United States Patent
Kanouni

(10) Patent No.: US 12,338,262 B2
(45) Date of Patent: *Jun. 24, 2025

(54) MODULATORS OF TNF-ALPHA ACTIVITY

(71) Applicant: Forward Therapeutics, Inc., Palm Beach Gardens, FL (US)

(72) Inventor: Toufike Kanouni, Palm Beach Gardens, FL (US)

(73) Assignee: FORWARD THERAPEUTICS, INC., Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/594,725

(22) Filed: Mar. 4, 2024

(65) Prior Publication Data
US 2024/0279258 A1    Aug. 22, 2024

Related U.S. Application Data

(63) Continuation of application No. 18/471,977, filed on Sep. 21, 2023, now Pat. No. 11,987,597, which is a continuation of application No. PCT/US2023/068223, filed on Jun. 9, 2023.

(60) Provisional application No. 63/351,116, filed on Jun. 10, 2022.

(51) Int. Cl.
| | |
|---|---|
| *C07D 471/12* | (2006.01) |
| *A61K 9/00* | (2006.01) |
| *A61K 9/08* | (2006.01) |
| *A61K 9/48* | (2006.01) |
| *C07D 471/02* | (2006.01) |
| *C07F 9/6558* | (2006.01) |
| *C07F 9/6561* | (2006.01) |
| *C07F 9/6584* | (2006.01) |

(52) U.S. Cl.
CPC ............ *C07F 9/6561* (2013.01); *A61K 9/08* (2013.01); *A61K 9/4825* (2013.01); *C07D 471/02* (2013.01); *C07D 471/12* (2013.01); *C07F 9/65583* (2013.01); *C07F 9/6584* (2013.01); *A61K 9/00* (2013.01)

(58) Field of Classification Search
None
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 9,242,968 B2 | 1/2016 | Boloor et al. |
| 9,447,046 B2 | 9/2016 | Boloor et al. |
| 9,586,902 B2 | 3/2017 | Boloor et al. |
| 9,815,828 B2 | 11/2017 | Boloor et al. |
| 2015/0132339 A1 | 5/2015 | Bufali et al. |
| 2024/0076306 A1 | 3/2024 | Kanouni |

FOREIGN PATENT DOCUMENTS

| | | |
|---|---|---|
| WO | WO-9310114 A1 | 5/1993 |
| WO | WO-2005099710 A1 | 10/2005 |
| WO | WO-2008005555 A1 | 1/2008 |
| WO | WO-2018119183 A2 | 6/2018 |
| WO | WO-2023240253 A2 | 12/2023 |

OTHER PUBLICATIONS

Berge et al., Pharmaceutical Salts. Journal of Pharmaceutical Sciences 66(1):1-19 (1977).
Braga et al., Overview of TNF Inhibitors for Treating Inflammatory Bowel Disease. US Pharm. 46(5):34-37 (2021).
Chemical Structure Search (SciFinder) dated Jun. 1, 2023, 2 pages.
Chemical Structure Search (SciFinder) dated Jun. 1, 2023 (p. 3).
Chemical Structure Search (SciFinder) dated May 30, 2023, 2 pages.
Dean et al. Recent Advances in the Synthesis and Applications of Radiolabeled Compounds for Drug Discovery and Development. Current Pharmaceutical Design 6:110 (2000).
Dietrich et al., Development of Orally Efficacious Allosteric Inhibitors of TNFα via Fragment-Based Drug Design. J Med Chem 64:417-429 (2021).
Dömling et al. TNF-α: The shape of small molecules to come? Drug Discov Today 27(1):3-7 (2022).
Evans. Synthesis Of Radiolabelled Compounds. Journal of Radioanalytical and Nuclear Chemistry 64(1-2):9-32 (1981).
Finkbeiner et al. Phosphine Oxides from a Medicinal Chemist's Perspective: Physicochemical and in Vitro Parameters Relevant for Drug Discovery. J Med Chem 63(13):7081-7107 (2020).
Fresegna et al., Re-Examining the Role of TNF in MS Pathogenesis and Therapy. Cells 9:2290 (2020).
He et al., Small-molecule inhibition of TNF-alpha. Science 310:1022-1025 (2015).
Kabalka et al., The synthesis of radiolabeled compounds via organometallic intermediates. Tetrahedron 45(21):6601-6621 (1989).
Lightwood et al. A conformation-selective monoclonal antibody against a small molecule-stabilised signalling-deficient form of TNF. Nat Commun 12(1):582 (2021).
O'Connell et al., Small molecules that inhibit TNF signalling by stabilising an asymmetric form of the trimer. Nature Commun 10:5795 (2019).
Orti-Casañ et al., Targeting TNFR2 as a Novel Therapeutic Strategy for Alzheimer's Disease. Front Neurosci. 13:49 (2019).
PCT/US2023/068223 International Invitation to Pay Additional Fees dated Sep. 13, 2023.
PCT/US2023/068223 International Search Report and Written Opinion dated Dec. 20, 2023.
Pubchem CID 154710039. 1-(2-Methyl-4,6-diphenylquinolin-3-yl)ethanone. Created Oct. 27, 2020, 10 pages.

(Continued)

*Primary Examiner* — Gigi G Huang
(74) *Attorney, Agent, or Firm* — WILSON SONSINI GOODRICH & ROSATI

(57) ABSTRACT

Provided herein are inhibitors of TNF-α, pharmaceutical compositions comprising the inhibitory compounds, and methods for using the TNF-α inhibitory compounds for the treatment of diseases or disorders.

20 Claims, No Drawings

(56) References Cited

OTHER PUBLICATIONS

Science IP Chemical Structure Search prepared May 12, 2022, 78 pages.

Shulman et al., Neuroinflammation and Tinnitus. Curr Top Behav Neurosci. 51:161-174 (2021).

Wang et al., Neuroinflammation mediates noise-induced synaptic imbalance and tinnitus in rodent models. PLoS Biol. 17(6):e3000307 (2019).

Xiao et al., Biologic-like In Vivo Efficacy with Small Molecule Inhibitors of TNFα Identified Using Scaffold Hopping and Structure-Based Drug Design Approaches. J Med Chem 63(23):15050-15071 (2020).

MODULATORS OF TNF-ALPHA ACTIVITY

CROSS-REFERENCE TO RELATED APPLICATION

This application is a continuation of U.S. patent application Ser. No. 18/471,977, filed Sep. 21, 2023, which is a continuation of PCT International Patent Application No. PCT/US2023/068223, filed Jun. 9, 2023, which claims the benefit of U.S. Patent Application No. 63/351,116, filed on Jun. 10, 2022, all of which are hereby incorporated by reference in their entirety.

BACKGROUND

Tumor necrosis factor alpha (TNF-α) is an inflammatory cytokine that is responsible for a wide range of signaling events within cells. Aberrant TNF-α signaling gives rise to inflammatory conditions and is thought to be an important component of inflammatory disease, such as rheumatoid arthritis.

BRIEF SUMMARY OF THE INVENTION

Provided herein are inhibitors of TNF-α, pharmaceutical compositions comprising said inhibitory compounds, and methods for using said inhibitory compounds for the treatment of inflammatory or autoimmune disease or disorder.

One embodiment provides a compound, or a pharmaceutically acceptable salt or solvate thereof, having the structure of Formula (I):

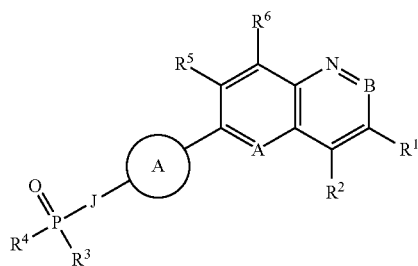

wherein,
A is N, C—F, or C—H;
B is N or C—R;
Ring A is optionally substituted C6 aryl, optionally substituted 6-membered heteroaryl, or optionally substituted 6-membered heterocyclyl;
J is a bond, —CH$_2$—, or —CH$_2$—O—;
R is selected from halogen, amino, or optionally substituted C1-C3 alkyl;
R$^1$ is selected from halogen, cyano, optionally substituted C1-C3 alkyl, optionally substituted C3-C5 cycloalkyl, optionally substituted C2-C3 alkenyl, or optionally substituted C2-C3 alkynyl;
R$^2$ is L-G; wherein L is a bond, —O—, —NH—, —NH(optionally substituted C1-C3 alkylene)-,

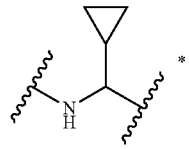 [SMILES: *NC(*)C1CC1]

wherein the * denotes the point of attachment of G, optionally substituted C1-C3 alkylene, or optionally substituted cyclopropyl; and G is an optionally substituted C6 aryl, or optionally substituted 5- or 6-membered heteroaryl;
R$^3$ is hydroxy, optionally substituted C1-C6 alkyl, or optionally substituted alkoxy;
R$^4$ is hydroxy, optionally substituted C1-C6 alkyl, or optionally substituted alkoxy; or R$^3$ and R$^4$ join to form optionally substituted phosphorus-containing 3- to 8-membered heterocyclyl; and
each R$^5$ and R$^6$ is independently selected from hydrogen, halogen, or optionally substituted C1-C3 alkyl.

One embodiment provides a compound, or a pharmaceutically acceptable salt or solvate thereof, having the structure of Formula (IA):

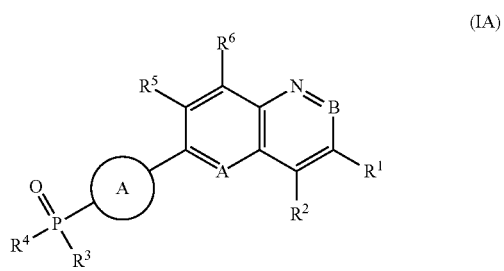

wherein,
A is N, C—F or C—H;
B is N or C—R;
Ring A is optionally substituted C6 aryl, optionally substituted 6-membered heteroaryl, or optionally substituted 6-membered heterocyclyl;
R is selected from halogen, amino or optionally substituted C1-C3 alkyl;
R$^1$ is selected from halogen, cyano, optionally substituted C1-C3 alkyl, or optionally substituted C3-C5 cycloalkyl, optionally substituted C2-C3 alkenyl, or optionally substituted C2-C3 alkynyl;
R$^2$ is L-G; wherein L is a bond, —O—, —NH—, —NH(optionally substituted C1-C3 alkylene)-, optionally substituted C1-C3 alkylene, or optionally substituted cyclopropyl; and G is an optionally substituted C6 aryl, or optionally substituted 5- or 6-membered heteroaryl;
R$^3$ is hydroxy or optionally substituted C1-C6 alkyl;
R$^4$ is hydroxy or optionally substituted C1-C6 alkyl; or R$^3$ and R$^4$ join to form optionally substituted phosphorus-containing 3- to 8-membered heterocyclyl; and
each R$^5$ and R$^6$ is independently selected from hydrogen, halogen, or optionally substituted C1-C3 alkyl.

One embodiment provides a pharmaceutical composition comprising compounds described herein (e.g., compounds of Formula (I)), or pharmaceutically acceptable salt or solvate thereof, and at least one pharmaceutically acceptable excipient.

One embodiment provides a method of treating a disease or disorder in a patient in need thereof comprising administering to the patient compounds described herein (e.g., compounds of Formula (I)), or pharmaceutically acceptable salt or solvate thereof. Another embodiment provides the method wherein the disease or disorder is rheumatoid arthritis.

One embodiment provides a method of treating an inflammatory or autoimmune disease or disorder in a patient in need thereof, comprising administering to the patient a therapeutically effectively amount of the compound (e.g., compounds of Formula (I)) or pharmaceutically acceptable salt or solvate thereof described herein.

One embodiment provides a method of inhibiting TNF-α activity comprising contacting the TNF-α protein with the compound (e.g., compounds of Formula (I)) or pharmaceutically acceptable salt or solvate thereof described herein, wherein the TNF-α protein is contacted in an in vitro setting.

One embodiment provides a method of inhibiting TNF-α activity comprising contacting the TNF-α protein with the compound (e.g., compounds of Formula (I)) or pharmaceutically acceptable salt or solvate thereof described herein, wherein the TNF-α protein is contacted in an in vivo setting.

One embodiment provides a method of treating or preventing a condition conducive to treatment or prevention by inhibition of TNF-α in a patient comprising administering to the patient a therapeutically effective amount of the compound (e.g., compounds of Formula (I)) or pharmaceutically acceptable salt or solvate thereof described herein.

One embodiment provides a compound (e.g., compounds of Formula (I)), or pharmaceutically acceptable salt or solvate or pharmaceutical composition described herein, for use in a method of treatment of the human or animal body.

One embodiment provides a compound (e.g., compounds of Formula (I)), or pharmaceutically acceptable salt or solvate, or pharmaceutical composition thereof, as described herein, for use in a method of treatment of inflammatory or immune disease or disorder disease.

One embodiment provides a compound (e.g., compounds of Formula (I)), or pharmaceutically acceptable salt or solvate thereof, as described herein, for use in treating or preventing a condition conducive to treatment or prevention by inhibition of TNF-α in a patient.

One embodiment provides use of a compound (e.g., compounds of Formula (I)), or pharmaceutically acceptable salt or solvate, or pharmaceutical composition thereof, as described herein, in the manufacture of a medicament for the treatment of an inflammatory or autoimmune disease or disorder.

One embodiment provides use of a compound (e.g., compounds of Formula (I)), or pharmaceutically acceptable salt or solvate thereof, as described herein, in the preparation of a medicament for treating or preventing a condition conducive to treatment or prevention by inhibition of TNF-α in a patient.

One embodiment provides a pharmaceutical composition comprising the compound (e.g., compounds of Formula (I)), or pharmaceutically acceptable salt or solvate as described herein, for use in an inflammatory or autoimmune disease or disorder in a patient in need thereof.

One embodiment provides a pharmaceutical composition comprising the compound (e.g., compounds of Formula (I)) described herein, for use in treating or preventing a condition conducive to treatment or prevention by inhibition of TNF-α in a patient.

One embodiment provides a method of preparing a pharmaceutical composition comprising mixing the compounds (e.g., compounds of Formula (I)), or pharmaceutically acceptable salt or solvate thereof, as described herein, and a pharmaceutically acceptable excipient or carrier.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —$CF_3$ group.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted cycloalkylalkyl, optionally substituted heterocyclylalkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—

N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the R$^a$, R$^b$, or R$^c$ substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

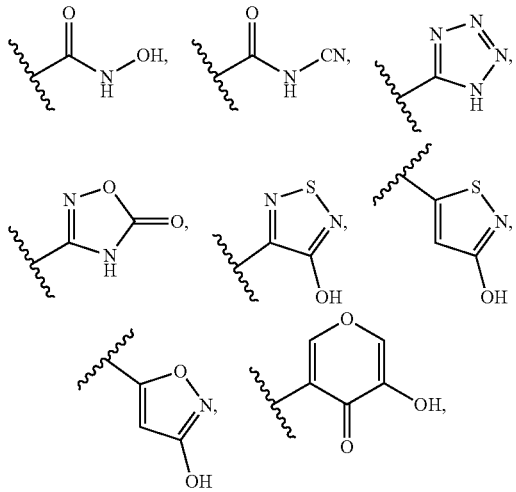

and the like.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

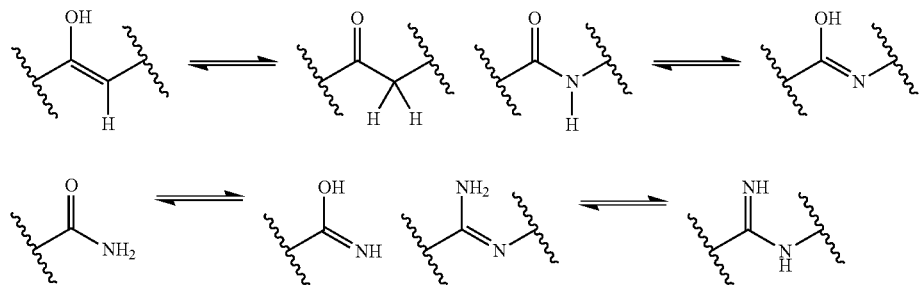

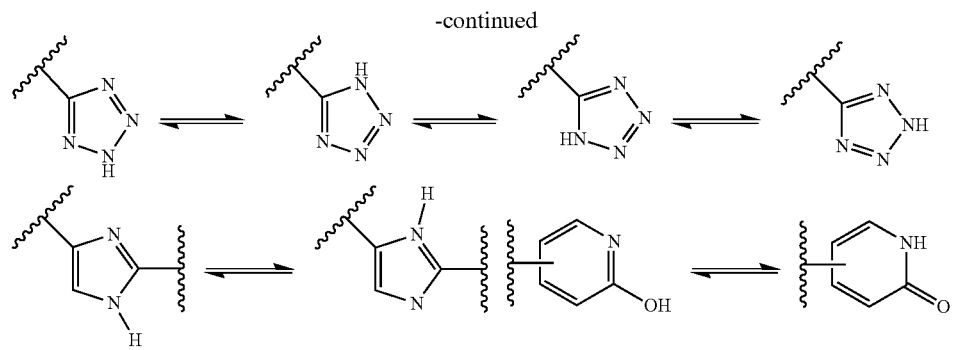

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium (2H), tritium (3H), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

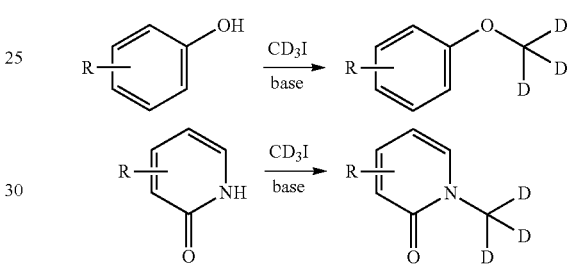

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

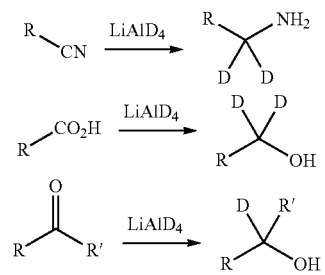

Deuterium gas and palladium catalyst are employed to reduce unsaturated carbon-carbon linkages and to perform a reductive substitution of aryl carbon-halogen bonds as illustrated, by way of example only, in the reaction schemes below.

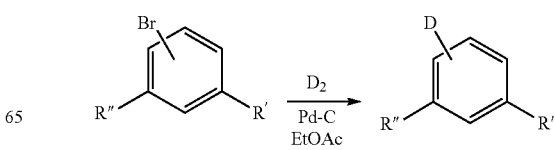

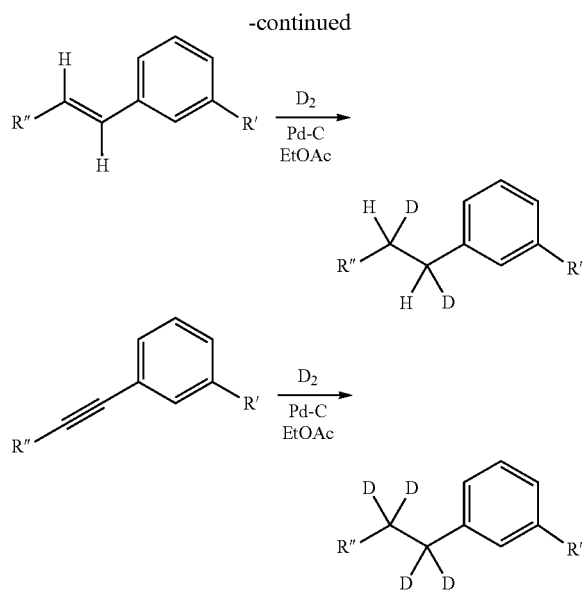

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the TNF-α inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein exist in either unsolvated or solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Tumor Necrosis Factor Alpha (TNFα) Protein and Function

Tumor necrosis factor alpha (TNFα) proteins are members of the TNF superfamily, comprising various transmembrane proteins with a homologous TNF domain forming trimers. The TNF superfamily comprises 19 family members, including, but not limited to tumor necrosis factor alpha (also known as tumor necrosis factor, or TNF), lymphotoxin alpha (TNFβ), lymphotoxin beta (TNFγ), OX40 ligand, CD40 ligand, Fas ligand, CD27 ligand, CD30 ligand, CD137 ligand, CD137 ligand, and TNF-related apoptosis-inducing ligand. TNFα proteins are cytokines and adipokines (cytokines secreted by adipose tissue).

TNFα is a transmembrane protein, with soluble TNFα (sTNFα) released via protein cleavage. The sTNFα can propagate signaling by binding to two receptors, TNFR1 and TNFR2. TNFα is a regulator of immune responses for cell signaling and can mediate cell survival and cell death inducing signaling. There are two receptors for TNF signaling, TNFR1 and TNFR2. sTNFα-TNFR1 signaling promotes immune cell activation and drives acute and chronic inflammation. Membrane TNFα-TNFR2 signaling promotes inflammation resolution, immune cell regulatory functions and cell survival.

The extracellular region of both TNFR1 and TNFR2 have four homologous cysteine-rich domains, but they have structurally different intracellular regions. TNFR1 has a protein binding region called a death domain which allows homo- and hetero-typic interactions with other death domain-containing proteins. In contrast, TNFR2 has a TNF Receptor Associated Factor TRAF) that interacts with TRAF family of signaling adaptors. The distinct profiles and differences of the two TNF receptors influence the cellular activity and physiological roles. TNFR1 can activate NF-κB and MAPK signaling, and cell death, and is important to regulate for inflammatory diseases. TNFR2 is highly regulated and restricted to specific cell types such as endothelial cells and T cells. TNFR1 primarily promotes tissue degeneration and inflammation and TNFR2 typically mediates local homeostatic effects such as tissue regeneration and cell survival (D. Fresegna et al., Cells, 2020, 9, 2290).

Binding of TNFα to TNFR1 can activate NF-κB for mediating transcription of various proteins involved in cell survival and proliferation, anti-apoptotic factors, and inflammatory response. Further, the MAPK pathway can also be activated by binding of TNFα to TNFR1, which is involved in cell differentiation and proliferation. When TNF binds to TNFR1, it triggers receptor trimerization, leading to the assembly of a TNFR1-associated signaling complex. This complex recruits the receptor interacting protein 1 (RIP2) and TNF receptor associated death domain (TRADD) to the TNFR1 through the receptive death domains. TRADD then recruits adaptor proteins TRAF2 and TRAF5, which can engage the E3 ligases cellular inhibitors of apoptosis (c-IAP1, c-IAP2). C-IAP1/2 are important for TNFR1 complex signaling, which can eventually lead to the recruitment of the signaling kinase complexes of kinase IKKα and IKKβ, which are inhibitors of kappa B kinase 1 and 2, and transforming growth factor beta-activated kinase 1 (TAK1) leading to activation of NF-κB and MAPK signaling. Activation of these signaling pathways can result in gene activation and expression of pro-inflammatory cytokines and pro-survival proteins.

TNF signaling is regulated by post-translational ubiquitination, which is essential for my biological processes. Post-translational modifications of TNFR1-associated signaling complexes can result in a change from inflammatory gene signaling to cell death. This switch is dependent upon the ubiquitination status of RIP1, which is formed as part of the TNFR1-associated signaling complex from TNFα binding.

TNF has long been known to be a key regulator of the inflammatory response, and recently has been known to be involved n brain functioning (D. Fresegna et al., Cells, 2020, 9, 2290). As a regulator of the inflammatory response, TNF can regulate many aspects of T cell biology including, but not limited to proliferation, survival, priming, and apoptotic fate. TNF is also known to play a role in conclusion of lymphocyte response, by the ability to promote cell death in both CD4 and CD8P T cells, through TNFR1. Specific inflammatory conditions can also result in TNFR2 promoting or supporting T cell apoptosis.

In normal adult brains, TNF is expressed at low levels, and it is believed that the expression could be influenced by presence or absence of cytokines that can cross the blood brain barrier. TNFRs in the brain are expressed by glia and neurons cells, and have regulatory functions, including, but not limited to homeostatic synaptic plasticity, astrocyte-mediated synaptic transmission, and neurogenesis. These functions are useful for regulating learning and memory functions amongst other roles.

TNF is recognized to be physiological gliotransmitter for the communication between neurons and glial cells, which in turn affects synaptic regulation. Glial TNF is important for maintenance of normal surface expression of AMPA receptors, and for homeostatic synaptic scaling, which allows for adjustment of the strength of all synapses on a neuron.

Prior Art Small Molecules Inhibitors

Diseases treated with biologic TNFα inhibitors include, but are not limited to rheumatoid arthritis, inflammatory bowel disease, psoriatic arthritis, psoriasis, and ankylosing spondylitis. Patients with neuroinflammatory conditions and degenerative disease, including, but not limited to Alzheimer's disease, Parkinson's disease, multiple sclerosis, treatment resistant depression, and tinnitus, may benefit from treatment with oral CNS sTNFα inhibitors by disrupting the sTNFα signaling and sparing the mTNFα signaling. Previous reports have also indicated targeting TNFR2 for treating Alzheimer's Disease (N. Orti-Casañ et al., Front Neurosci. 2019; 13: 49).

Small molecules have been developed for treatment of rheumatoid arthritis as some patients have responded poorly to monotherapy of approved anti-TNFα drugs (J. D. Dietrich et al., J. Med. Chem. 2021, 64, 417-429). Anti-TNFα drugs have also been expanded for use in other chronic autoimmune diseases, including, but not limited to, Crohn's disease, psoriasis, psoriatic arthritis, ulcerative colitis inflammatory bowel disease, ankylosing spondylitis, and juvenile rheumatoid arthritis. Small molecules have been developed as an alternative to anti-TNFα biologics since the long-term clinical response rate is generally around 60-70% for rheumatoid arthritis.

Previous research has also indicated that TNFα inhibitors can be therapeutic for treatment of multiple sclerosis (D.

Fresegna et al., Cells, 2020, 9, 2290). There has been evidence of the involvement of TNF in various pathological issues of multiple sclerosis, including immune dysregulation, demyelination, synaptopathy, and neuroinflammation. TNFα inhibitors have the potential for treatment of multiple sclerosis, other potential chronic neurodegenerative diseases of the central nervous system.

More than 50 million Americans struggle with tinnitus, which is the hearing of a sound with no external source. It has been shown that TNFα is necessary for noise-induced neuroinflammation and synaptic imbalance (W. Wang et al., PLoS Biol. 2019 Jun. 18; 17(6): e3000307; A. Shulman et al., Curr Top Behav Neurosci. 2021; 51:161-174). It is believed that certain inhibitors of TNFα have activities for treating tinnitus.

Recent reports also indicate that TNFα inhibitors can be used alone or in combination for treatment with inflammatory bowel disease (S. F. Fowler Braga and K. J. Clark, US Pharm. 2021; 46(5):34-37). TNFα is a mediator of the abnormal immune response of inflammatory bowel disease, which leads to disruption of the intestinal mucosa and epithelial wall barrier. The anti-TNF agents can block TNF-mediated activation of the proinflammatory pathways to result in decreased immune-mediated inflammation.

Small molecule sTNF α inhibitors are active in pharmacology models of sTNFα/TNFR1 signaling in addition to demonstrating efficacy in a model of collagen antibody induced arthritis. There is currently limited data in the public domain for small molecule sTNF α inhibitors. Some TNFα inhibitors include, but are not limited to XPro1595, Etanercept, Infliximab, Adalimumab, Certolizumab pegol, Golimumamb, and other inhibitors described in "TNF-α: The Shape of Small Molecules to Come?" (A. Dömling and X. Li, Drug Discov Today 2022 January; 27(1):3-7) and "Small Molecules that Inhibit TNF Signalling by Stabilising an Asymmetric Form of the Trimer (J. O'Connell et al., Nature Communications 10, 5795 (2019)). Additional small molecule inhibitors of TNFα include, but are not limited to the inhibitors described in "Biologic-like In Vivo Efficacy with Small Molecule Inhibitors of TNFα Identified Using Scaffold Hopping and Structure-Based Drug Design Approaches" (H—Y Xiao et al., J. Med. Chem. 2020, 15050-15071), "Development of Orally Efficacious Allosteric Inhibitors of TNFα via Fragment-Based Drug Design" (J. D. Dietrich et al., J. Med. Chem. 2021, 64, 417-429), and "Small-Molecule Inhibition of TNF-α" (M. M. He et al., Science, 310 (2015), 1022-1025).

Small molecule sTNFα inhibitors have potential as a valuable therapy for patients currently treated with biologic TNFα inhibitors which affect mTNFα with the ability to fine tune oral dosing requirements and avoid anti-drug antibody responses, thereby improving short and long responses (A. Dömling and X. Li, Drug Discov Today 2022 January; 27(1):3-7).

Novel Compounds Inhibiting TNF-α

In one aspect, provided herein are TNF-α inhibitory compounds.

One embodiment provides a compound, or a pharmaceutically acceptable salt or solvate thereof, having the structure of Formula (I):

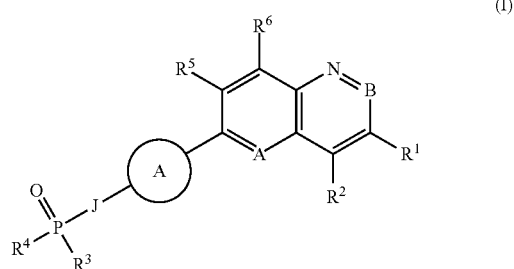

wherein,
A is N, C—F, or C—H;
B is N or C—R;
Ring A is optionally substituted C6 aryl, optionally substituted 6-membered heteroaryl, or optionally substituted 6-membered heterocyclyl;
J is a bond, —CH$_2$—, or —CH$_2$—O—;
R is selected from halogen, amino, or optionally substituted C1-C3 alkyl;
R$^1$ is selected from halogen, cyano, optionally substituted C1-C3 alkyl, optionally substituted C3-C5 cycloalkyl, optionally substituted C2-C3 alkenyl, or optionally substituted C2-C3 alkynyl;
R$^2$ is L-G; wherein L is a bond, —O—, —NH—, —NH(optionally substituted C1-C3 alkylene)-,

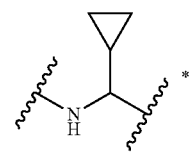 [SMILES: *NC(*)C1CC1]

wherein the * denotes the point of attachment of G, optionally substituted C1-C3 alkylene, or optionally substituted cyclopropyl; and G is an optionally substituted C6 aryl, or optionally substituted 5- or 6-membered heteroaryl;
R$^3$ is hydroxy, optionally substituted C1-C6 alkyl, or optionally substituted alkoxy;
R$^4$ is hydroxy, optionally substituted C1-C6 alkyl, or optionally substituted alkoxy; or R$^3$ and R$^4$ join to form optionally substituted phosphorus-containing 3- to 8-membered heterocyclyl; and
each R$^5$ and R$^6$ is independently selected from hydrogen, halogen, or optionally substituted C1-C3 alkyl.

One embodiment provides a compound, or pharmaceutically acceptable salt or solvate thereof, having the structure of Formula (IA):

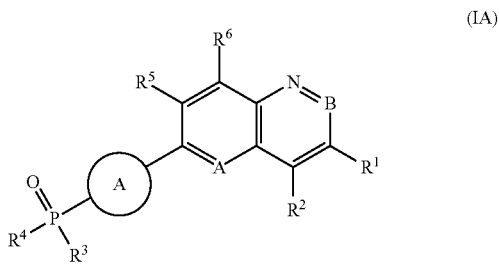

wherein,
A is N, C—F, or C—H;
B is N or C—R;
Ring A is optionally substituted C6 aryl, optionally substituted 6-membered heteroaryl, or optionally substituted 6-membered heterocyclyl;
R is selected from halogen, amino, or optionally substituted C1-C3 alkyl;
R$^1$ is selected from halogen, cyano, optionally substituted C1-C3 alkyl, optionally substituted C3-C5 cycloalkyl, optionally substituted C2-C3 alkenyl, or optionally substituted C2-C3 alkynyl;
R$^2$ is L-G; wherein L is a bond, —O—, —NH—, —NH(optionally substituted C1-C3 alkylene)-, optionally substituted C1-C3 alkylene, or optionally substituted cyclopropyl; and G is an optionally substituted C6 aryl, or optionally substituted 5- or 6-membered heteroaryl;
R$^3$ is hydroxy or optionally substituted C1-C6 alkyl;
R$^4$ is hydroxy or optionally substituted C1-C6 alkyl; or R$^3$ and R$^4$ join to form optionally substituted phosphorus-containing 3- to 8-membered heterocyclyl; and
each R$^5$ and R$^6$ is independently selected from hydrogen, halogen, or optionally substituted C1-C3 alkyl.

In some embodiments, Ring A is optionally substituted C6 aryl or optionally substituted 6-membered heteroaryl.

In some embodiments, the compound of Formula (I), or pharmaceutically acceptable salt, or solvate thereof, has a structure of Formula (IB):

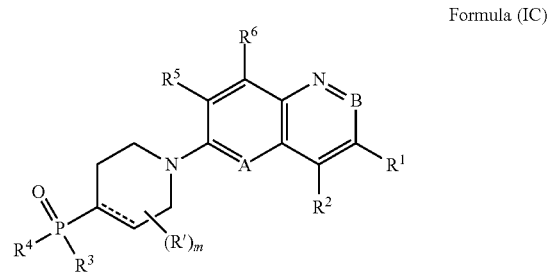

Formula (IB)

wherein:
A is N, C—F, or C—H;
B is N or C—R;
R is selected from halogen, amino, or optionally substituted C1-C3 alkyl;
R$^1$ is selected from halogen, cyano, optionally substituted C1-C3 alkyl, optionally substituted C3-C5 cycloalkyl, optionally substituted C2-C3 alkenyl, or optionally substituted C2-C3 alkynyl;
R$^2$ is L-G; wherein L is a bond, —O—, —NH—, —NH(optionally substituted C1-C3 alkylene)-, optionally substituted C1-C3 alkylene, or optionally substituted cyclopropyl; and G is an optionally substituted C6 aryl, or optionally substituted 5- or 6-membered heteroaryl;
R$^3$ is hydroxy or optionally substituted C1-C6 alkyl;
R$^4$ is hydroxy or optionally substituted C1-C6 alkyl; or R$^3$ and R$^4$ join to form optionally substituted phosphorus-containing 3- to 8-membered heterocyclyl;
each R$^5$ and R$^6$ is independently selected from hydrogen, halogen, or optionally substituted C1-C3 alkyl;
W is N or C—R$^7$;
X is N or C—R$^8$;
Y is N or C—R$^9$;
Z is N or C—R$^{10}$;
each R$^7$ and R$^8$ is independently selected from hydrogen, halogen, —CN, optionally substituted C1-C3 alkyl, optionally substituted C1-C3 alkoxy, or —NH (optionally substituted C1-C3 alkyl); and
each R$^9$ and R$^{10}$ is independently selected from hydrogen, halogen, —CN, optionally substituted C1-C3 alkyl, optionally substituted C3-C7 cycloalkyl, optionally substituted C1-C3 alkoxy, or —NH(optionally substituted C1-C3 alkyl).

In some embodiments, Ring A is optionally substituted C6 aryl, optionally substituted 6-membered heteroaryl, or optionally substituted 6-membered heterocyclyl. In some embodiments, Ring A is optionally substituted 6-membered heterocyclyl.

In some embodiments, the compound of Formula (I), or pharmaceutically acceptable salt, or solvate thereof, has a structure of Formula (IC):

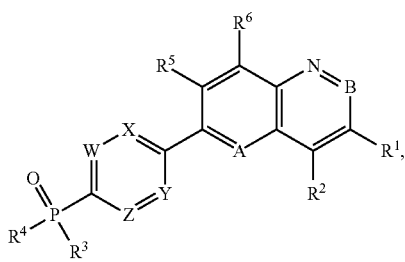

Formula (IC)

wherein:
A is N, C—F, or C—H;
B is N or C—R;
R is selected from halogen, amino, or optionally substituted C1-C3 alkyl;
R$^1$ is selected from halogen, cyano, optionally substituted C1-C3 alkyl, optionally substituted C3-C5 cycloalkyl, optionally substituted C2-C3 alkenyl, or optionally substituted C2-C3 alkynyl;
R$^2$ is L-G; wherein L is a bond, —O—, —NH—, —NH(optionally substituted C1-C3 alkylene)-, optionally substituted C1-C3 alkylene, or optionally substituted cyclopropyl; and G is an optionally substituted C6 aryl, or optionally substituted 5- or 6-membered heteroaryl;
R$^3$ is hydroxy or optionally substituted C1-C6 alkyl;
R$^4$ is hydroxy or optionally substituted C1-C6 alkyl; or R$^3$ and R$^4$ join to form optionally substituted phosphorus-containing 3- to 8-membered heterocyclyl;
each R$^5$ and R$^6$ is independently selected from hydrogen, halogen, or optionally substituted C1-C3 alkyl;
each ═ is independently a single or a double bond;
each R' is independently selected from halogen or optionally substituted C1-C3 alkyl; and
m is 0, 1, 2, 3 or 4.

In some embodiments, A is N, C—F, or C—H. In some embodiments, A is N or C—F. In some embodiments, A is C—F or C—H. In some embodiments, A is N or C—H. In some embodiments, A is N. In some embodiments, A is C—H. In some embodiments, B is N or C—R. In some embodiments, B is N. In some embodiments, B is C—R.

In some embodiments, W is N or C—R$^7$. In some embodiments, W is N. In some embodiments, W is C—R$^7$. In some embodiments, X is N or C—R$^8$. In some embodiments, X is N. In some embodiments, X is C—R⁸. In some embodiments, Y is N or C—R⁹. In some embodiments, Y is N. In some embodiments, Y is C—R⁹. In some embodiments, Z is N or C—R¹⁰. In some embodiments, Z is N. In some embodiments, Z is C—R¹⁰. In some embodiments, W is N, X is C—R⁸, Y is C—R⁹, and Z is C—R¹⁰. In some embodiments, W is C—R⁷, X is N, Y is C—R⁹, and Z is C—R¹⁰. In some embodiments, W is C—R⁷, X is C—R⁸, Y is N, and Z is C—R¹⁰. In some embodiments, W is C—R⁷, X is C—R⁸, Y is C—R⁹, and Z is N. In some embodiments, W is N, X is C—R⁸, Y is C—R⁹, and Z is N. In some embodiments, W is C—R⁷, X is C—R⁸, Y is C—R⁹, and Z is C—R¹⁰. In some embodiments, W, X, Y, and Z are each CH. In some embodiments, W is N, and X, Y, and Z are each independently CH, CF, CCl, or C(CH₃). In some embodiments, W is N, Z is N, and X and Y are each independently CH, CF, CCl, or C(CH₃).

In some embodiments, R is selected from halogen, amino, or optionally substituted C1-C3 alkyl. In some embodiments, R is selected from amino or optionally substituted C1-C3 alkyl. In some embodiments, R is selected from halogen or optionally substituted C1-C3 alkyl. In some embodiments, R is halogen. In some embodiments, R is F, Cl or Br. In some embodiments, R is F or Cl. In some embodiments, R is optionally substituted C1-C3 alkyl. In some embodiments, R is unsubstituted C1-C3 alkyl. In some embodiments, R is substituted C1-C3 alkyl. In some embodiments, R is C1-C3 alkyl optionally substituted with a halo, hydroxy, $C_{6-14}$ aryl, $C_{6-14}$ aryloxy, or heterocyclyl. In some embodiments, R is selected from the group consisting of F, Cl, Br, I, NH₂, methyl, ethyl, n-propyl, i-propyl, —CH₂F, —CHF₂, and —CF₃. In some embodiments, R is selected from the group consisting of F, Cl, NH₂, methyl, ethyl, and n-propyl. In some embodiments, R is methyl, ethyl, or n-propyl. In some embodiments, R is methyl or ethyl. In some embodiments, R is methyl. In some embodiments, R is ethyl. In some embodiments, R is n-propyl.

In some embodiments, R¹ is selected from halogen, cyano, optionally substituted C1-C3 alkyl, optionally substituted C3-C5 cycloalkyl, optionally substituted C2-C3 alkenyl, or optionally substituted C2-C3 alkynyl. In some embodiments, R¹ is selected from halogen, optionally substituted C1-C3 alkyl, optionally substituted C3-C5 cycloalkyl, optionally substituted C2-C3 alkenyl, or optionally substituted C2-C3 alkynyl. In some embodiments, R¹ is selected from halogen, optionally substituted C1-C3 alkyl, or optionally substituted C1-C3 alkenyl. In some embodiments, R¹ is selected from halogen, optionally substituted C1-C3 alkyl, or optionally substituted C3-C5 cycloalkyl. In some embodiments, R¹ is selected from halogen or optionally substituted C1-C3 alkyl. In some embodiments, R¹ is selected from halogen, or optionally substituted C3-C5 cycloalkyl. In some embodiments, R¹ is selected from optionally substituted C1-C3 alkyl, or optionally substituted C3-C5 cycloalkyl. In some embodiments, R¹ is halogen. In some embodiments, R¹ is optionally substituted C1-C3 alkyl. In some embodiments, R¹ is optionally substituted C3-C5 cycloalkyl. In some embodiments, R¹ is cyano. In some embodiments, R¹ is optionally substituted C1-C3 alkenyl. In some embodiments, R¹ is optionally substituted C2-C3 alkynyl. In some embodiments, R¹ is selected from F, Cl, Br, I, cyano, methyl, ethyl, n-propyl, i-propyl, cyclopropyl, —CH₂F, —CHF₂, —CF₃, and —CH=CH₂. In some embodiments, R¹ is selected from F, Cl, Br, I, methyl, ethyl, n-propyl, i-propyl, —CH₂F, —CHF₂, —CF₃, and —CH=CH₂. In some embodiments, R¹ is selected from F, Cl, Br, I, methyl, ethyl, n-propyl, i-propyl, —CH₂F, —CHF₂, or —CF₃. In some embodiments, R¹ is selected from F, Cl, methyl, ethyl, n-propyl, i-propyl, and —CF₃. In some embodiments, R¹ is selected from F, Cl, methyl, and ethyl. In some embodiments, R¹ is selected from F, Cl, and methyl. In some embodiments, R¹ is F. In some embodiments, R¹ is Cl. In some embodiments, R¹ is methyl.

In some embodiments, R² is L-G. In some embodiments, L is a bond, —O—, —NH—, —NH(optionally substituted C1-C3 alkylene)-, optionally substituted C1-C3 alkylene, or optionally substituted cyclopropyl. In some embodiments, L is a bond, —O—, —NH—, —NH(optionally substituted C1-C3 alkylene)-, or optionally substituted C1-C3 alkylene. In some embodiments, L is —O—, —NH—, or —NH (optionally substituted C1-C3 alkylene)-. In some embodiments, L is —O—. In some embodiments, L is —N—. In some embodiments, L is —NH(optionally substituted C1-C3 alkylene)-. In some embodiments, L is —NH—CH(CH₃)—. In some embodiments, L is

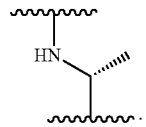

In some embodiments, G is an optionally substituted C6 aryl, or optionally substituted 5- or 6-membered heteroaryl. G is C6 aryl or 5- or 6-membered heteroaryl, optionally substituted with one, two, three, four, or five substituents $Q^4$; wherein each $Q^4$ is independently selected from (a) cyano, halo, hydroxy, and nitro; (b) $C_{1-6}$ alkyl, $C_{1-6}$ alkoxy, $C_{2-6}$ alkenyl, $C_{2-6}$ alkynyl, $C_{3-10}$ cycloalkyl, $C_{3-10}$ cycloalkyloxy, $C_{6-14}$ aryl, $C_{6-14}$ aryloxy, $C_{7-15}$ aralkyl, heteroaryl, and heterocyclyl. In some embodiments, G is C6 aryl optionally substituted with one, two, three, four, or five substituents $Q^4$; wherein each $Q^4$ is independently selected from cyano, F, Cl, Br, hydroxy, nitro, CH₃, CH₂OH, CHF₂, CH₂F, CF₃, C₂H₅, C(CH₃)₂, OCH₃, OC₂H₅, OCHF₂, OCH₂F, OCF₃, OC₂H₅, OC(CH₃)₂, cyclopropyl, and cyclopropoxy.

In some embodiments, G is phenyl optionally substituted with one, two, three, or four substituents $Q^4$; wherein each $Q^4$ is independently selected from cyano, F, Cl, Br, hydroxy, nitro, CH₃, CH₂OH, CHF₂, CH₂F, CF₃, C₂H₅, C(CH₃)₂, OCH₃, OC₂H₅, OCHF₂, OCH₂F, OCF₃, OC₂H₅, OC(CH₃)₂, cyclopropyl, and cyclopropoxy. In some embodiments, G is phenyl substituted with one $Q^4$. In some embodiments, G is phenyl substituted with two $Q^4$. In some embodiments, G is phenyl substituted with three or four $Q^4$.

In some embodiments, G is 5- to 10-membered heteroaryl optionally substituted with one, two, three, four, or five substituents $Q^4$; wherein each $Q^4$ is independently selected from (a) cyano, halo, hydroxy, and nitro; (b) $C_{1-6}$ alkyl, $C_{1-6}$ alkoxy, $C_{2-6}$ alkenyl, $C_{2-6}$ alkynyl, $C_{3-10}$ cycloalkyl, $C_{6-14}$ aryl, $C_{6-14}$ aryloxy, $C_{7-15}$ aralkyl, heteroaryl, and heterocyclyl. In some embodiments, G is 5- or 6-membered heteroaryl optionally substituted with one, two, three, four, or five substituents $Q^4$; wherein each $Q^4$ is independently selected from (a) cyano, halo, hydroxy, and nitro; (b) $C_{1-6}$ alkyl, $C_{1-6}$ alkoxy, $C_{2-6}$ alkenyl, $C_{2-6}$ alkynyl, $C_{3-10}$ cycloalkyl, $C_{3-10}$ cycloalkyloxy, $C_{6-14}$ aryl, $C_{6-14}$ aryloxy, $C_{7-15}$ aralkyl, heteroaryl, and heterocyclyl. In some embodiments, G is 5- or 6-membered heteroaryl substituted with one $Q^4$. In some embodiments, G is 5- or 6-membered heteroaryl substituted with two $Q^4$. In some embodiments, G is 5- or 6-membered heteroaryl substituted with three or four $Q^4$.

In some embodiments, $R^3$ is hydroxy or optionally substituted C1-C6 alkyl; or $R^3$ and $R^4$ join to form optionally substituted phosphorus-containing 3- to 8-membered heterocyclyl. In some embodiments, $R^3$ is hydroxy. In some embodiments, $R^3$ is optionally substituted C1-C6 alkyl. In some embodiments, $R^3$ is methyl, ethyl, n-propyl, iso-propyl, n-butyl, or isobutyl. In some embodiments, $R^3$ is methyl or ethyl.

In some embodiments, $R^4$ is hydroxy or optionally substituted C1-C6 alkyl; or $R^3$ and $R^4$ join to form optionally substituted phosphorus-containing 3- to 8-membered heterocyclyl. In some embodiments, $R^4$ is hydroxy. In some embodiments, $R^4$ is optionally substituted C1-C6 alkyl. In some embodiments, $R^4$ is methyl, ethyl, n-propyl, iso-propyl, n-butyl, or isobutyl. In some embodiments, $R^4$ is methyl or ethyl.

In some embodiments, $R^3$ and $R^4$ are each independently hydroxy or optionally substituted C1-C6 alkyl. In some embodiments, $R^3$ and $R^4$ are each independently optionally substituted C1-C6 alkyl. In some embodiments, $R^3$ and $R^4$ are each independently methyl, ethyl, n-propyl, iso-propyl, n-butyl, or iso-butyl. In some embodiments, $R^3$ and $R^4$ are each methyl. In some embodiments, $R^3$ and $R^4$ are each ethyl. In some embodiments, $R^3$ is hydroxy and $R^4$ is methyl, ethyl, n-propyl, iso-propyl, n-butyl, or iso-butyl.

In some embodiments, $R^3$ and $R^4$ join to form optionally substituted phosphorus-containing 3- to 8-membered heterocyclyl. In some embodiments, $R^3$ and $R^4$ join to form optionally substituted phosphorus-containing 3- to 8-membered heterocyclyl which comprises 1 or 2 additional heteroatoms each independently selected from N, O, and S. In some embodiments, $R^3$ and $R^4$ join to form optionally substituted phosphorus-containing 4- to 6-membered heterocyclyl. In some embodiments, $R^3$ and $R^4$ join to form optionally substituted phosphorus-containing 4-membered heterocyclyl. In some embodiments, $R^3$ and $R^4$ join to form optionally substituted phosphorus-containing 5-membered heterocyclyl. In some embodiments, $R^3$ and $R^4$ join to form optionally substituted phosphorus-containing 6-membered heterocyclyl. In some embodiments, $R^3$ and $R^4$ are each methyl or ethyl; or $R^3$ is OH and $R^4$ is methyl; or $R^3$ and $R^4$ taken together with the phosphorus atom to which they are attached to join to form

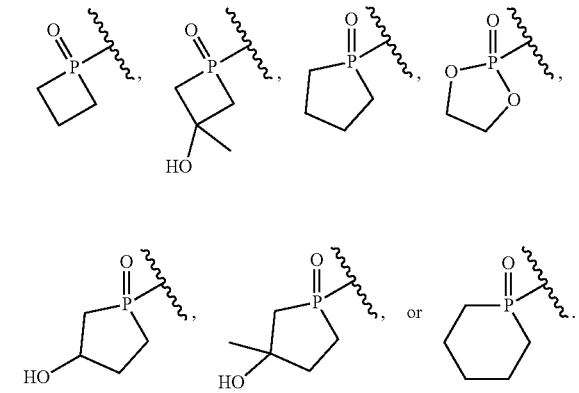

In some embodiments, each $R^5$ and $R^6$ is independently selected from hydrogen, halogen, or optionally substituted C1-C3 alkyl. In some embodiments, each $R^5$ and $R^6$ is independently hydrogen or halogen. In some embodiments, each $R^5$ and $R^6$ are independently selected from hydrogen, F, Cl, and Br. In some embodiments, each $R^5$ and $R^6$ are hydrogen. In some embodiments, $R^5$ is F and $R^6$ are hydrogen.

In some embodiments, $R^5$ is hydrogen. In some embodiments $R^5$ is halogen. In some embodiments, $R^5$ is F, Cl, or Br. In some embodiments, $R^5$ is optionally substituted C1-C3 alkyl.

In some embodiments, $R^5$ is methyl or ethyl. In some embodiments, $R^6$ is hydrogen. In some embodiments, $R^6$ is halogen. In some embodiments, $R^6$ is F, Cl, or Br. In some embodiments, $R^6$ is optionally substituted C1-C3 alkyl. In some embodiments, $R^6$ is methyl or ethyl.

One embodiment provides a TNF-α, inhibitory compound, or a pharmaceutically acceptable salt or solvate thereof, having a structure presented in Table 1.

TABLE 1

| Synthetic Chemistry Example | Compound Structure | Compound Name |
|---|---|---|
| 1 | 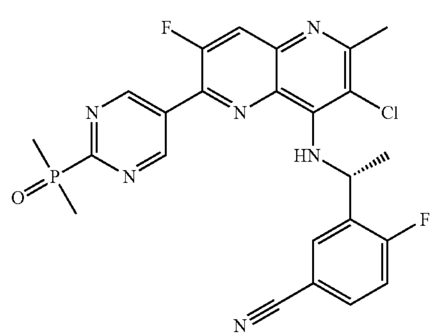 [SMILES: Cc1nc2cc(F)c(-c3cnc(P(C)(C)=O)nc3)nc2c(N[C@H](C)c2cc(C#N)ccc2F)c1Cl] | 3-[(1R)-1-({3-chloro-6-[2-(dimethylphosphoryl)pyrimidin-5-yl]-7-fluoro-2-methyl-1,5-naphthyridin-4-yl}amino)ethyl]-4-fluorobenzonitrile |

TABLE 1-continued

| Synthetic Chemistry Example | Compound Structure | Compound Name |
|---|---|---|
| 2 | 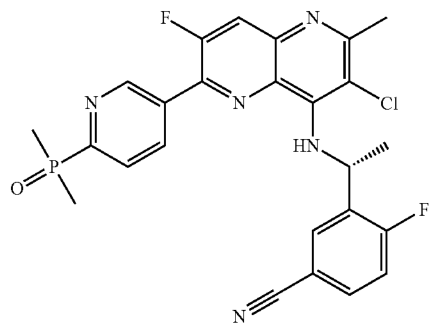 [SMILES: Cc1nc2cc(F)c(-c3ccc(P(C)(C)=O)nc3)nc2c(N[C@H](C)c2cc(C#N)ccc2F)c1Cl] | 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile |
| 3 | 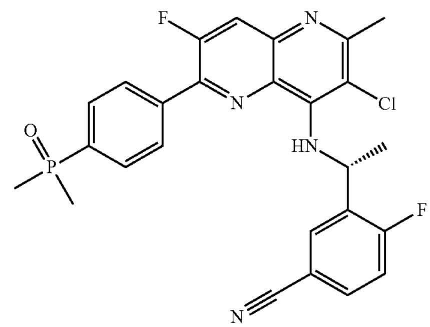 [SMILES: Cc1nc2cc(F)c(-c3ccc(P(C)(C)=O)cc3)nc2c(N[C@H](C)c2cc(C#N)ccc2F)c1Cl] | 3-[(1R)-1-({3-chloro-6-[4-(dimethylphosphoryl)phenyl]-7-fluoro-2-methyl-1,5-naphthyridin-4-yl}amino)ethyl]-4-fluorobenzonitrile |
| 4 | 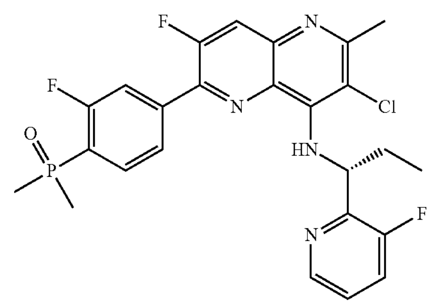 [SMILES: CC[C@@H](Nc1c(Cl)c(C)nc2cc(F)c(-c3ccc(P(C)(C)=O)c(F)c3)nc12)c1ncccc1F] | 3-chloro-6-[4-(dimethylphosphoryl)-3-fluorophenyl]-7-fluoro-N-[(1R)-1-(3-fluoropyridin-2-yl)propyl]-2-methyl-1,5-naphthyridin-4-amine |
| 5 | 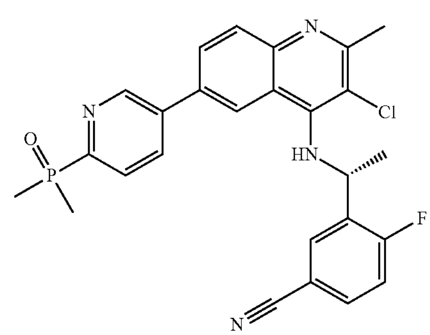 [SMILES: Cc1nc2ccc(-c3ccc(P(C)(C)=O)nc3)cc2c(N[C@H](C)c2cc(C#N)ccc2F)c1Cl] | 3-[(1R)-1-({3-chloro-6-[6-(dimethylphosphoryl)pyridin-3-yl]-2-methylquinolin-4-yl}amino)ethyl]-4-fluorobenzonitrile |

TABLE 1-continued

| Synthetic Chemistry Example | Compound Structure | Compound Name |
|---|---|---|
| 6 | 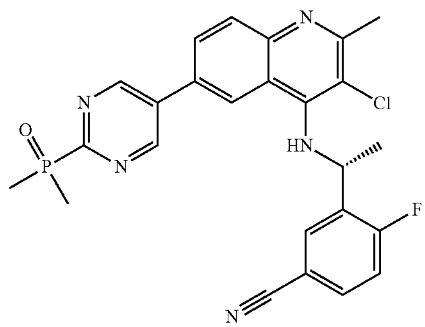 | 3-[(1R)-1-({3-chloro-6-[2-(dimethylphosphoryl)pyrimidin-5-yl]-2-methylquinolin-4-yl}amino)ethyl]-4-fluorobenzonitrile |
| 7 | 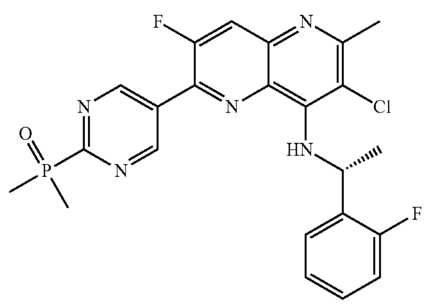 [SMILES: Cc1nc2cc(F)c(-c3cnc(P(C)(C)=O)nc3)nc2c(N[C@H](C)c2ccccc2F)c1Cl] | 3-chloro-6-[2-(dimethylphosphoryl)pyrimidin-5-yl]-7-fluoro-N-[(1R)-1-(2-fluorophenyl)ethyl]-2-methyl-1,5-naphthyridin-4-amine |
| 8 | 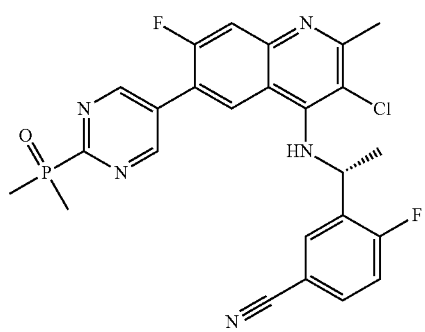 [SMILES: Cc1nc2cc(F)c(-c3cnc(P(C)(C)=O)nc3)cc2c(N[C@H](C)c2cc(C#N)ccc2F)c1Cl] | 3-[(1R)-1-({3-chloro-6-[2-(dimethylphosphoryl)pyrimidin-5-yl]-7-fluoro-2-methylquinolin-4-yl}amino)ethyl]-4-fluorobenzonitrile |
| 9 | 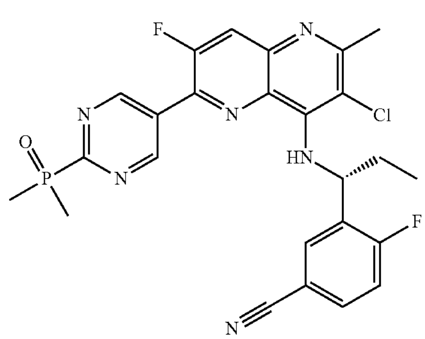 [SMILES: CC[C@@H](Nc1c(Cl)c(C)nc2cc(F)c(-c3cnc(P(C)(C)=O)nc3)nc12)c1cc(C#N)ccc1F] | 3-[(1R)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile |

TABLE 1-continued

| Synthetic Chemistry Example | Compound Structure | Compound Name |
|---|---|---|
| 10 | 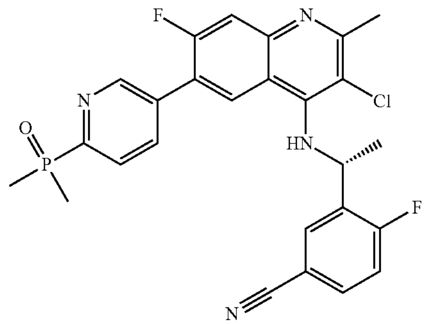 [SMILES: Cc1nc2cc(F)c(-c3ccc(P(C)(C)=O)nc3)cc2c(N[C@H](C)c2cc(C#N)ccc2F)c1Cl] | 3-[(1R)-1-({3-chloro-6-[6-(dimethylphosphoryl)pyridin-3-yl]-7-fluoro-2-methylquinolin-4-yl}amino)ethyl]-4-fluorobenzonitrile |
| 11 | 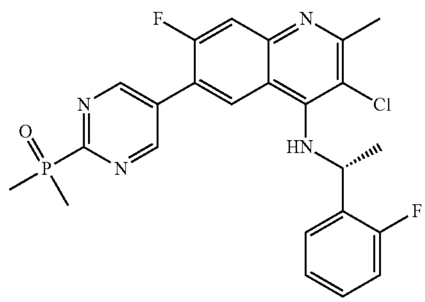 [SMILES: Cc1nc2cc(F)c(-c3cnc(P(C)(C)=O)nc3)cc2c(N[C@H](C)c2ccccc2F)c1Cl] | 3-chloro-6-[2-(dimethylphosphoryl)pyrimidin-5-yl]-7-fluoro-N-[(1R)-1-(2-fluorophenyl)ethyl]-2-methylquinolin-4-amine |
| 12 | 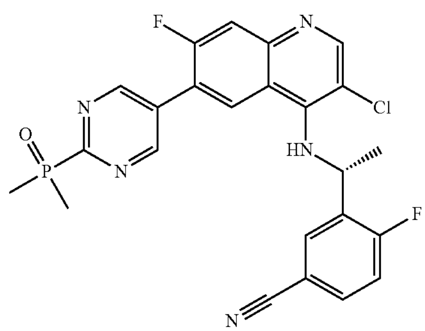 [SMILES: C[C@@H](Nc1c(Cl)cnc2cc(F)c(-c3cnc(P(C)(C)=O)nc3)cc12)c1cc(C#N)ccc1F] | 3-[(1R)-1-({3-chloro-6-[2-(dimethylphosphoryl)pyrimidin-5-yl]-7-fluoroquinolin-4-yl}amino)ethyl]-4-fluorobenzonitrile |
| 13 | 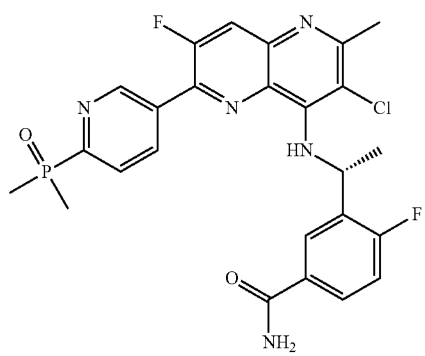 [SMILES: Cc1nc2cc(F)c(-c3ccc(P(C)(C)=O)nc3)nc2c(N[C@H](C)c2cc(C(N)=O)ccc2F)c1Cl] | 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzamide |

TABLE 1-continued

| Synthetic Chemistry Example | Compound Structure | Compound Name |
|---|---|---|
| 14 | 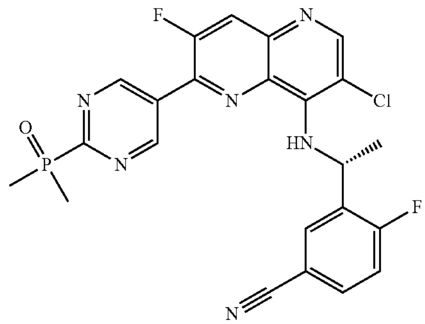 | 3-[(1R)-1-({3-chloro-6-[2-(dimethylphosphoryl) pyrimidin-5-yl]-7-fluoro-1,5-naphthyridin-4-yl}amino)ethyl]-4-fluorobenzonitrile |
| 15 | 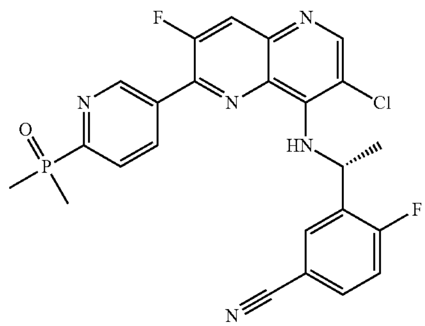 [SMILES: C[C@@H](Nc1c(Cl)cnc2cc(F)c(-c3ccc(P(C)(C)=O)nc3)nc12)c1cc(C#N)ccc1F] | 3-[(1R)-1-({3-chloro-6-[6-(dimethylphosphoryl)pyridin-3-yl]-7-fluoro-1,5-naphthyridin-4-yl}amino)ethyl]-4-fluorobenzonitrile |
| 16 | 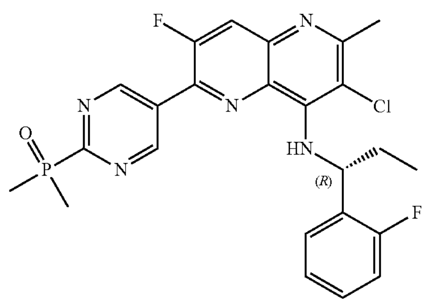 | 3-chloro-6-[2-(dimethylphosphoryl)pyrimidin-5-yl]-7-fluoro-N-[(1R)-1-(2-fluorophenyl)propyl]-2-methyl-1,5-naphthyridin-4-amine |
| 17 | 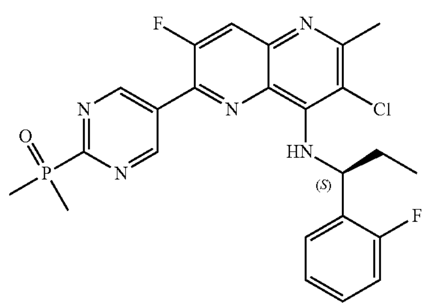 | 3-chloro-6-[2-(dimethylphosphoryl)pyrimidin-5-yl]-7-fluoro-N-[(1S)-1-(2-fluorophenyl)propyl]-2-methyl-1,5-naphthyridin-4-amine |
| 18 | 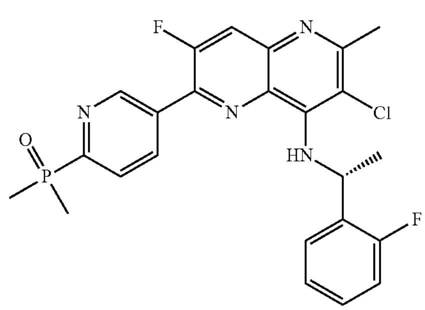 [SMILES: Cc1nc2cc(F)c(-c3ccc(P(C)(C)=O)nc3)nc2c(N[C@H](C)c2ccccc2F)c1Cl] | 3-chloro-6-[6-(dimethylphosphoryl)pyridin-3-yl]-7-fluoro-N-[(1R)-1-(2-fluorophenyl)ethyl]-2-methyl-1,5-naphthyridin-4-amine |

TABLE 1-continued

| Synthetic Chemistry Example | Compound Structure | Compound Name |
|---|---|---|
| 19 | 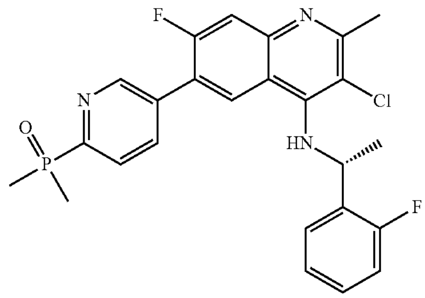 [SMILES: Cc1nc2cc(F)c(-c3ccc(P(C)(C)=O)nc3)cc2c(N[C@H](C)c2ccccc2F)c1Cl] | 3-chloro-6-[6-(dimethylphosphoryl)pyridin-3-yl]-7-fluoro-N-[(1R)-1-(2-fluorophenyl)ethyl]-2-methylquinolin-4-amine |
| 20 | 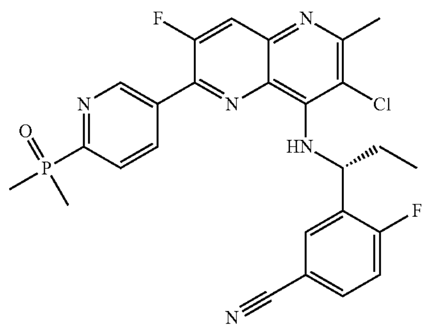 [SMILES: CC[C@@H](Nc1c(Cl)c(C)nc2cc(F)c(-c3ccc(P(C)(C)=O)nc3)nc12)c1cc(C#N)ccc1F] | 3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile |
| 21 | 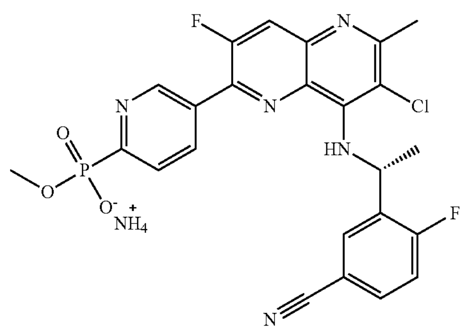 [SMILES: COP(=O)([O-])c1ccc(-c2nc3c(N[C@H](C)c4cc(C#N)ccc4F)c(Cl)c(C)nc3cc2F)cn1 ; [NH4+]] | ammonium methyl5-(7-chloro-8-{[(1R)-1-(5-cyano-2-fluorophenyl)ethyl]amino}-3-fluoro-6-methyl-1,5-naphthyridin-2-yl)pyridin-2-ylphosphonate |
| 22 | 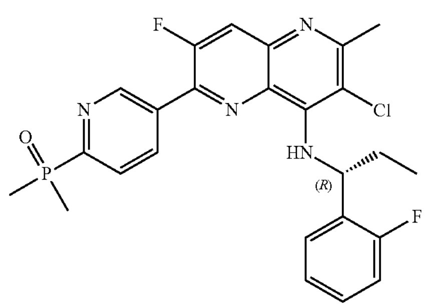 | 3-chloro-6-[6-(dimethylphosphoryl)pyridin-3-yl]-7-fluoro-N-[(1R)-1-(2-fluorophenyl)propyl]-2-methyl-1,5-naphthyridin-4-amine |
| 23 | 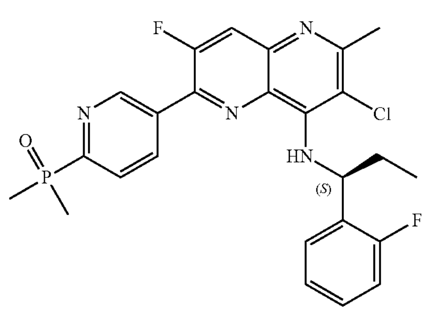 | 3-chloro-6-[6-(dimethylphosphoryl)pyridin-3-yl]-7-fluoro-N-[(1S)-1-(2-fluorophenyl)propyl]-2-methyl-1,5-naphthyridin-4-amine |

TABLE 1-continued

| Synthetic Chemistry Example | Compound Structure | Compound Name |
|---|---|---|
| 24 | 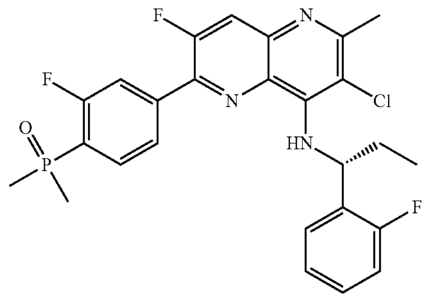 [SMILES: CC[C@@H](Nc1c(Cl)c(C)nc2cc(F)c(-c3ccc(P(C)(C)=O)c(F)c3)nc12)c1ccccc1F] | 3-chloro-6-[4-(dimethylphosphoryl)-3-fluorophenyl]-7-fluoro-N-[(1R)-1-(2-fluorophenyl)propyl]-2-methyl-1,5-naphthyridin-4-amine |
| 25 | 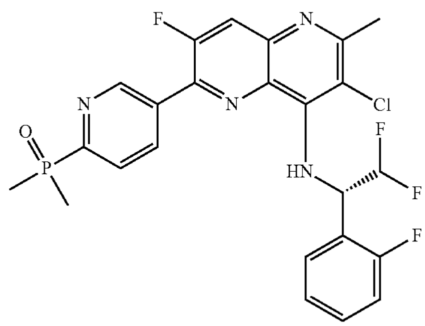 [SMILES: Cc1nc2cc(F)c(-c3ccc(P(C)(C)=O)nc3)nc2c(N[C@@H](c2ccccc2F)C(F)F)c1Cl] | (S)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide |
| and | + | And |
| 26 | 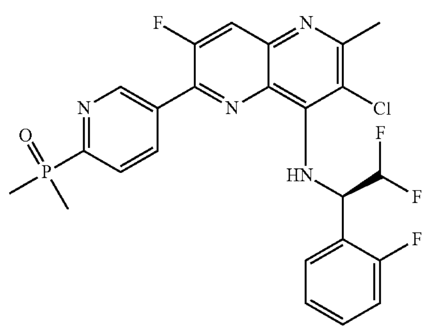 [SMILES: Cc1nc2cc(F)c(-c3ccc(P(C)(C)=O)nc3)nc2c(N[C@H](c2ccccc2F)C(F)F)c1Cl] | (R)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide |
| 27 | 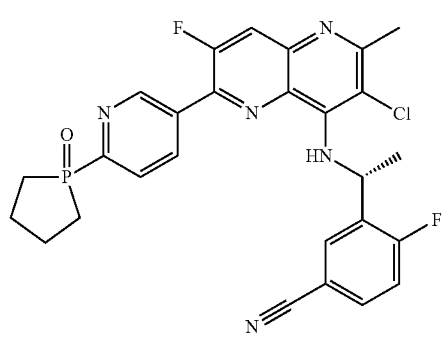 [SMILES: Cc1nc2cc(F)c(-c3ccc(P4(=O)CCCC4)nc3)nc2c(N[C@H](C)c2cc(C#N)ccc2F)c1Cl] | 3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile |

TABLE 1-continued

| Synthetic Chemistry Example | Compound Structure | Compound Name |
|---|---|---|
| 28 | 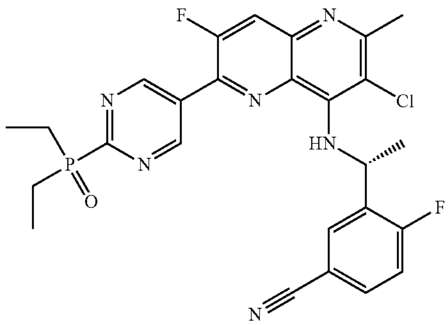 [SMILES: CCP(=O)(CC)c1ncc(-c2nc3c(N[C@H](C)c4cc(C#N)ccc4F)c(Cl)c(C)nc3cc2F)cn1] | 3-[(1R)-1-({3-chloro-6-[2-(diethylphosphoryl)pyrimidin-5-yl]-7-fluoro-2-methyl-1,5-naphthyridin-4-yl}amino)ethyl]-4-fluorobenzonitrile |
| 29 | 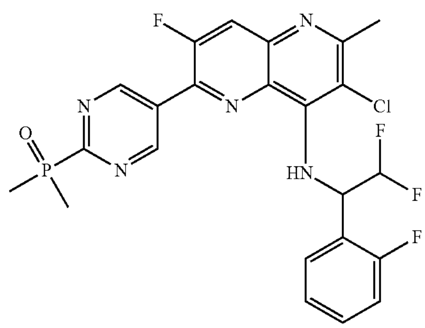 [SMILES: Cc1nc2cc(F)c(-c3cnc(P(C)(C)=O)nc3)nc2c(NC(c2ccccc2F)C(F)F)c1Cl] | 3-chloro-N-[2,2-difluoro-1-(2-fluorophenyl)ethyl]-6-[2-(dimethylphosphoryl)pyrimidin-5-yl]-7-fluoro-2-methyl-1,5-naphthyridin-4-amine |
| 30 | 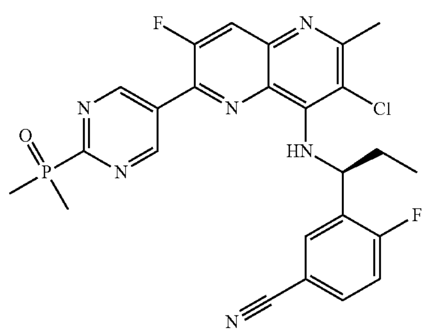 [SMILES: CC[C@H](Nc1c(Cl)c(C)nc2cc(F)c(-c3cnc(P(C)(C)=O)nc3)nc12)c1cc(C#N)ccc1F] | 3-[(1S)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile |
| 31 | 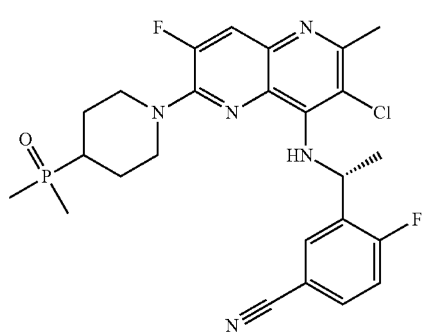 [SMILES: Cc1nc2cc(F)c(N3CCC(P(C)(C)=O)CC3)nc2c(N[C@H](C)c2cc(C#N)ccc2F)c1Cl] | 3-[(1R)-1-({3-chloro-6-[4-(dimethylphosphoryl)piperidin-1-yl]-7-fluoro-2-methyl-1,5-naphthyridin-4-yl}amino)ethyl]-4-fluorobenzonitrile |

TABLE 1-continued

| Synthetic Chemistry Example | Compound Structure | Compound Name |
|---|---|---|
| 32 | 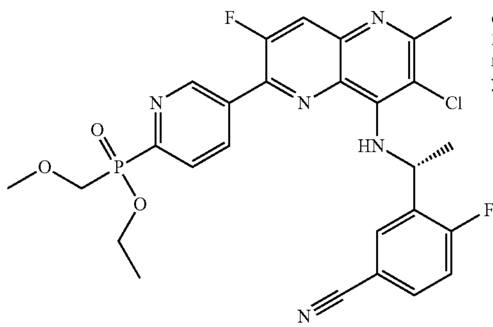 [SMILES: CCOP(=O)(COC)c1ccc(-c2nc3c(N[C@H](C)c4cc(C#N)ccc4F)c(Cl)c(C)nc3cc2F)cn1] | diethyl5-(7-chloro-8-{[(1R)-1-(5-cyano-2-fluorophenyl)ethyl]amino}-3-fluoro-6-methyl-1,5-naphthyridin-2-yl)pyridin-2-ylphosphonate |
| 33 | 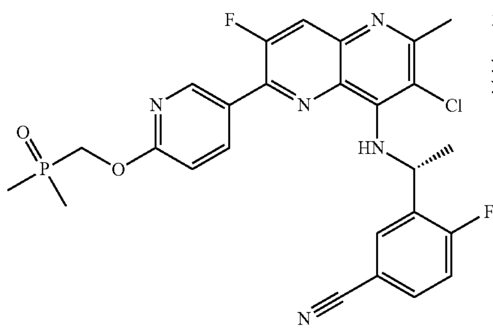 | 3-[(1R)-1-[(3-chloro-6-{6-[(dimethylphosphoryl)methoxy]pyridin-3-yl}-7-fluoro-2-methyl-1,5-naphthyridin-4-yl)amino]ethyl]-4-fluorobenzonitrile |
| 34 | 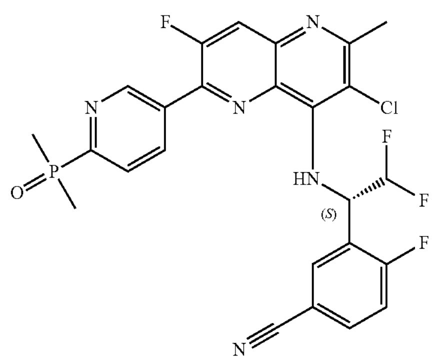 | (S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile |
| 35 | 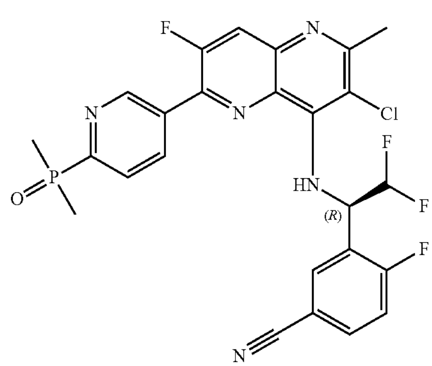 | (R)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile |

TABLE 1-continued

| Synthetic Chemistry Example | Compound Structure | Compound Name |
|---|---|---|
| 36 | 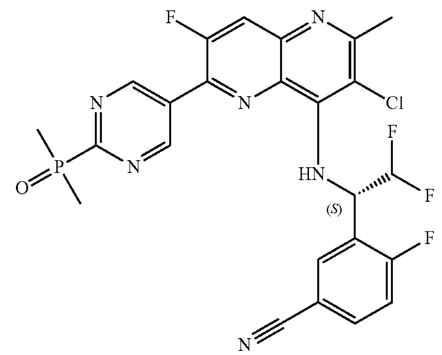 | (S)-3-(1-((3-chloro-6-(2-(dimethylphosphoryl)pyrimidin-5-yl)-7-fluoro-2-methyl-1,5-naphthyridin-4-yl)amino)-2,2-difluoroethyl)-4-fluorobenzonitrile |
| 37 | 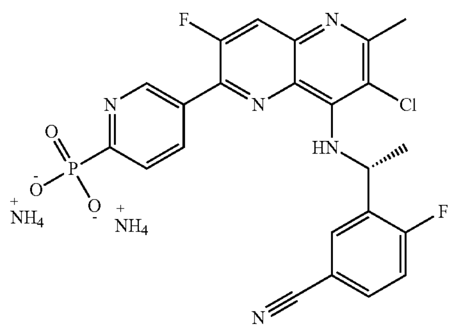 | diammonium 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate |
| 38 | 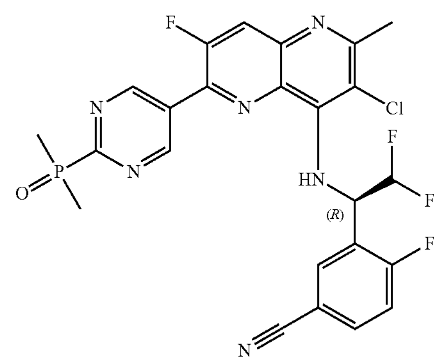 | (R)-3-(1-((3-chloro-6-(2-(dimethylphosphoryl)pyrimidin-5-yl)-7-fluoro-2-methyl-1,5-naphthyridin-4-yl)amino)-2,2-difluoroethyl)-4-fluorobenzonitrile |
| 39 | 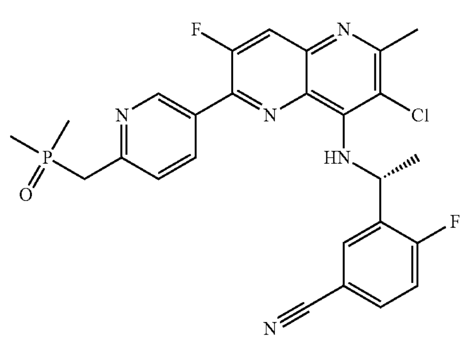 [SMILES: Cc1nc2cc(F)c(-c3ccc(CP(C)(C)=O)nc3)nc2c(N[C@H](C)c2cc(C#N)ccc2F)c1Cl] | (R)-3-(1-((3-chloro-6-(6-((dimethylphosphoryl)methyl)pyridin-3-yl)-7-fluoro-2-methyl-1,5-naphthyridin-4-yl)amino)ethyl)-4-fluorobenzonitrile |

TABLE 1-continued

| Synthetic Chemistry Example | Compound Structure | Compound Name |
|---|---|---|
| 40 | 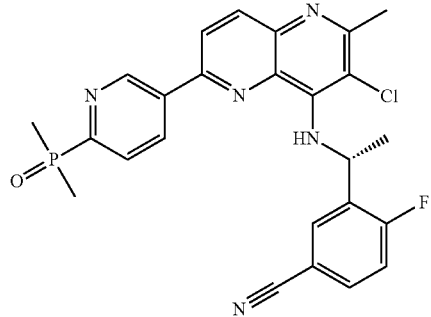 [SMILES: Cc1nc2ccc(-c3ccc(P(C)(C)=O)nc3)nc2c(N[C@H](C)c2cc(C#N)ccc2F)c1Cl] | 3-[(1R)-1-({3-chloro-6-[6-(dimethylphosphoryl)pyridin-3-yl]-2-methyl-1,5-naphthyridin-4-yl}amino)ethyl]-4-fluorobenzonitrile |
| 41 | 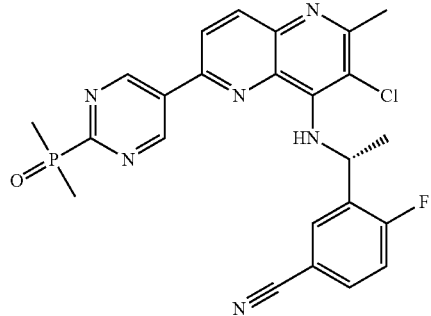 [SMILES: Cc1nc2ccc(-c3cnc(P(C)(C)=O)nc3)nc2c(N[C@H](C)c2cc(C#N)ccc2F)c1Cl] | 3-[(1R)-1-({3-chloro-6-[2-(dimethylphosphoryl)pyrimidin-5-yl]-2-methyl-1,5-naphthyridin-4-yl}amino)ethyl]-4-fluorobenzonitrile |
| 42 | 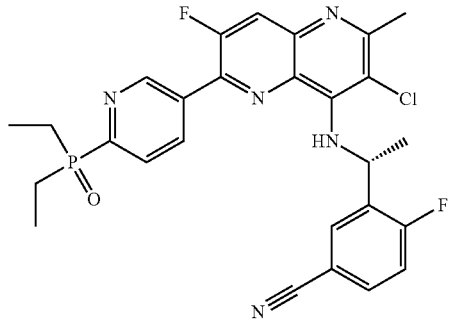 [SMILES: CCP(=O)(CC)c1ccc(-c2nc3c(N[C@H](C)c4cc(C#N)ccc4F)c(Cl)c(C)nc3cc2F)cn1] | 3-[(1R)-1-({3-chloro-6-[6-(diethylphosphoryl)pyridin-3-yl]-7-fluoro-2-methyl-1,5-naphthyridin-4-yl}amino)ethyl]-4-fluorobenzonitrile |
| 43 | 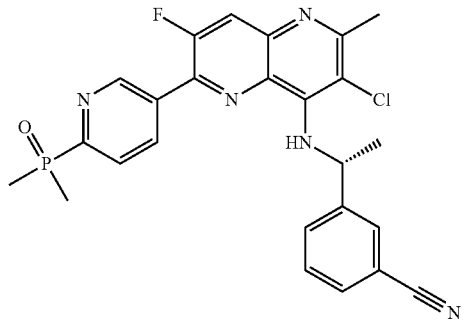 [SMILES: Cc1nc2cc(F)c(-c3ccc(P(C)(C)=O)nc3)nc2c(N[C@H](C)c2cccc(C#N)c2)c1Cl] | 3-[(1R)-1-({3-chloro-6-[6-(dimethylphosphoryl)pyridin-3-yl]-7-fluoro-2-methyl-1,5-naphthyridin-4-yl}amino)ethyl]benzonitrile |

TABLE 1-continued

| Synthetic Chemistry Example | Compound Structure | Compound Name |
|---|---|---|
| 44 | 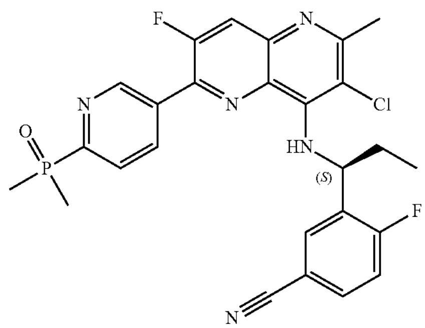 | 3-[(1S)-1-({3-chloro-6-[6-(dimethylphosphoryl)pyridin-3-yl]-7-fluoro-2-methyl-1,5-naphthyridin-4-yl}amino)propyl]-4-fluorobenzonitrile |
| 45 | 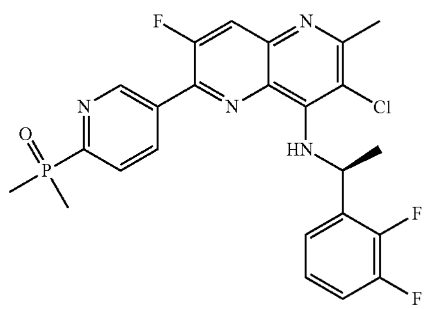 [SMILES: Cc1nc2cc(F)c(-c3ccc(P(C)(C)=O)nc3)nc2c(N[C@@H](C)c2cccc(F)c2F)c1Cl] | 3-chloro-N-[(1S)-1-(2,3-difluorophenyl)ethyl]-6-[6-(dimethylphosphoryl)pyridin-3-yl]-7-fluoro-2-methyl-1,5-naphthyridin-4-amine |
| 46 | 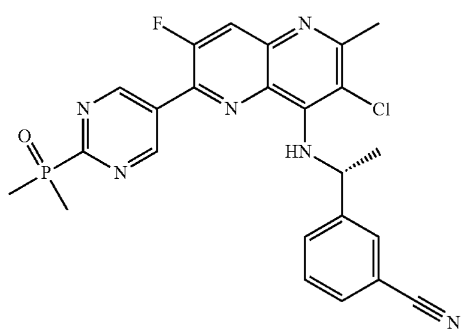 | 3-[(1R)-1-({3-chloro-6-[2-(dimethylphosphoryl)pyrimidin-5-yl]-7-fluoro-2-methyl-1,5-naphthyridin-4-yl}amino)ethyl]benzonitrile |
| 47 | 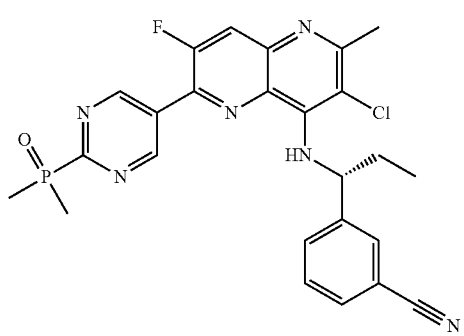 [SMILES: CC[C@@H](Nc1c(Cl)c(C)nc2cc(F)c(-c3cnc(P(C)(C)=O)nc3)nc12)c1cccc(C#N)c1] | 3-[(1R)-1-({3-chloro-6-[2-(dimethylphosphoryl)pyrimidin-5-yl]-7-fluoro-2-methyl-1,5-naphthyridin-4-yl}amino)ethyl]benzonitrile |

TABLE 1-continued

| Synthetic Chemistry Example | Compound Structure | Compound Name |
|---|---|---|
| 48 | 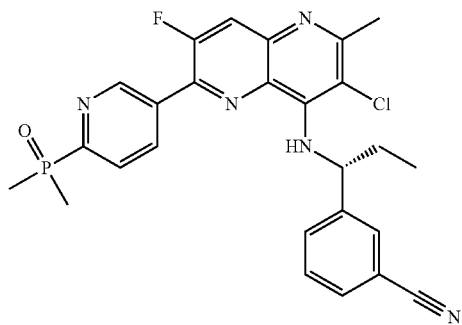 [SMILES: CC[C@@H](Nc1c(Cl)c(C)nc2cc(F)c(-c3ccc(P(C)(C)=O)nc3)nc12)c1cccc(C#N)c1] | 3-[(1R)-1-({3-chloro-6-[6-(dimethylphosphoryl)pyridin-3-yl]-7-fluoro-2-methyl-1,5-naphthyridin-4-yl}amino)propyl]benzonitrile |
| 49 | 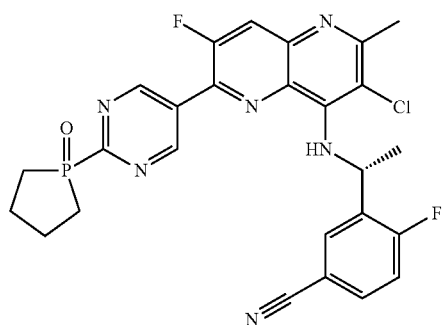 [SMILES: Cc1nc2cc(F)c(-c3cnc(P4(=O)CCCC4)nc3)nc2c(N[C@H](C)c2cc(C#N)ccc2F)c1Cl] | 3-[(1R)-1-({3-chloro-7-fluoro-2-methyl-6-[2-(1-oxo-1lambda5-phospholan-1-yl)pyrimidin-5-yl]-1,5-naphthyridin-4-yl}amino)ethyl]-4-fluorobenzonitrile |
| 50 | 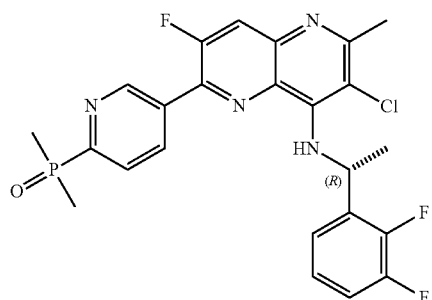 | 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine |
| 51 | 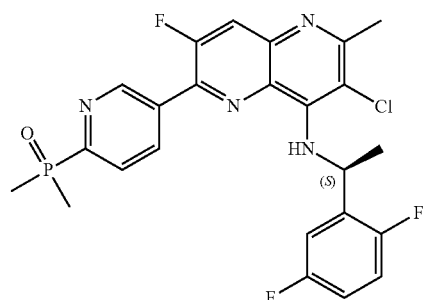 | 3-chloro-N-[(1S)-1-(2,5-difluorophenyl)ethyl]-6-[6-(dimethylphosphoryl)pyridin-3-yl]-7-fluoro-2-methyl-1,5-naphthyridin-4-amine |
| 52 | 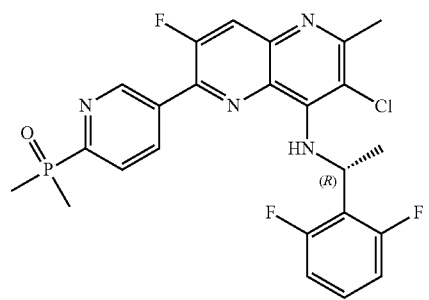 | 3-chloro-N-[(1R)-1-(2,6-difluorophenyl)ethyl]-6-[6-(dimethylphosphoryl)pyridin-3-yl]-7-fluoro-2-methyl-1,5-naphthyridin-4-amine |

TABLE 1-continued

| Synthetic Chemistry Example | Compound Structure | Compound Name |
|---|---|---|
| 53 | 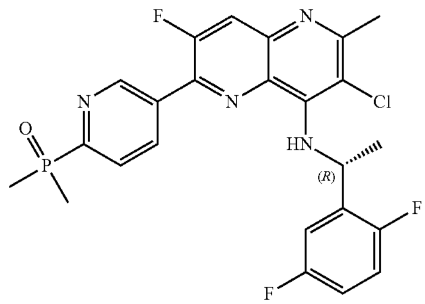 | 3-chloro-N-[(1R)-1-(2,5-difluorophenyl)ethyl]-6-[6-(dimethylphosphoryl)pyridin-3-yl]-7-fluoro-2-methyl-1,5-naphthyridin-4-amine |
| 54 | 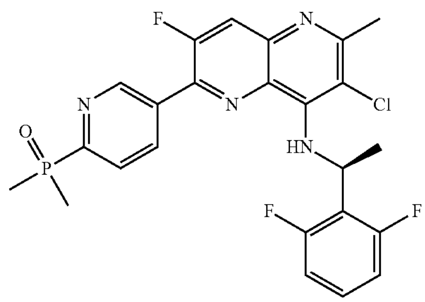 [SMILES: Cc1nc2cc(F)c(-c3ccc(P(C)(C)=O)nc3)nc2c(N[C@@H](C)c2c(F)cccc2F)c1Cl] | 3-chloro-N-[(1S)-1-(2,6-difluorophenyl)ethyl]-6-[6-(dimethylphosphoryl)pyridin-3-yl]-7-fluoro-2-methyl-1,5-naphthyridin-4-amine |
| 55 | 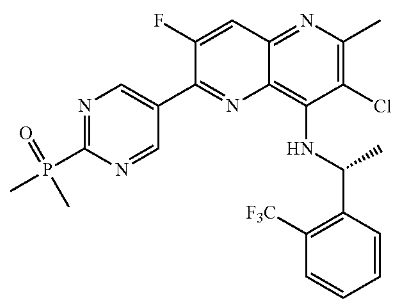 | 3-chloro-6-[2-(dimethylphosphoryl)pyrimidin-5-yl]-7-fluoro-2-methyl-N-[(1R)-1-[2-(trifluoromethyl)phenyl]ethyl]-1,5-naphthyridin-4-amine |
| 56 | 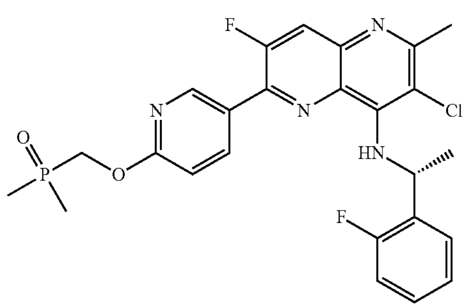 | 3-chloro-6-{6-[(dimethylphosphoryl)methoxy]pyridin-3-yl}-7-fluoro-N-[(1R)-1-(2-fluorophenyl)ethyl]-2-methyl-1,5-naphthyridin-4-amine |
| 57 | 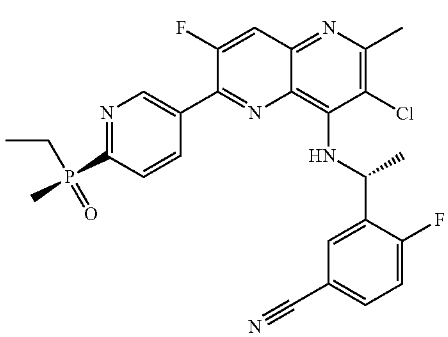 [SMILES: CC[P@@](C)(=O)c1ccc(-c2nc3c(N[C@H](C)c4cc(C#N)ccc4F)c(Cl)c(C)nc3cc2F)cn1] | (R)-3-(1-((3-chloro-6-(6-(diethylphosphoryl)pyridin-3-yl)-7-fluoro-2-methyl-1,5-naphthyridin-4-yl)amino)ethyl)-4-fluorobenzonitrile |

TABLE 1-continued

| Synthetic Chemistry Example | Compound Structure | Compound Name |
|---|---|---|
| and | + | And |
| 58 | 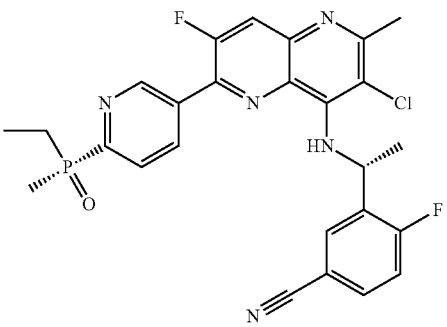 | 3-((R)-1-((3-chloro-6-(6-((S)-ethyl(methyl)phosphoryl)pyridin-3-yl)-7-fluoro-2-methyl-1,5-naphthyridin-4-yl)amino)ethyl)-4-fluorobenzonitrile |
| 59 | 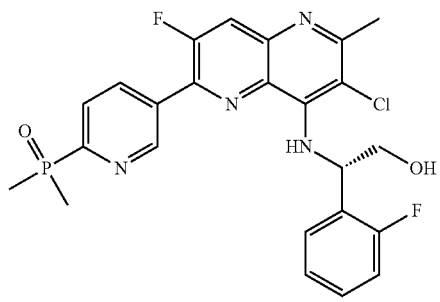 [SMILES: Cc1nc2cc(F)c(-c3ccc(P(C)(C)=O)nc3)nc2c(N[C@H](CO)c2ccccc2F)c1Cl] | (2S)-2-({3-chloro-6-[6-(dimethylphosphoryl)pyridin-3-yl]-7-fluoro-2-methyl-1,5-naphthyridin-4-yl}amino)-2-(2-fluorophenyl)ethanol |
| 60 | 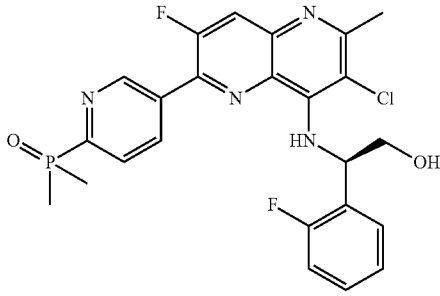 [SMILES: Cc1nc2cc(F)c(-c3ccc(P(C)(C)=O)nc3)nc2c(N[C@@H](CO)c2ccccc2F)c1Cl] | (2R)-2-({3-chloro-6-[6-(dimethylphosphoryl)pyridin-3-yl]-7-fluoro-2-methyl-1,5-naphthyridin-4-yl}amino)-2-(2-fluorophenyl)ethanol |
| 61 | 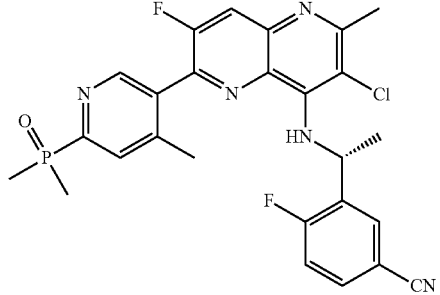 [SMILES: Cc1cc(P(C)(C)=O)ncc1-c1nc2c(N[C@H](C)c3cc(C#N)ccc3F)c(Cl)c(C)nc2cc1F] | 3-[(1R)-1-({3-chloro-6-[6-(dimethylphosphoryl)-4-methylpyridin-3-yl]-7-fluoro-2-methyl-1,5-naphthyridin-4-yl}amino)ethyl]-4-fluorobenzonitrile |
| 62 | 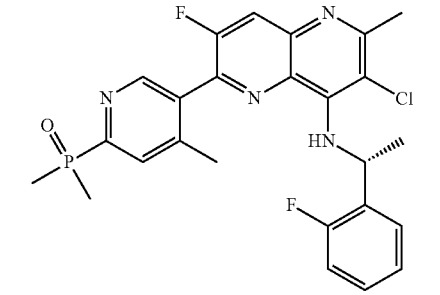 | 3-chloro-6-[6-(dimethylphosphoryl)-4-methylpyridin-3-yl]-7-fluoro-N-[(1R)-1-(2-fluorophenyl)ethyl]-2-methyl-1,5-naphthyridin-4-amine |

TABLE 1-continued

| Synthetic Chemistry Example | Compound Structure | Compound Name |
|---|---|---|
| 63 | 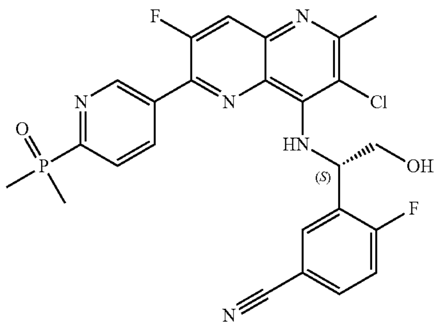 | (S)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile |
| and | + | And |
| 64 | 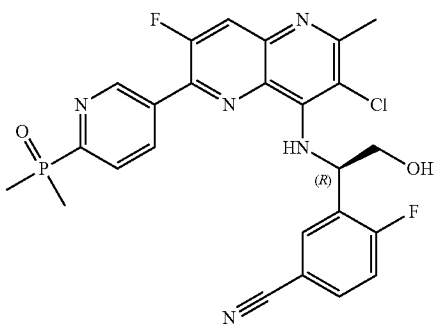 | (R)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile |
| 65 | 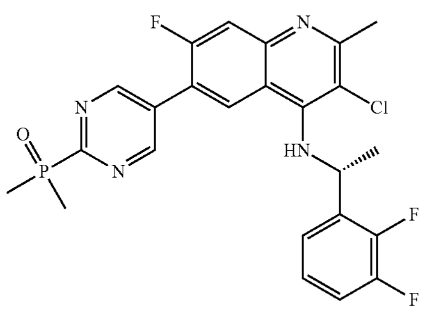 [SMILES: Cc1nc2cc(F)c(-c3cnc(P(C)(C)=O)nc3)cc2c(N[C@H](C)c2cccc(F)c2F)c1Cl] | 3-chloro-N-[(1R)-1-(2,3-difluorophenyl)ethyl]-6-[2-(dimethylphosphoryl)pyrimidin-5-yl]-7-fluoro-2-methylquinolin-4-amine |
| 66 | 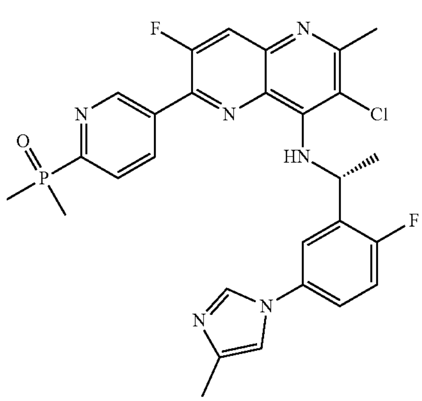 [SMILES: Cc1cn(-c2ccc(F)c([C@@H](C)Nc3c(Cl)c(C)nc4cc(F)c(-c5ccc(P(C)(C)=O)nc5)nc34)c2)cn1] | 3-chloro-6-[6-(dimethylphosphoryl)pyridin-3-yl]-7-fluoro-N-[(1R)-1-[2-fluoro-5-(4-methylimidazol-1-yl)phenyl]ethyl]-2-methyl-1,5-naphthyridin-4-amine |

TABLE 1-continued

| Synthetic Chemistry Example | Compound Structure | Compound Name |
|---|---|---|
| 67 | 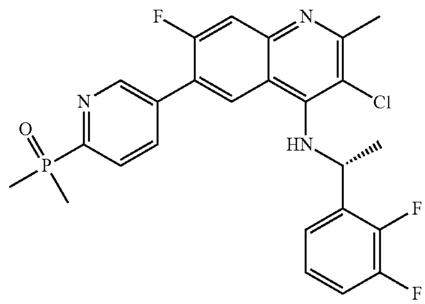 [SMILES: Cc1nc2cc(F)c(-c3ccc(P(C)(C)=O)nc3)cc2c(N[C@H](C)c2cccc(F)c2F)c1Cl] | 3-chloro-N-[(1R)-1-(2,3-difluorophenyl)ethyl]-6-[6-(dimethylphosphoryl)pyridin-3-yl]-7-fluoro-2-methylquinolin-4-amine |
| 68 | 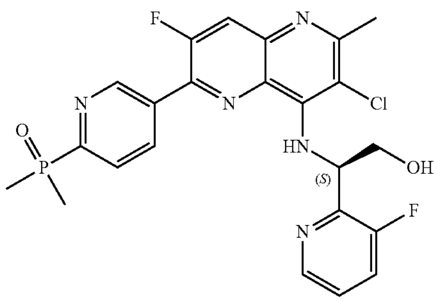 | (S)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide |
| 69 | 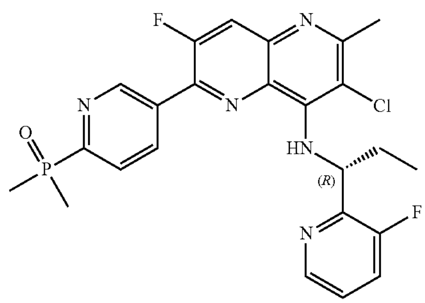 | (R)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide |
| 70 | 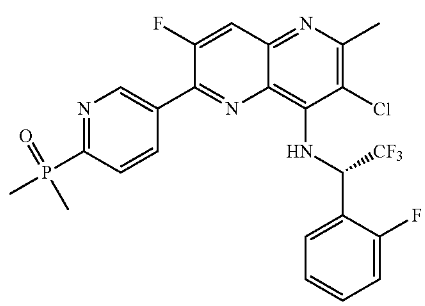 [SMILES: Cc1nc2cc(F)c(-c3ccc(P(C)(C)=O)nc3)nc2c(N[C@@H](c2ccccc2F)C(F)(F)F)c1Cl] | 3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine |
| 71 | 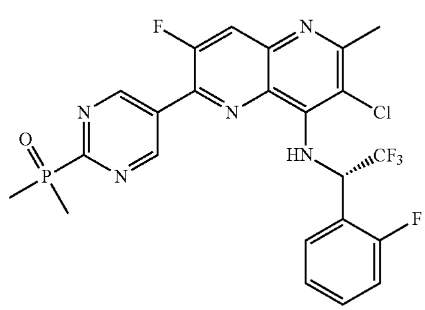 | 3-chloro-6-[2-(dimethylphosphoryl)pyrimidin-5-yl]-7-fluoro-2-methyl-N-[(1S)-2,2,2-trifluoro-1-(2-fluorophenyl)ethyl]-1,5-naphthyridin-4-amine |

TABLE 1-continued

| Synthetic Chemistry Example | Compound Structure | Compound Name |
|---|---|---|
| 72 | 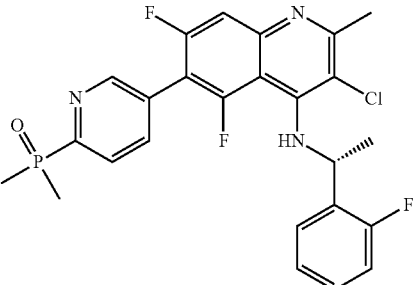 | 3-chloro-6-[6-(dimethylphosphoryl)pyridin-3-yl]-5,7-difluoro-N-[(1R)-1-(2-fluorophenyl)ethyl]-2-methylquinolin-4-amine |
| 73 | 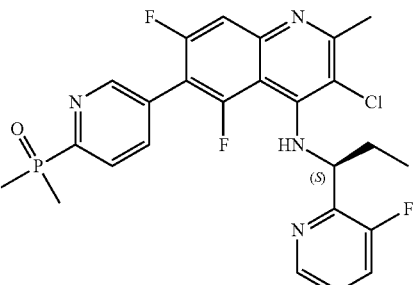 | (S)-(5-(3-chloro-5,7-difluoro-4-((1-(3-fluoropyridin-2-yl)propyl)amino)-2-methylquinolin-6-yl)pyridin-2-yl)dimethylphosphine oxide |
| 74 | 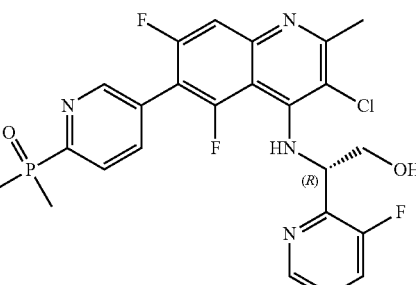 | (R)-(5-(3-chloro-5,7-difluoro-4-((1-(3-fluoropyridin-2-yl)propyl)amino)-2-methylquinolin-6-yl)pyridin-2-yl)dimethylphosphine oxide |
| 75 | 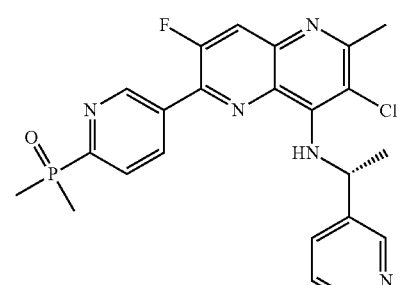 | 3-chloro-6-[6-(dimethylphosphoryl)pyridin-3-yl]-7-fluoro-2-methyl-N-[(1R)-1-(pyridin-3-yl)ethyl]-1,5-naphthyridin-4-amine |
| 76 | 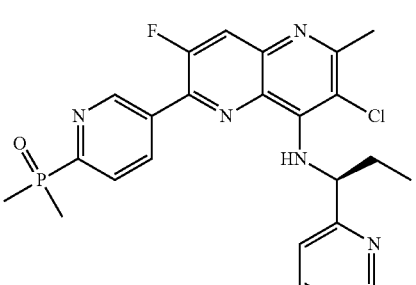 | 3-chloro-6-[6-(dimethylphosphoryl)pyridin-3-yl]-7-fluoro-2-methyl-N-[(1S)-1-(pyridin-2-yl)propyl]-1,5-naphthyridin-4-amine |

TABLE 1-continued

| Synthetic Chemistry Example | Compound Structure | Compound Name |
|---|---|---|
| 77 | 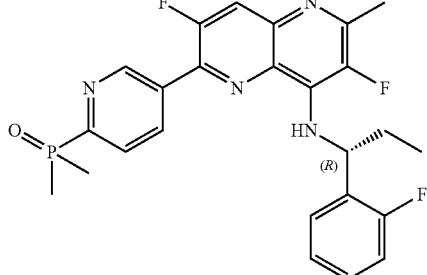 | 6-[6-(dimethylphosphoryl)pyridin-3-yl]-3,7-difluoro-N-[(1R)-1-(2-fluorophenyl)propyl]-2-methyl-1,5-naphthyridin-4-amine |
| 78 | 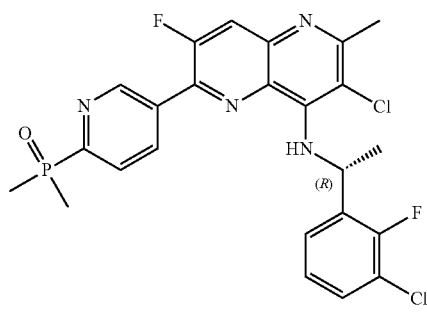 | 3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine |
| 79 | 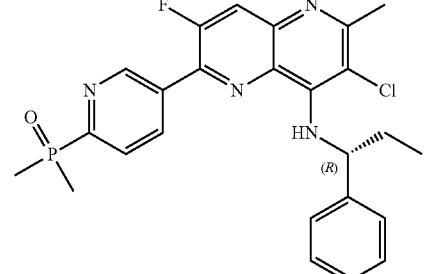 | 3-chloro-6-[6-(dimethylphosphoryl)pyridin-3-yl]-7-fluoro-2-methyl-N-[(1R)-1-phenylpropyl]-1,5-naphthyridin-4-amine |
| 80 | 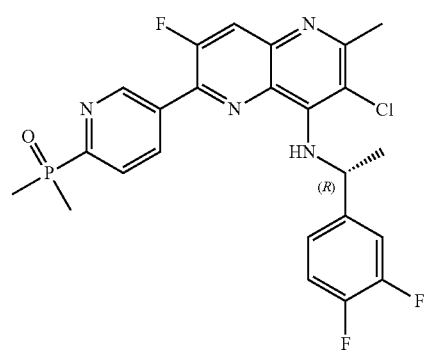 | 3-chloro-N-[(1R)-1-(3,4-difluorophenyl)ethyl]-6-[6-(dimethylphosphoryl)pyridin-3-yl]-7-fluoro-2-methyl-1,5-naphthyridin-4-amine |
| 81 | 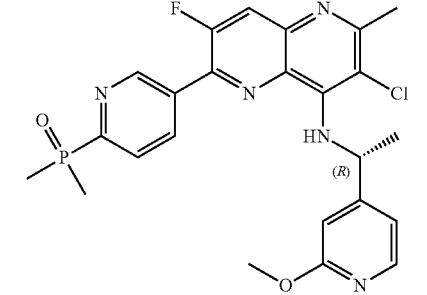 | 3-chloro-6-[6-(dimethylphosphoryl)pyridin-3-yl]-7-fluoro-N-[(1R)-1-(2-methoxypyridin-4-yl)ethyl]-2-methyl-1,5-naphthyridin-4-amine |

TABLE 1-continued

| Synthetic Chemistry Example | Compound Structure | Compound Name |
|---|---|---|
| 82 | 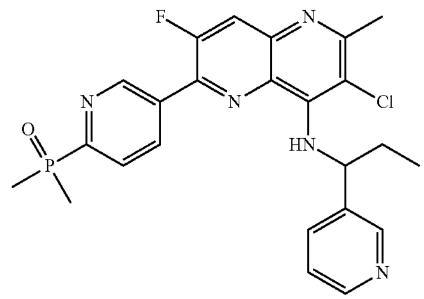 [SMILES: CCC(Nc1c(Cl)c(C)nc2cc(F)c(-c3ccc(P(C)(C)=O)nc3)nc12)c1cccnc1] | 3-chloro-6-[6-(dimethylphosphoryl)pyridin-3-yl]-7-fluoro-2-methyl-N-[1-(pyridin-3-yl)propyl]-1,5-naphthyridin-4-amine |
| 83 | 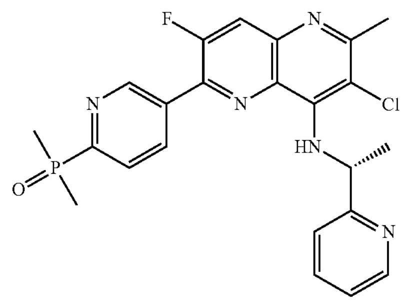 [SMILES: Cc1nc2cc(F)c(-c3ccc(P(C)(C)=O)nc3)nc2c(N[C@H](C)c2ccccn2)c1Cl] | 3-chloro-6-[6-(dimethylphosphoryl)pyridin-3-yl]-7-fluoro-2-methyl-N-[(1R)-1-(pyridin-2-yl)ethyl]-1,5-naphthyridin-4-amine |
| 84 | 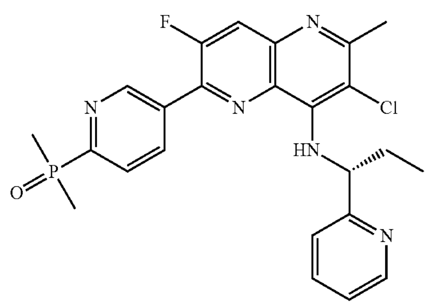 [SMILES: CC[C@@H](Nc1c(Cl)c(C)nc2cc(F)c(-c3ccc(P(C)(C)=O)nc3)nc12)c1ccccn1] | 3-chloro-6-[6-(dimethylphosphoryl)pyridin-3-yl]-7-fluoro-2-methyl-N-[(1R)-1-(pyridin-2-yl)propyl]-1,5-naphthyridin-4-amine |
| 85 | 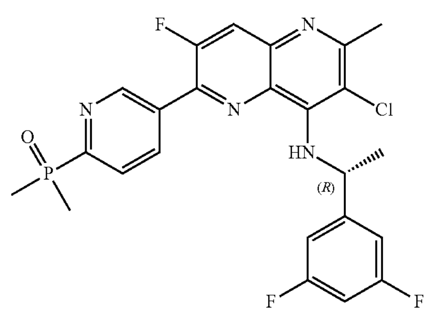 | 3-chloro-N-[(1R)-1-(3,5-difluorophenyl)ethyl]-6-[6-(dimethylphosphoryl)pyridin-3-yl]-7-fluoro-2-methyl-1,5-naphthyridin-4-amine |
| 86 | 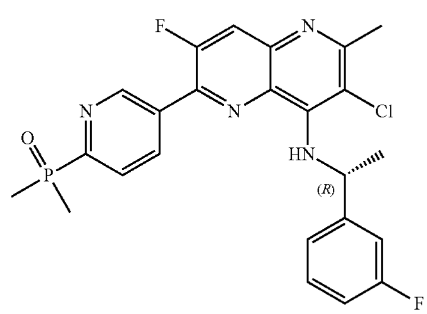 | 3-chloro-6-[6-(dimethylphosphoryl)pyridin-3-yl]-7-fluoro-N-[(1R)-1-(3-fluorophenyl)ethyl]-2-methyl-1,5-naphthyridin-4-amine |

TABLE 1-continued

| Synthetic Chemistry Example | Compound Structure | Compound Name |
|---|---|---|
| 87 | 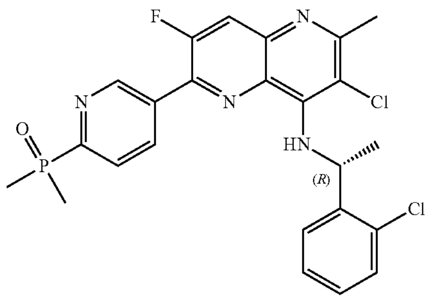 | 3-chloro-N-[(1R)-1-(2-chlorophenyl)ethyl]-6-[6-(dimethylphosphoryl)pyridin-3-yl]-7-fluoro-2-methyl-1,5-naphthyridin-4-amine |
| 88 | 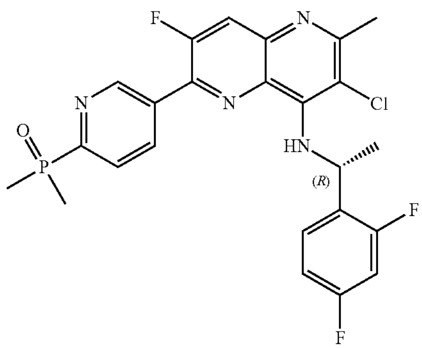 | 3-chloro-N-[(1R)-1-(2,4-difluorophenyl)ethyl]-6-[6-(dimethylphosphoryl)pyridin-3-yl]-7-fluoro-2-methyl-1,5-naphthyridin-4-amine |
| 89 | 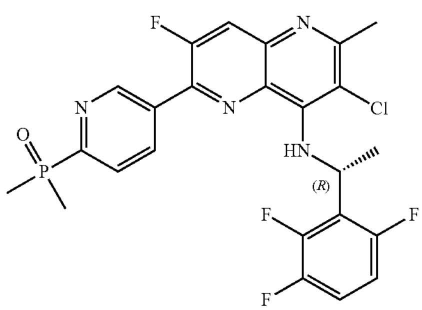 | 3-chloro-6-[6-(dimethylphosphoryl)pyridin-3-yl]-7-fluoro-2-methyl-N-[(1R)-1-(2,3,6-trifluorophenyl)ethyl]-1,5-naphthyridin-4-amine |
| 90 | 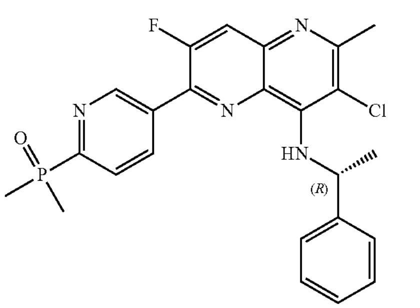 | 3-chloro-6-[6-(dimethylphosphoryl)pyridin-3-yl]-7-fluoro-2-methyl-N-[(1R)-1-phenylethyl]-1,5-naphthyridin-4-amine |
| 91 | 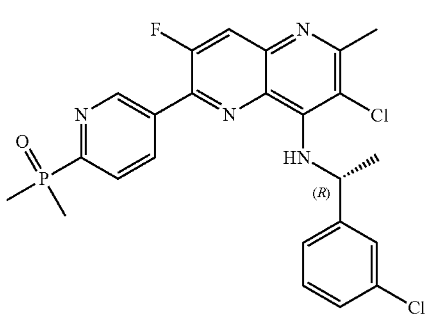 | 3-chloro-N-[(1R)-1-(3-chlorophenyl)ethyl]-6-[6-(dimethylphosphoryl)pyridin-3-yl]-7-fluoro-2-methyl-1,5-naphthyridin-4-amine |

TABLE 1-continued

| Synthetic Chemistry Example | Compound Structure | Compound Name |
|---|---|---|
| 92 | 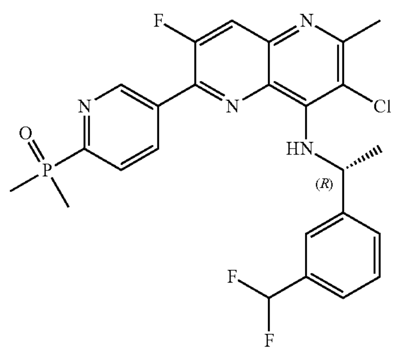 | 3-chloro-N-[(1R)-1-[3-(difluoromethyl)phenyl]ethyl]-6-[6-(dimethylphosphoryl)pyridin-3-yl]-7-fluoro-2-methyl-1,5-naphthyridin-4-amine |
| 93 | 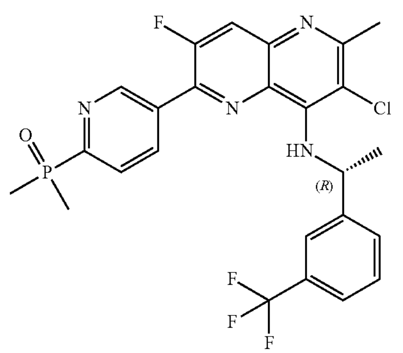 | 3-chloro-6-[6-(dimethylphosphoryl)pyridin-3-yl]-7-fluoro-2-methyl-N-[(1R)-1-[3-(trifluoromethyl)phenyl]ethyl]-1,5-naphthyridin-4-amine |
| 94 | 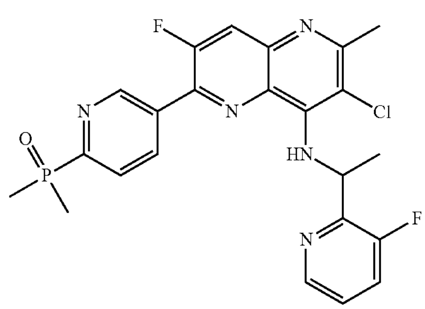 [SMILES: Cc1nc2cc(F)c(-c3ccc(P(C)(C)=O)nc3)nc2c(NC(C)c2ncccc2F)c1Cl] | 3-chloro-6-[6-(dimethylphosphoryl)pyridin-3-yl]-7-fluoro-N-[1-(3-fluoropyridin-2-yl)ethyl]-2-methyl-1,5-naphthyridin-4-amine |
| 95 | 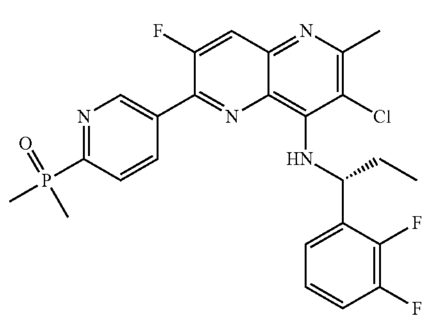 [SMILES: CC[C@@H](Nc1c(Cl)c(C)nc2cc(F)c(-c3ccc(P(C)(C)=O)nc3)nc12)c1cccc(F)c1F] | (R)-(5-(7-chloro-8-((1-(2,3-difluorophenyl)propyl)amino)-3-fluoro-6-methyl-1,5-naphthyridin-2-yl)pyridin-2-yl)dimethylphosphine oxide |

TABLE 1-continued

| Synthetic Chemistry Example | Compound Structure | Compound Name |
|---|---|---|
| 96 | 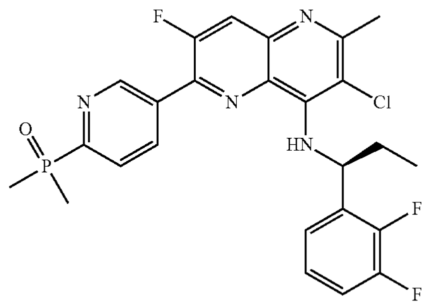 | (S)-(5-(7-chloro-8-((1-(2,3-difluorophenyl)propyl)amino)-3-fluoro-6-methyl-1,5-naphthyridin-2-yl)pyridin-2-yl)dimethylphosphine oxide |
| 97 | 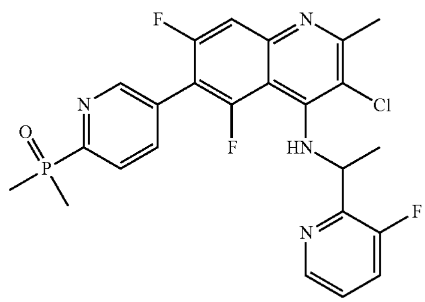 [SMILES: Cc1nc2cc(F)c(-c3ccc(P(C)(C)=O)nc3)c(F)c2c(NC(C)c2ncccc2F)c1Cl] | 3-chloro-6-[6-(dimethylphosphoryl)pyridin-3-yl]-5,7-difluoro-N-[1-(3-fluoropyridin-2-yl)ethyl]-2-methylquinolin-4-amine |
| 98 | 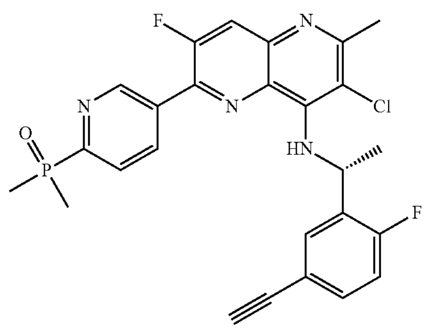 [SMILES: C#Cc1ccc(F)c([C@@H](C)Nc2c(Cl)c(C)nc3cc(F)c(-c4ccc(P(C)(C)=O)nc4)nc23)c1] | 3-chloro-6-[6-(dimethylphosphoryl)pyridin-3-yl]-N-[(1R)-1-(5-ethynyl-2-fluorophenyl)ethyl]-7-fluoro-2-methyl-1,5-naphthyridin-4-amine |
| 99 | 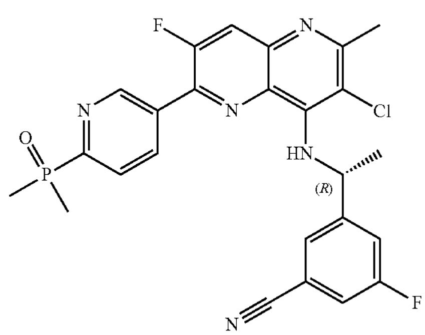 | 3-[(1R)-1-({3-chloro-6-[6-(dimethylphosphoryl)pyridin-3-yl]-7-fluoro-2-methyl-1,5-naphthyridin-4-yl}amino)ethyl]-5-fluorobenzonitrile |
| 100 | 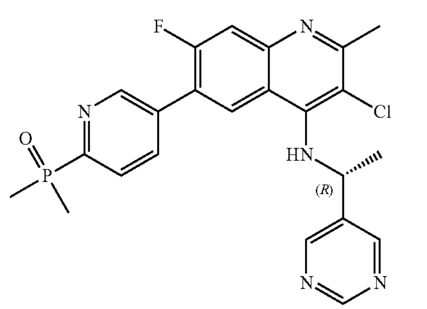 | (R)-(5-(3-chloro-7-fluoro-2-methyl-4-((1-(pyrimidin-5-yl)ethyl)amino)quinolin-6-yl)pyridin-2-yl)dimethylphosphine oxide |

TABLE 1-continued

| Synthetic Chemistry Example | Compound Structure | Compound Name |
|---|---|---|
| and | + | And |
| 101 | 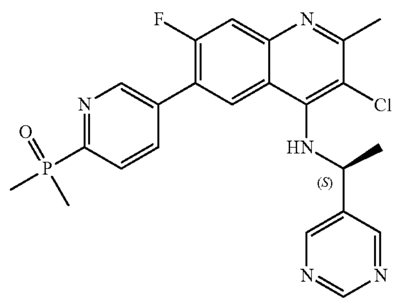 | (S)-(5-(3-chloro-7-fluoro-2-methyl-4-((1-(pyrimidin-5-yl)ethyl)amino)quinolin-6-yl)pyridin-2-yl)dimethylphosphine oxide |
| 102 | 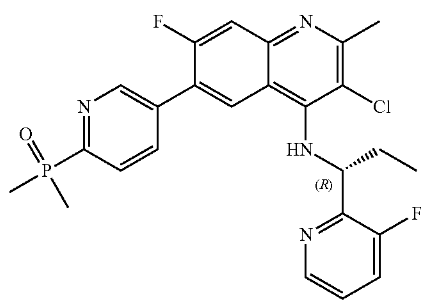 | 3-chloro-6-[6-(dimethylphosphoryl)pyridin-3-yl]-7-fluoro-N-[(1R)-1-(3-fluoropyridin-2-yl)propyl]-2-methylquinolin-4-amine |
| 103 | 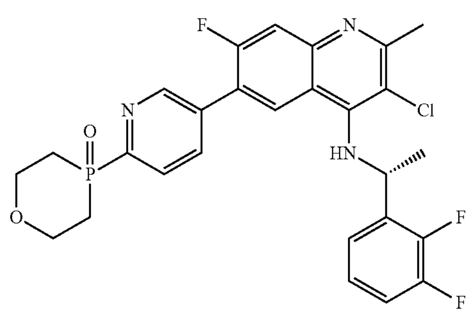 [SMILES: Cc1nc2cc(F)c(-c3ccc(P4(=O)CCOCC4)nc3)cc2c(N[C@H](C)c2cccc(F)c2F)c1Cl] | 4-[5-(3-chloro-4-{[(1R)-1-(2,3-difluorophenyl)ethyl]amino}-7-fluoro-2-methylquinolin-6-yl)pyridin-2-yl]-1,4lambda5-oxaphosphinan-4-one |
| 104 | 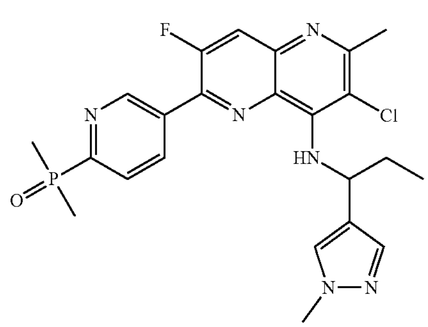 [SMILES: CCC(Nc1c(Cl)c(C)nc2cc(F)c(-c3ccc(P(C)(C)=O)nc3)nc12)c1cnn(C)c1] | 3-chloro-6-[6-(dimethylphosphoryl)pyridin-3-yl]-7-fluoro-2-methyl-N-[1-(1-methylpyrazol-4-yl)propyl]-1,5-naphthyridin-4-amine |

TABLE 1-continued

| Synthetic Chemistry Example | Compound Structure | Compound Name |
|---|---|---|
| 105 | 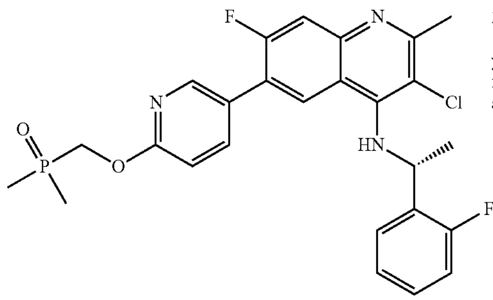 [SMILES: Cc1nc2cc(F)c(-c3ccc(OCP(C)(C)=O)nc3)cc2c(N[C@H](C)c2ccccc2F)c1Cl] | 3-chloro-6-{6-[(dimethylphosphoryl)methoxy]pyridin-3-yl}-7-fluoro-N-[(1R)-1-(2-fluorophenyl)ethyl]-2-methylquinolin-4-amine |
| 106 | 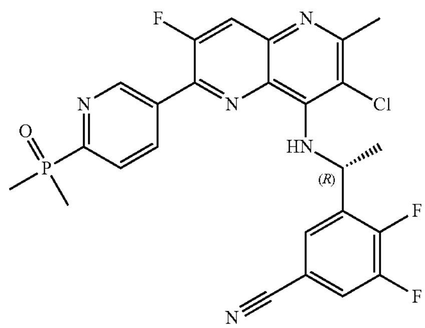 | 3-[(1R)-1-({3-chloro-6-[6-(dimethylphosphoryl)pyridin-3-yl]-7-fluoro-2-methyl-1,5-naphthyridin-4-yl}amino)ethyl]-4,5-difluorobenzonitrile |
| 107 | 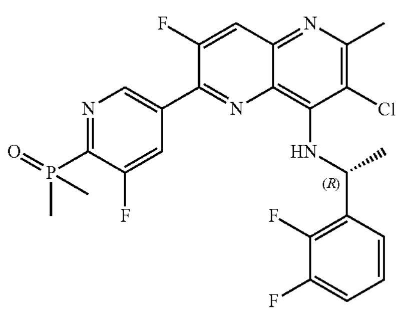 | 3-chloro-N-[(1R)-1-(2,3-difluorophenyl)ethyl]-6-[6-(dimethylphosphoryl)-5-fluoropyridin-3-yl]-7-fluoro-2-methyl-1,5-naphthyridin-4-amine |
| 108 | 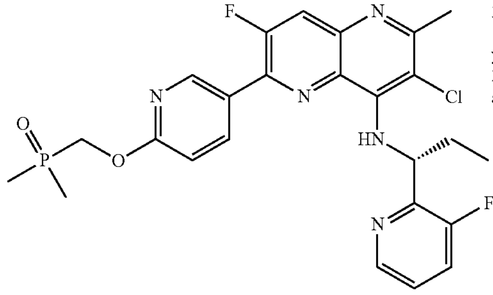 [SMILES: CC[C@@H](Nc1c(Cl)c(C)nc2cc(F)c(-c3ccc(OCP(C)(C)=O)nc3)nc12)c1ncccc1F] | 3-chloro-6-{6-[(dimethylphosphoryl)methoxy]pyridin-3-yl}-7-fluoro-N-[(1R)-1-(3-fluoropyridin-2-yl)propyl]-2-methyl-1,5-naphthyridin-4-amine |

TABLE 1-continued

| Synthetic Chemistry Example | Compound Structure | Compound Name |
|---|---|---|
| 109 | 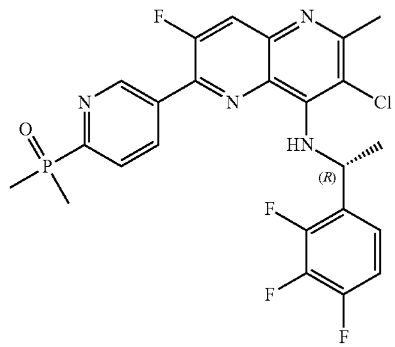 | (R)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide |
| and | + | And |
| 110 | 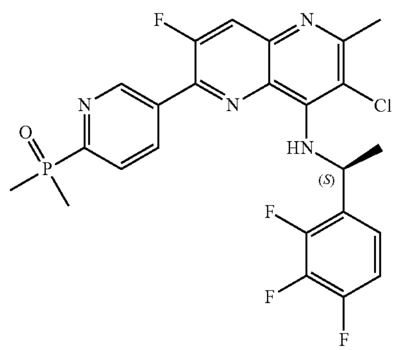 | (S)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide |
| 111 | 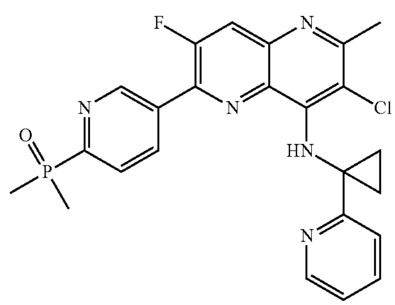 [SMILES: Cc1nc2cc(F)c(-c3ccc(P(C)(C)=O)nc3)nc2c(NC2(c3ccccn3)CC2)c1Cl] | 3-chloro-6-[6-(dimethylphosphoryl)pyridin-3-yl]-7-fluoro-2-methyl-N-[1-(pyridin-2-yl)cyclopropyl]-1,5-naphthyridin-4-amine |
| 112 | 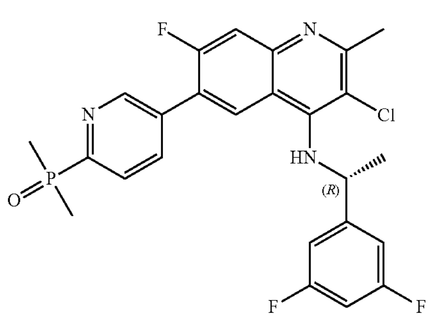 | 3-chloro-N-[(1R)-1-(3,5-difluorophenyl)ethyl]-6-[6-(dimethylphosphoryl)pyridin-3-yl]-7-fluoro-2-methylquinolin-4-amine |

TABLE 1-continued

| Synthetic Chemistry Example | Compound Structure | Compound Name |
|---|---|---|
| 113 | 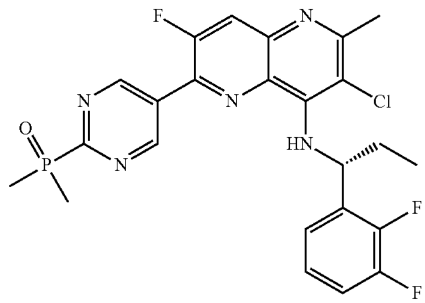 [SMILES: CC[C@@H](Nc1c(Cl)c(C)nc2cc(F)c(-c3cnc(P(C)(C)=O)nc3)nc12)c1cccc(F)c1F] | (R)-(5-(7-chloro-8-((1-(2,3-difluorophenyl)propyl)amino)-3-fluoro-6-methyl-1,5-naphthyridin-2-yl)pyrimidin-2-yl)dimethylphosphine oxide |
| 114 | 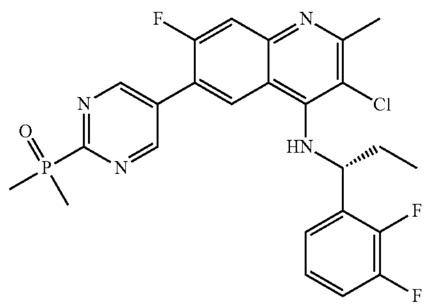 [SMILES: CC[C@@H](Nc1c(Cl)c(C)nc2cc(F)c(-c3cnc(P(C)(C)=O)nc3)cc12)c1cccc(F)c1F] | (R)-(5-(3-chloro-4-((1-(2,3-difluorophenyl)propyl)amino)-7-fluoro-2-methylquinolin-6-yl)pyrimidin-2-yl)dimethylphosphine oxide |
| 115 | 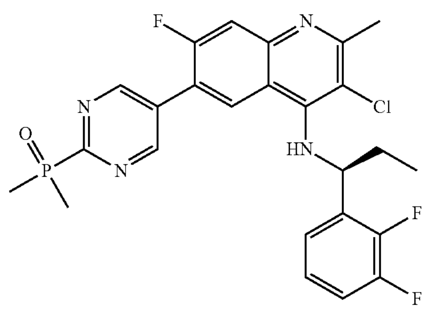 [SMILES: CC[C@H](Nc1c(Cl)c(C)nc2cc(F)c(-c3cnc(P(C)(C)=O)nc3)cc12)c1cccc(F)c1F] | (S)-(5-(3-chloro-4-((1-(2,3-difluorophenyl)propyl)amino)-7-fluoro-2-methylquinolin-6-yl)pyrimidin-2-yl)dimethylphosphine oxide |
| 116 | 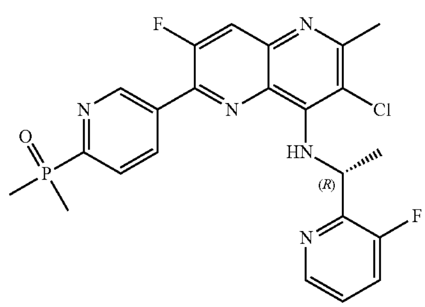 | (R)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide |
| and | + | And |
| 117 | 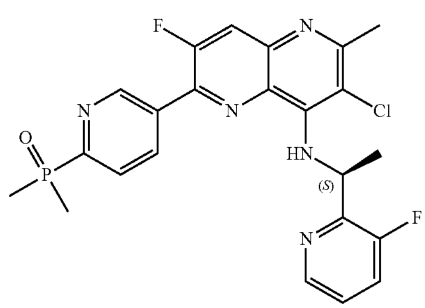 | (S)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide |

TABLE 1-continued

| Synthetic Chemistry Example | Compound Structure | Compound Name |
|---|---|---|
| 118 | 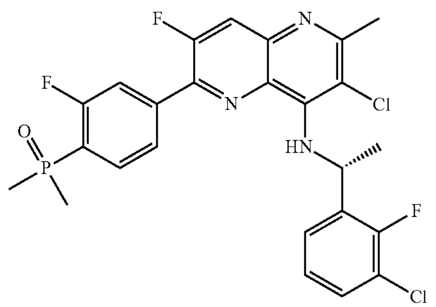 [SMILES: Cc1nc2cc(F)c(-c3ccc(P(C)(C)=O)c(F)c3)nc2c(N[C@H](C)c2cccc(Cl)c2F)c1Cl] | 3-chloro-N-[(1R)-1-(3-chloro-2-fluorophenyl)ethyl]-6-[4-(dimethylphosphoryl)-3-fluorophenyl]-7-fluoro-2-methyl-1,5-naphthyridin-4-amine |
| 119 | 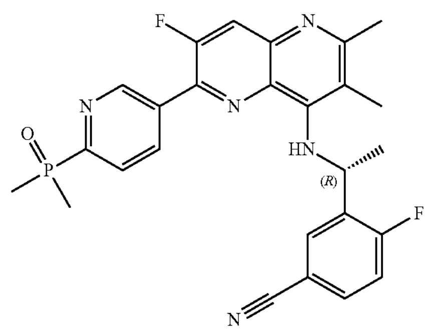 | 3-[(1R)-1-({6-[6-(dimethylphosphoryl)pyridin-3-yl]-7-fluoro-2,3-dimethyl-1,5-naphthyridin-4-yl}amino)ethyl]-4-fluorobenzonitrile |
| 120 | 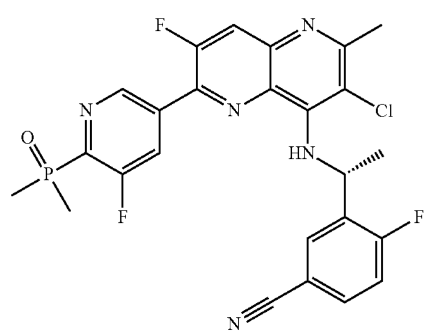 [SMILES: Cc1nc2cc(F)c(-c3cnc(P(C)(C)=O)c(F)c3)nc2c(N[C@H](C)c2cc(C#N)ccc2F)c1Cl] | 3-[(1R)-1-({3-chloro-6-[6-(dimethylphosphoryl)-5-fluoropyridin-3-yl]-7-fluoro-2-methyl-1,5-naphthyridin-4-yl}amino)ethyl]-4-fluorobenzonitrile |
| 121 | 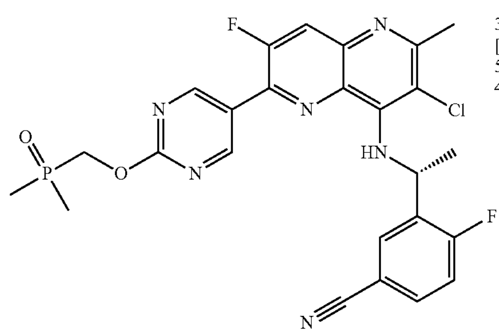 | 3-[(1R)-1-[(3-chloro-6-{2-[(dimethylphosphoryl)methoxy]pyrimidin-5-yl}-7-fluoro-2-methyl-1,5-naphthyridin-4-yl)amino]ethyl]-4-fluorobenzonitrile |

TABLE 1-continued

| Synthetic Chemistry Example | Compound Structure | Compound Name |
|---|---|---|
| 122 | 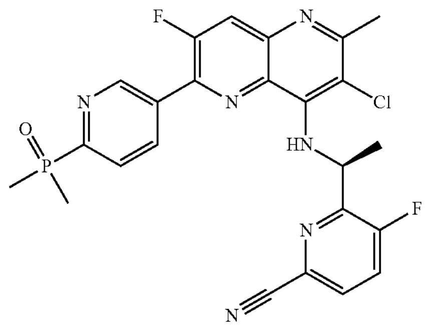 [SMILES: Cc1nc2cc(F)c(-c3ccc(P(C)(C)=O)nc3)nc2c(N[C@@H](C)c2nc(C#N)ccc2F)c1Cl] | 6-[(1S)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile |
| 123 | 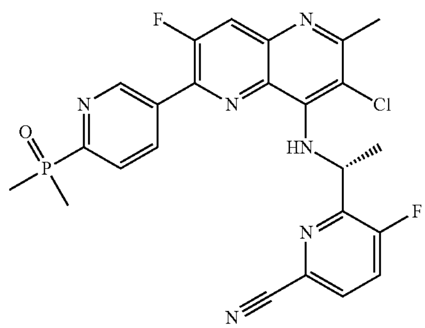 [SMILES: Cc1nc2cc(F)c(-c3ccc(P(C)(C)=O)nc3)nc2c(N[C@H](C)c2nc(C#N)ccc2F)c1Cl] | 6-[(1R)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile |
| 124 | 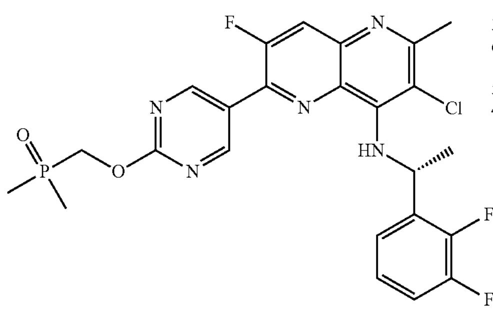 [SMILES: Cc1nc2cc(F)c(-c3cnc(OCP(C)(C)=O)nc3)nc2c(N[C@H](C)c2cccc(F)c2F)c1Cl] | 3-chloro-N-[(1R)-1-(2,3-difluorophenyl)ethyl]-6-{2-[(dimethylphosphoryl)methoxy]pyrimidin-5-yl}-7-fluoro-2-methyl-1,5-naphthyridin-4-amine |
| 125 | 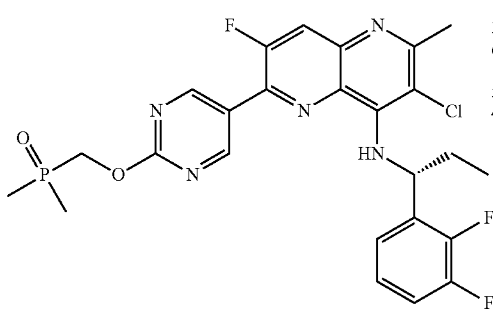 [SMILES: CC[C@@H](Nc1c(Cl)c(C)nc2cc(F)c(-c3cnc(OCP(C)(C)=O)nc3)nc12)c1cccc(F)c1F] | 3-chloro-N-[(1R)-1-(2,3-difluorophenyl)propyl]-6-{2-[(dimethylphosphoryl)methoxy]pyrimidin-5-yl}-7-fluoro-2-methyl-1,5-naphthyridin-4-amine |
| 126 | 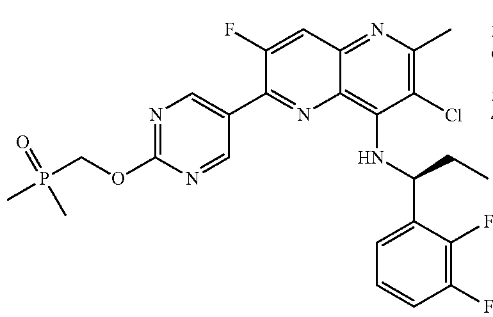 [SMILES: CC[C@H](Nc1c(Cl)c(C)nc2cc(F)c(-c3cnc(OCP(C)(C)=O)nc3)nc12)c1cccc(F)c1F] | 3-chloro-N-[(1S)-1-(2,3-difluorophenyl)propyl]-6-{2-[(dimethylphosphoryl)methoxy]pyrimidin-5-yl}-7-fluoro-2-methyl-1,5-naphthyridin-4-amine |

TABLE 1-continued

| Synthetic Chemistry Example | Compound Structure | Compound Name |
|---|---|---|
| 127 | 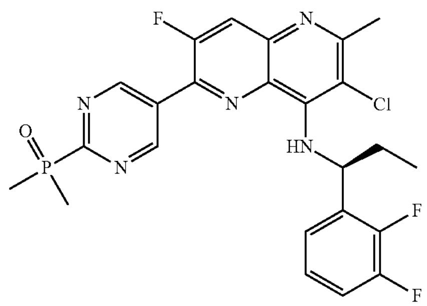 [SMILES: CC[C@H](Nc1c(Cl)c(C)nc2cc(F)c(-c3cnc(P(C)(C)=O)nc3)nc12)c1cccc(F)c1F] | 3-chloro-N-[(1S)-1-(2,3-difluorophenyl)propyl]-6-[2-(dimethylphosphoryl)pyrimidin-5-yl]-7-fluoro-2-methyl-1,5-naphthyridin-4-amine |
| 128 | 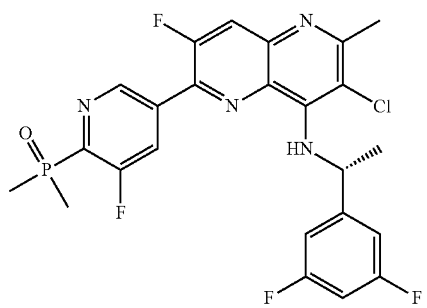 [SMILES: Cc1nc2cc(F)c(-c3cnc(P(C)(C)=O)c(F)c3)nc2c(N[C@H](C)c2cc(F)cc(F)c2)c1Cl] | 3-chloro-N-[(1R)-1-(3,5-difluorophenyl)ethyl]-6-[6-(dimethylphosphoryl)-5-fluoropyridin-3-yl]-7-fluoro-2-methyl-1,5-naphthyridin-4-amine |
| 129 | 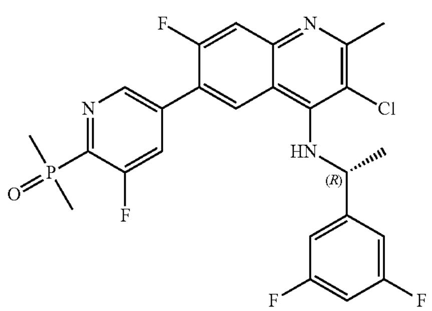 | 3-chloro-N-[(1R)-1-(3,5-difluorophenyl)ethyl]-6-[6-(dimethylphosphoryl)-5-fluoropyridin-3-yl]-7-fluoro-2-methylquinolin-4-amine |
| 130 | 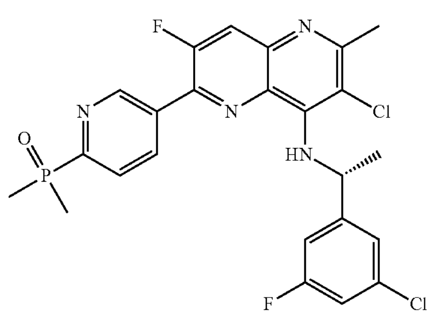 [SMILES: Cc1nc2cc(F)c(-c3ccc(P(C)(C)=O)nc3)nc2c(N[C@H](C)c2cc(F)cc(Cl)c2)c1Cl] | 3-chloro-N-[(1R)-1-(3-chloro-5-fluorophenyl)ethyl]-6-[6-(dimethylphosphoryl)pyridin-3-yl]-7-fluoro-2-methyl-1,5-naphthyridin-4-amine |
| 131 | 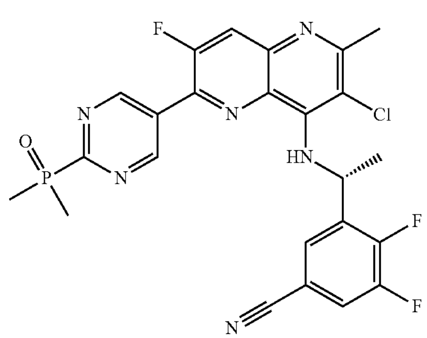 [SMILES: Cc1nc2cc(F)c(-c3cnc(P(C)(C)=O)nc3)nc2c(N[C@H](C)c2cc(C#N)cc(F)c2F)c1Cl] | 3-[(1R)-1-({3-chloro-6-[2-(dimethylphosphoryl)pyrimidin-5-yl]-7-fluoro-2-methyl-1,5-naphthyridin-4-yl}amino)ethyl]-4,5-difluorobenzonitrile |

TABLE 1-continued

| Synthetic Chemistry Example | Compound Structure | Compound Name |
|---|---|---|
| 132 | 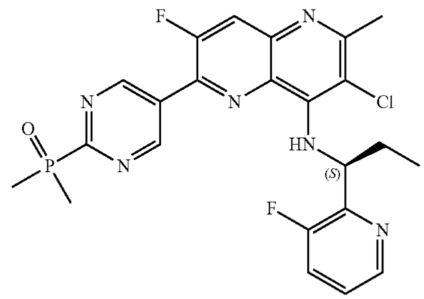 | 3-chloro-6-[2-(dimethylphosphoryl)pyrimidin-5-yl]-7-fluoro-N-[(1S)-1-(3-fluoropyridin-2-yl)propyl]-2-methyl-1,5-naphthyridin-4-amine |
| 133 | 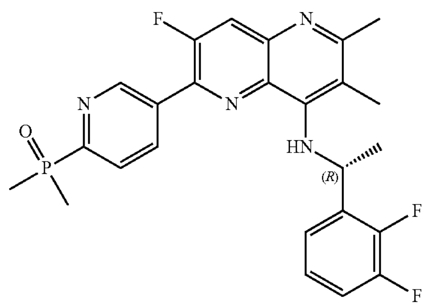 | N-[(1R)-1-(2,3-difluorophenyl)ethyl]-6-[6-(dimethylphosphoryl)pyridin-3-yl]-7-fluoro-2,3-dimethyl-1,5-naphthyridin-4-amine |
| 134 | 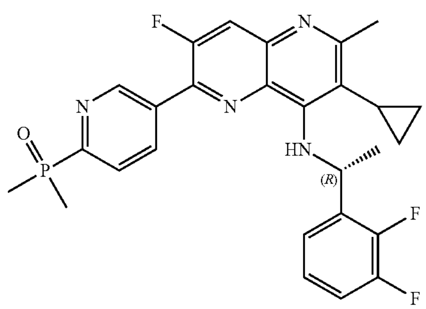 | 3-cyclopropyl-N-[(1R)-1-(2,3-difluorophenyl)ethyl]-6-[6-(dimethylphosphoryl)pyridin-3-yl]-7-fluoro-2-methyl-1,5-naphthyridin-4-amine |
| 135 | 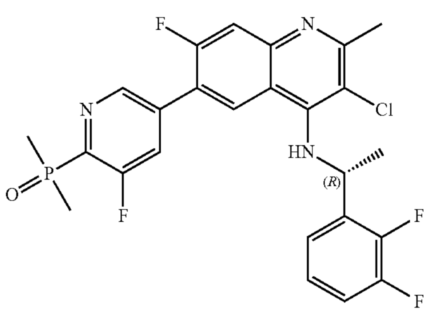 | 3-chloro-N-[(1R)-1-(2,3-difluorophenyl)ethyl]-6-[6-(dimethylphosphoryl)-5-fluoropyridin-3-yl]-7-fluoro-2-methylquinolin-4-amine |
| 136 | 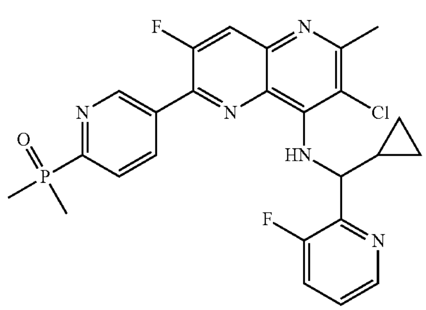 [SMILES: Cc1nc2cc(F)c(-c3ccc(P(C)(C)=O)nc3)nc2c(NC(c2ncccc2F)C2CC2)c1Cl] | 3-chloro-N-[cyclopropyl(3-fluoropyridin-2-yl)methyl]-6-[6-(dimethylphosphoryl)pyridin-3-yl]-7-fluoro-2-methyl-1,5-naphthyridin-4-amine |

TABLE 1-continued

| Synthetic Chemistry Example | Compound Structure | Compound Name |
|---|---|---|
| 137 | 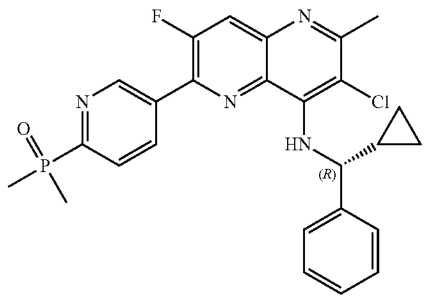 | 3-chloro-N-[(R)-cyclopropyl(phenyl)methyl]-6-[6-(dimethylphosphoryl)pyridin-3-yl]-7-fluoro-2-methyl-1,5-naphthyridin-4-amine |
| 138 | 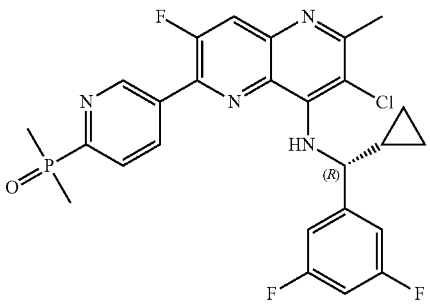 | 3-chloro-N-[(R)-cyclopropyl(3,5-difluorophenyl)methyl]-6-[6-(dimethylphosphoryl)pyridin-3-yl]-7-fluoro-2-methyl-1,5-naphthyridin-4-amine |
| 139 | 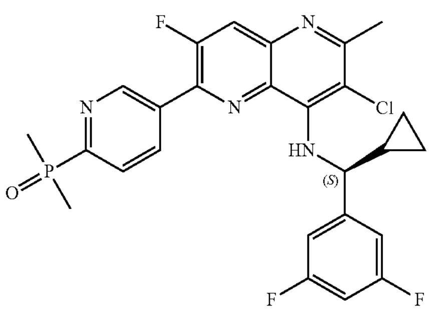 | 3-chloro-N-[(S)-cyclopropyl(3,5-difluorophenyl)methyl]-6-[6-(dimethylphosphoryl)pyridin-3-yl]-7-fluoro-2-methyl-1,5-naphthyridin-4-amine |
| 140 | 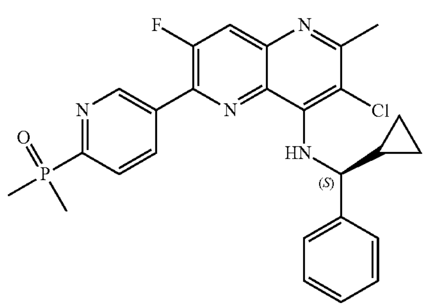 | 3-chloro-N-[(S)-cyclopropyl(phenyl)methyl]-6-[6-(dimethylphosphoryl)pyridin-3-yl]-7-fluoro-2-methyl-1,5-naphthyridin-4-amine |
| 141 | 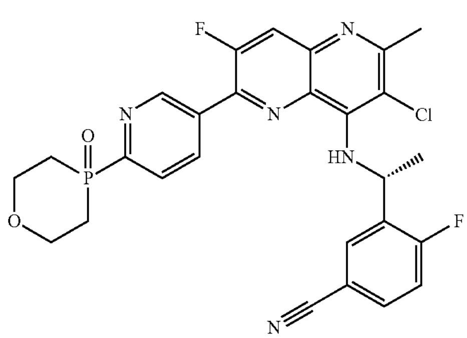 [SMILES: Cc1nc2cc(F)c(-c3ccc(P4(=O)CCOCC4)nc3)nc2c(N[C@H](C)c2cc(C#N)ccc2F)c1Cl] | 3-[(1R)-1-({3-chloro-7-fluoro-2-methyl-6-[6-(4-oxo-1,4lambda5-oxaphosphinan-4-yl)pyridin-3-yl]-1,5-naphthyridin-4-yl}amino)ethyl]-4-fluorobenzonitrile |

TABLE 1-continued

| Synthetic Chemistry Example | Compound Structure | Compound Name |
|---|---|---|
| 142 | 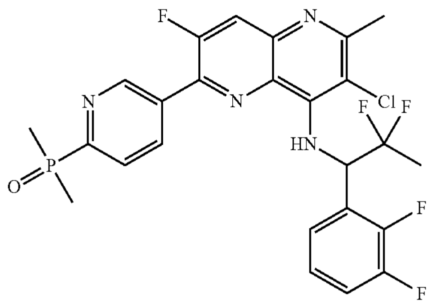 [SMILES: Cc1nc2cc(F)c(-c3ccc(P(C)(C)=O)nc3)nc2c(NC(c2cccc(F)c2F)C(C)(F)F)c1Cl] | 3-chloro-N-[1-(2,3-difluorophenyl)-2,2-difluoropropyl]-6-[6-(dimethylphosphoryl)pyridin-3-yl]-7-fluoro-2-methyl-1,5-naphthyridin-4-amine |
| 143 | 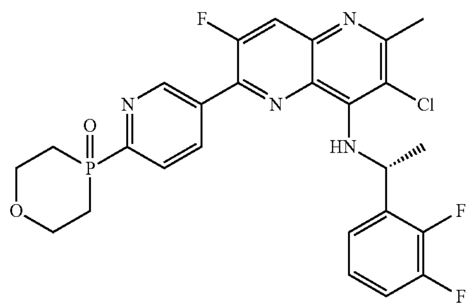 [SMILES: Cc1nc2cc(F)c(-c3ccc(P4(=O)CCOCC4)nc3)nc2c(N[C@H](C)c2cccc(F)c2F)c1Cl] | 4-[5-(7-chloro-8-{[(1R)-1-(2,3-difluorophenyl)ethyl]amino}-3-fluoro-6-methyl-1,5-naphthyridin-2-yl)pyridin-2-yl]-1,4lambda5-oxaphosphinan-4-one |
| 144 | 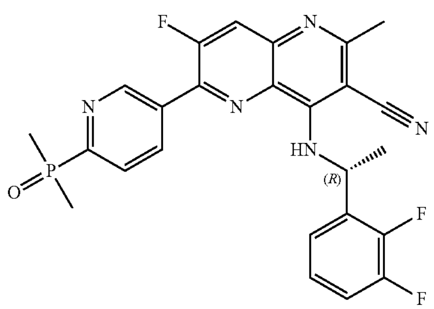 | 4-{[(1R)-1-(2,3-difluorophenyl)ethyl]amino}-6-[6-(dimethylphosphoryl)pyridin-3-yl]-7-fluoro-2-methyl-1,5-naphthyridine-3-carbonitrile |
| 145 | 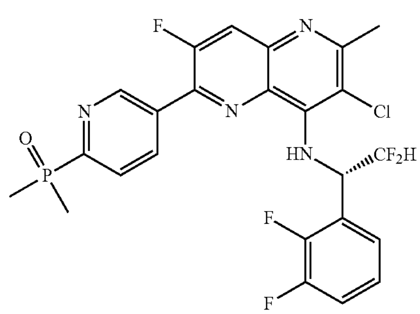 [SMILES: Cc1nc2cc(F)c(-c3ccc(P(C)(C)=O)nc3)nc2c(N[C@@H](c2cccc(F)c2F)C(F)F)c1Cl] | (S)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide |
| and | + | And |
| 146 | 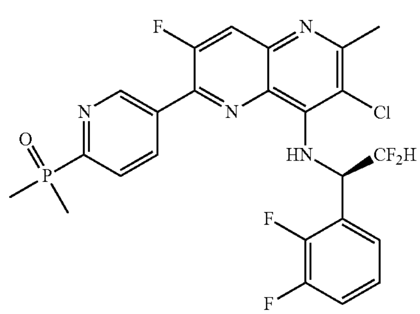 [SMILES: Cc1nc2cc(F)c(-c3ccc(P(C)(C)=O)nc3)nc2c(N[C@H](c2cccc(F)c2F)C(F)F)c1Cl] | (R)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide |

TABLE 1-continued

| Synthetic Chemistry Example | Compound Structure | Compound Name |
|---|---|---|
| 147 | 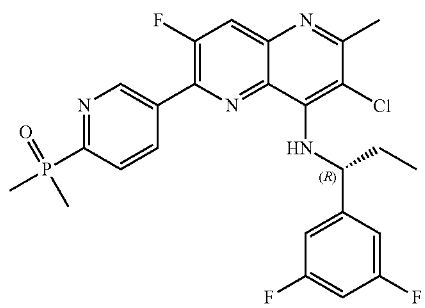 | 3-chloro-N-[(1R)-1-(3,5-difluorophenyl)propyl]-6-[6-(dimethylphosphoryl)pyridin-3-yl]-7-fluoro-2-methyl-1,5-naphthyridin-4-amine |
| 148 | 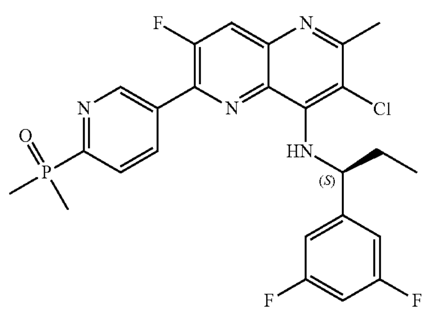 | 3-chloro-N-[(1S)-1-(3,5-difluorophenyl)propyl]-6-[6-(dimethylphosphoryl)pyridin-3-yl]-7-fluoro-2-methyl-1,5-naphthyridin-4-amine |
| 149 | 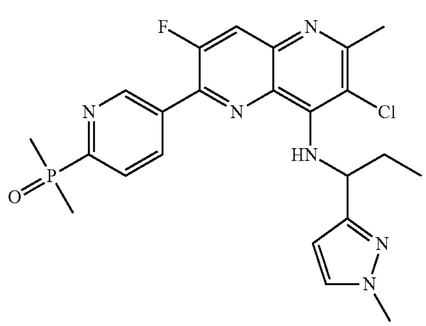 [SMILES: CCC(Nc1c(Cl)c(C)nc2cc(F)c(-c3ccc(P(C)(C)=O)nc3)nc12)c1ccn(C)n1] | 3-chloro-6-[6-(dimethylphosphoryl)pyridin-3-yl]-7-fluoro-2-methyl-N-[1-(1-methylpyrazol-3-yl)propyl]-1,5-naphthyridin-4-amine |
| 150 | 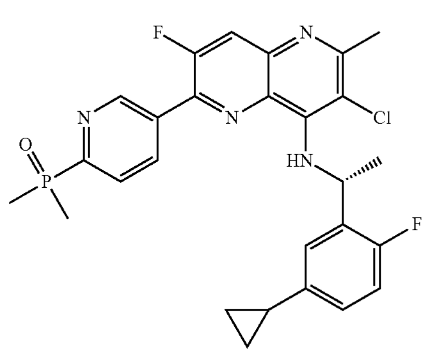 [SMILES: Cc1nc2cc(F)c(-c3ccc(P(C)(C)=O)nc3)nc2c(N[C@H](C)c2cc(C3CC3)ccc2F)c1Cl] | 3-chloro-N-[(1R)-1-(5-cyclopropyl-2-fluorophenyl)ethyl]-6-[6-(dimethylphosphoryl)pyridin-3-yl]-7-fluoro-2-methyl-1,5-naphthyridin-4-amine |

Another embodiment provides a TNF-α, inhibitory compound, or a pharmaceutically acceptable salt or solvate thereof, having a structure presented in Table 2.

TABLE 2

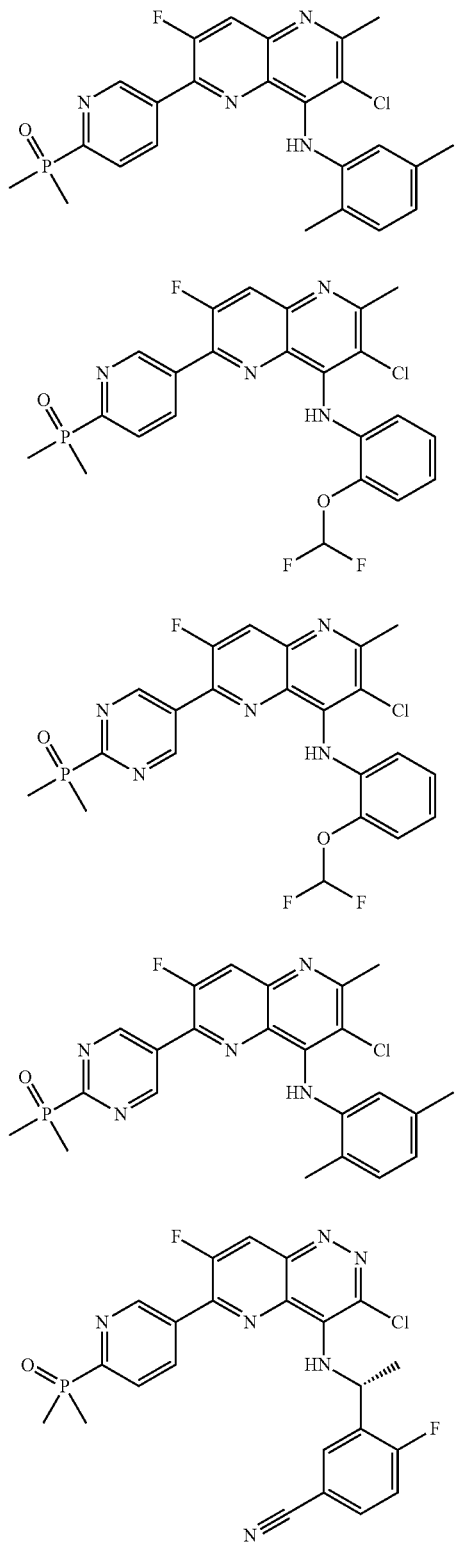

TABLE 2-continued

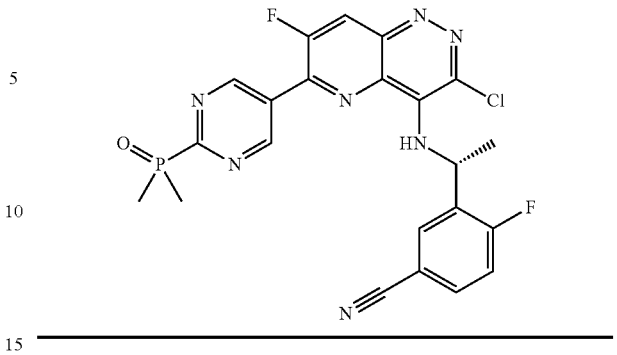

Preparation of Compounds

The compounds used in the synthetic chemistry reactions described herein are made according to organic synthesis techniques known to those skilled in this art, start from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, Nil), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

General Synthetic Schemes

The TNF-α inhibitory compound disclosed herein can be prepared by a variety of synthetic routes including, but not limited to, the routes described below in Scheme I.

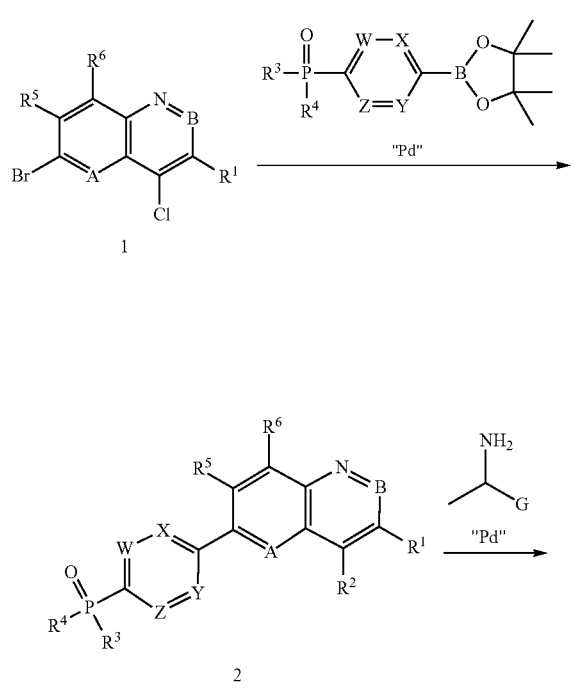

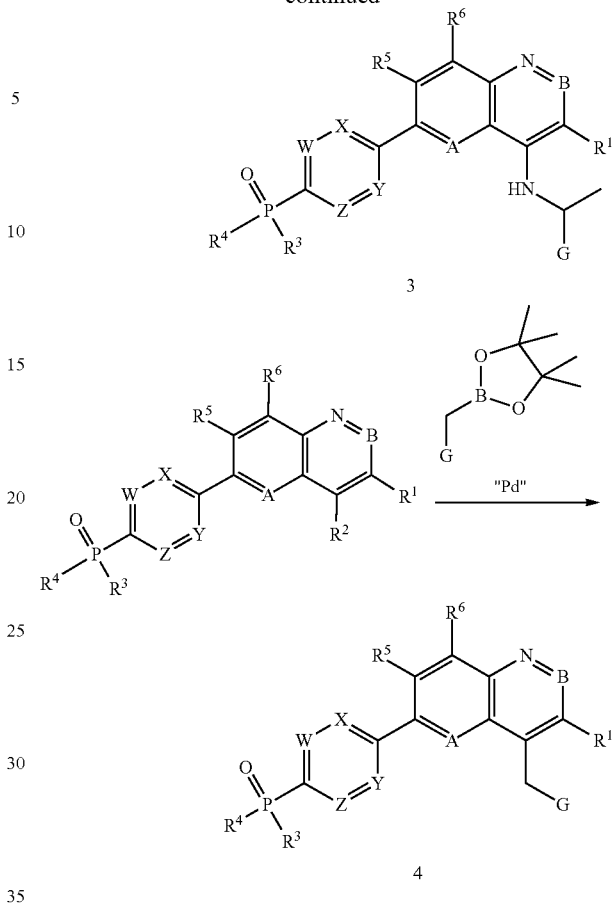

Starting with quinoline derivative 1, palladium-catalyzed boronic acid coupling affords tricyclic compound 2. Buchwald-type palladium-mediated coupling with a suitable amine provides 4-aminoquinoline derivative 3. Alternatively, palladium-catalyzed boronic acid coupling with an alkyl boronic acid derivative provides 4-substituted quinoline derivative 4. Using appropriate starting materials, the TNF-α inhibitory compounds described herein by Formula (I), or within Tables 1 or Table 2, can be synthesized using the methods described above in Scheme I.

Pharmaceutical Compositions

In certain embodiments, the TNF-α inhibitory compound described herein is administered as a pure chemical. In other embodiments, the TNF-α inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Provided herein is a pharmaceutical composition comprising at least one TNF-α inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a method of preparing a pharmaceutical composition comprising mixing a compound of Formula (I), or a pharmaceutically acceptable salt or solvate thereof, and a pharmaceutically acceptable carrier.

In certain embodiments, the TNF-α inhibitory compound as described by Formula (I), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1 or Table 2, or a pharmaceutically acceptable salt or solvate thereof.

One embodiment provides a method of preparing a pharmaceutical composition comprising mixing a compound of Table 1 or Table 2, or a pharmaceutically acceptable salt or solvate thereof, and a pharmaceutically acceptable carrier.

In certain embodiments, the TNF-α inhibitory compound as described by Table 1 or Table 2, or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

In some embodiments, the TNF-α inhibitory compound as described by Formula (I) or Table 1 or Table 2, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one TNF-α inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), or a pharmaceutically acceptable salt or solvate thereof, for use in a method of treatment of the human or animal body.

One embodiment provides a compound of Formula (I), or a pharmaceutically acceptable salt or solvate thereof, for use in a method of treatment of inflammatory or autoimmune disease or disorder. Another embodiment provides a compound of Formula (I), or a pharmaceutically acceptable salt or solvate thereof, for use in a method of treatment of inflammatory disease or disorder. Yet another embodiment provides a compound of Formula (I), or a pharmaceutically acceptable salt or solvate thereof, for use in a method of treatment of autoimmune disease or disorder.

One embodiment provides a pharmaceutical composition comprising a compound of Formula (I), or a pharmaceutically acceptable salt or solvate thereof, and a pharmaceutically acceptable excipient for use in a method of treatment of inflammatory or autoimmune disease or disorder.

One embodiment provides a use of a compound of Formula (I), or a pharmaceutically acceptable salt or solvate thereof, in the manufacture of a medicament for the treatment of inflammatory or autoimmune disease or disorder.

In some embodiments is provided a method of treating an inflammatory or autoimmune disease or disorder, in a patient in need thereof, comprising administering to the patient a compound of Formula (I), or a pharmaceutically acceptable salt or solvate thereof. In some embodiments is provided a method of treating inflammatory or autoimmune disease or disorder, in a patient in need thereof, comprising administering to the patient a pharmaceutical composition comprising a compound of Formula (I), or a pharmaceutically acceptable salt or solvate thereof, and a pharmaceutically acceptable excipient. One embodiment provides a method of treating an inflammatory disease or disorder. Another embodiment provides a method of treating an autoimmune disease or disorder.

One embodiment provides a compound of Table 1 or Table 2, or a pharmaceutically acceptable salt or solvate thereof, for use in a method of treatment of the human or animal body.

One embodiment provides a compound of Table 1 or Table 2, or a pharmaceutically acceptable salt or solvate thereof, for use in a method of treatment of inflammatory or autoimmune disease or disorder.

One embodiment provides a pharmaceutical composition comprising a compound of Table 1 or Table 2, or a pharmaceutically acceptable salt or solvate thereof, and a pharmaceutically acceptable excipient for use in a method of treatment of inflammatory or autoimmune disease or disorder.

One embodiment provides a use of a compound of Table 1 or Table 2, or a pharmaceutically acceptable salt or solvate thereof, in the manufacture of a medicament for the treatment of inflammatory or autoimmune disease or disorder.

In some embodiments is provided a method of treating an inflammatory or autoimmune disease or disorder in a patient in need thereof, comprising administering to the patient a compound of Table 1 or Table 2, or a pharmaceutically acceptable salt or solvate thereof. In some embodiments is provided a method of treating an inflammatory or autoimmune disease or disorder, in a patient in need thereof, comprising administering to the patient a pharmaceutical composition comprising a compound of Table 1 or Table 2, or a pharmaceutically acceptable salt or solvate thereof, and a pharmaceutically acceptable excipient.

In some embodiments the inflammatory and autoimmune disease or disorder is selected from, but are not limited to: rheumatoid arthritis, psoriatic arthritis, systemic onset juvenile idiopathic arthritis, multiple sclerosis, lupus nephritis, systemic lupus erythematosus, psoriasis, Crohn's disease, colitis, asthma, graft versus host disease, allograft rejection, chronic obstructive pulmonary disease, multiple sclerosis, Alzheimer's disease, Graves' disease, cutaneous lupus, ankylosing spondylitis, cryopyrin-associated periodic syndromes (CAPS), gout, and gouty arthritis, ulcerative TNF receptor associated periodic syndrome (TRAPS), Wegener's granulomatosis, sarcoidosis, familial Mediterranean fever (FMF), neuropathic pain, and adult onset stills.

Provided herein is the method wherein the pharmaceutical composition is administered orally. Provided herein is the method wherein the pharmaceutical composition is administered by injection.

One embodiment provides a method of inhibiting TNF-α activity comprising contacting the TNF-α protein with a compound of Formula (I) or Table 1 or Table 2. Another embodiment provides the method of inhibiting TNF-α activity, wherein the TNF-α protein is contacted in an in vivo setting. Another embodiment provides the method of inhibiting TNF-α activity, wherein the TNF-α protein is contacted in an in vitro setting.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the TNF-α inhibitory compounds disclosed herein are synthesized according to the following examples. As used below, and throughout the description of the invention, the following abbreviations, unless otherwise indicated, shall be understood to have the following meanings:

| | |
|---|---|
| ACN | acetonitrile |
| ° C. | degrees Celsius |
| δ$_H$ | chemical shift in parts per million downfield from tetramethylsilane |
| DCM | dichloromethane (CH$_2$Cl$_2$) |
| DIAD | diisopropyl azodicarboxylate |
| DIEA | diisopropylethylamine |
| DMF | dimethylformamide |
| DMSO | dimethylsulfoxide |
| EA | ethyl acetate |
| EtOAc | ethyl acetate |
| ESI | electrospray ionization |
| Et | ethyl |
| g | gram(s) |
| h | hour(s) |
| HPLC | high performance liquid chromatography |
| Hz | hertz |
| J | coupling constant (in NMR spectrometry) |
| LCMS | liquid chromatography mass spectrometry |
| μ | micro |
| m | multiplet (spectral); meter(s); milli |
| M | molar |
| M$^+$ | parent molecular ion |
| Me | methyl |
| MsCl | methanesulfonyl chloride |
| MHz | megahertz |
| min | minute(s) |
| mol | mole(s); molecular (as in mol wt) |
| mL | milliliter |
| MS | mass spectrometry |
| nm | nanometer(s) |
| NMR | nuclear magnetic resonance |
| pH | potential of hydrogen; a measure of the acidity or basicity of an aqueous solution |
| PE | petroleum ether |
| RT | room temperature |
| s | singlet (spectral) |
| t | triplet (spectral) |
| SFC | Supercritical fluid chromatography |
| T | temperature |
| TFA | trifluoroacetic acid |
| THF | tetrahydrofuran |
| TPP | Triphenylphosphine |

Example 1: 5-(3-{[2-(difluoromethoxy)phenyl]methyl}-7-fluoro-2-methylimidazo[1,2-a]pyridin-6-yl)-2-(dimethylphosphoryl)pyrimidine

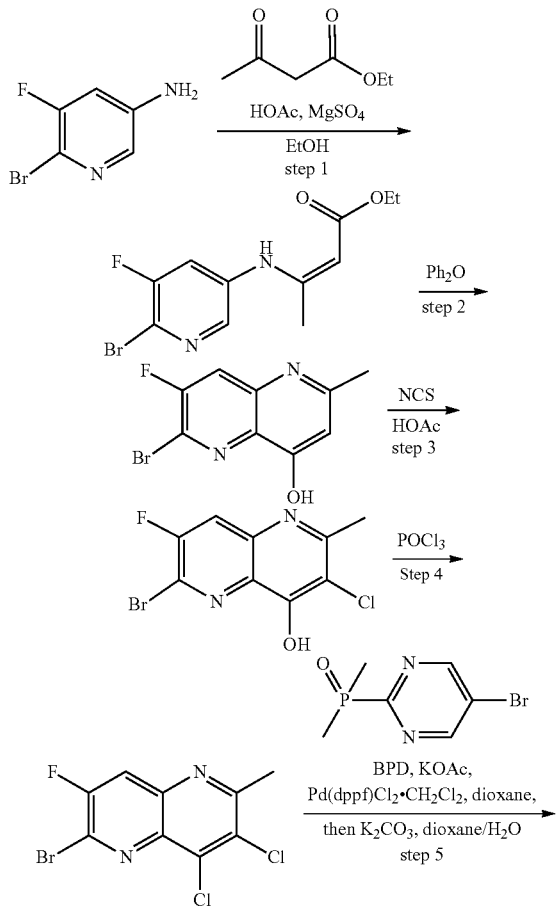

-continued

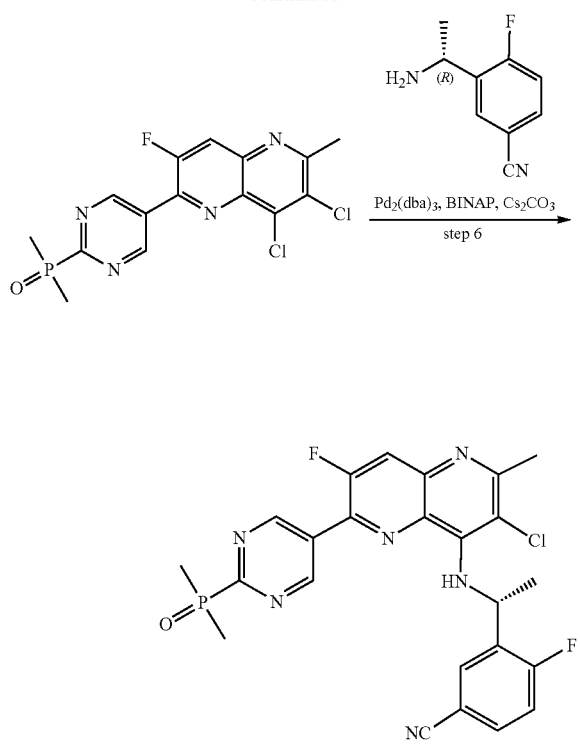

Preparation 1A: ethyl (2Z)-3-[(6-bromo-5-fluoro-pyridin-3-yl)amino]but-2-enoate

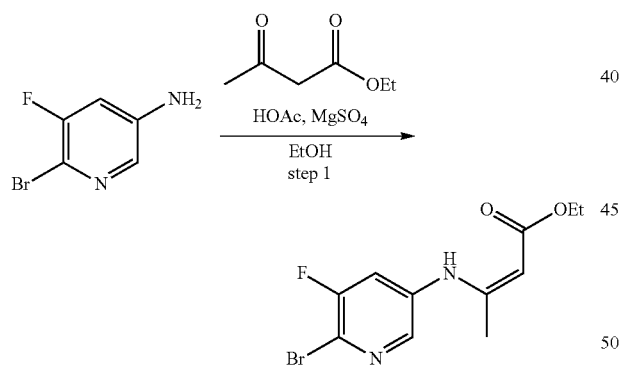

A solution of 6-bromo-5-fluoropyridin-3-amine (10.00 g, 52.355 mmol), ethyl acetoacetate (10.22 g, 78.532 mmol), acetic acid (0.31 g, 5.236 mmol) and MgSO₄ (12.60 g, 104.710 mmol) in EtOH (100 mL) was stirred for 3 days at 80° C. under nitrogen atmosphere. The resulting mixture was concentrated under reduced pressure. The residue was purified by silica gel column chromatography, eluted with PE/EA (3/1), to afford ethyl (2Z)-3-[(6-bromo-5-fluoropyridin-3-yl)amino]but-2-enoate (4.40 g, 28%) as a white solid. MS ESI calculated for C$_{11}$H$_{12}$BrFN$_2$O$_2$[M+H]$^+$, 303.01 305.01, found 303.00 305.00. $^1$H NMR (400 MHz, chloroform-d) δ 10.58 (s, 1H), 8.10-7.97 (m, 1H), 7.23-7.10 (m, 1H), 4.86 (s, 1H), 4.27-4.12 (m, 2H), 2.08 (s, 3H), 1.39-1.20 (m, 3H).

Preparation 1B: 6-bromo-7-fluoro-2-methyl-1,5-naphthyridin-4-ol

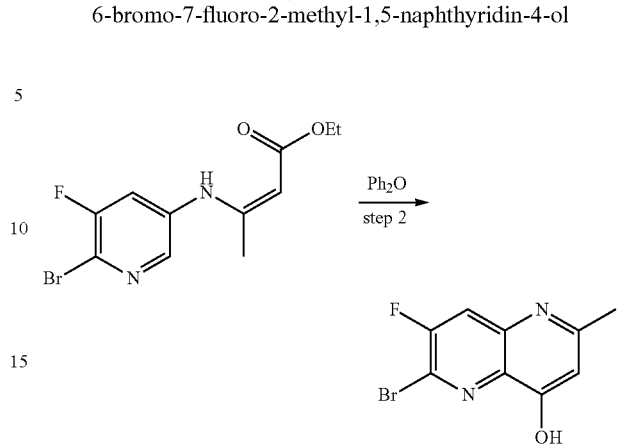

A solution of ethyl (2Z)-3-[(6-bromo-5-fluoropyridin-3-yl)amino]but-2-enoate (4.20 g, 13.855 mmol) in diphenylether (40 mL) was stirred for 2 h at 250° C. under air atmosphere. The mixture was allowed to cool down to room temperature. The precipitated solids were collected by filtration and washed with ethyl ether (2×50 mL). The resulting solid was dried under vacuum. This resulted in 6-bromo-7-fluoro-2-methyl-1,5-naphthyridin-4-ol (1.80 g, 51%) as a brown solid. MS ESI calculated for C$_9$H$_6$BrFN$_2$O [M+H]$^+$, 256.96 258.96 found 257.05 259.00. $^1$H NMR (400 MHz, DMSO-d6) δ 11.92 (s, 1H), 7.81 (d, J=8.4 Hz, 1H), 6.13 (s, 1H), 2.35 (s, 3H).

Preparation 1C: 6-bromo-3-chloro-7-fluoro-2-methyl-1,5-naphthyridin-4-ol

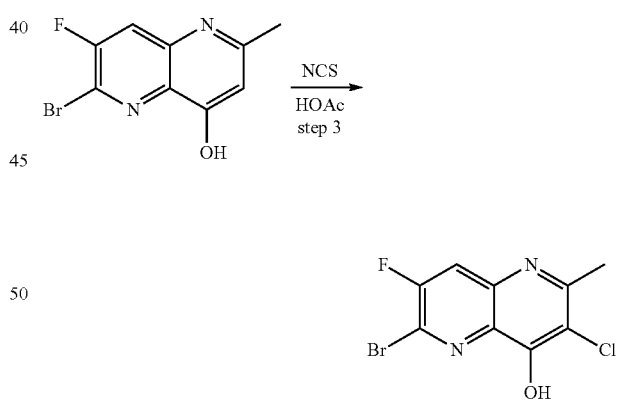

A solution of 6-bromo-7-fluoro-2-methyl-1,5-naphthyridin-4-ol (1.84 g, 7.158 mmol) and NCS (1.05 g, 7.874 mmol) in HOAc (20 mL) was stirred for 3 h at 65° C. under nitrogen atmosphere. The precipitated solids were collected by filtration and washed with water (3×20 mL). The resulting solid was dried under vacuum to give 6-bromo-3-chloro-7-fluoro-2-methyl-1,5-naphthyridin-4-ol (1.66 g, 80%) as a grey solid. MS ESI calculated for C$_9$H$_5$BrClFN$_2$O [M+H]$^+$ 290.93 292.93, found 290.95 292.95. $^1$H NMR (400 MHz, DMSO-d6) δ 12.50 (s, 1H), 7.88 (d, J=8.1 Hz, 1H), 2.53 (s, 3H).

Preparation 1D: 6-bromo-3,4-dichloro-7-fluoro-2-methyl-1,5-naphthyridine

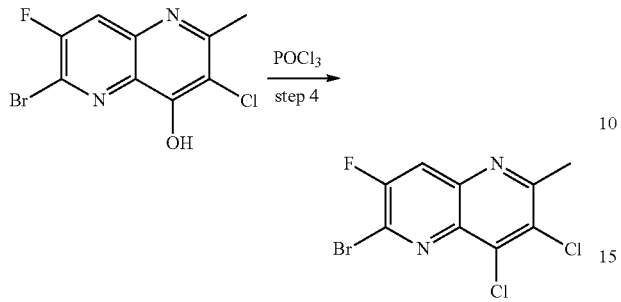

A solution of 6-bromo-3-chloro-7-fluoro-2-methyl-1,5-naphthyridin-4-ol (1.60 g, 5.489 mmol) in phosphorus oxychloride (15 mL) was stirred for 2 h at 105° C. under nitrogen atmosphere. The mixture was allowed to cool down to room temperature. The resulting mixture was concentrated under reduced pressure. The residue was dissolved in water (100 mL) and the mixture was neutralized to pH 6 with NaOH (1 N). The precipitated solids were collected by filtration and washed with water (2×10 mL). The residue was purified by silica gel column chromatography, eluted with PE/EA (3/1), to afford 6-bromo-3,4-dichloro-7-fluoro-2-methyl-1,5-naphthyridine (1.16 g, 68%) as a yellow solid. $^1$H NMR (400 MHz, chloroform-d) δ 8.03 (d, J=7.9 Hz, 1H), 2.87 (s, 3H).

Preparation 1E: 3,4-dichloro-6-[2-(dimethylphosphoryl)pyrimidin-5-yl]-7-fluoro-2-methyl-1,5-naphthyridine

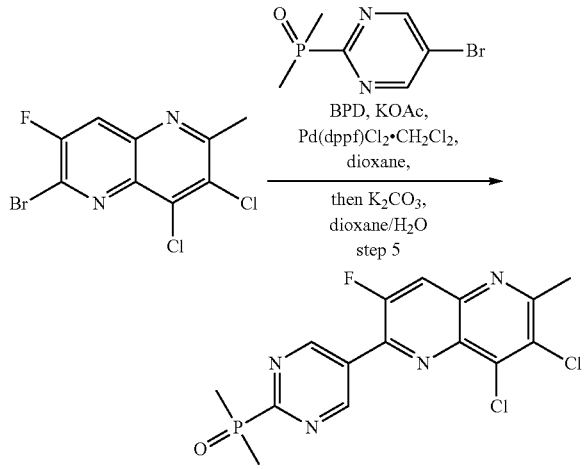

A solution of 5-bromo-2-(dimethylphosphoryl)pyrimidine (190 mg, 0.806 mmol), bis(pinacolato)diboron (328 mg, 1.290 mmol), potassium acetate (127 mg, 1.290 mmol) and Pd(dppf)Cl$_2$·CH$_2$Cl$_2$ (68 mg, 0.084 mmol) in 1,4-dioxane (8 mL) was stirred for 3 h at 80° C. under nitrogen atmosphere. After cooling to room temperature, to the above mixture was added 6-bromo-3,4-dichloro-7-fluoro-2-methyl-1,5-naphthyridine (200 mg, 0.645 mmol), potassium carbonate (225 mg, 1.613 mmol) and water (1.6 mL). The reaction mixture was stirred for additional 4 h at 100° C. The resulting mixture was concentrated under reduced pressure. The residue was purified by silica gel column chromatography, eluted with CH$_2$Cl$_2$/MeOH (10/1) to afford 3,4-dichloro-6-[2-(dimethylphosphoryl)pyrimidin-5-yl]-7-fluoro-2-methyl-1,5-naphthyridine (45 mg, 18%) as a yellow solid. MS ESI calculated for C$_{15}$H$_{12}$Cl$_2$FN$_4$OP [M+H]$^+$ 385.01 387.01, found 385.15 387.15. $^1$H NMR (300 MHz, Chloroform-d) δ 9.68 (d, J=1.3 Hz, 2H), 8.17 (d, J=11.0 Hz, 1H), 2.92 (s, 3H), 1.98 (s, 3H), 1.93 (s, 3H).

Example 1: 3-[(1R)-1-({3-chloro-6-[2-(dimethylphosphoryl)pyrimidin-5-yl]-7-fluoro-2-methyl-1,5-naphthyridin-4-yl}amino)ethyl]-4-fluorobenzonitrile

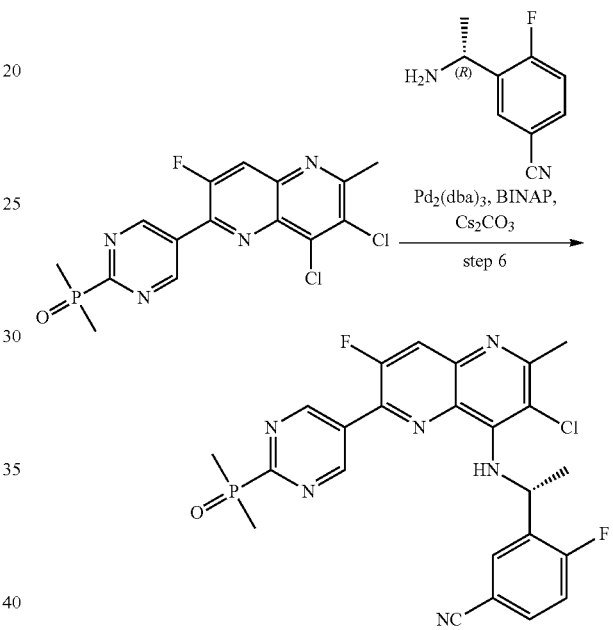

A solution of 3,4-dichloro-6-[2-(dimethylphosphoryl)pyrimidin-5-yl]-7-fluoro-2-methyl-1,5-naphthyridine (40 mg, 0.104 mmol), 3-[(1R)-1-aminoethyl]-4-fluorobenzonitrile (20 mg, 0.125 mmol), Pd$_2$(dba)$_3$ (9 mg, 0.010 mmol), BINAP (13 mg, 0.021 mmol) and Cs$_2$CO$_3$ (50 mg, 0.156 mmol) in toluene (2 mL) was stirred for 4 h at 100° C. under nitrogen atmosphere. The resulting mixture was concentrated under reduced pressure. The residue was purified by silica gel column chromatography, eluted with CH$_2$Cl$_2$/MeOH (10/1) to afford crude product. The residue was purified by reversed-phase flash chromatography: C18 silica gel; ACN in Water (10 mmol/L NH$_4$HCO$_3$), 40% to 50% gradient in 10 min; detector, UV 254 nm. The desired fractions were collected and concentrated to give 3-[(1R)-1-({3-chloro-6-[2-(dimethylphosphoryl)pyrimidin-5-yl]-7-fluoro-2-methyl-1,5-naphthyridin-4-yl}amino)ethyl]-4-fluorobenzonitrile (11 mg, 22%). MS ESI calculated for C$_{24}$H$_{20}$ClF$_2$N$_6$OP [M+H]$^+$ 513.11 515.11, found 513.00 515.00. $^1$H NMR (400 MHz, DMSO-d$_6$) δ 9.39 (d, J=1.4 Hz, 2H), 8.23 (d, J=11.6 Hz, 1H), 8.06-8.01 (m, 1H), 7.80-7.75 (m, 1H), 7.31-7.24 (m, 1H), 7.04 (d, J=8.5 Hz, 1H), 6.36-6.27 (m, 1H), 2.65 (s, 3H), 1.88 (s, 3H), 1.85 (s, 3H), 1.66 (d, J=6.8 Hz, 3H). $^{19}$F NMR (377 MHz, DMSO-d$_6$) δ −109.63 (1F), −121.08 (1F). $^{31}$P NMR (162 MHz, DMSO-d$_6$) δ 34.37.

Example 2: 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile

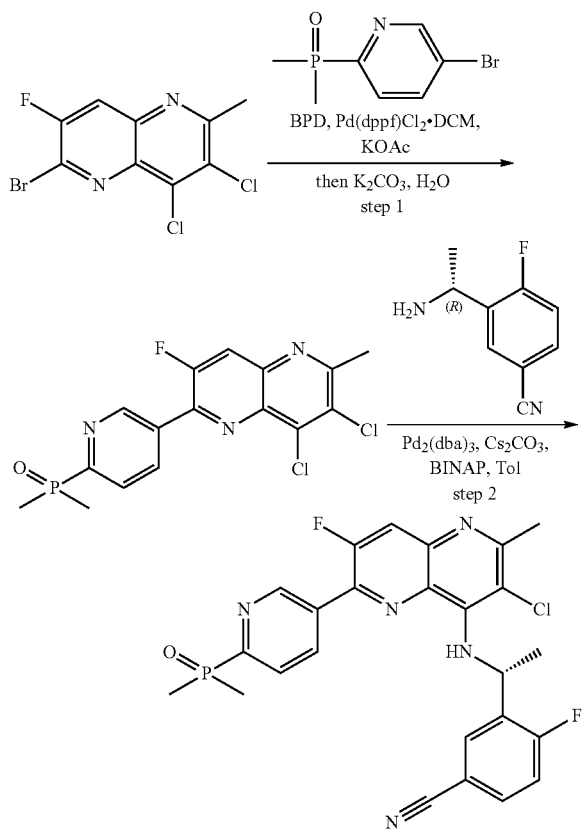

Preparation 2A: 4-dichloro-6-[6-(dimethylphosphoryl)pyridin-3-yl]-7-fluoro-2-methyl-1,5-naphthyridine

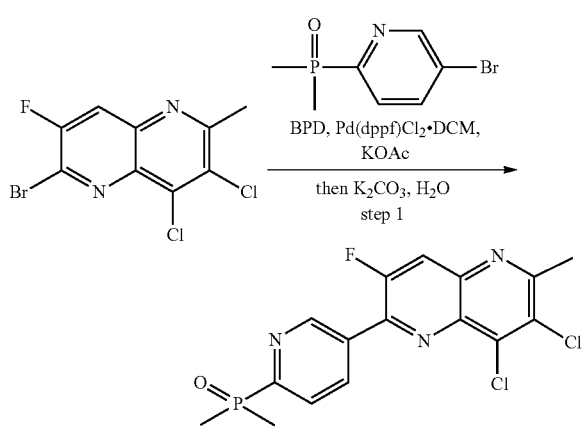

To a stirred solution of bis(pinacolato)diboron (196 mg, 0.774 mmol), 5-bromo-2-(dimethylphosphoryl)pyridine (226 mg, 0.968 mmol) and AcOK (126 mg, 1.290 mmol) in 1,4-dioxane (8 mL) was added Pd(dppf)Cl$_2$·CH$_2$Cl$_2$ (52 mg, 0.065 mmol) at room temperature under nitrogen atmosphere. The resulting mixture was stirred for 1 h at 80° C. under nitrogen atmosphere. The mixture was allowed to cool down to room temperature. To the above mixture was added 6-bromo-3,4-dichloro-7-fluoro-2-methyl-1,5-naphthyridine (200 mg, 0.645 mmol), K$_2$CO$_3$ (267 mg, 1.935 mmol) and H$_2$O (2 mL) under nitrogen atmosphere. The resulting mixture was stirred for additional 2 h at 100° C., and then concentrated under vacuum. The residue was purified by silica gel column chromatography (CH$_2$Cl$_2$/MeOH, 10:1) to afford 3,4-dichloro-6-[6-(dimethylphosphoryl)pyridin-3-yl]-7-fluoro-2-methyl-1,5-naphthyridine (150 mg, 60%) as a light brown solid. MS ESI calculated for C$_{16}$H$_{13}$Cl$_2$FN$_3$OP [M+H]$^+$, 384.02 386.02 found 384.25 386.25. $^1$H NMR (300 MHz, Chloroform-d) δ 9.58 (s, 1H), 8.66 (d, J=7.0 Hz, 1H), 8.41-8.27 (m, 1H), 8.14 (d, J=11.0 Hz, 1H), 2.92 (s, 3H), 1.90 (s, 3H), 1.86 (s, 3H).

Example 2: 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile

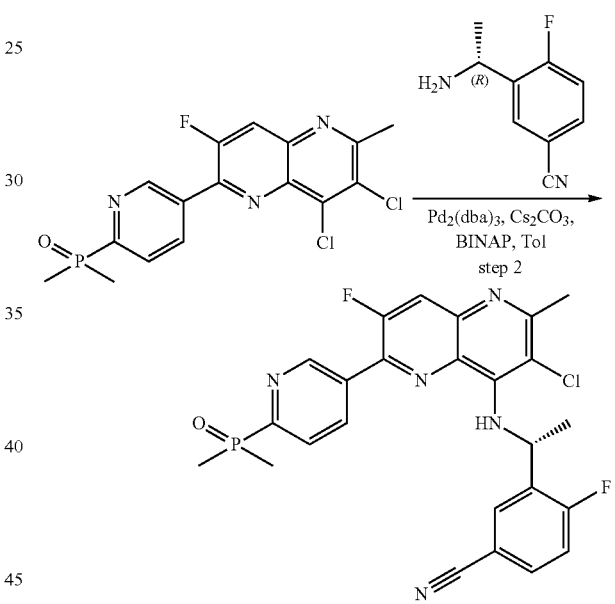

To a stirred solution of 3,4-dichloro-6-[6-(dimethylphosphoryl)pyridin-3-yl]-7-fluoro-2-methyl-1,5-naphthyridine (100 mg, 0.260 mmol), 3-[(1R)-1-aminoethyl]-4-fluorobenzonitrile (51 mg, 0.312 mmol), Cs$_2$CO$_3$ (127 mg, 0.390 mmol) and BINAP (32 mg, 0.052 mmol) in toluene (3 mL) was added Pd$_2$(dba)$_3$ (24 mg, 0.026 mmol) at room temperature under nitrogen atmosphere. The resulting mixture was stirred for 3 h at 100° C. under nitrogen atmosphere. The resulting mixture was concentrated under vacuum. The residue was purified by silica gel column chromatography (CH$_2$Cl$_2$/MeOH, 10:1) to give crude product. The residue was purified by reversed-phase flash chromatography: C18 silica gel; mobile phase, ACN in Water (10 mmol/L NH$_4$HCO$_3$), 10% to 50% gradient in 10 min; detector, UV 254 nm. This desired fractions were collected and concentrated to give 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile (88 mg, 66%). MS ESI calculated for C$_{25}$H$_{21}$ClF$_2$N$_5$OP [M+H]$^+$ 512.11 514.11, found 512.05 514.05. $^1$H NMR (300 MHz, Chloroform-d) δ

9.24 (s, 1H), 8.35-8.26 (m, 2H), 8.15-8.00 (m, 1H), 7.62-7.51 (m, 2H), 7.15-7.03 (m, 1H), 6.46-6.38 (m, 2H), 2.79 (s, 3H), 1.92 (s, 3H), 1.87 (s, 3H), 1.75 (d, J=6.2 Hz, 3H). $^{19}$F NMR (282 MHz, chloroform-d) δ −108.55 (1F), −120.41 (1F). $^{31}$P NMR (121 MHz, chloroform-d) δ 36.67 (1P).

Example 3: 3-[(1R)-1-({3-chloro-6-[4-(dimethylphosphoryl)phenyl]-7-fluoro-2-methyl-1,5-naphthyridin-4-yl}amino)ethyl]-4-fluorobenzonitrile

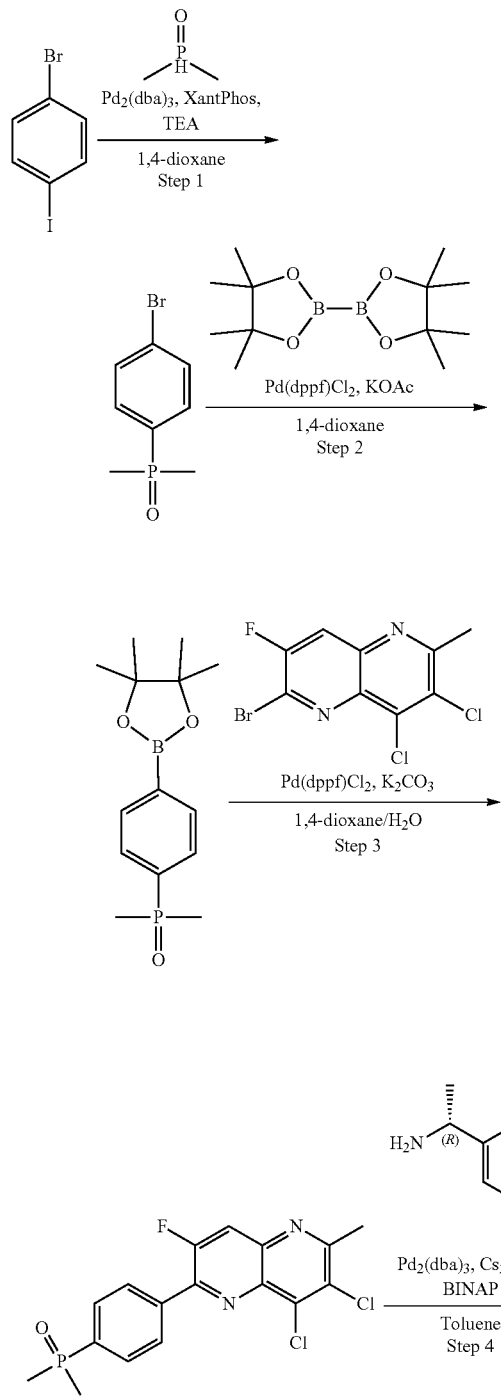

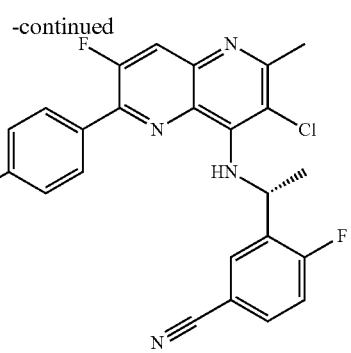

Preparation 3A:
1-bromo-4-(dimethylphosphoryl)benzene

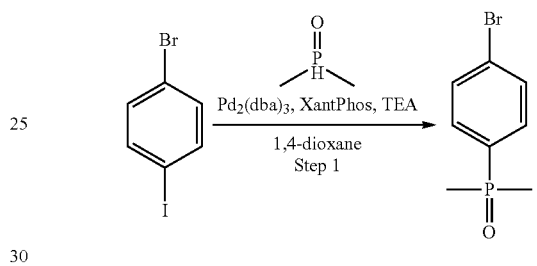

A mixture of Xantphos (2.05 g, 3.535 mmol) and TEA (4.29 g, 42.416 mmol) in 1,4-dioxane was treated with Pd$_2$(dba)$_3$ (1.76 g, 1.922 mmol) for 10 min at room temperature under nitrogen atmosphere followed by the addition of 4-bromoiodobenzene (10.00 g, 35.347 mmol) and (methylphosphonoyl)methane (2.76 g, 35.347 mmol) at room temperature. The resulting mixture was stirred for 2 h at 100° C. under nitrogen atmosphere. The resulting mixture was filtered, and the filter cake was washed with CH$_2$Cl$_2$ (3×20 mL). The filtrate was concentrated under reduced pressure. The residue was purified by silica gel column chromatography, eluted with CH$_2$Cl$_2$/MeOH (10:1) to afford 1-bromo-4-(dimethylphosphoryl)benzene (5.70 g, 69%) as a brown oil. MS ESI calculated for C$_8$H$_{10}$BrOP [M+H]$^+$, 232.97 234.97, found 233.00 235.00. $^1$H NMR (300 MHz, Chloroform-d) δ 7.76-7.51 (m, 4H), 1.74 (s, 3H), 1.70 (s, 3H).

Preparation 3B: 2-[4-(dimethylphosphoryl)phenyl]-4,4,5,5-tetramethyl-1,3,2-dioxaborolane

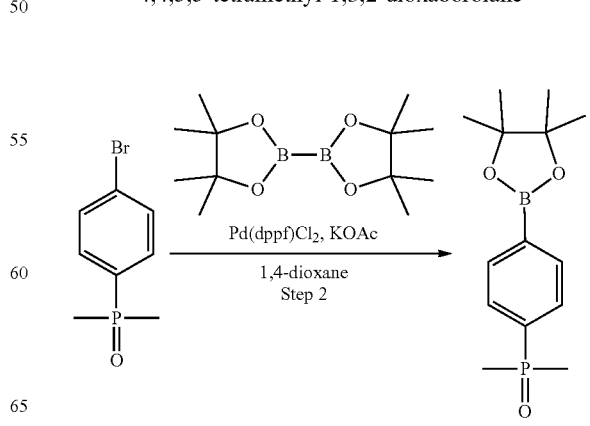

To a stirred mixture of 1-bromo-4-(dimethylphosphoryl)benzene (1.56 g, 6.720 mmol), BPD (2.22 g, 8.736 mmol) and KOAc (1.98 g, 20.160 mmol) in 1,4-dioxane (15 mL) was added Pd(dppf)Cl$_2$·CH$_2$Cl$_2$ (0.55 g, 0.672 mmol) at room temperature under nitrogen atmosphere. The resulting mixture was stirred for 2 h at 60° C. under nitrogen atmosphere. The resulting mixture was concentrated under reduced pressure. The residue was purified by silica gel column chromatography, eluted with CH$_2$Cl$_2$/MeOH (10:1) to afford 2-[4-(dimethylphosphoryl)phenyl]-4,4,5,5-tetramethyl-1,3,2-dioxaborolane (1.50 g, 79%) as a yellow oil. MS ESI calculated for C$_{14}$H$_{22}$BO$_3$P [M+H]$^+$, 281.14, found 281.40.

Preparation 3C: 3,4-dichloro-6-[4-(dimethylphosphoryl)phenyl]-7-fluoro-2-methyl-1,5-naphthyridine

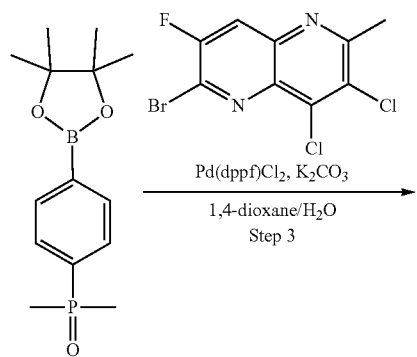

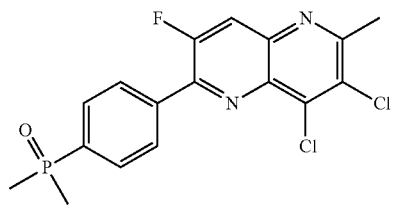

To a stirred mixture of 6-bromo-3,4-dichloro-7-fluoro-2-methyl-1,5-naphthyridine (150 mg, 0.484 mmol) and 2-[4-(dimethylphosphoryl)phenyl]-4,4,5,5-tetramethyl-1,3,2-dioxaborolane (176 mg, 0.629 mmol) in 1,4-dioxane (2 mL) were added H$_2$O (0.5 mL), K$_2$CO$_3$ (133 mg, 0.968 mmol) and Pd(dppf)Cl$_2$·CH$_2$Cl$_2$ (39 mg, 0.048 mmol) at room temperature under nitrogen atmosphere. The resulting mixture was stirred for 3 h at 80° C. under nitrogen atmosphere. The resulting mixture was concentrated under reduced pressure. The residue was purified by silica gel column chromatography, eluted with CH$_2$Cl$_2$/MeOH (9:1) to afford 3,4-dichloro-6-[4-(dimethylphosphoryl)phenyl]-7-fluoro-2-methyl-1,5-naphthyridine (130 mg, 70%) as a red solid. MS ESI calculated for C$_{17}$H$_{14}$Cl$_2$FN$_2$OP [M+H]$^+$, 383.02, found 383.30. $^1$H NMR (300 MHz, Chloroform-d) δ 8.38-8.28 (m, 2H), 8.10 (d, J=11.1 Hz, 1H), 8.01-7.88 (m, 2H), 2.91 (s, 3H), 1.84 (s, 3H), 1.80 (s, 3H).

Example 3: 3-[(1R)-1-({3-chloro-6-[4-(dimethylphosphoryl)phenyl]-7-fluoro-2-methyl-1,5-naphthyridin-4-yl}amino)ethyl]-4-fluorobenzonitrile

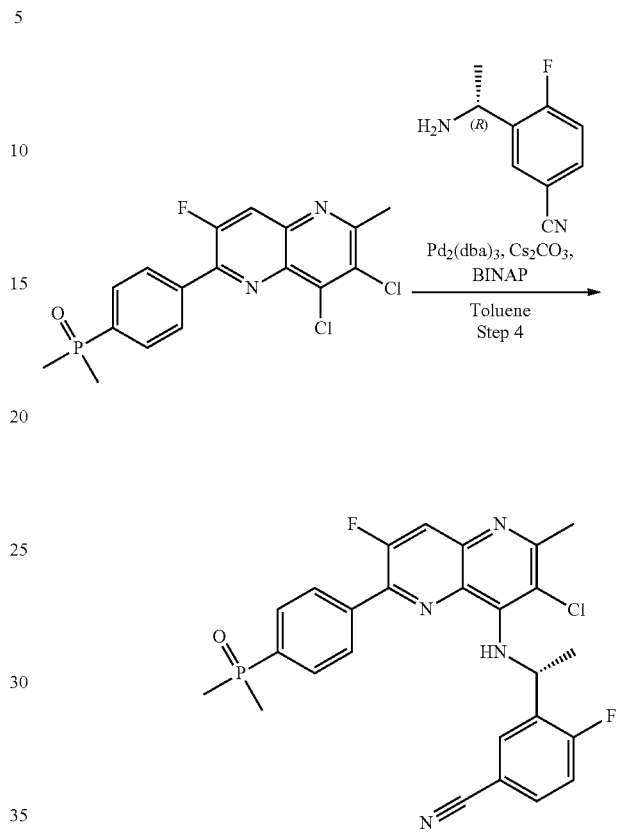

To a stirred mixture of 3,4-dichloro-6-[4-(dimethylphosphoryl)phenyl]-7-fluoro-2-methyl-1,5-naphthyridine (100 mg, 0.261 mmol) and 3-[(1R)-1-aminoethyl]-4-fluorobenzonitrile (51 mg, 0.313 mmol) in Toluene (2 mL) were added BINAP (32 mg, 0.052 mmol), Cs$_2$CO$_3$ (255 mg, 0.783 mmol) and Pd$_2$(dba)$_3$ (24 mg, 0.026 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% FA), Mobile Phase B: CH$_3$CN; Flow rate: 60 mL/min; Gradient: 30 B to 50 B in 40 min; 254/220 nm to afford 3-[(1R)-1-({3-chloro-6-[4-(dimethylphosphoryl)phenyl]-7-fluoro-2-methyl-1,5-naphthyridin-4-yl}amino)ethyl]-4-fluorobenzonitrile (30 mg, 22%) as a white solid. MS ESI calculated for C$_{26}$H$_{22}$ClF$_2$N$_4$OP [M+H]$^+$, 511.12, found 511.05. $^1$H NMR (300 MHz, DMSO-d$_6$) δ 8.18-8.12 (m, 1H), 8.02-7.97 (m, 1H), 7.95-7.91 (m, 2H), 7.90-7.85 (m, 2H), 7.82-7.77 (m, 1H), 7.36-7.31 (m, 1H), 6.89 (d, J=8.6 Hz, 1H), 6.40 (t, J=7.5 Hz, 1H), 2.64 (d, J=1.4 Hz, 3H), 1.76 (s, 3H), 1.71 (s, 3H), 1.66 (d, J=6.8 Hz, 3H). $^{19}$F NMR (282 MHz, DMSO-d$_6$) δ −108.86, −120.67. $^{31}$P NMR (122 MHz, DMSO-d$_6$) δ 32.40.

Example 4: 3-chloro-6-[4-(dimethylphosphoryl)-3-fluorophenyl]-7-fluoro-N-[(1R)-1-(3-fluoropyridin-2-yl)propyl]-2-methyl-1,5-naphthyridin-4-amine

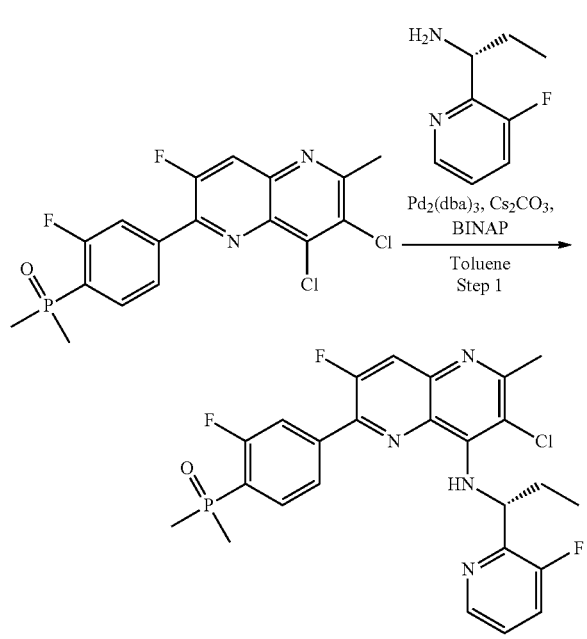

To a solution of 3,4-dichloro-6-[4-(dimethylphosphoryl)-3-fluorophenyl]-7-fluoro-2-methyl-1,5-naphthyridine (50 mg, 0.125 mmol), BINAP (16 mg, 0.025 mmol) and (1R)-1-(3-fluoropyridin-2-yl)propan-1-amine (21 mg, 0.138 mmol) in Toluene (1 mL) were added $Cs_2CO_3$ (61 mg, 0.188 mmol) and $Pd_2(dba)_3$ (11 mg, 0.013 mmol). After stirring for 16 h at 100° C. under a nitrogen atmosphere. The resulting mixture was filtered, and the filter cake was washed with MeOH (3×5 mL). The filtrate was concentrated under reduced pressure. The residue was purified by reversed-phase flash chromatography with the following conditions: column, C18 silica gel; mobile phase, $CH_3CN$ in water (10 mmol/L $NH_4HCO_3$), 40% to 70% gradient in 30 min; detector, 254 nm. This resulted in 3-chloro-6-[4-(dimethylphosphoryl)-3-fluorophenyl]-7-fluoro-N-[(1R)-1-(3-fluoropyridin-2-yl)propyl]-2-methyl-1,5-naphthyridin-4-amine (11 mg, 17%) as a yellow solid. MS ESI calculated for $C_{25}H_{23}ClF_3N_4OP$ $[M+H]^+$, 519.13, found 519.00. $^1H$ NMR (400 MHz, Chloroform-d) δ 8.58-8.51 (m, 1H), 8.23-8.14 (m, 3H), 8.05-7.97 (m, 1H), 7.50-7.42 (m, 1H), 7.36-7.29 (m, 1H), 6.88-6.61 (m, 2H), 2.81 (s, 3H), 2.18-1.99 (m, 2H), 1.91 (s, 3H), 1.88 (s, 3H), 0.84-0.76 (m, 3H). $^{19}F$ NMR (377 MHz, Chloroform-d) δ −75.72, −105.59, −126.24. $^{31}P$ NMR (162 MHz, Chloroform-d) δ 30.43.

Example 5: 3-[(1R)-1-({3-chloro-6-[6-(dimethylphosphoryl)pyridin-3-yl]-2-methylquinolin-4-yl}amino)ethyl]-4-fluorobenzonitrile

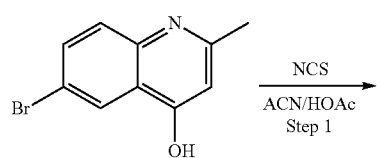

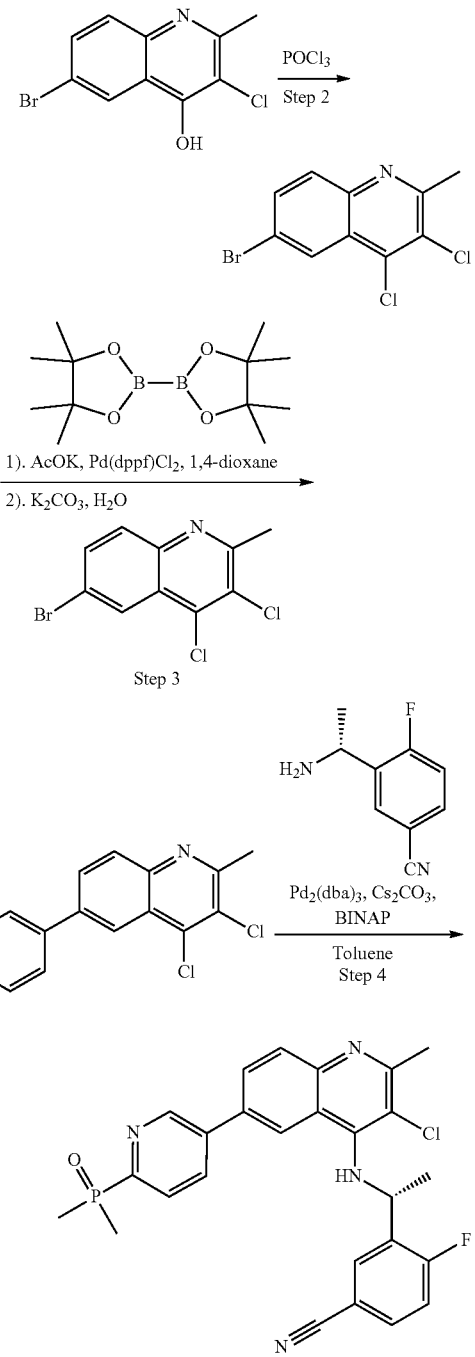

Preparation 5A: 6-bromo-3-chloro-2-methylquinolin-4-ol

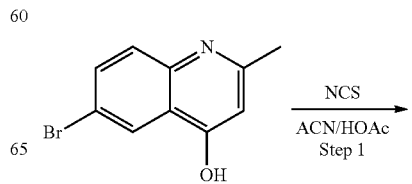

-continued

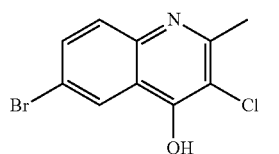

A solution of 6-bromo-2-methylquinolin-4-ol (5.30 g, 22.261 mmol) and NCS (3.12 g, 23.374 mmol) in HOAc (10 mL) and ACN (200 mL) was stirred for 6 h at 80° C. under nitrogen atmosphere. The precipitated solids were collected by filtration and washed with ACN (3×50 mL). The resulting solid was dried under vacuum. This resulted in 6-bromo-3-chloro-2-methylquinolin-4-ol (5.20 g, 86%) as a white solid. MS ESI calculated for $C_{10}H_7BrClNO$ [M+H]$^+$, 271.94 273.94, found 272.00 274.00. $^1$H NMR (400 MHz, DMSO-$d_6$) δ 12.28 (s, 1H), 8.18 (d, J=2.4 Hz, 1H), 7.84-7.80 (m, 1H), 7.53 (d, J=8.8 Hz, 1H), 2.52 (s, 3H).

Preparation 5B:
6-bromo-3,4-dichloro-2-methylquinoline

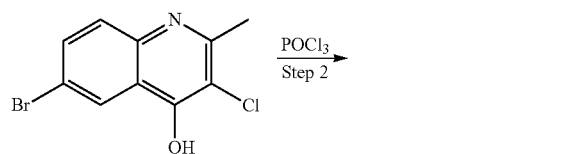

A solution of 6-bromo-3-chloro-2-methylquinolin-4-ol (4.70 g, 17.246 mmol) in POCl$_3$ (20 mL) was stirred for 3 h at 100° C. under nitrogen atmosphere. The resulting mixture was concentrated under reduced pressure. The residue was dissolved in water/ice (100 mL). The mixture was basified to pH 10 with (2 M) aq. NaOH at 0° C. The precipitated solids were collected by filtration and washed with water (2×20 mL). The residue was purified by silica gel column chromatography, eluted with PE/EA (10:1) to afford 6-bromo-3,4-dichloro-2-methylquinoline (4.90 g, 98%) as a yellow solid. MS ESI calculated for $C_{10}H_6BrCl_2N$ [M+H]$^+$, 289.91 291.91, found 290.10 292.10. $^1$H NMR (400 MHz, Chloroform-d) δ 8.29 (d, J=2.1 Hz, 1H), 7.88 (d, J=9.0 Hz, 1H), 7.78-7.77 (m, 1H), 2.83 (s, 3H).

Preparation 5C: 3,4-dichloro-6-[6-(dimethylphosphoryl)pyridin-3-yl]-2-methylquinoline

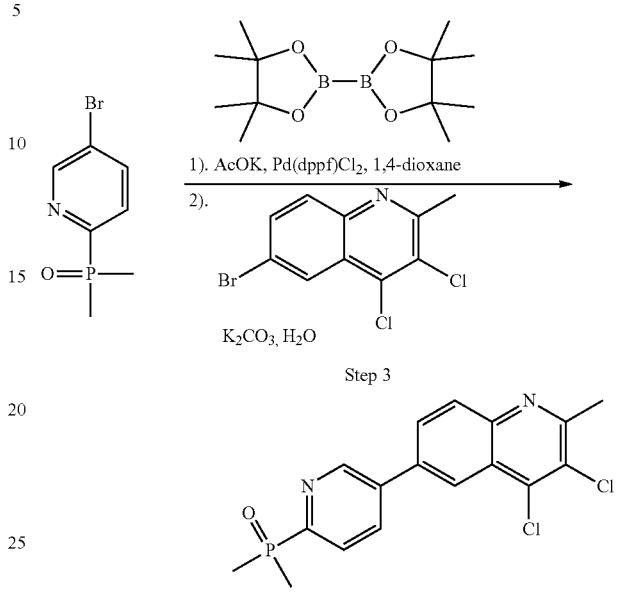

To a stirred mixture of 5-bromo-2-(dimethylphosphoryl)pyridine (198 mg, 0.846 mmol), bis(pinacolato)diboron (145 mg, 0.571 mmol) and KOAc (101 mg, 1.029 mmol) in 1,4-dioxane (4 mL) was added Pd(dppf)Cl$_2$·CH$_2$Cl$_2$ (42 mg, 0.052 mmol) at room temperature under nitrogen atmosphere. The resulting mixture was stirred for 2 h at 80° C. To the above mixture were added 6-bromo-3,4-dichloro-2-methylquinoline (150 mg, 0.516 mmol), H$_2$O (1 mL) and K$_2$CO$_3$ (214 mg, 1.548 mmol) at room temperature under nitrogen atmosphere. The resulting mixture was stirred for 12 h at 80° C. under nitrogen atmosphere. The resulting mixture was concentrated under vacuum. The residue was purified by silica gel column chromatography, eluted with CH$_2$Cl$_2$/MeOH (10:1) to afford 3,4-dichloro-6-[6-(dimethylphosphoryl)pyridin-3-yl]-2-methylquinoline (180 mg, 95%) as a brown solid. MS ESI calculated for $C_{17}H_{15}Cl_2N_2OP$ [M+H]$^+$, 365.03, found 365.00. $^1$H NMR (300 MHz, Chloroform-d) δ 9.12 (s, 1H), 8.38 (d, J=1.8 Hz, 1H), 8.28 (s, 1H), 8.17 (d, J=8.7 Hz, 2H), 7.98 (d, J=8.7, 2.0 Hz, 1H), 3.49 (s, 3H), 2.89 (s, 3H), 1.24 (s, 3H).

Example 5: 3-[(1R)-1-({3-chloro-6-[6-(dimethylphosphoryl)pyridin-3-yl]-2-methylquinolin-4-yl}amino)ethyl]-4-fluorobenzonitrile

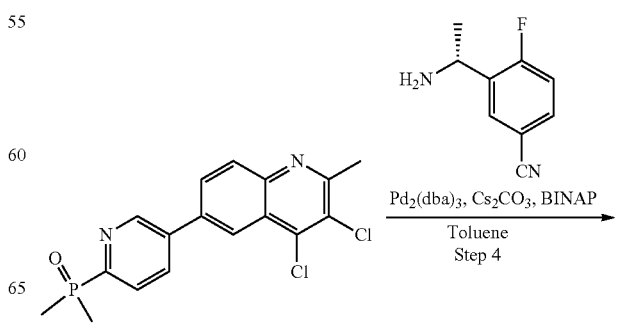

-continued

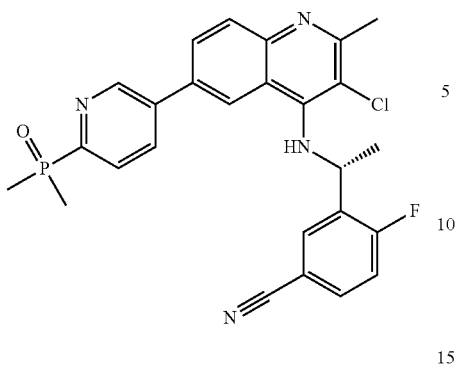

To a stirred solution of 3,4-dichloro-6-[6-(dimethylphosphoryl)pyridin-3-yl]-2-methylquinoline (94 mg, 0.257 mmol), 3-[(1R)-1-aminoethyl]-4-fluorobenzonitrile (51 mg, 0.308 mmol), $Cs_2CO_3$ (126 mg, 0.386 mmol) and BINAP (32 mg, 0.051 mmol) in toluene (1 mL) was added $Pd_2(dba)_3$ (23.57 mg, 0.026 mmol) at room temperature under nitrogen atmosphere. The resulting mixture was stirred for 12 h at 100° C. under nitrogen atmosphere. The resulting mixture was concentrated under vacuum. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in water (10 mmol/L $NH_4HCO_3$), 10% to 50% gradient in 30 min; detector, 254 nm. This resulted in 3-[(1R)-1-({3-chloro-6-[6-(dimethylphosphoryl)pyridin-3-yl]-2-methylquinolin-4-yl}amino)ethyl]-4-fluorobenzonitrile (40 mg, 32%) as a white solid. MS ESI calculated for $C_{26}H_{23}ClFN_4OP$ $[M+H]^+$, 493.13, found 493.05. $^1H$ NMR (300 MHz, Chloroform-d) δ 8.87 (d, J=2.1 Hz, 1H), 8.19-8.07 (m, 2H), 7.96-7.76 (m, 4H), 7.70-7.60 (m, 1H), 7.24-7.15 (m, 1H), 5.39-5.28 (m, 1H), 5.22-5.09 (m, 1H), 2.81 (s, 3H), 1.85 (s, 3H), 1.80 (s, 3H), 1.72 (d, J=6.6 Hz, 3H). $^{19}F$ NMR (282 MHz, Chloroform-d) δ –108.66. $^{31}P$ NMR (122 MHz, Chloroform-d) δ 36.67.

Example 6: 3-[(1R)-1-({3-chloro-6-[2-(dimethylphosphoryl)pyrimidin-5-yl]-2-methylquinolin-4-yl}amino)ethyl]-4-fluorobenzonitrile

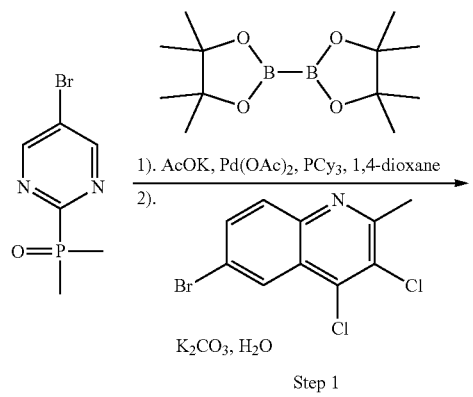

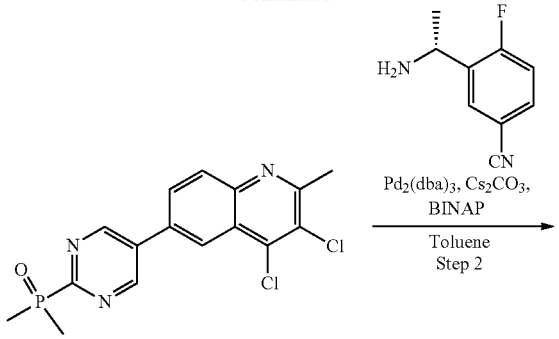

Preparation 6A: 3,4-dichloro-6-[2-(dimethylphosphoryl)pyrimidin-5-yl]-2-methylquinoline

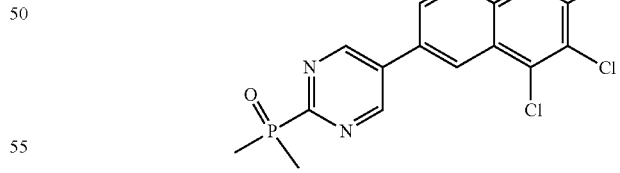

To a stirred mixture of 5-bromo-2-(dimethylphosphoryl)pyrimidine (182 mg, 0.774 mmol), KOAc (142 mg, 1.445 mmol) and $PCy_3$ (22 mg, 0.077 mmol) in 1,4-dioxane (5 mL) was added $Pd(OAc)_2$ (17 mg, 0.077 mmol) at room temperature. The resulting mixture was stirred for 1 h at 100° C. under nitrogen atmosphere. To the above mixture were added 6-bromo-3,4-dichloro-2-methylquinoline (150 mg, 0.516 mmol), $K_2CO_3$ (178 mg, 1.290 mmol) and $H_2O$ (1 mL) at room temperature. The resulting mixture was stirred for additional 4 h at 70° C. The resulting mixture was concentrated under vacuum. The residue was purified by silica gel column chromatography, eluted with $CH_2Cl_2$/MeOH (9/1) followed by reversed-phase flash chromatography with the following conditions: column, C18 silica gel; mobile phase, $CH_3CN$ in water (10 mmol/L $NH_4HCO_3$), 35% to 50% gradient in 30 min; detector, 254 nm. This resulted in 3,4-dichloro-6-[2-(dimethylphosphoryl)pyrimidin-5-yl]-2-methylquinoline (89 mg, 47%) as a white solid. MS ESI calculated for $C_{16}H_{14}Cl_2N_3OP$ $[M+H]^+$, 366.03. found 366.20. $^1H$ NMR (400 MHz, Chloroform-d) δ 9.23 (s, 2H), 8.43-8.35 (m, 2H), 8.01 (d, J=8.4 Hz, 1H), 2.97 (s, 3H), 1.96 (d, J=13.6 Hz, 6H).

Example 6: 3-[(1R)-1-({3-chloro-6-[2-(dimethylphosphoryl)pyrimidin-5-yl]-2-methylquinolin-4-yl}amino)ethyl]-4-fluorobenzonitrile

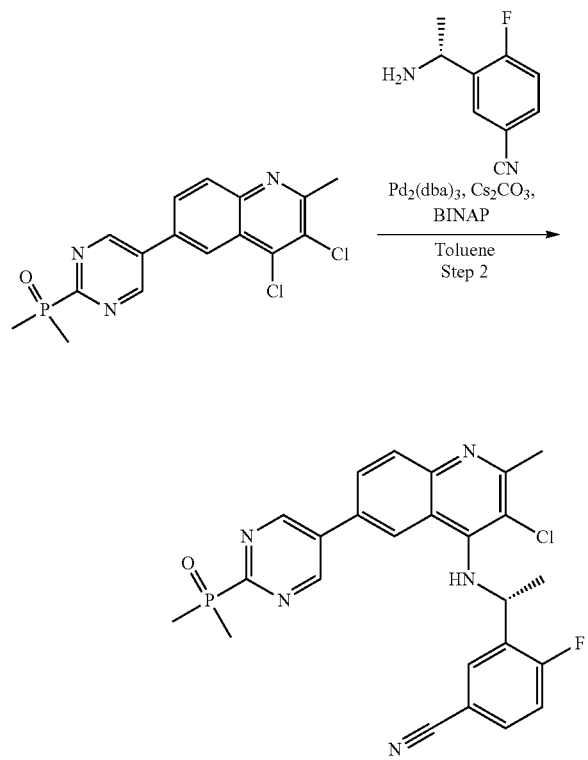

To a stirred mixture of 3,4-dichloro-6-[2-(dimethylphosphoryl)pyrimidin-5-yl]-2-methylquinoline (70 mg, 0.191 mmol), 3-[(1R)-1-aminoethyl]-4-fluorobenzonitrile (38 mg, 0.229 mmol), BINAP (24 mg, 0.038 mmol) and $Cs_2CO_3$ (124.57 mg, 0.382 mmol) in Toluene (2 mL) was added $Pd_2(dba)_3$ (18 mg, 0.019 mmol) at room temperature under nitrogen atmosphere. The resulting mixture was stirred for 4 h at 110° C. under nitrogen atmosphere. The resulting mixture was concentrated under vacuum. The residue was purified by silica gel column chromatography, eluted with $CH_2Cl_2$/MeOH (9/1) followed by reversed-phase flash chromatography with the following conditions: column, C18 silica gel; mobile phase, $CH_3CN$ in water (10 mmol/L $NH_4HCO_3$), 10% to 50% gradient in 30 min; detector, 254 nm. This resulted in 3-[(1R)-1-({3-chloro-6-[2-(dimethylphosphoryl)pyrimidin-5-yl]-2-methylquinolin-4-yl}amino)ethyl]-4-fluorobenzonitrile (36 mg, 38%) as a white solid. MS ESI calculated for $C_{25}H_{22}ClFN_5OP$ $[M+H]^+$, 494.12, found 494.10. $^1H$ NMR (400 MHz, Chloroform-d) δ 8.97 (s, 2H), 8.13 (d, J=8.8 Hz, 1H), 8.00 (s, 1H), 7.91-7.80 (m, 2H), 7.69-7.60 (m, 1H), 7.26-7.20 (m, 1H), 5.33 (d, J=8.0 Hz, 1H), 5.20 (s, 1H), 2.81 (s, 3H), 1.94 (d, J=13.6 Hz, 6H), 1.72 (d, J=6.6 Hz, 3H). $^{19}F$ NMR (377 MHz, Chloroform-d) δ −108.75. $^{31}P$ NMR (162 MHz, Chloroform-d) δ 35.75.

Example 7: 3-chloro-6-[2-(dimethylphosphoryl)pyrimidin-5-yl]-7-fluoro-N-[(1R)-1-(2-fluorophenyl)ethyl]-2-methyl-1,5-naphthyridin-4-amine

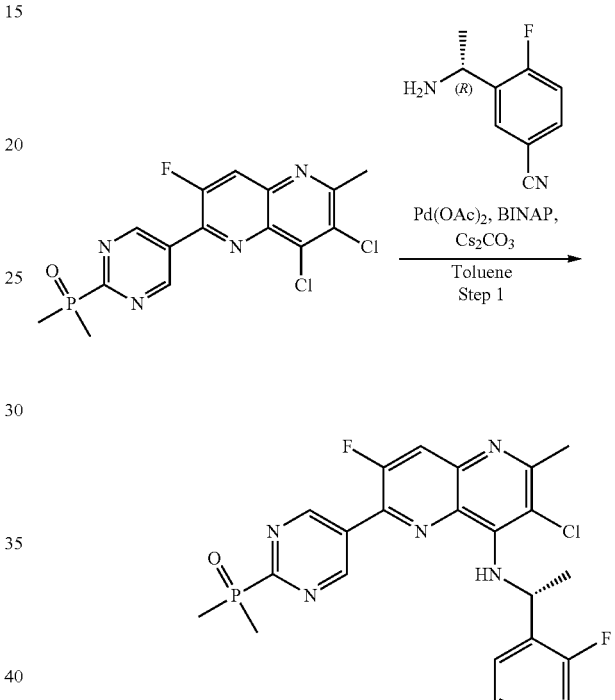

A mixture of 3,4-dichloro-6-[2-(dimethylphosphoryl)pyrimidin-5-yl]-7-fluoro-2-methyl-1,5-naphthyridine (80 mg, 0.208 mmol), (1R)-1-(2-fluorophenyl)ethanamine (35 mg, 0.250 mmol), $Pd(OAc)_2$ (5 mg, 0.021 mmol), BINAP (13 mg, 0.021 mmol) and $Cs_2CO_3$ (203 mg, 0.624 mmol) in Toluene (1 mL) was stirred for 2 h at 100° C. under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 50% to 60% gradient in 10 min; detector, 254 nm. This resulted in 3-chloro-6-[2-(dimethylphosphoryl)pyrimidin-5-yl]-7-fluoro-N-[(1R)-1-(2-fluorophenyl)ethyl]-2-methyl-1,5-naphthyridin-4-amine (36 mg, 36%) as a yellow solid. MS ESI calculated for $C_{23}H_{21}ClF_2N_5OP$ $[M+H]^+$, 488.11, found 488.05. $^1H$ NMR (400 MHz, DMSO-$d_6$) δ 9.47-9.42 (m, 2H), 8.24 (d, J=11.6 Hz, 1H), 7.46-7.40 (m, 1H), 7.26-7.18 (m, 1H), 7.13-7.01 (m, 2H), 7.00-6.94 (m, 1H), 6.46-6.36 (m, 1H), 2.63 (s, 3H), 1.88 (s, 3H), 1.84 (s, 3H), 1.67 (d, J=6.8 Hz, 3H). $^{19}F$ NMR (377 MHz, DMSO-$d_6$) δ −119.50, −120.99. $^{31}P$ NMR (162 MHz, DMSO-$d_6$) δ 34.39.

Example 8: 3-[(1R)-1-({3-chloro-6-[2-(dimethylphosphoryl)pyrimidin-5-yl]-7-fluoro-2-methylquinolin-4-yl}amino)ethyl]-4-fluorobenzonitrile

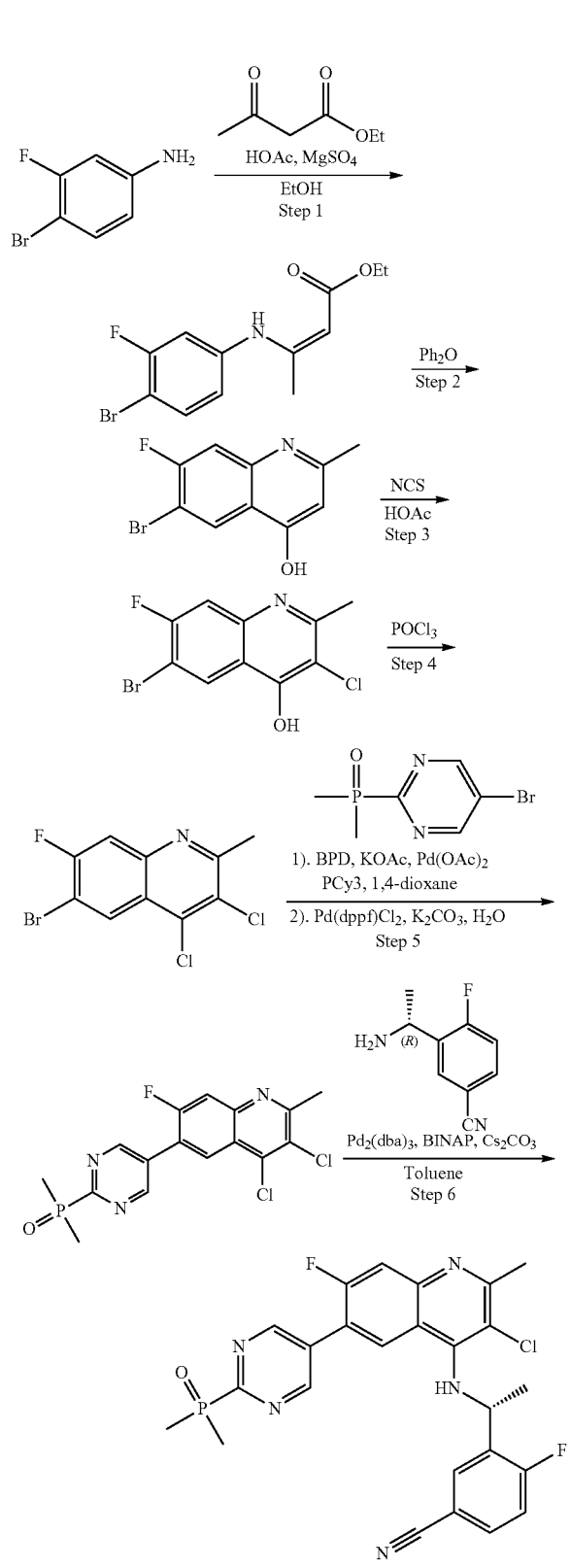

Preparation 8A: ethyl (2Z)-3-[(4-bromo-3-fluorophenyl)amino]but-2-enoate

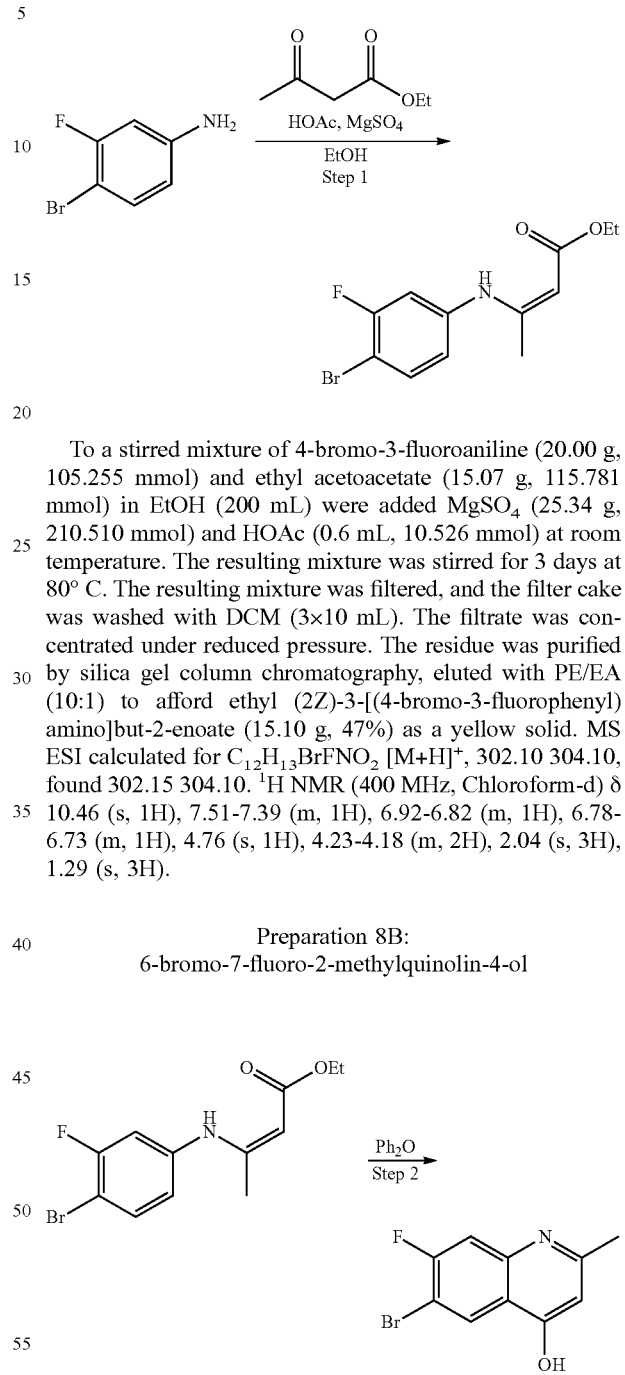

To a stirred mixture of 4-bromo-3-fluoroaniline (20.00 g, 105.255 mmol) and ethyl acetoacetate (15.07 g, 115.781 mmol) in EtOH (200 mL) were added MgSO$_4$ (25.34 g, 210.510 mmol) and HOAc (0.6 mL, 10.526 mmol) at room temperature. The resulting mixture was stirred for 3 days at 80° C. The resulting mixture was filtered, and the filter cake was washed with DCM (3×10 mL). The filtrate was concentrated under reduced pressure. The residue was purified by silica gel column chromatography, eluted with PE/EA (10:1) to afford ethyl (2Z)-3-[(4-bromo-3-fluorophenyl)amino]but-2-enoate (15.10 g, 47%) as a yellow solid. MS ESI calculated for C$_{12}$H$_{13}$BrFNO$_2$ [M+H]$^+$, 302.10 304.10, found 302.15 304.10. $^1$H NMR (400 MHz, Chloroform-d) δ 10.46 (s, 1H), 7.51-7.39 (m, 1H), 6.92-6.82 (m, 1H), 6.78-6.73 (m, 1H), 4.76 (s, 1H), 4.23-4.18 (m, 2H), 2.04 (s, 3H), 1.29 (s, 3H).

Preparation 8B: 6-bromo-7-fluoro-2-methylquinolin-4-ol

A solution of ethyl (2Z)-3-[(4-bromo-3-fluorophenyl)amino]but-2-enoate (17.00 g, 56.265 mmol) in diphenylether (150 mL) was stirred for 1 h at 250° C. The precipitated solids were collected by filtration and washed with Et$_2$O (3×50 mL). This resulted in 6-bromo-7-fluoro-2-methylquinolin-4-ol (11.00 g, 76%) as a brown solid. The crude product was used in the next step directly. MS ESI calculated for C$_{10}$H$_7$BrFNO [M+H]$^+$, 255.97, 257.97, found 256.10, 258.10.

Preparation 8C: 6-bromo-3-chloro-7-fluoro-2-methylquinolin-4-ol

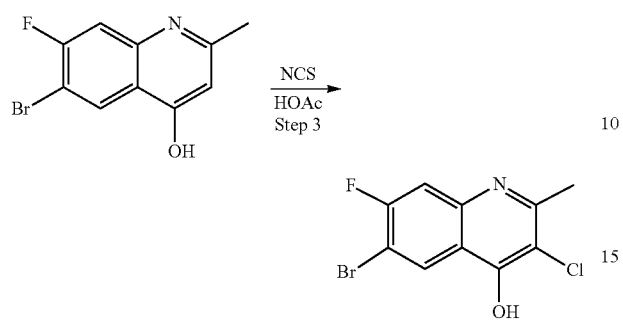

A solution of 6-bromo-7-fluoro-2-methylquinolin-4-ol (6.00 g, 23.431 mmol) and NCS (4.70 g, 35.147 mmol) in HOAc (120 mL) was stirred for 3 h at 65° C. The precipitated solids were collected by filtration and washed with water (3×20 mL). The resulting solid was dried under vacuum. This resulted in 6-bromo-3-chloro-7-fluoro-2-methylquinolin-4-ol (3.90 g, 57%) as a brown solid. MS ESI calculated for $C_{10}H_6BrClFNO$ [M+H]$^+$, 289.93 291.93, found 289.95 292.00.

Preparation 8D: 6-bromo-3,4-dichloro-7-fluoro-2-methylquinoline

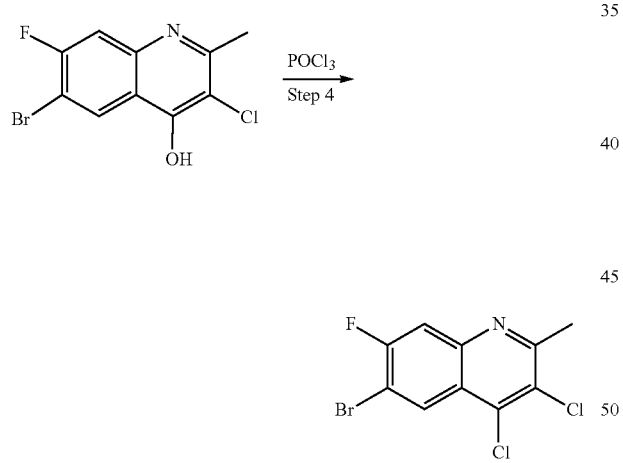

A solution of 6-bromo-3-chloro-7-fluoro-2-methylquinolin-4-ol (3.90 g, 13.424 mmol) in phosphorus oxychloride (39 mL) was stirred for 2 h at 100° C. The reaction was quenched with Water/Ice at 0° C. The residue was basified to pH 8 with saturated $Na_2CO_3$ (aq.). The aqueous layer was extracted with EtOAc (3×100 mL). The resulting mixture was concentrated under reduced pressure. The residue was purified by silica gel column chromatography, eluted with PE/EA (20:1) to afford 6-bromo-3,4-dichloro-7-fluoro-2-methylquinoline (1.30 g, 31%) as a white solid. MS ESI calculated for $C_{10}H_5BrCl_2FN$ [M+H]$^+$, 307.90 309.89, found 307.90 309.95. $^1$H NMR (300 MHz, Chloroform-d) δ 8.40 (d, J=7.2 Hz, 1H), 7.74 (d, J=9.1 Hz, 1H), 2.83 (s, 3H).

Preparation 8E: 3,4-dichloro-6-[2-(dimethylphosphoryl)pyrimidin-5-yl]-7-fluoro-2-methylquinoline

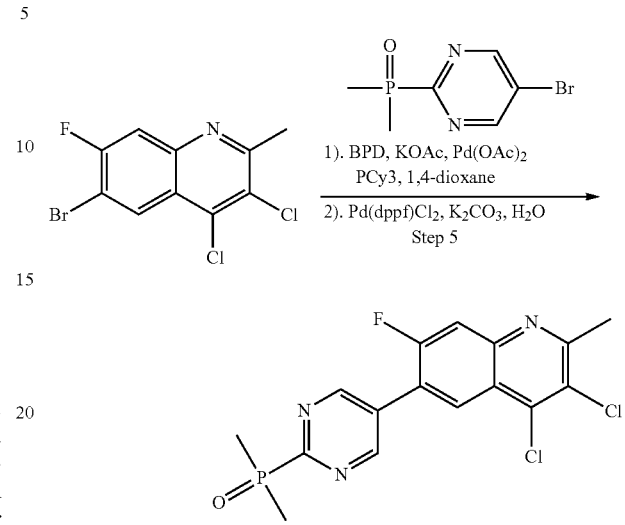

To a stirred solution of 5-bromo-2-(dimethylphosphoryl)pyrimidine (449 mg, 1.912 mmol) and BPD (728 mg, 2.869 mmol) in 1,4-dioxane (10 mL) were added KOAc (375 mg, 3.825 mmol), PCy$_3$ (107 mg, 0.382 mmol) and Pd(OAc)$_2$ (43 mg, 0.191 mmol) at room temperature. The resulting mixture was stirred for overnight at 80° C. under nitrogen atmosphere. To the above mixture was added 6-bromo-3-chloro-7-fluoro-2-methylquinoline (350 mg, 1.275 mmol), H$_2$O (2 mL), K$_2$CO$_3$ (352 mg, 2.550 mmol) and Pd(dppf)Cl$_2$·CH$_2$Cl$_2$ (104 mg, 0.128 mmol) in portions over 10 min at room temperature. The resulting mixture was stirred for additional 3 h at 100° C. The resulting mixture was concentrated under reduced pressure. The residue was purified by silica gel column chromatography, eluted with CH$_2$Cl$_2$/MeOH (10:1) to afford 3,4-dichloro-6-[2-(dimethylphosphoryl)pyrimidin-5-yl]-7-fluoro-2-methylquinoline (257 mg, 52%) as a yellow solid. MS ESI calculated for $C_{16}H_{13}Cl_2FN_3OP$ [M+H]$^+$, 384.02, 386.01, found 384.00, 386.00. $^1$H NMR (300 MHz, Chloroform-d) δ 9.19 (s, 2H), 8.26 (d, J=7.8 Hz, 1H), 7.86 (d, J=11.1 Hz, 1H), 2.89 (s, 3H), 1.97 (d, J=12.7 Hz, 6H).

Example 8: 3-[(1R)-1-({3-chloro-6-[2-(dimethylphosphoryl)pyrimidin-5-yl]-7-fluoro-2-methylquinolin-4-yl}amino)ethyl]-4-fluorobenzonitrile

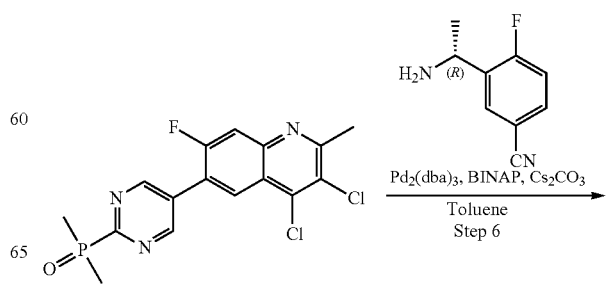

-continued

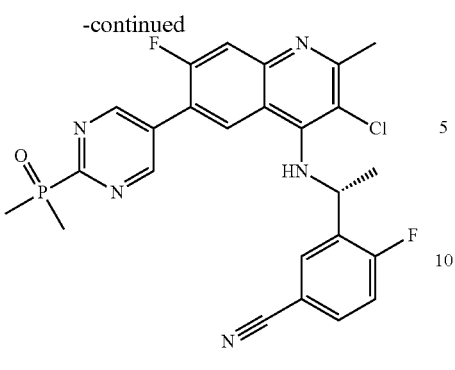

To a stirred solution of 3,4-dichloro-6-[2-(dimethylphosphoryl)pyrimidin-5-yl]-7-fluoro-2-methylquinoline (100 mg, 0.260 mmol) and 3-[(1R)-1-aminoethyl]-4-fluorobenzonitrile (51 mg, 0.312 mmol) in Toluene (3 mL) were added $Cs_2CO_3$ (127 mg, 0.390 mmol), BINAP (32 mg, 0.052 mmol) and $Pd_2(dba)_3$ (24 mg, 0.026 mmol) at room temperature. The resulting mixture was stirred for overnight at 100° C. under nitrogen atmosphere. The resulting mixture was concentrated under reduced pressure. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in water (10 mmol/L $NH_4HCO_3$), 30% to 60% gradient in 30 min; detector, 254 nm. This resulted in 3-[(1R)-1-({3-chloro-6-[2-(dimethylphosphoryl)pyrimidin-5-yl]-7-fluoro-2-methylquinolin-4-yl}amino)ethyl]-4-fluorobenzonitrile (56 mg, 41%) as a white solid. ESI calculated for $C_{25}H_{21}ClF_2N_5OP$ $[M+H]^+$, 512.11, found 512.10. $^1H$ NMR (400 MHz, DMSO-$d_6$) δ 9.28 (d, J=1.6 Hz, 2H), 8.47 (d, J=8.0 Hz, 1H), 8.22-8.15 (m, 1H), 7.87-7.74 (m, 2H), 7.42-7.31 (m, 1H), 6.57 (d, J=9.2 Hz, 1H), 5.65-5.53 (m, 1H), 2.62 (s, 3H), 1.86 (s, 3H), 1.83 (s, 3H), 1.64 (d, J=6.7 Hz, 3H). $^{19}F$ NMR (377 MHz, DMSO-$d_6$) δ −109.89, −116.14. $^{31}P$ NMR (162 MHz, DMSO-$d_6$) δ 34.14.

Example 9: 3-[(1R)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile Synthetic Scheme

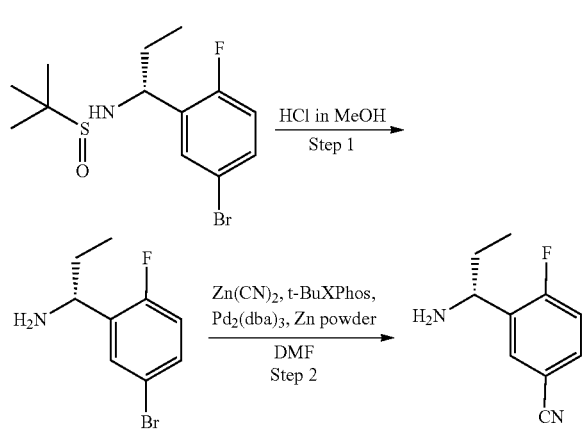

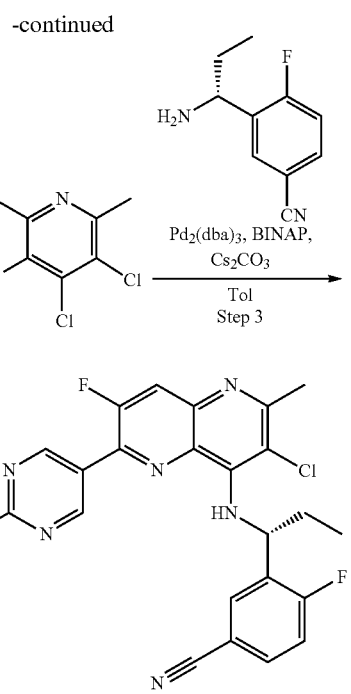

Preparation 9A: (1R)-1-(5-bromo-2-fluorophenyl)propan-1-amine

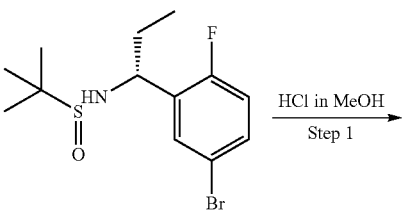

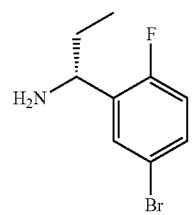

A solution of (S)—N-[(1R)-1-(5-bromo-2-fluorophenyl)propyl]-2-methylpropane-2-sulfinamide (520 mg, 1.546 mmol) and HCl in MeOH (6 mL) was stirred for 1 h at room temperature. The resulting mixture was concentrated under reduced pressure. The residue was dissolved in DCM (3 mL). The mixture was basified to pH 10 with sat. $NaHCO_3$. The resulting mixture was washed with 3×10 mL of water. The organic layer was concentrated under reduced pressure. The residue was purified by silica gel column chromatography, eluted with $CH_2Cl_2$/MeOH (10/1) to afford (1R)-1-(5-bromo-2-fluorophenyl)propan-1-amine (310 mg, 86%) as a colorless oil. MS ESI calculated for $C_9H_{11}BrFN$ $[M+H]^+$, 232.01 234.01, found 232.05 234.05. $^1H$ NMR (400 MHz, Chloroform-d) δ 7.57-7.49 (m, 1H), 7.36-7.28 (m, 1H), 6.95-6.86 (m, 1H), 4.10 (t, J=6.9 Hz, 1H), 1.72-1.67 (m, 2H), 0.90 (t, J=7.4 Hz, 3H).

Preparation 9B: 3-[(1R)-1-aminopropyl]-4-fluorobenzonitrile

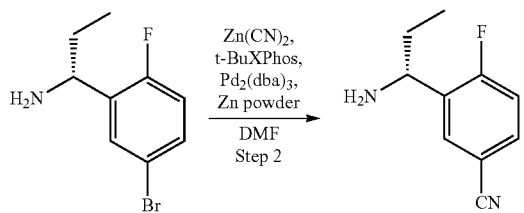

A mixture of (1R)-1-(5-bromo-2-fluorophenyl)propan-1-amine (300 mg, 1.293 mmol), Zn (169 mg, 2.586 mmol), Zn(CN)$_2$ (304 mg, 2.586 mmol), Pd$_2$(dba)$_3$ (118 mg, 0.129 mmol) and t-BuXPhos (110 mg, 0.259 mmol) in DMF (3 mL) was stirred for 1 h at 95° C. under nitrogen atmosphere. The resulting mixture was diluted with EtOAc (20 mL). The resulting mixture was washed with 3×10 mL of water. The organic layer was concentrated under reduced pressure. The residue was purified by silica gel column chromatography, eluted with CH$_2$Cl$_2$/PE (10/1) to afford 3-[(1R)-1-aminopropyl]-4-fluorobenzonitrile (150 mg, 65%) as a yellow oil. MS ESI calculated for C$_{10}$H$_{11}$FN$_2$ [M+H]$^+$, 179.09, found 179.21.

Example 9: 3-[(1R)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile

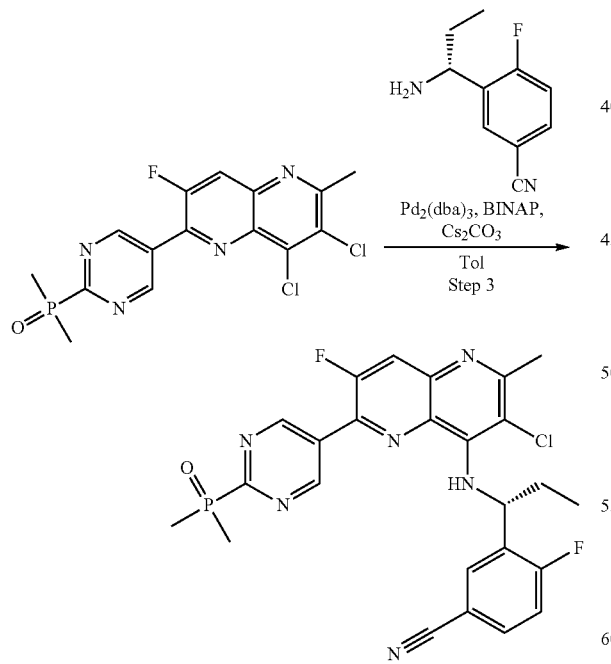

A solution of 3,4-dichloro-6-[2-(dimethylphosphoryl)pyrimidin-5-yl]-7-fluoro-2-methyl-1,5-naphthyridine (80 mg, 0.208 mmol), 3-[(1R)-1-aminopropyl]-4-fluorobenzonitrile (45 mg, 0.250 mmol), Pd$_2$(dba)$_3$ (19 mg, 0.021 mmol), BINAP (26 mg, 0.042 mmol) and Cs$_2$CO$_3$ (136 mg, 0.416 mmol) in Toluene (2 mL) was stirred for 2 h at 100° C. under nitrogen atmosphere. The resulting mixture was concentrated under reduced pressure. The residue was purified by silica gel column chromatography, eluted with CH$_2$Cl$_2$/MeOH followed by reversed-phase flash chromatography with the following conditions: column, C18 silica gel; mobile phase, CH$_3$CN in water (10 mmol/L NH$_4$HCO$_3$), 35% to 50% gradient in 20 min; detector, 254 nm. This resulted in 3-[(1R)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile (14 mg, 13%) as a yellow solid. MS ESI calculated for C$_{25}$H$_{22}$ClF$_2$N$_6$OP [M+H]$^+$, 527.12, found 526.90. $^1$H NMR (400 MHz, DMSO-d$_6$) δ 9.43-9.34 (m, 2H), 8.31-8.20 (m, 1H), 8.15-8.09 (m, 1H), 7.83-7.76 (m, 1H), 7.32-7.23 (m, 1H), 7.10-7.02 (m, 1H), 6.03-5.93 (m, 1H), 2.65 (s, 3H), 2.14-2.00 (m, 1H), 1.96-1.89 (m, 1H), 1.88 (s, 3H), 1.85 (s, 3H), 0.98 (t, J=7.3 Hz, 3H). $^{19}$F NMR (377 MHz, DMSO-d$_6$) δ −119.56, −121.01. $^{31}$P NMR (162 MHz, DMSO-d$_6$) δ 34.45.

Example 10: 3-[(1R)-1-({3-chloro-6-[6-(dimethylphosphoryl)pyridin-3-yl]-7-fluoro-2-methylquinolin-4-yl}amino)ethyl]-4-fluorobenzonitrile Synthetic Scheme

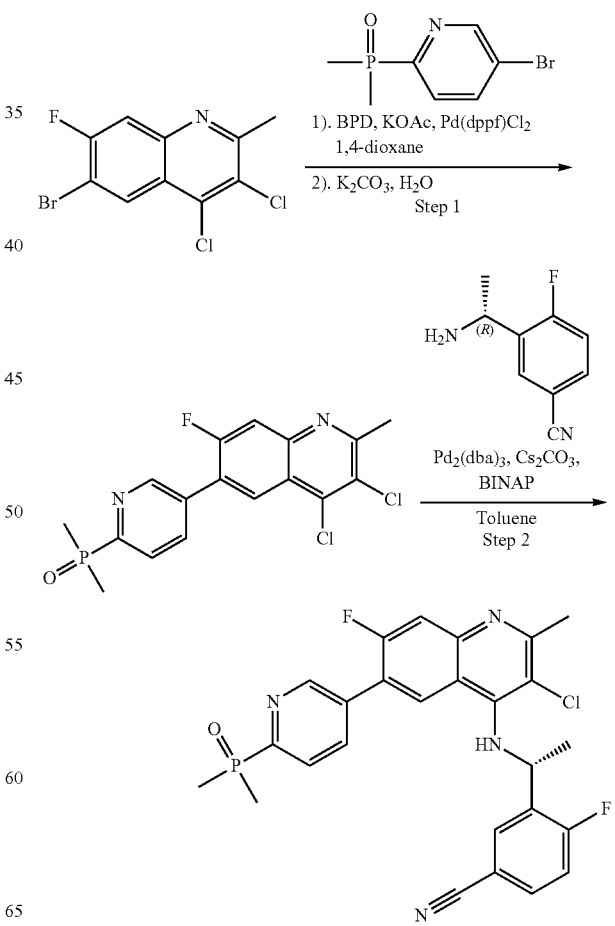

Preparation 10A: 3,4-dichloro-6-[6-(dimethylphosphoryl)pyridin-3-yl]-7-fluoro-2-methylquinoline

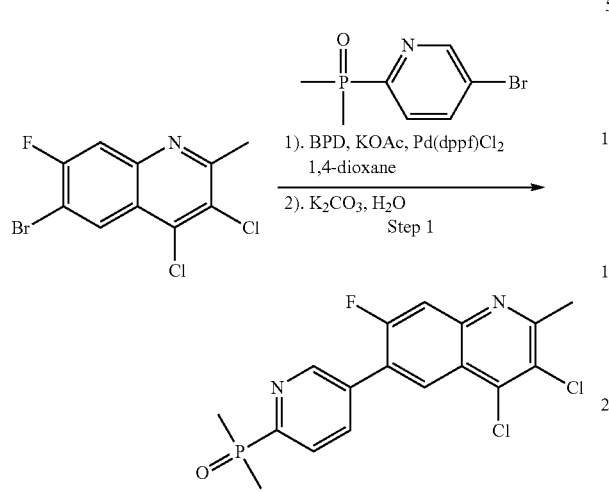

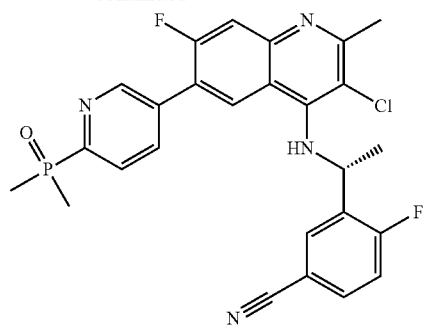

To a stirred solution of 5-bromo-2-(dimethylphosphoryl)pyridine (192 mg, 0.819 mmol) and BPD (277 mg, 1.092 mmol) in 1,4-dioxane (5 mL) were added Pd(dppf)Cl$_2$·CH$_2$Cl$_2$ (67 mg, 0.082 mmol) and KOAc (134 mg, 1.365 mmol) at room temperature under nitrogen atmosphere. The resulting mixture was stirred for 3 h at 100° C. under nitrogen atmosphere. To the above mixture were added K$_2$CO$_3$ (151 mg, 1.092 mmol), 6-bromo-3-chloro-7-fluoro-2-methylquinoline (150 mg, 0.546 mmol), H$_2$O (1 mL) at room temperature. The resulting mixture was stirred for additional 2 h at 80° C. under nitrogen atmosphere. The resulting mixture was concentrated under reduced pressure. The residue was purified by silica gel column chromatography, eluted with CH$_2$Cl$_2$/MeOH (10/1) to afford 3,4-dichloro-6-[6-(dimethylphosphoryl)pyridin-3-yl]-7-fluoro-2-methylquinoline (155 mg, 74%) as a yellow solid. MS ESI calculated for C$_{17}$H$_{14}$Cl$_2$FN$_2$OP [M+H]$^+$, 383.02 found 382.85. $^1$H NMR (400 MHz, Chloroform-d) δ 8.99 (d, J=2.0 Hz, 1H), 8.30-8.18 (m, 2H), 8.15-8.07 (m, 1H), 7.81 (d, J=11.2 Hz, 1H), 2.85 (s, 3H), 1.83 (d, J=13.6 Hz, 6H).

Example 10: 3-[(1R)-1-({3-chloro-6-[6-(dimethylphosphoryl)pyridin-3-yl]-7-fluoro-2-methylquinolin-4-yl}amino)ethyl]-4-fluorobenzonitrile To a stirred solution of 3,4-dichloro-6-[6-(dimethylphosphoryl)pyridin-3-yl]-7-fluoro-2-methylquinoline (150 mg, 0.391 mmol), BINAP (48.75 mg, 0.078 mmol) and 3-[(1R)-1-aminoethyl]-4-fluorobenzonitrile (77 mg, 0.469 mmol) in Toluene (5 mL) were added Cs$_2$CO$_3$ (191 mg, 0.587 mmol) and Pd(OAc)$_2$ (9 mg, 0.039 mmol) at room temperature under nitrogen atmosphere. The resulting mixture was stirred for 3 h at 110° C. under nitrogen atmosphere. The resulting mixture was concentrated under reduced pressure. The residue was purified by silica gel column chromatography, eluted with CH$_2$Cl$_2$/MeOH (10/1) followed by reversed-phase flash chromatography with the following conditions (column, C18 silica gel; mobile phase, CH$_3$CN in water (10 mmol/L NH$_4$HCO$_3$), 10% to 70% gradient in 25 min; detector, 254 nm) to afford 3-[(1R)-1-({3-chloro-6-[6-(dimethylphosphoryl)pyridin-3-yl]-7-fluoro-2-methylquinolin-4-yl}amino)ethyl]-4-fluorobenzonitrile (63 mg, 31%) as a white solid. MS ESI calculated for C$_{26}$H$_{22}$ClF$_2$N$_4$OP [M+H]$^+$, 511.12 found 511.05. $^1$H NMR (400 MHz, Chloroform-d) δ 8.82 (s, 1H), 8.19-8.11 (m, 1H), 7.91-7.68 (m, 4H), 7.66-7.59 (m, 1H), 7.22-7.13 (m, 1H), 5.31 (s, 1H), 5.15 (s, 1H), 2.79 (s, 3H), 1.83 (d, J=13.6 Hz, 6H), 1.71 (d, J=6.4 Hz, 3H). $^{19}$F NMR (376 MHz, Chloroform-d) δ −108.91, −114.75. $^{31}$P NMR (162 MHz, Chloroform-d) δ 36.58.

Example 11: 3-chloro-6-[2-(dimethylphosphoryl)pyrimidin-5-yl]-7-fluoro-N-[(1R)-1-(2-fluorophenyl)ethyl]-2-methylquinolin-4-amine

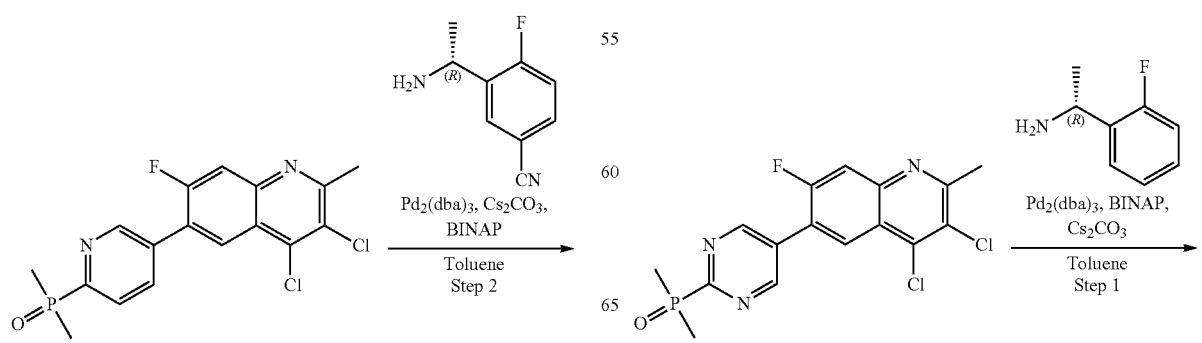

-continued

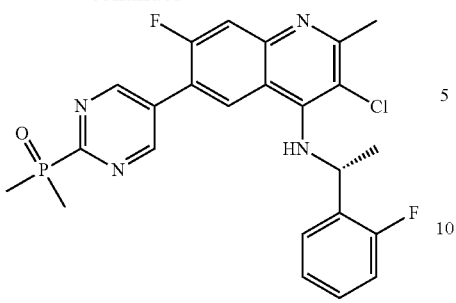

To a stirred solution of 3,4-dichloro-6-[2-(dimethylphosphoryl)pyrimidin-5-yl]-7-fluoro-2-methylquinoline (100 mg, 0.260 mmol) and (1R)-1-(2-fluorophenyl)ethanamine (43.47 mg, 0.312 mmol) in Toluene (2 mL) were added BINAP (32 mg, 0.052 mmol), Cs$_2$CO$_3$ (127 mg, 0.390 mmol) and Pd$_2$(dba)$_3$ (24 mg, 0.026 mmol) at room temperature under nitrogen atmosphere. The resulting mixture was stirred for overnight at 100° C. under nitrogen atmosphere. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 10% to 50% gradient in 30 min; detector, 254 nm. This resulted in 3-chloro-6-[2-(dimethylphosphoryl)pyrimidin-5-yl]-7-fluoro-N-[(1R)-1-(2-fluorophenyl)ethyl]-2-methylquinolin-4-amine (56 mg, 44%) as a white solid. MS ESI calculated for C$_{24}$H$_{22}$ClF$_2$N$_4$OP [M+H]$^+$, 487.12, found 487.10. $^1$H NMR (400 MHz, Chloroform-d) δ 8.90 (s, 2H), 8.01-7.95 (m, 1H), 7.82-7.70 (m, 1H), 7.44 (t, J=7.5 Hz, 1H), 7.30 (d, J=5.7 Hz, 2H), 7.20-7.12 (m, 1H), 7.08 (t, J=9.3 Hz, 1H), 5.42-5.25 (s, 1H), 2.79 (s, 3H), 1.96 (s, 3H), 1.92 (s, 3H), 1.70 (d, J=4.7 Hz, 3H). $^{19}$F NMR (376 MHz, Chloroform-d) δ -115.42, -119.07. $^{31}$P NMR (162 MHz, Chloroform-d) δ 34.70.

Example 12: 3-[(1R)-1-({3-chloro-6-[2-(dimethylphosphoryl)pyrimidin-5-yl]-7-fluoroquinolin-4-yl}amino)ethyl]-4-fluorobenzonitrile Synthetic Scheme

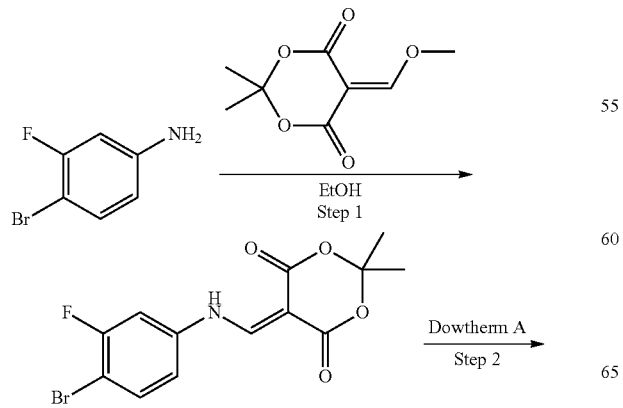

-continued

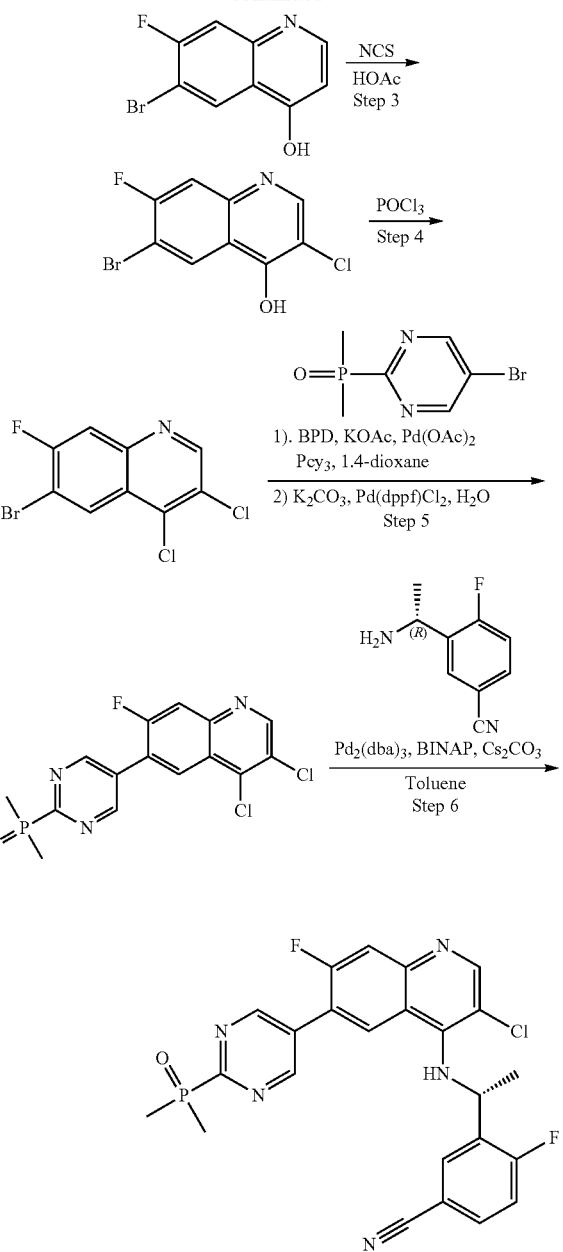

Preparation 12A: 5-{[(4-bromo-3-fluorophenyl)amino]methylidene}-2,2-dimethyl-1,3-dioxane-4,6-dione

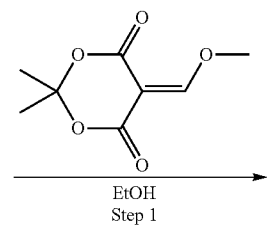

-continued

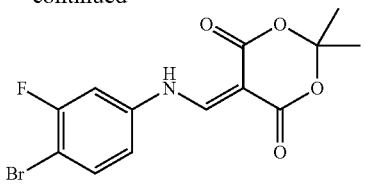

A solution of 4-bromo-3-fluoroaniline (20.00 g, 105.255 mmol) and 5-(methoxymethylidene)-2,2-dimethyl-1,3-dioxane-4,6-dione (23.51 g, 126.306 mmol) in EtOH (200 mL) was stirred for 3 h at 100° C. The mixture was allowed to cool down to room temperature. The resulting mixture was filtered, and the filter cake was washed with ethyl ether (3×50 mL). The filtrate was concentrated under reduced pressure to afford 5-{[(4-bromo-3-fluorophenyl)amino]methylidene}-2,2-dimethyl-1,3-dioxane-4,6-dione (33.00 g, 91%) as a light yellow solid. MS ESI calculated for $C_{13}H_{11}BrFNO_4$ [M+H]$^+$, 343.99 345.99, found 344.10 346.10. $^1$H NMR (300 MHz, Chloroform-d) δ 11.24 (d, J=14.0 Hz, 1H), 8.59 (d, J=14.0 Hz, 1H), 7.73-7.54 (m, 1H), 7.14-7.05 (m, 1H), 7.02-6.93 (m, 1H), 1.78 (s, 6H).

Preparation 12B: 6-bromo-7-fluoroquinolin-4-ol

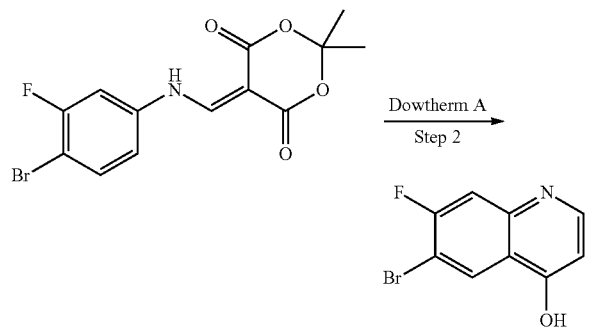

A solution of 5-{[(4-bromo-3-fluorophenyl)amino]methylidene}-2,2-dimethyl-1,3-dioxane-4,6-dione (32.00 g, 92.986 mmol) in 1,1'-biphenyl; phenoxybenzene (160 mL) was stirred for 15 min at 245° C. The mixture was allowed to cool down to room temperature. The resulting mixture was diluted with hexane (300 mL). The resulting mixture was filtered, This result in 6-bromo-7-fluoroquinolin-4-ol (16.80 g, 74%) as a brown solid. MS ESI calculated for $C_9H_5BrFNO$ [M+H]$^+$, 241.95, 243.95 found 241.97, 243.97. $^1$H NMR (300 MHz, DMSO-d$_6$) δ 11.91 (s, 1H), 8.28 (d, J=7.7 Hz, 1H), 7.96 (t, J=6.6 Hz, 1H), 7.47 (d, J=9.7 Hz, 1H), 6.08 (d, J=7.5 Hz, 1H).

Preparation 12C: 6-bromo-3-chloro-7-fluoroquinolin-4-ol

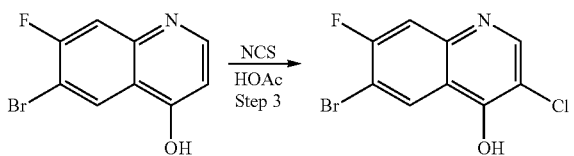

A solution of 6-bromo-7-fluoroquinolin-4-ol (16.30 g, 67.342 mmol) and NCS (13.49 g, 101.013 mmol) in HOAc (300 mL) was stirred for 3 h at 65° C. The mixture was allowed to cool down to room temperature. The resulting mixture was quenched with water and filtered, the filter cake was washed with water (3×200 mL). The filter cake was dried under vacuum. This result in 6-bromo-3-chloro-7-fluoroquinolin-4-ol (7.70 g, 41%) as a light yellow solid. MS ESI calculated for $C_9H_4BrClFNO$ [M+H]$^+$, 275.91 277.91, found 276.00 278.00. $^1$H NMR (400 MHz, DMSO-d$_6$) δ 12.46 (s, 1H), 8.48 (d, J=4.4 Hz, 1H), 8.35 (d, J=7.6 Hz, 1H), 7.52 (d, J=9.5 Hz, 1H).

Preparation 12D: 6-bromo-3,4-dichloro-7-fluoroquinoline

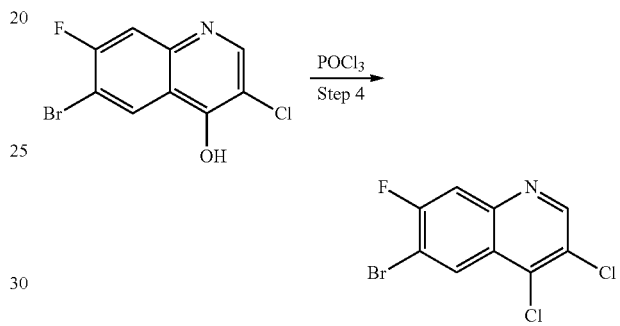

A solution of 6-bromo-3-chloro-7-fluoroquinolin-4-ol (2.00 g, 7.234 mmol) in POCl$_3$ (25 mL) was stirred for 2 h at 100° C. under nitrogen atmosphere. The resulting mixture was concentrated under reduced pressure. The resulting mixture was diluted with DCM (50 mL). The mixture was basified to pH 10 with NaOH (1 M). The resulting mixture was extracted with CH$_2$Cl$_2$ (3×50 mL). The combined organic layers were washed with brine (1×100 mL), dried over anhydrous Na$_2$SO$_4$. After filtration, the filtrate was concentrated under reduced pressure. The residue was purified by silica gel column chromatography, eluted with PE/EA (15/1) to afford 6-bromo-3,4-dichloro-7-fluoroquinoline (1.10 g, 46%) as a white solid. MS ESI calculated for $C_9H_3BrCl_2FN$ [M+H]$^+$, 293.88 295.88, found 293.90 295.90. $^1$H NMR (300 MHz, Chloroform-d) δ 8.85 (s, 1H), 8.48 (d, J=7.1 Hz, 1H), 7.81 (d, J=8.9 Hz, 1H).

Preparation 12E: 3,4-dichloro-6-[2-(dimethylphosphoryl)pyrimidin-5-yl]-7-fluoroquinoline

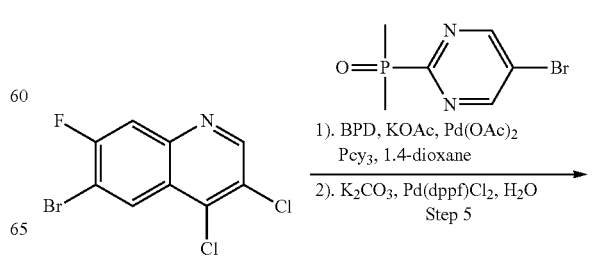

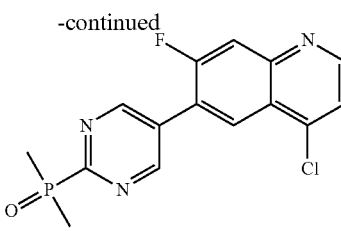

A solution of 5-bromo-2-(dimethylphosphoryl)pyrimidine (358 mg, 1.525 mmol), BPD (581 mg, 2.288 mmol), Pd(OAc)$_2$ (34 mg, 0.153 mmol), KOAc (299 mg, 3.051 mmol) and PCy$_3$ (85 mg, 0.305 mmol) in 1,4-dioxane (5 mL) was stirred for 3 h at 80° C. under nitrogen atmosphere. To the above mixture were added 6-bromo-3,4-dichloro-7-fluoroquinoline (300 mg, 1.017 mmol), Pd(dppf)Cl$_2$·CH$_2$Cl$_2$ (82 mg, 0.102 mmol) and K$_2$CO$_3$ (281 mg, 2.034 mmol) in H$_2$O (1 mL) at room temperature. The resulting mixture was stirred for additional 2 h at 100° C. The resulting mixture was concentrated under reduced pressure. The residue was purified by silica gel column chromatography, eluted with CH$_2$Cl$_2$/MeOH (12/1) to afford 3,4-dichloro-6-[2-(dimethylphosphoryl)pyrimidin-5-yl]-7-fluoroquinoline (210 mg, 55%) as a light yellow solid. MS ESI calculated for C$_{15}$H$_{11}$Cl$_2$FN$_3$OP [M+H]$^+$, 370.00, found 370.20. $^1$H NMR (400 MHz, Chloroform-d) δ 9.18 (s, 2H), 8.93 (s, 1H), 8.34 (d, J=7.7 Hz, 1H), 7.98 (d, J=10.9 Hz, 1H), 1.98 (s, 3H), 1.95 (s, 3H).

Example 12: 3-[(1R)-1-({3-chloro-6-[2-(dimethylphosphoryl)pyrimidin-5-yl]-7-fluoroquinolin-4-yl}amino)ethyl]-4-fluorobenzonitrile

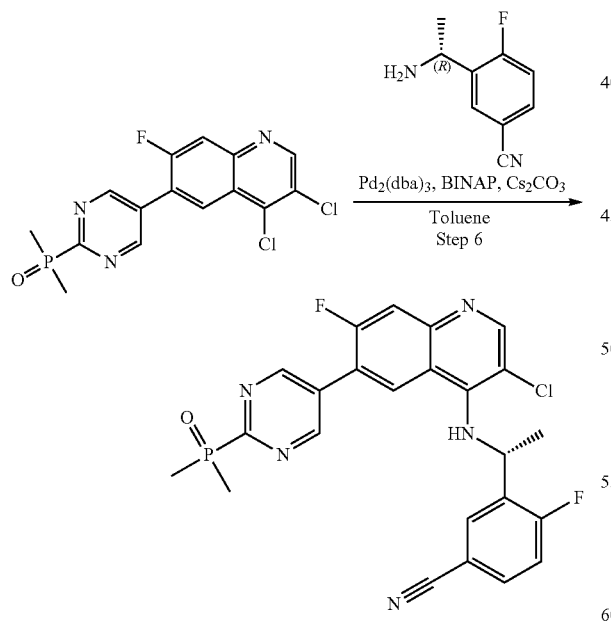

A mixture of 3,4-dichloro-6-[2-(dimethylphosphoryl)pyrimidin-5-yl]-7-fluoroquinoline (200 mg, 0.540 mmol), 3-[(1R)-1-aminoethyl]-4-fluorobenzonitrile (106 mg, 0.648 mmol), Pd$_2$(dba)$_3$ (49 mg, 0.054 mmol), BINAP (67.29 mg, 0.108 mmol) and Cs$_2$CO$_3$ (264 mg, 0.810 mmol) in Toluene (2 mL) was stirred for 2 h at 100° C. under nitrogen atmosphere. The resulting mixture was concentrated under reduced pressure. The residue was purified by silica gel column chromatography, eluted with CH$_2$Cl$_2$/MeOH (12/1) followed by reversed phase flash with the following conditions (column, C18 silica gel; mobile phase, CH$_3$CN in water (10 mmol/L NH$_4$HCO$_3$), 30% to 70% gradient in 20 min; detector, 254 nm) to afford 3-[(1R)-1-({3-chloro-6-[2-(dimethylphosphoryl)pyrimidin-5-yl]-7-fluoroquinolin-4-yl}amino)ethyl]-4-fluorobenzonitrile (66 mg, 24%) as a white solid. MS ESI calculated for C$_{24}$H$_{19}$ClF$_2$N$_5$OP [M+H]$^+$, 498.10, found 498.05. $^1$H NMR (400 MHz, DMSO-d$_6$) δ 9.33 (s, 2H), 8.66 (d, J=8.0 Hz, 1H), 8.53 (d, J=2.8 Hz, 1H), 8.14-8.08 (m, 1H), 7.88-7.80 (m, 2H), 7.45-7.37 (m, 1H), 6.90 (d, J=8.7 Hz, 1H), 5.82-5.72 (m, 1H), 1.86 (s, 3H), 1.83 (s, 3H), 1.65 (d, J=6.8 Hz, 3H). $^{19}$F NMR (376 MHz, DMSO-d$_6$) δ −109.84, −116.09. $^{31}$P NMR (162 MHz, DMSO-d$_6$) δ 34.14.

Example 13: 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzamide

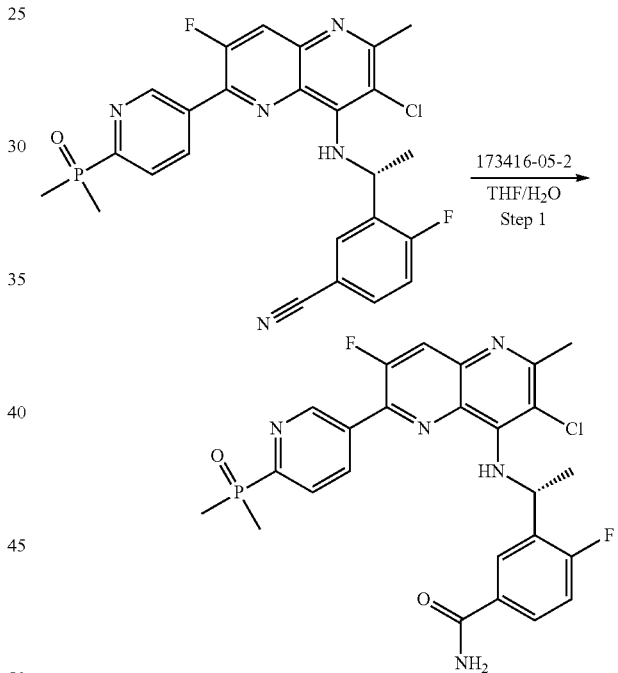

To a stirred solution of 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile (100 mg, 0.195 mmol) in THF (5 mL) and H$_2$O (1 mL) was added CAS #: 173416-05-2 (4 mg, 0.010 mmol) at room temperature. The resulting mixture was stirred for 2 h at 60° C. The resulting mixture was concentrated under reduced pressure. The residue was purified by reversed-phase flash chromatography with the following conditions: column, C18 silica gel; mobile phase, CH$_3$CN in water (10 mmol/L NH$_4$HCO$_3$), 45% to 60% gradient in 20 min; detector, 254 nm to afford 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzamide (46 mg, 44%) as a light yellow solid. MS ESI calculated for C$_{25}$H$_{23}$ClF$_2$N$_5$O$_2$P [M+H]$^+$, 530.12, found 529.95. $^1$H NMR (400 MHz, DMSO-d$_6$) δ 9.19 (s, 1H), 8.38-8.32 (m, 1H), 8.20 (d, J=11.7 Hz, 1H), 8.14-8.08 (m, 1H), 8.06-8.00 (m, 1H), 7.91 (s, 1H), 7.79-7.72 (m, 1H), 7.33 (s, 1H), 7.18-7.10 (m, 1H), 6.94 (d, J=8.6 Hz, 1H), 6.44-6.32 (m, 1H), 2.64 (s, 3H), 1.77 (s, 3H), 1.73 (s, 3H), 1.67 (d, J=6.8 Hz, 3H). $^{19}$F NMR (377 MHz, DMSO-$d_6$) δ −115.43, −121.04.

Example 14: 3-[(1R)-1-({3-chloro-6-[2-(dimethylphosphoryl) pyrimidin-5-yl]-7-fluoro-1,5-naphthyridin-4-yl}amino)ethyl]-4-fluorobenzonitrile Synthetic Scheme

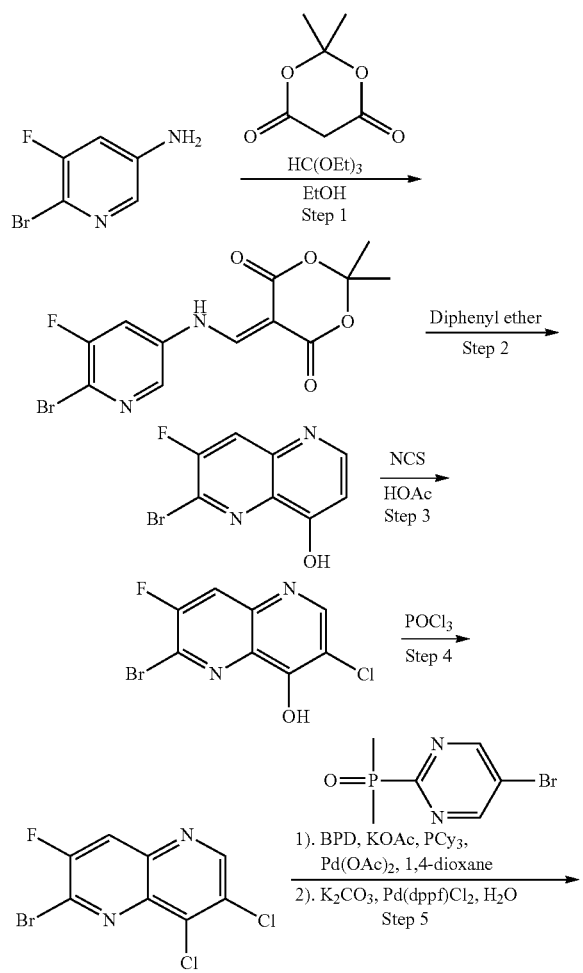

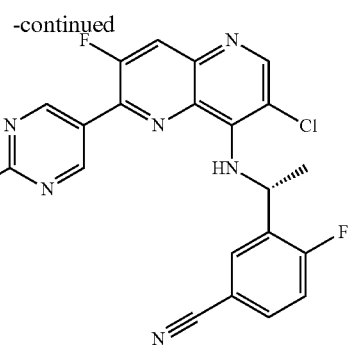

Preparation 14A: 5-{[(6-bromo-5-fluoropyridin-3-yl)amino]methylidene}-2,2-dimethyl-1,3-dioxane-4,6-dione A mixture of 6-bromo-5-fluoropyridin-3-amine (12.00 g, 62.826 mmol), meldrum's acid (11.32 g, 78.532 mmol) and triethyl orthoformate (7 mL, 42.722 mmol) in EtOH (120 mL) was stirred for 16 h at 80° C. under nitrogen atmosphere. The mixture was allowed to cool down to room temperature. The precipitated solids were collected by filtration and washed with Et$_2$O (3×50 mL). This resulted in 5-{[(6-bromo-5-fluoropyridin-3-yl)amino]methylidene}-2,2-dimethyl-1,3-dioxane-4,6-dione (18.00 g, 83%) as a yellow solid. MS ESI calculated for $C_{12}H_{10}BrFN_2O_4$[M−H]$^−$, 342.98 344.98, found 342.90 344.90. $^1$H NMR (400 MHz, DMSO-$d_6$) δ 11.32 (s, 1H), 8.61 (s, 1H), 8.53 (d, J=2.3 Hz, 1H), 8.27-8.21 (m, 1H), 1.67 (s, 6H).

Preparation 14B: 6-bromo-7-fluoro-1,5-naphthyridin-4-ol

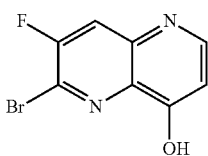

A mixture of 5-{[(6-bromo-5-fluoropyridin-3-yl)amino]methylidene}-2,2-dimethyl-1,3-dioxane-4,6-dione (18.00 g, 52.155 mmol) in phenoxybenzene (180 mL) was stirred for 20 min at 180° C. under nitrogen atmosphere. The mixture was allowed to cool down to room temperature. The precipitated solids were collected by filtration and washed with Et$_2$O (3×50 mL). This resulted in 6-bromo-7-fluoro-1,5-naphthyridin-4-ol (8.50 g, 67%) as a brown solid. MS ESI calculated for C$_8$H$_4$BrFN$_2$O [M+H]$^+$, 242.95 244.95, found 243.05 245.05. $^1$H NMR (300 MHz, DMSO-d$_6$) δ 7.96 (d, J=8.0 Hz, 1H), 7.46-7.34 (m, 1H), 7.05-6.96 (m, 1H).

Preparation 14C:
6-bromo-3-chloro-7-fluoroquinolin-4-ol

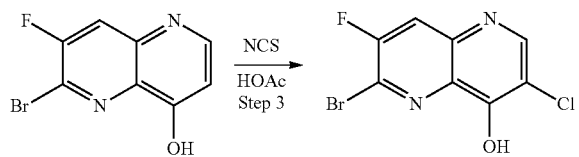

A mixture of 6-bromo-7-fluoro-1,5-naphthyridin-4-ol (8.50 g, 34.974 mmol) and NCS (5.14 g, 38.471 mmol) in HOAc (90 mL) was stirred for 3 h at 60° C. under nitrogen atmosphere. The resulting mixture was concentrated under vacuum. The precipitated solids were collected by filtration and washed with water (3×50 mL). This resulted in 6-bromo-3-chloro-7-fluoroquinolin-4-ol (7.50 g, 77%) as a yellow solid. MS ESI calculated for C$_8$H$_3$BrClFN$_2$O [M+H]$^+$, 276.91 278.91, found 276.90 278.90. $^1$H NMR (300 MHz, DMSO-d$_6$) δ 12.61 (s, 1H), 8.55 (s, 1H), 7.98 (d, J=8.1 Hz, 1H).

Preparation 14D:
2-bromo-7,8-dichloro-3-fluoro-1,5-naphthyridine

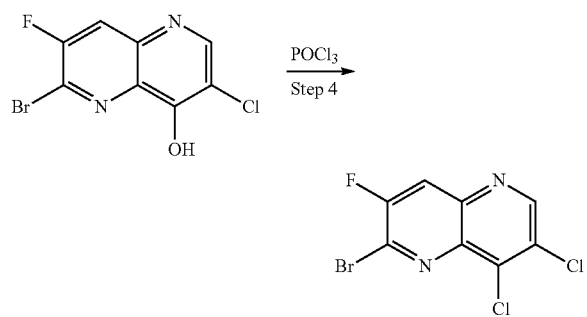

A mixture of 6-bromo-3-chloro-7-fluoro-1,5-naphthyridin-4-ol (7.50 g, 27.029 mmol) in phosphorus oxychloride (45 mL) was stirred for 2 h at 110° C. under nitrogen atmosphere. The resulting mixture was concentrated under vacuum. After add water, the mixture was basified to pH 9 with sat. NaOH. The precipitated solids were collected by filtration and washed with water (3×40 mL). The residue was purified by silica gel column chromatography, eluted with PE/EA (8/1) to afford 2-bromo-7,8-dichloro-3-fluoro-1,5-naphthyridine (6.20 g, 77%) as a white solid. MS ESI calculated for C$_8$H$_2$BrCl$_2$FN$_2$ [M+H]$^+$, 294.88 296.88, found N/A. $^1$H NMR (300 MHz, Chloroform-d) δ 8.93 (s, 1H), 8.13 (d, J=7.7 Hz, 1H).

Preparation 14E: 7,8-dichloro-2-[2-(dimethylphosphoryl) pyrimidin-5-yl]-3-fluoro-1,5-naphthyridine

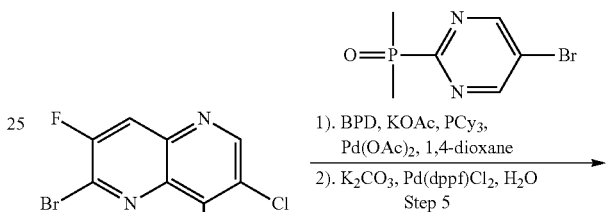

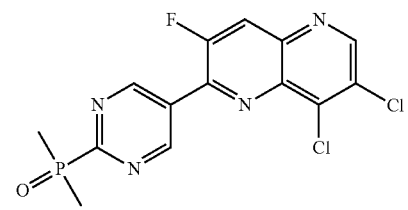

To a solution of 5-bromo-2-(dimethylphosphoryl) pyrimidine (477 mg, 2.028 mmol) and BPD (772 mg, 3.042 mmol) in 1,4-dioxane (5 mL) were added KOAc (398 mg, 4.056 mmol), PCy3 (114 mg, 0.406 mmol) and Pd(OAc)$_2$ (46 mg, 0.203 mmol). After stirring for 2 h at 80° C. under a nitrogen atmosphere. To the above mixture was added 2-bromo-7,8-dichloro-3-fluoro-1,5-naphthyridine (400 mg, 1.352 mmol), K$_2$CO$_3$ (374 mg, 2.704 mmol), Pd(dppf)Cl$_2$·CH$_2$Cl$_2$ (110 mg, 0.135 mmol) and H$_2$O (1 mL) at room temperature. The resulting mixture was stirred for additional 3 h at 80° C. The resulting mixture was concentrated under vacuum. The residue was purified by silica gel column chromatography, eluted with CH$_2$Cl$_2$/MeOH (9/1) to afford 7,8-dichloro-2-[2-(dimethylphosphoryl) pyrimidin-5-yl]-3-fluoro-1,5-naphthyridine (360 mg, 71%) as a yellow solid. MS ESI calculated for C$_{14}$H$_{10}$Cl$_2$FN$_4$OP [M+H]$^+$, 371.00, found 370.80. $^1$H NMR (400 MHz, Chloroform-d) δ 9.71 (s, 2H), 8.99 (s, 1H), 8.28 (d, J=10.8 Hz, 1H), 1.99 (s, 3H), 1.97 (s, 3H).

Example 14: 3-[(1R)-1-({3-chloro-6-[2-(dimethylphosphoryl) pyrimidin-5-yl]-7-fluoro-1,5-naphthyridin-4-yl}amino) ethyl]-4-fluorobenzonitrile

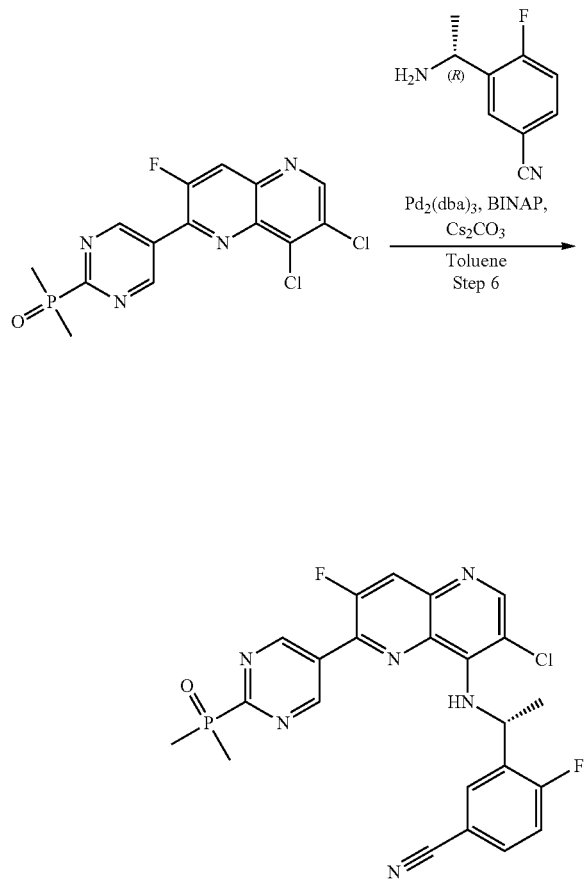

To a solution of 7,8-dichloro-2-[2-(dimethylphosphoryl)pyrimidin-5-yl]-3-fluoro-1,5-naphthyridine (100 mg, 0.269 mmol) and 3-[(1R)-1-aminoethyl]-4-fluorobenzonitrile (53 mg, 0.323 mmol) in Toluene (2 mL) were added BINAP (34 mg, 0.054 mmol), Cs$_2$CO$_3$ (132 mg, 0.404 mmol) and Pd$_2$(dba)$_3$ (25 mg, 0.027 mmol). After stirring for 2 h at 95° C. under a nitrogen atmosphere, the resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 10% to 50% gradient in 30 min; detector, 254 nm. This resulted in 3-[(1R)-1-({3-chloro-6-[2-(dimethylphosphoryl) pyrimidin-5-yl]-7-fluoro-1,5-naphthyridin-4-yl}amino) ethyl]-4-fluorobenzonitrile (20 mg, 14%) as a yellow solid. MS ESI calculated for C$_{23}$H$_{18}$ClF$_2$N$_6$OP [M+H]$^+$, 499.09, found 498.85. $^1$H NMR (300 MHz, Chloroform-d) δ 9.45 (s, 2H), 8.56 (s, 1H), 8.15 (d, J=11.0 Hz, 1H), 7.57 (d, J=7.2 Hz, 2H), 7.15 (t, J=9.5 Hz, 1H), 6.85 (d, J=8.1 Hz, 1H), 6.25 (t, J=7.4 Hz, 1H), 2.00 (s, 3H), 1.96 (s, 3H), 1.75 (d, J=6.8 Hz, 3H). $^{19}$F NMR (282 MHz, Chloroform-d) δ −108.86, −120.06. $^{31}$P NMR (122 MHz, Chloroform-d) δ 35.01.

Example 15: 3-[(1R)-1-({3-chloro-6-[6-(dimethylphosphoryl)pyridin-3-yl]-7-fluoro-1,5-naphthyridin-4-yl}amino) ethyl]-4-fluorobenzonitrile Synthetic Scheme

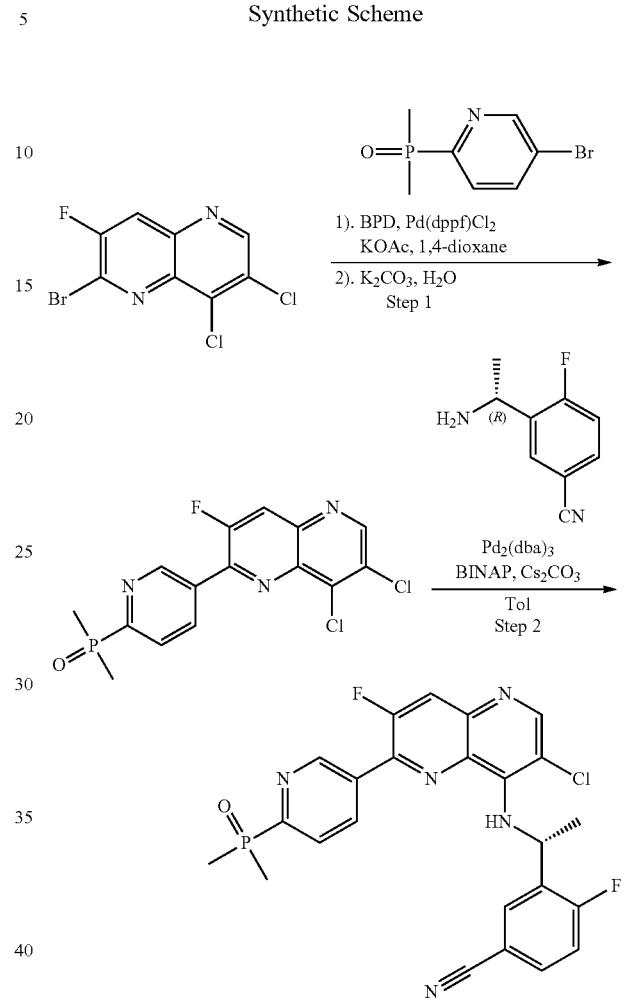

Preparation 15A: 7,8-dichloro-2-[6-(dimethylphosphoryl)pyridin-3-yl]-3-fluoro-1,5-naphthyridine

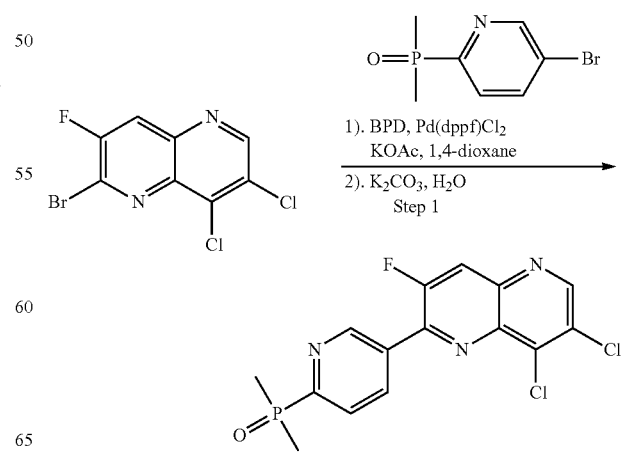

To a solution of 5-bromo-2-(dimethylphosphoryl)pyridine (178 mg, 0.760 mmol) and BPD (290 mg, 1.141 mmol) in 1,4-dioxane (3 mL) were added KOAc (149 mg, 1.521 mmol) and Pd(dppf)Cl$_2$·CH$_2$Cl$_2$ (62 mg, 0.076 mmol). After stirring for 2 h at 80° C. under a nitrogen atmosphere. To the above mixture was added 2-bromo-7,8-dichloro-3-fluoro-1,5-naphthyridine (150 mg, 0.507 mmol), K$_2$CO$_3$ (140 mg, 1.014 mmol) and H$_2$O (0.6 mL) at room temperature. The resulting mixture was stirred for additional 3 h at 80° C. The resulting mixture was concentrated under vacuum. The residue was purified by silica gel column chromatography, eluted with CH$_2$Cl$_2$/MeOH (9/1) to afford 7,8-dichloro-2-[6-(dimethylphosphoryl)pyridin-3-yl]-3-fluoro-1,5-naphthyridine (120 mg, 63%) as a yellow solid. MS ESI calculated for C$_{15}$H$_{11}$Cl$_2$FN$_3$OP [M+H]$^+$, 370.00, found 370.00. $^1$H NMR (400 MHz, Chloroform-d) δ 9.59 (s, 1H), 8.97 (s, 1H), 8.67 (s, 1H), 8.35 (s, 1H), 8.24 (d, J=10.8 Hz, 1H), 1.91 (s, 3H), 1.88 (s, 3H).

Example 15: 3-[(1R)-1-({3-chloro-6-[6-(dimethylphosphoryl)pyridin-3-yl]-7-fluoro-1,5-naphthyridin-4-yl}amino) ethyl]-4-fluorobenzonitrile

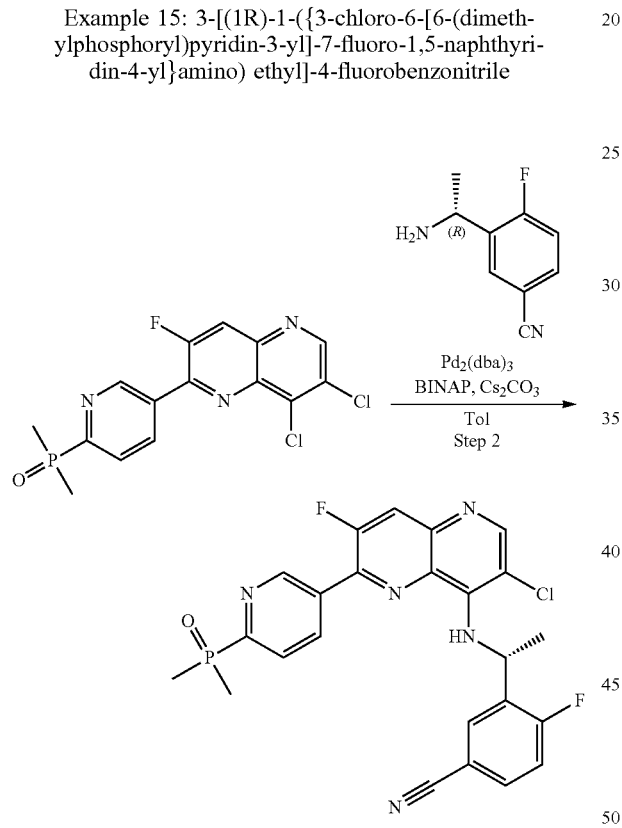

To a solution of 7,8-dichloro-2-[6-(dimethylphosphoryl)pyridin-3-yl]-3-fluoro-1,5-naphthyridine (100 mg, 0.270 mmol) and 3-[(1R)-1-aminoethyl]-4-fluorobenzonitrile (53 mg, 0.324 mmol) in Toluene (2 mL) were added Cs$_2$CO$_3$ (132 mg, 0.405 mmol), BINAP (34 mg, 0.054 mmol) and Pd$_2$(dba)$_3$ (25 mg, 0.027 mmol). After stirring for 2 h at 95° C. under a nitrogen atmosphere, the resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 10% to 50% gradient in 30 min; detector, 254 nm. This resulted in 3-[(1R)-1-({3-chloro-6-[6-(dimethylphosphoryl)pyridin-3-yl]-7-fluoro-1,5-naphthyridin-4-yl}amino) ethyl]-4-fluorobenzonitrile (20 mg, 14%) as a yellow solid. MS ESI calculated for C$_{24}$H$_{19}$ClF$_2$N$_5$OP [M+H]$^+$, 498.10, found 497.90. $^1$H NMR (300 MHz, Chloroform-d) δ 9.29 (s, 1H), 8.54 (s, 1H), 8.42-8.25 (m, 2H), 8.11 (d, J=11.1 Hz, 1H), 7.64-7.50 (m, 2H), 7.19-7.07 (m, 1H), 6.83 (d, J=7.6 Hz, 1H), 6.31-6.21 (m, 1H), 1.90 (s, 3H), 1.85 (s, 3H), 1.74 (d, J=6.8 Hz, 3H). $^{19}$F NMR (282 MHz, Chloroform-d) δ -108.79, -119.71. $^{31}$P NMR (122 MHz, Chloroform-d) δ 36.74.

Example 16: 3-chloro-6-[2-(dimethylphosphoryl)pyrimidin-5-yl]-7-fluoro-N-[(1R)-1-(2-fluorophenyl)propyl]-2-methyl-1,5-naphthyridin-4-amine Synthetic Scheme

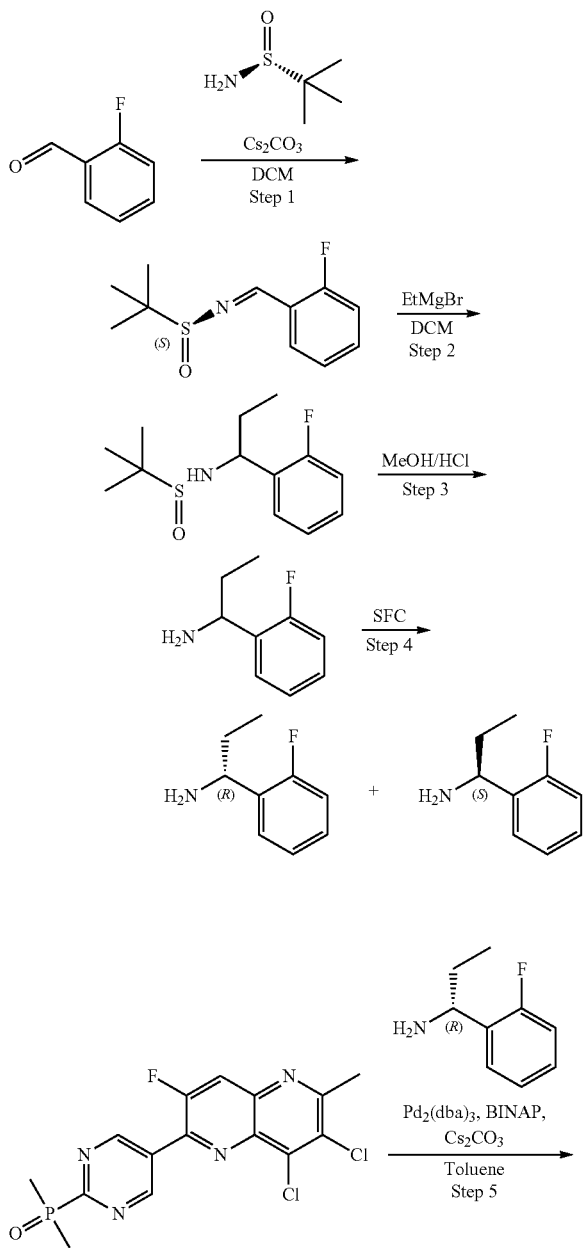

-continued

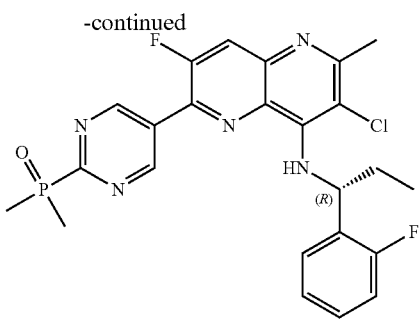

Preparation 16A: (S)—N-[(2-fluorophenyl)methyl-idene]-2-methylpropane-2-sulfinamide

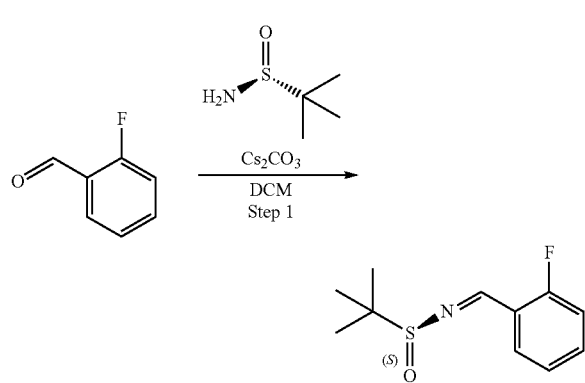

A solution of 2-fluor-benzaldehyde (10.00 g, 80.571 mmol), tert-butanesulfinamide (11.72 g, 96.685 mmol) and Cs$_2$CO$_3$ (52.50 g, 161.142 mmol) in DCM (200 mL) was stirred for overnight at room temperature under nitrogen atmosphere. The resulting mixture was filtered, and the filter cake was washed with DCM (2×100 mL). The filtrate was concentrated under reduced pressure. The residue was purified by silica gel column chromatography, eluted with PE/EA (5/1) to afford (S)—N-[(2-fluorophenyl)methyl-idene]-2-methylpropane-2-sulfinamide (17.40 g, 95%) as a yellow oil. MS ESI calculated for C$_{11}$H$_{14}$FNOS [M+H]$^+$, 228.08, found 228.21. $^1$H NMR (400 MHz, Chloroform-d) δ 8.91 (s, 1H), 8.05-7.95 (m, 1H), 7.57-7.49 (m, 1H), 7.26-7.21 (m, 1H), 7.19-7.12 (m, 1H), 1.28 (s, 9H).

Preparation 16B: (S)—N-[1-(2-fluorophenyl)pro-pyl]-2-methylpropane-2-sulfinamide

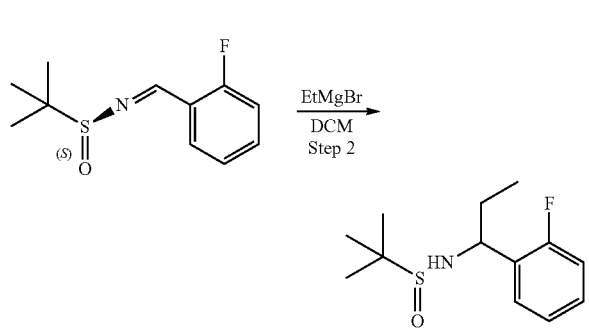

To a stirred solution of (S)—N-[(2-fluorophenyl)methyl-idene]-2-methylpropane-2-sulfinamide (3.00 g, 13.198 mmol) in DCM (30 mL) was added EtMgBr (7.8 mL, 26.396 mmol) dropwise at −78° C. under nitrogen atmosphere. The resulting mixture was stirred for 30 min at room temperature under nitrogen atmosphere. The reaction was quenched with sat. NH$_4$Cl (aq.) at 0° C. The resulting mixture was extracted with CH$_2$Cl$_2$ (4×50 mL). The combined organic layers were dried over anhydrous Na$_2$SO$_4$. After filtration, the filtrate was concentrated under reduced pressure. This resulted in (S)—N-[1-(2-fluorophenyl)propyl]-2-methylpropane-2-sul-finamide (2.80 g, 82%) as a yellow oil. MS ESI calculated for C$_{13}$H$_{20}$FNOS [M+H]$^+$, 258.12, found 258.21.

Preparation 16C: 1-(2-fluorophenyl)propan-1-amine

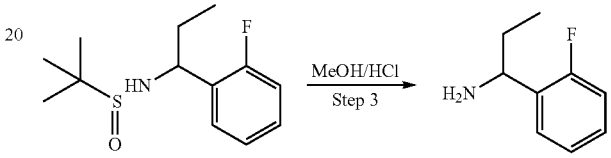

To a stirred solution of (S)—N-[1-(2-fluorophenyl)pro-pyl]-2-methylpropane-2-sulfinamide (2.80 g, 10.879 mmol) in MeOH (20 mL) was added conc. HCl (5 mL) dropwise at room temperature. The resulting mixture was stirred for 1 h at room temperature. The resulting mixture was concentrated under reduced pressure. The residue was dissolved in MeOH (3 mL). The mixture was basified to pH 9 with saturated NaHCO$_3$ (aq.). The resulting mixture was extracted with CH$_2$Cl$_2$ (4×50 mL). The combined organic layers were dried over anhydrous Na$_2$SO$_4$. After filtration, the filtrate was concentrated under reduced pressure. The residue was purified by silica gel column chromatography, eluted with CH$_2$Cl$_2$/MeOH (10/1) to afford 1-(2-fluorophe-nyl)propan-1-amine (1.30 g, 78%) as a yellow oil. MS ESI calculated for C$_9$H$_{12}$FN [M+H]$^+$, 154.10, found 154.23.

Preparation 16D: (1R)-1-(2-fluorophenyl)propan-1-amine and (1S)-1-(2-fluorophenyl)propan-1-amine

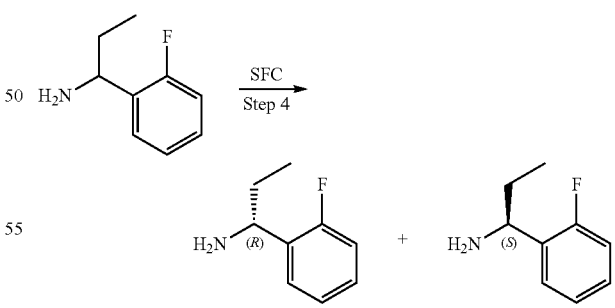

The 1-(2-fluorophenyl)propan-1-amine (1.30 g) was resolved by SFC with the following conditions (Column: NB_Lux 5 um Cellulose-4, 5*25 cm, 5 m; Mobile Phase A: CO$_2$, Mobile Phase B: MeOH (0.1% 2M NH$_3$-MeOH); Flow rate: 140 mL/min; Gradient: isocratic 20% B; Column Temperature(° C.): 30; Back Pressure(bar): 100; Wave Length: 202/262 nm). The first peak afforded 390 mg (30%) as a yellow oil. MS ESI calculated for C$_9$H$_{12}$FN [M+H]$^+$, 154.10, found 154.31. ¹H NMR (400 MHz, Chloroform-d) δ 7.40-7.34 (m, 1H), 7.24-7.18 (m, 1H), 7.15-7.09 (m, 1H), 7.05-6.97 (m, 1H), 4.14-4.08 (m, 1H), 1.79-1.70 (m, 2H), 0.93-0.86 (m, 3H). ¹⁹F NMR (377 MHz, Chloroform-d) δ −119.57.

The second peak afforded 60 mg (4%) as a yellow oil. MS ESI calculated for $C_9H_{12}FN$ [M+H]⁺, 154.10, found 154.27. ¹H NMR (400 MHz, Chloroform-d) δ 7.40-7.33 (m, 1H), 7.24-7.18 (m, 1H), 7.15-7.09 (m, 1H), 7.05-6.97 (m, 1H), 4.14-4.08 (m, 1H), 1.79-1.70 (m, 2H), 0.93-0.86 (m, 3H). ¹⁹F NMR (377 MHz, Chloroform-d) δ −119.57.

Example 16: 3-chloro-6-[2-(dimethylphosphoryl) pyrimidin-5-yl]-7-fluoro-N-[(1R)-1-(2-fluorophenyl) propyl]-2-methyl-1,5-naphthyridin-4-amine

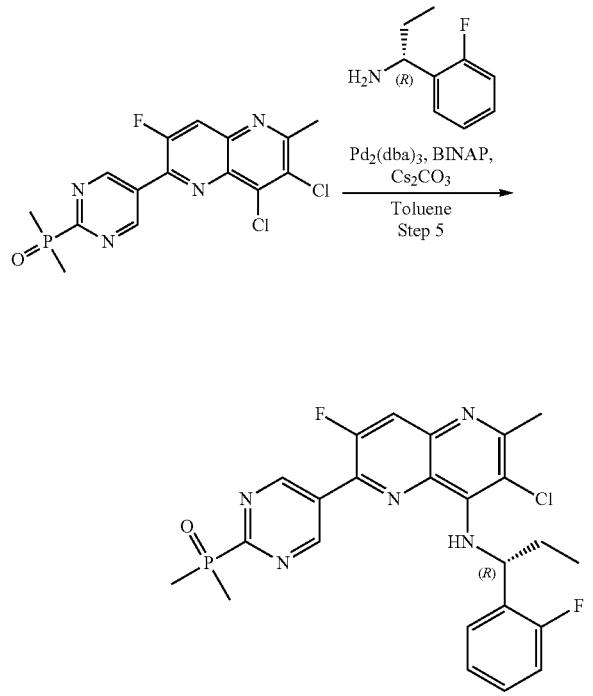

A mixture of 3,4-dichloro-6-[2-(dimethylphosphoryl)pyrimidin-5-yl]-7-fluoro-2-methyl-1,5-naphthyridine (100 mg, 0.260 mmol), (1R)-1-(2-fluorophenyl)propan-1-amine (48 mg, 0.312 mmol), Pd(OAc)₂ (6 mg, 0.026 mmol), BINAP (32 mg, 0.052 mmol) and Cs₂CO₃ (127 mg, 0.390 mmol) in Toluene (2 mL) was stirred for 3 h at 100° C. under nitrogen atmosphere. The resulting mixture was concentrated under reduced pressure. The residue was purified by silica gel column chromatography, eluted with CH₂Cl₂/MeOH (10/1) followed by reversed-phase flash chromatography with the following conditions: column, C18 silica gel; mobile phase, CH₃CN in water (10 mmol/L NH₄HCO₃), 40% to 60% gradient in 20 min; detector, 254 nm. This resulted in 3-chloro-6-[2-(dimethylphosphoryl)pyrimidin-5-yl]-7-fluoro-N-[(1R)-1-(2-fluorophenyl)propyl]-2-methyl-1,5-naphthyridin-4-amine (29 mg, 22%) as a yellow solid. MS ESI calculated for $C_{24}H_{23}ClF_2N_5OP$ [M+H]⁺, 502.13, found 501.95. ¹H NMR (400 MHz, DMSO-d₆) δ 9.48-9.44 (m, 2H), 8.27-8.23 (m, 1H), 7.51-7.44 (m, 1H), 7.28-7.21 (m, 1H), 7.14-6.93 (m, 3H), 6.18-6.09 (m, 1H), 2.63 (s, 3H), 2.15-2.03 (m, 1H), 1.99-1.91 (m, 1H), 1.88 (s, 3H), 1.85 (s, 3H), 0.98 (t, J=7.3 Hz, 3H). ¹⁹F NMR (377 MHz, DMSO-d₆) δ −119.30, −126.33. ³¹P NMR (162 MHz, DMSO-d₆) δ 34.42.

Example 17: 3-chloro-6-[2-(dimethylphosphoryl) pyrimidin-5-yl]-7-fluoro-N-[(1S)-1-(2-fluorophenyl) propyl]-2-methyl-1,5-naphthyridin-4-amine

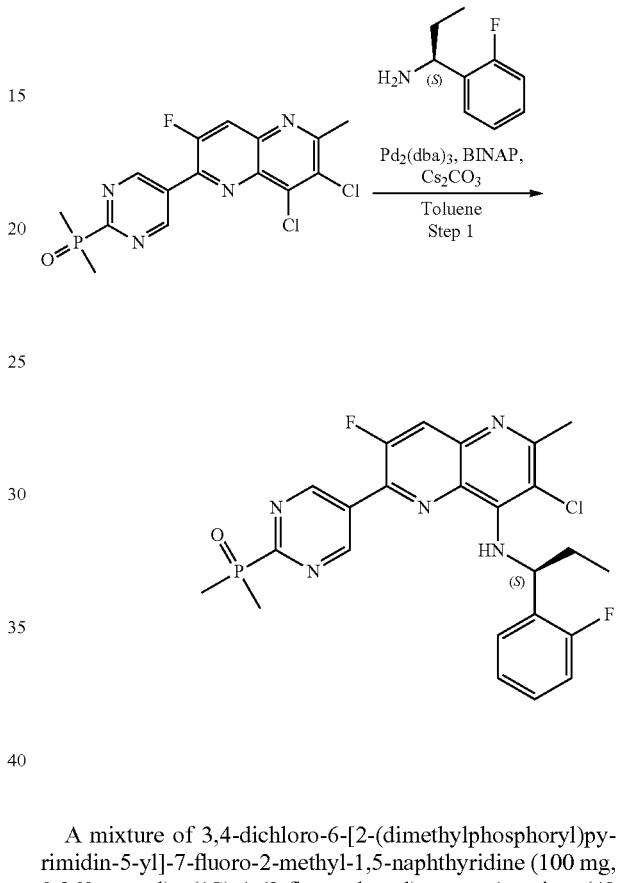

A mixture of 3,4-dichloro-6-[2-(dimethylphosphoryl)pyrimidin-5-yl]-7-fluoro-2-methyl-1,5-naphthyridine (100 mg, 0.260 mmol), (1S)-1-(2-fluorophenyl)propan-1-amine (48 mg, 0.312 mmol), Pd(OAc)₂ (6 mg, 0.026 mmol), BINAP (32 mg, 0.052 mmol) and Cs₂CO₃ (127 mg, 0.390 mmol) in Toluene (2 mL) was stirred for 3 h at 100° C. under nitrogen atmosphere. The resulting mixture was concentrated under reduced pressure. The residue was purified by silica gel column chromatography, eluted with CH₂Cl₂/MeOH (10/1) followed by reversed-phase flash chromatography with the following conditions: column, C18 silica gel; mobile phase, CH₃CN in water (10 mmol/L NH₄HCO₃), 40% to 60% gradient in 20 min; detector, 254 nm. This resulted in 3-chloro-6-[2-(dimethylphosphoryl)pyrimidin-5-yl]-7-fluoro-N-[(1S)-1-(2-fluorophenyl)propyl]-2-methyl-1,5-naphthyridin-4-amine (41 mg, 31%) as a yellow solid. MS ESI calculated for $C_{24}H_{23}ClF_2N_5OP$ [M+H]⁺, 502.13, found 501.95. ¹H NMR (400 MHz, DMSO-d₆) δ 9.48-9.44 (m, 2H), 8.27-8.23 (m, 1H), 7.51-7.44 (m, 1H), 7.28-7.21 (m, 1H), 7.14-6.93 (m, 3H), 6.18-6.09 (m, 1H), 2.63 (s, 3H), 2.15-2.03 (m, 1H), 1.99-1.91 (m, 1H), 1.88 (s, 3H), 1.85 (s, 3H), 0.98 (t, J=7.3 Hz, 3H). ¹⁹F NMR (377 MHz, DMSO-d₆) δ −119.30, −126.33. ³¹P NMR (162 MHz, DMSO-d₆) δ 34.42.

Example 18: 3-chloro-6-[6-(dimethylphosphoryl)pyridin-3-yl]-7-fluoro-N-[(1R)-1-(2-fluorophenyl)ethyl]-2-methyl-1,5-naphthyridin-4-amine

Example 19: 3-chloro-6-[6-(dimethylphosphoryl)pyridin-3-yl]-7-fluoro-N-[(1R)-1-(2-fluorophenyl)ethyl]-2-methylquinolin-4-amine

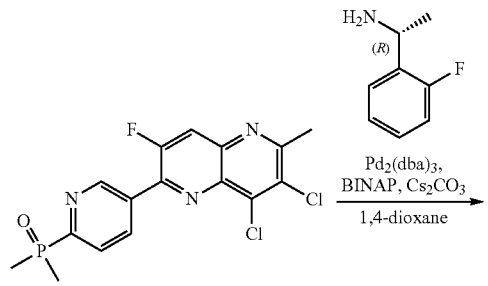

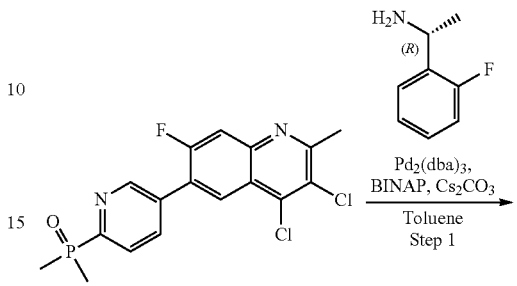

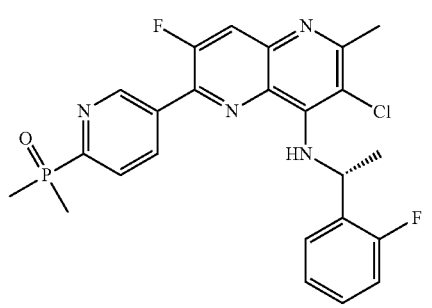

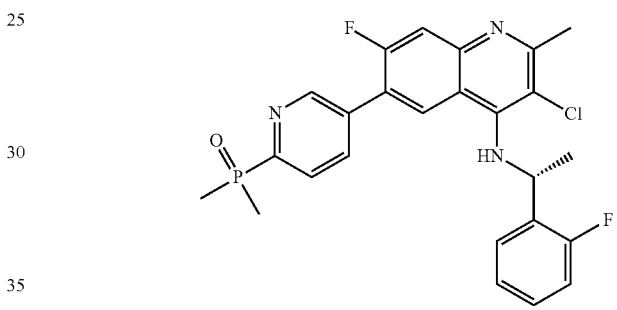

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-(2-fluorophenyl)ethanamine (43 mg, 0.312 mmol) in 1,4-dioxane (2 mL) were added BINAP (32.42 mg, 0.052 mmol), Pd$_2$(dba)$_3$ (23.84 mg, 0.026 mmol) and Cs$_2$CO$_3$ (127.22 mg, 0.390 mmol) at room temperature under nitrogen atmosphere. The resulting mixture was stirred for overnight at 100° C. under nitrogen atmosphere. The resulting mixture was concentrated under vacuum. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 10% to 50% gradient in 10 min; detector, 254 nm. This resulted in 3-chloro-6-[6-(dimethylphosphoryl)pyridin-3-yl]-7-fluoro-N-[(1R)-1-(2-fluorophenyl)ethyl]-2-methyl-1,5-naphthyridin-4-amine (60 mg, 47%) as a yellow solid. MS ESI calculated for C$_{24}$H$_{22}$ClF$_2$N$_4$OP [M+H]$^+$, 487.12, found 487.05. $^1$H NMR (400 MHz, Chloroform-d) n 9.29 (s, 1H), 8.35-8.23 (m, 2H), 7.95 (d, J=11.5 Hz, 1H), 7.25-7.14 (m, 2H), 7.06-6.95 (m, 2H), 6.59 (s, 1H), 6.48-6.38 (m, 1H), 2.73 (s, 3H), 1.88 (s, 3H), 1.84 (s, 3H), 1.72 (d, J=6.7 Hz, 3H). 19F NMR (377 MHz, Chloroform-d) δ −118.51, −120.85. $^{31}$p NMR (162 MHz, Chloroform-d) s 36.53.

To a stirred solution of 3,4-dichloro-6-[6-(dimethylphosphoryl)pyridin-3-yl]-7-fluoro-2-methylquinoline (100 mg, 0.261 mmol) and (1R)-1-(2-fluorophenyl)ethanamine (44 mg, 0.313 mmol) in Toluene (1 mL) were added BINAP (33 mg, 0.052 mmol), Cs$_2$CO$_3$ (128 mg, 0.392 mmol) and Pd$_2$(dba)$_3$ (24 mg, 0.026 mmol) at room temperature under nitrogen atmosphere. The resulting mixture was stirred for overnight at 100° C. under nitrogen atmosphere. The resulting mixture was concentrated under vacuum. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 10% to 95% gradient in 35 min; detector, 254 nm. This resulted in 3-chloro-6-[6-(dimethylphosphoryl)pyridin-3-yl]-7-fluoro-N-[(1R)-1-(2-fluorophenyl)ethyl]-2-methylquinolin-4-amine (60 mg, 47%) as a white solid. MS ESI calculated for C$_{25}$H$_{23}$ClF$_2$N$_3$OP [M+H]$^+$, 486.12, found 486.05. $^1$H NMR (400 MHz, Chloroform-d) δ 8.80 (s, 1H), 8.16-8.10 (m, 1H), 7.94 (d, J=7.9 Hz, 1H), 7.90-7.67 (m, 2H), 7.46 (t, J=7.6 Hz, 1H), 7.34-7.26 (m, 1H), 7.20-7.12 (m, 1H), 7.12-7.03 (m, 1H), 5.42-5.30 (m, 1H), 2.83 (s, 3H), 1.85 (s, 3H), 1.81 (s, 3H), 1.71 (d, J=6.3 Hz, 3H). $^{19}$F NMR (377 MHz, Chloroform-d) δ −115.07, −119.25. $^{31}$P NMR (162 MHz, Chloroform-d) δ 36.58.

Example 20: 3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile

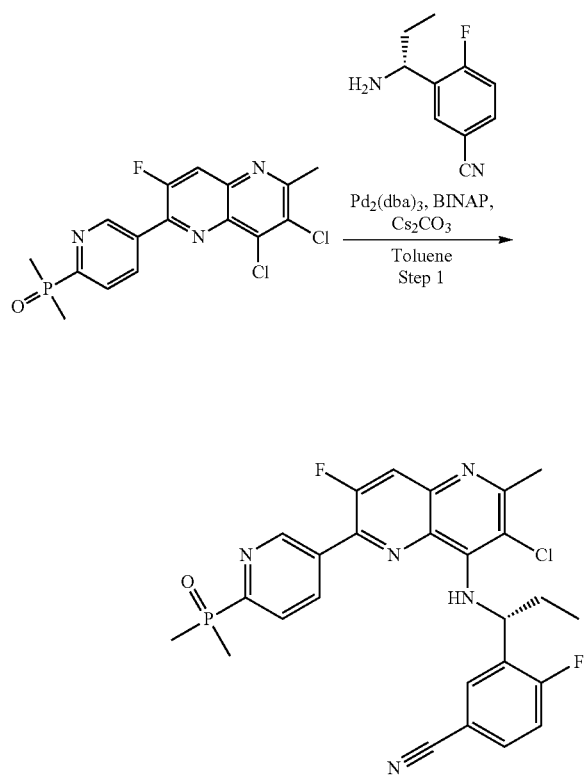

A mixture of 3,4-dichloro-6-[6-(dimethylphosphoryl)pyridin-3-yl]-7-fluoro-2-methyl-1,5-naphthyridine (100 mg, 0.260 mmol), 3-[(1R)-1-aminopropyl]-4-fluorobenzonitrile (56 mg, 0.312 mmol), BINAP (33 mg, 0.052 mmol), $Cs_2CO_3$ (128 mg, 0.390 mmol) and $Pd_2(dba)_3$ (24 mg, 0.026 mmol) in Toluene (1 mL) was stirred for overnight at 80° C. under nitrogen atmosphere. The resulting mixture was concentrated under vacuum. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 10% to 50% gradient in 30 min; detector, 254 nm. This resulted in 3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile (23 mg, 34%) as a light yellow solid. MS ESI calculated for $C_{26}H_{23}ClF_2N_5OP$ [M+H]$^+$, 526.13, found 526.10. $^1$H NMR (400 MHz, DMSO-$d_6$) δ 9.15 (s, 1H), 8.36 (d, J=8.0 Hz, 1H), 8.25-8.19 (m, 1H), 8.13-8.09 (m, 2H), 7.82-7.76 (m, 1H), 7.32-7.26 (m, 1H), 6.97 (d, J=8.7 Hz, 1H), 6.04-5.97 (m, 1H), 2.65 (s, 3H), 2.10-20.1 (m, 1H), 1.94-1.86 (m, 1H), 1.77 (d, J=3.6 Hz, 3H), 1.74 (d, J=3.6 Hz, 3H), 0.10-0.95 (m, 3H). $^{19}$F NMR (377 MHz, DMSO-$d_6$) δ −109.37, −121.00. $^{31}$P NMR (162 MHz, DMSO-$d_6$) δ 34.28.

Example 21: ammonium methyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate Synthetic Scheme

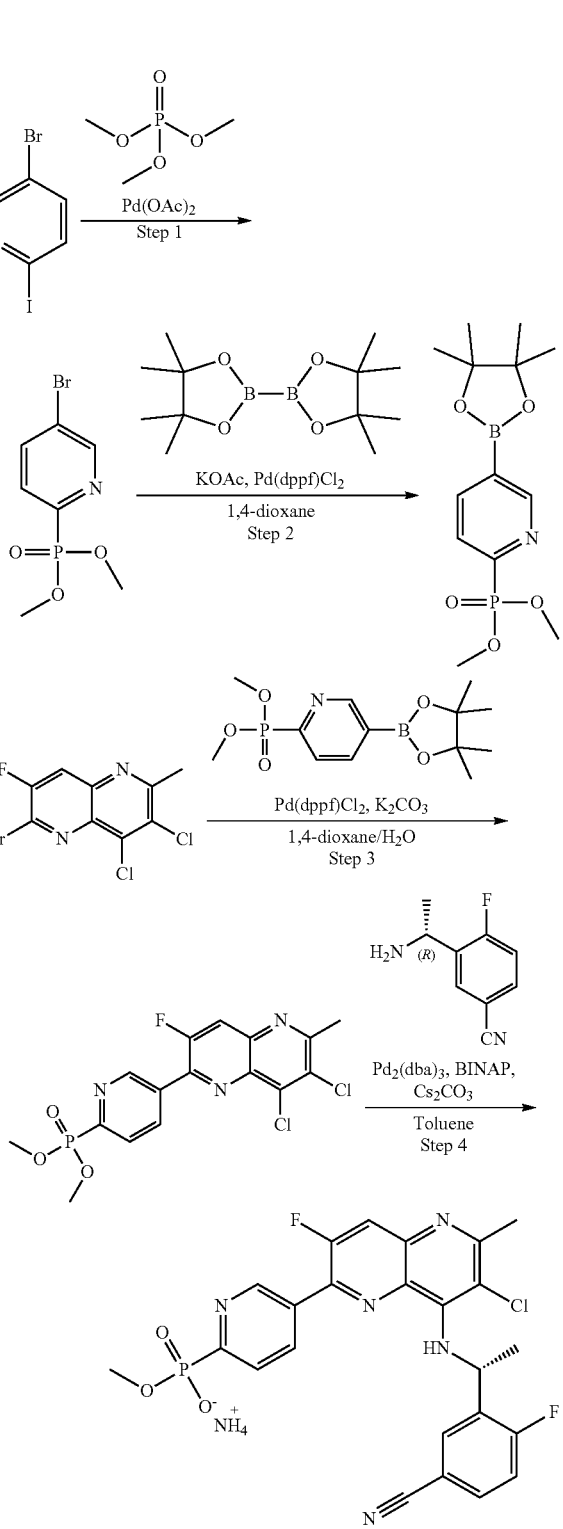

Preparation 21A: dimethyl 5-bromopyridin-2-ylphosphonate

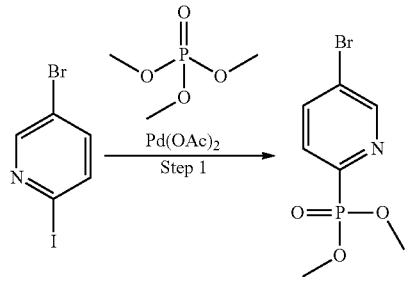

To a stirred solution of 5-bromo-2-iodopyridine (500 mg, 1.761 mmol) in trimethyl phosphate (0.74 g, 5.283 mmol) was added Pd(OAc)$_2$ (0.08 g, 0.352 mmol) at room temperature under nitrogen atmosphere. The resulting mixture was stirred for 3 h at 70° C. under nitrogen atmosphere. The resulting mixture was concentrated under vacuum. The residue was purified by silica gel column chromatography, eluted with CH$_2$Cl$_2$/MeOH (12/1) to afford dimethyl 5-bromopyridin-2-ylphosphonate (250 mg, 29%) as a yellow oil. MS ESI calculated for C$_7$H$_9$BrNO$_3$P [M+H]$^+$, 265.95 267.95, found 266.00 268.00. $^1$H NMR (400 MHz, Chloroform-d) δ 8.86 (d, J=2.4 Hz, 1H), 8.02-7.93 (m, 1H), 7.90-7.80 (m, 1H), 3.89 (s, 3H), 3.86 (s, 3H).

Preparation 21B: dimethyl 5-(4,4,5,5-tetramethyl-1,3,2-dioxaborolan-2-yl)pyridin-2-ylphosphonate

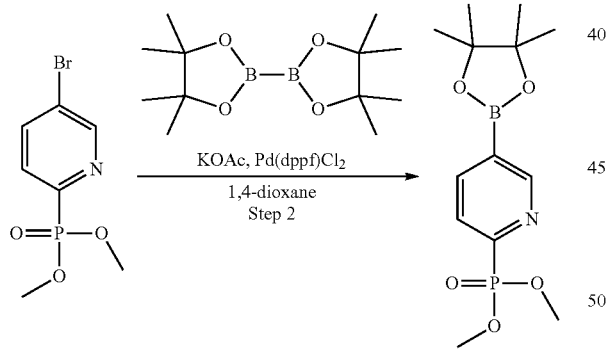

To a solution of dimethyl 5-bromopyridin-2-ylphosphonate (250 mg, 0.940 mmol) and BPD (358 mg, 1.410 mmol) in 1,4-dioxane (5 mL) were added KOAc (277 mg, 2.820 mmol) and Pd(dppf)Cl$_2$·CH$_2$Cl$_2$ (77 mg, 0.094 mmol). After stirring for 3 h at 100° C. under a nitrogen atmosphere. The mixture was allowed to cool down to room temperature. The resulting mixture was filtered, and the filter cake was washed with EtOAc (2×15 mL). The filtrate was concentrated under reduced pressure to afford dimethyl 5-(4,4,5,5-tetramethyl-1,3,2-dioxaborolan-2-yl)pyridin-2-ylphosphonate (380 mg, 90%) as a dark grey solid. The crude product was used in the next step without purification. MS ESI calculated for C$_{13}$H$_{21}$BNO$_5$P [M+H]$^+$, 314.13, found 314.20.

Preparation 21C: dimethyl 5-(7,8-dichloro-3-fluoro-6-methyl-1,5-naphthyridin-2-yl)pyridin-2-ylphosphonate

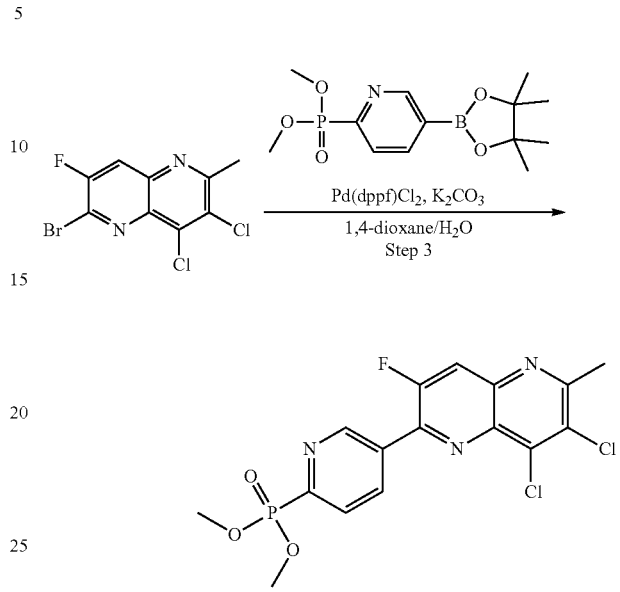

To a solution of 6-bromo-3,4-dichloro-7-fluoro-2-methyl-1,5-naphthyridine (200 mg, 0.645 mmol) and dimethyl 5-(4,4,5,5-tetramethyl-1,3,2-dioxaborolan-2-yl)pyridin-2-ylphosphonate (375 mg, 0.839 mmol) in 1,4-dioxane (5 mL) and H$_2$O (1 mL) were added Pd(dppf)Cl$_2$·CH$_2$Cl$_2$ (52 mg, 0.065 mmol) and K$_2$CO$_3$ (178 mg, 1.290 mmol). After stirring for 2 h at 80° C. under a nitrogen atmosphere. The resulting mixture was concentrated under reduced pressure. The residue was purified by silica gel column chromatography, eluted with CH$_2$Cl$_2$/MeOH (12/1) to afford dimethyl 5-(7,8-dichloro-3-fluoro-6-methyl-1,5-naphthyridin-2-yl)pyridin-2-ylphosphonate (80 mg, 29%) as a pink solid. MS ESI calculated for C$_{16}$H$_{13}$Cl$_2$FN$_3$O$_3$P [M+H]$^+$, 416.01, found 416.00. $^1$H NMR (400 MHz, Chloroform-d) δ 9.61 (s, 1H), 8.64 (t, J=6.8 Hz, 1H), 8.22-8.08 (m, 2H), 3.95 (s, 3H), 3.92 (s, 3H), 2.91 (s, 3H).

Example 21: ammonium methyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate

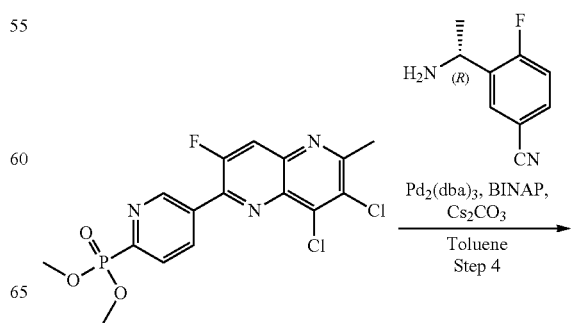

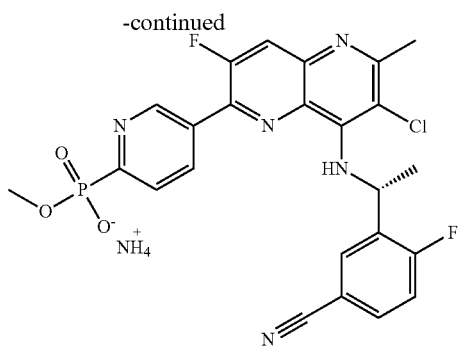

To a solution of dimethyl 5-(7,8-dichloro-3-fluoro-6-methyl-1,5-naphthyridin-2-yl)pyridin-2-ylphosphonate (80 mg, 0.192 mmol), BINAP (24 mg, 0.038 mmol) and 3-[(1R)-1-aminoethyl]-4-fluorobenzonitrile (38 mg, 0.230 mmol) in Toluene (2 mL) were added $Cs_2CO_3$ (94 mg, 0.288 mmol) and $Pd_2(dba)_3$ (18 mg, 0.019 mmol). After stirring for overnight at 100° C. under a nitrogen atmosphere. The resulting mixture was concentrated under reduced pressure. The residue was purified by silica gel column chromatography, eluted with $CH_2Cl_2$/MeOH (12/1) followed by reversed-phase flash chromatography with the following conditions: column, C18 silica gel; mobile phase, $CH_3CN$ in water (10 mmol/L $NH_4HCO_3$), 10% to 50% gradient in 10 min; detector, 254 nm to afford ammonium methyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate (30 mg, 29%) as a light yellow solid. MS ESI calculated for $C_{24}H_{19}ClF_2OP$ [M+H]$^+$, 530.09, found 530.05. $^1$H NMR (400 MHz, DMSO-$d_6$) δ 9.07 (s, 1H), 8.09 (s, 3H), 7.90-7.68 (m, 2H), 7.54-7.07 (m, 3H), 6.93 (s, 1H), 6.32 (s, 1H), 3.51 (s, 3H), 2.61 (s, 3H), 1.66 (d, J=6.8 Hz, 3H). $^{19}$F NMR (376 MHz, DMSO-$d_6$) δ −109.18, −120.89. $^{31}$P NMR (162 MHz, DMSO-$d_6$) δ 5.69.

Example 22: 3-chloro-6-[6-(dimethylphosphoryl)pyridin-3-yl]-7-fluoro-N-[(1R)-1-(2-fluorophenyl)propyl]-2-methyl-1,5-naphthyridin-4-amine

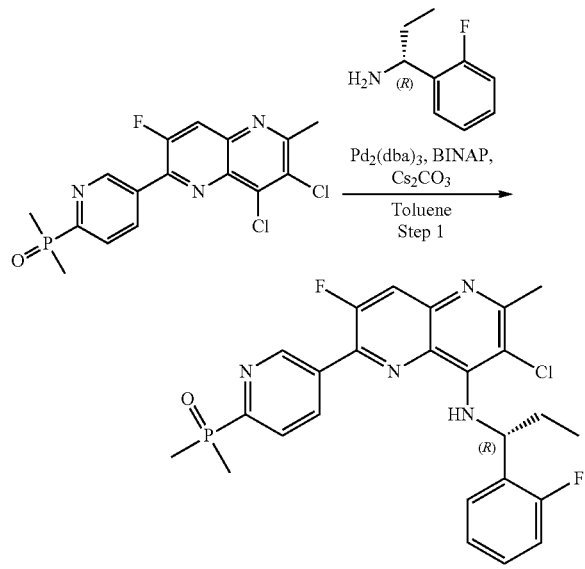

A mixture of 3,4-dichloro-6-[6-(dimethylphosphoryl)pyridin-3-yl]-7-fluoro-2-methyl-1,5-naphthyridine (100 mg, 0.260 mmol), (1R)-1-(2-fluorophenyl)propan-1-amine (48 mg, 0.312 mmol), $Pd_2(dba)_3$ (24 mg, 0.026 mmol), BINAP (32 mg, 0.052 mmol) and $Cs_2CO_3$ (127 mg, 0.390 mmol) in Toluene (2 mL) was stirred for 3 h at 100° C. under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 45% to 60% gradient in 20 min; detector, 254 nm. This resulted in 3-chloro-6-[6-(dimethylphosphoryl)pyridin-3-yl]-7-fluoro-N-[(1R)-1-(2-fluorophenyl)propyl]-2-methyl-1,5-naphthyridin-4-amine (48 mg, 36%) as a yellow solid. MS ESI calculated for $C_{25}H_{24}ClF_2N_4OP$ [M+H]$^+$, 501.13, found 500.95. $^1$H NMR (400 MHz, DMSO-$d_6$) δ 9.26 (s, 1H), 8.44-8.39 (m, 1H), 8.20 (d, J=11.8 Hz, 1H), 8.17-8.11 (m, 1H), 7.49-7.42 (m, 1H), 7.29-7.21 (m, 1H), 7.15-7.04 (m, 2H), 6.96-6.87 (m, 1H), 6.30-6.11 (m, 1H), 2.62 (s, 3H), 2.16-2.01 (m, 1H), 2.00-1.87 (m, 1H), 1.77 (s, 3H), 1.74 (s, 3H), 0.97 (t, J=7.3 Hz, 3H). $^{19}$F NMR (377 MHz, DMSO-$d_6$) δ −119.04, −120.91. $^{31}$P NMR (162 MHz, DMSO-$d_6$) δ 34.25.

Example 23: 3-chloro-6-[6-(dimethylphosphoryl)pyridin-3-yl]-7-fluoro-N-[(1S)-1-(2-fluorophenyl)propyl]-2-methyl-1,5-naphthyridin-4-amine

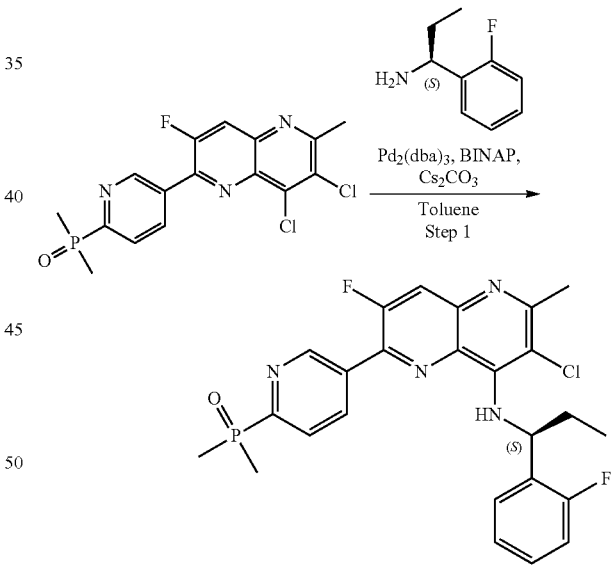

A mixture of 3,4-dichloro-6-[6-(dimethylphosphoryl)pyridin-3-yl]-7-fluoro-2-methyl-1,5-naphthyridine (100 mg, 0.260 mmol), (1S)-1-(2-fluorophenyl)propan-1-amine (48 mg, 0.312 mmol), $Pd_2(dba)_3$ (24 mg, 0.026 mmol), BINAP (32 mg, 0.052 mmol) and $Cs_2CO_3$ (127 mg, 0.390 mmol) in Toluene (1.5 mL) was stirred for 3 h at 100° C. under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 45% to 60% gradient in 20 min; detector, 254 nm. This resulted in 3-chloro-6-[6-(dimethylphosphoryl)pyridin-3-yl]-7-fluoro-N-[(1S)-1-(2-fluorophenyl)propyl]-2-methyl-1,5-naphthyridin-4-amine (54 mg, 41%) as a yellow solid. MS ESI calculated for C$_{25}$H$_{24}$ClF$_2$N$_4$OP [M+H]$^+$, 500.13, found 500.95. $^1$H NMR (400 MHz, DMSO-d$_6$)) δ 9.26 (s, 1H), 8.44-8.39 (m, 1H), 8.20 (d, J=11.8 Hz, 1H), 8.17-8.11 (m, 1H), 7.49-7.42 (m, 1H), 7.29-7.21 (m, 1H), 7.15-7.04 (m, 2H), 6.96-6.87 (m, 1H), 6.30-6.11 (m, 1H), 2.62 (s, 3H), 2.16-2.01 (m, 1H), 2.00-1.87 (m, 1H), 1.77 (s, 3H), 1.74 (s, 3H), 0.97 (t, J=7.3 Hz, 3H). $^{19}$F NMR (377 MHz, DMSO-d$_6$) δ −119.04, −120.91. $^{31}$P NMR (162 MHz, DMSO-d$_6$) δ 34.25.

Example 24: 3-chloro-6-[4-(dimethylphosphoryl)-3-fluorophenyl]-7-fluoro-N-[(1R)-1-(2-fluorophenyl)propyl]-2-methyl-1,5-naphthyridin-4-amine

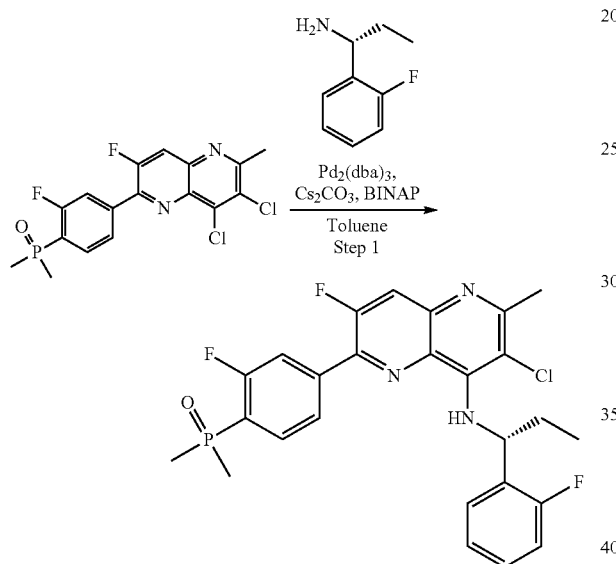

To a solution of 3,4-dichloro-6-[4-(dimethylphosphoryl)-3-fluorophenyl]-7-fluoro-2-methyl-1,5-naphthyridine (50 mg, 0.125 mmol), BINAP (16 mg, 0.025 mmol) and (1R)-1-(2-fluorophenyl)propan-1-amine (21 mg, 0.138 mmol) in Toluene (1 mL) were added Cs$_2$CO$_3$ (61 mg, 0.188 mmol) and Pd$_2$(dba)$_3$ (11 mg, 0.013 mmol). After stirring for 16 h at 100° C. under a nitrogen atmosphere. The resulting mixture was filtered, and the filter cake was washed with MeOH (3×5 mL). The filtrate was concentrated under reduced pressure. The residue was purified by reversed-phase flash chromatography with the following conditions: column, C$_{18}$ silica gel; mobile phase, CH$_3$CN in water (10 mmol/L NH$_4$HCO$_3$), 40% to 90% gradient in 30 min; detector, 254 nm. This resulted in 3-chloro-6-[4-(dimethylphosphoryl)-3-fluorophenyl]-7-fluoro-N-[(1R)-1-(2-fluorophenyl)propyl]-2-methyl-1,5-naphthyridin-4-amine (9 mg, 14%) as a yellow solid. MS ESI calculated for C$_{26}$H$_{24}$ClF$_3$N$_3$OP [M+H]$^+$, 518.13, found 518.05. $^1$H NMR (400 MHz, Chloroform-d) δ 8.19-8.07 (m, 1H), 8.02-7.86 (m, 2H), 7.82-7.71 (m, 1H), 7.26-7.17 (m, 2H), 7.07-6.98 (m, 2H), 6.88-6.62 (m, 1H), 6.33-6.17 (m, 1H), 2.71 (s, 3H), 2.12-1.99 (m, 2H), 1.90 (s, 3H), 1.87 (s, 3H), 1.03 (t, J=7.4 Hz, 3H). $^{19}$F NMR (376 MHz, Chloroform-d) δ −105.60, −118.03, −120.19. $^{31}$P NMR (162 MHz, Chloroform-d) δ 30.55.

Example 25 and 26: (S)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide and (R)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide Synthetic Scheme

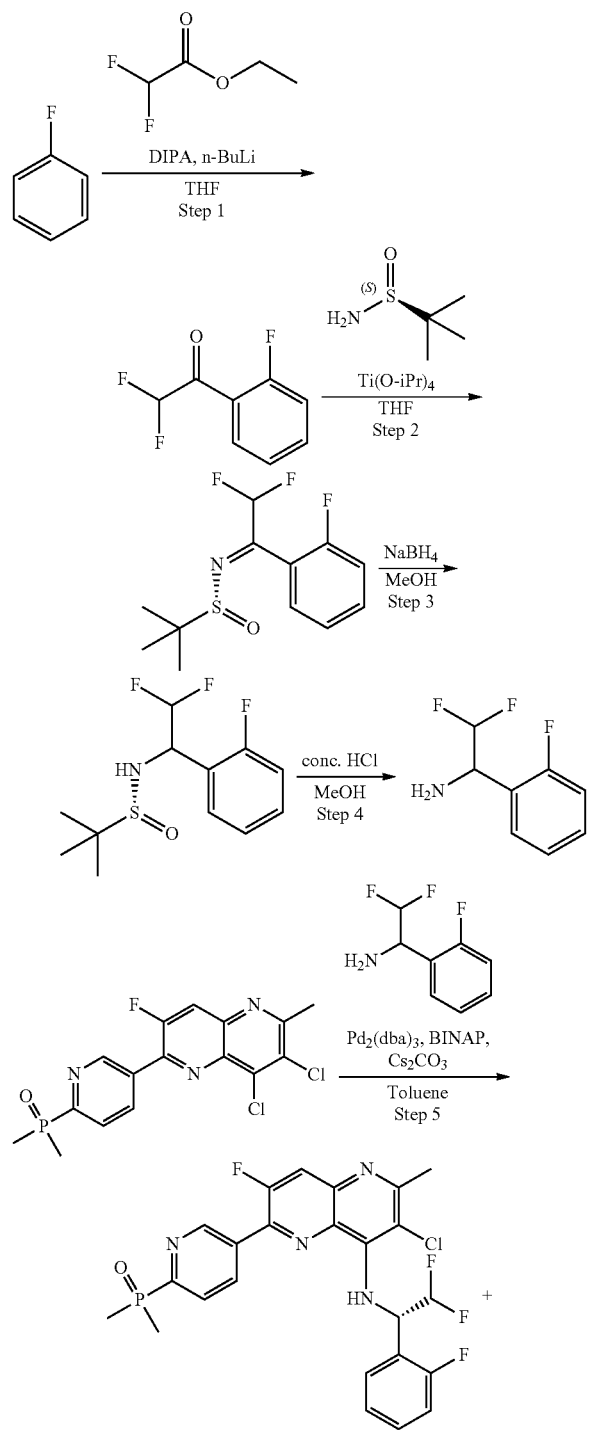

-continued

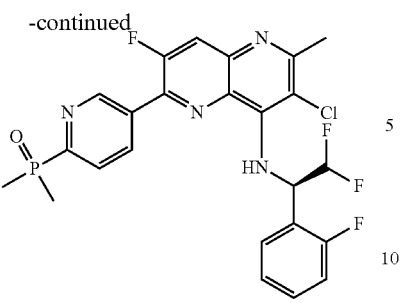

Preparation 25A:
2,2-difluoro-1-(2-fluorophenyl)ethanone

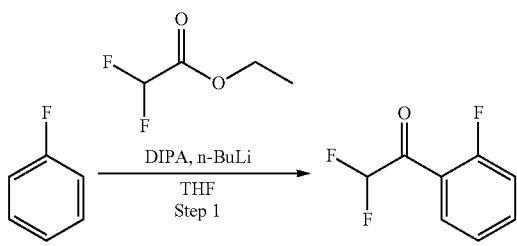

To a stirred solution of DIPA (16.2 mL, 114.459 mmol) in THF (350 mL) was added 2.5 M of n-BuLi in hexanes (45.8 mL, 114.459 mmol) dropwise at −78° C. under nitrogen atmosphere. The resulting mixture was stirred for 30 min at 0° C. under nitrogen atmosphere. To the above mixture was added fluorobenzene (10.00 g, 104.054 mmol) dropwise at −78° C. The resulting mixture was stirred for additional 2.5 h at −78° C. To the above mixture was added ethyl 2,2-difluoroacetate (15.49 g, 124.865 mmol) dropwise at −78° C. The resulting mixture was stirred for additional 20 min at −50° C. The reaction was quenched with HCl (2 M) at 0° C. The resulting mixture was extracted with EtOAc (3×300 mL). The combined organic layers were washed with brine (1×500 mL), dried over anhydrous Na$_2$SO$_4$. After filtration, the filtrate was concentrated under reduced pressure. The residue was purified by silica gel column chromatography, eluted with PE/EA (10:1) to afford 2,2-difluoro-1-(2-fluorophenyl)ethanone (1.47 g, 8%) as a yellow liquid. $^1$H NMR (300 MHz, Chloroform-d) δ 7.99-7.94 (m, 1H), 7.70-7.63 (m, 1H), 7.37-7.29 (m, 1H), 7.26-7.17 (m, 1H), 6.63-6.26 (m, 1H).

Preparation 25B: (R)—N-[2,2-difluoro-1-(2-fluorophenyl)ethylidene]-2-methylpropane-2-sulfinamide

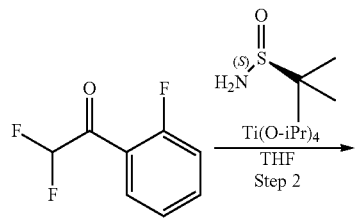

-continued

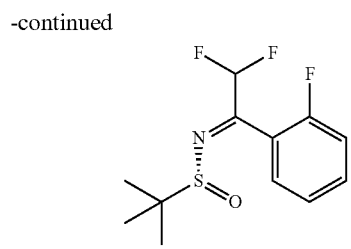

To a stirred solution of 2,2-difluoro-1-(2-fluorophenyl)ethanone (1.70 g, 9.763 mmol) and (S)-2-methylpropane-2-sulfinamide (1.42 g, 11.716 mmol) in THF (15 mL) was added Ti(O-iPr)$_4$ (5.55 g, 19.526 mmol) dropwise at room temperature under nitrogen atmosphere. The resulting mixture was stirred for 2 h at 80° C. under nitrogen atmosphere. The reaction was quenched with water at 0° C. The resulting mixture was filtered, and the filter cake was washed with EtOAc (3×100 mL). The filtrate was concentrated under reduced pressure. The residue was purified by silica gel column chromatography, eluted with PE/EA (10/1) to afford (R)—N-[2,2-difluoro-1-(2-fluorophenyl)ethylidene]-2-methylpropane-2-sulfinamide (425 mg, 15%) as a yellow liquid. $^1$H NMR (300 MHz, Chloroform-d) δ 7.55-7.31 (m, 2H), 7.25-7.08 (m, 2H), 6.25 (t, J=55.7 Hz, 1H), 1.31 (s, 9H).

Preparation 25C: (R)—N-[(1S)-2,2-difluoro-1-(2-fluorophenyl)ethyl]-2-methylpropane-2-sulfinamide

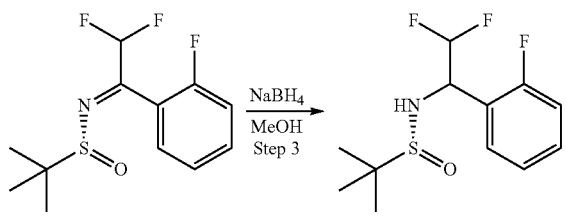

To a solution of (R)—N-[2,2-difluoro-1-(2-fluorophenyl)ethylidene]-2-methylpropane-2-sulfinamide (870 mg, 3.137 mmol) in MeOH (10 mL) was added NaBH$_4$ (142 mg, 3.764 mmol) at room temperature under nitrogen atmosphere. The resulting mixture was stirred for 2 h at 80° C. under nitrogen atmosphere. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 60% B in 20 min; 254/220 nm to afford (R)—N-[(1S)-2,2-difluoro-1-(2-fluorophenyl)ethyl]-2-methylpropane-2-sulfinamide (750 mg, 85%) as a yellow liquid. MS ESI calculated for C$_{12}$H$_{16}$F$_3$NOS [M+H]$^+$, 280.09, found 280.10. $^1$H NMR (400 MHz, Chloroform-d) δ 7.45-7.32 (m, 2H), 7.24-7.18 (m, 1H), 7.16-7.08 (m, 1H), 6.27-5.84 (m, 1H), 5.03-4.81 (m, 1H), 4.01-3.89 (m, 1H), 1.24 (d, J=9.0 Hz, 9H).

Preparation 25D: 2,2-difluoro-1-(2-fluorophenyl)ethanamine

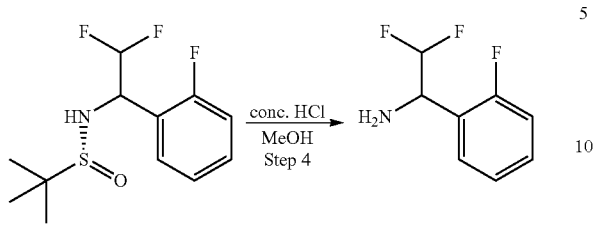

To a stirred solution of (R)—N-[2,2-difluoro-1-(2-fluorophenyl)ethyl]-2-methylpropane-2-sulfinamide (750 mg, 2.685 mmol) in MeOH (8 mL) was added conc. HCl (2 mL, 65.826 mmol) dropwise at 0° C. The resulting mixture was stirred for 1 h at room temperature. The resulting mixture was concentrated under reduced pressure. The residue was basified to pH 8 with saturated NaHCO$_3$ (aq.). The resulting mixture was extracted with CH$_2$Cl$_2$ (4×30 mL). The combined organic layers were dried over anhydrous Na$_2$SO$_4$. After filtration, the filtrate was concentrated under reduced pressure. The residue was purified by silica gel column chromatography, eluted with CH$_2$Cl$_2$/MeOH (10/1) to afford 2,2-difluoro-1-(2-fluorophenyl)ethanamine (350 mg, 74%) as a yellow oil. MS ESI calculated for C$_8$H$_8$F$_3$N [M+H]$^+$, 176.06, found 176.21. $^1$H NMR (400 MHz, DMSO-d$_6$) δ 7.64-7.55 (m, 1H), 7.41-7.32 (m, 1H), 7.26-7.15 (m, 2H), 6.20-5.86 (m, 1H), 4.44-4.30 (m, 1H). $^{19}$F NMR (376 MHz, DMSO-d$_6$) δ −118.40, −124.75.

Example 25 and 26: (S)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide and (R)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide

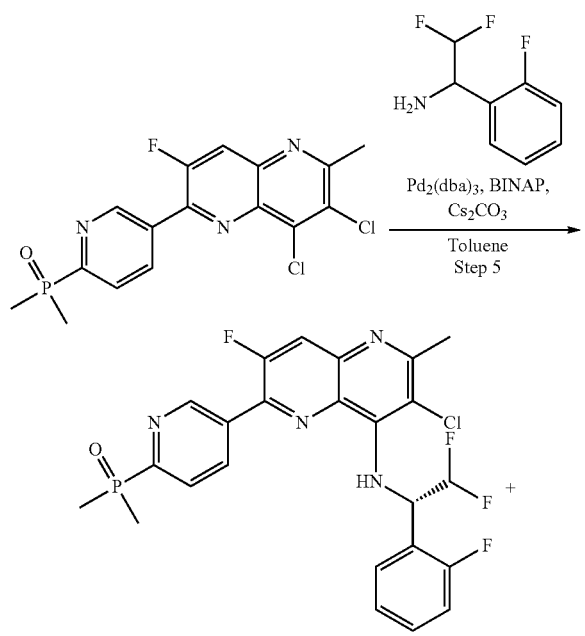

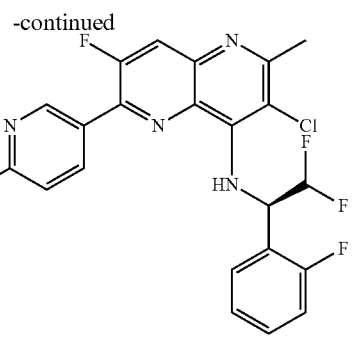

A mixture of 3,4-dichloro-6-[6-(dimethylphosphoryl)pyridin-3-yl]-7-fluoro-2-methyl-1,5-naphthyridine (200 mg, 0.521 mmol), Pd$_2$(dba)$_3$ (47 mg, 0.052 mmol), BINAP (65 mg, 0.104 mmol) and Cs$_2$CO$_3$ (254 mg, 0.782 mmol) in Toluene (3 mL) was stirred for 3 h at 100° C. under nitrogen atmosphere. The resulting mixture was concentrated under reduced pressure. The residue was purified by silica gel column chromatography, eluted with CH$_2$Cl$_2$/MeOH (10/1) followed by SFC with the following conditions (Column: CHIRALPAK IG, 3*25 cm, 5 m; Mobile Phase A: CO$_2$, Mobile Phase B: MeOH (0.1% 2M NH$_3$-MeOH); Flow rate: 100 mL/min; Gradient: isocratic 30% B; Column Temperature(° C.): 35; Back Pressure(bar): 100; Wave Length: 206/328 nm). The first peak afforded 87 mg (32%) as a white solid. MS ESI calculated for C$_{24}$H$_{20}$ClF$_4$N$_4$OP [M+H]$^+$, 523.10, found 522.95. $^1$H NMR (400 MHz, Methanol-d$_4$) δ 9.28 (s, 1H), 8.50-8.42 (m, 1H), 8.20-8.14 (m, 1H), 8.05-7.95 (m, 1H), 7.52-7.46 (m, 1H), 7.41-7.32 (m, 1H), 7.21-7.15 (m, 1H), 7.14-7.07 (m, 1H), 7.03-6.91 (m, 1H), 6.55-6.19 (m, 1H), 2.72 (s, 3H), 1.91 (s, 3H), 1.88 (s, 3H). $^{19}$F NMR (377 MHz, Methanol-d$_4$) δ −118.96, −121.58, −125.95, −126.66, −130.35, −131.11. $^{31}$P NMR (162 MHz, Methanol-d$_4$) δ 41.63.

The last peak afforded 77 mg (28%) as a white solid. MS ESI calculated for C$_{24}$H$_{20}$ClF$_4$N$_4$OP [M+H]$^+$, 523.10, found 522.95. $^1$H NMR (400 MHz, Methanol-d$_4$) δ 9.28 (s, 1H), 8.48-8.43 (m, 1H), 8.20-8.14 (m, 1H), 7.99 (d, J=11.5 Hz, 1H), 7.52-7.46 (m, 1H), 7.41-7.32 (m, 1H), 7.21-7.15 (m, 1H), 7.14-7.07 (m, 1H), 7.03-6.91 (m, 1H), 6.55-6.19 (m, 1H), 2.72 (s, 3H), 1.92 (s, 3H), 1.88 (s, 3H). $^{19}$F NMR (377 MHz, Methanol-d$_4$) δ −118.96, −121.47, −125.92, −126.65, −130.30, −131.03. $^{31}$P NMR (162 MHz, Methanol-d$_4$) δ 41.63.

Example 27: 3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile Synthetic Scheme

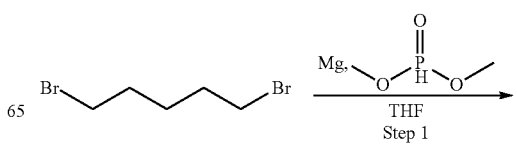

Step 1

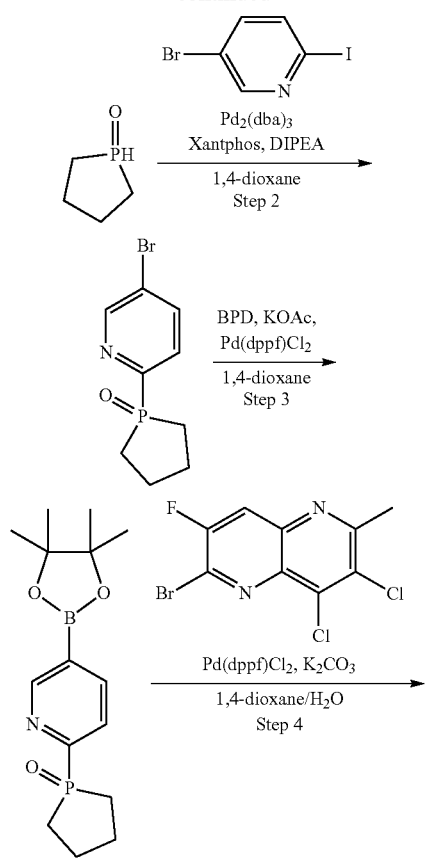

Preparation 27A: 1lambda5-phospholan-1-one

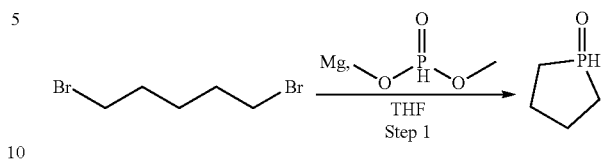

To a solution of 1,4-dibromobutane (19.62 g, 90.868 mmol) in THF (100 mL) was added activated Mg (4.42 g, 181.736 mmol) in ports. The mixture was stirred at <30° C. for 2 h. To the above mixture was added dimethyl phosphite (5.00 g, 45.434 mmol) in 5 mL THF dropwise over 0.5 h at <30° C. The resulting mixture was stirred for additional 1 h at room temperature. The reaction was quenched by the addition of 20 g of $K_2CO_3$ in water (50 mL) at 20° C. The resulting mixture was filtered, and the filter cake was washed with EtOH (3×10 mL). The filtrate was concentrated under reduced pressure. This resulted in 1lambda5-phospholan-1-one (3.10 g, 51%) as a colorless oil. $^{31}P$ NMR (162 MHz, Chloroform-d) δ 47.78.

Preparation 27B: 1-(5-bromopyridin-2-yl)-1lambda5-phospholan-1-one

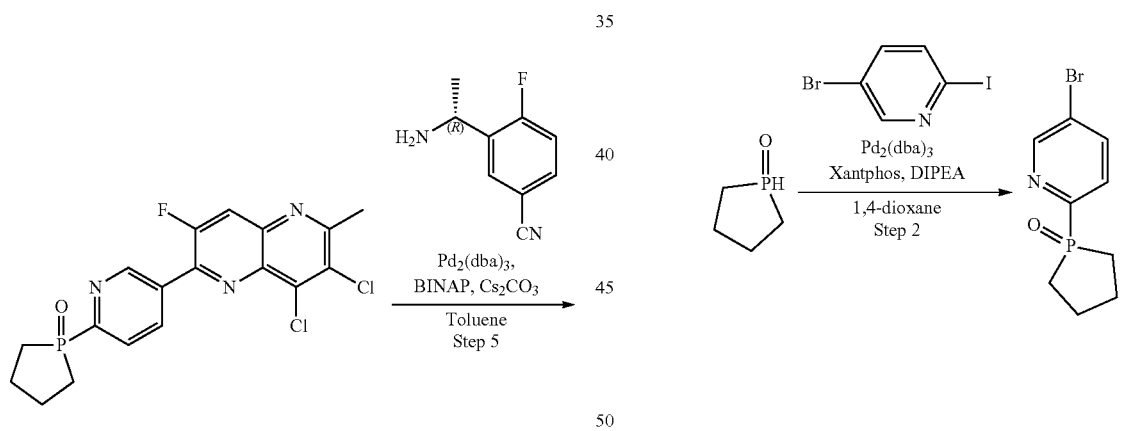

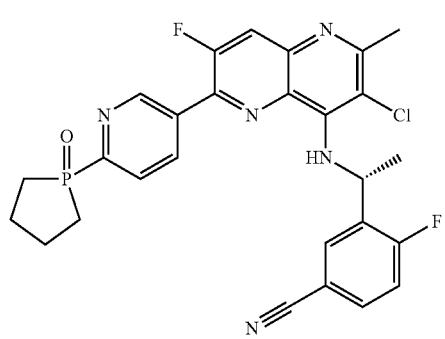

A mixture of $Pd_2(dba)_3$ (97 mg, 0.106 mmol), DIPEA (164 mg, 1.268 mmol), XantPhos (122 mg, 0.211 mmol), 5-bromo-2-iodopyridine (300 mg, 1.057 mmol) and 1lambda5-phospholan-1-one (330 mg, 3.171 mmol) in 1,4-dioxane (6 mL) was stirred for overnight at 80° C. The resulting mixture was concentrated under reduced pressure. The residue was purified by silica gel column chromatography, eluted with $CH_2Cl_2$/MeOH (16/1) to afford 1-(5-bromopyridin-2-yl)-1lambda5-phospholan-1-one (88 mg, 32%) as a yellow solid. MS ESI calculated for $C_9H_{11}BrNOP$ $[M+H]^+$, 259.98 261.98, found 259.90 261.90. $^1H$ NMR (400 MHz, Chloroform-d) δ 8.78 (s, 1H), 8.12-8.04 (m, 1H), 8.02-7.89 (m, 1H), 2.24-1.87 (m, 8H). $^{31}P$ NMR (162 MHz, Chloroform-d) δ 62.02.

Preparation 27C: 1-[5-(4,4,5,5-tetramethyl-1,3,2-dioxaborolan-2-yl)pyridin-2-yl]-1lambda5-phospholan-1-one

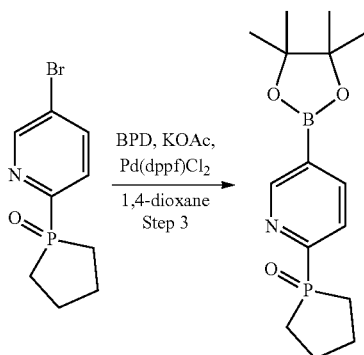

To a solution of 1-(5-bromopyridin-2-yl)-1lambda5-phospholan-1-one (250 mg, 0.961 mmol) and BPD (366 mg, 1.442 mmol) in 1,4-dioxane (5 mL) were added KOAc (189 mg, 1.923 mmol) and Pd(dppf)Cl$_2$·CH$_2$Cl$_2$ (78 mg, 0.096 mmol). After stirring for 3 h at 100° C. under a nitrogen atmosphere. The resulting mixture was allowed to cool down to room temperature. The resulting mixture was concentrated under reduced pressure. The residue was purified by trituration with PE (10 mL) to afford 1-[5-(4,4,5,5-tetramethyl-1,3,2-dioxaborolan-2-yl)pyridin-2-yl]-1lambda5-phospholan-1-one (420 mg, 99%) as a brown solid which was used in the next step directly. MS ESI calculated for C$_{15}$H$_{23}$BNO$_3$P [M+H]$^+$, 308.15, found N/A.

Preparation 27D: 1-[5-(7,8-dichloro-3-fluoro-6-methyl-1,5-naphthyridin-2-yl)pyridin-2-yl]-1lambda5-phospholan-1-one

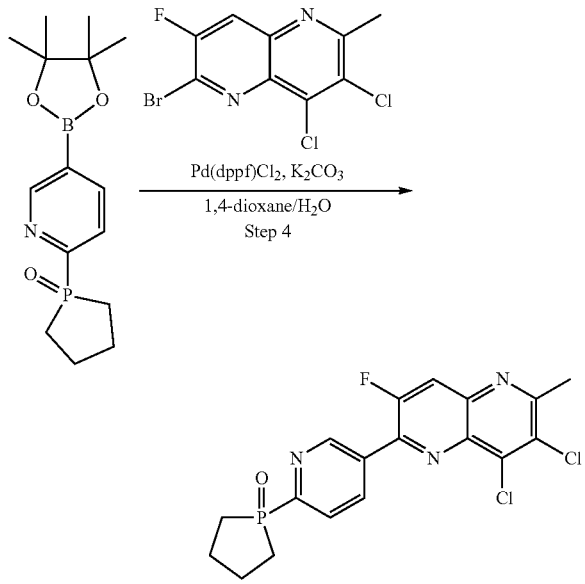

To a solution of 6-bromo-3,4-dichloro-7-fluoro-2-methyl-1,5-naphthyridine (250 mg, 0.807 mmol) and 1-[5-(4,4,5,5-tetramethyl-1,3,2-dioxaborolan-2-yl)pyridin-2-yl]-1lambda5-phospholan-1-one (347 mg, 1.130 mmol) in 1,4-dioxane (5 mL) and H$_2$O (1 mL) were added K$_2$CO$_3$ (223 mg, 1.614 mmol) and Pd(dppf)Cl$_2$·CH$_2$Cl$_2$ (66 mg, 0.081 mmol). After stirring for 2 h at 80° C. under a nitrogen atmosphere. The resulting mixture was concentrated under reduced pressure. The residue was purified by silica gel column chromatography, eluted with CH$_2$Cl$_2$/MeOH (15:1) to afford 1-[5-(7,8-dichloro-3-fluoro-6-methyl-1,5-naphthyridin-2-yl)pyridin-2-yl]-1lambda5-phospholan-1-one (160 mg, 48%) as a pink solid. MS ESI calculated for C$_{18}$H$_{15}$Cl$_2$FN$_3$OP [M+H]$^+$, 410.03, found 410.10. $^1$H NMR (400 MHz, Chloroform-d) δ 9.57 (s, 1H), 8.64 (s, 1H), 8.46-8.31 (m, 1H), 8.12 (d, J=11.0 Hz, 1H), 2.90 (s, 3H), 2.45-1.92 (m, 8H).

Example 27: 3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile

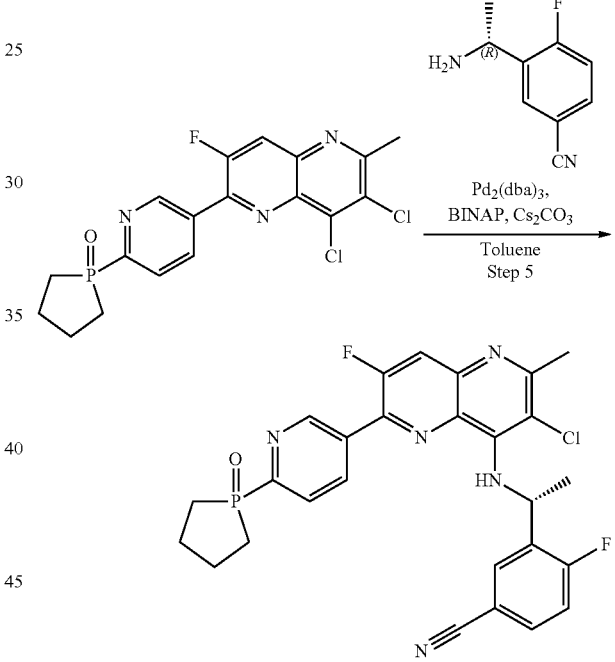

To a stirred solution of 1-[5-(7,8-dichloro-3-fluoro-6-methyl-1,5-naphthyridin-2-yl)pyridin-2-yl]-1lambda5-phospholan-1-one (80 mg, 0.195 mmol) and 3-[(1R)-1-aminoethyl]-4-fluorobenzonitrile (38 mg, 0.234 mmol) in Toluene (2 mL) were added BINAP (24 mg, 0.039 mmol), Cs$_2$CO$_3$ (95 mg, 0.292 mmol) and Pd$_2$(dba)$_3$ (18 mg, 0.020 mmol) in portions at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (15/1) followed by reversed-phase flash chromatography with the following conditions: column, C18 silica gel; mobile phase, CH$_3$CN in water (10 mmol/L NH$_4$HCO$_3$), 40% to 70% gradient in 30 min; detector, 254 nm. This resulted in 3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile (40 mg, 36%) as a yellow green solid. MS ESI calculated for $C_{27}H_{23}ClF_2N_5OP$ [M+H]+, 538.13, found 537.95. $^1$H NMR (400 MHz, DMSO-$d_6$) δ 9.16 (s, 1H), 8.39-8.32 (m, 1H), 8.23-8.12 (m, 2H), 8.05-7.98 (m, 1H), 7.82-7.75 (m, 1H), 7.30-7.20 (m, 1H), 6.98 (d, J=8.5 Hz, 1H), 6.40-6.30 (m, 1H), 2.65 (s, 3H), 2.24-1.76 (m, 8H), 1.66 (d, J=6.8 Hz, 3H). $^{19}$F NMR (377 MHz, DMSO-$d_6$) δ −109.29, −120.92. $^{31}$P NMR (162 MHz, DMSO-$d_6$) δ 58.99.

Example 28: 3-[(1R)-1-({3-chloro-6-[2-(diethylphosphoryl)pyrimidin-5-yl]-7-fluoro-2-methyl-1,5-naphthyridin-4-yl}amino)ethyl]-4-fluorobenzonitrile Synthetic Scheme

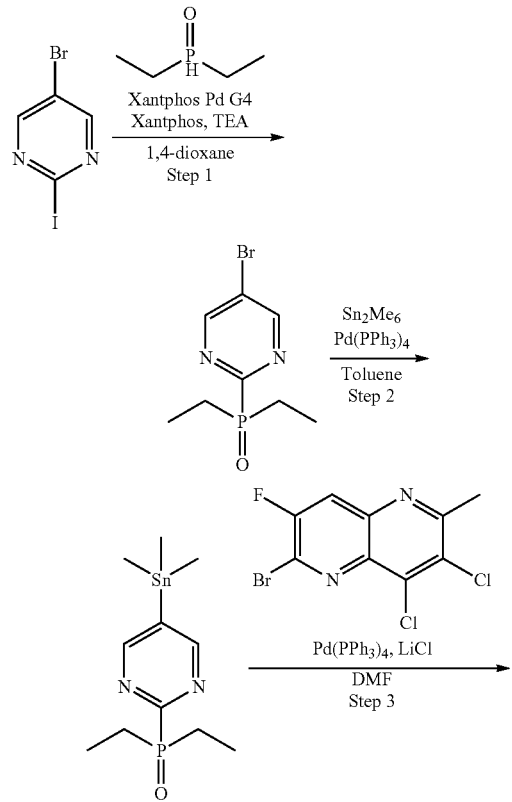

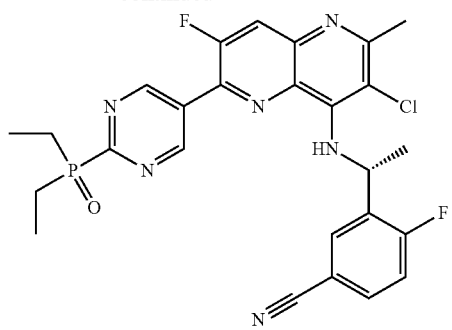

Preparation 28A: 5-bromo-2-(diethylphosphoryl)pyrimidine

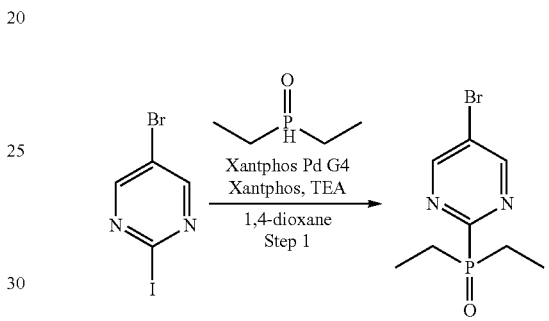

To a stirred mixture of 5-bromo-2-iodopyrimidine (10.00 g, 35.102 mmol) and (ethylphosphonoyl)ethane (5.59 g, 52.653 mmol) in 1,4-dioxane (200 mL) were added Et$_3$N (5.33 g, 52.653 mmol), Xantphos (4.06 g, 7.020 mmol) and Xantphos Pd G$_4$ (3.38 g, 3.510 mmol) at room temperature under nitrogen atmosphere. The resulting mixture was stirred for overnight at 90° C. under nitrogen atmosphere. The resulting mixture was concentrated under reduced pressure. The residue was purified by silica gel column chromatography, eluted with $CH_2Cl_2$/MeOH (9/1) to afford 5-bromo-2-(diethylphosphoryl)pyrimidine (2.70 g, 29%) as a Brown yellow solid. MS ESI calculated for $C_8H_{12}BrN_2OP$ [M+H]+, 262.99, found 262.95. $^1$H NMR (400 MHz, Chloroform-d) δ 8.96 (s, 2H), 2.22-2.08 (m, 4H), 1.28-1.11 (m, 6H). $^{31}$P NMR (162 MHz, Chloroform-d) δ 44.36.

Preparation 28B: 2-(diethylphosphoryl)-5-(trimethylstannyl)pyrimidine

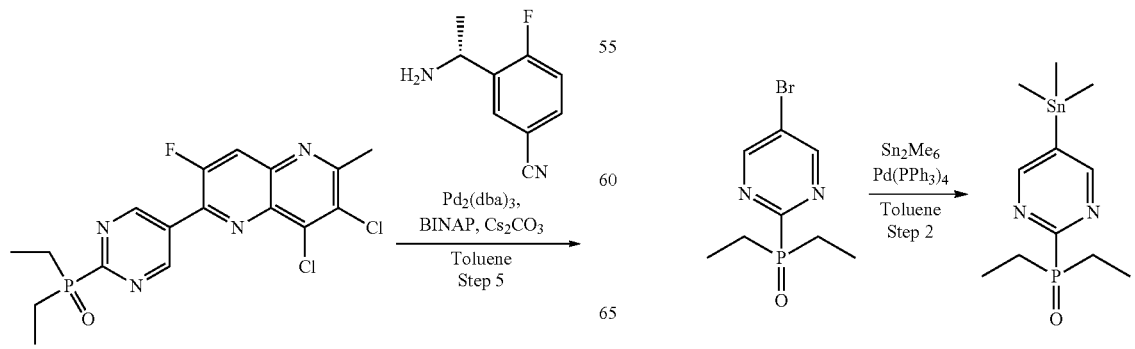

To a stirred solution of 5-bromo-2-(diethylphosphoryl) pyrimidine (500 mg, 1.901 mmol) and hexamethyldistannane (809 mg, 2.471 mmol) in toluene (5 mL) was added Pd(PPh$_3$)$_4$(220 mg, 0.190 mmol) at room temperature under nitrogen atmosphere. The resulting mixture was stirred for overnight at 110° C. under nitrogen atmosphere. The resulting mixture was concentrated under reduced pressure. The residue was used in the next step without further purification. MS ESI calculated for C$_{11}$H$_{21}$N$_2$OPSn [M+H]$^+$, 349.04, found 349.15.

Preparation 28C: 3,4-dichloro-6-[2-(diethylphosphoryl)pyrimidin-5-yl]-7-fluoro-2-methyl-1,5-naphthyridine

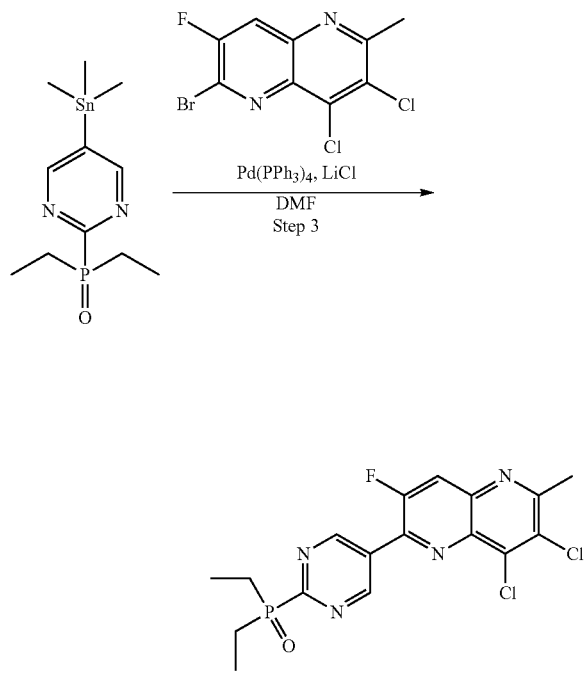

To a stirred solution of 2-(diethylphosphoryl)-5-(trimethylstannyl)pyrimidine (160 mg, 0.461 mmol) and 6-bromo-3,4-dichloro-7-fluoro-2-methyl-1,5-naphthyridine (114 mg, 0.369 mmol) in DMF (2 mL) were added LiCl (31 mg, 0.738 mmol) and Pd(PPh$_3$)$_4$(43 mg, 0.037 mmol) at room temperature. The resulting mixture was stirred for 3 h at 100° C. under nitrogen atmosphere. The resulting mixture was concentrated under reduced pressure. The residue was purified by silica gel column chromatography, eluted with CH$_2$Cl$_2$/MeOH (9/1) to afford 3,4-dichloro-6-[2-(diethylphosphoryl)pyrimidin-5-yl]-7-fluoro-2-methyl-1,5-naphthyridine (60 mg, 39%) as a brown yellow solid. MS ESI calculated for C$_{17}$H$_{16}$Cl$_2$FN$_4$OP [M+H]$^+$, 413.04, found 413.30. $^1$H NMR (400 MHz, Chloroform-d) δ 9.69 (s, 2H), 8.17 (d, J=11.0 Hz, 1H), 2.92 (s, 3H), 2.36-2.11 (m, 4H), 1.36-1.12 (m, 6H).

Example 28: 3-[(1R)-1-({3-chloro-6-[2-(diethylphosphoryl)pyrimidin-5-yl]-7-fluoro-2-methyl-1,5-naphthyridin-4-yl}amino)ethyl]-4-fluorobenzonitrile

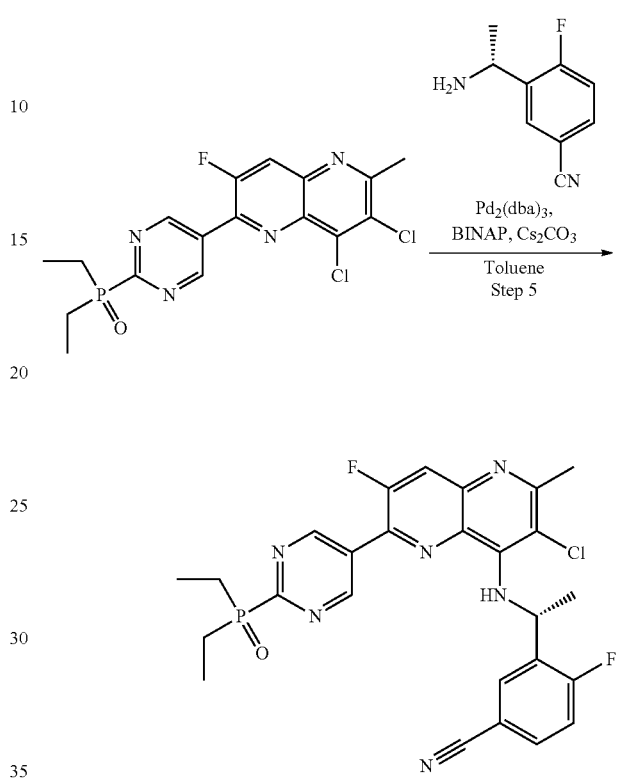

To a stirred solution of 3,4-dichloro-6-[2-(diethylphosphoryl)pyrimidin-5-yl]-7-fluoro-2-methyl-1,5-naphthyridine (50 mg, 0.121 mmol) and 3-[(1R)-1-aminoethyl]-4-fluorobenzonitrile (30 mg, 0.181 mmol) in Toluene (1 mL) were added BINAP (15 mg, 0.024 mmol), Cs$_2$CO$_3$ (59 mg, 0.181 mmol) and Pd$_2$(dba)$_3$ (11 mg, 0.012 mmol) in portions at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (9/1) to afford 3-[(1R)-1-({3-chloro-6-[2-(diethylphosphoryl)pyrimidin-5-yl]-7-fluoro-2-methyl-1,5-naphthyridin-4-yl}amino)ethyl]-4-fluorobenzonitrile as a brown solid. The residue was purified by reversed-phase flash chromatography with the following conditions: column, C18 silica gel; mobile phase, CH$_3$CN in water (10 mmol/L NH$_4$HCO$_3$), 30% to 60% gradient in 30 min; detector, 254 nm. This resulted in 3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile (6 mg, 8%) as a yellow solid. MS ESI calculated for C$_{26}$H$_{24}$ClF$_2$N$_6$OP [M+H]$^+$, 541.14, found 541.05. $^1$H NMR (300 MHz, Methanol-d$_4$) δ 9.34 (d, J=1.5 Hz, 2H), 7.97 (d, J=11.4 Hz, 1H), 7.83-7.75 (m, 1H), 7.65-7.56 (m, 1H), 7.21-7.04 (m, 1H), 6.52-6.39 (m, 1H), 2.72 (s, 3H), 2.50-2.16 (m, 4H), 1.72 (d, J=6.8 Hz, 3H), 1.36-1.13 (m, 6H). $^{19}$F NMR (282 MHz, Methanol-d$_4$) δ −110.96, −122.35. $^{31}$P NMR (162 MHz, Methanol-d$_4$) δ 48.64.

171

Example 29: 3-chloro-N-[2,2-difluoro-1-(2-fluoro-phenyl)ethyl]-6-[2-(dimethylphosphoryl)pyrimidin-5-yl]-7-fluoro-2-methyl-1,5-naphthyridin-4-amine

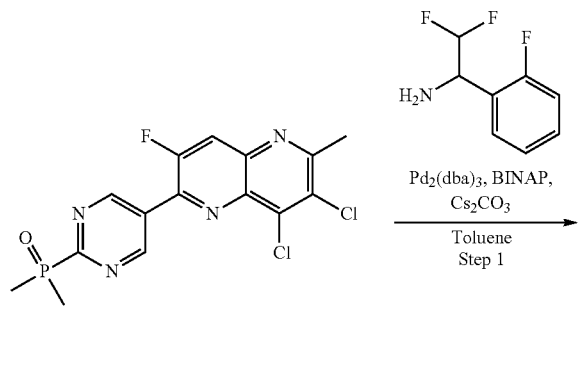

172

Example 30: 3-[(1S)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile

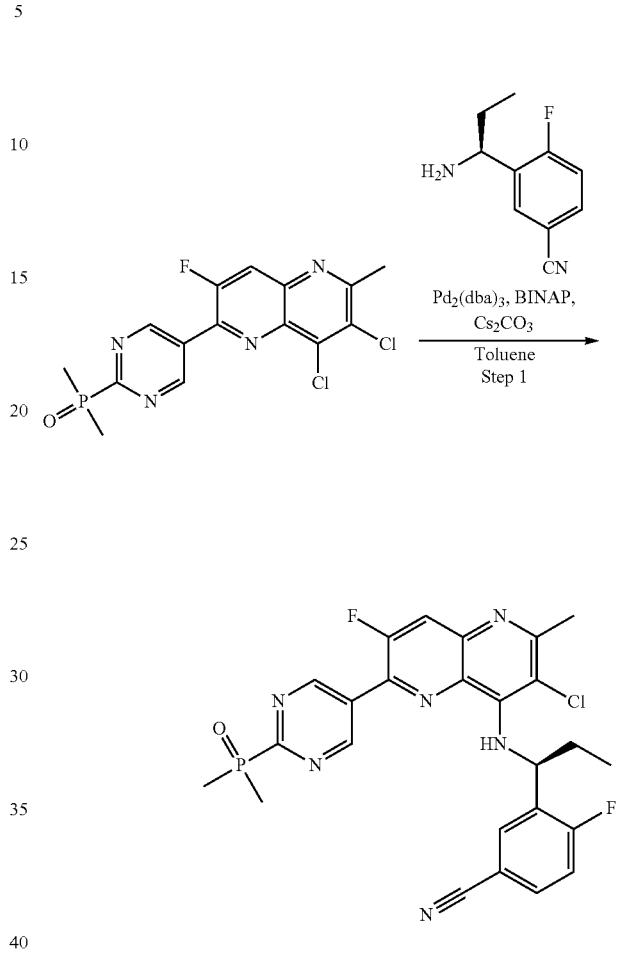

A mixture of 3,4-dichloro-6-[2-(dimethylphosphoryl)pyrimidin-5-yl]-7-fluoro-2-methyl-1,5-naphthyridine (110 mg, 0.286 mmol), 2,2-difluoro-1-(2-fluorophenyl)ethanamine (75 mg, 0.429 mmol), Pd$_2$(dba)$_3$ (26 mg, 0.029 mmol,), Xantphos (33 mg, 0.057 mmol) and Cs$_2$CO$_3$ (139 mg, 0.429 mmol) in Toluene (2 mL) was stirred for 3 h at 100° C. under nitrogen atmosphere. The resulting mixture was concentrated under reduced pressure. The residue was purified by silica gel column chromatography, eluted with CH$_2$Cl$_2$/MeOH (10/1) followed by reversed-phase flash chromatography with the following conditions: column, C18 silica gel; mobile phase, CH$_3$CN in water (10 mmol/L NH$_4$HCO$_3$), 45% to 60% gradient in 20 min; detector, 254 nm. This resulted in 3-chloro-N-[2,2-difluoro-1-(2-fluorophenyl)ethyl]-6-[2-(dimethylphosphoryl)pyrimidin-5-yl]-7-fluoro-2-methyl-1,5-naphthyridin-4-amine (90 mg, 60%) as a yellow solid. MS ESI calculated for C$_{23}$H$_{19}$ClF$_4$N$_5$OP [M+H]$^+$, 524.10, found 523.95. $^1$H NMR (400 MHz, DMSO-d$_6$) δ 9.50-9.46 (m, 2H), 8.37-8.31 (m, 1H), 7.72-7.65 (m, 1H), 7.43-7.35 (m, 1H), 7.27-7.10 (m, 3H), 6.97-6.84 (m, 1H), 6.81-6.48 (m, 1H), 2.72-2.65 (m, 3H), 1.89 (s, 3H), 1.85 (s, 3H). $^{19}$F NMR (376 MHz, DMSO-d$_6$) δ −117.32, −117.34, −125.19, −125.21, −125.27, −125.28. $^{31}$P NMR (162 MHz, DMSO-d$_6$) δ 34.53.

A mixture of 3,4-dichloro-6-2-(dimethylphosphorylpyrimidin-5-yl-7-fluoro-2-methyl-1,5-naphthyridine (80 mg, 0.208 mmol), 3-[(1S)-1-aminopropyl]-4-fluorobenzonitrile (45 mg, 0.250 mmol), Pd$_2$(dba)$_3$ (19 mg, 0.021 mmol), BINAP (26 mg, 0.042 mmol) and Cs$_2$CO$_3$ (102 mg, 0.312 mmol) in Toluene (1 mL) was stirred for 4 h at 100° C. under nitrogen atmosphere. The resulting mixture was concentrated under reduced pressure. The residue was purified by silica gel column chromatography, eluted with CH$_2$Cl$_2$/MeOH (10/1) followed by reversed-phase flash chromatography with the following conditions: column, C18 silica gel; mobile phase, CH$_3$CN in water (10 mmol/L NH$_4$HCO$_3$), 30% to 50% gradient in 20 min; detector, 254 nm. This resulted in 3-[(1S)-1-({3-chloro-6-[2-(dimethylphosphoryl)pyrimidin-5-yl]-7-fluoro-2-methyl-1,5-naphthyridin-4-yl}amino)propyl]-4-fluorobenzonitrile (19 mg, 17%) as a light yellow solid. MS ESI calculated for C$_{25}$H$_{22}$ClF$_2$N$_6$OP [M+H]$^+$, 527.12, found 527.10. $^1$H NMR (400 MHz, Chloroform-d) δ 9.39 (d, J=1.4 Hz, 2H), 8.03 (d, J=11.2 Hz, 1H), 7.57-7.48 (m, 2H), 7.16-7.04 (m, 1H), 6.62 (s, 1H), 6.15-6.08 (m, 1H), 2.74 (s, 3H), 2.12-2.00 (m, 2H), 1.99 (s, 3H), 1.96 (s, 3H), 1.13-1.07 (m, 3H). $^{19}$F NMR (376 MHz, Chloroform-d) δ −108.34, −120.82. $^{31}$P NMR (162 MHz, Chloroform-d) δ 34.90.

Example 31: 3-[(1R)-1-({3-chloro-6-[4-(dimethylphosphoryl)piperidin-1-yl]-7-fluoro-2-methyl-1,5-naphthyridin-4-yl}amino)ethyl]-4-fluorobenzonitrile Synthetic Scheme

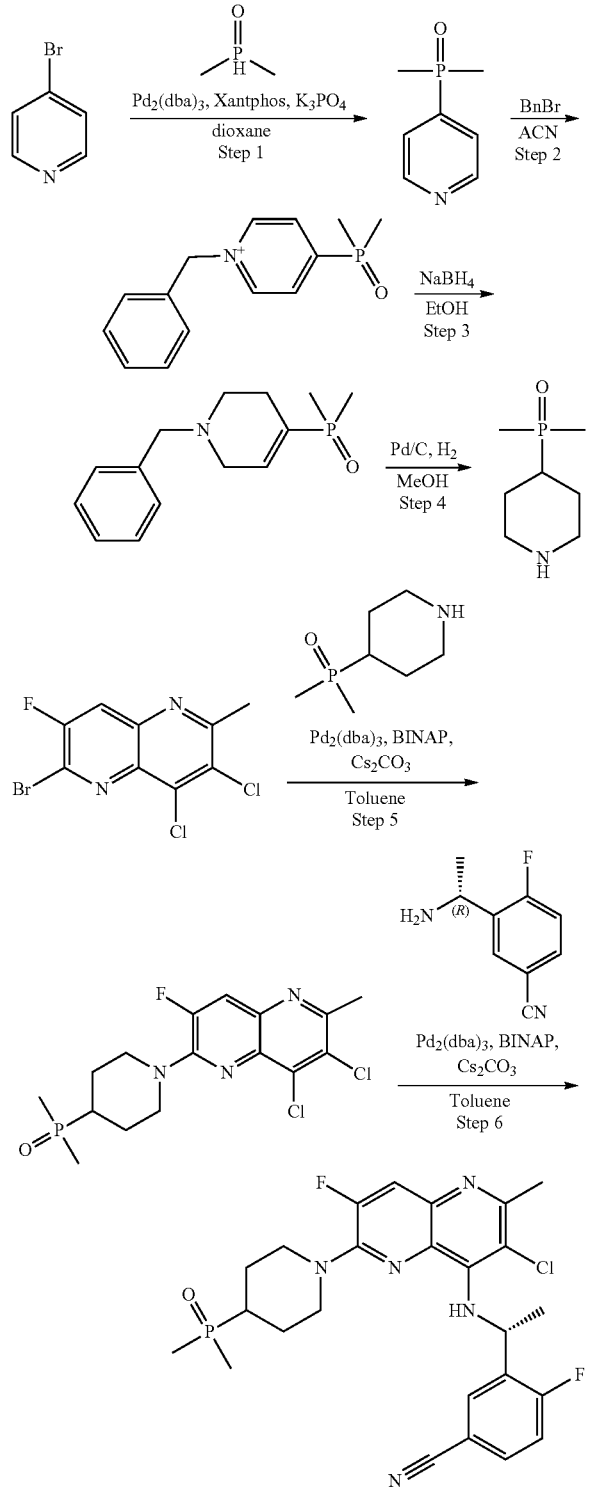

Preparation 31A: 4-(dimethylphosphoryl)pyridine

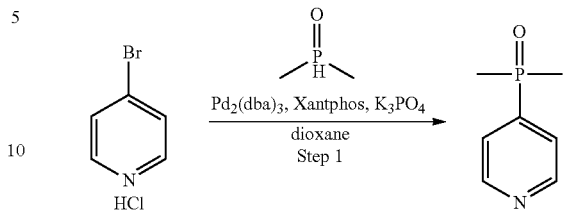

To a stirred solution of 4-bromopyridine hydrochloride (5.00 g, 25.712 mmol) and (methylphosphonoyl)methane (2.21 g, 28.283 mmol) in Toluene (5 mL) were added $Pd_2(dba)_3$ (0.71 g, 0.771 mmol), Xantphos (0.89 g, 1.543 mmol) and $K_3PO_4$ (10.92 g, 51.424 mmol) at room temperature. The resulting mixture was stirred for 16 h at 100° C. under nitrogen atmosphere. The resulting mixture was concentrated under reduced pressure. The residue was purified by silica gel column chromatography, eluted with $CH_2Cl_2$/MeOH (10:1) to afford 4-(dimethylphosphoryl) pyridine (3.60 g, 90%) as a yellow solid. MS ESI calculated for $C_7H_{10}NOP$ $[M+H]^+$, 156.05, found 156.10. $^1H$ NMR (300 MHz, DMSO-$d_6$) δ 8.78-8.72 (m, 2H), 7.80-7.69 (m, 2H), 1.73 (s, 3H), 1.68 (s, 3H).

Preparation 31B: 1-benzyl-4-(dimethylphosphoryl)pyridin-1-ium

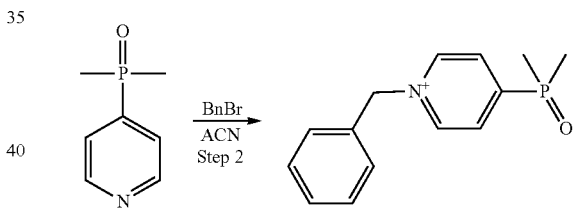

A solution of 4-(dimethylphosphoryl)pyridine (3.50 g, 22.561 mmol) and BnBr (4.24 g, 24.817 mmol) in ACN (35 mL) was stirred for 16 h at 80° C. The precipitated solids were collected by filtration and washed with EtOAc (2×30 mL). This resulted in 1-benzyl-4-(dimethylphosphoryl)pyridin-1-ium (2.80 g, 50%) as a white solid. MS ESI calculated for $C_{14}H_{17}NOP^+$ $[M]^+$, 246.10, found 246.00. $^1H$ NMR (300 MHz, Methanol-$d_4$) δ 9.37-9.27 (m, 2H), 8.58-8.47 (m, 2H), 7.65-7.57 (m, 2H), 7.50-7.44 (m, 3H), 6.00 (s, 2H), 1.99 (s, 3H), 1.94 (s, 3H).

Preparation 31C: 1-benzyl-4-(dimethylphosphoryl)-3,6-dihydro-2H-pyridine

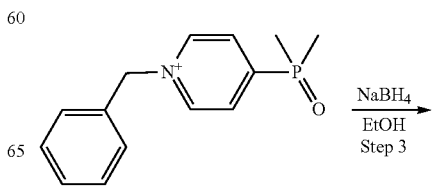

-continued

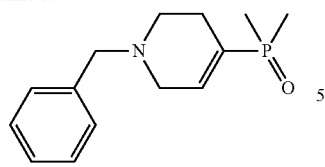

To a stirred solution of 1-benzyl-4-(dimethylphosphoryl) pyridin-1-ium (2.50 g, 10.152 mmol) in EtOH (25 mL) was added NaBH$_4$ (3.84 g, 101.520 mmol) in EtOH (15 mL) dropwise at 0° C. The resulting mixture was stirred for 16 h at room temperature. The reaction was quenched with Water/Ice at room temperature. The resulting mixture was filtered, and the filter cake was washed with EtOH (3×20 mL). The filtrate was concentrated under reduced pressure. The residue was purified by silica gel column chromatography, eluted with CH$_2$Cl$_2$/MeOH (10:1) to afford 1-benzyl-4-(dimethylphosphoryl)-3,6-dihydro-2H-pyridine (1.70 g, 67%) as a yellow oil. MS ESI calculated for C$_{14}$H$_{20}$NOP [M+H]$^+$, 250.13, found 250.15. $^1$H NMR (300 MHz, Chloroform-d) δ 7.42-7.26 (m, 5H), 6.62-6.51 (m, 1H), 3.62 (s, 2H), 3.20-3.12 (m, 2H), 2.69-2.60 (m, 2H), 2.33-2.24 (m, 2H), 1.53 (s, 3H), 1.49 (s, 3H).

Preparation 31D: 4-(dimethylphosphoryl)piperidine

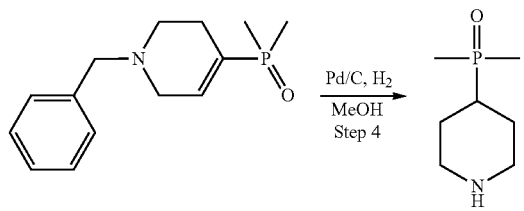

To a solution of 1-benzyl-4-(dimethylphosphoryl)-3,6-dihydro-2H-pyridine (600 mg, 2.407 mmol) in 5 mL MeOH was added Pd/C (61 mg, 0.058 mmol, 10%) under nitrogen atmosphere. The mixture was hydrogenated at room temperature for 16 h under hydrogen atmosphere. The resulting mixture was filtered, and the filter cake was washed with MeOH (3×10 mL). The filtrate was concentrated under reduced pressure. The residue was purified by reverse flash chromatography with the following conditions: column, C18 silica gel; mobile phase, CH$_3$CN in water (10 mmol/L NH$_4$HCO$_3$), 5% to 10% gradient in 10 min; detector, 254 nm. This resulted in 4-(dimethylphosphoryl)piperidine (300 mg, 77%) as a white solid. MS ESI calculated for C$_7$H$_{16}$NOP [M+H]$^+$, 162.10, found 162.10. $^1$H NMR (300 MHz, Chloroform-d) δ 3.28-3.15 (m, 2H), 2.71-2.60 (m, 2H), 1.95-1.79 (m, 3H), 1.60-1.49 (m, 2H), 1.47 (s, 3H), 1.43 (s, 3H).

Preparation 31E: 3,4-dichloro-6-[4-(dimethylphosphoryl)piperidin-1-yl]-7-fluoro-2-methyl-1,5-naphthyridine

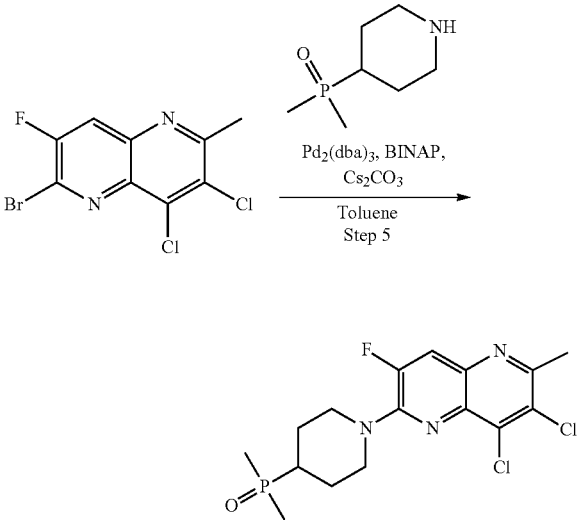

To a stirred solution of 6-bromo-3,4-dichloro-7-fluoro-2-methyl-1,5-naphthyridine (500 mg, 1.613 mmol) and 4-(dimethylphosphoryl)piperidine (312 mg, 1.936 mmol) in Toluene (10 mL) were added BINAP (201 mg, 0.323 mmol), Pd$_2$(dba)$_3$ (148 mg, 0.161 mmol) and Cs$_2$CO$_3$ (788 mg, 2.420 mmol) at room temperature. The resulting mixture was stirred for 4 h at 100° C. under nitrogen atmosphere. The resulting mixture was concentrated under vacuum. The residue was purified by silica gel column chromatography, eluted with CH$_2$Cl$_2$/MeOH (10:1) to afford 3,4-dichloro-6-[4-(dimethylphosphoryl)piperidin-1-yl]-7-fluoro-2-methyl-1,5-naphthyridine (230 mg, 37%) as a white solid. MS ESI calculated for C$_{16}$H$_{19}$Cl$_2$FN$_3$OP [M+H]$^+$, 390.06, found 390.00. $^1$H NMR (400 MHz, Chloroform-d) δ 7.72 (d, J=13.5 Hz, 1H), 4.66 (d, J=13.2 Hz, 2H), 3.07 (t, J=12.7 Hz, 2H), 2.78 (s, 3H), 2.10-2.02 (m, 2H), 2.02-1.93 (m, 1H), 1.87-1.75 (m, 2H), 1.50 (s, 3H), 1.47 (s, 3H).

Example 31: 3-[(1R)-1-({3-chloro-6-[4-(dimethylphosphoryl)piperidin-1-yl]-7-fluoro-2-methyl-1,5-naphthyridin-4-yl}amino)ethyl]-4-fluorobenzonitrile

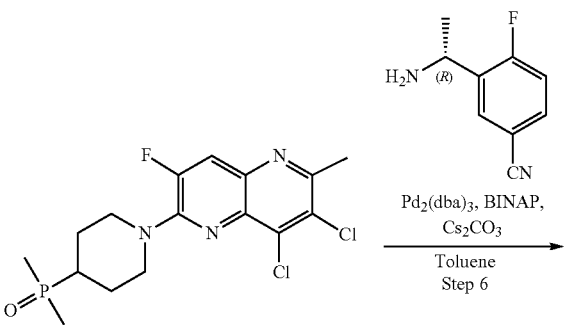

177

-continued

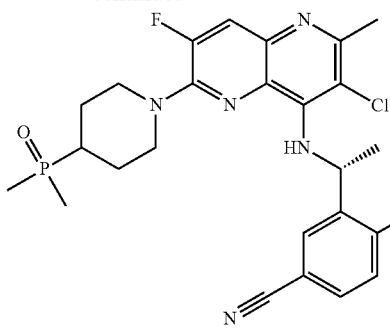

To a stirred solution of 3,4-dichloro-6-[4-(dimethylphosphoryl)piperidin-1-yl]-7-fluoro-2-methyl-1,5-naphthyridine (200 mg, 0.513 mmol) and 3-[(1R)-1-aminoethyl]-4-fluorobenzonitrile (101 mg, 0.616 mmol) in Toluene (3 mL) were added $Cs_2CO_3$ (250 mg, 0.770 mmol), $Pd_2(dba)_3$ (47 mg, 0.051 mmol) and BINAP (64 mg, 0.103 mmol). The resulting mixture was stirred for 16 h at 100° C. under nitrogen atmosphere. The resulting mixture was concentrated under reduced pressure. The residue was purified by silica gel column chromatography, eluted with $CH_2Cl_2$/ MeOH (10/1) followed by reversed-phase flash chromatography with the following conditions: column, C18 silica gel; mobile phase, $CH_3CN$ in water (10 mmol/L $NH_4HCO_3$), 40% to 50% gradient in 20 min; detector, 254 nm. This resulted in 3-[(1R)-1-({3-chloro-6-[4-(dimethylphosphoryl)piperidin-1-yl]-7-fluoro-2-methyl-1,5-naphthyridin-4-yl}amino)ethyl]-4-fluorobenzonitrile (91 mg, 34%) as a white solid. MS ESI calculated for $C_{25}H_{27}ClF_2N_5OP$ $[M+H]^+$, 518.16, found 518.25. $^1H$ NMR (400 MHz, DMSO-$d_6$) δ 8.06-8.00 (m, 1H), 7.87-7.78 (m, 2H), 7.46-7.39 (m, 1H), 6.45 (d, J=9.3 Hz, 1H), 6.34-6.23 (m, 1H), 4.24-4.12 (m, 2H), 3.01-2.89 (m, 2H), 2.54 (s, 3H), 1.97-1.82 (m, 3H), 167-1.52 (m, 5H), 1.37 (s, 3H), 1.34 (s, 3H). $^{19}F$ NMR (377 MHz, DMSO-$d_6$) δ −109.28, −121.97. $^{31}P$ NMR (162 MHz, DMSO-$d_6$) δ 42.94.

Example 32: diethyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate

Synthetic Scheme

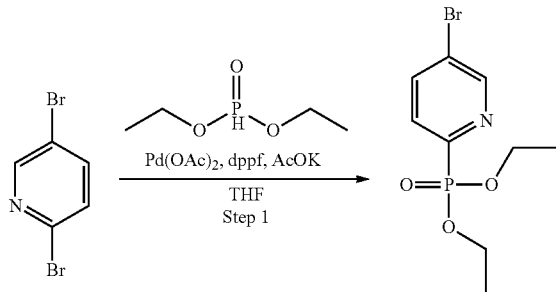

178

-continued

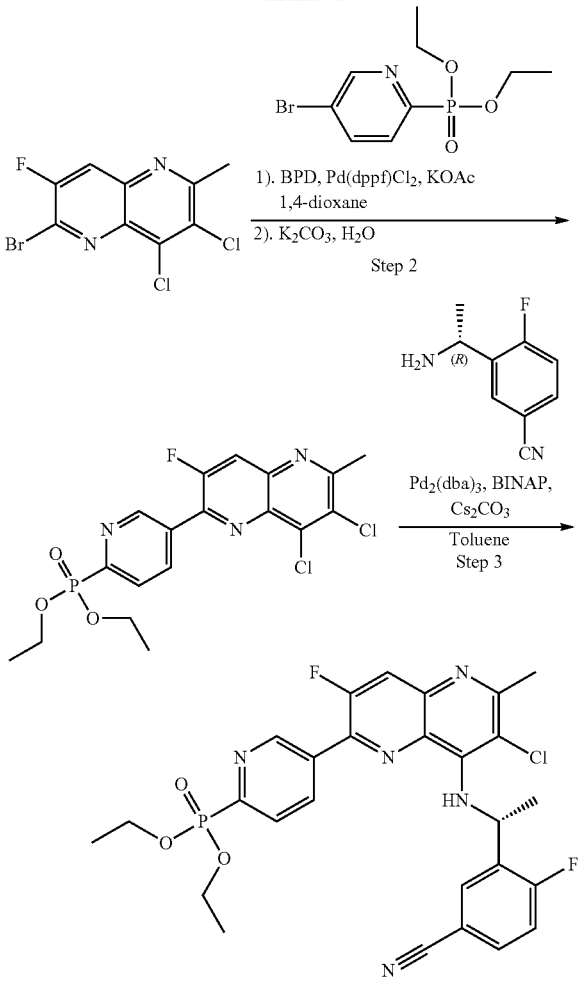

Preparation 32A: diethyl 5-bromopyridin-2-ylphosphonate

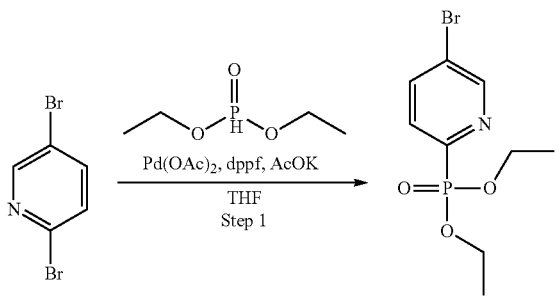

To a stirred mixture of $Pd(OAc)_2$ (280 mg, 1.266 mmol) and Dppf (1.40 g, 2.533 mmol) in THF (100 mL) were added TEA (5.13 g, 50.656 mmol), KOAc (410 mg, 4.221 mmol), 2,5-dibromopyridine (10.00 g, 42.213 mmol) and diethyl phosphonate (5.83 g, 42.213 mmol) over 5 min at room temperature. The resulting mixture was stirred for additional overnight at 68° C. The resulting mixture was concentrated under reduced pressure. The residue was purified by silica gel column chromatography, eluted with PE/EA (1:2) to afford diethyl 5-bromopyridin-2-ylphosphonate (9.89 g, 79%) as a brown oil. MS ESI calculated for $C_9H_{13}BrNO_3P$ [M+H]$^+$, 293.98, 295.98, found 293.95, 295.90. $^1$H NMR (400 MHz, Chloroform-d) δ 8.86 (d, J=2.1 Hz, 1H), 7.98-7.94 (m, 1H), 7.90-7.83 (m, 1H), 4.30-4.17 (m, 4H), 1.36 (t, J=7.0 Hz, 6H).

Preparation 32B: diethyl 5-(7,8-dichloro-3-fluoro-6-methyl-1,5-naphthyridin-2-yl)pyridin-2-ylphosphonate

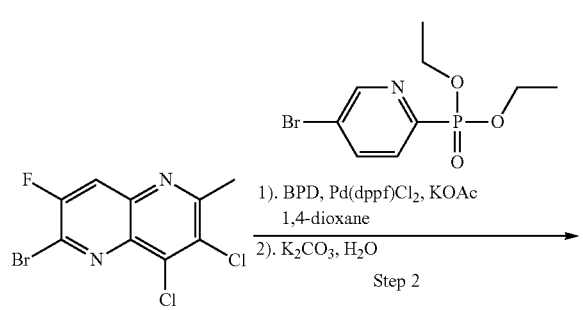

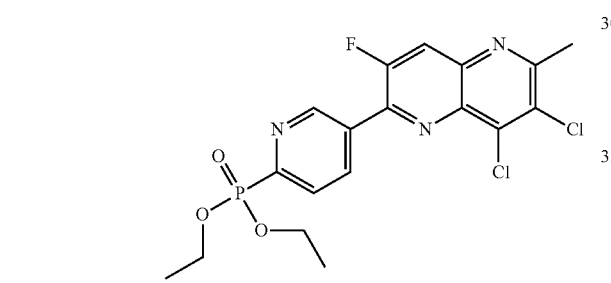

To a stirred mixture of diethyl 5-bromopyridin-2-ylphosphonate (512 mg, 1.742 mmol) and BPD (553 mg, 2.178 mmol) in 1,4-dioxane (10 mL) were added Pd(dppf)Cl$_2$·CH$_2$Cl$_2$ (118 mg, 0.145 mmol) and KOAc (285 mg, 2.904 mmol) at room temperature under nitrogen atmosphere. The resulting mixture was stirred for 3 h at 90° C. under nitrogen atmosphere. The mixture was allowed to cool down to room temperature. To the above mixture was added 6-bromo-3,4-dichloro-7-fluoro-2-methyl-1,5-naphthyridine (450 mg, 1.452 mmol), K$_2$CO$_3$ (502 mg, 3.630 mmol) and H$_2$O (1 mL) over 10 min at room temperature. The resulting mixture was stirred for additional 3 h at 80° C. The resulting mixture was concentrated under reduced pressure. The residue was purified by silica gel column chromatography, eluted with CH$_2$Cl$_2$/MeOH (10:1) to afford diethyl 5-(7,8-dichloro-3-fluoro-6-methyl-1,5-naphthyridin-2-yl)pyridin-2-ylphosphonate (390 mg, 60%) as a red solid. MS ESI calculated for $C_{18}H_{17}Cl_2FN_3O_3P$ [M+H]$^+$, 444.04, found 444.25. $^1$H NMR (400 MHz, Chloroform-d) δ 9.62 (s, 1H), 8.63 (s, 1H), 8.25-8.07 (m, 2H), 4.30 (s, 4H), 2.91 (s, 3H), 1.40 (d, J=6.3 Hz, 6H). $^{19}$F NMR (376 MHz, Chloroform-d) δ −118.32. $^{31}$P NMR (162 MHz, Chloroform-d) δ 10.15.

Example 32: diethyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate

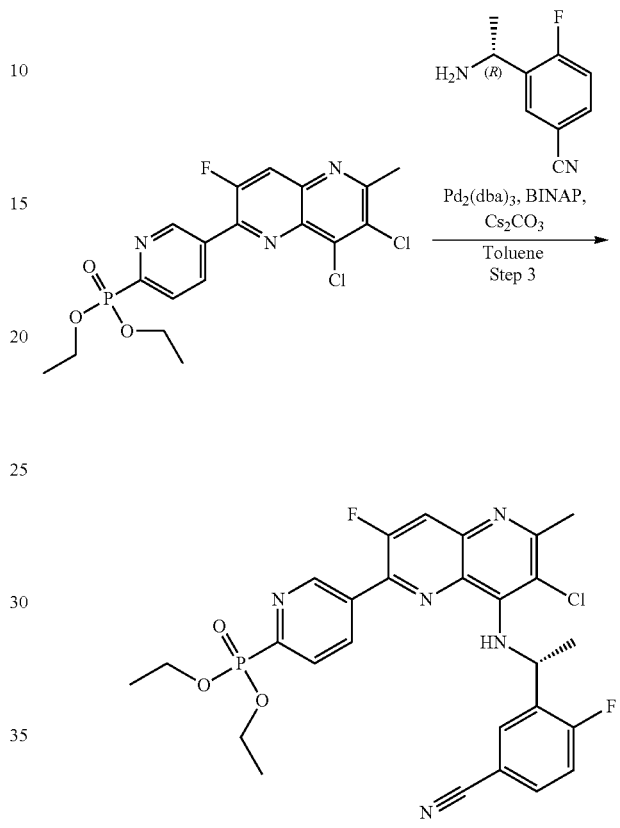

To a stirred solution of diethyl 5-(7,8-dichloro-3-fluoro-6-methyl-1,5-naphthyridin-2-yl)pyridin-2-ylphosphonate (390 mg, 0.878 mmol) and 3-[(1R)-1-aminoethyl]-4-fluorobenzonitrile (173 mg, 1.054 mmol,) in Toluene (8 mL, 75.189 mmol) were added Cs$_2$CO$_3$ (429 mg, 1.317 mmol), BINAP (109 mg, 0.176 mmol,) and Pd$_2$(dba)$_3$ (80 mg, 0.088 mmol) at room temperature. The resulting mixture was stirred for 5 h at 100° C. under nitrogen atmosphere. The resulting mixture was concentrated under vacuum. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 30% to 60% gradient in 30 min; detector, 254 nm. The resulting mixture was concentrated under vacuum. This resulted in diethyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate (330 mg, 64%) as a yellow solid. MS ESI calculated for $C_{27}H_{25}ClF_2N_5O_3P$ [M+H]$^+$, 572.14, found 572.15. $^1$H NMR (400 MHz, DMSO-d$_6$) δ 9.20 (s, 1H), 8.37-8.31 (m, 1H), 8.21-8.12 (m, 1H), 8.08-7.98 (m, 2H), 7.82-7.75 (m, 1H), 7.30-7.21 (m, 1H), 6.96 (d, J=8.6 Hz, 1H), 6.37 (t, J=7.6 Hz, 1H), 4.28-4.10 (m, 4H), 2.63 (s, 3H), 1.66 (d, J=6.8 Hz, 3H), 1.31 (t, J=7.0 Hz, 6H). $^{19}$F NMR (377 MHz, DMSO-d$_6$) δ −109.35, −120.99. $^{31}$P NMR (162 MHz, DMSO-d$_6$) δ 9.76.

181

Example 33: 3-[(1R)-1-[(3-chloro-6-{6-[(dimethylphosphoryl)methoxy]pyridin-3-yl}-7-fluoro-2-methyl-1,5-naphthyridin-4-yl)amino]ethyl]-4-fluorobenzonitrile Synthetic Scheme

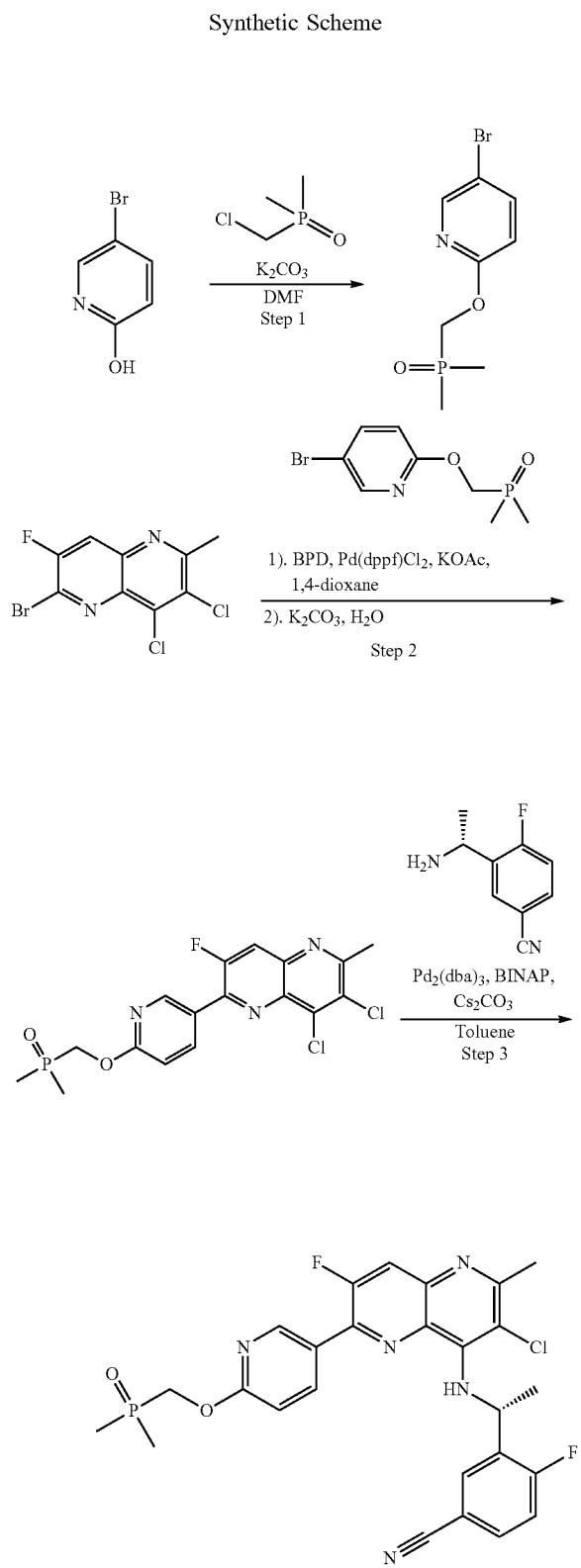

182

Preparation 33A: 5-bromo-2-[(dimethylphosphoryl)methoxy]pyridine

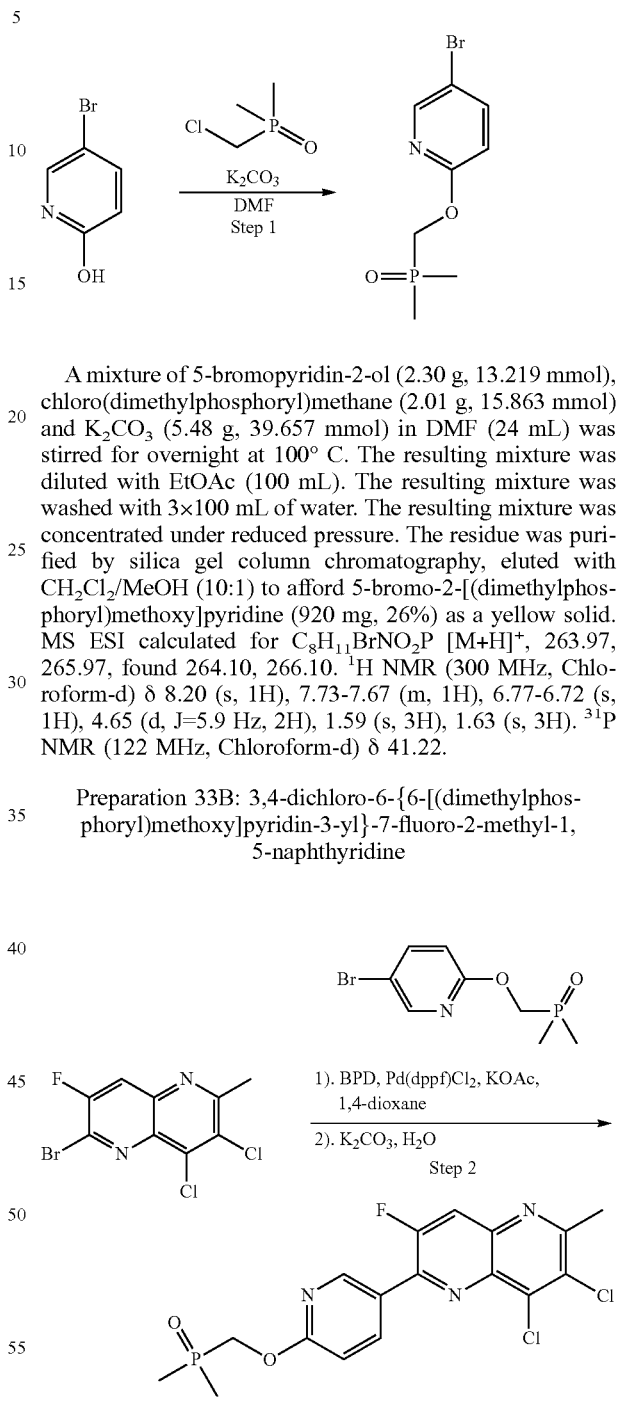

A mixture of 5-bromopyridin-2-ol (2.30 g, 13.219 mmol), chloro(dimethylphosphoryl)methane (2.01 g, 15.863 mmol) and $K_2CO_3$ (5.48 g, 39.657 mmol) in DMF (24 mL) was stirred for overnight at 100° C. The resulting mixture was diluted with EtOAc (100 mL). The resulting mixture was washed with 3×100 mL of water. The resulting mixture was concentrated under reduced pressure. The residue was purified by silica gel column chromatography, eluted with $CH_2Cl_2$/MeOH (10:1) to afford 5-bromo-2-[(dimethylphosphoryl)methoxy]pyridine (920 mg, 26%) as a yellow solid. MS ESI calculated for $C_8H_{11}BrNO_2P$ $[M+H]^+$, 263.97, 265.97, found 264.10, 266.10. $^1H$ NMR (300 MHz, Chloroform-d) δ 8.20 (s, 1H), 7.73-7.67 (m, 1H), 6.77-6.72 (s, 1H), 4.65 (d, J=5.9 Hz, 2H), 1.59 (s, 3H), 1.63 (s, 3H). $^{31}P$ NMR (122 MHz, Chloroform-d) δ 41.22.

Preparation 33B: 3,4-dichloro-6-{6-[(dimethylphosphoryl)methoxy]pyridin-3-yl}-7-fluoro-2-methyl-1,5-naphthyridine To a stirred mixture of 5-bromo-2-[(dimethylphosphoryl)methoxy]pyridine (497 mg, 1.882 mmol) and BPD (597 mg, 2.352 mmol) in 1,4-dioxane (10 mL) were added Pd(dppf)Cl$_2$·CH$_2$Cl$_2$ (128 mg, 0.157 mmol) and KOAc (308 mg, 3.136 mmol) at room temperature. The resulting mixture was stirred for 3 h at 90° C. under nitrogen atmosphere. The mixture was allowed to cool down to room temperature. To the above mixture was added 6-bromo-3,4-dichloro-7-fluoro-2-methyl-1,5-naphthyridine (486 mg, 1.568 mmol), K$_2$CO$_3$ (542 mg, 3.920 mmol) and H$_2$O (1 mL) over 10 min at room temperature. The resulting mixture was stirred for additional 3 h at 80° C. under nitrogen atmosphere. The resulting mixture was concentrated under reduced pressure. The residue was purified by silica gel column chromatography, eluted with CH$_2$Cl$_2$/MeOH (10:1) to afford 3,4-dichloro-6-{6-[(dimethylphosphoryl)methoxy]pyridin-3-yl}-7-fluoro-2-methyl-1,5-naphthyridine (400 mg, 61%) as a yellow solid. MS ESI calculated for C$_{17}$H$_{15}$Cl$_2$FN$_3$O$_2$P [M+H]$^+$, 414.03, found 414.00. $^1$H NMR (400 MHz, Chloroform-d) δ 9.04 (s, 1H), 8.55 (d, J=7.7 Hz, 1H), 8.06 (d, J=11.2 Hz, 1H), 7.01 (d, J=7.6 Hz, 1H), 4.88 (s, 2H), 2.89 (s, 3H), 1.83 (s, 3H), 1.65 (s, 3H). $^{19}$F NMR (376 MHz, Chloroform-d) δ −118.03.

Example 33: 3-[(1R)-1-[(3-chloro-6-{6-[(dimethylphosphoryl)methoxy]pyridin-3-yl}-7-fluoro-2-methyl-1,5-naphthyridin-4-yl)amino]ethyl]-4-fluorobenzonitrile

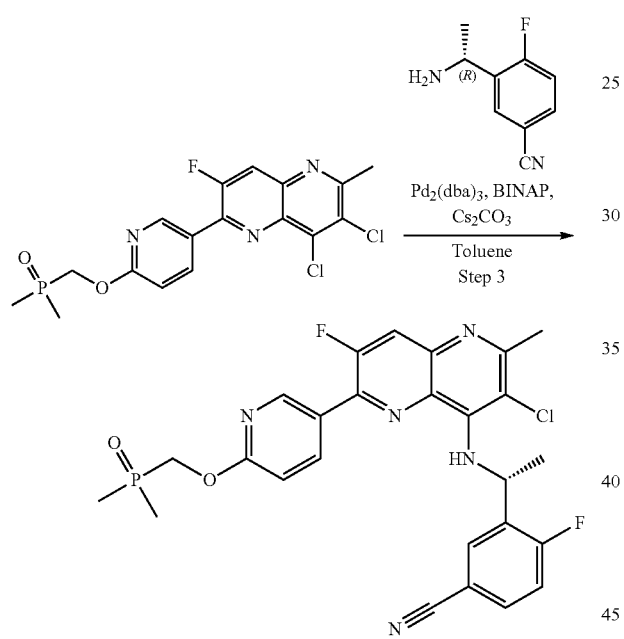

To a stirred solution of 3,4-dichloro-6-{6-[(dimethylphosphoryl)methoxy]pyridin-3-yl}-7-fluoro-2-methyl-1,5-naphthyridine (100 mg, 0.241 mmol) and 3-[(1R)-1-aminoethyl]-4-fluorobenzonitrile (48 mg, 0.289 mmol) in Toluene (2 mL) were added Cs$_2$CO$_3$ (118 mg, 0.361 mmol), BINAP (30 mg, 0.048 mmol) and Pd$_2$(dba)$_3$ (22 mg, 0.024 mmol) at room temperature. The resulting mixture was stirred for 5 h at 100° C. under nitrogen atmosphere. The resulting mixture was concentrated under reduced pressure. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 30% to 60% gradient in 30 min; detector, 254 nm. The resulting mixture was concentrated under vacuum. This resulted in 3-[(1R)-1-[(3-chloro-6-{6-[(dimethylphosphoryl)methoxy]pyridin-3-yl}-7-fluoro-2-methyl-1,5-naphthyridin-4-yl)amino]ethyl]-4-fluorobenzonitrile (62 mg, 47%) as a white solid. MS ESI calculated for C$_{26}$H$_{23}$ClF$_2$N$_5$O$_2$P [M+H]$^+$, 542.12, found 542.10. $^1$H NMR (400 MHz, DMSO-d$_6$) δ 8.66 (s, 1H), 8.16 (d, J=8.7 Hz, 1H), 8.13-8.06 (m, 1H), 8.05-8.00 (m, 1H), 7.83-7.76 (m, 1H), 7.40-7.32 (m, 1H), 7.09 (d, J=8.7 Hz, 1H), 6.89 (d, J=8.6 Hz, 1H), 6.40-6.31 (m, 1H), 4.71 (d, J=5.1 Hz, 2H), 2.62 (s, 3H), 1.66 (d, J=6.8 Hz, 3H), 1.56 (s, 3H), 1.53 (s, 3H). $^{19}$F NMR (377 MHz, DMSO-d$_6$) δ −109.28, −120.64. $^{31}$P NMR (162 MHz, DMSO-d$_6$) δ 37.96.

Example 34: (S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile Synthetic Scheme

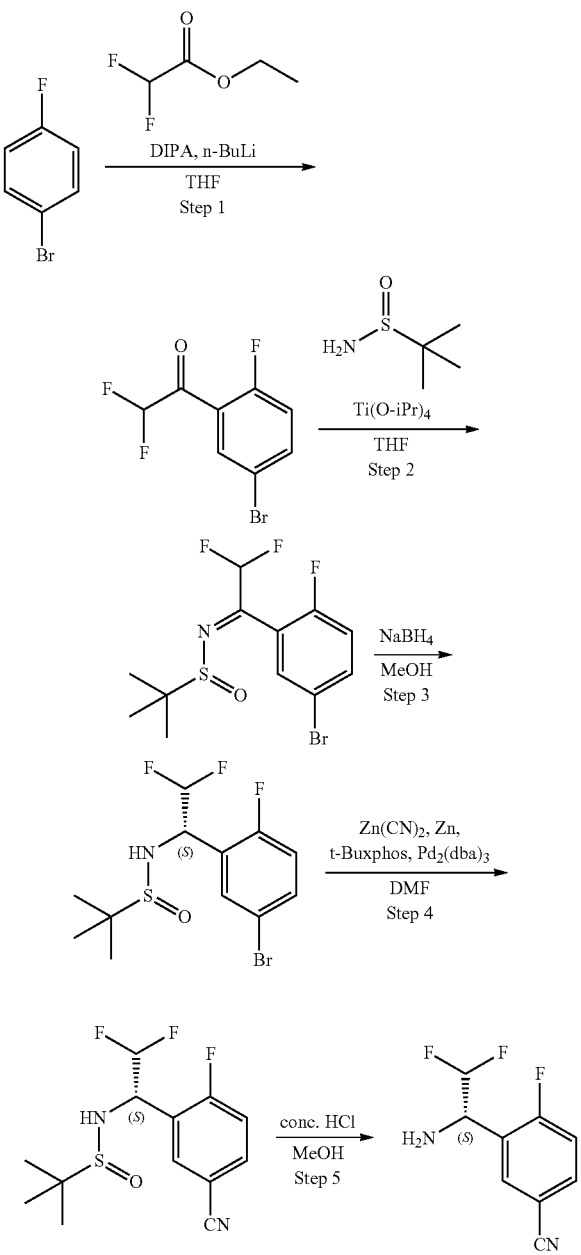

185

-continued

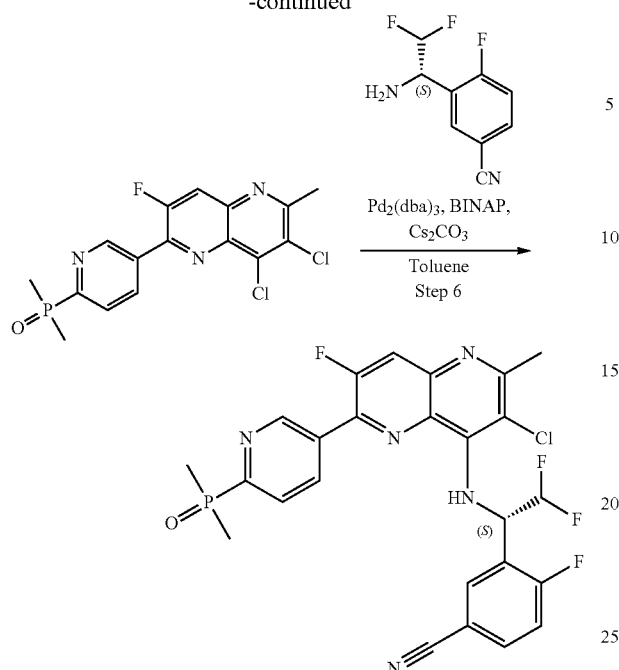

Preparation 34A:
1-(5-bromo-2-fluorophenyl)-2,2-difluoroethanone

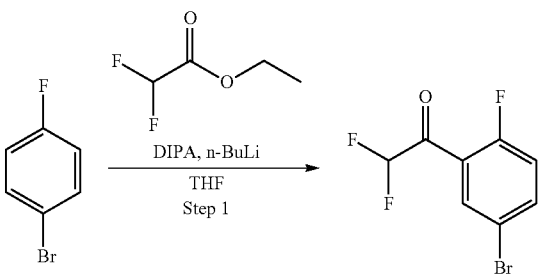

To a stirred solution of DIPA (17 mL, 125.715 mmol) in THF (380 mL) was added 2.5 M of n-BuLi in hexanes (50 mL, 125.715 mmol) dropwise at −78° C. under nitrogen atmosphere. The resulting mixture was stirred for 30 min at 0° C. under nitrogen atmosphere. To the above mixture was added 4-bromofluorobenzene (20.00 g, 114.286 mmol) dropwise at −78° C. The resulting mixture was stirred for additional 2 h at −78° C. To the above mixture was added ethyl 2,2-difluoroacetate (17.02 g, 137.143 mmol) dropwise at −78° C. The resulting mixture was stirred for additional 20 min at −78° C. The reaction was quenched with 2N HCl (aq.) at 0° C. The resulting mixture was extracted with EtOAc (3×300 mL). The combined organic layers were washed with brine (1×300 mL), dried over anhydrous Na$_2$SO$_4$. After filtration, the filtrate was concentrated under reduced pressure. The residue was purified by silica gel column chromatography, eluted with PE/EA (5/1) to afford 1-(5-bromo-2-fluorophenyl)-2,2-difluoroethanone (23.10 g, 79%) as a yellow liquid. $^1$H NMR (400 MHz, Chloroform-d) δ 8.09-8.02 (m, 1H), 7.78-7.72 (m, 1H), 7.17-7.10 (m, 1H), 6.56-6.26 (m, 1H).

186

Preparation 34B: N-[1-(5-bromo-2-fluorophenyl)-2,2-difluoroethylidene]-2-methylpropane-2-sulfinamide

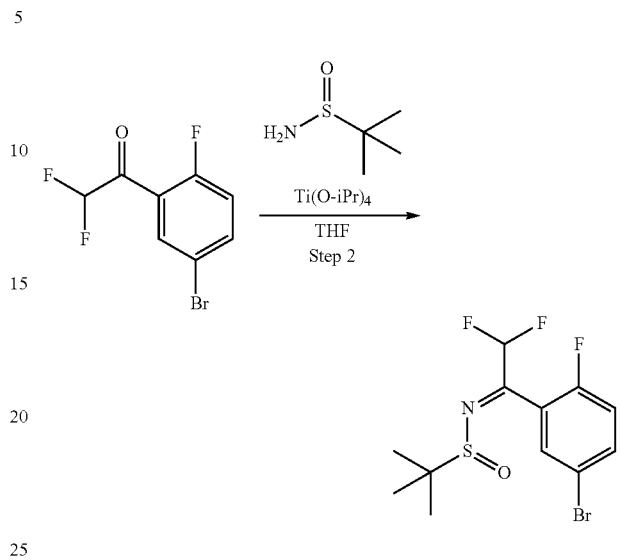

To a stirred solution of 1-(5-bromo-2-fluorophenyl)-2,2-difluoroethanone (10.00 g, 39.523 mmol) and 2-methylpropane-2-sulfinamide (5.75 g, 47.428 mmol) in THF (100 mL) was added Ti(O-iPr)$_4$ (22.47 g, 79.046 mmol) dropwise at room temperature under nitrogen atmosphere. The resulting mixture was stirred for 16 h at 80° C. under nitrogen atmosphere. The reaction was quenched with water at 0° C. The resulting mixture was filtered, and the filter cake was washed with EtOAc (3×200 mL). The filtrate was concentrated under reduced pressure. The residue was purified by silica gel column chromatography, eluted with PE/EA (10/1) to afford N-[1-(5-bromo-2-fluorophenyl)-2,2-difluoroethylidene]-2-methylpropane-2-sulfinamide (8.40 g, 59%) as a yellow liquid. $^1$H NMR (300 MHz, Chloroform-d) δ 7.59-7.53 (m, 1H), 7.49-7.44 (m, 1H), 6.41-6.03 (m, 1H), 6.47-5.99 (m, 1H), 1.31 (s, 9H).

Preparation 34C: N-[(1S)-1-(5-bromo-2-fluorophenyl)-2,2-difluoroethyl]-2-methylpropane-2-sulfinamide

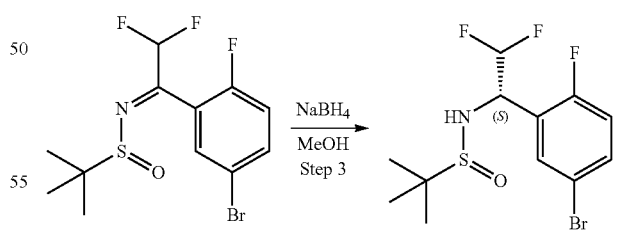

A solution of N-[1-(5-bromo-2-fluorophenyl)-2,2-difluoroethylidene]-2-methylpropane-2-sulfinamide (3.92 g, 11.005 mmol) and NaBH$_4$ (499 mg, 13.206 mmol) in MeOH (45 mL) was stirred for 2 h at room temperature. The resulting mixture was concentrated under reduced pressure. The residue was purified by silica gel column chromatography, eluted with PE/EA (10/1) followed by reversed phase flash with the following conditions (column, C18 silica gel; mobile phase, CH$_3$CN in water (10 mmol/L NH$_4$HCO$_3$), 30% to 70% gradient in 20 min; detector, 254 nm) to afford N-[(1S)-1-(5-bromo-2-fluorophenyl)-2,2-difluoroethyl]-2-methylpropane-2-sulfinamide (1.95 g, 54%) as a light yellow liquid. MS ESI calculated for $C_{12}H_{15}BrF_3NOS$ [M+H]$^+$, 358.00 360.00, found 357.90 359.90. $^1$H NMR (400 MHz, Chloroform-d) δ 7.54-7.45 (m, 2H), 7.06-6.97 (m, 1H), 6.26-5.80 (m, 1H), 5.04-4.77 (m, 1H), 3.93 (t, J=7.1 Hz, 1H), 1.25 (s, 9H).

Preparation 34D: N—((S)-1-(5-cyano-2-fluorophenyl)-2,2-difluoroethyl)-2-methylpropane-2-sulfinamide

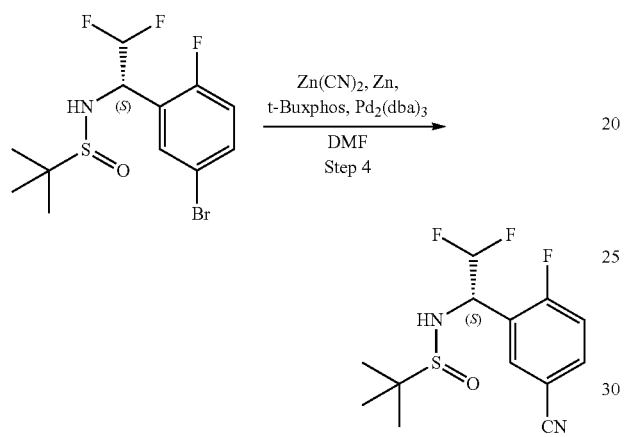

A mixture of N-[(1S)-1-(5-bromo-2-fluorophenyl)-2,2-difluoroethyl]-2-methylpropane-2-sulfinamide (4 g, 11.166 mmol), Zn(CN)$_2$ (2.62 g, 22.332 mmol), Zn (1.46 g, 22.332 mmol), t-BuXPhos (0.95 g, 2.233 mmol) and Pd$_2$(dba)$_3$ (1.02 g, 1.117 mmol) in DMF (20 mL) was stirred for 16 h at 95° C. under nitrogen atmosphere. The resulting mixture was filtered, and the filter cake was washed with CH$_2$Cl$_2$ (3×100 mL). The filtrate was concentrated under reduced pressure. The residue was purified by silica gel column chromatography, eluted with CH$_2$Cl$_2$/MeOH (12/1) to afford N—((S)-1-(5-cyano-2-fluorophenyl)-2,2-difluoroethyl)-2-methylpropane-2-sulfinamide (1.90 g, 55%) as a light yellow liquid. MS ESI calculated for $C_{13}H_{15}F_3N_2OS$ [M+H]$^+$, 305.09, found 305.10. $^1$H NMR (300 MHz, Chloroform-d) δ 7.76-7.69 (m, 2H), 7.29-7.23 (m, 1H), 6.29-5.91 (m, 1H), 5.10-4.98 (m, 1H), 4.07 (d, J=6.2 Hz, 1H), 1.26 (s, 9H).

Preparation 34E: (S)-3-(1-amino-2,2-difluoroethyl)-4-fluorobenzonitrile

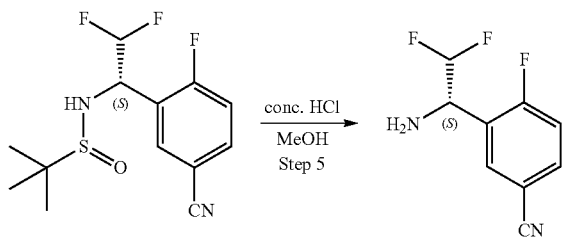

A solution of N—((S)-1-(5-cyano-2-fluorophenyl)-2,2-difluoroethyl)-2-methylpropane-2-sulfinamide (2.00 g, 3.549 mmol) in conc. HCl (4 mL) and MeOH (12 mL) was stirred for 2 h at room temperature. The resulting mixture was concentrated under reduced pressure. The resulting mixture was adjusted PH=8 with sat. NaHCO$_3$ aq. (100 mL). The resulting mixture was extracted with EtOAc (3×50 mL). The combined organic layers were washed with brine (3×100 mL), dried over anhydrous Na$_2$SO$_4$. The organic layer was concentrated under reduced pressure. The residue was purified by silica gel column chromatography, eluted with CH$_2$Cl$_2$/MeOH (12/1) to afford (S)-3-(1-amino-2,2-difluoroethyl)-4-fluorobenzonitrile (445 mg, 62%) as light yellow solids. $^1$H NMR (400 MHz, Chloroform-d) δ 7.87 (d, J=6.5 Hz, 1H), 7.68-7.65 (m, 1H), 7.24-7.17 (m, 1H), 6.03-5.74 (m, 1H), 4.60-4.53 (m, 1H).

Example 34: (S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile

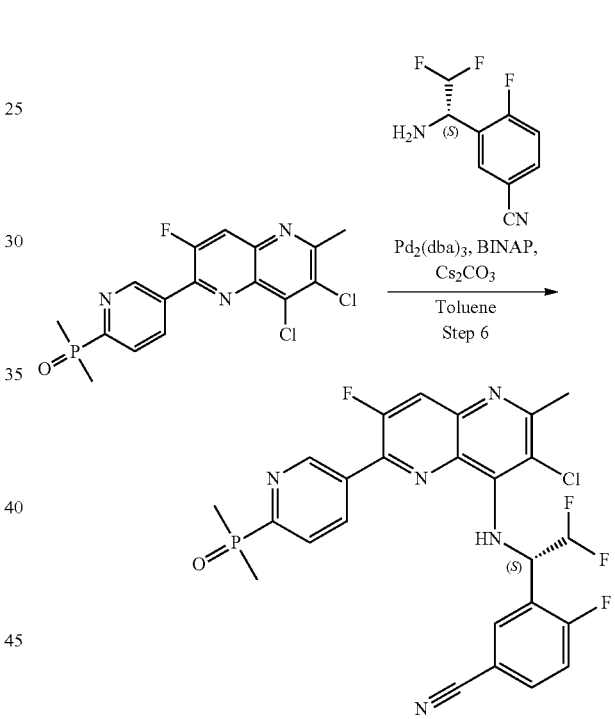

A mixture of (S)-3-(1-amino-2,2-difluoroethyl)-4-fluorobenzonitrile (62 mg, 0.312 mmol), 3,4-dichloro-6-[6-(dimethylphosphoryl)pyridin-3-yl]-7-fluoro-2-methyl-1,5-naphthyridine (100 mg, 0.260 mmol), Pd$_2$(dba)$_3$ (23 mg, 0.026 mmol), BINAP (32 mg, 0.052 mmol) and Cs$_2$CO$_3$ (127 mg, 0.390 mmol) in Toluene (2 mL) was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C$_{18}$ Column 120 g; Mobile Phase A: water (0.1% NH$_4$HCO$_3$), Mobile Phase B: CH$_3$CN; Flow rate: 60 mL/min; Gradient: 30% B to 70% B in 20 min; 254/220 nm to afford (R or S) 3-[(1S)-1-({3-chloro-6-[6-(dimethylphosphoryl)pyridin-3-yl]-7-fluoro-2-methyl-1,5-naphthyridin-4-yl}amino)-2,2-difluoroethyl]-4-fluorobenzonitrile (78 mg, 52%) as a white solid. MS ESI calculated for $C_{25}H_{19}ClF_4N_5OP$, $[M+H]^+$, 548.10, found 547.95. $^1$H NMR (400 MHz, DMSO-$d_6$) δ 9.16 (s, 1H), 8.41-8.37 (m, 2H), 8.28 (d, J=11.6 Hz, 1H), 8.15-8.11 (m, 1H), 7.98-7.94 (m, 1H), 7.41-7.37 (m, 1H), 7.22 (d, J=9.6 Hz, 1H), 6.83-6.42 (m, 2H), 2.69 (s, 3H), 1.79-1.74 (m, 6H). $^{19}$F NMR (376 MHz, DMSO-$d_6$) δ −107.05, −120.48, −125.14, −125.16, −125.33, −125.35. $^{31}$P NMR (162 MHz, DMSO-$d_6$) δ 34.37.

Example 35: (R)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile Synthetic Scheme

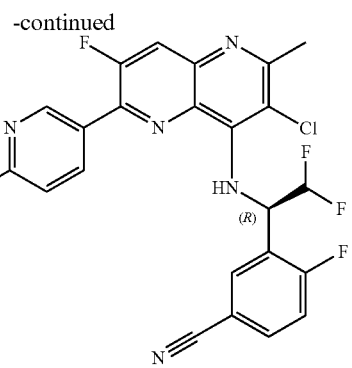

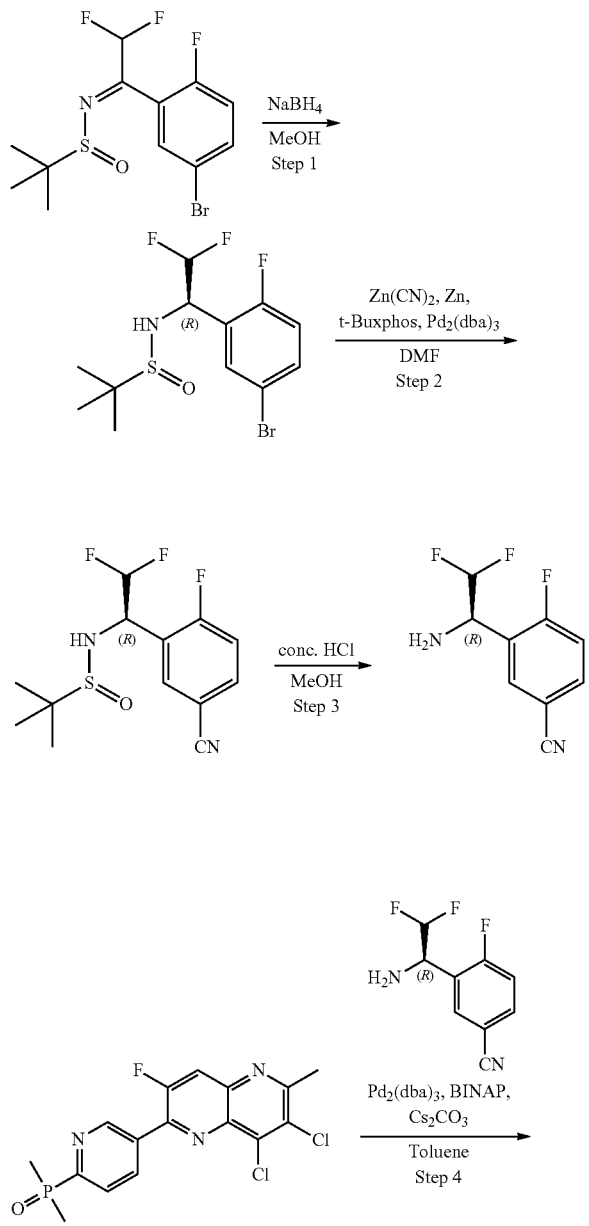

Preparation 35A: N-[(1R)-1-(5-bromo-2-fluorophenyl)-2,2-difluoroethyl]-2-methylpropane-2-sulfinamide

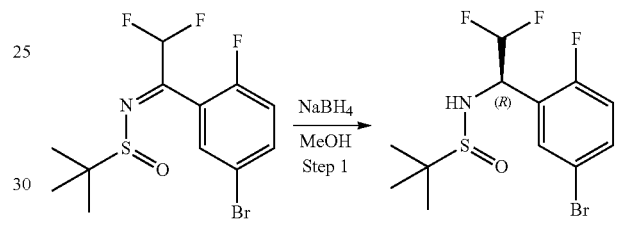

A solution of N-[1-(5-bromo-2-fluorophenyl)-2,2-difluoroethylidene]-2-methylpropane-2-sulfinamide (3.92 g, 11.005 mmol) and NaBH$_4$ (499 mg, 13.206 mmol) in MeOH (45 mL) was stirred for 2 h at room temperature. The resulting mixture was concentrated under reduced pressure. The residue was purified by silica gel column chromatography, eluted with PE/EA (10/1) followed by reversed phase flash with the following conditions (column, C18 silica gel; mobile phase, CH$_3$CN in water (10 mmol/L NH$_4$HCO$_3$), 30% to 70% gradient in 20 min; detector, 254 nm) to afford N-[(1R)-1-(5-bromo-2-fluorophenyl)-2,2-difluoroethyl]-2-methylpropane-2-sulfinamide (1.85 g, 51%) as a light yellow liquid. MS ESI calculated for $C_{12}H_{15}BrF_3NOS$ $[M+H]^+$, 358.00 360.00, found 357.90 359.90. $^1$H NMR (400 MHz, Chloroform-d) δ 7.54-7.45 (m, 2H), 7.06-6.97 (m, 1H), 6.26-5.80 (m, 1H), 5.04-4.77 (m, 1H), 3.93 (t, J=7.1 Hz, 1H), 1.25 (s, 9H).

Preparation 35B: N—((R)-1-(5-cyano-2-fluorophenyl)-2,2-difluoroethyl)-2-methylpropane-2-sulfinamide

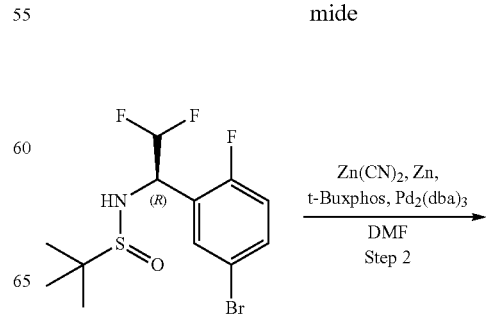

-continued

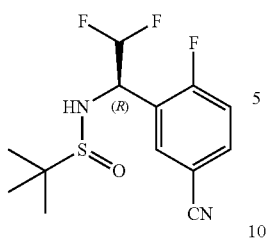

A mixture of N-[(1R)-1-(5-bromo-2-fluorophenyl)-2,2-difluoroethyl]-2-methylpropane-2-sulfinamide (4 g, 11.166 mmol), Zn(CN)$_2$ (2.62 g, 22.332 mmol), Zn (1.46 g, 22.332 mmol), t-BuXphos (0.95 g, 2.233 mmol) and Pd$_2$(dba)$_3$ (1.02 g, 1.117 mmol) in DMF (20 mL) was stirred for 16 h at 95° C. under nitrogen atmosphere. The resulting mixture was filtered, and the filter cake was washed with CH$_2$Cl$_2$ (3×100 mL). The filtrate was concentrated under reduced pressure. The residue was purified by silica gel column chromatography, eluted with CH$_2$Cl$_2$/MeOH (12/1) to afford N—((R)-1-(5-cyano-2-fluorophenyl)-2,2-difluoroethyl)-2-methylpropane-2-sulfinamide (1.90 g, 55%) as a light yellow liquid. MS ESI calculated for C$_{13}$H$_{15}$F$_3$N$_2$OS [M+H]$^+$, 305.09, found 305.10. $^1$H NMR (300 MHz, Chloroform-d) δ 7.76-7.69 (m, 2H), 7.29-7.23 (m, 1H), 6.29-5.91 (m, 1H), 5.10-4.98 (m, 1H), 4.07 (d, J=6.2 Hz, 1H), 1.26 (s, 9H).

Preparation 35C: (R)-3-(1-amino-2,2-difluoroethyl)-4-fluorobenzonitrile

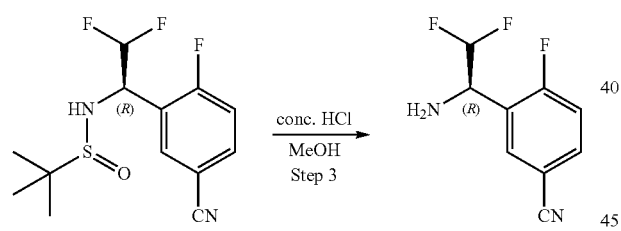

A solution of N—((R)-1-(5-cyano-2-fluorophenyl)-2,2-difluoroethyl)-2-methylpropane-2-sulfinamide (2.00 g, 3.549 mmol) in conc. HCl (4 mL) and MeOH (12 mL) was stirred for 2 h at room temperature. The resulting mixture was concentrated under reduced pressure. The resulting mixture was adjusted PH=8 with sat. NaHCO$_3$ aq. (100 mL). The resulting mixture was extracted with EtOAc (3×50 mL). The combined organic layers were washed with brine (3×100 mL), dried over anhydrous Na$_2$SO$_4$. The organic layer was concentrated under reduced pressure. The residue was purified by silica gel column chromatography, eluted with CH$_2$Cl$_2$/MeOH (12/1) to afford (R)-3-(1-amino-2,2-difluoroethyl)-4-fluorobenzonitrile (445 mg, 62%) as light yellow solids. $^1$H NMR (400 MHz, DMSO-d$_6$) δ 8.19-8.13 (m, 1H), 7.94-7.89 (m, 1H), 7.50-7.43 (m, 1H), 6.29-5.90 (m, 1H), 4.52-4.33 (m, 1H), 2.43 (s, 2H).

Example 35: (R)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile

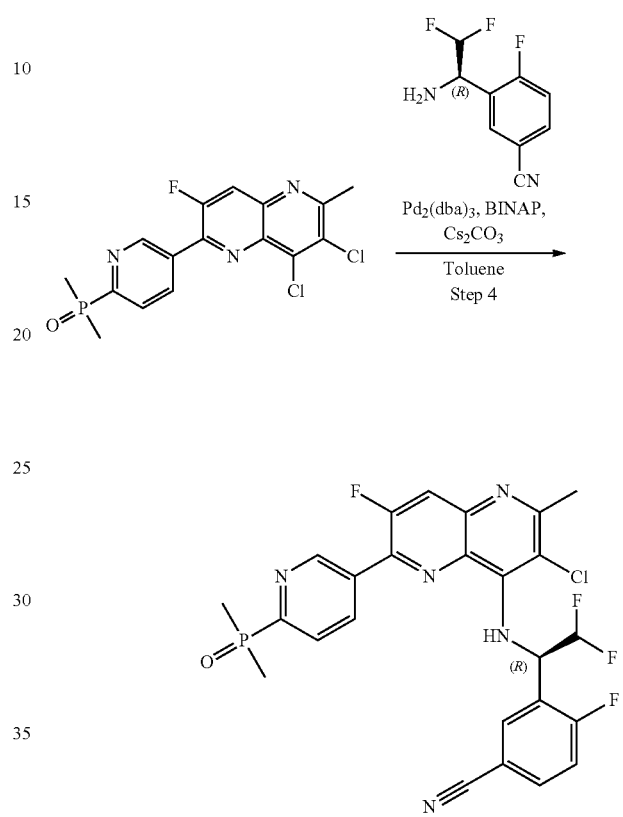

A mixture of (R)-3-(1-amino-2,2-difluoroethyl)-4-fluorobenzonitrile (62 mg, 0.312 mmol), 3,4-dichloro-6-[6-(dimethylphosphoryl)pyridin-3-yl]-7-fluoro-2-methyl-1,5-naphthyridine (100 mg, 0.260 mmol), Pd$_2$(dba)$_3$ (23 mg, 0.026 mmol), BINAP (32 mg, 0.052 mmol) and Cs$_2$CO$_3$ (127 mg, 0.390 mmol) in Toluene (2 mL) was stirred for 4 h at 100° C. under nitrogen atmosphere. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 30% B to 70% B in 20 min; 254/220 nm to afford (R)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile (58 mg, 40%) as a light yellow solid. MS ESI calculated for C$_{25}$H$_{19}$ClF$_4$N$_5$OP, [M+H]$^+$, 548.10, found 548.10. $^1$H NMR (400 MHz, DMSO-d$_6$) δ 9.15 (s, 1H), 8.42-8.35 (m, 2H), 8.29 (d, J=11.6 Hz, 1H), 8.15-8.11 (m, 1H), 7.98-7.94 (m, 1H), 7.41-7.37 (m, 1H), 7.22 (d, J=9.6 Hz, 1H), 6.83-6.43 (m, 2H), 2.69 (s, 3H), 1.79-1.74 (m, 6H). $^{19}$F NMR (376 MHz, DMSO-d$_6$) δ −107.05, −120.48, −125.14, −125.16, −125.33, −125.35. $^{31}$P NMR (162 MHz, DMSO-d$_6$) δ 34.37.

Example 36: (S)-3-(1-((3-chloro-6-(2-(dimeth-ylphosphoryl)pyrimidin-5-yl)-7-fluoro-2-methyl-1,5-naphthyridin-4-yl)amino)-2,2-difluoroethyl)-4-fluorobenzonitrile

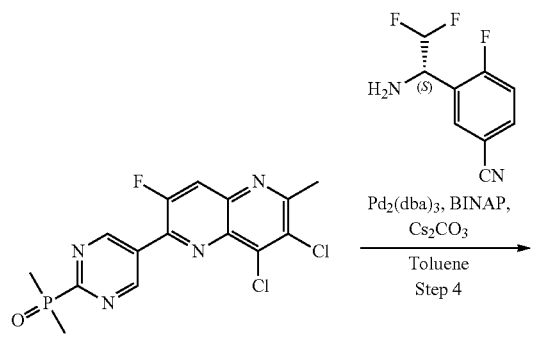

Example 37: diammonium 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate

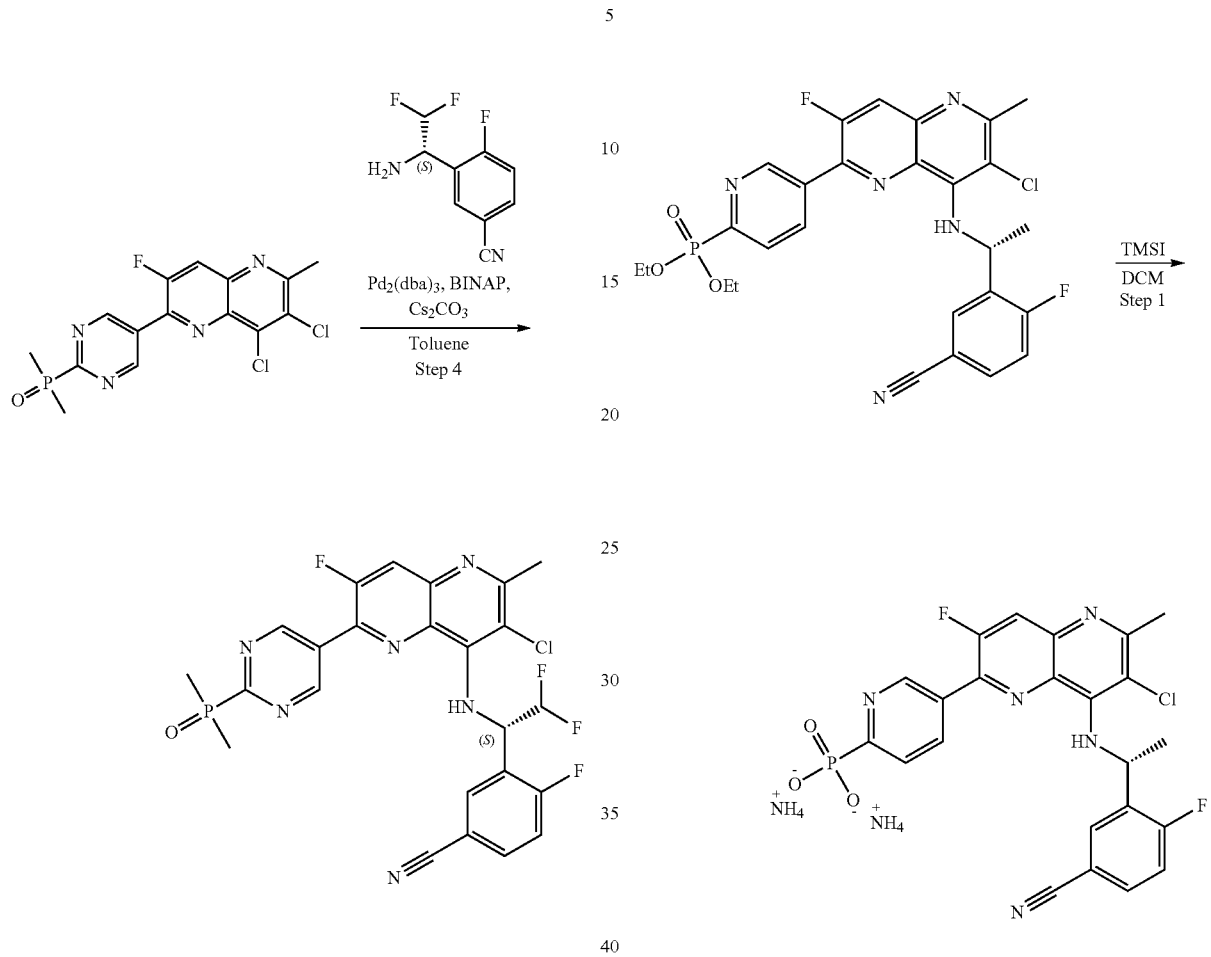

A mixture of (S)-3-(1-amino-2,2-difluoroethyl)-4-fluorobenzonitrile (62 mg, 0.312 mmol), 3,4-dichloro-6-[2-(dimethylphosphoryl)pyrimidin-5-yl]-7-fluoro-2-methyl-1,5-naphthyridine (100 mg, 0.260 mmol), $Pd_2(dba)_3$ (23 mg, 0.026 mmol), BINAP (32 mg, 0.052 mmol) and $Cs_2CO_3$ (126 mg, 0.390 mmol) in Toluene (2 mL) was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L $NH_4HCO_3$), Mobile Phase B: $CH_3CN$; Flow rate: 60 mL/min; Gradient: 30% B to 70% B in 20 min; 254/220 nm to afford (S)-3-(1-((3-chloro-6-(2-(dimethylphosphoryl)pyrimidin-5-yl)-7-fluoro-2-methyl-1,5-naphthyridin-4-yl)amino)-2,2-difluoroethyl)-4-fluorobenzonitrile (22 mg, 15%) as a light yellow solid. MS ESI calculated for $C_{24}H_{18}ClF_4N_6OP$ [M+H]$^+$, 549.09, found 548.85. $^1$H NMR (400 MHz, DMSO-$d_6$) δ 9.40 (d, J=1.5 Hz, 2H), 8.41-8.32 (m, 2H), 7.98-7.94 (m, 1H), 7.42-7.31 (m, 2H), 6.76 (d, J=13.0 Hz, 1H), 6.60-6.45 (m, 1H), 2.71 (s, 3H), 1.87 (d, J=13.8 Hz, 6H). $^{19}$F NMR (377 MHz, DMSO-$d_6$) δ −74.85, −107.24, −120.20, −124.15, −124.89, −126.07. $^{31}$P NMR (162 MHz, DMSO-$d_6$) δ 34.55.

A solution of diethyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate (100 mg, 0.175 mmol) in DCM (2 mL) was added TMSI (350 mg, 1.750 mmol) at 0 degree under nitrogen atmosphere. The reaction was stirred for 2 h at room temperature under nitrogen atmosphere. The resulting mixture was quenched with MeOH (5 mL). The resulting mixture was concentrated under reduced pressure. The residue was purified by reversed-phase flash chromatography with the following conditions: column, C18 silica gel; mobile phase, $CH_3CN$ in water (10 mmol/L $NH_4HCO_3$), 5% to 35% gradient in 25 min; detector, 254 nm. The resulting mixture was concentrated under reduced pressure. This resulted in diammonium 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate (29 mg, 29%) as a yellow solid. MS ESI calculated for $C_{23}H_{17}ClF_2N_5O_3P$ [M+H]$^+$, 516.07, found 516.05. $^1$H NMR (400 MHz, DMSO-$d_6$) δ 8.94 (s, 1H), 7.99-7.93 (m, 1H), 7.92-7.83 (m, 2H), 7.78-7.65 (m, 2H), 7.42-7.27 (m, 3H), 6.82 (d, J=8.6 Hz, 1H), 6.32-6.25 (m, 1H), 2.60 (s, 3H), 1.62 (d, J=6.7 Hz, 3H). $^{19}$F NMR (377 MHz, DMSO-$d_6$) δ −109.17, −120.92. $^{31}$P NMR (162 MHz, DMSO-$d_6$) δ 4.35.

Example 38: (R)-3-(1-((3-chloro-6-(2-(dimethylphosphoryl)pyrimidin-5-yl)-7-fluoro-2-methyl-1,5-naphthyridin-4-yl)amino)-2,2-difluoroethyl)-4-fluorobenzonitrile

Example 39: (R)-3-(1-((3-chloro-6-(6-((dimethylphosphoryl)methyl)pyridin-3-yl)-7-fluoro-2-methyl-1,5-naphthyridin-4-yl)amino)ethyl)-4-fluorobenzonitrile Synthetic Scheme

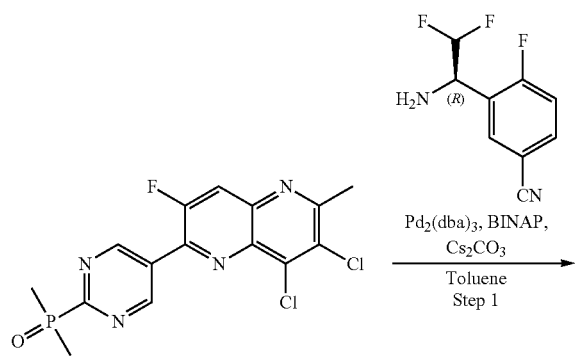

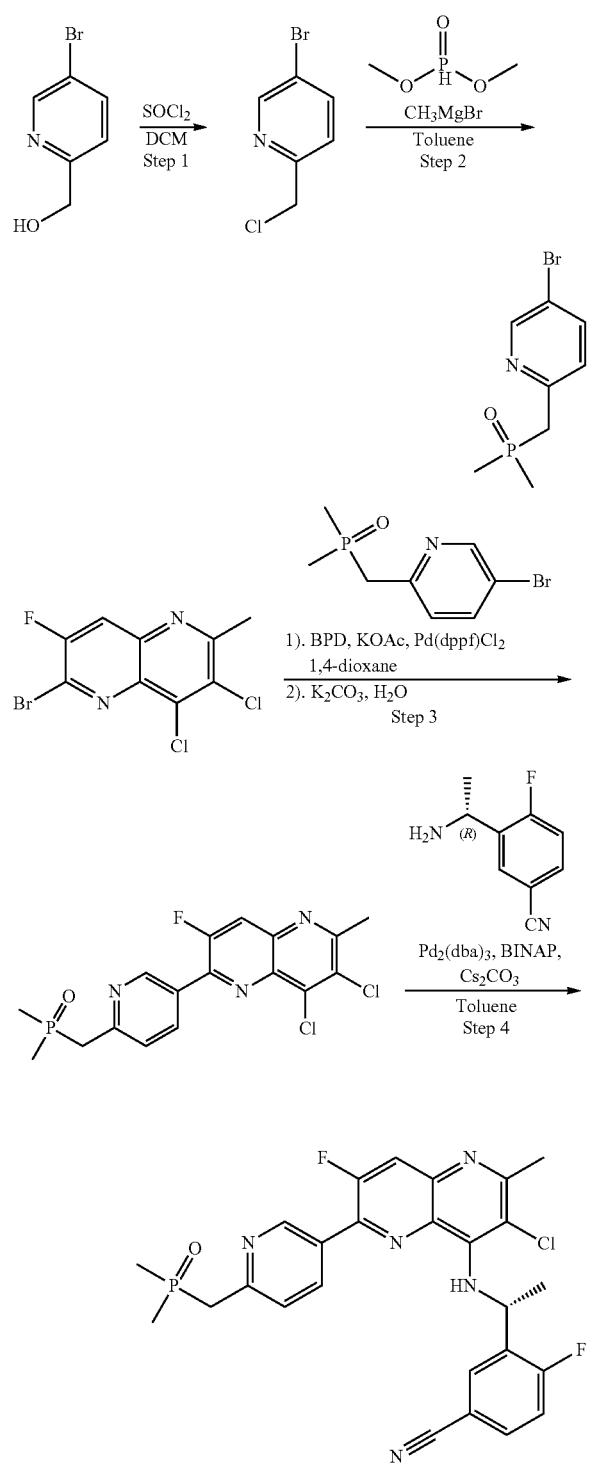

A mixture of (R)-3-(1-amino-2,2-difluoroethyl)-4-fluorobenzonitrile (62 mg, 0.312 mmol), 3,4-dichloro-6-[2-(dimethylphosphoryl)pyrimidin-5-yl]-7-fluoro-2-methyl-1,5-naphthyridine (100 mg, 0.260 mmol), Pd$_2$(dba)$_3$ (23 mg, 0.026 mmol), BINAP (32 mg, 0.052 mmol) and Cs$_2$CO$_3$ (126 mg, 0.390 mmol) in Toluene (2 mL) was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford (R)-3-(1-((3-chloro-6-(2-(dimethylphosphoryl)pyrimidin-5-yl)-7-fluoro-1,5-naphthyridin-4-yl)amino)-2,2-difluoroethyl)-4-fluorobenzonitrile (13 mg, 8%) as a light yellow solid. MS ESI calculated for C$_{24}$H$_{18}$ClF$_4$N$_6$OP [M+H]$^+$, 549.09, found 549.05. $^1$H NMR (400 MHz, DMSO-d$_6$) δ 9.40 (s, 2H), 8.42-8.31 (m, 2H), 7.98-7.94 (m, 1H), 7.42-7.29 (m, 2H), 6.75 (d, J=10.1 Hz, 1H), 6.60-6.45 (m, 1H), 2.71 (s, 3H), 1.87 (d, J=13.7 Hz, 6H). $^{19}$F NMR (377 MHz, DMSO-d$_6$) δ −74.85, −107.24, −120.20, −124.15, −124.89, −126.07. $^{31}$P NMR (162 MHz, DMSO-d$_6$) δ 34.55.

Preparation 39A: 5-bromo-2-(chloromethyl)pyridine

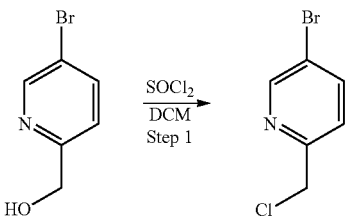

To a stirred mixture of (5-bromopyridin-2-yl)methanol (10.00 g, 53.185 mmol) in DCM (200 mL) was added thionyl chloride (9.49 g, 79.778 mmol) dropwise at 0° C. under nitrogen atmosphere. The resulting mixture was stirred for overnight at room temperature under nitrogen atmosphere. The mixture was basified to pH 9 with saturated NaHCO$_3$ (aq.). The resulting mixture was extracted with CH$_2$Cl$_2$ (3×200 mL). The combined organic layers were washed with brine (2×200 mL), dried over anhydrous Na$_2$SO$_4$. After filtration, the filtrate was concentrated under reduced pressure. This resulted in 5-bromo-2-(chloromethyl)pyridine (10.30 g, 93%) as a brown oil. $^1$H NMR (400 MHz, Chloroform-d) δ 8.64 (d, J=2.3 Hz, 1H), 7.90-7.78 (m, 1H), 7.39 (d, J=8.3 Hz, 1H), 4.63 (s, 2H).

Preparation 39B: 5-bromo-2-[(dimethylphosphoryl)methyl]pyridine

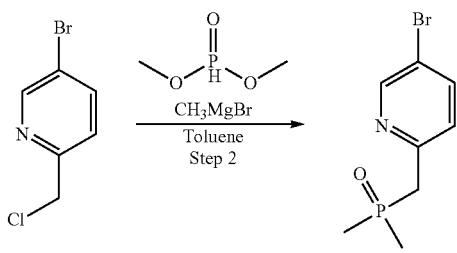

To a stirred mixture of 3M of bromo(methyl)magnesium (9.69 mL, 29.061 mmol) in THF (15 mL) was added dimethylphosphite (1.17 g, 10.656 mmol) in Toluene (5 mL) dropwise at room temperature under nitrogen atmosphere. The resulting mixture was stirred for 1 h at 70° C. under nitrogen atmosphere. To the above mixture was added 5-bromo-2-(chloromethyl)pyridine (2.00 g, 9.687 mmol) in Toluene (5 mL) dropwise at room temperature. The resulting mixture was stirred for additional 16 h at 70° C. The reaction was quenched with sat. NH$_4$Cl (aq.) at 0° C. The resulting mixture was extracted with EtOAc (3×50 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with PE/EA (1/1) to afford 5-bromo-2-[(dimethylphosphoryl)methyl]pyridine (1.10 g, 45%) as a brown solid. $^1$H NMR (400 MHz, Chloroform-d) δ 8.60 (d, J=2.4 Hz, 1H), 7.83-7.77 (m, 1H), 7.30-7.23 (m, 1H), 3.36 (d, J=15.1 Hz, 2H), 1.56 (s, 3H), 1.52 (s, 3H). $^{31}$P NMR (162 MHz, Chloroform-d) δ 42.08.

Preparation 39C: 3,4-dichloro-6-{6-[(dimethylphosphoryl)methyl]pyridin-3-yl}-7-fluoro-2-methyl-1,5-naphthyridine

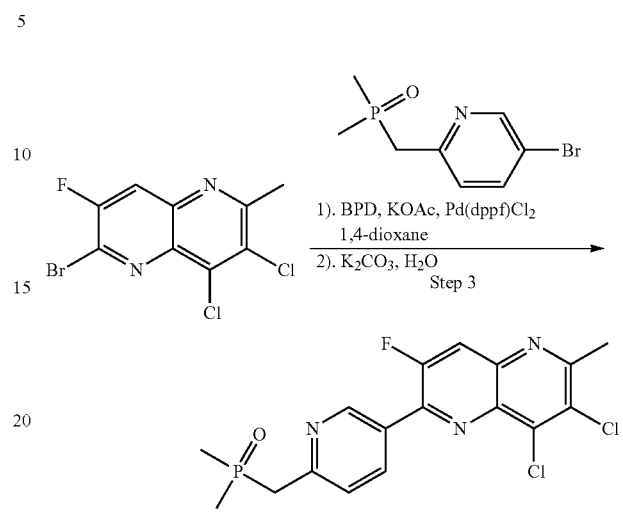

To a solution of 5-bromo-2-[(dimethylphosphoryl)methyl]pyridine (418 mg, 1.684 mmol) and BPD (513 mg, 2.020 mmol) in 1,4-dioxane (10 mL) were added potassium acetate (413 mg, 4.209 mmol) and Pd(dppf)Cl$_2$·CH$_2$Cl$_2$ (114 mg, 0.140 mmol). The resulting mixture was stirred for 2 h at 90° C. under nitrogen atmosphere. To the above mixture was added 6-bromo-3,4-dichloro-7-fluoro-2-methyl-1,5-naphthyridine (435 mg, 1.403 mmol), K$_2$CO$_3$ (388 mg, 2.806 mmol) and H$_2$O (2 mL) at room temperature. The resulting mixture was stirred for additional 16 h at 80° C. The resulting mixture was concentrated under vacuum. The residue was purified by silica gel column chromatography, eluted with CH$_2$Cl$_2$/MeOH (10/1) to afford 3,4-dichloro-6-{6-[(dimethylphosphoryl)methyl]pyridin-3-yl}-7-fluoro-2-methyl-1,5-naphthyridine (150 mg, 26%) as a yellow solid. MS ESI calculated for C$_{17}$H$_{15}$Cl$_2$FN$_3$OP [M+H]$^+$, 398.03, found 397.9. $^1$H NMR (400 MHz, Chloroform-d) δ 9.38 (s, 1H), 8.53 (d, J=7.8 Hz, 1H), 8.09 (d, J=11.1 Hz, 1H), 7.56 (d, J=8.2 Hz, 1H), 3.53 (d, J=14.8 Hz, 2H), 2.89 (s, 3H), 1.61 (d, J=12.1 Hz, 6H).

Example 39: (R)-3-(1-((3-chloro-6-(6-((dimethylphosphoryl)methyl)pyridin-3-yl)-7-fluoro-2-methyl-1,5-naphthyridin-4-yl)amino)ethyl)-4-fluorobenzonitrile

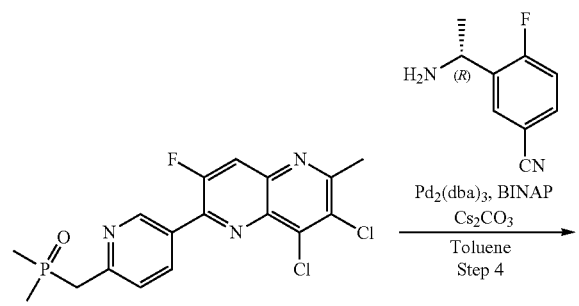

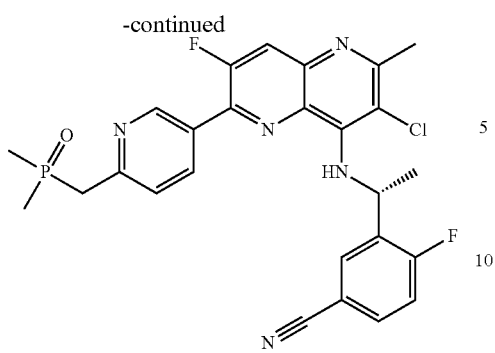

To a solution of 3,4-dichloro-6-{6-[(dimethylphosphoryl)methyl]pyridin-3-yl}-7-fluoro-2-methyl-1,5-naphthyridine (75 mg, 0.188 mmol), BINAP (23 mg, 0.038 mmol) and 3-[(1R)-1-aminoethyl]-4-fluorobenzonitrile (37 mg, 0.226 mmol) in Toluene (1 mL) were added $Cs_2CO_3$ (92 mg, 0.282 mmol) and $Pd_2(dba)_3$ (17 mg, 0.019 mmol). After stirring for 16 h at 100° C. under a nitrogen atmosphere. The resulting mixture was concentrated under reduced pressure. The residue was purified by reversed-phase flash chromatography with the following conditions: column, C18 silica gel; mobile phase, $CH_3CN$ in water (10 mmol/L $NH_4HCO_3$), 20% to 60% gradient in 30 min; detector, 254 nm. This resulted in (R)-3-(1-((3-chloro-6-(6-((dimethylphosphoryl)methyl)pyridin-3-yl)-7-fluoro-2-methyl-1,5-naphthyridin-4-yl)amino)ethyl)-4-fluorobenzonitrile (70 mg, 70%) as a white solid. MS ESI calculated for $C_{26}H_{23}ClF_2N_5OP$ [M+H]$^+$, 526.13, found 525.95. $^1$H NMR (300 MHz, DMSO-$d_6$) δ 8.90 (s, 1H), 8.16 (d, J=11.8 Hz, 1H), 8.08 (d, J=8.2 Hz, 1H), 8.03-7.98 (m, 1H), 7.80-7.73 (m, 1H), 7.50 (d, J=7.3 Hz, 1H), 7.38-7.29 (m, 1H), 6.91 (d, J=8.5 Hz, 1H), 6.42-6.31 (m, 1H), 3.48 (d, J=15.4 Hz, 2H), 2.65 (s, 3H), 1.65 (d, J=6.8 Hz, 3H), 1.50 (s, 3H), 1.46 (s, 3H). $^{19}$F NMR (282 MHz, DMSO-$d_6$) δ −109.12, −120.96. $^{31}$P NMR (121 MHz, DMSO-$d_6$) δ 39.08.

Example 40: 3-[(1R)-1-({3-chloro-6-[6-(dimethylphosphoryl)pyridin-3-yl]-2-methyl-1,5-naphthyridin-4-yl}amino)ethyl]-4-fluorobenzonitrile Synthetic Scheme

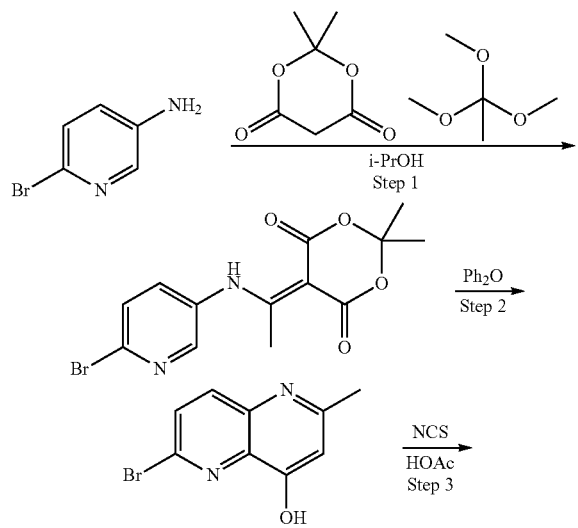

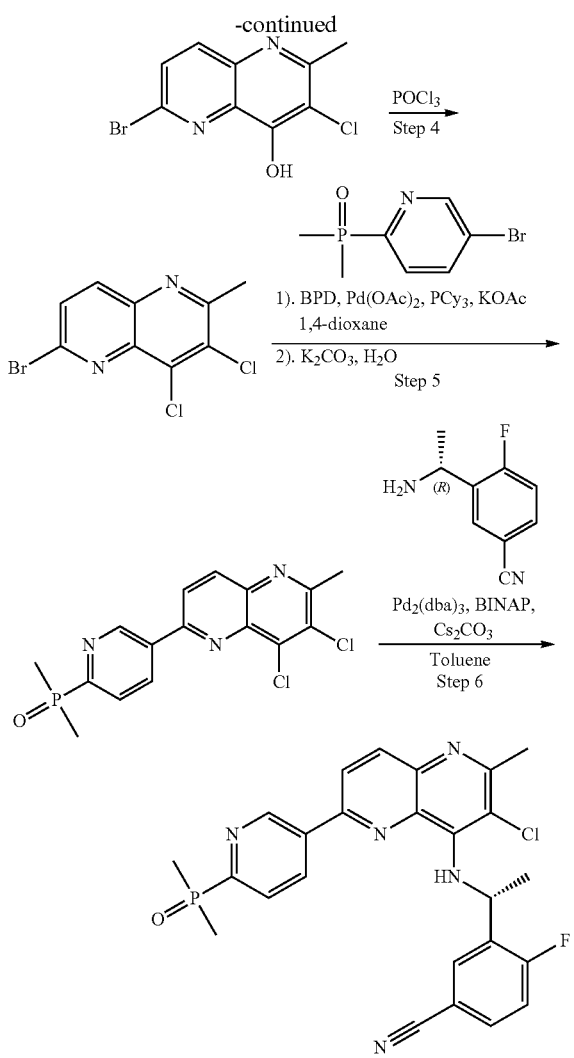

Preparation 40A. 5-{1-[(6-bromopyridin-3-yl)amino]ethylidene}-2,2-dimethyl-1,3-dioxane-4,6-dione A solution of 1,1,1-trimethoxyethane (18.32 g, 152.588 mmol) and meldrum's acid (21.99 g, 152.588 mmol) was stirred for 4 h at 100° C. under nitrogen atmosphere. The resulting mixture was concentrated under reduced pressure.

To a stirred solution of 6-bromopyridin-3-amine (6.60 g, 38.147 mmol) in IPA (60 mL) was added the resulting mixture at room temperature. The resulting mixture was stirred for 2 h at room temperature. The precipitated solids were collected by filtration and washed with ethyl ether (3×50 mL). The resulting solid was dried under vacuum. This resulted in 5-{1-[(6-bromopyridin-3-yl)amino]ethyl-idene}-2,2-dimethyl-1,3-dioxane-4,6-dione (9.88 g, 76%) as a yellow solid. MS ESI calculated for $C_{13}H_{13}BrN_2O_4$ [M−H]⁻, 339.01 341.01, found 338.92 340.92. ¹H NMR (300 MHz, Chloroform-d) δ 12.85 (s, 1H), 8.30 (d, J=2.8 Hz, 1H), 7.65-7.60 (m, 1H), 7.44-7.40 (m, 1H), 2.59 (s, 3H), 1.75 (s, 6H).

Preparation 40B3:
6-bromo-2-methyl-1,5-naphthyridin-4-ol

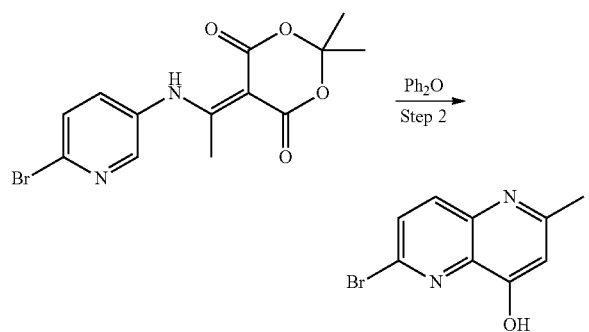

A solution of 5-{1-[(6-bromopyridin-3-yl)amino]ethyl-idene}-2,2-dimethyl-1,3-dioxane-4,6-dione (12.60 g, 36.933 mmol) in diphenyl-ether (120 mL) was stirred for 1 h at 180° C. The mixture was allowed to cool down to room temperature. The precipitated solids were collected by filtration and washed with ethyl ether (3×50 mL). The resulting solid was dried under vacuum. This resulted in 6-bromo-2-methyl-1,5-naphthyridin-4-ol (6.90 g, 78%) as a yellow solid. MS ESI calculated for $C_9H_7BrN_2O$ [M+H]⁺, 238.97 240.97, found 239.10 241.10. ¹H NMR (400 MHz, DMSO-$d_6$) δ 11.85 (s, 1H), 7.91-7.83 (m, 1H), 7.82-7.78 (m, 1H), 6.14 (s, 1H), 2.35 (s, 3H).

Preparation 40C:
6-bromo-3-chloro-2-methyl-1,5-naphthyridin-4-ol

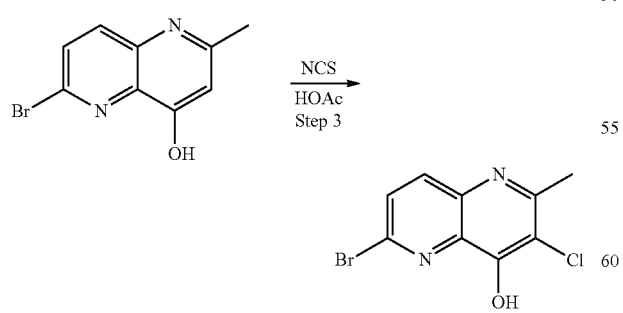

A solution of 6-bromo-2-methyl-1,5-naphthyridin-4-ol (7.80 g, 32.626 mmol) and NCS (5.23 g, 39.151 mmol) in HOAc (150 mL) was stirred for 3 h at 65° C. The mixture was allowed to cool down to room temperature. The precipitated solids were collected by filtration and washed with water (3×100 mL). The resulting solid was dried under vacuum. This resulted in 6-bromo-3-chloro-2-methyl-1,5-naphthyridin-4-ol (7.30 g, 82%) as a white solid. MS ESI calculated for $C_9H_6BrClN_2O$ [M−H]⁻, 270.94 272.94, found 270.90 272.90. ¹H NMR (400 MHz, DMSO-$d_6$) δ 12.42 (s, 1H), 8.01-7.68 (m, 2H), 2.53 (s, 3H).

Preparation 40D:
6-bromo-3,4-dichloro-2-methyl-1,5-naphthyridine

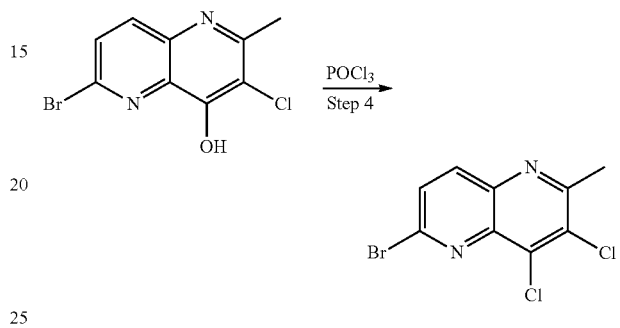

A solution of 6-bromo-3-chloro-2-methyl-1,5-naphthyridin-4-ol (3.00 g, 10.969 mmol) in POCl₃ (30 mL) was stirred for 2 h at 100° C. under nitrogen atmosphere. The mixture was allowed to cool down to room temperature. The resulting mixture was concentrated under reduced pressure. The residue was dissolved in water (100 mL). The mixture was basified to pH 8 with saturated NaHCO₃ (aq.). The resulting mixture was extracted with EtOAc (3×100 mL). The combined organic layers were dried over anhydrous Na₂SO₄. After filtration, the filtrate was concentrated under reduced pressure. The residue was purified by silica gel column chromatography, eluted with PE/EA (10/1) to afford 6-bromo-3,4-dichloro-2-methyl-1,5-naphthyridine (2.30 g, 72%) as a white solid. MS ESI calculated for $C_9H_5BrCl_2N_2$ [M+H]⁺, 290.90 292.90, found N/A. ¹H NMR (400 MHz, Chloroform-d) δ 8.28 (d, J=8.8 Hz, 1H), 7.64 (d, J=8.7 Hz, 1H), 2.87 (s, 3H).

Preparation 40E: 3,4-dichloro-6-[6-(dimethylphosphoryl)pyridin-3-yl]-2-methyl-1,5-naphthyridine

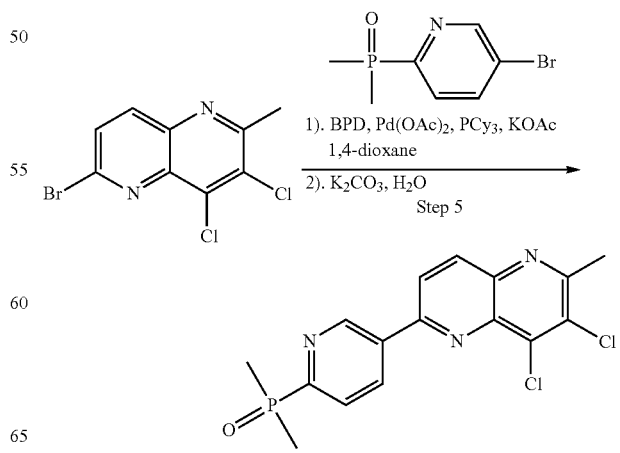

To a solution of 5-bromo-2-(dimethylphosphoryl)pyridine (481 mg, 2.056 mmol) and BPD (652 mg, 2.570 mmol) in 1,4-dioxane (10 mL) were added Pd(OAc)$_2$ (38 mg, 0.171 mmol), PCy$_3$ (96 mg, 0.343 mmol) and KOAc (420 mg, 4.283 mmol). After stirring for 16 h at 80° C. under a nitrogen atmosphere. To the above mixture were added 6-bromo-3,4-dichloro-2-methyl-1,5-naphthyridine (500 mg, 1.713 mmol), K$_2$CO$_3$ (592 mg, 4.283 mmol) and H$_2$O (2 mL) at room temperature. The resulting mixture was stirred for additional 2 h at 80° C. The resulting mixture was concentrated under reduced pressure. The residue was purified by silica gel column chromatography, eluted with CH$_2$Cl$_2$/MeOH (10/1) to afford 3,4-dichloro-6-[6-(dimethylphosphoryl)pyridin-3-yl]-2-methyl-1,5-naphthyridine (165 mg, 26%) as a yellow solid. MS ESI calculated for C$_{16}$H$_{14}$Cl$_2$N$_3$OP [M+H]$^+$, 366.03, found 366.15. $^1$H NMR (300 MHz, Chloroform-d) δ 9.60 (s, 1H), 8.72-8.65 (m, 1H), 8.52-8.47 (m, 1H), 8.36-8.27 (m, 1H), 8.23-8.17 (m, 1H), 2.92 (s, 3H), 1.88 (s, 3H), 1.83 (s, 3H).

Example 40: 3-[(1R)-1-({3-chloro-6-[6-(dimethylphosphoryl)pyridin-3-yl]-2-methyl-1,5-naphthyridin-4-yl}amino)ethyl]-4-fluorobenzonitrile

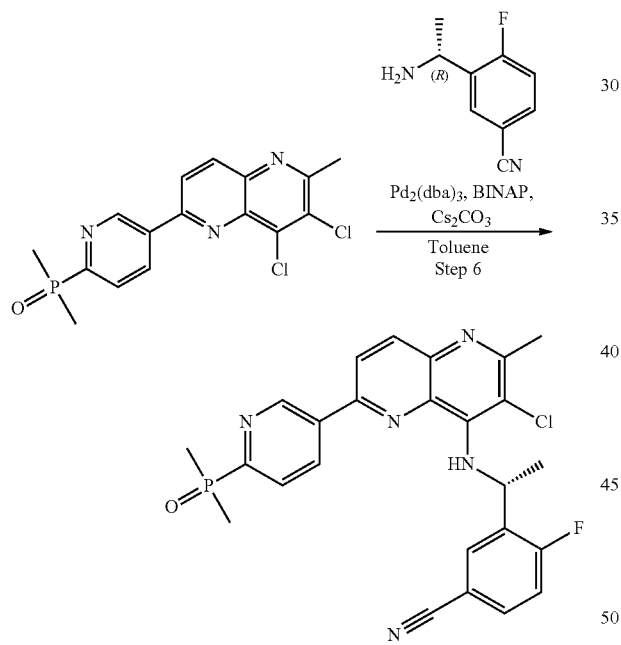

To a solution of 3,4-dichloro-6-[6-(dimethylphosphoryl)pyridin-3-yl]-2-methyl-1,5-naphthyridine (100 mg, 0.273 mmol) and 3-[(1R)-1-aminoethyl]-4-fluorobenzonitrile (54 mg, 0.328 mmol) in Toluene (2 mL) were added Pd$_2$(dba)$_3$ (25 mg, 0.027 mmol), BINAP (34 mg, 0.055 mmol) and Cs$_2$CO$_3$ (133 mg, 0.410 mmol) at room temperature. The resulting mixture was stirred for 16 h at 100° C. under nitrogen atmosphere. The resulting mixture was concentrated under reduced pressure. The residue was purified by silica gel column chromatography, eluted with CH$_2$Cl$_2$/MeOH (10/1) followed by reversed-phase flash chromatography with the following conditions: column, C18 silica gel; mobile phase, CH$_3$CN in water (10 mmol/L NH$_4$HCO$_3$), 45% to 55% gradient in 10 min; detector, 254 nm. This resulted in 3-[(1R)-1-({3-chloro-6-[6-(dimethylphosphoryl) pyridin-3-yl]-2-methyl-1,5-naphthyridin-4-yl}amino) ethyl]-4-fluorobenzonitrile (80 mg, 59%) as a yellow solid. MS ESI calculated for C$_{25}$H$_{22}$ClFN$_5$OP [M+H]$^+$, 494.12, found 494.05. $^1$H NMR (400 MHz, DMSO-d$_6$) δ 9.55-9.51 (m, 1H), 8.67-8.59 (m, 1H), 8.41-8.35 (m, 1H), 8.34-8.28 (m, 1H), 8.14-8.05 (m, 2H), 7.85-7.76 (m, 1H), 7.43-7.33 (m, 1H), 7.16-6.98 (m, 1H), 6.41-6.29 (m, 1H), 2.63 (s, 3H), 1.76 (s, 3H), 1.74-1.69 (m, 6H). $^{19}$F NMR (376 MHz, DMSO-d$_6$) δ −109.59. $^{31}$P NMR (162 MHz, DMSO-d$_6$) δ 34.23.

Example 41: 3-[(1R)-1-({3-chloro-6-[2-(dimethylphosphoryl)pyrimidin-5-yl]-2-methyl-1,5-naphthyridin-4-yl}amino)ethyl]-4-fluorobenzonitrile Synthetic Scheme

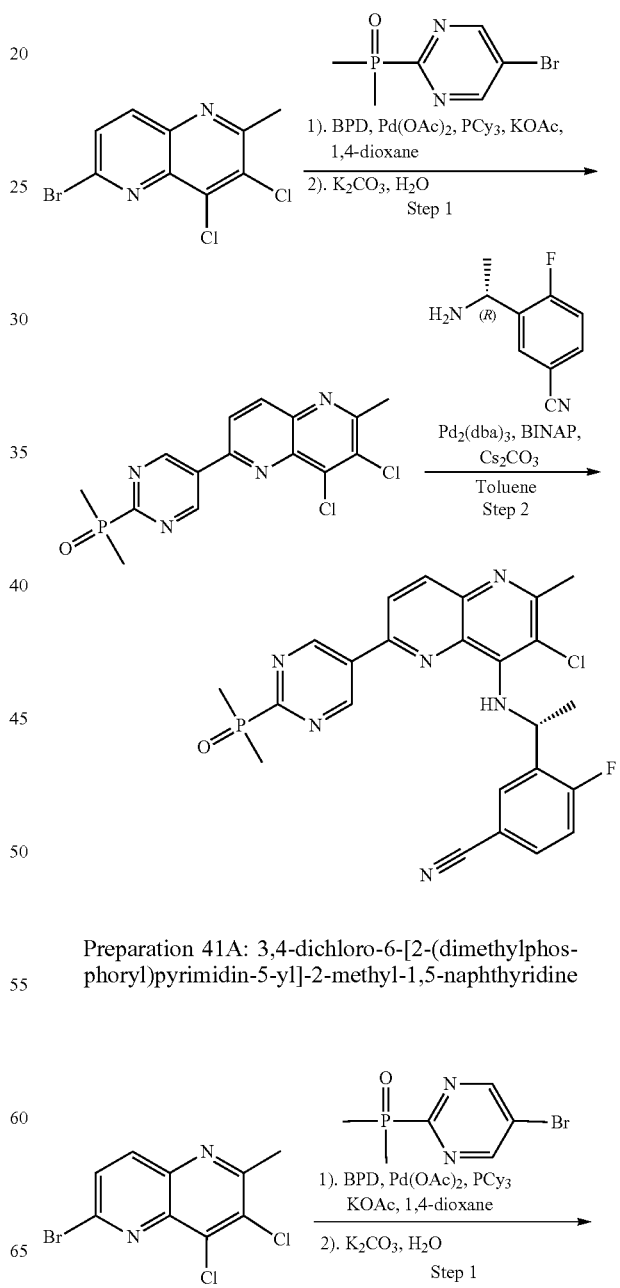

Preparation 41A: 3,4-dichloro-6-[2-(dimethylphosphoryl)pyrimidin-5-yl]-2-methyl-1,5-naphthyridine

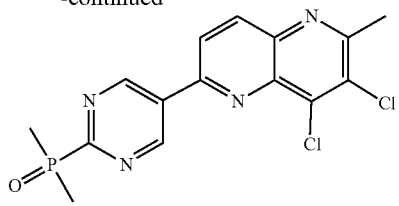

To a solution of 5-bromo-2-(dimethylphosphoryl)pyrimidine (483 mg, 2.056 mmol) and BPD (652 mg, 2.570 mmol) in 1,4-dioxane (10 mL) were added Pd(OAc)$_2$ (38 mg, 0.171 mmol), PCy$_3$ (96 mg, 0.343 mmol) and KOAc (420 mg, 4.283 mmol). After stirring for 16 h at 80° C. under a nitrogen atmosphere. To the above mixture was added 6-bromo-3,4-dichloro-2-methyl-1,5-naphthyridine (500 mg, 1.713 mmol), K$_2$CO$_3$ (592 mg, 4.283 mmol) and H$_2$O (2 mL) in portions at room temperature. The resulting mixture was stirred for additional 2 h at 80° C. The resulting mixture was concentrated under reduced pressure. The residue was purified by silica gel column chromatography, eluted with CH$_2$Cl$_2$/MeOH (10/1) to afford 3,4-dichloro-6-[2-(dimethylphosphoryl)pyrimidin-5-yl]-2-methyl-1,5-naphthyridine (180 mg, 28%) as a yellow solid. MS ESI calculated for C$_{15}$H$_{13}$C$_{12}$N$_4$OP [M+H]$^+$, 367.02, found 367.05. $^1$H NMR (300 MHz, Chloroform-d) δ 9.69 (s, 2H), 8.54 (d, J=8.7 Hz, 1H), 8.21 (d, J=8.8 Hz, 1H), 2.93 (s, 3H), 1.97 (s, 3H), 1.92 (s, 3H).

Example 41: 3-[(1R)-1-({3-chloro-6-[2-(dimethylphosphoryl)pyrimidin-5-yl]-2-methyl-1,5-naphthyridin-4-yl}amino)ethyl]-4-fluorobenzonitrile

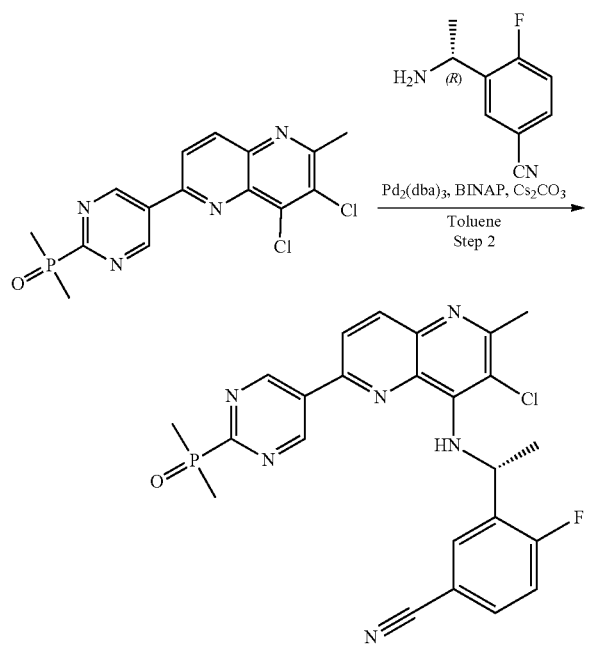

A mixture of 3,4-dichloro-6-[2-(dimethylphosphoryl)pyrimidin-5-yl]-2-methyl-1,5-naphthyridine (100 mg, 0.272 mmol), 3-[(1R)-1-aminoethyl]-4-fluorobenzonitrile (54 mg, 0.326 mmol), Pd$_2$(dba)$_3$ (25 mg, 0.027 mmol), BINAP (34 mg, 0.054 mmol) and Cs$_2$CO$_3$ (133 mg, 0.408 mmol) in Toluene (2 mL) was stirred for overnight at 100° C. under nitrogen atmosphere. The resulting mixture was concentrated under reduced pressure. The residue was purified by silica gel column chromatography, eluted with CH$_2$Cl$_2$/MeOH (10/1) followed by reversed-phase flash chromatography with the following conditions: column, C18 silica gel; mobile phase, CH$_3$CN in water (10 mmol/L NH$_4$HCO$_3$), 45% to 55% gradient in 10 min; detector, 254 nm. This resulted in 3-[(1R)-1-({3-chloro-6-[2-(dimethylphosphoryl)pyrimidin-5-yl]-2-methyl-1,5-naphthyridin-4-yl}amino)ethyl]-4-fluorobenzonitrile (29 mg, 21%) as a yellow solid. MS ESI calculated for C$_{24}$H$_{21}$ClFN$_6$OP [M+H]$^+$, 495.12, found 494.95. $^1$H NMR (400 MHz, DMSO-d$_6$) δ 9.73 (s, 2H), 8.49-8.43 (m, 1H), 8.39-8.33 (m, 1H), 8.13-8.08 (m, 1H), 7.83-7.77 (m, 1H), 7.41-7.35 (m, 1H), 7.24-7.05 (m, 1H), 6.40-6.27 (m, 1H), 2.64 (s, 3H), 1.87 (s, 3H), 1.83 (s, 3H), 1.71 (d, J=6.8 Hz, 3H). $^{19}$F NMR (376 MHz, DMSO-d$_6$) δ -109.84. $^{31}$P NMR (162 MHz, DMSO-d$_6$) δ34.14.

Example 42: 3-[(1R)-1-({3-chloro-6-[6-(diethylphosphoryl)pyridin-3-yl]-7-fluoro-2-methyl-1,5-naphthyridin-4-yl}amino)ethyl]-4-fluorobenzonitrile Synthetic Scheme

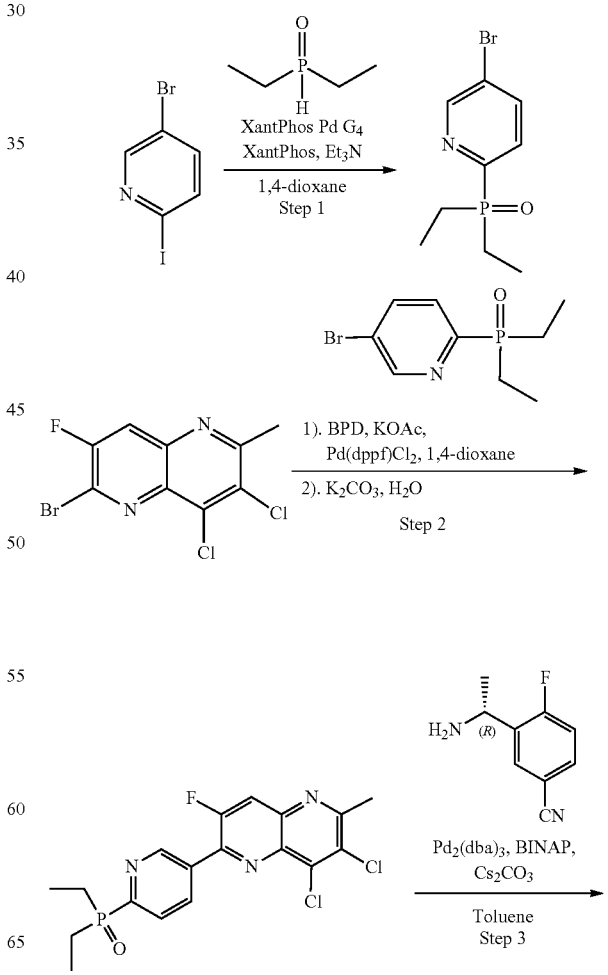

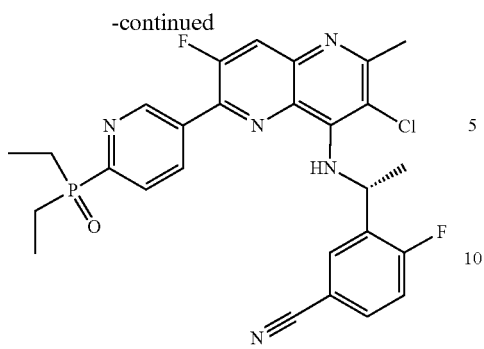

Preparation 42A:
5-bromo-2-(diethylphosphoryl)pyridine

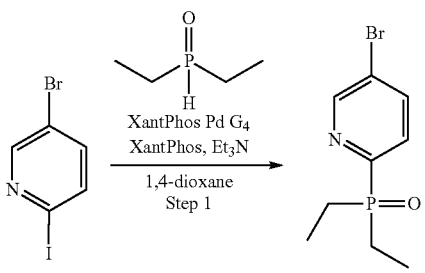

To a stirred mixture of 5-bromo-2-iodopyridine (3.00 g, 10.567 mmol) and (ethylphosphonoyl)ethane (1.35 g, 12.680 mmol) in 1,4-dioxane (60 mL) were added TEA (1.60 g, 15.851 mmol), Xantphos (1.22 g, 2.113 mmol) and Xantphos Pd $G_4$ (1.02 g, 1.057 mmol) at room temperature under nitrogen atmosphere. The resulting mixture was stirred for overnight at 90° C. under nitrogen atmosphere. The residue was basified to pH 9 with saturated NaHCO$_3$ (aq.). The resulting mixture was washed with 3×100 mL of CH$_2$Cl$_2$. After filtration, the filtrate was concentrated under reduced pressure. The residue was purified by silica gel column chromatography, eluted with CH$_2$Cl$_2$/MeOH (9:1) to afford 5-bromo-2-(diethylphosphoryl)pyridine (2.26 g, 81%) as a brown oil. MS ESI calculated for C$_9$H$_{13}$BrNOP [M+H]$^+$, 261.99 263.99, found 264.20 266.20. $^1$H NMR (300 MHz, Chloroform-d) δ 8.81 (s, 1H), 8.11-7.99 (m, 2H), 2.12-1.95 (m, 4H), 1.20-1.03 (m, 6H). $^{31}$P NMR (121 MHz, Chloroform-d) δ 45.89.

Preparation 42B: 3,4-dichloro-6-[6-(diethylphosphoryl)pyridin-3-yl]-7-fluoro-2-methyl-1,5-naphthyridine

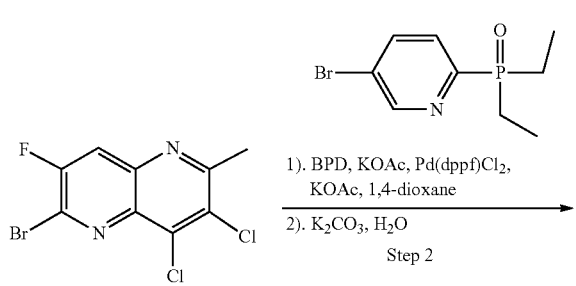

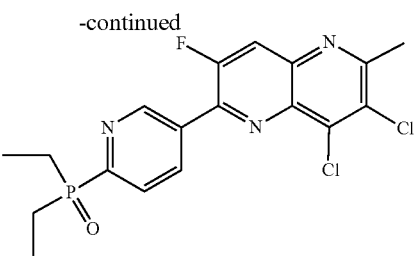

To a stirred solution of 5-bromo-2-(diethylphosphoryl)pyridine (220 mg, 0.839 mmol) and BPD (295 mg, 1.161 mmol) in 1,4-dioxane (4 mL) were added KOAc (158 mg, 1.613 mmol) and Pd(dppf)Cl$_2$·CH$_2$Cl$_2$ (53 mg, 0.065 mmol) at room temperature. After stirring for 2 h at 90° C. under a nitrogen atmosphere. To the above mixture was added K$_2$CO$_3$ (223 mg, 1.613 mmol), 6-bromo-3,4-dichloro-7-fluoro-2-methyl-1,5-naphthyridine (200 mg, 0.645 mmol) and H$_2$O (0.4 mL) at room temperature. The resulting mixture was stirred for additional 2 h at 80° C. The resulting mixture was concentrated under reduced pressure. The residue was purified by silica gel column chromatography, eluted with CH$_2$Cl$_2$/MeOH (5/1) to afford 3,4-dichloro-6-[6-(diethylphosphoryl)pyridin-3-yl]-7-fluoro-2-methyl-1,5-naphthyridine (200 mg, 75%) as a brown yellow solid. MS ESI calculated for C$_{18}$H$_{17}$Cl$_2$FN$_3$OP [M+H]$^+$, 412.05, found 412.30. $^1$H NMR (400 MHz, Chloroform-d) δ 9.55 (s, 1H), 8.64 (d, J=7.6 Hz, 1H), 8.37-8.27 (m, 1H), 8.13 (d, J=11.1 Hz, 1H), 2.90 (s, 3H), 2.21-2.03 (m, 4H), 1.22-1.10 (m, 6H).

Example 42: 3-[(1R)-1-({3-chloro-6-[6-(diethylphosphoryl)pyridin-3-yl]-7-fluoro-2-methyl-1,5-naphthyridin-4-yl}amino)ethyl]-4-fluorobenzonitrile

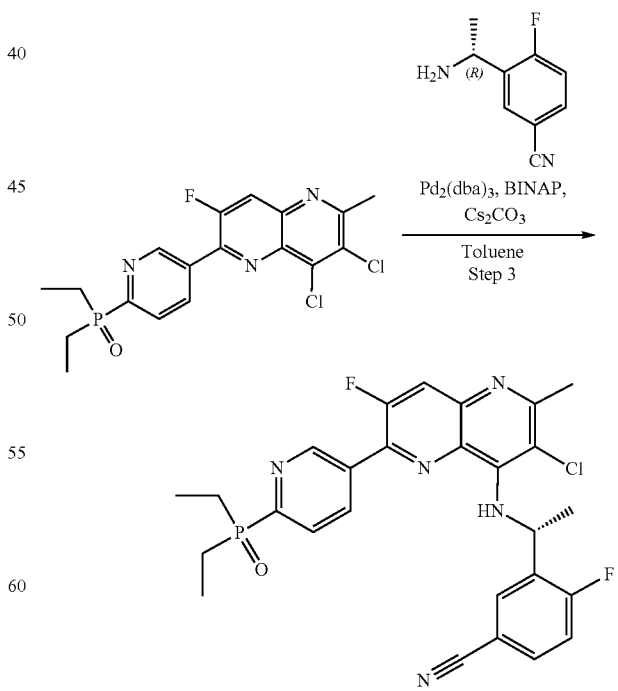

To a stirred solution of 3,4-dichloro-6-[2-(diethylphosphoryl)pyrimidin-5-yl]-7-fluoro-2-methyl-1,5-naphthyridine (100 mg, 0.243 mmol) and 3-[(1R)-1-aminoethyl]-4-fluorobenzonitrile (60 mg, 0.364 mmol) in Toluene (2 mL) were added BINAP (30 mg, 0.049 mmol), Cs₂CO₃ (118 mg, 0.364 mmol) and Pd₂(dba)₃ (22 mg, 0.024 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH₂Cl₂/MeOH (9/1) followed by reversed-phase flash chromatography with the following conditions: column, C18 silica gel; mobile phase, CH₃CN in water (10 mmol/L NH₄HCO₃), 40% to 60% gradient in 30 min; detector, 254 nm. This resulted in 3-[(1R)-1-({3-chloro-6-[6-(diethylphosphoryl)pyridin-3-yl]-7-fluoro-2-methyl-1,5-naphthyridin-4-yl}amino)ethyl]-4-fluorobenzonitrile (56 mg, 42%) as a light yellow solid. MS ESI calculated for C₂₇H₂₅ClF₂N₅OP [M+H]+, 540.15, found 540.00. ¹H NMR (400 MHz, Chloroform-d) δ 9.20 (s, 1H), 8.32-8.16 (m, 2H), 7.98 (d, J=11.4 Hz, 1H), 7.61-7.46 (m, 2H), 7.09-7.00 (m, 1H), 6.50-6.28 (m, 2H), 2.75 (s, 3H), 2.23-2.05 (m, 4H), 1.72 (d, J=6.2 Hz, 3H), 1.25-1.11 (m, 6H). ¹⁹F NMR (377 MHz, Chloroform-d) 6-108.55, −120.35. ³¹P NMR (162 MHz, Chloroform-d) δ 45.63.

Example 43: 3-[(1R)-1-({3-chloro-6-[6-(dimethylphosphoryl)pyridin-3-yl]-7-fluoro-2-methyl-1,5-naphthyridin-4-yl}amino)ethyl]benzonitrile

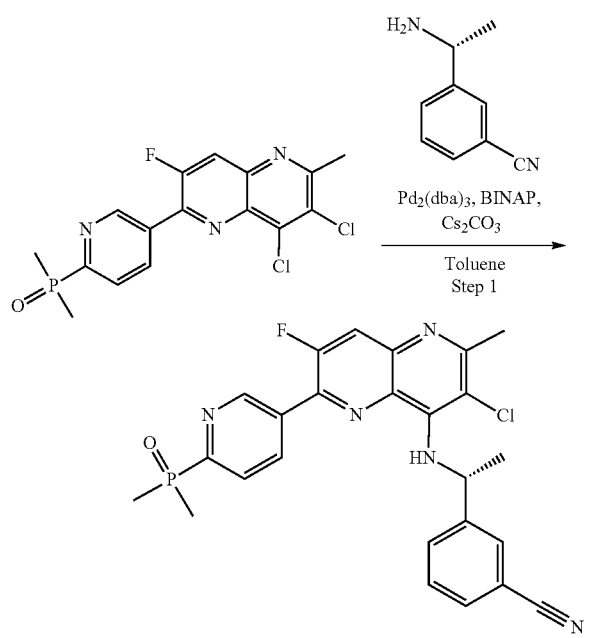

A mixture of 3,4-dichloro-6-[6-(dimethylphosphoryl)pyridin-3-yl]-7-fluoro-2-methyl-1,5-naphthyridine (100 mg, 0.260 mmol), 3-[(1R)-1-aminoethyl]benzonitrile hydrochloride (57 mg, 0.312 mmol), Pd₂(dba)₃ (23 mg, 0.026 mmol), BINAP (32 mg, 0.052 mmol) and Cs₂CO₃ (212 mg, 0.650 mmol) in Toluene (2 mL) was stirred for 3 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH₄HCO₃), Mobile Phase B: CH₃CN; Flow rate: 60 mL/min; Gradient: 30% B to 70% B in 20 min; 254/220 nm to afford 3-[(1R)-1-({3-chloro-6-[6-(dimethylphosphoryl)pyridin-3-yl]-7-fluoro-2-methyl-1,5-naphthyridin-4-yl}amino)ethyl]benzonitrile (44 mg, 34%) as a yellow solid. MS ESI calculated for C₂₅H₂₂ClFN₅OP [M+H]+, 494.12, found 494.19. ¹H NMR (400 MHz, DMSO-d₆) δ 9.15-9.13 (m, 1H), 8.37-8.33 (m, 1H), 8.18-8.10 (m, 2H), 7.81-7.80 (m, 1H), 7.68-7.60 (m, 2H), 7.44-7.40 (m, 1H), 6.90 (d, J=8.4 Hz, 1H), 6.24-6.17 (m 1H), 2.64 (s, 3H), 1.77 (s, 3H), 1.73 (s, 3H), 1.68 (d, J=6.9 Hz, 3H). ¹⁹F NMR (377 MHz, DMSO-d₆) δ −121.11. ³¹P NMR (162 MHz, DMSO-d₆) δ 34.26.

Example 44: 3-[(1S)-1-({3-chloro-6-[6-(dimethylphosphoryl)pyridin-3-yl]-7-fluoro-2-methyl-1,5-naphthyridin-4-yl}amino)propyl]-4-fluorobenzonitrile

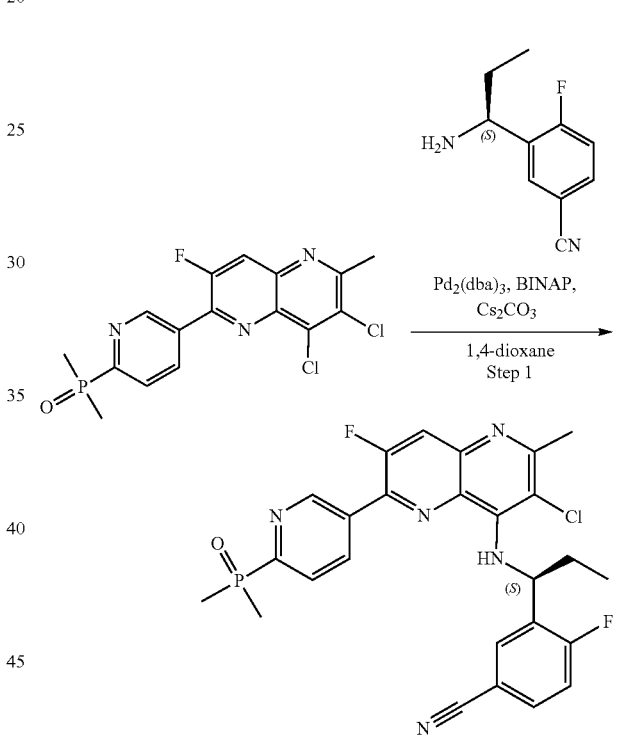

To a stirred solution of 3,4-dichloro-6-[6-(dimethylphosphoryl)pyridin-3-yl]-7-fluoro-2-methyl-1,5-naphthyridine (100 mg, 0.260 mmol) and 3-[(1S)-1-aminopropyl]-4-fluorobenzonitrile (56 mg, 0.312 mmol,) in 1,4-dioxane (1 mL) were added Pd₂(dba)₃ (24 mg, 0.026 mmol), BINAP (33 mg, 0.052 mmol) and Cs₂CO₃ (128 mg, 0.390 mmol) at room temperature under nitrogen atmosphere. The resulting mixture was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH₄HCO₃), Mobile Phase B: CH₃CN; Flow rate: 60 mL/min; Gradient: 20 B to 50 B in 30 min; 254/220 nm to afford 3-[(1S)-1-({3-chloro-6-[6-(dimethylphosphoryl)pyridin-3-yl]-7-fluoro-2-methyl-1,5-naphthyridin-4-yl}amino)

propyl]-4-fluorobenzonitrile (30 mg, 21%) as a white solid. MS ESI calculated for $C_{26}H_{23}ClF_2N_5OP$ [M+H]$^+$, 526.13, found 526.15. $^1$H NMR (400 MHz, DMSO-d$_6$) δ 9.15 (s, 1H), 8.38-8.34 (m, 1H), 8.23-8.20 (m, 1H), 8.13-8.09 (m, 2H), 7.81-7.78 (m, 1H), 7.31-7.26 (m, 1H), 6.97 (d, J=8.7 Hz, 1H), 6.04-5.98 (m, 1H), 2.65 (s, 3H), 2.12-2.01 (m, 1H), 1.96-1.86 (m, 1H), 1.77 (d, J=3.6 Hz, 3H), 1.74 (d, J=3.6 Hz, 3H), 0.97 (t, J=7.3 Hz, 3H). $^{19}$F NMR (377 MHz, DMSO-d$_6$) δ −109.37, −121.00. $^{31}$P NMR (162 MHz, DMSO-d$_6$) δ 34.28.

Example 45: 3-chloro-N-[(1S)-1-(2,3-difluorophenyl)ethyl]-6-[6-(dimethylphosphoryl)pyridin-3-yl]-7-fluoro-2-methyl-1,5-naphthyridin-4-amine

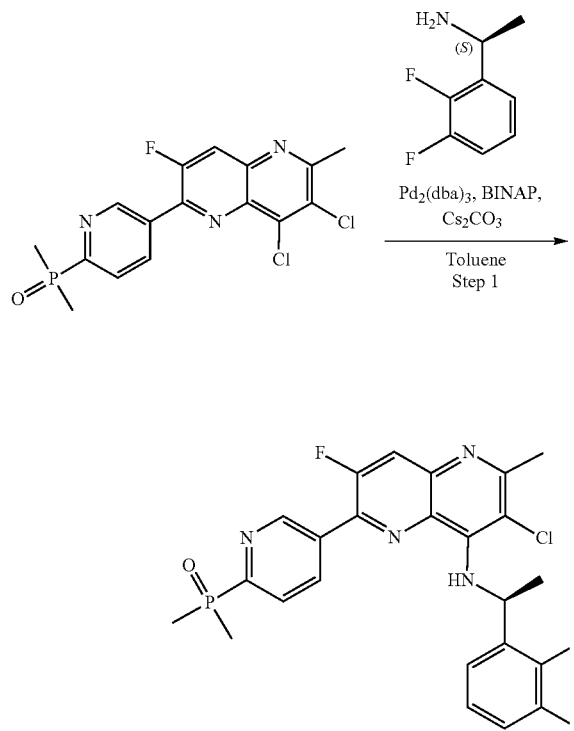

To a stirred solution of 3,4-dichloro-6-[6-(dimethylphosphoryl)pyridin-3-yl]-7-fluoro-2-methyl-1,5-naphthyridine (100 mg, 0.260 mmol) and (1S)-1-(2,3-difluorophenyl)ethanamine hydrochloride (60 mg, 0.312 mmol) in Toluene (1 mL) were added BINAP (32 mg, 0.052 mmol), Cs$_2$CO$_3$ (212 mg, 0.650 mmol,) and Pd$_2$(dba)$_3$ (23.84 mg, 0.026 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 40% to 60% gradient in 30 min; detector, 254 nm. This resulted in 3-chloro-N-[(1S)-1-(2,3-difluorophenyl)ethyl]-6-[6-(dimethylphosphoryl)pyridin-3-yl]-7-fluoro-2-methyl-1,5-naphthyridin-4-amine (47 mg, 35%) as a light yellow solid. MS ESI calculated for $C_{24}H_{21}ClF_3N_4OP$ [M+H]$^+$, 505.11, found 505.00. $^1$H NMR (400 MHz, Chloroform-d) δ 9.20 (s, 1H), 8.34-8.25 (m, 2H), 7.94 (d, J=11.4 Hz, 1H), 7.02-6.90 (m, 3H), 6.48-6.36 (m, 2H), 2.73 (s, 3H), 1.88 (s, 3H), 1.84 (s, 3H), 1.72 (d, J=6.5 Hz, 3H). $^{19}$F NMR (377 MHz, Chloroform-d) δ −120.73, −137.86, −137.91, −144.11, −144.16. $^{31}$P NMR (162 MHz, Chloroform-d) δ 36.65.

Example 46: 3-[(1R)-1-({3-chloro-6-[2-(dimethylphosphoryl)pyrimidin-5-yl]-7-fluoro-2-methyl-1,5-naphthyridin-4-yl}amino)ethyl]benzonitrile A mixture of 3,4-dichloro-6-[2-(dimethylphosphoryl)pyrimidin-5-yl]-7-fluoro-2-methyl-1,5-naphthyridine (100 mg, 0.260 mmol), 3-[(1R)-1-aminoethyl]benzonitrile hydrochloride (56 mg, 0.312 mmol), Pd$_2$(dba)$_3$ (23 mg, 0.026 mmol), BINAP (32 mg, 0.052 mmol) and Cs$_2$CO$_3$ (211 mg, 0.650 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-[(1R)-1-({3-chloro-6-[2-(dimethylphosphoryl)pyrimidin-5-yl]-7-fluoro-2-methyl-1,5-naphthyridin-4-yl}amino)ethyl]benzonitrile (15 mg, 11%) as a yellow solid. MS ESI calculated for $C_{24}H_{21}ClFN_6OP$ [M+H]$^+$, 495.12, found 494.95. $^1$H NMR (400 MHz, DMSO-d$_6$) δ 9.38 (s, 2H), 8.25-8.20 (m, 1H), 7.84-7.83 (m, 1H), 7.70-7.67 (m, 1H), 7.64-7.61 (m, 1H), 7.45-7.41 (m, 1H), 7.00 (d, J=8.4 Hz, 1H), 6.20-6.12 (m, 1H), 2.65-2.64 (m, 3H), 1.88 (d, J=3.3 Hz, 3H), 1.84 (d, J=3.3 Hz, 3H), 1.68 (d, J=6.8 Hz, 3H). $^{19}$F NMR (377 MHz, DMSO-d$_6$) δ −121.13. $^{31}$P NMR (162 MHz, DMSO-d$_6$) δ 34.36.

Example 47: 3-[(1R)-1-({3-chloro-6-[2-(dimethylphosphoryl)pyrimidin-5-yl]-7-fluoro-2-methyl-1,5-naphthyridin-4-yl}amino)propyl]benzonitrile

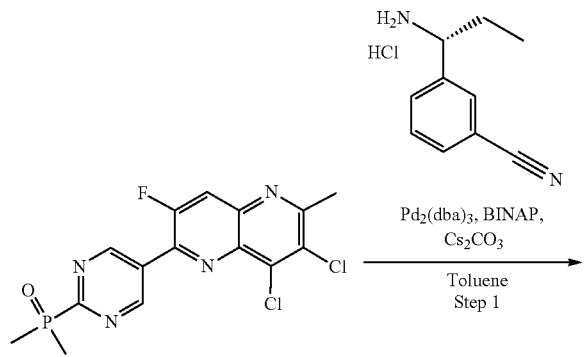

Example 48: 3-[(1R)-1-({3-chloro-6-[6-(dimethylphosphoryl)pyridin-3-yl]-7-fluoro-2-methyl-1,5-naphthyridin-4-yl}amino)propyl]benzonitrile

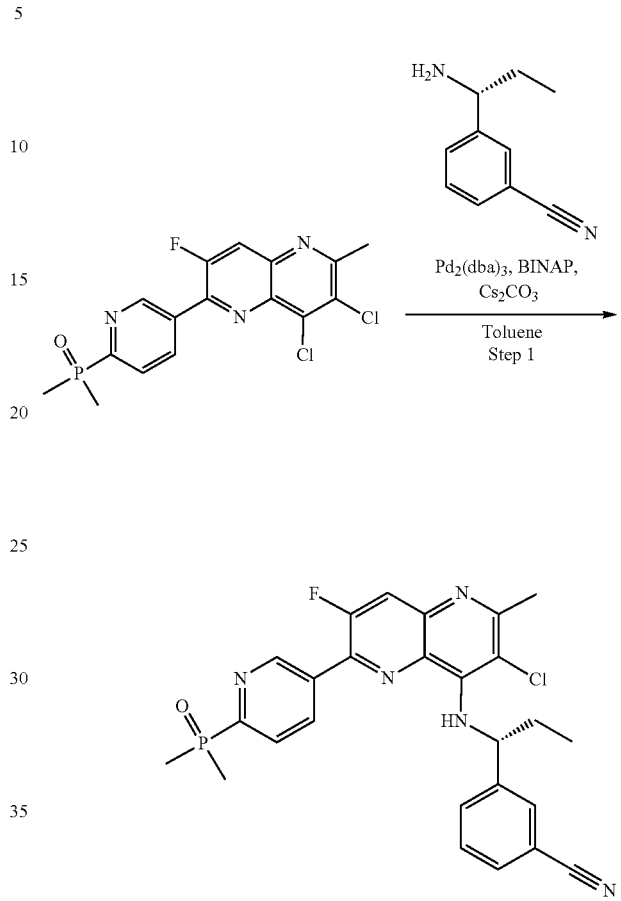

A mixture of 3,4-dichloro-6-[2-(dimethylphosphoryl)pyrimidin-5-yl]-7-fluoro-2-methyl-1,5-naphthyridine (100 mg, 0.260 mmol), 3-[(1R)-1-aminopropyl]benzonitrile hydrochloride (61 mg, 0.312 mmol), Pd$_2$(dba)$_3$ (23 mg, 0.026 mmol), BINAP (32 mg, 0.052 mmol) and Cs$_2$CO$_3$ (211 mg, 0.650 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-[(1R)-1-({3-chloro-6-[2-(dimethylphosphoryl)pyrimidin-5-yl]-7-fluoro-2-methyl-1,5-naphthyridin-4-yl}amino)propyl]benzonitrile (25 mg, 19%) as a yellow solid. MS ESI calculated for C$_{25}$H$_{23}$ClFN$_6$OP [M+H]$^+$, 509.13, found 508.95. $^1$H NMR (400 MHz, DMSO-d$_6$) δ 9.39 (s, 2H), 8.26-8.21 (m, 1H), 7.87-7.86 (m, 1H), 7.71 (d, J=8.1 Hz, 1H), 7.63 (d, J=7.8 Hz, 1H), 7.46-7.42 (m, 1H), 6.99 (d, J=8.6 Hz, 1H), 5.86-5.80 (m, 1H), 2.64-2.63 (m, 3H), 2.13-1.91 (m, 2H), 1.88 (d, J=3.4 Hz, 3H), 1.85 (d, J=3.4 Hz, 3H) 0.97 (t, J=7.2 Hz, 3H). $^{19}$F NMR (377 MHz, DMSO-d$_6$) δ −121.08. $^{31}$P NMR (162 MHz, DMSO-d$_6$) δ 34.38.

A mixture of 3,4-dichloro-6-[6-(dimethylphosphoryl)pyridin-3-yl]-7-fluoro-2-methyl-1,5-naphthyridine (100 mg, 0.260 mmol), 3-[(1R)-1-aminopropyl]benzonitrile hydrochloride (61 mg, 0.312 mmol), Pd$_2$(dba)$_3$ (23 mg, 0.026 mmol), BINAP (32.42 mg, 0.052 mmol) and Cs$_2$CO$_3$ (212 mg, 0.650 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-[(1R)-1-({3-chloro-6-[6-(dimethylphosphoryl)pyridin-3-yl]-7-fluoro-2-methyl-1,5-naphthyridin-4-yl}amino)propyl]benzonitrile (46 mg, 33%) as a yellow solid. MS ESI calculated for C$_{26}$H$_{24}$ClFN$_5$OP [M+H]$^+$, 508.14, found 507.95. $^1$H NMR (400 MHz, DMSO-d$_6$) δ 9.16 (s, 1H), 8.38-8.35 (m, 1H), 8.21-8.10 (m, 2H), 7.83 (s, 1H), 7.69-7.67 (m, 1H), 7.64-7.61 (m, 1H), 7.45-7.41 (m, 1H), 6.90 (d, J=8.6 Hz, 1H), 5.92-5.86 (m, 1H), 2.64-2.63 (m, 3H), 2.12-1.92 (m, 2H), 1.77 (d, J=1.8 Hz, 3H), 1.74 (d, J=1.8 Hz, 3H), 0.97 (t, J=7.3 Hz, 3H). $^{19}$F NMR (377 MHz, DMSO-d$_6$) δ −121.06. $^{31}$P NMR (162 MHz, DMSO-d$_6$) δ 34.26.

Example 49: 3-[(1R)-1-({3-chloro-7-fluoro-2-methyl-6-[2-(1-oxo-1lambda5-phospholan-1-yl)pyrimidin-5-yl]-1,5-naphthyridin-4-yl}amino)ethyl]-4-fluorobenzonitrile Synthetic Scheme

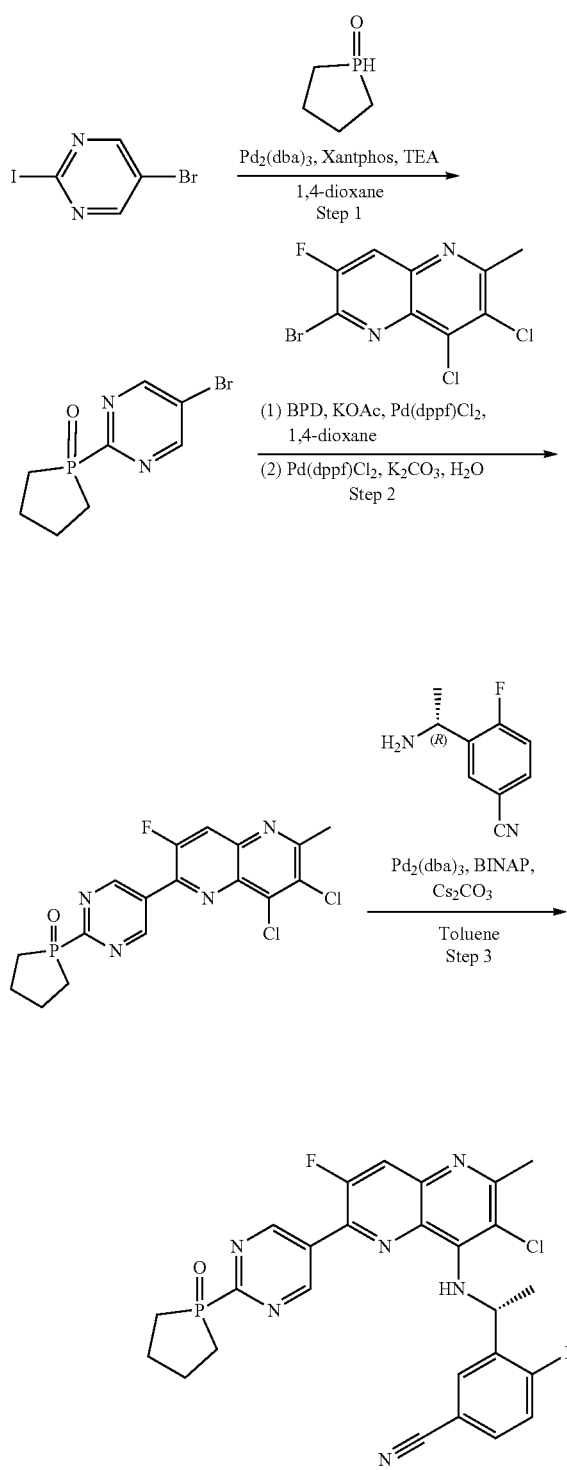

Preparation 49A: 1-(5-bromopyrimidin-2-yl)-1lambda5-phospholan-1-one

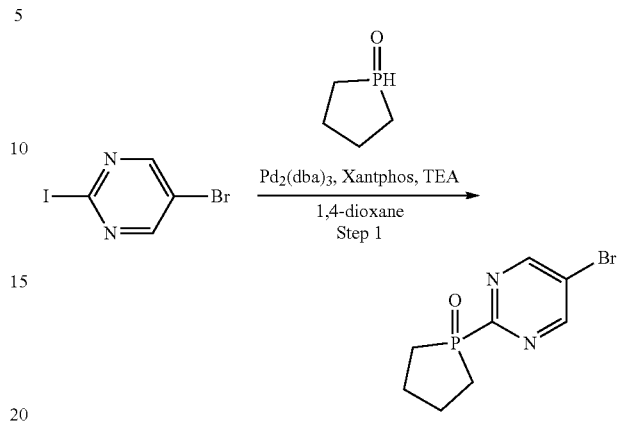

A mixture of Pd$_2$(dba)$_3$ (92 mg, 0.100 mmol), TEA (1.60 g, 15.797 mmol) and Xantphos (116 mg, 0.199 mmol) in 1,4-dioxane (3 mL) was stirred for 15 min at room temperature under nitrogen atmosphere. To the above mixture were added 5-bromo-2-iodopyrimidine (284 mg, 0.997 mmol) and 1lambda5-phospholan-1-one (1.64 g, 15.797 mmol) at room temperature. The resulting mixture was stirred for additional overnight at 90° C. The resulting mixture was concentrated under reduced pressure. The residue was purified by silica gel column chromatography, eluted with CH$_2$Cl$_2$/MeOH (10:1) to afford 1-(5-bromopyrimidin-2-yl)-1lambda5-phospholan-1-one (1.15 g, 42%) as a brown oil. MS ESI calculated for C$_8$H$_{10}$BrN$_2$OP [M+H]$^+$, 260.97 262.97, found 261.10 263.10. $^1$H NMR (400 MHz, Chloroform-d) δ 8.95 (s, 2H), 2.37-2.30 (m, 2H), 2.19-1.60 (m, 4H), 1.51-1.42 (m, 1H), 0.97-0.93 (m, 1H).

Preparation 49B: 1-[5-(7,8-dichloro-3-fluoro-6-methyl-1,5-naphthyridin-2-yl)pyrimidin-2-yl]-1lambda5-phospholan-1-one

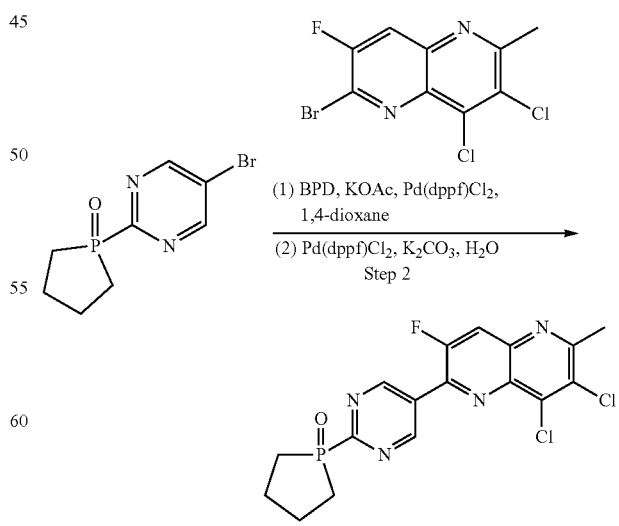

To a stirred solution of 1-(5-bromopyrimidin-2-yl)-1lambda5-phospholan-1-one (455 mg, 1.742 mmol) and BPD (2.21 g, 8.712 mmol) in 1,4-dioxane (5 mL) were added KOAc (285 mg, 2.904 mmol) and Pd(dppf)Cl$_2$·CH$_2$Cl$_2$ (119 mg, 0.145 mmol) at room temperature under nitrogen atmosphere. The resulting mixture was stirred for 2 h at 80° C. under nitrogen atmosphere. The mixture was allowed to cool down to room temperature. To the above mixture were added 6-bromo-3,4-dichloro-7-fluoro-2-methyl-1,5-naphthyridine (450 mg, 1.452 mmol), K$_2$CO$_3$ (502 mg, 3.630 mmol), Pd(dppf)Cl$_2$·CH$_2$Cl$_2$ (119 mg, 0.145 mmol) and H$_2$O (1 mL) at room temperature. The resulting mixture was stirred for additional 16 h at 100° C. The resulting mixture was concentrated under reduced pressure. The residue was purified by silica gel column chromatography, eluted with CH$_2$Cl$_2$/MeOH (10/1) to afford 1-[5-(7,8-dichloro-3-fluoro-6-methyl-1,5-naphthyridin-2-yl)pyrimidin-2-yl]-1lambda5-phospholan-1-one (80 mg, 13%) as a yellow solid. MS ESI calculated for C$_{17}$H$_{14}$Cl$_2$FN$_4$OP [M+H]$^+$, 411.03 413.03, found 410.85 412.85. $^1$H NMR (400 MHz, Chloroform-d) δ 9.68 (s, 2H), 8.21 (d, J=10.9 Hz, 1H), 2.93 (s, 3H), 2.51-2.40 (m, 2H), 2.24-1.99 (m, 6H).

Example 49: 3-[(1R)-1-({3-chloro-7-fluoro-2-methyl-6-[2-(1-oxo-1lambda5-phospholan-1-yl)pyrimidin-5-yl]-1,5-naphthyridin-4-yl}amino)ethyl]-4-fluorobenzonitrile

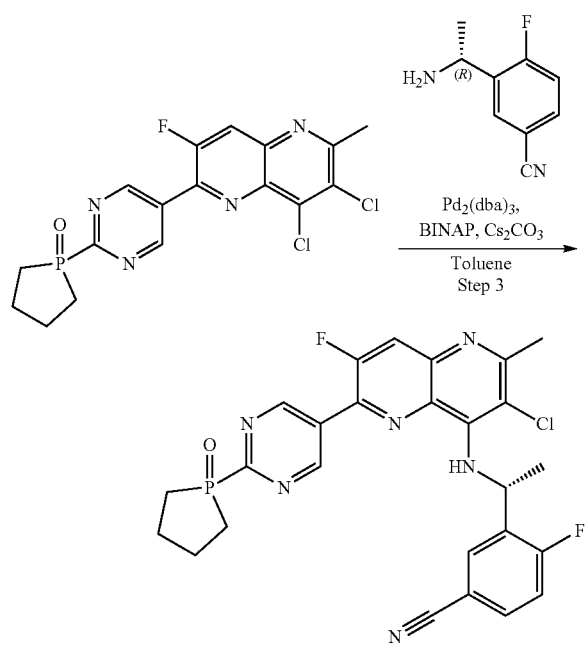

To a stirred solution of 1-[5-(7,8-dichloro-3-fluoro-6-methyl-1,5-naphthyridin-2-yl)pyrimidin-2-yl]-1lambda5-phospholan-1-one (80 mg, 0.195 mmol) and 3-[(1R)-1-aminoethyl]-4-fluorobenzonitrile (39 mg, 0.234 mmol) in Toluene (1 mL) were added Pd$_2$(dba)$_3$ (18 mg, 0.020 mmol), BINAP (25 mg, 0.039 mmol,) and Cs$_2$CO$_3$ (95 mg, 0.292 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 30% to 70% gradient in 30 min; detector, 254 nm to afford 3-[(1R)-1-({3-chloro-7-fluoro-2-methyl-6-[2-(1-oxo-1lambda5-phospholan-1-yl)pyrimidin-5-yl]-1,5-naphthyridin-4-yl}amino)ethyl]-4-fluorobenzonitrile (42 mg, 40%) as a light yellow solid. MS ESI calculated for C$_{26}$H$_{22}$ClF$_2$N$_6$OP [M+H]$^+$, 539.12, found 539.15. $^1$H NMR (400 MHz, DMSO-d$_6$) δ 9.42 (s, 2H), 8.25 (d, J=11.6 Hz, 1H), 8.04-8.02 (m, 1H), 7.80-7.76 (m, 1H), 7.28-7.23 (m, 1H), 7.06 (d, J=8.5 Hz, 1H), 6.36-6.29 (m, 1H), 2.65 (s, 3H), 2.47-2.40 (m, 2H), 2.08-1.75 (m, 6H), 1.67 (d, J=6.7 Hz, 3H). $^{19}$F NMR (377 MHz, DMSO-d$_6$) δ −109.64, −120.98. $^{31}$P NMR (162 MHz, DMSO-d$_6$) δ 60.29.

Example 50: 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine

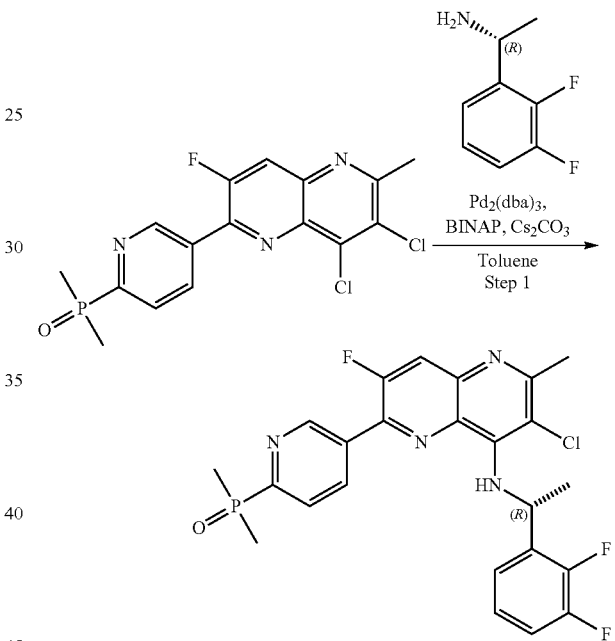

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-(2,3-difluorophenyl)ethanamine (49 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: ACN; Flow rate: 60 mL/min; Gradient: 30 B to 70 B in 30 min; 254/220 nm to afford 3-chloro-N-[1-(2,3-difluorophenyl)ethyl]-6-[6-(dimethylphosphoryl)pyridin-3-yl]-7-fluoro-2-methyl-1,5-naphthyridin-4-amine (53 mg, 40%) as a light yellow semi-solid. MS ESI calculated for C$_{24}$H$_{21}$ClF$_3$N$_4$OP [M+H]$^+$, 505.11, found 505.10. $^1$H NMR (400 MHz, Chloroform-d) δ 9.26-

9.25 (m, 1H), 8.32-8.25 (m, 2H), 7.95 (d, J=11.5 Hz, 1H), 6.96-6.90 (m, 2H), 6.88-6.82 (m, 1H), 6.47-6.45 (m, 1H), 6.39-6.32 (m, 1H), 2.73 (s, 3H), 1.88 (s, 3H), 1.84 (s, 3H), 1.70 (d, J=6.6 Hz, 3H). $^{19}$F NMR (377 MHz, Chloroform-d) δ −117.85, −117.89, −120.69, −124.53, −124.57. $^{31}$P NMR (162 MHz, Chloroform-d) δ 36.54.

Example 51: 3-chloro-N-[(1S)-1-(2,5-difluorophenyl)ethyl]-6-[6-(dimethylphosphoryl)pyridin-3-yl]-7-fluoro-2-methyl-1,5-naphthyridin-4-amine

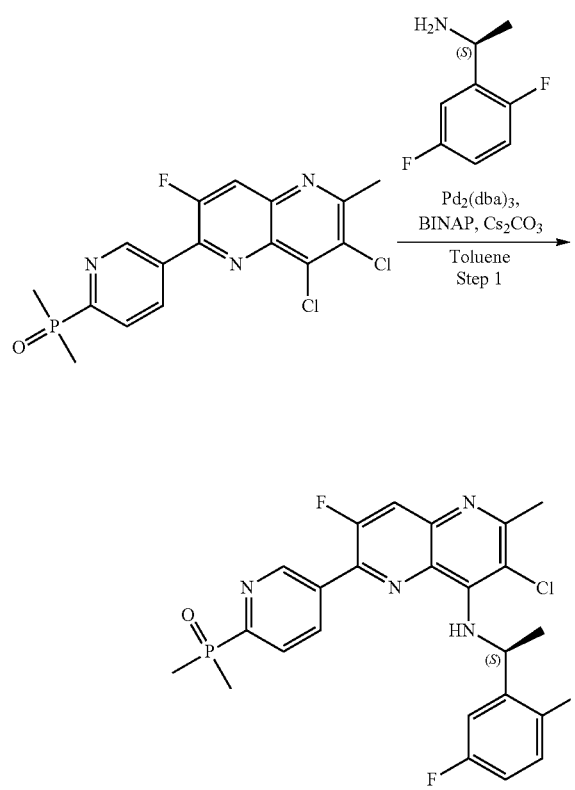

To a stirred solution of 3,4-dichloro-6-[6-(dimethylphosphoryl)pyridin-3-yl]-7-fluoro-2-methyl-1,5-naphthyridine (100 mg, 0.260 mmol) and (1S)-1-(2,5-difluorophenyl)ethanamine (49 mg, 0.312 mmol) in Toluene (1 mL) were added Pd$_2$(dba)$_3$ (24 mg, 0.026 mmol), BINAP (33 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 30 B to 70 B in 30 min; 254/220 nm to afford 3-chloro-N-[(1S)-1-(2,5-difluorophenyl)ethyl]-6-[6-(dimethylphosphoryl)pyridin-3-yl]-7-fluoro-2-methyl-1,5-naphthyridin-4-amine (61 mg, 46%) as a white solid. as a light yellow semi-solid. MS ESI calculated for C$_{24}$H$_{21}$ClF$_3$N$_4$OP [M+H]$^+$, 505.11, found 504.90. $^1$H NMR (400 MHz, Chloroform-d) δ 9.20 (s, 1H), 8.34-8.26 (m, 2H), 7.97 (d, J=11.4 Hz, 1H), 7.03-6.91 (m, 3H), 6.52-6.38 (m, 2H), 2.74 (s, 3H), 1.88 (s, 3H), 1.84 (s, 3H), 1.72 (d, J=6.6 Hz, 3H). $^{19}$F NMR (377 MHz, Chloroform-d) δ −120.62, −137.80, −137.86, −144.07, −144.13. $^{31}$P NMR (162 MHz, Chloroform-d) δ 36.56.

Example 52: 3-chloro-N-[(1R)-1-(2,6-difluorophenyl)ethyl]-6-[6-(dimethylphosphoryl)pyridin-3-yl]-7-fluoro-2-methyl-1,5-naphthyridin-4-amine

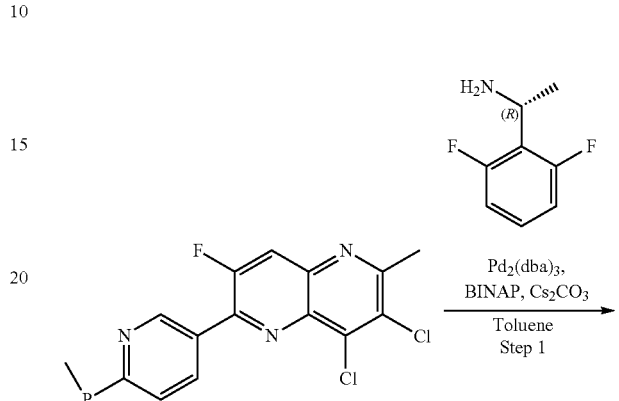

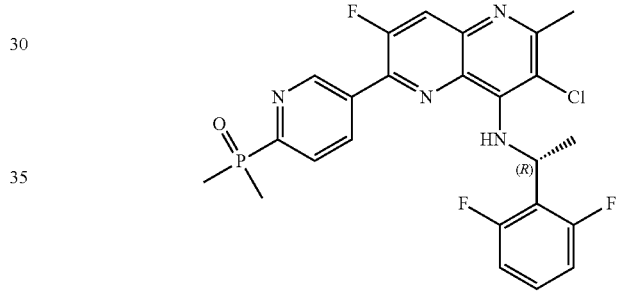

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-(2,6-difluorophenyl)ethanamine (49 mg, 0.312 mmol) in Toluene (1 mL) were added BINAP (32 mg, 0.052 mmol), Cs$_2$CO$_3$ (212 mg, 0.650 mmol) and Pd$_2$(dba)$_3$ (24 mg, 0.026 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 40% to 60% gradient in 30 min; detector, 254 nm to afford 3-chloro-N-[(1R)-1-(2,6-difluorophenyl)ethyl]-6-[6-(dimethylphosphoryl)pyridin-3-yl]-7-fluoro-2-methyl-1,5-naphthyridin-4-amine (34 mg, 25%) as a yellow solid. MS ESI calculated for C$_{24}$H$_{21}$ClF$_3$N$_4$OP [M+H]$^+$, 505.11, found 504.90. $^1$H NMR (400 MHz, DMSO-d$_6$) δ 9.32 (s, 1H), 8.54-8.50 (m, 1H), 8.25 (d, J=11.8 Hz, 1H), 8.21-8.17 (m, 1H), 7.35-7.28 (m, 1H), 7.06-6.99 (m, 2H), 6.94 (d, J=9.8 Hz, 1H), 6.64-6.56 (m, 1H), 2.64 (s, 3H), 1.78 (s, 3H), 1.75 (s, 3H), 1.71 (d, J=6.9 Hz, 3H). $^{19}$F NMR (377 MHz, DMSO-d$_6$) δ −115.52, −120.61. $^{31}$P NMR (162 MHz, DMSO-d$_6$) δ 34.47.

Example 53: 3-chloro-N-[(1R)-1-(2,5-difluorophenyl)ethyl]-6-[6-(dimethylphosphoryl)pyridin-3-yl]-7-fluoro-2-methyl-1,5-naphthyridin-4-amine

Example 54: 3-chloro-N-[(1S)-1-(2,6-difluorophenyl)ethyl]-6-[6-(dimethylphosphoryl)pyridin-3-yl]-7-fluoro-2-methyl-1,5-naphthyridin-4-amine

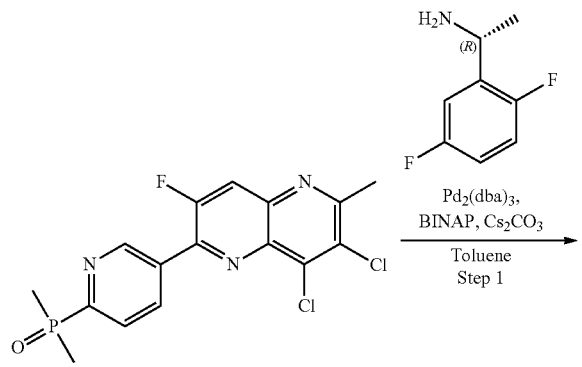

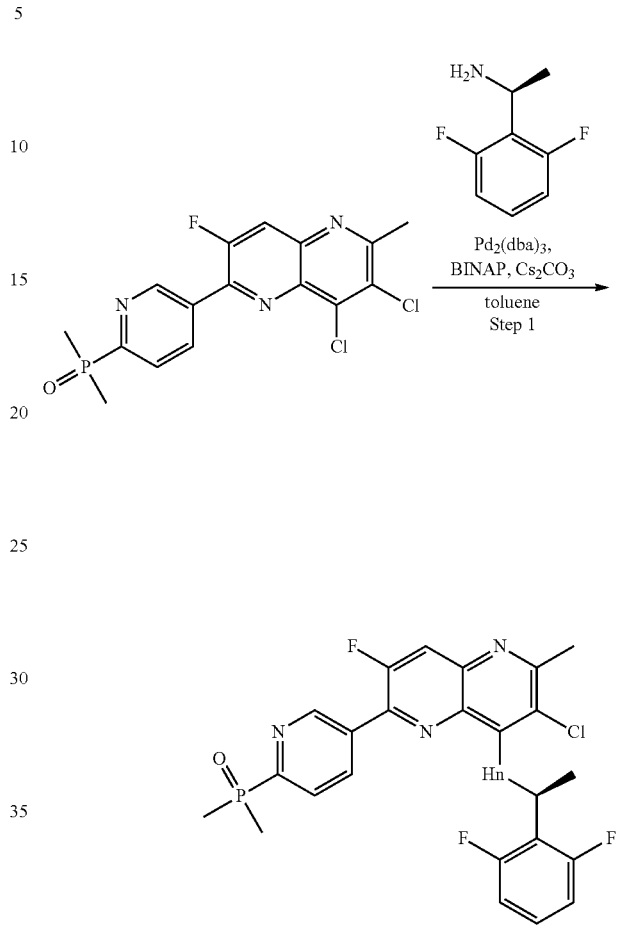

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-(2,5-difluorophenyl)ethanamine (49 mg, 0.312 mmol) in Toluene (1 mL) were added BINAP (32 mg, 0.052 mmol), $Cs_2CO_3$ (212 mg, 0.650 mmol) and $Pd_2(dba)_3$ (24 mg, 0.026 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, $CH_3CN$ in water (10 mmol/L $NH_4HCO_3$), 40% to 60% gradient in 30 min; detector, 254 nm to afford 3-chloro-N-[(1R)-1-(2,5-difluorophenyl)ethyl]-6-[6-(dimethylphosphoryl)pyridin-3-yl]-7-fluoro-2-methyl-1,5-naphthyridin-4-amine (56 mg, 42%) as a light yellow solid. MS ESI calculated for $C_{24}H_{21}ClF_3N_4OP$ [M+H]$^+$, 505.11, found 505.10. $^1$H NMR (400 MHz, Chloroform-d) δ 9.26-9.25 (m, 1H), 8.32-8.25 (m, 2H), 7.97 (d, J=11.4 Hz, 1H), 6.96-6.90 (m, 2H), 6.88-6.82 (m, 1H), 6.49-6.46 (m, 1H), 6.40-6.33 (m, 1H), 2.74 (s, 3H), 1.88 (s, 3H), 1.84 (s, 3H), 1.70 (d, J=6.7 Hz, 3H). $^{19}$F NMR (377 MHz, Chloroform-d) δ −117.82, −117.87, −120.51, −124.52, −124.56. $^{31}$P NMR (162 MHz, Chloroform-d) δ 36.68.

A mixture of 3,4-dichloro-6-[6-(dimethylphosphoryl)pyridin-3-yl]-7-fluoro-2-methyl-1,5-naphthyridine (200 mg, 0.521 mmol), (1S)-1-(2,6-difluorophenyl)ethanamine hydrochloride (120 mg, 0.625 mmol), $Pd_2(dba)_3$ (47 mg, 0.052 mmol), BINAP (64 mg, 0.104 mmol) and $Cs_2CO_3$ (424 mg, 1.302 mmol) in toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L $NH_4HCO_3$), Mobile Phase B: $CH_3CN$; Flow rate: 70 mL/min; Gradient: 5 B to 70 B in 30 min; 254/220 nm to afford 3-chloro-N-[(1S)-1-(2,6-difluorophenyl)ethyl]-6-[6-(dimethylphosphoryl)pyridin-3-yl]-7-fluoro-2-methyl-1,5-naphthyridin-4-amine (51 mg, 19%) as a green solid. MS ESI calculated for $C_{24}H_{21}ClF_3N_4OP$ [M+H]$^+$, 505.11, found 504.95. $^1$H NMR (400 MHz, Methanol-d$_4$) δ 9.39-9.38 (m, 1H), 8.60-8.56 (m, 1H), 8.23-8.20 (m, 1H), 7.93 (d, J=11.7 Hz, 1H), 7.29-7.21 (m, 1H), 6.93-6.86 (m, 2H), 6.78-6.73 (m, 1H), 2.67 (s, 3H), 1.92 (s, 3H), 1.89 (s, 3H), 1.73 (d, J=6.9 Hz, 3H). $^{19}$F NMR (377 MHz, Methanol-d$_4$) δ −117.15, −121.80. $^{31}$P NMR (162 MHz, Methanol-d$_4$) δ 41.60.

Example 55: 3-chloro-6-[2-(dimethylphosphoryl)pyrimidin-5-yl]-7-fluoro-2-methyl-N-[(1R)-1-[2-(trifluoromethyl)phenyl]ethyl]-1,5-naphthyridin-4-amine

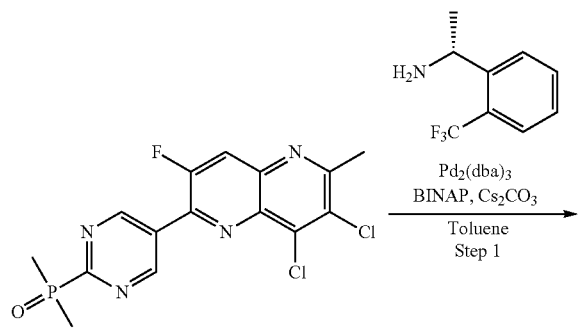

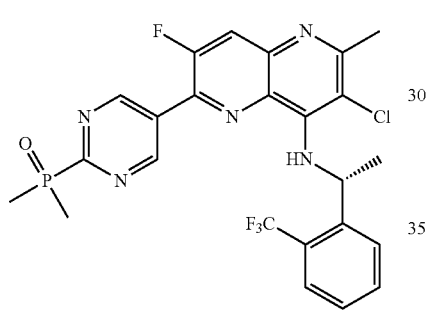

A mixture of 3,4-dichloro-6-[2-(dimethylphosphoryl)pyrimidin-5-yl]-7-fluoro-2-methyl-1,5-naphthyridine (200 mg, 0.519 mmol), (1R)-1-[2-(trifluoromethyl)phenyl]ethanamine (117 mg, 0.623 mmol), Pd$_2$(dba)$_3$ (47 mg, 0.052 mmol), BINAP (64 mg, 0.104 mmol) and Cs$_2$CO$_3$ (253 mg, 0.778 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 70 mL/min; Gradient: 5 B to 70 B in 30 min; 254/220 nm to afford 3-chloro-6-[2-(dimethylphosphoryl)pyrimidin-5-yl]-7-fluoro-2-methyl-N-[(1R)-1-[2-(trifluoromethyl)phenyl]ethyl]-1,5-naphthyridin-4-amine (59 mg, 20%) as a green solid. MS ESI calculated for C$_{24}$H$_{21}$ClF$_4$N$_5$OP [M+H]$^+$, 538.11, found 537.95. $^1$H NMR (400 MHz, DMSO-d$_6$) δ 9.50 (s, 2H), 8.34-8.26 (m, 1H), 8.09 (d, J=8.0 Hz, 1H), 7.70 (t, J=7.7 Hz, 1H), 7.63 (d, J=7.5 Hz, 1H), 7.47 (t, J=7.7 Hz, 1H), 7.01 (d, J=8.8 Hz, 1H), 6.45-6.33 (m, 1H), 2.63 (s, 3H), 1.87 (s, 3H), 1.84 (s, 3H), 1.71 (d, J=6.7 Hz, 3H). $^{19}$F NMR (377 MHz, DMSO-d$_6$) δ −57.17, −120.75. $^{31}$P NMR (162 MHz, DMSO-d$_6$) δ 34.39.

Example 56: 3-chloro-6-{6-[(dimethylphosphoryl)methoxy]pyridin-3-yl}-7-fluoro-N-[(1R)-1-(2-fluorophenyl)ethyl]-2-methyl-1,5-naphthyridin-4-amine

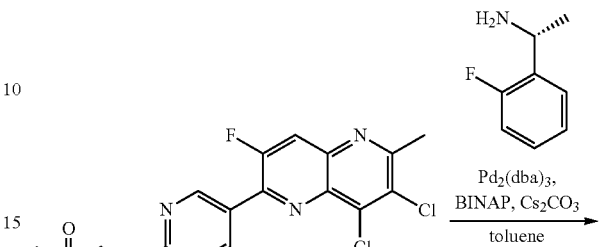

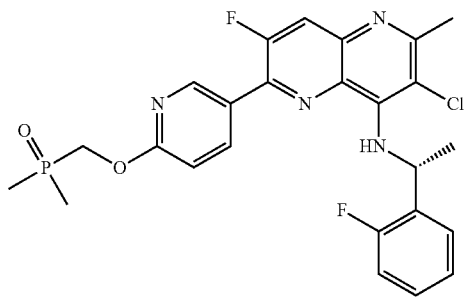

A mixture of 3,4-dichloro-6-{6-[(dimethylphosphoryl)methoxy]pyridin-3-yl}-7-fluoro-2-methyl-1,5-naphthyridine (200 mg, 0.483 mmol), (1R)-1-(2-fluorophenyl)ethanamine (80 mg, 0.580 mmol), Pd$_2$(dba)$_3$ (44 mg, 0.048 mmol), BINAP (60 mg, 0.097 mmol) and Cs$_2$CO$_3$ (235 mg, 0.724 mmol) in toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 70 mL/min; Gradient: 5 B to 70 B in 30 min; 254/220 nm to afford 3-chloro-6-{6-[(dimethylphosphoryl)methoxy]pyridin-3-yl}-7-fluoro-N-[(1R)-1-(2-fluorophenyl)ethyl]-2-methyl-1,5-naphthyridin-4-amine (33 mg, 13%) as a yellow solid. MS ESI calculated for C$_{25}$H$_{24}$ClF$_2$N$_4$O$_2$P [M+H]$^+$, 517.13, found 516.95. $^1$H NMR (400 MHz, DMSO-d$_6$) δ 8.76-8.75 (m, 1H), 8.25-8.22 (m, 1H), 8.12 (d, J=12.0 Hz, 1H), 7.43-7.39 (m, 1H), 7.27-7.21 (m, 1H), 7.14-7.08 (m, 3H), 6.83 (d, J=9.0 Hz, 1H), 6.46-6.39 (m, 1H), 4.71 (d, J=5.1 Hz, 2H), 2.61 (s, 3H), 1.66 (d, J=6.8 Hz, 3H), 1.56 (s, 3H), 1.52 (s, 3H). $^{19}$F NMR (377 MHz, DMSO-d$_6$) δ −119.20, −120.57. $^{31}$P NMR (162 MHz, DMSO-d$_6$) δ 38.00.

Example 57 and 58: (R)-3-(1-((3-chloro-6-(6-(diethylphosphoryl)pyridin-3-yl)-7-fluoro-2-methyl-1,5-naphthyridin-4-yl)amino)ethyl)-4-fluorobenzonitrile and 3-((R)-1-((3-chloro-6-(6-((S)-ethyl(methyl)phosphoryl)pyridin-3-yl)-7-fluoro-2-methyl-1,5-naphthyridin-4-yl)amino)ethyl)-4-fluorobenzonitrile
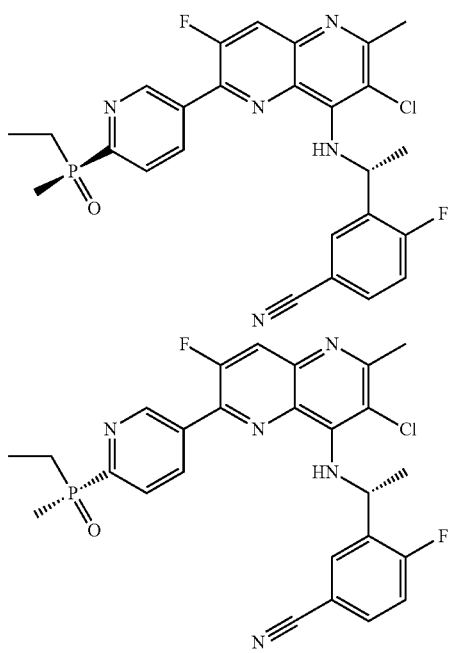
Synthetic Scheme
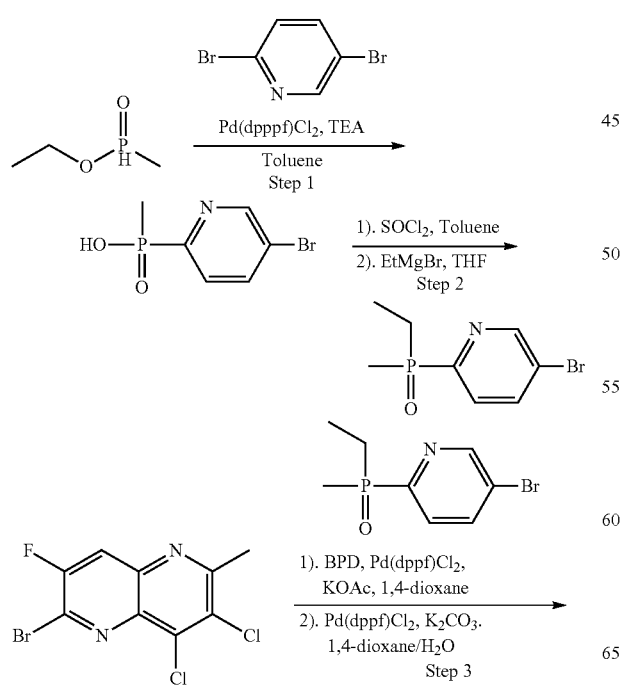
Preparation 57A:
5-bromopyridin-2-yl(methyl)phosphinic acid
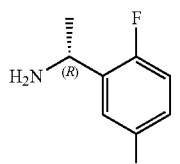

-continued

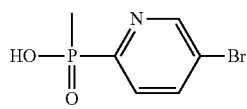

To a solution of 2,5-dibromopyridine (2.19 g, 9.253 mmol) and ethyl methylphosphinate (1.00 g, 9.253 mmol) in Toluene (20 mL) were added TEA (1.40 g, 13.880 mmol) and Pd(dppf)Cl$_2$·CH$_2$Cl$_2$ (0.75 g, 0.925 mmol). After stirring for overnight at 70° C. under a nitrogen atmosphere, the resulting mixture was concentrated under reduced pressure. The residue was purified by reversed-phase flash chromatography with the following conditions: column, C18 silica gel; mobile phase, CH$_3$CN in water (0.1% NH$_3$·H$_2$O), 0% to 25% gradient in 30 min; detector, 254 nm to afford 5-bromopyridin-2-yl(methyl)phosphinic acid (1.30 g, 59%) as a white solid. $^1$H NMR (300 MHz, Methanol-d$_4$) δ 8.73 (d, J=2.3 Hz, 1H), 8.04-8.00 (m, 1H), 7.85-7.80 (m, 1H), 1.50 (d, J=14.6 Hz, 3H). $^{31}$P NMR (122 MHz, Methanol-d$_4$) δ 26.83.

Preparation 57B: 5-bromo-2-[ethyl(methyl)phosphoryl]pyridine

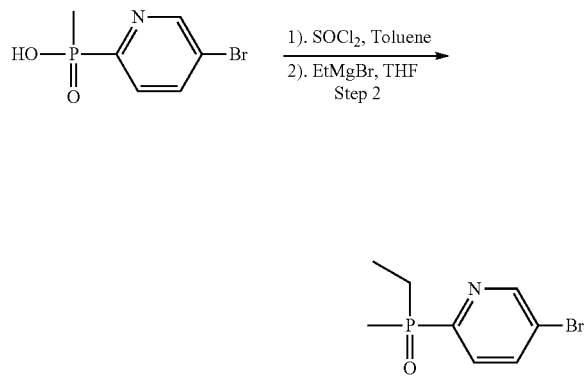

A solution of 5-bromopyridin-2-yl(methyl)phosphinic acid (600 mg, 2.542 mmol) and SOCl$_2$ (1.84 mL, 25.420 mmol) in Toluene (5 mL) was stirred for overnight at 80° C. under nitrogen atmosphere. The resulting mixture was concentrated under reduced pressure. The residue was dissolved in THF (9 mL) and then to the above mixture was added EtMgBr (9.2 mL, 5.084 mmol) dropwise over 10 min at 0° C. The resulting mixture was stirred for additional 30 min at room temperature. The reaction was quenched with water (20 mL) at 0° C. and extracted with EtOAc (2×20 mL). The combined organic layers were washed with brine (1×25 mL), dried over anhydrous Na$_2$SO$_4$. After filtration, the filtrate was concentrated under reduced pressure. The residue was purified by silica gel column chromatography, eluted with CH$_2$Cl$_2$/MeOH (12/1) to afford 5-bromo-2-[ethyl(methyl)phosphoryl]pyridine (210 mg, 33%) as a light yellow liquid. MS ESI calculated for C$_8$H$_{11}$BrNOP [M+H]$^+$, 247.98 249.97, found 248.00 250.10. $^1$H NMR (400 MHz, Chloroform-d) δ 8.79-8.78 (m, 1H), 8.01-7.99 (m, 2H), 2.07-1.99 (m, 2H), 1.73 (d, J=13.2 Hz, 3H), 1.16-1.08 (m, 3H).

Preparation 57C: 3,4-dichloro-6-{6-[ethyl(methyl)phosphoryl]pyridin-3-yl}-7-fluoro-2-methyl-1,5-naphthyridine

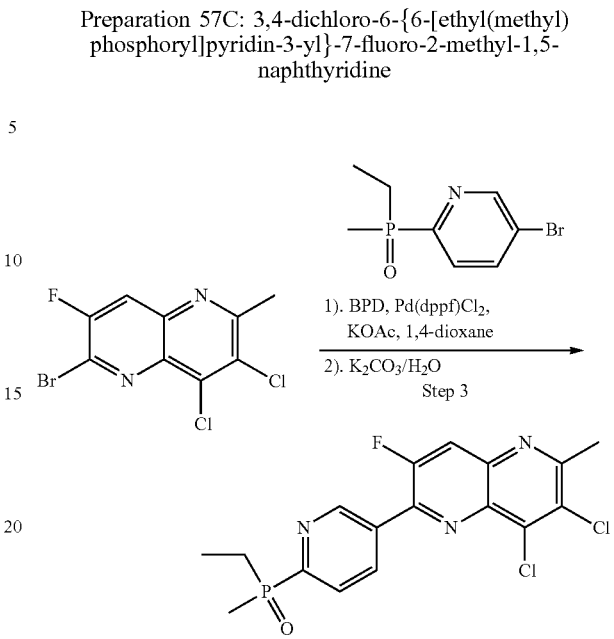

A solution of 5-bromo-2-[ethyl(methyl)phosphoryl]pyridine (202 mg, 0.816 mmol), BPD (283 mg, 1.113 mmol), KOAc (146 mg, 1.484 mmol) and Pd(dppf)Cl$_2$·CH$_2$Cl$_2$ (60 mg, 0.074 mmol) in 1,4-dioxane (5 mL) was stirred for 3 h at 100° C. under nitrogen atmosphere. The mixture was allowed to cool down to room temperature. To the above mixture were added 6-bromo-3,4-dichloro-7-fluoro-2-methyl-1,5-naphthyridine (230 mg, 0.742 mmol), K$_2$CO$_3$ (205 mg, 1.484 mmol) and H$_2$O (1 mL) at room temperature under nitrogen atmosphere. The resulting mixture was stirred for additional 2 h at 80° C. The resulting mixture was concentrated under reduced pressure. The residue was purified by silica gel column chromatography, eluted with CH$_2$Cl$_2$/MeOH (12:1) to afford 3,4-dichloro-6-{6-[ethyl(methyl)phosphoryl]pyridin-3-yl}-7-fluoro-2-methyl-1,5-naphthyridine (160 mg, 54%) as an orange solid. MS ESI calculated for C$_{17}$H$_{15}$Cl$_2$FN$_3$OP [M+H]$^+$, 398.03, found 398.10. $^1$H NMR (400 MHz, Chloroform-d) δ 9.63-9.55 (m, 1H), 8.67-8.63 (m, 1H), 8.40-8.29 (m, 1H), 8.13 (d, J=10.8 Hz, 1H), 2.91 (s, 3H), 2.29-2.17 (m, 2H), 1.92-1.85 (m, 3H), 1.24-1.17 (m, 3H).

Preparation 57D: 3-[(1R)-1-[(3-chloro-6-{6-[ethyl(methyl)phosphoryl]pyridin-3-yl}-7-fluoro-2-methyl-1,5-naphthyridin-4-yl)amino]ethyl]-4-fluorobenzonitrile

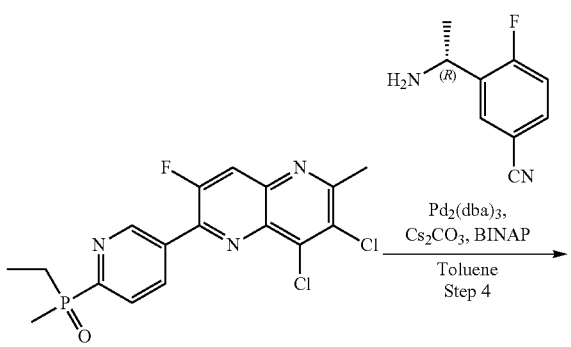

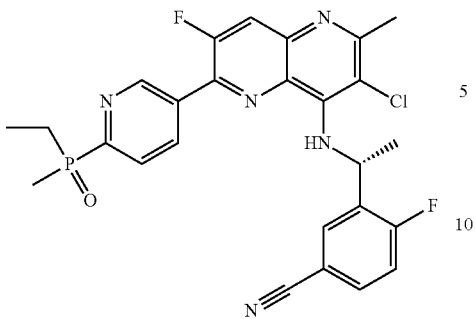

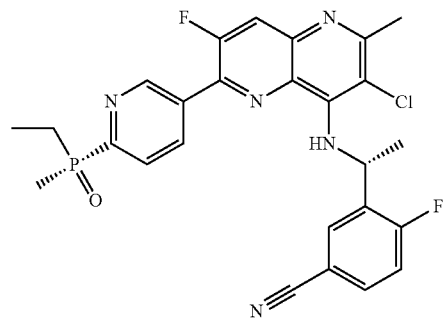

To a solution of 3,4-dichloro-6-{6-[ethyl(methyl)phosphoryl]pyridin-3-yl}-7-fluoro-2-methyl-1,5-naphthyridine (160 mg, 0.402 mmol) and 3-[(1R)-1-aminoethyl]-4-fluorobenzonitrile (79 mg, 0.482 mmol) in toluene (5 mL) were added $Pd_2(dba)_3$ (37 mg, 0.040 mmol), BINAP (50 mg, 0.080 mmol) and $Cs_2CO_3$ (196 mg, 0.603 mmol). After stirring for 3 h at 100° C. under a nitrogen atmosphere, the resulting mixture was concentrated under reduced pressure. The residue was purified by silica gel column chromatography, eluted with $CH_2Cl_2$/MeOH (10:1) to afford 3-[(1R)-1-[(3-chloro-6-{6-[ethyl(methyl)phosphoryl]pyridin-3-yl}-7-fluoro-2-methyl-1,5-naphthyridin-4-yl)amino]ethyl]-4-fluorobenzonitrile (140 mg, 66%) as a light yellow solid. MS ESI calculated for $C_{26}H_{23}ClF_2N_5OP$ [M+H]$^+$, 526.13, found 526.15.

Example 57 and 58: (R)-3-(1-((3-chloro-6-(6-(diethylphosphoryl)pyridin-3-yl)-7-fluoro-2-methyl-1,5-naphthyridin-4-yl)amino)ethyl)-4-fluorobenzonitrile and 3-((R)-1-((3-chloro-6-(6-((S)-ethyl(methyl)phosphoryl)pyridin-3-yl)-7-fluoro-2-methyl-1,5-naphthyridin-4-yl)amino)ethyl)-4-fluorobenzonitrile

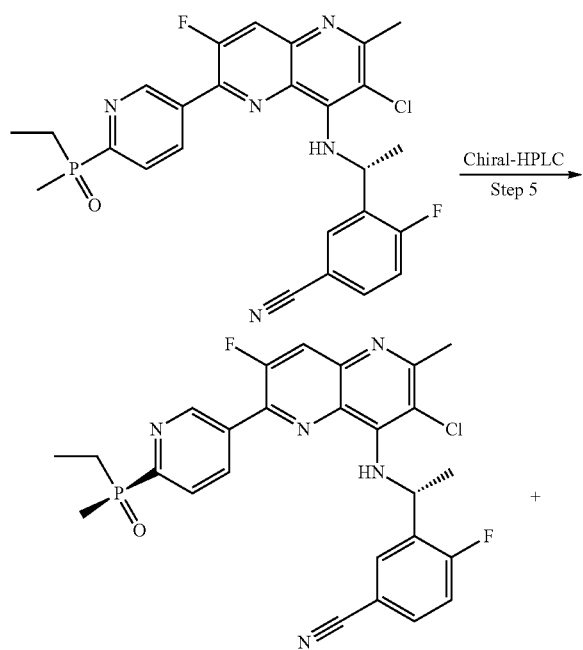

The mixture of 3-[(1R)-1-[(3-chloro-6-{6-[ethyl(methyl)phosphoryl]pyridin-3-yl}-7-fluoro-2-methyl-1,5-naphthyridin-4-yl)amino]ethyl]-4-fluorobenzonitrile (140 mg, 0.266 mmol) was resolved by Chiral Separation with following Conditions: (Column: CHIRAL ART Cellulose-SZ, 3*25 cm, 5 m; Mobile Phase A: Hex(10 mM $NH_3$-MeOH), Mobile Phase B: EtOH; Flow rate: 40 mL/min; Gradient: 20% B to 20% B in 27 min; Wave Length: 209/207 nm; RT1(min): 20.5; RT2(min): 23.6;). The fast peak afforded (45 mg, 32%) as a light yellow solid. MS ESI calculated for $C_{26}H_{23}ClF_2N_5OP$ [M+H]$^+$, 526.13, found 526.00. $^1$H NMR (300 MHz, Chloroform-d) δ 9.21 (s, 1H), 8.28-8.26 (m, 2H), 7.97 (d, J=11.3 Hz, 1H), 7.58-7.47 (m, 2H), 7.05 (t, J=9.2 Hz, 1H), 6.45-6.34 (m, 2H), 2.75 (s, 3H), 2.20-2.07 (m, 2H), 1.83 (d, J=13.2 Hz, 3H), 1.72 (d, J=6.2 Hz, 3H), 1.26-1.15 (m, 3H). $^{19}$F NMR (282 MHz, Chloroform-d) δ −108.61, −120.41. $^{31}$P NMR (122 MHz, Chloroform-d) δ 41.25.

The second peak afforded (48 mg, 34%) as a light yellow solid. MS ESI calculated for $C_{26}H_{23}ClF_2N_5OP$ [M+H]$^+$, 526.13, found 525.95. $^1$H NMR (300 MHz, Chloroform-d) δ 9.20 (s, 1H), 8.28-8.26 (m, 2H), 7.98 (d, J=11.3 Hz, 1H), 7.57-7.47 (m, 2H), 7.08-7.02 (m, 1H), 6.45-6.33 (m, 2H), 2.75 (s, 3H), 2.19-2.07 (m, 2H), 1.83 (d, J=13.2 Hz, 3H), 1.72 (d, J=6.4 Hz, 3H), 1.25-1.14 (m, 3H). $^{19}$F NMR (282 MHz, Chloroform-d) δ −108.53, −120.37. $^{31}$P NMR (122 MHz, Chloroform-d) δ 41.23.

Example 59: (2S)-2-({3-chloro-6-[6-(dimethylphosphoryl)pyridin-3-yl]-7-fluoro-2-methyl-1,5-naphthyridin-4-yl}amino)-2-(2-fluorophenyl)ethanol

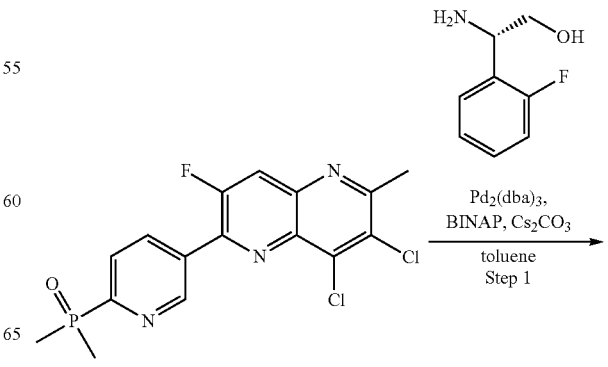

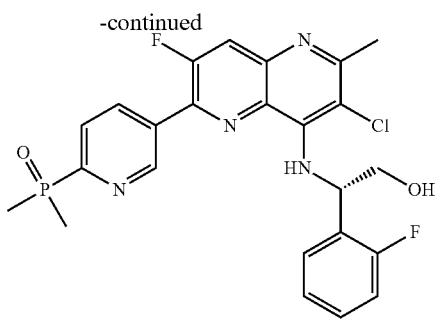

To a stirred solution of 3,4-dichloro-6-[6-(dimethylphosphoryl)pyridin-3-yl]-7-fluoro-2-methyl-1,5-naphthyridine (100 mg, 0.260 mmol) and (2S)-2-amino-2-(2-fluorophenyl)ethanol hydrochloride (60 mg, 0.312 mmol) in Toluene (1 mL) were added BINAP (32 mg, 0.052 mmol), Cs$_2$CO$_3$ (212 mg, 0.650 mmol) and Pd$_2$(dba)$_3$ (24 mg, 0.026 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: Column: column, C18 silica gel; mobile phase, CH$_3$CN in water (10 mmol/L NH$_4$HCO$_3$), 30% to 50% gradient in 30 min; detector, 254 nm to afford (2S)-2-({3-chloro-6-[6-(dimethylphosphoryl)pyridin-3-yl]-7-fluoro-2-methyl-1,5-naphthyridin-4-yl}amino)-2-(2-fluorophenyl)ethanol (51 mg, 3 8%) as a light yellow solid. MS ESI calculated for C$_{24}$H$_{22}$ClF$_2$N$_4$O$_2$P [M+H]$^+$, 503.11, found 503.10. $^1$H NMR (400 MHz, Chloroform-d) δ 9.26 (s, 1H), 8.30-8.21 (m, 2H), 7.97 (d, J=11.4 Hz, 1H), 7.29-7.20 (m, 3H), 7.06-7.00 (m, 2H), 6.54-6.50 (m, 1H), 4.20-4.14 (m, 1H), 4.10-4.05 (m, 1H), 2.74 (s, 3H), 2.27 (br s, 1H), 1.86 (s, 3H), 1.83 (s, 3H). $^{19}$F NMR (377 MHz, Chloroform-d) δ −118.06, −120.54. $^{31}$P NMR (162 MHz, Chloroform-d) δ 36.90.

Example 60: (2R)-2-({3-chloro-6-[6-(dimethylphosphoryl)pyridin-3-yl]-7-fluoro-2-methyl-1,5-naphthyridin-4-yl}amino)-2-(2-fluorophenyl)ethanol

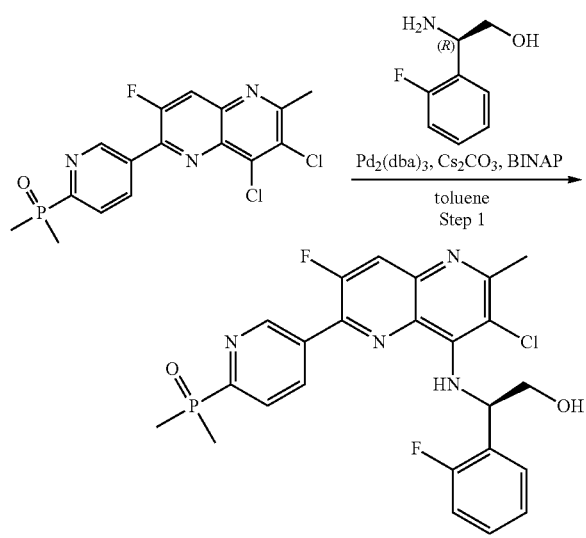

To a stirred solution of 3,4-dichloro-6-[6-(dimethylphosphoryl)pyridin-3-yl]-7-fluoro-2-methyl-1,5-naphthyridine (100 mg, 0.260 mmol) and (2R)-2-amino-2-(2-fluorophenyl)ethanol hydrochloride (60 mg, 0.312 mmol) in Toluene (1 mL) were added BINAP (32 mg, 0.052 mmol), Cs$_2$CO$_3$ (212 mg, 0.650 mmol) and Pd$_2$(dba)$_3$ (24 mg, 0.026 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 30% to 50% gradient in 30 min; detector, 254 nm to afford (2R)-2-({3-chloro-6-[6-(dimethylphosphoryl)pyridin-3-yl]-7-fluoro-2-methyl-1,5-naphthyridin-4-yl}amino)-2-(2-fluorophenyl)ethanol (35 mg, 26%) as a light yellow solid. MS ESI calculated for C$_{24}$H$_{22}$ClF$_2$N$_4$O$_2$P [M+H]$^+$, 503.11, found 503.10. $^1$H NMR (400 MHz, Chloroform-d) δ 9.26 (s, 1H), 8.30-8.21 (m, 2H), 7.95 (d, J=11.5 Hz, 1H), 7.29-7.20 (m, 3H), 7.06-7.00 (m, 2H), 6.54-6.50 (m, 1H), 4.20-4.14 (m, 1H), 4.09-4.06 (m, 1H), 2.73 (s, 3H), 2.40 (br s, 1H), 1.86 (s, 3H), 1.82 (s, 3H). $^{19}$F NMR (377 MHz, Chloroform-d) δ −118.08, −120.51. $^{31}$P NMR (162 MHz, Chloroform-d) δ 36.91.

Example 61: 3-[(1R)-1-({3-chloro-6-[6-(dimethylphosphoryl)-4-methylpyridin-3-yl]-7-fluoro-2-methyl-1,5-naphthyridin-4-yl}amino)ethyl]-4-fluorobenzonitrile Synthetic Scheme

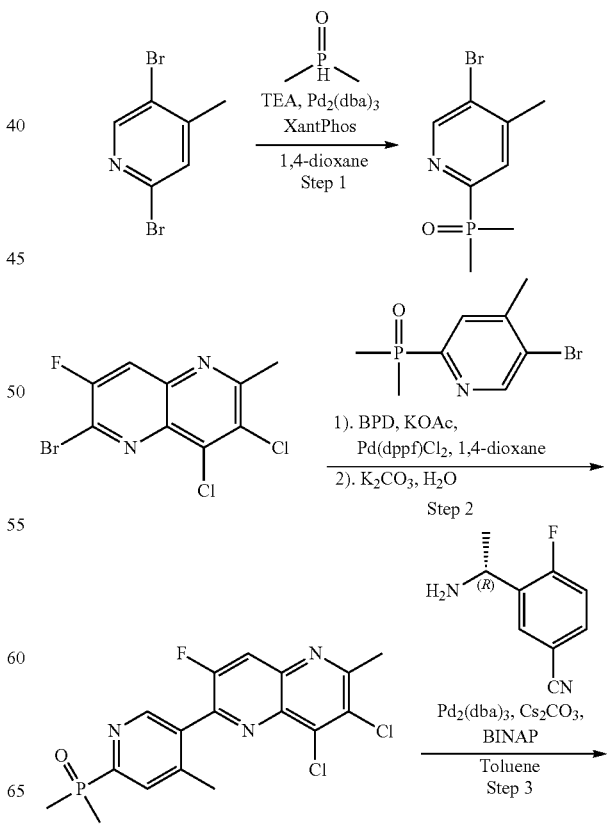

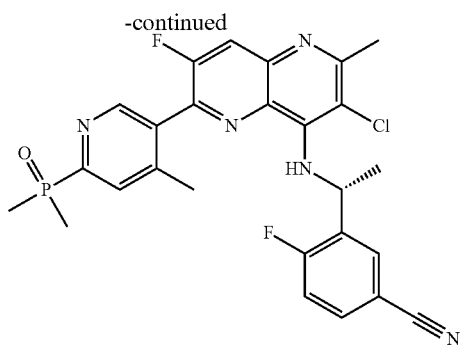

Preparation 61A:
5-bromo-2-dimethylphosphoryl-4-methylpyridine

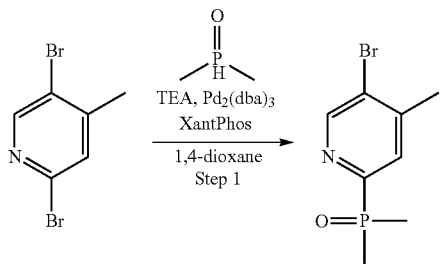

A mixture of Pd$_2$(dba)$_3$ (0.91 g, 0.996 mmol) and Xantphos (1.15 g, 1.993 mmol) in 1,4-dioxane (100 mL) was stirred for 15 min at room temperature under nitrogen atmosphere. To the above mixture were added 2,5-dibromo-4-methylpyridine (5.00 g, 19.927 mmol), TEA (2.42 g, 23.912 mmol) and dimethylphosphine oxide (1.56 g, 19.927 mmol) at room temperature. The resulting mixture was stirred for additional 16 h at 90° C. The resulting mixture was concentrated under reduced pressure. The residue was purified by silica gel column chromatography, eluted with CH$_2$Cl$_2$/MeOH (12:1) to afford 5-bromo-2-(dimethylphosphoryl)-4-methylpyridine (3.50 g, 70%) as a yellow solid. MS ESI calculated for C$_8$H$_{11}$BrNOP [M+H]$^+$, 247.98 249.97, found 248.00 250.00 $^1$H NMR (400 MHz, Chloroform-d) δ 8.73 (s, 1H), 8.00-7.98 (m, 1H), 2.47 (s, 3H), 1.77 (s, 3H), 1.74 (s, 3H). $^{31}$P NMR (162 MHz, Chloroform-d) δ 36.38.

Preparation 61B: 3,4-dichloro-6-[6-(dimethylphosphoryl)-4-methylpyridin-3-yl]-7-fluoro-2-methyl-1,5-naphthyridine

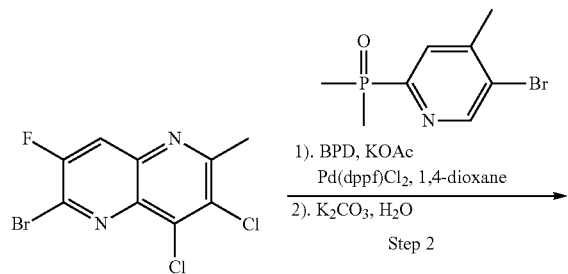

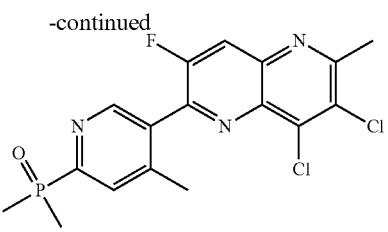

A mixture of 5-bromo-2-(dimethylphosphoryl)-4-methylpyridine (224 mg, 0.903 mmol), BPD (328 mg, 1.290 mmol), KOAc (190 mg, 1.935 mmol) and Pd(dppf)Cl$_2$·CH$_2$Cl$_2$ (74 mg, 0.090 mmol) in 1,4-dioxane (5 mL) was stirred for 3 h at 100° C. under nitrogen atmosphere. The mixture was allowed to cool down to room temperature. To the above mixture were added 6-bromo-3,4-dichloro-7-fluoro-2-methyl-1,5-naphthyridine (200 mg, 0.645 mmol), K$_2$CO$_3$ (178 mg, 1.290 mmol) and H$_2$O (1 mL) at room temperature under nitrogen atmosphere. The resulting mixture was stirred for additional 2 h at 80° C. The resulting mixture was concentrated under reduced pressure. The residue was purified by silica gel column chromatography, eluted with CH$_2$Cl$_2$/MeOH (12:1) to afford 3,4-dichloro-6-[6-(dimethylphosphoryl)-4-methylpyridin-3-yl]-7-fluoro-2-methyl-1,5-naphthyridine (180 mg, 70%) as an orange solid. MS ESI calculated for C$_{17}$H$_{15}$Cl$_2$FN$_3$OP [M+H]$^+$, 398.03, found 398.10. $^1$H NMR (400 MHz, Chloroform-d) δ 8.81 (s, 1H), 8.16-8.13 (m, 2H), 2.92 (s, 3H), 2.48 (s, 3H), 1.86 (s, 3H), 1.83 (s, 3H). $^{19}$F NMR (377 MHz, Chloroform-d) δ −117.62.

Example 61: 3-[(1R)-1-({3-chloro-6-[6-(dimethylphosphoryl)-4-methylpyridin-3-yl]-7-fluoro-2-methyl-1,5-naphthyridin-4-yl}amino)ethyl]-4-fluorobenzonitrile

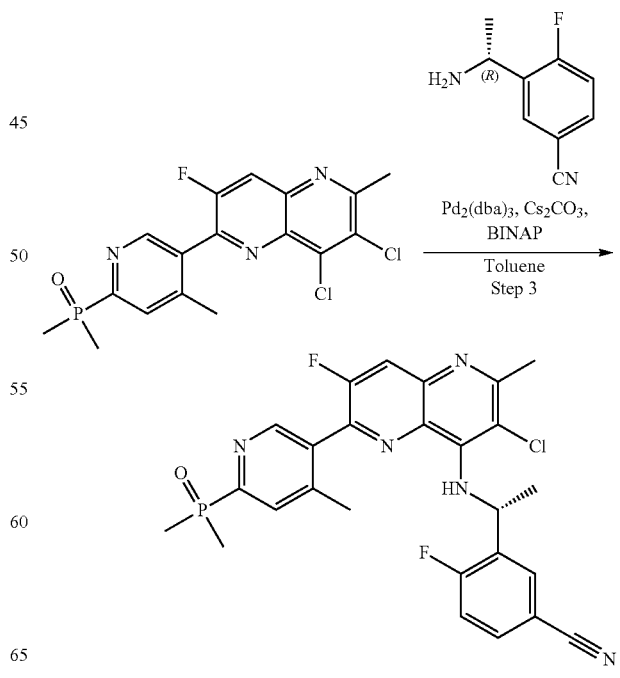

To a solution of 3,4-dichloro-6-[6-(dimethylphosphoryl)-4-methylpyridin-3-yl]-7-fluoro-2-methyl-1,5-naphthyridine (90 mg, 0.226 mmol), BINAP (28 mg, 0.045 mmol) and 3-[(1R)-1-aminoethyl]-4-fluorobenzonitrile (45 mg, 0.271 mmol) in Toluene (4 mL) were added Cs$_2$CO$_3$ (221 mg, 0.678 mmol) and Pd$_2$(dba)$_3$ (21 mg, 0.023 mmol). After stirring for overnight at 100° C. under a nitrogen atmosphere, the resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 10% to 70% gradient in 25 min; detector, 254 nm to afford 3-[(1R)-1-({3-chloro-6-[6-(dimethylphosphoryl)-4-methylpyridin-3-yl]-7-fluoro-2-methyl-1,5-naphthyridin-4-yl}amino)ethyl]-4-fluorobenzonitrile (45 mg, 37%) as a light yellow solid. MS ESI calculated for C$_{26}$H$_{23}$ClF$_2$N$_5$OP [M+H]$^+$, 526.13, found 525.95. $^1$H NMR (400 MHz, Chloroform-d) δ 8.50 (s, 1H), 8.11 (d, J=5.6 Hz, 1H), 7.94 (d, J=10.0 Hz, 1H), 7.50-7.43 (m, 2H), 6.87 (t, J=9.2 Hz, 1H), 6.28-6.18 (m, 2H), 2.76 (s, 3H), 2.24 (s, 3H), 1.89 (s, 3H), 1.85 (s, 3H), 1.63 (d, J=6.4 Hz, 3H). $^{19}$F NMR (377 MHz, Chloroform-d) δ −109.51, −119.59. $^{31}$P NMR (162 MHz, Chloroform-d) δ 36.57.

Example 62: 3-chloro-6-[6-(dimethylphosphoryl)-4-methylpyridin-3-yl]-7-fluoro-N-[(1R)-1-(2-fluorophenyl)ethyl]-2-methyl-1,5-naphthyridin-4-amine

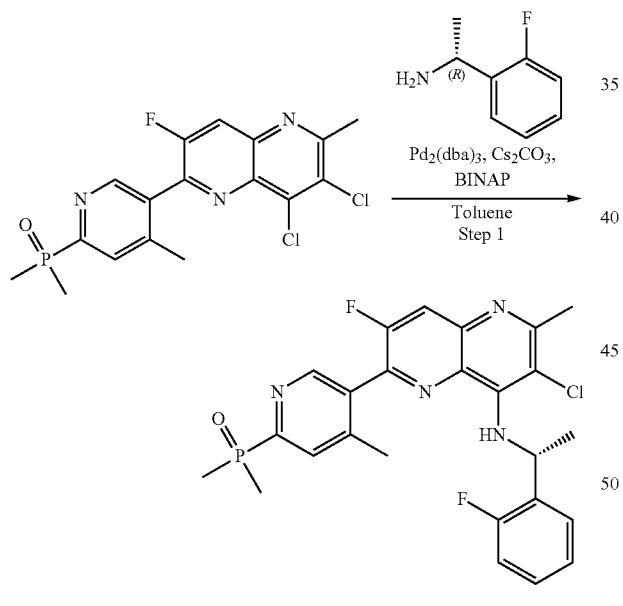

To a solution of 3,4-dichloro-6-[6-dimethylphosphoryl)-4-methylpyridin-3-yl]-7-fluoro-2-methyl-1,5-naphthyridine (90 mg, 0.226 mmol), BINAP (28 mg, 0.045 mmol) and (1R)-1-(2-fluorophenyl)ethanamine (38 mg, 0.271 mmol) in Toluene (3 mL) were added Cs$_2$CO$_3$ (221 mg, 0.678 mmol) and Pd$_2$(dba)$_3$ (21 mg, 0.023 mmol). After stirring for overnight at 100° C. under a nitrogen atmosphere, the resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 10% to 70% gradient in 25 min; detector, 254 nm to afford 3-chloro-6-[6-(dimethylphosphoryl)-4-methylpyridin-3-yl]-7-fluoro-N-[(1R)-1-(2-fluorophenyl)ethyl]-2-methyl-1,5-naphthyridin-4-amine (50 mg, 44%) as a light yellow solid. MS ESI calculated for C$_{25}$H$_{24}$ClF$_2$N$_4$OP [M+H]$^+$, 501.13, found 500.95. $^1$H NMR (400 MHz, Chloroform-d) δ 8.60 (s, 1H), 8.11 (d, J=6.0 Hz, 1H), 7.89 (d, J=10.0 Hz, 1H), 7.15-7.10 (m, 2H), 6.96-6.92 (m, 1H), 6.85-6.80 (m, 1H), 6.44-6.40 (m, 1H), 6.30-6.23 (m, 1H), 2.73 (s, 3H), 2.26 (s, 3H), 1.88 (d, J=2.0 Hz, 3H), 1.85 (d, J=2.0 Hz, 3H), 1.63 (d, J=6.7 Hz, 3H). $^{19}$F NMR (377 MHz, Chloroform-d) δ −119.42, −120.08. $^{31}$P NMR (162 MHz, Chloroform-d) δ 36.65.

Example 63 and 64: (S)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile and (R)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile Synthetic Scheme

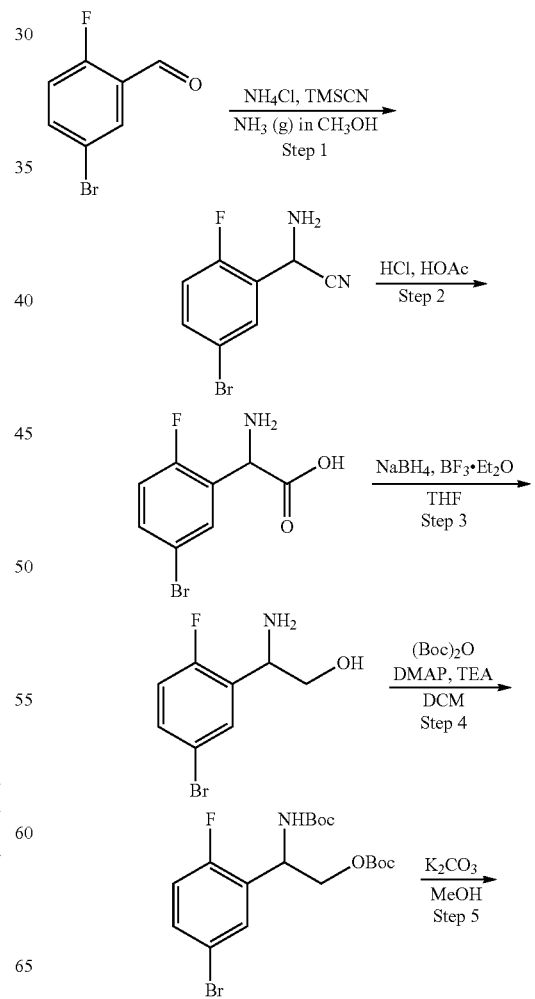

237
-continued

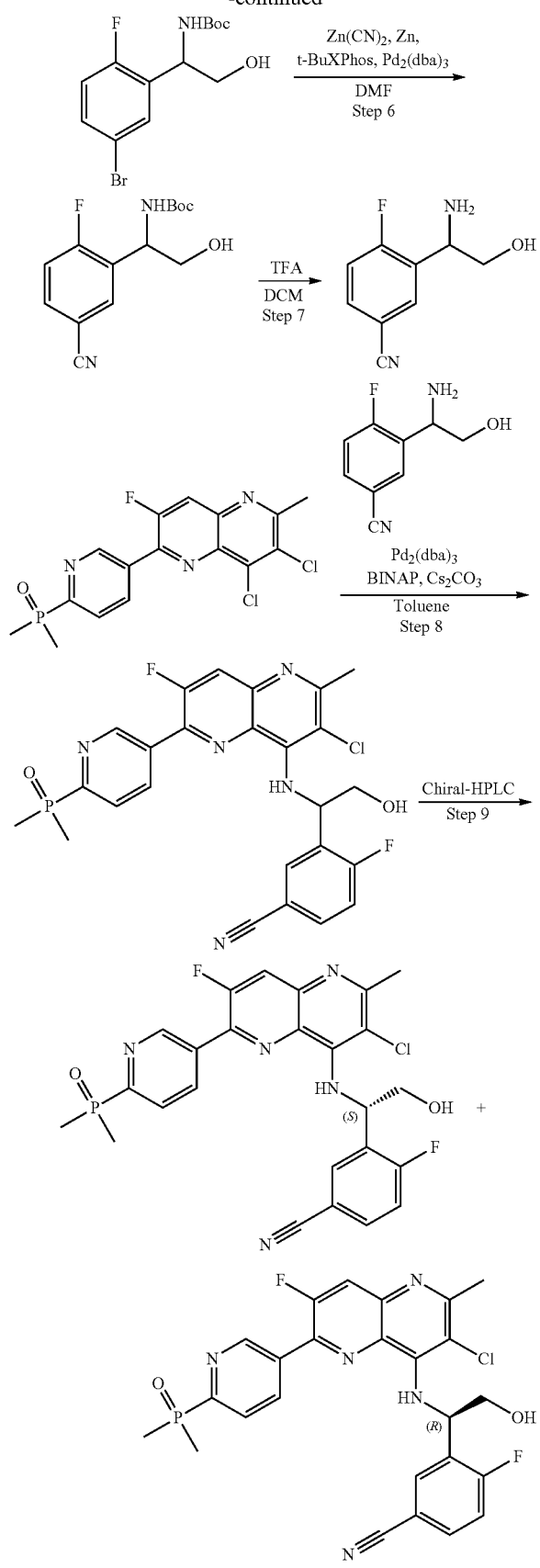

238

Preparation 63A.
2-amino-2-(5-bromo-2-fluorophenyl)acetonitrile

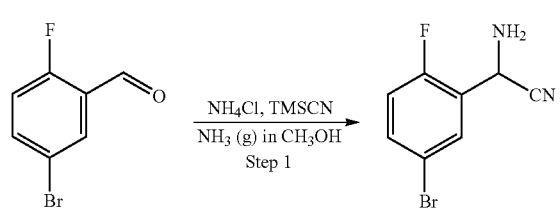 [SMILES: O=Cc1cc(Br)ccc1F ; N#CC(N)c1cc(Br)ccc1F]

A mixture of 5-bromo-2-fluorobenzaldehyde (20.00 g, 98.517 mmol), NH$_4$Cl (15.81 g, 295.551 mmol) and trimethylsilanecarbonitrile (19.55 g, 197.034 mmol) in solution of 4N of NH$_3$(g) in MeOH (250 mL) was stirred for 16 h at room temperature. The resulting mixture was concentrated under reduced pressure. The residue was diluted with EtOAc (100 mL) and water (100 mL). The aqueous layer was extracted with EtOAc (4×250 mL). The combined organic layers were dried over anhydrous Na$_2$SO$_4$. After filtration, the filtrate was concentrated under reduced pressure to afford 2-amino-2-(5-bromo-2-fluorophenyl)acetonitrile (15.50 g, 69%) as a yellow solid. MS ESI calculated for C$_8$H$_6$BrFN$_2$ [M+H]$^+$, 228.97 230.97 found 229.05 231.05. $^1$H NMR (400 MHz, Chloroform-d) δ 7.71-7.68 (m, 1H), 7.53-7.48 (m, 1H), 7.06-7.01 (m, 1H), 5.07-5.06 (m, 1H), 2.00 (s, 2H).

Preparation 63B:
amino(5-bromo-2-fluorophenyl)acetic acid

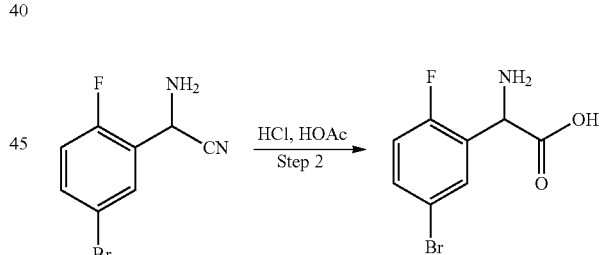

A solution of 2-amino-2-(5-bromo-2-fluorophenyl)acetonitrile (15.50 g, 67.670 mmol) in conc. HCl (80 mL) and HOAc (80 mL) was stirred for 16 h at 100° C. The resulting mixture was concentrated under reduced pressure. The mixture was neutralized to pH 7 with 1N NaOH (aq.). The aqueous layer was extracted with EtOAc (5×100 mL). The combined organic layers were dried over anhydrous Na$_2$SO$_4$. After filtration, the filtrate was concentrated under reduced pressure to afford amino(5-bromo-2-fluorophenyl) acetic acid (12.50 g, 74%) as a white solid. MS ESI calculated for C$_8$H$_7$BrFNO$_2$ [M+H]$^+$, 247.96 249.96 found 247.95 249.95.

Preparation 63C: 2-amino-2-(5-bromo-2-fluorophenyl)ethanol

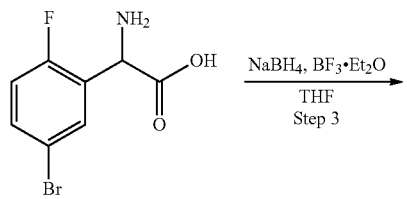

A solution of amino(5-bromo-2-fluorophenyl)acetic acid (12.50 g, 50.393 mmol) in THF (200 ml) was treated with NaBH₄ (5.72 g, 151.179 mmol) for 30 min at 0° C. under nitrogen atmosphere. To the above mixture was added BF₃·Et₂O (21.46 g, 151.179 mmol) dropwise at 0° C. The resulting mixture was stirred for additional 3 h at room temperature. The reaction was quenched by the addition of water (50 mL) at room temperature. The aqueous layer was extracted with EtOAc (3×150 mL). The combined organic layers were dried over anhydrous Na₂SO₄. After filtration, the filtrate was concentrated under reduced pressure to afford 2-amino-2-(5-bromo-2-fluorophenyl)ethanol (10.00 g, 85%) as a light yellow solid. MS ESI calculated for $C_8H_9BrFNO$ [M+H]⁺, 233.99 235.99 found 234.05 236.00. ¹H NMR (400 MHz, Chloroform-d) δ 7.57-7.54 (m, 1H), 7.38-7.34 (m, 1H), 6.96-6.91 (m, 1H), 4.33-4.30 (m, 1H), 3.81-3.77 (m, 1H), 3.62-3.57 (m, 1H), 2.52 (s, 1H).

Preparation 63D: 4-bromo-2-{1-[(tert-butoxycarbonyl)amino]-2-[(tert-butoxycarbonyl)oxy]ethyl}-1-fluorobenzene

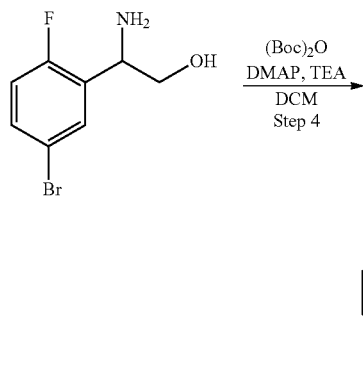

A solution of 2-amino-2-(5-bromo-2-fluorophenyl)ethanol (10.00 g, 42.723 mmol), (Boc)₂O (23.31 g, 106.808 mmol), TEA (12.97 g, 128.169 mmol) and DMAP (0.52 g, 4.272 mmol) in DCM (100 ml) was stirred for 2 h at room temperature. The resulting mixture was concentrated under reduced pressure. The residue was purified by silica gel column chromatography, eluted with CH₂Cl₂/PE (5:1) to afford 4-bromo-2-{1-[(tert-butoxycarbonyl)amino]-2-[(tert-butoxycarbonyl)oxy]ethyl}-1-fluorobenzene (8.90 g, 48%) as a yellow oil. MS ESI calculated for $C_{26}H_{23}ClF_2N_5OP$ [M−H]⁻, 432.09 434.09, found 431.85 433.90.

Preparation 63E: tert-butyl N-[1-(5-bromo-2-fluorophenyl)-2-hydroxyethyl]carbamate

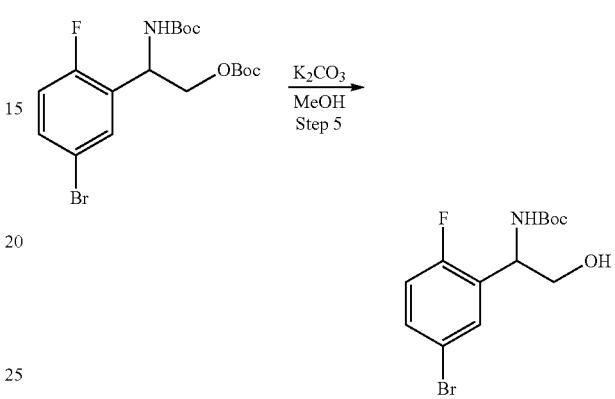

A mixture of 4-bromo-2-{1-[(tert-butoxycarbonyl)amino]-2-[(tert-butoxycarbonyl)oxy]ethyl}-1-fluorobenzene (8.90 g, 20.493 mmol) and K₂CO₃ (8.50 g, 61.479 mmol) in MeOH (100 mL) was stirred for 2 h at room temperature. The resulting mixture was filtered, and the filter cake was washed with EA (3×50 mL). The filtrate was concentrated under reduced pressure. The residue was purified by silica gel column chromatography, eluted with CH₂Cl₂/MeOH (12:1) to afford tert-butyl N-[1-(5-bromo-2-fluorophenyl)-2-hydroxyethyl]carbamate (4.00 g, 58%) as a yellow solid. MS ESI calculated for $C_{13}H_{17}BrFNO_3$ [M−H]⁻, 332.04 334.04, found 331.90 333.90. ¹H NMR (400 MHz, Chloroform-d) δ 7.46-7.43 (m, 1H), 7.40-7.36 (m, 1H), 6.97-6.93 (m, 1H), 5.39-5.35 (m, 1H), 5.05-5.00 (m, 1H), 3.89-3.85 (m, 1H), 3.83-3.78 (m, 1H), 1.44 (s, 9H).

Preparation 63F: tert-butyl N-[1-(5-cyano-2-fluorophenyl)-2-hydroxyethyl]carbamate

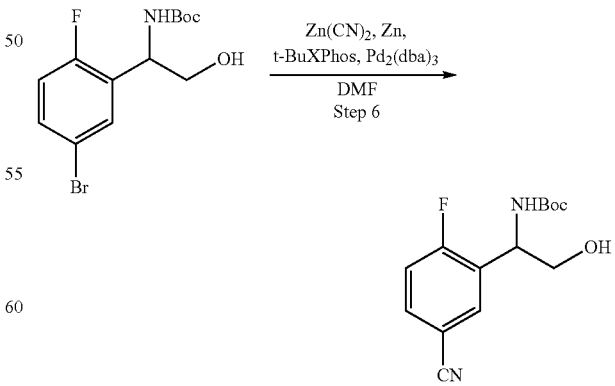

A mixture of tert-butyl N-[1-(5-bromo-2-fluorophenyl)-2-hydroxyethyl]carbamate (3.50 g, 10.473 mmol), Zn (1.37 g, 20.946 mmol), Zn(CN)₂ (2.46 g, 20.946 mmol), t-BuX- Phos (890 mg, 2.095 mmol) and Pd$_2$(dba)$_3$ (959 mg, 1.047 mmol) in DMF (30 ml) was stirred for 2 h at 80° C. under nitrogen atmosphere. The resulting mixture was filtered, and the filter cake was washed with DCM (2×30 mL). The filtrate was concentrated under reduced pressure. The residue was purified by reversed-phase flash chromatography with the following conditions: column, C18 silica gel; mobile phase, CH$_3$CN in water (10 mmol/L NH$_4$HCO$_3$), 5% to 80% gradient in 40 min; detector, 220 nm to afford tert-butyl N-[1-(5-cyano-2-fluorophenyl)-2-hydroxyethyl] carbamate (1.70 g, 58%) as a colorless oil. MS ESI calculated for C$_{14}$H$_{17}$FN$_2$O$_3$[M−H]$^-$, 279.12, found 279.10. $^1$H NMR (300 MHz, Chloroform-d) δ 7.73-7.69 (m, 1H), 7.64-7.58 (m, 1H), 7.21-7.15 (m, 1H), 5.10-5.04 (m, 1H), 4.86-4.82 (m, 1H), 3.94-3.77 (m, 2H), 1.45 (s, 9H).

Preparation 63G:
3-(1-amino-2-hydroxyethyl)-4-fluorobenzonitrile

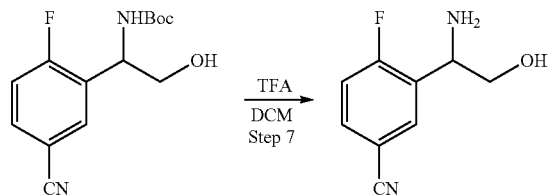 [SMILES: CC(C)(C)OC(=O)NC(CO)c1cc(C#N)ccc1F ; N#Cc1ccc(F)c(C(N)CO)c1]

To a stirred solution of tert-butyl N-[1-(5-cyano-2-fluorophenyl)-2-hydroxyethyl]carbamate (1.70 g, 6.065 mmol) in DCM (20 mL) was added TFA (4 mL) at room temperature. The resulting mixture was stirred for 2 h at room temperature. The resulting mixture was concentrated under reduced pressure. The residue was purified by reversed-phase flash chromatography with the following conditions: column, C18 silica gel; mobile phase, CH$_3$CN in water (10 mmol/L NH$_4$HCO$_3$), 5% to 5% gradient in 20 min; detector, 220 nm to afford 3-(1-amino-2-hydroxyethyl)-4-fluorobenzonitrile (1.00 g, 92%) as a colorless oil. MS ESI calculated for C$_9$H$_9$FN$_2$O [M+H]$^+$, 181.07, found 181.20.

Preparation 63H: 3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile

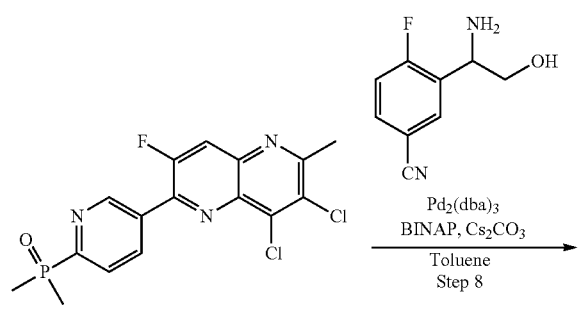

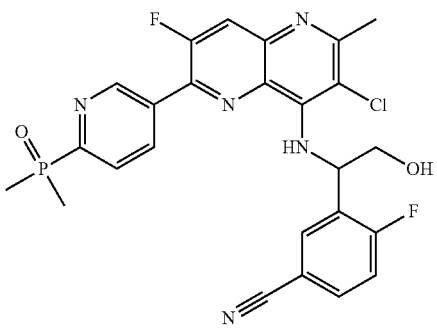

To a stirred solution of 3-(1-amino-2-hydroxyethyl)-4-fluorobenzonitrile (400 mg, 2.220 mmol) and 3,4-dichloro-6-[6-(dimethylphosphoryl)pyridin-3-yl]-7-fluoro-2-methyl-1,5-naphthyridine (1.02 g, 2.664 mmol) in Toluene (8 mL) were added BINAP (276 mg, 0.444 mmol), Cs$_2$CO$_3$ (1.08 g, 3.330 mmol) and Pd$_2$(dba)$_3$ (203 mg, 0.222 mmol) at room temperature under nitrogen atmosphere. The resulting mixture was stirred for 2 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 40% to 80% gradient in 30 min; detector, 254 nm to afford 3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile (200 mg, 17%) as a yellow solid. MS ESI calculated for C$_{25}$H$_{21}$ClF$_2$N$_5$O$_2$P [M+H]$^+$, 528.11, found 527.95.

Example 63 and 64: (S)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile and (R)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile

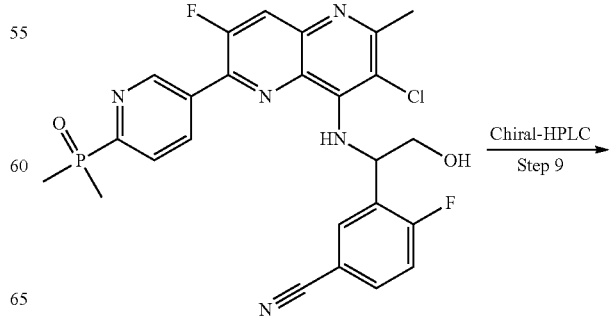

-continued

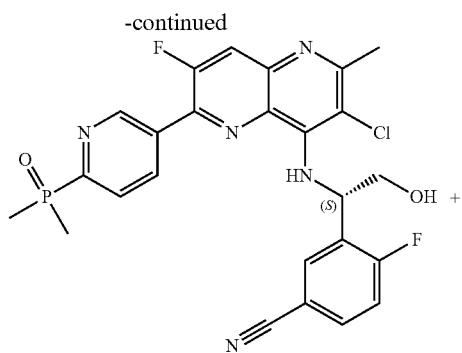

+

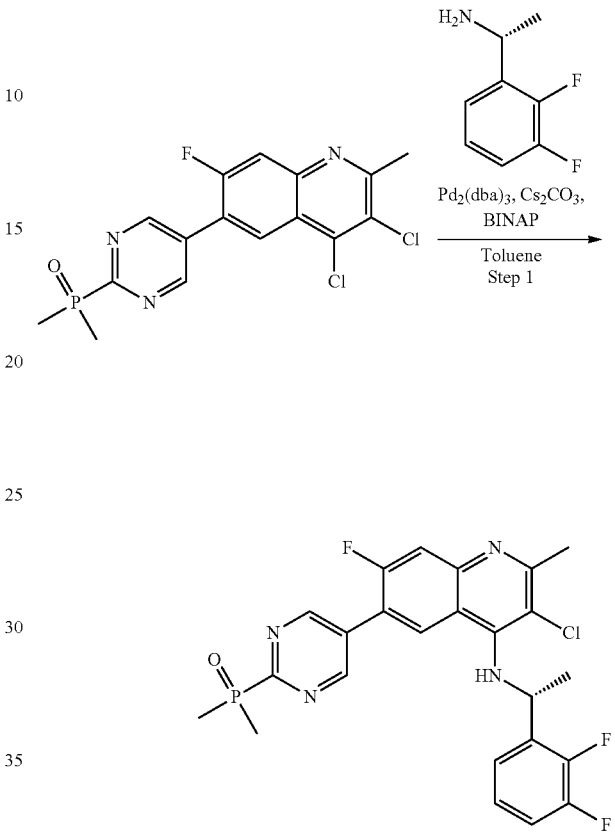

3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile (50 mg) was resolved by Chiral-Prep-HPLC with the following conditions (Column: Lux 5 um Cellulose-2, 2.12*25 cm, 5 m; Mobile Phase A: Hex(10 mM $NH_3$-MeOH), Mobile Phase B: EtOH; Flow rate: 20 mL/min; Gradient: 30% B to 30% B in 32 min; Wave Length: 280/218 nm; RT1(min): 25.09; RT2(min): 28.55). The first peak afforded 5 mg (10%) as a yellow solid. MS ESI calculated for $C_{25}H_{21}ClF_2N_5O_2P$ [M+H]$^+$, 528.11, found 528.20. $^1$H NMR (400 MHz, Chloroform-d) δ 9.24-9.21 (m, 1H), 8.32-8.28 (m, 1H), 8.21-8.16 (m, 1H), 7.99-7.94 (m, 1H), 7.67-7.62 (m, 1H), 7.56-7.51 (m, 1H), 7.44-7.39 (m, 1H), 7.13-7.07 (m, 1H), 6.44-6.39 (m, 1H), 4.23-4.19 (m, 1H), 4.05-4.01 (m, 1H), 3.85-3.62 (m, 1H), 2.75-2.71 (m, 3H), 1.85-1.80 (m, 6H). $^{19}$F NMR (377 MHz, Chloroform-d) δ -108.40, -120.00. $^{31}$P NMR (162 MHz, Chloroform-d) δ 37.65.

The second peak afforded 7 mg (14%) as a yellow solid. MS ESI calculated for $C_{25}H_{21}ClF_2N_5O_2P$ [M+H]$^+$, 528.11, found 527.95. $^1$H NMR (400 MHz, Chloroform-d) δ 9.24-9.21 (m, 1H), 8.32-8.28 (m, 1H), 8.19-8.15 (m, 1H), 7.96-7.92 (m, 1H), 7.66-7.63 (m, 1H), 7.55-7.51 (m, 1H), 7.42-7.39 (m, 1H), 7.13-7.06 (m, 1H), 6.43-6.39 (m, 1H), 4.23-4.18 (m, 1H), 4.05-4.00 (m, 1H), 3.74-3.69 (m, 1H), 2.73-2.69 (m, 3H), 1.84-1.79 (m, 6H). $^{19}$F NMR (377 MHz, Chloroform-d) δ -108.42, -120.12. $^{31}$P NMR (162 MHz, Chloroform-d) δ 37.72.

Example 65: 3-chloro-N-[(1R)-1-(2,3-difluorophenyl)ethyl]-6-[2-(dimethylphosphoryl)pyrimidin-5-yl]-7-fluoro-2-methylquinolin-4-amine To a stirred solution of 3,4-dichloro-6-[2-(dimethylphosphoryl)pyrimidin-5-yl]-7-fluoro-2-methylquinoline (60 mg, 0.156 mmol) and (1R)-1-(2,3-difluorophenyl)ethanamine hydrochloride (36 mg, 0.187 mmol) in Toluene (1 mL) were added Pd$_2$(dba)$_3$ (14 mg, 0.016 mmol) and Cs$_2$CO$_3$ (127 mg, 0.390 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 40% to 60% gradient in 30 min; detector, 254 nm. This resulted in 3-chloro-N-[(1R)-1-(2,3-difluorophenyl)ethyl]-6-[2-(dimethylphosphoryl)pyrimidin-5-yl]-7-fluoro-2-methylquinolin-4-amine (16 mg, 20%) as a white solid. MS ESI calculated for $C_{24}H_{21}ClF_3N_4OP$ [M+H]$^+$, 505.11, found 505.10. $^1$H NMR (300 MHz, Chloroform-d) δ 8.94-8.93 (m, 2H), 7.95 (d, J=7.9 Hz, 1H), 7.77 (d, J=11.7 Hz, 1H), 7.27-7.19 (m, 1H), 7.17-7.11 (m, 2H), 5.33-5.28 (m, 2H), 2.81 (s, 3H), 1.99 (s, 3H), 1.94 (s, 3H), 1.70 (d, J=6.4 Hz, 3H). $^{19}$F NMR (282 MHz, Chloroform-d) δ -115.10, -136.88, -136.96, -144.27, -144.34. $^{31}$P NMR (121 MHz, Chloroform-d) δ 34.77.

Example 66: 3-chloro-6-[6-(dimethylphosphoryl) pyridin-3-yl]-7-fluoro-N-[(1R)-1-[2-fluoro-5-(4-methylimidazol-1-yl)phenyl]ethyl]-2-methyl-1,5-naphthyridin-4-amine Synthetic Scheme

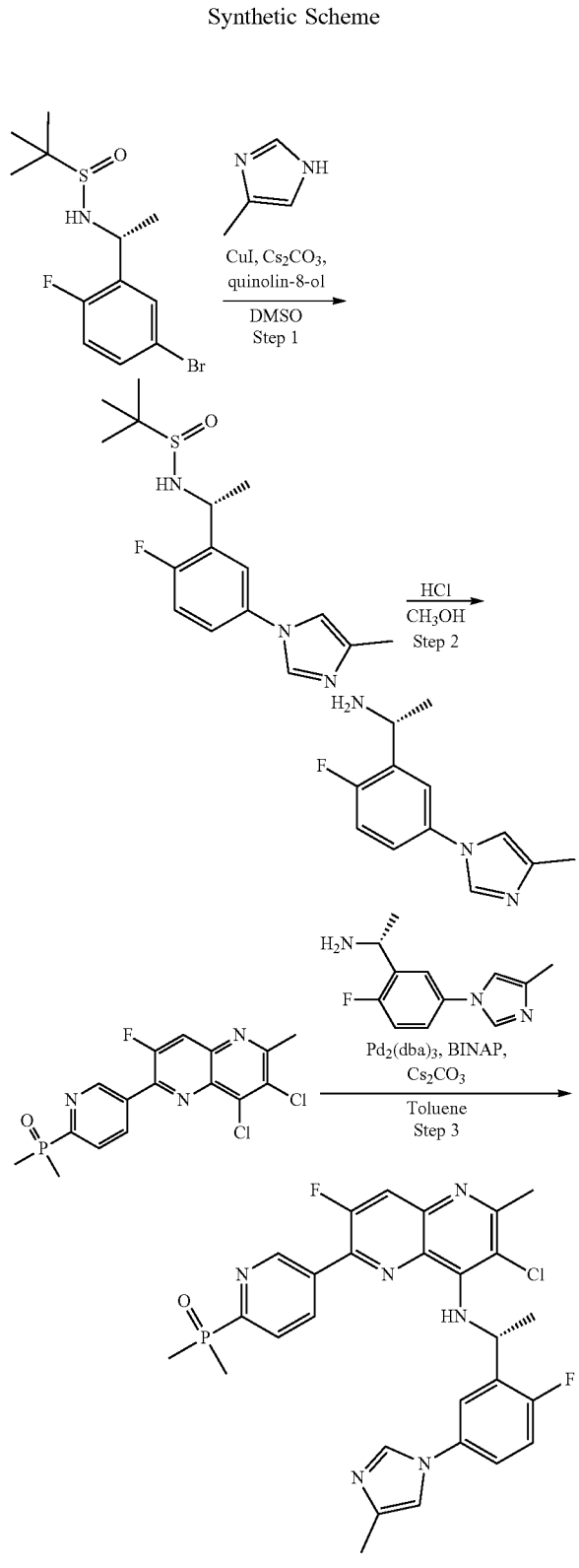

Preparation 66A: N-[(1R)-1-[2-fluoro-5-(4-methylimidazol-1-yl)phenyl]ethyl]-2-methylpropane-2-sulfinamide

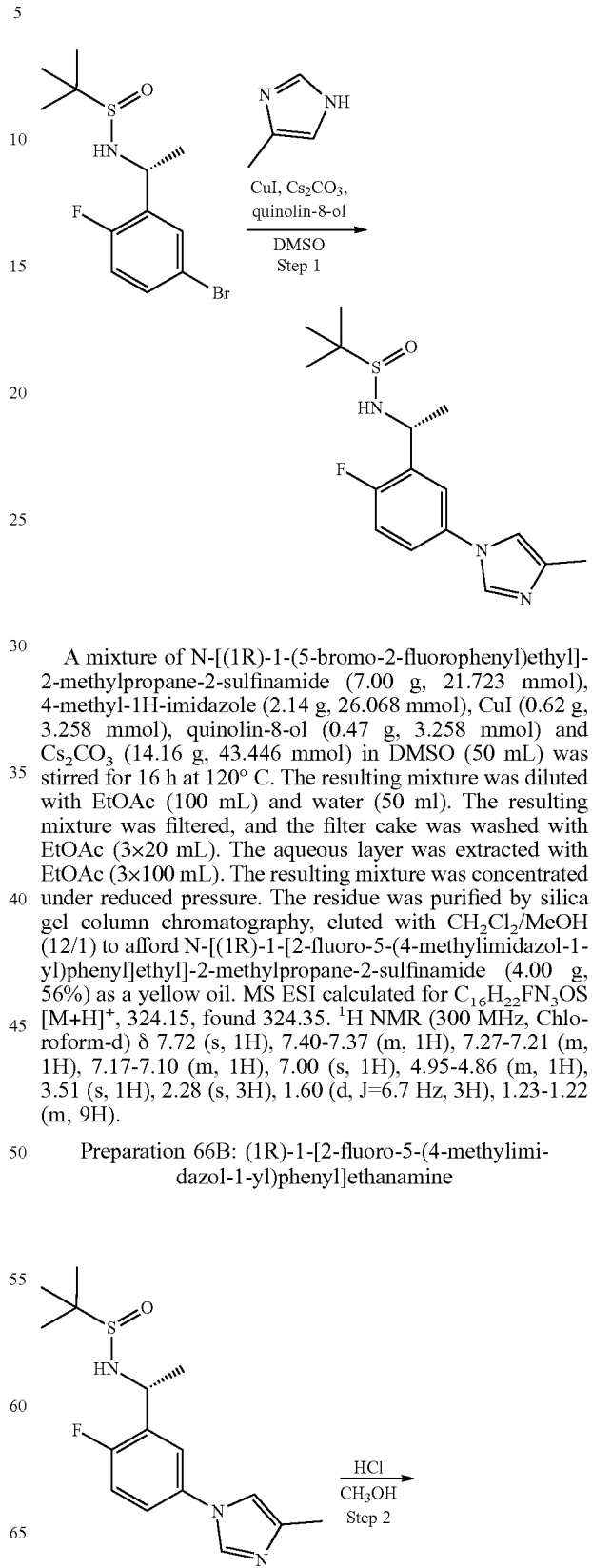

A mixture of N-[(1R)-1-(5-bromo-2-fluorophenyl)ethyl]-2-methylpropane-2-sulfinamide (7.00 g, 21.723 mmol), 4-methyl-1H-imidazole (2.14 g, 26.068 mmol), CuI (0.62 g, 3.258 mmol), quinolin-8-ol (0.47 g, 3.258 mmol) and $Cs_2CO_3$ (14.16 g, 43.446 mmol) in DMSO (50 mL) was stirred for 16 h at 120° C. The resulting mixture was diluted with EtOAc (100 mL) and water (50 ml). The resulting mixture was filtered, and the filter cake was washed with EtOAc (3×20 mL). The aqueous layer was extracted with EtOAc (3×100 mL). The resulting mixture was concentrated under reduced pressure. The residue was purified by silica gel column chromatography, eluted with $CH_2Cl_2$/MeOH (12/1) to afford N-[(1R)-1-[2-fluoro-5-(4-methylimidazol-1-yl)phenyl]ethyl]-2-methylpropane-2-sulfinamide (4.00 g, 56%) as a yellow oil. MS ESI calculated for $C_{16}H_{22}FN_3OS$ [M+H]$^+$, 324.15, found 324.35. $^1$H NMR (300 MHz, Chloroform-d) δ 7.72 (s, 1H), 7.40-7.37 (m, 1H), 7.27-7.21 (m, 1H), 7.17-7.10 (m, 1H), 7.00 (s, 1H), 4.95-4.86 (m, 1H), 3.51 (s, 1H), 2.28 (s, 3H), 1.60 (d, J=6.7 Hz, 3H), 1.23-1.22 (m, 9H).

Preparation 66B: (1R)-1-[2-fluoro-5-(4-methylimidazol-1-yl)phenyl]ethanamine

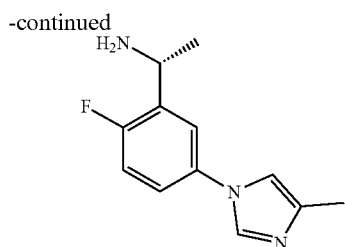

A solution of N-[(1R)-1-[2-fluoro-5-(4-methylimidazol-1-yl)phenyl]ethyl]-2-methylpropane-2-sulfinamide (4.00 g, 12.367 mmol) and conc. HCl (10 mL) in MeOH (30 mL) was stirred for 30 min at room temperature. The resulting mixture was concentrated under reduced pressure. The mixture was neutralized to pH 7 with saturated NaHCO$_3$ (aq.). The aqueous layer was extracted with EtOAc (5×50 mL). The resulting mixture was concentrated under reduced pressure to afford (1R)-1-[2-fluoro-5-(4-methylimidazol-1-yl)phenyl] ethanamine (2.50 g, 92%) as a yellow oil. MS ESI calculated for C$_{12}$H$_{14}$FN$_3$ [M+H]$^+$, 220.12, found 220.30. $^1$H NMR (400 MHz, Chloroform-d) δ 7.70 (s, 1H), 7.50-7.47 (m, 1H), 7.21-7.17 (m, 1H), 7.12-7.08 (m, 1H), 6.97 (s, 1H), 4.50-4.44 (m, 1H), 2.29 (s, 3H), 1.44 (d, J=6.6 Hz, 3H).

Example 66: 3-chloro-6-[6-(dimethylphosphoryl)pyridin-3-yl]-7-fluoro-N-[(1R)-1-[2-fluoro-5-(4-methylimidazol-1-yl)phenyl]ethyl]-2-methyl-1,5-naphthyridin-4-amine

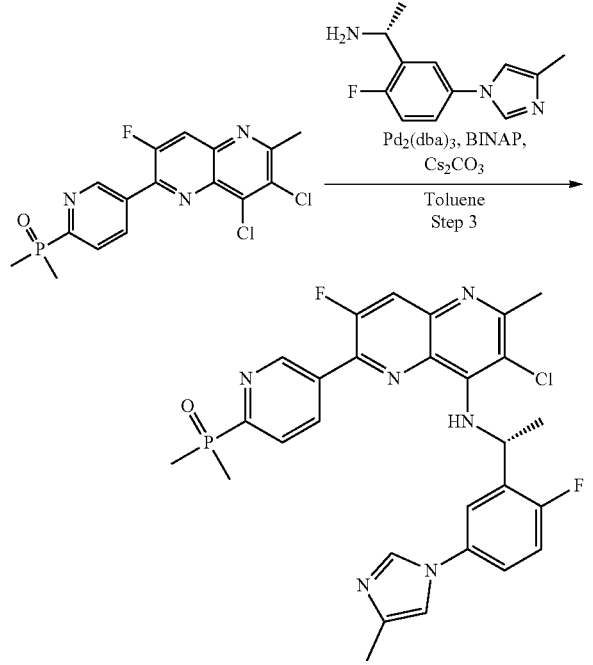

A mixture of 3,4-dichloro-6-[6-(dimethylphosphoryl)pyridin-3-yl]-7-fluoro-2-methyl-1,5-naphthyridine (100 mg, 0.260 mmol), (1R)-1-[2-fluoro-5-(4-methylimidazol-1-yl)phenyl]ethanamine (68 mg, 0.312 mmol), Pd$_2$(dba)$_3$ (23 mg, 0.026 mmol), BINAP (32 mg, 0.052 mmol) and Cs$_2$CO$_3$ (127 mg, 0.390 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-chloro-6-[6-(dimethylphosphoryl)pyridin-3-yl]-7-fluoro-N-[(1R)-1-[2-fluoro-5-(4-methylimidazol-1-yl)phenyl]ethyl]-2-methyl-1,5-naphthyridin-4-amine (61 mg, 41%) as a yellow solid. MS ESI calculated for C$_{28}$H$_{26}$ClF$_2$N$_6$OP [M+H]$^+$, 567.16, found 567.10. $^1$H NMR (400 MHz, DMSO-d$_6$) δ 9.24 (s, 1H), 8.43-8.39 (m, 1H), 8.22-8.18 (m, 1H), 8.13-8.09 (m, 1H), 7.93 (d, J=1.4 Hz, 1H), 7.74-7.72 (m, 1H), 7.48-7.43 (m, 1H), 7.25-7.18 (m, 2H), 6.93 (d, J=8.9 Hz, 1H), 6.42-6.34 (m, 1H), 2.64 (s, 3H), 2.11 (s, 3H), 1.77 (s, 3H), 1.74 (s, 3H), 1.70 (d, J=6.8 Hz, 3H). $^{19}$F NMR (377 MHz, DMSO-d$_6$) δ −120.90, −122.07. $^{31}$P NMR (162 MHz, DMSO-d$_6$) δ 34.27.

Example 67: 3-chloro-N-[(1R)-1-(2,3-difluorophenyl)ethyl]-6-[6-(dimethylphosphoryl)pyridin-3-yl]-7-fluoro-2-methylquinolin-4-amine

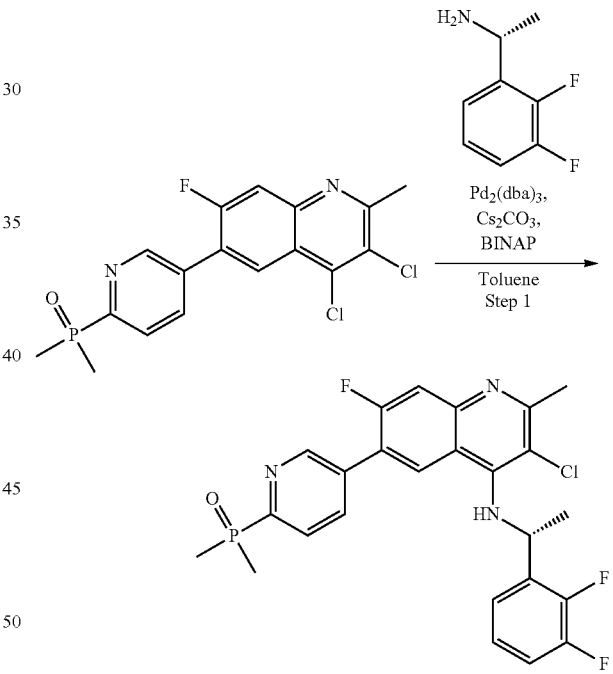

To a stirred solution of 3,4-dichloro-6-[6-(dimethylphosphoryl)pyridin-3-yl]-7-fluoro-2-methylquinoline (80 mg, 0.209 mmol) and (1R)-1-(2,3-difluorophenyl)ethanamine hydrochloride (49 mg, 0.251 mmol) in Toluene (1 mL) were added Pd$_2$(dba)$_3$ (19 mg, 0.021 mmol) and Cs$_2$CO$_3$ (170 mg, 0.522 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: column, C18 silica gel; mobile phase, CH$_3$CN in water (10 mmol/L NH$_4$HCO$_3$), 40% to 60% gradient in 30 min; detector, 254 nm. This resulted in 3-chloro-N-[(1R)-1-(2,3-difluorophenyl)ethyl]-6-[6-(dimethylphosphoryl)pyridin-3-yl]-7-fluoro-2-methylquinolin-4-amine (37 mg, 35%) as a white solid. MS ESI calculated for $C_{25}H_{22}ClF_3N_3OP$ [M+H]$^+$, 504.11, found 504.10. $^1$H NMR (400 MHz, Chloroform-d) δ 8.75 (s, 1H), 8.18-8.15 (m, 1H), 7.88-7.83 (m, 2H), 7.71 (d, J=12.0 Hz, 1H), 7.26-7.22 (m, 1H), 7.15-7.06 (m, 2H), 5.32-5.20 (m, 2H), 2.78 (s, 3H), 1.85 (d, J=2.5 Hz, 3H), 1.82 (d, J=2.5 Hz, 3H), 1.70 (d, J=6.4 Hz, 3H). $^{19}$F NMR (377 MHz, Chloroform-d) δ −115.05, −137.11, −137.16, −144.18, −144.23. $^{31}$P NMR (162 MHz, Chloroform-d) δ 36.59.

Example 68: (S)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide Synthetic Scheme

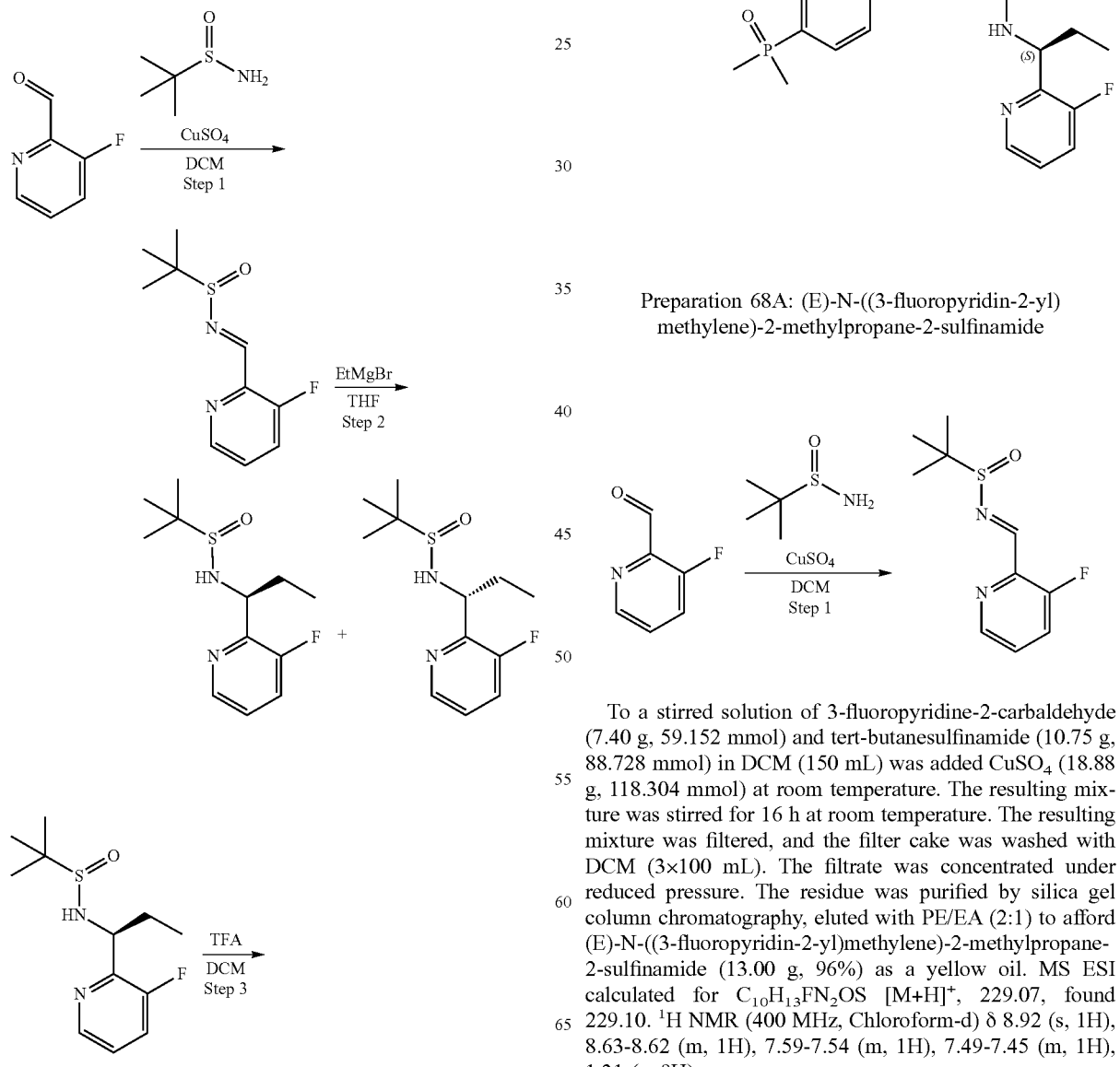

Preparation 68A: (E)-N-((3-fluoropyridin-2-yl)methylene)-2-methylpropane-2-sulfinamide

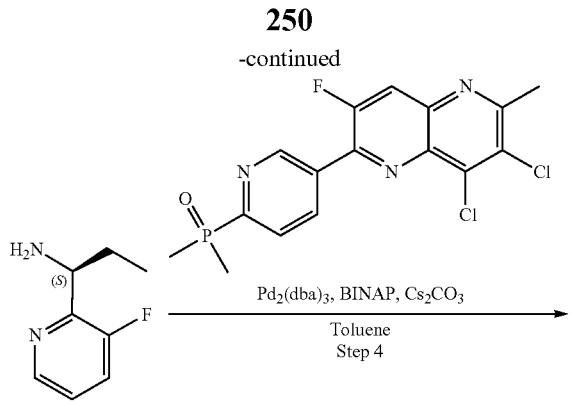

To a stirred solution of 3-fluoropyridine-2-carbaldehyde (7.40 g, 59.152 mmol) and tert-butanesulfinamide (10.75 g, 88.728 mmol) in DCM (150 mL) was added CuSO$_4$ (18.88 g, 118.304 mmol) at room temperature. The resulting mixture was stirred for 16 h at room temperature. The resulting mixture was filtered, and the filter cake was washed with DCM (3×100 mL). The filtrate was concentrated under reduced pressure. The residue was purified by silica gel column chromatography, eluted with PE/EA (2:1) to afford (E)-N-((3-fluoropyridin-2-yl)methylene)-2-methylpropane-2-sulfinamide (13.00 g, 96%) as a yellow oil. MS ESI calculated for $C_{10}H_{13}FN_2OS$ [M+H]$^+$, 229.07, found 229.10. $^1$H NMR (400 MHz, Chloroform-d) δ 8.92 (s, 1H), 8.63-8.62 (m, 1H), 7.59-7.54 (m, 1H), 7.49-7.45 (m, 1H), 1.31 (s, 9H).

Preparation 68B: N—((S or R)-1-(3-fluoropyridin-2-yl)propyl)-2-methylpropane-2-sulfinamide, N—((R or S)-1-(3-fluoropyridin-2-yl)propyl)-2-methylpropane-2-sulfinamide

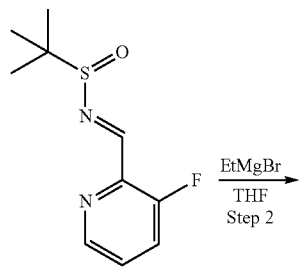

To a stirred solution of (E)-N-((3-fluoropyridin-2-yl)methylene)-2-methylpropane-2-sulfinamide (13.00 g, 56.945 mmol) in THF (100 mL) was added 3.4 N ethylmagnesium bromide in THF (34 mL, 115.600 mmol) dropwise at −78° C. under nitrogen atmosphere. The resulting mixture was stirred for 16 h at room temperature under nitrogen atmosphere. The reaction was quenched with water/ice at 0° C. The resulting mixture was extracted with EtOAc (3×500 mL). The combined organic layers were washed with brine (3×100 mL), dried over anhydrous $Na_2SO_4$. After filtration, the filtrate was concentrated under reduced pressure. The residue was purified by silica gel column chromatography, eluted with PE/EA (1/1) to afford two isomers. The first peak afforded (1.80 g, 12%) as the yellow oil. MS ESI calculated for $C_{12}H_{19}FN_2OS$ [M+H]$^+$, 259.12, found 259.20. The second peak afforded (880 mg, 6%) as the yellow oil. MS ESI calculated for $C_{12}H_{19}FN_2OS$ [M+H]$^+$, 259.12, found 259.20.

Preparation 68C: (S)-1-(3-fluoropyridin-2-yl)propan-1-amine

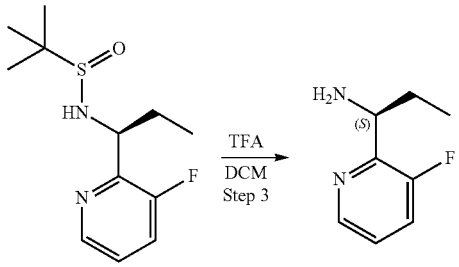

To a stirred solution of N—((S)-1-(3-fluoropyridin-2-yl)propyl)-2-methylpropane-2-sulfinamide (880 mg, 3.406 mmol) in DCM (9 mL) was added TFA (3 mL) dropwise at 0° C. The resulting mixture was stirred for 2 h at room temperature. The resulting mixture was concentrated under reduced pressure. The residue was purified by reversed-phase flash chromatography with the following conditions: column, C18 silica gel; mobile phase, $CH_3CN$ in water (10 mmol/L $NH_4HCO_3$), 35% to 50% gradient in 30 min; detector, 254 nm to afford (S)-1-(3-fluoropyridin-2-yl)propan-1-amine (170 mg, 32%) as a colorless oil. MS ESI calculated for $C_8H_{11}FN_2$ [M+H]$^+$, 155.09, found 155.30.

Example 68: (S)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide

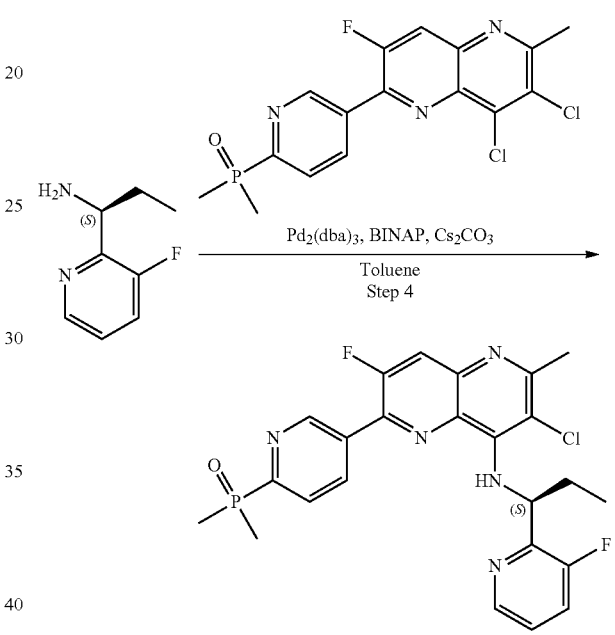

To a stirred mixture of 3,4-dichloro-6-[6-(dimethylphosphoryl)pyridin-3-yl]-7-fluoro-2-methyl-1,5-naphthyridine (100 mg, 0.260 mmol) and (S)-1-(3-fluoropyridin-2-yl)propan-1-amine (48 mg, 0.312 mmol) in Toluene (2 mL) were added $Pd_2(dba)_3$ (24 mg, 0.026 mmol), BINAP (33 mg, 0.052 mmol) and $Cs_2CO_3$ (128 mg, 0.390 mmol) at room temperature under nitrogen atmosphere. The resulting mixture was stirred for 3 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: CH3CN; Flow rate: 60 mL/min; Gradient: 30 B to 60 B in 30 min; 254/220 nm to afford (S)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide (78 mg, 60%) as a white solid. MS ESI calculated for $C_{24}H_{23}ClF_2N_5OP$ [M+H]$^+$, 502.13, found 501.95. $^1$H NMR (400 MHz, DMSO-$d_6$) δ 9.37 (s, 1H), 8.58-8.53 (m, 2H), 8.23-8.18 (m, 2H), 7.81-7.75 (m, 1H), 7.71-7.67 (m, 1H), 7.51-7.47 (m, 1H), 6.62-6.57 (m, 1H), 2.65 (s, 3H), 2.05-1.90 (m, 2H), 1.78 (s, 3H), 1.75 (s, 3H), 0.72 (t, J=7.3 Hz, 3H). $^{19}$F NMR (377 MHz, DMSO-d$_6$) δ −120.74, −126.98. $^{31}$P NMR (162 MHz, DMSO) δ 34.30.

Example 69: (R)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide Synthetic Scheme

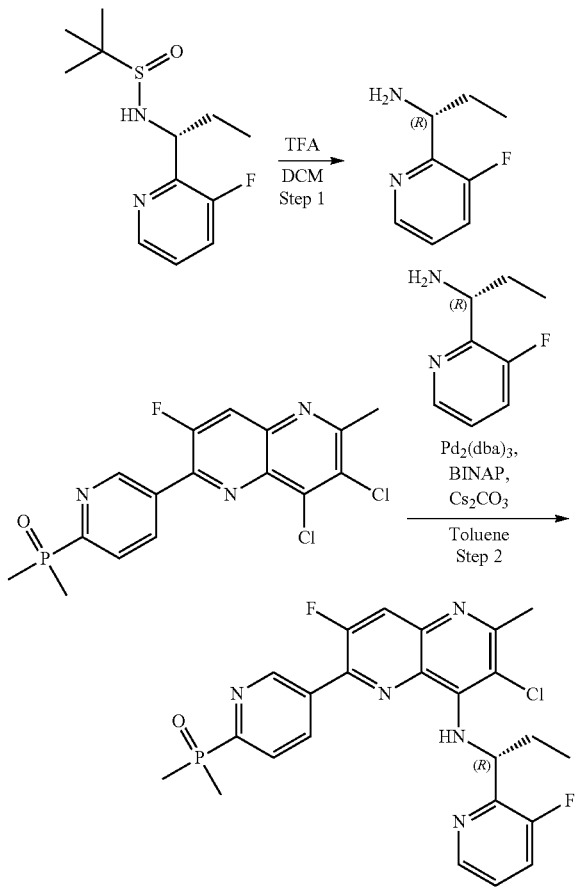

Preparation 69A: (R)-1-(3-fluoropyridin-2-yl)propan-1-amine

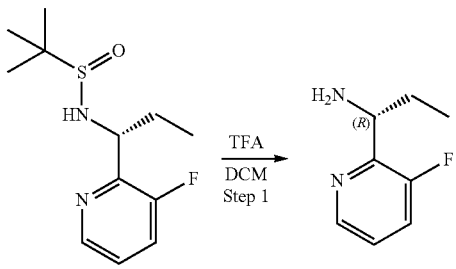

To a stirred solution of N-[(1R)-1-(3-fluoropyridin-2-yl)propyl]-2-methylpropane-2-sulfinamide (880 mg, 3.406 mmol) in DCM (9 mL) was added TFA (3 mL) dropwise at 0° C. The resulting mixture was stirred for 2 h at room temperature. The resulting mixture was concentrated under reduced pressure. The residue was purified by reversed-phase flash chromatography with the following conditions: column, C18 silica gel; mobile phase, CH$_3$CN in water (10 mmol/L NH$_4$HCO$_3$), 35% to 50% gradient in 30 min; detector, 254 nm to afford (R)-1-(3-fluoropyridin-2-yl)propan-1-amine (170 mg, 32%) as a colorless oil. MS ESI calculated for C$_8$H$_{11}$FN$_2$ [M+H]$^+$, 155.09, found 155.20.

Example 69: (R)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide

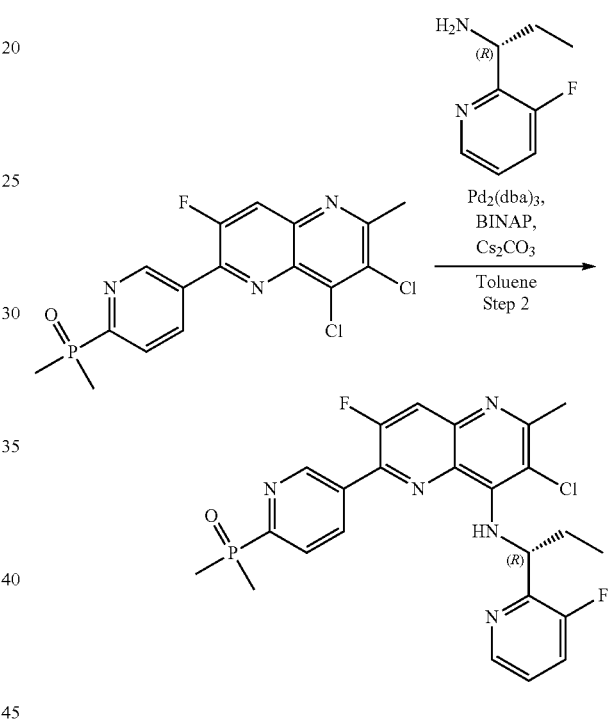

To a stirred mixture of 3,4-dichloro-6-[6-(dimethylphosphoryl)pyridin-3-yl]-7-fluoro-2-methyl-1,5-naphthyridine (100 mg, 0.260 mmol) and (R)-1-(3-fluoropyridin-2-yl)propan-1-amine (48 mg, 0.312 mmol) in Toluene (2 mL) were added Pd$_2$(dba)$_3$ (24 mg, 0.026 mmol), BINAP (33 mg, 0.052 mmol) and Cs$_2$CO$_3$ (128 mg, 0.390 mmol) at room temperature under nitrogen atmosphere. The resulting mixture was stirred for 3 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH3CN; Flow rate: 60 mL/min; Gradient: 30 B to 60 B in 30 min; 254/220 nm to afford (R)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide (42 mg, 32%) as a white solid. MS ESI calculated for C$_{24}$H$_{23}$ClF$_2$N$_5$OP [M+H]$^+$, 502.13, found 501.95. $^1$H NMR (400 MHz, DMSO-d$_6$) δ 9.38 (s, 1H), 8.58-8.53 (m, 2H), 8.24-8.18 (m, 2H), 7.81-

7.75 (m, 1H), 7.72-7.68 (m, 1H), 7.51-7.47 (m, 1H), 6.62-6.57 (m, 1H), 2.66 (s, 3H), 2.05-1.91 (m, 2H), 1.78 (s, 3H), 1.75 (s, 3H), 0.72 (t, J=7.4 Hz, 3H). $^{19}$F NMR (377 MHz, DMSO-$d_6$) δ -120.75, -126.98. $^{31}$P NMR (162 MHz, DMSO-$d_6$) δ 34.31.

Example 70: 3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine

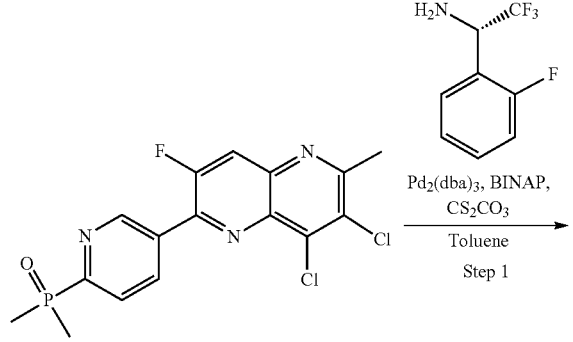

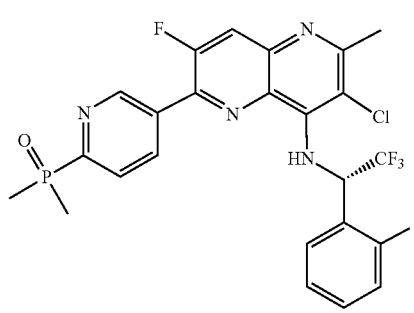

To a stirred mixture of 3,4-dichloro-6-[6-(dimethylphosphoryl)pyridin-3-yl]-7-fluoro-2-methyl-1,5-naphthyridine (100 mg, 0.260 mmol) and (1S)-2,2,2-trifluoro-1-(2-fluorophenyl)ethanamine (60 mg, 0.312 mmol) in Toluene (2 mL) were added Pd$_2$(dba)$_3$ (24 mg, 0.026 mmol), BINAP (33 mg, 0.052 mmol) and Cs$_2$CO$_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 30 B to 60 B in 30 min; 254/220 nm to afford 3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine (67 mg, 47%) as a white solid. MS ESI calculated for C$_{24}$H$_{19}$ClF$_5$N$_4$OP [M+H]$^+$, 541.09, found 540.90. $^1$H NMR (400 MHz, DMSO-$d_6$) δ 9.24 (s, 1H), 8.46 (d, J=8.0 Hz, 1H), 8.39-8.32 (m, 1H), 8.19-8.13 (m, 1H), 7.96-7.89 (m, 1H), 7.55-7.48 (m, 1H), 7.35-7.29 (m, 1H), 7.29-7.19 (m, 2H), 7.12 (d, J=10.6 Hz, 1H), 2.71 (s, 3H), 1.78 (s, 3H), 1.75 (s, 3H). $^{19}$F NMR (376 MHz, DMSO-$d_6$) δ -73.64, -116.85, -119.83. $^{31}$P NMR (162 MHz, DMSO-$d_6$) δ 34.33.

Example 71: 3-chloro-6-[2-(dimethylphosphoryl)pyrimidin-5-yl]-7-fluoro-2-methyl-N-[(1S)-2,2,2-trifluoro-1-(2-fluorophenyl)ethyl]-1,5-naphthyridin-4-amine

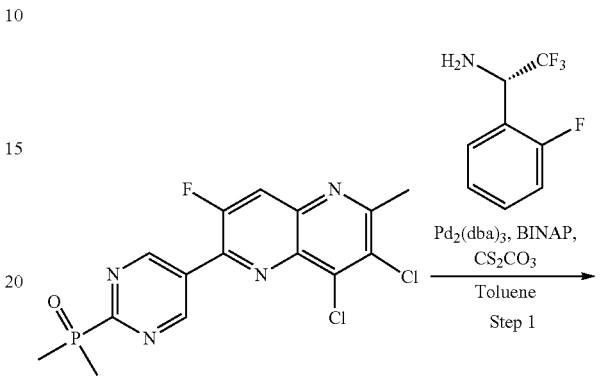

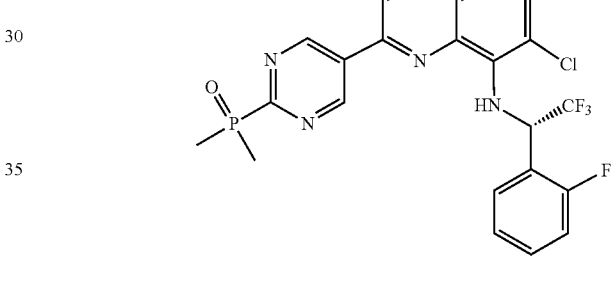

To a stirred mixture of 3,4-dichloro-6-[2-(dimethylphosphoryl)pyrimidin-5-yl]-7-fluoro-2-methyl-1,5-naphthyridine (100 mg, 0.260 mmol) and (1S)-2,2,2-trifluoro-1-(2-fluorophenyl)ethanamine (60 mg, 0.312 mmol) in Toluene (2 mL) were added Pd$_2$(dba)$_3$ (24 mg, 0.026 mmol), BINAP (32, 0.052 mmol) and Cs$_2$CO$_3$ (127 mg, 0.390 mmol) at room temperature under nitrogen atmosphere. The resulting mixture was stirred for 2 h at 100° C. under nitrogen atmosphere. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 30 B to 60 B in 30 min; 254/220 nm to afford 3-chloro-6-[2-(dimethylphosphoryl)pyrimidin-5-yl]-7-fluoro-2-methyl-N-[(1S)-2,2,2-trifluoro-1-(2-fluorophenyl)ethyl]-1,5-naphthyridin-4-amine (16 mg, 11%) as a white solid. MS ESI calculated for C$_{23}$H$_{18}$ClF$_5$N$_5$OP [M+H]$^+$, 542.09, found 541.90. $^1$H NMR (400 MHz, DMSO-$d_6$) δ 9.45 (d, J=1.6 Hz, 2H), 8.43-8.39 (m, 1H), 7.98-7.93 (m, 1H), 7.56-7.46 (m, 1H), 7.35-7.29 (m, 1H), 7.27-7.22 (m, 1H), 7.19-7.14 (m, 2H), 2.72 (s, 3H), 1.89 (s, 3H), 1.86 (s, 3H). $^{19}$F NMR (376 MHz, DMSO-$d_6$) δ -73.60, -117.18, -120.08. $^{31}$P NMR (162 MHz, DMSO-$d_6$) δ 34.73.

Example 72: 3-chloro-6-[6-(dimethylphosphoryl)pyridin-3-yl]-5,7-difluoro-N-[(1R)-1-(2-fluorophenyl)ethyl]-2-methylquinolin-4-amine Synthetic Scheme

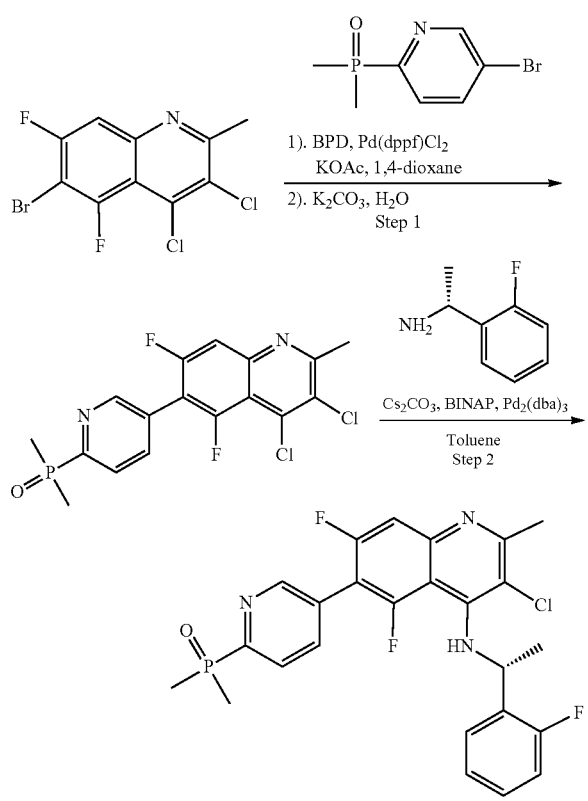

Preparation 72A: 3,4-dichloro-6-[6-(dimethylphosphoryl)pyridin-3-yl]-5,7-difluoro-2-methylquinoline

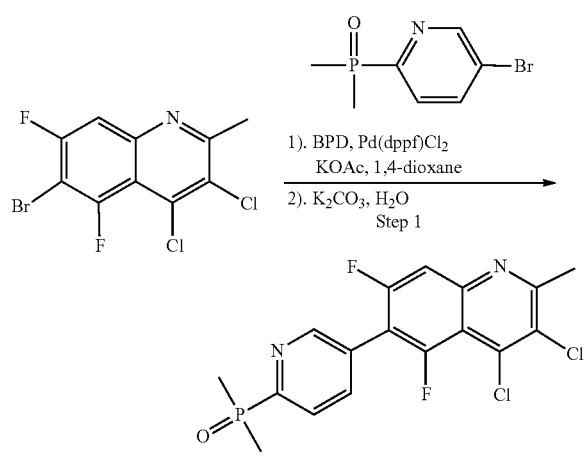

To a solution of 5-bromo-2-(dimethyl phosphoryl) pyridine (859 mg, 3.671 mmol) and BPD (1.17 g, 4.588 mmol) in 1,4-dioxane (15 mL) were added KOAc (750 mg, 7.648 mmol) and Pd(dppf)Cl₂·CH₂Cl₂ (299 mg, 0.367 mmol). After stirring for 2 h at 100° C. under a nitrogen atmosphere, the resulting mixture was concentrated under reduced pressure. To the above mixture was added 6-bromo-3,4-dichloro-5,7-difluoro-2-methylquinoline (1.00 g, 3.059 mmol), K₂CO₃ (1.06 g, 7.648 mmol) and H₂O (3 mL) at room temperature. The resulting mixture was stirred for additional 3 h at 100° C. The resulting mixture was concentrated under vacuum. The residue was purified by silica gel column chromatography, eluted with CH₂Cl₂/MeOH (12/1) to afford 3,4-dichloro-6-[6-(dimethylphosphoryl)pyridin-3-yl]-5,7-difluoro-2-methylquinoline (800 mg, 65%) as a yellow solid. MS ESI calculated for $C_{17}H_{13}Cl_2F_2N_2OP$ [M+H]⁺, 401.01, found 401.05. ¹H NMR (400 MHz, Chloroform-d) δ 8.89 (s, 1H), 8.32-8.24 (m, 1H), 8.09-7.99 (m, 1H), 7.70-7.64 (m, 1H), 2.87 (s, 3H), 1.87 (s, 3H), 1.84 (s, 3H).

Example 72: 3-chloro-6-[6-(dimethylphosphoryl)pyridin-3-yl]-5,7-difluoro-N-[(1R)-1-(2-fluorophenyl)ethyl]-2-methylquinolin-4-amine

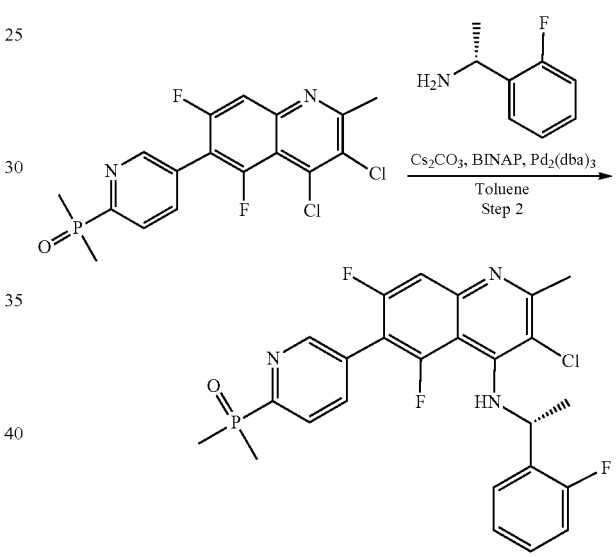

To a solution of 3,4-dichloro-6-[6-(dimethylphosphoryl)pyridin-3-yl]-5,7-difluoro-2-methylquinoline (100 mg, 0.249 mmol), BINAP (31 mg, 0.050 mmol) and (1R)-1-(2-fluorophenyl) ethanamine (42 mg, 0.299 mmol) in Toluene (2 mL) were added Cs₂CO₃ (122 mg, 0.373 mmol) and Pd₂(dba)₃ (23 mg, 0.025 mmol). After stirring for 3 h at 100° C. under a nitrogen atmosphere. The resulting mixture was concentrated under reduced pressure. The residue was purified by reversed-phase flash chromatography with the following conditions: column, C18 silica gel; mobile phase, CH₃CN in water (10 mmol/L NH₄HCO₃), 30% to 70% gradient in 30 min; detector, 254 nm. This resulted in 3-chloro-6-[6-(dimethylphosphoryl)pyridin-3-yl]-5,7-difluoro-N-[(1R)-1-(2-fluorophenyl)ethyl]-2-methylquinolin-4-amine (33 mg, 26%) as a yellow solid. MS ESI calculated for $C_{25}H_{22}ClF_3N_3OP$ [M+H]⁺, 504.11, found 503.90. ¹H NMR (400 MHz, Chloroform-d) δ 8.87 (s, 1H), 8.30-8.23 (m, 1H), 8.05-7.97 (m, 1H), 7.64-7.43 (m, 1H), 7.29-7.23 (m, 1H), 7.23-7.17 (m, 1H), 7.09-7.03 (m, 1H), 7.02-6.95 (m, 1H), 6.13-5.86 (m, 1H), 5.58-5.43 (m, 1H), 2.69 (s, 3H), 1.87 (s, 3H), 1.83 (s, 3H), 1.64 (d, J=6.7 Hz, 3H). ¹⁹F NMR (377 MHz, Chloroform-d) δ −113.38, −113.81, −119.00, −119.01. $^{31}$P NMR (162 MHz, Chloroform-d) δ 36.57.

Example 73: (S)-(5-(3-chloro-5,7-difluoro-4-((1-(3-fluoropyridin-2-yl)propyl)amino)-2-methylquinolin-6-yl)pyridin-2-yl)dimethylphosphine oxide

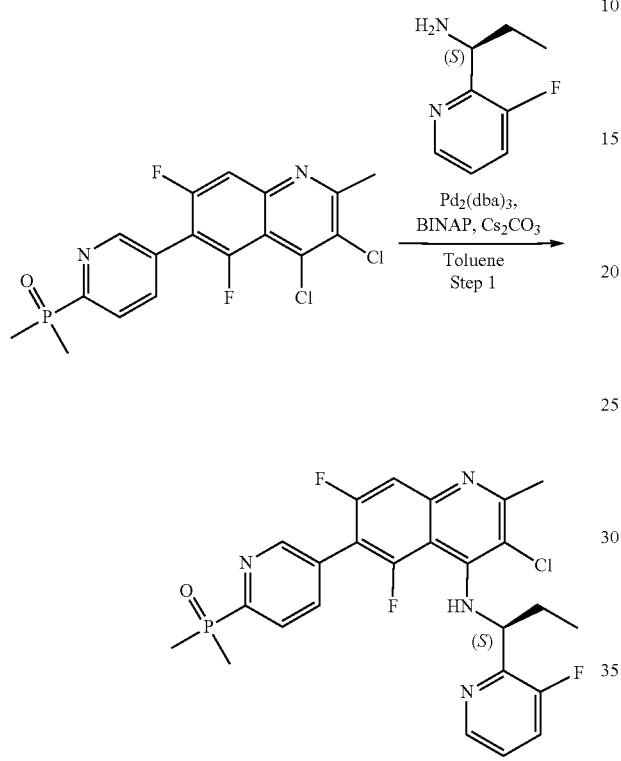

Example 74: (R)-(5-(3-chloro-5,7-difluoro-4-((1-(3-fluoropyridin-2-yl)propyl)amino)-2-methylquinolin-6-yl)pyridin-2-yl)dimethylphosphine oxide

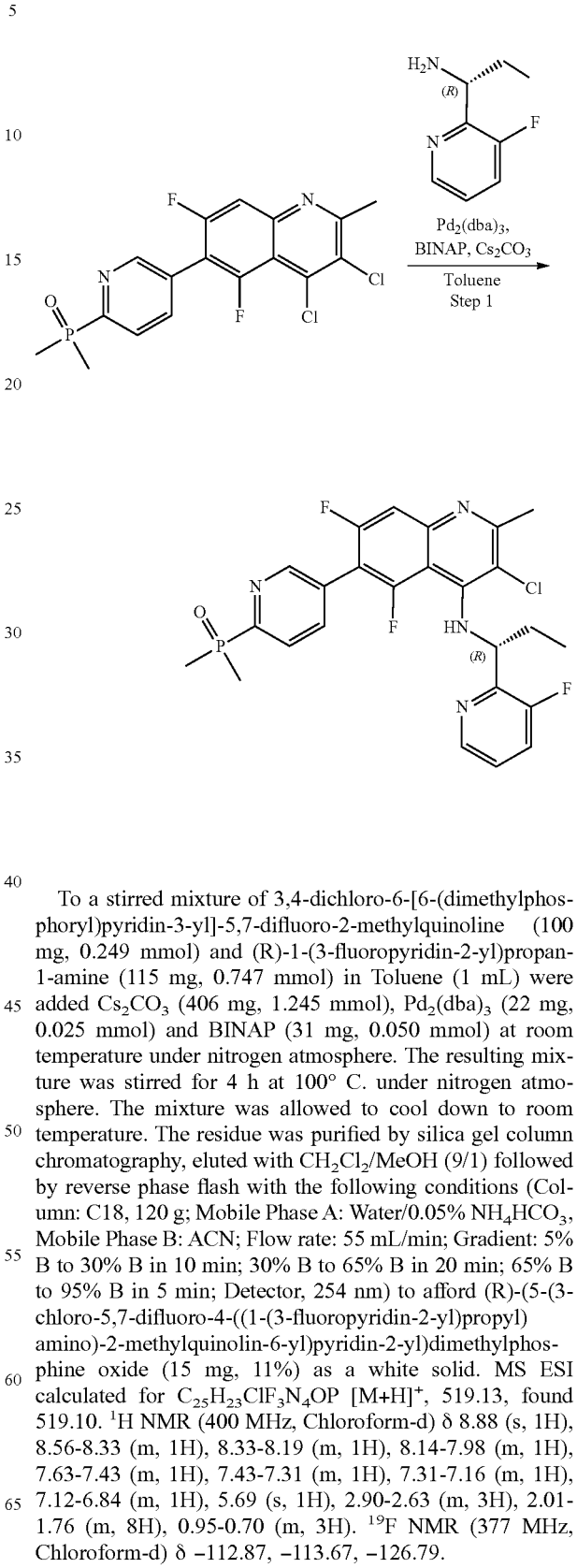

To a stirred mixture of 3,4-dichloro-6-[6-(dimethylphosphoryl)pyridin-3-yl]-5,7-difluoro-2-methylquinoline (100 mg, 0.249 mmol) and (S)-1-(3-fluoropyridin-2-yl)propan-1-amine (46 mg, 0.299 mmol) in Toluene (1 mL) were added Pd$_2$(dba)$_3$ (22 mg, 0.025 mmol), BINAP (31 mg, 0.050 mmol) and Cs$_2$CO$_3$ (121 mg, 0.373 mmol) at room temperature under nitrogen atmosphere. The resulting mixture was stirred for 4 h at 100° C. under nitrogen atmosphere. The mixture was allowed to cool down to room temperature. The residue was purified by silica gel column chromatography, eluted with CH$_2$Cl$_2$/MeOH (9/1) followed by reverse phase flash with the following conditions (Column: C18, 120 g; Mobile Phase A: Water/0.05% NH$_4$HCO$_3$, Mobile Phase B: ACN; Flow rate: 60 mL/min; Gradient: 5% B to 30% B in 5 min; 30% B to 65% B in 20 min; 65% B to 95% B in 5 min; Detector, 254 nm) to afford (S)-(5-(3-chloro-5,7-difluoro-4-((1-(3-fluoropyridin-2-yl)propyl)amino)-2-methylquinolin-6-yl)pyridin-2-yl)dimethylphosphine oxide (14 mg, 10%) as a white solid. MS ESI calculated for C$_{25}$H$_{23}$ClF$_3$N$_4$OP [M+H]$^+$, 519.13, found 519.10. $^1$H NMR (300 MHz, Chloroform-d) δ 8.88 (s, 1H), 8.46-8.38 (m, 1H), 8.32-8.23 (m, 1H), 8.08-7.99 (m, 1H), 7.60 (s, 1H) 7.44-7.32 (m, 1H), 7.25-7.20 (m, 1H), 5.74 (s, 1H), 2.75 (s, 3H), 2.08-1.91 (m, 2H), 1.88 (s, 3H), 1.83 (s, 3H), 0.80 (t, J=7.2 Hz, 3H). $^{19}$F NMR (282 MHz, Chloroform-d) δ −112.73, −113.51, −126.72.

To a stirred mixture of 3,4-dichloro-6-[6-(dimethylphosphoryl)pyridin-3-yl]-5,7-difluoro-2-methylquinoline (100 mg, 0.249 mmol) and (R)-1-(3-fluoropyridin-2-yl)propan-1-amine (115 mg, 0.747 mmol) in Toluene (1 mL) were added Cs$_2$CO$_3$ (406 mg, 1.245 mmol), Pd$_2$(dba)$_3$ (22 mg, 0.025 mmol) and BINAP (31 mg, 0.050 mmol) at room temperature under nitrogen atmosphere. The resulting mixture was stirred for 4 h at 100° C. under nitrogen atmosphere. The mixture was allowed to cool down to room temperature. The residue was purified by silica gel column chromatography, eluted with CH$_2$Cl$_2$/MeOH (9/1) followed by reverse phase flash with the following conditions (Column: C18, 120 g; Mobile Phase A: Water/0.05% NH$_4$HCO$_3$, Mobile Phase B: ACN; Flow rate: 55 mL/min; Gradient: 5% B to 30% B in 10 min; 30% B to 65% B in 20 min; 65% B to 95% B in 5 min; Detector, 254 nm) to afford (R)-(5-(3-chloro-5,7-difluoro-4-((1-(3-fluoropyridin-2-yl)propyl)amino)-2-methylquinolin-6-yl)pyridin-2-yl)dimethylphosphine oxide (15 mg, 11%) as a white solid. MS ESI calculated for C$_{25}$H$_{23}$ClF$_3$N$_4$OP [M+H]$^+$, 519.13, found 519.10. $^1$H NMR (400 MHz, Chloroform-d) δ 8.88 (s, 1H), 8.56-8.33 (m, 1H), 8.33-8.19 (m, 1H), 8.14-7.98 (m, 1H), 7.63-7.43 (m, 1H), 7.43-7.31 (m, 1H), 7.31-7.16 (m, 1H), 7.12-6.84 (m, 1H), 5.69 (s, 1H), 2.90-2.63 (m, 3H), 2.01-1.76 (m, 8H), 0.95-0.70 (m, 3H). $^{19}$F NMR (377 MHz, Chloroform-d) δ −112.87, −113.67, −126.79.

Example 75: 3-chloro-6-[6-(dimethylphosphoryl)pyridin-3-yl]-7-fluoro-2-methyl-N-[(1R)-1-(pyridin-3-yl)ethyl]-1,5-naphthyridin-4-amine

Example 76: 3-chloro-6-[6-(dimethylphosphoryl)pyridin-3-yl]-7-fluoro-2-methyl-N-[(1S)-1-(pyridin-2-yl)propyl]-1,5-naphthyridin-4-amine

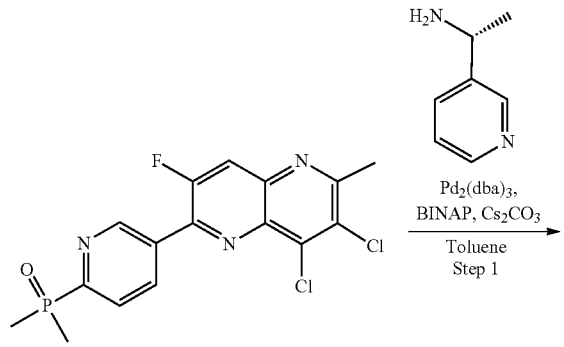

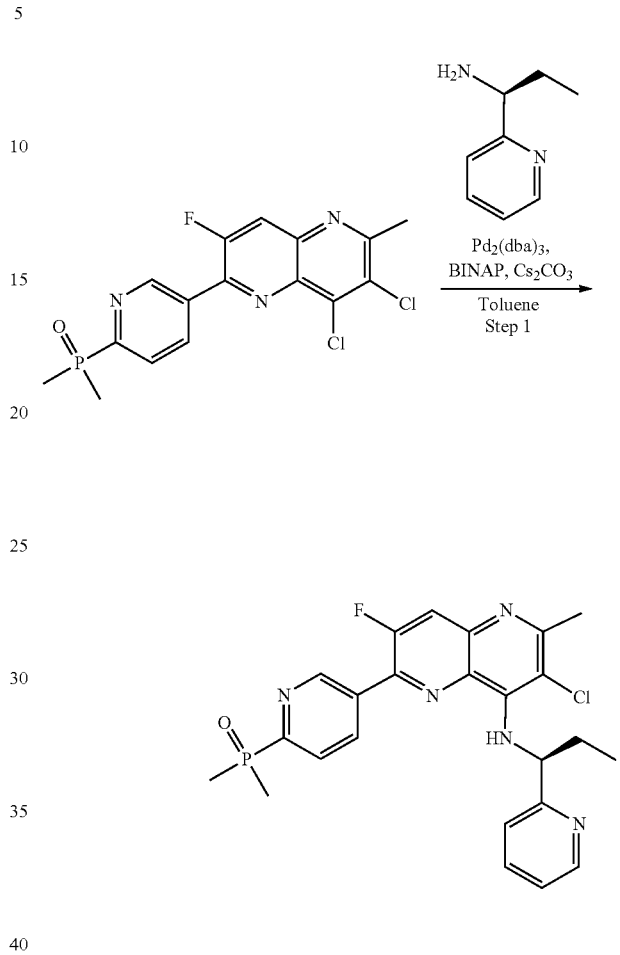

A solution of 3,4-dichloro-6-[6-(dimethylphosphoryl)pyridin-3-yl]-7-fluoro-2-methyl-1,5-naphthyridine (102 mg, 0.265 mmol), (1R)-1-(pyridin-3-yl)ethanamine (27 mg, 0.221 mmol), Pd$_2$(dba)$_3$ (20 mg, 0.022 mmol), BINAP (27 mg, 0.044 mmol) and Cs$_2$CO$_3$ (108 mg, 0.332 mmol) in Toluene (2 mL) was stirred for overnight at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-chloro-6-[6-(dimethylphosphoryl)pyridin-3-yl]-7-fluoro-2-methyl-N-[(1R)-1-(pyridin-3-yl)ethyl]-1,5-naphthyridin-4-amine (59 mg, 57%) as a yellow solid. MS ESI calculated for C$_{23}$H$_{22}$ClFN$_5$OP [M+H]$^+$, 470.12, found 470.20. $^1$H NMR (400 MHz, DMSO-d$_6$) δ 9.27 (s, 1H), 8.55 (d, J=2.4 Hz, 1H), 8.40-8.37 (m, 2H), 8.22-8.18 (m, 1H), 8.14-8.10 (m, 1H), 7.77-7.74 (m, 1H), 7.28-7.24 (m, 1H), 6.93 (d, J=8.8 Hz, 1H), 6.28-6.17 (m, 1H), 2.63 (s, 3H), 1.76 (s, 3H), 1.73 (s, 3H), 1.70 (d, J=6.8 Hz, 3H). $^{19}$F NMR (377 MHz, DMSO-d6) δ −120.95. $^{31}$P NMR (162 MHz, DMSO-d$_6$) δ 34.24.

A mixture of 3,4-dichloro-6-[6-(dimethylphosphoryl)pyridin-3-yl]-7-fluoro-2-methyl-1,5-naphthyridine (102 mg, 0.264 mmol), (1S)-1-(pyridin-2-yl)propan-1-amine (30 mg, 0.220 mmol), Pd$_2$(dba)$_3$ (21 mg, 0.022 mmol,), BINAP (28 mg, 0.044 mmol) and Cs$_2$CO$_3$ (108 mg, 0.330 mmol) in Toluene (2 mL) was stirred for overnight at 100° C. under nitrogen atmosphere. The resulting mixture was concentrated under reduced pressure. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-chloro-6-[6-(dimethylphosphoryl)pyridin-3-yl]-7-fluoro-2-methyl-N-[(1S)-1-(pyridin-2-yl)propyl]-1,5-naphthyridin-4-amine (57 mg, 53%) as a yellow solid MS ESI calculated for C$_{24}$H$_{24}$ClFN$_5$OP [M+H]$^+$, 484.14, found 484.25. $^1$H NMR (400 MHz, DMSO-d$_6$) δ 9.34 (s, 1H), 8.65-8.63 (m, 1H), 8.56-8.48 (m, 1H), 8.24-8.13 (m, 2H), 7.82-7.79 (m, 2H), 7.46 (d, J=8.0 Hz, 1H), 7.36-7.32 (m, 1H), 6.04 (s, 1H), 2.64 (s, 3H), 2.09-1.90 (m, 2H), 1.78 (s, 3H), 1.75 (s, 3H), 0.74 (t, J=7.2 Hz, 3H). $^{19}$F NMR (377 MHz, DMSO-d$_6$) δ −120.87. $^{31}$P NMR (162 MHz, DMSO-d$_6$) δ 34.26.

Example 77: 6-[6-(dimethylphosphoryl)pyridin-3-yl]-3,7-difluoro-N-[(1R)-1-(2-fluorophenyl)propyl]-2-methyl-1,5-naphthyridin-4-amine Synthetic Scheme

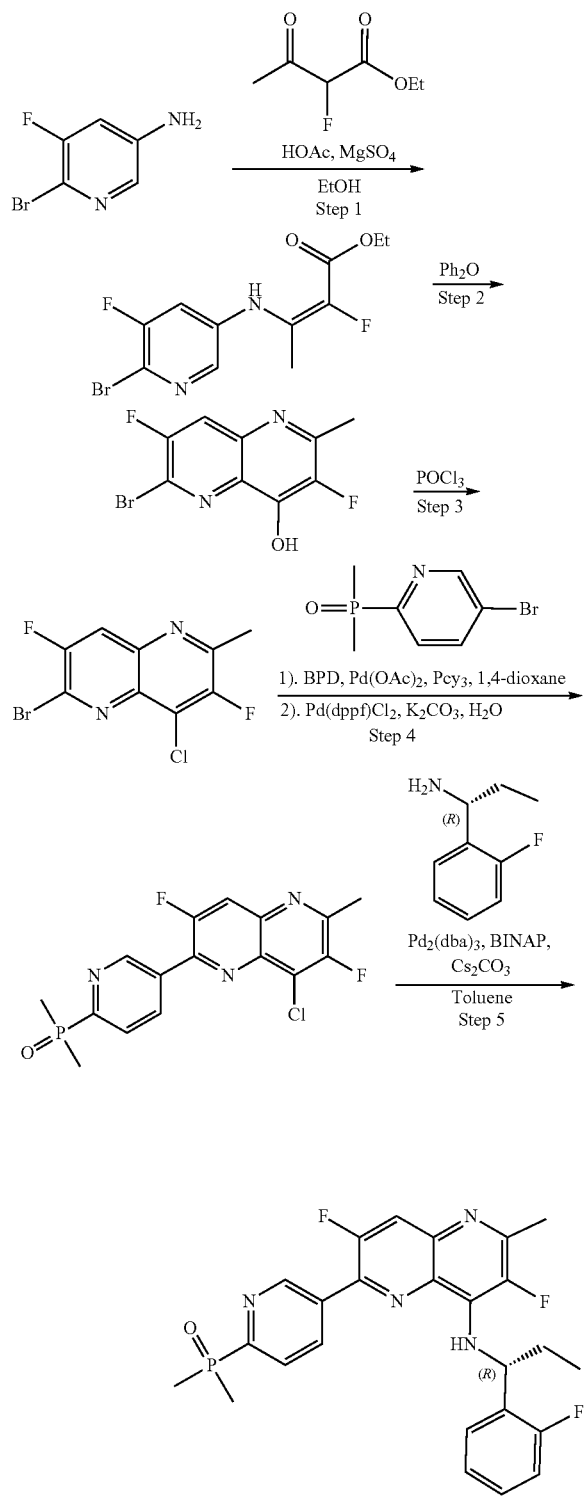

Preparation 77A: ethyl (2E)-3-[(6-bromo-5-fluoropyridin-3-yl)amino]-2-fluorobut-2-enoate

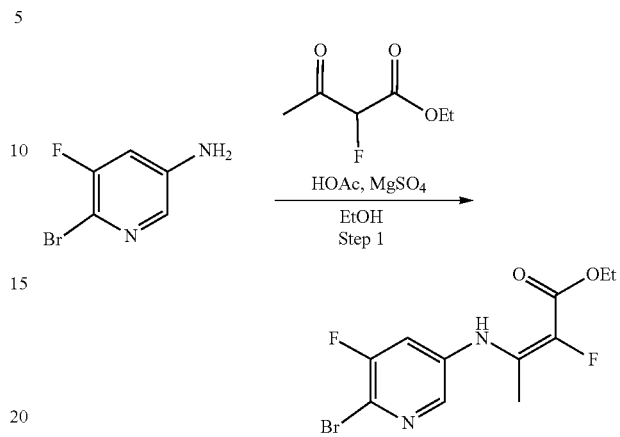

A mixture of 6-bromo-5-fluoropyridin-3-amine (80.00 g, 418.842 mmol), HOAc (2.52 g, 41.884 mmol) and MgSO$_4$ (151.24 g, 1256.526 mmol) in EtOH (100 mL) was stirred for 36 h at 85° C. under nitrogen atmosphere. The resulting mixture were collected by filtration and washed with ethyl acetate (3×100 mL). The organic layer was concentrated under reduced pressure. The residue was purified by silica gel column chromatography, eluted with PE/EA (10/1) to afford ethyl (2E)-3-[(6-bromo-5-fluoropyridin-3-yl)amino]-2-fluorobut-2-enoate (6.00 g, 4%) as a yellow oil. MS ESI calculated for $C_{11}H_{11}BrF_2N_2O_2$ [M+H]$^+$, 321.00, 323.00, found 321.10, 323.10.

Preparation 77B: 6-bromo-3,7-difluoro-2-methyl-1,5-naphthyridin-4-ol

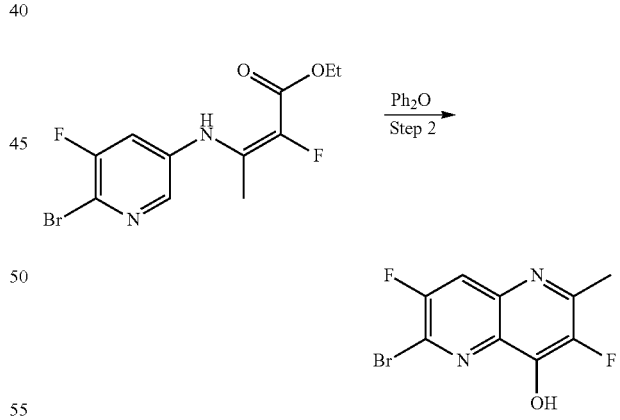

A solution of ethyl (2E)-3-[(6-bromo-5-fluoropyridin-3-yl)amino]-2-fluorobut-2-enoate (1.60 g, 4.983 mmol) in diphenyl-ether (20 mL) was stirred for 3 h at 230° C. The mixture was allowed to cool down to room temperature. The precipitated solids were collected by filtration and washed with ethyl ether (3×50 mL). The resulting solid was dried under vacuum. This resulted in 6-bromo-3,7-difluoro-2-methyl-1,5-naphthyridin-4-ol (320 mg, 23%) as a black solid. MS ESI calculated for $C_9H_5BrF_2N_2O$ [M−H]$^−$, 272.96, 274.96, found 272.92, 274.92.

Preparation 77C: 6-bromo-4-chloro-3,7-difluoro-2-methyl-1,5-naphthyridine

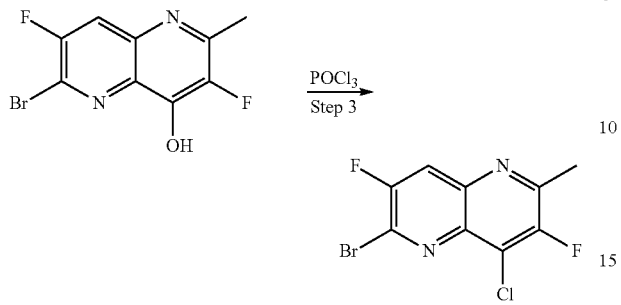

A mixture of 6-bromo-3,7-difluoro-2-methyl-1,5-naphthyridin-4-ol (420 mg, 1.527 mmol) in POCl₃ (2 mL) was stirred for 2 h at 100° C. The mixture was allowed to cool down to room temperature. The resulting mixture was concentrated under reduced pressure. The reaction was quenched with Water/Ice at 0° C. The mixture was neutralized to pH 7 with NaOH (2 M). The resulting mixture was extracted with EtOAc (3×50 mL). The combined organic layers were dried over anhydrous Na₂SO₄. After filtration, the filtrate was concentrated under reduced pressure. The residue was purified by silica gel column chromatography, eluted with PE/EA (10/1) to afford 6-bromo-4-chloro-3,7-difluoro-2-methyl-1,5-naphthyridine (20 mg, 4%) as a white solid. $^1$H NMR (300 MHz, Chloroform-d) δ 8.12-7.98 (m, 1H), 2.81-2.73 (m, 3H).

Preparation 77D: 4-chloro-6-[6-(dimethylphosphoryl)pyridin-3-yl]-3,7-difluoro-2-methyl-1,5-naphthyridine

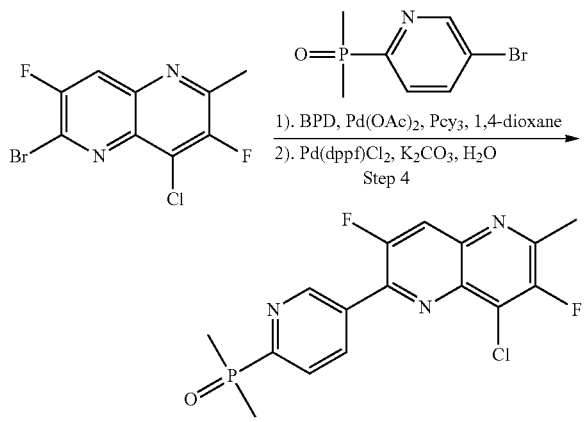

A mixture of 5-bromo-2-(dimethylphosphoryl)pyridine (19 mg, 0.082 mmol), BPD (26 mg, 0.102 mmol), Pd(OAc)₂ (2 mg, 0.007 mmol), PCy₃ (4 mg, 0.014 mmol) and KOAc (17 mg, 0.170 mmol) in 1,4-dioxane (0.5 mL) was stirred for 4 h at 80° C. under nitrogen atmosphere. The mixture was allowed to cool down to room temperature. To the above mixture were added 6-bromo-4-chloro-3,7-difluoro-2-methyl-1,5-naphthyridine (20 mg, 0.068 mmol), Pd(dppf)Cl₂·CH₂Cl₂ (5 mg, 0.007 mmol), K₂CO₃ (23 mg, 0.170 mmol) and water (0.1 mL) in portions at room temperature. The resulting mixture was stirred for additional 2 h at 80° C. The residue was purified by silica gel column chromatography, eluted with CH₂Cl₂/MeOH (10/1) to afford 4-chloro-6-[6-(dimethylphosphoryl)pyridin-3-yl]-3,7-difluoro-2-methyl-1,5-naphthyridine (25 mg, 99%) as a yellow solid. MS ESI calculated for C₁₆H₁₃ClF₂N₃OP [M+H]⁺, 368.05, found 367.95.

Example 77: 6-[6-(dimethylphosphoryl)pyridin-3-yl]-3,7-difluoro-N-[(1R)-1-(2-fluorophenyl)propyl]-2-methyl-1,5-naphthyridin-4-amine

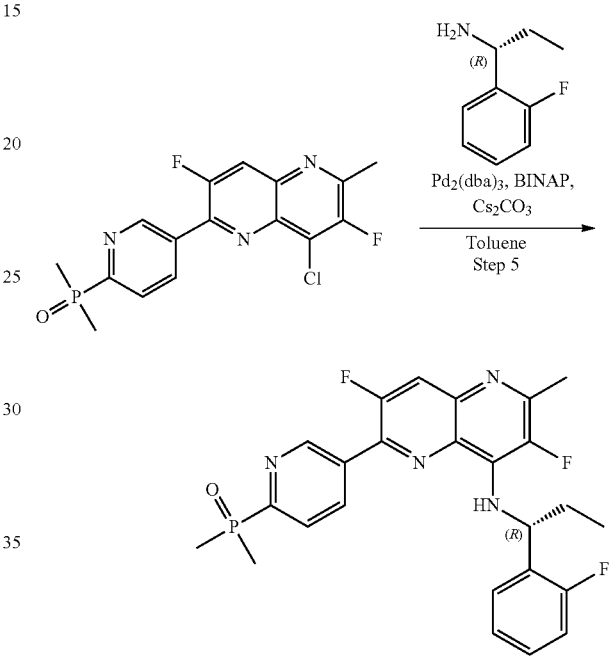

A mixture of 4-chloro-6-[6-(dimethylphosphoryl)pyridin-3-yl]-3,7-difluoro-2-methyl-1,5-naphthyridine (20 mg, 0.054 mmol), (1R)-1-(2-fluorophenyl)propan-1-amine (10 mg, 0.065 mmol), Pd₂(dba)₃ (5 mg, 0.005 mmol), Xantphos (6 mg, 0.011 mmol) and Cs₂CO₃ (26, 0.081 mmol) in Toluene (0.5 mL) was stirred for 4 h at 100° C. under nitrogen atmosphere. The resulting mixture was concentrated under reduced pressure. The residue was purified by silica gel column chromatography, eluted with CH₂Cl₂/MeOH (10/1) followed by reversed-phase flash chromatography with the following conditions: column, C18 silica gel; mobile phase, CH₃CN in water (10 mmol/L NH₄HCO₃), 40% to 60% gradient in 20 min; detector, 254 nm. This resulted in 6-[6-(dimethylphosphoryl)pyridin-3-yl]-3,7-difluoro-N-[(1R)-1-(2-fluorophenyl)propyl]-2-methyl-1,5-naphthyridin-4-amine (10 mg, 38%) as a white solid. MS ESI calculated for C₂₅H₂₄F₃N₄OP [M+H]⁺, 485.16, found 485.00. $^1$H NMR (400 MHz, Methanol-d₄) δ 9.44 (s, 1H), 8.69-8.62 (m, 1H), 8.25-8.18 (m, 1H), 8.00-7.92 (m, 1H), 7.42-7.35 (m, 1H), 7.30-7.20 (m, 1H), 7.14-7.03 (m, 2H), 5.44-5.36 (m, 1H), 2.54-2.48 (m, 3H), 2.18-2.04 (m, 1H), 2.04-1.96 (m, 7.0 Hz, 1H), 1.91 (s, 3H), 1.88 (s, 3H), 1.10-1.03 (m, 3H). $^{19}$F NMR (376 MHz, Methanol-d₄) δ -121.31, -123.40, -147.27. $^{31}$P NMR (162 MHz, Methanol-d₄) δ41.59.

Example 78: 3-chloro-N-[(1R)-1-(3-chloro-2-fluoro-phenyl)ethyl]-6-[6-(dimethylphosphoryl)pyridin-3-yl]-7-fluoro-2-methyl-1,5-naphthyridin-4-amine

Example 79: 3-chloro-6-[6-(dimethylphosphoryl)pyridin-3-yl]-7-fluoro-2-methyl-N-[(1R)-1-phenyl-propyl]-1,5-naphthyridin-4-amine

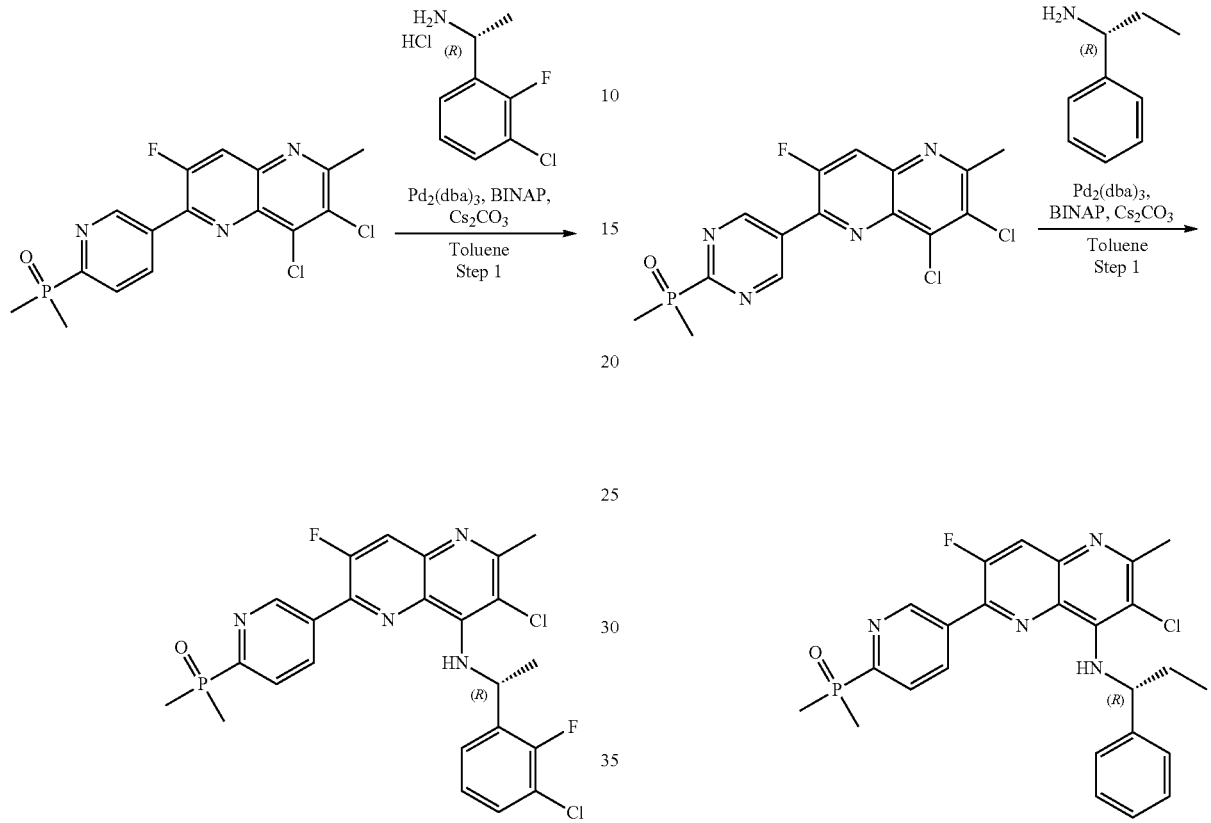

To a stirred mixture of 3,4-dichloro-6-[6-(dimethylphosphoryl)pyridin-3-yl]-7-fluoro-2-methyl-1,5-naphthyridine (100 mg, 0.260 mmol) and (1R)-1-(3-chloro-2-fluorophenyl)ethanamine (54 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 30 B to 70 B in 40 min; 254/220 nm to afford 3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine (58 mg, 42%) as a light yellow solid. MS ESI calculated for $C_{24}H_{21}Cl_2F_2N_4OP$ $[M+H]^+$, 521.08, found 520.90. $^1H$ NMR (400 MHz, DMSO-$d_6$) δ 9.14 (s, 1H), 8.31-8.24 (m, 1H), 8.19-8.14 (m, 1H), 8.12-8.08 (m, 1H), 7.38-7.33 (m, 2H), 7.12-7.07 (m, 1H), 6.90-6.81 (m, 1H), 6.43-6.35 (m, 1H), 2.68-2.61 (m, 3H), 1.76 (s, 3H), 1.72 (s, 3H), 1.66 (d, J=6.8 Hz, 3H). $^{19}F$ NMR (377 MHz, DMSO-$d_6$) δ −121.08, −121.76. $^{31}P$ NMR (162 MHz, DMSO-$d_6$) δ 34.19.

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-phenylpropan-1-amine (42 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 30 B to 70 B in 40 min; 254/220 nm to afford 3-chloro-6-[6-(dimethylphosphoryl)pyridin-3-yl]-7-fluoro-2-methyl-N-[(1R)-1-phenylpropyl]-1,5-naphthyridin-4-amine (19 mg, 15%) as a light yellow solid. MS ESI calculated for $C_{25}H_{25}ClFN_4OP$ $[M+H]^+$, 483.14, found 483.05. $^1H$ NMR (400 MHz, DMSO-$d_6$) δ 9.30 (s, 1H), 8.45-8.38 (m, 1H), 8.20 (d, J=11.8 Hz, 1H), 8.17-8.11 (m, 1H), 7.36-7.30 (m, 2H), 7.28-7.21 (m, 2H), 7.21-7.14 (m, 1H), 6.93-6.82 (m, 1H), 5.96-5.84 (m, 1H), 2.62 (s, 3H), 2.11-2.02 (m, 1H), 1.97-1.89 (m, 1H), 1.77 (s, 3H), 1.73 (s, 3H), 0.95 (t, J=7.3 Hz, 3H). $^{19}F$ NMR (377 MHz, DMSO-$d_6$) δ −120.95. $^{31}P$ NMR (162 MHz, DMSO-$d_6$) δ 34.20.

269

Example 80: 3-chloro-N-[(1R)-1-(3,4-difluorophenyl)ethyl]-6-[6-(dimethylphosphoryl)pyridin-3-yl]-7-fluoro-2-methyl-1,5-naphthyridin-4-amine

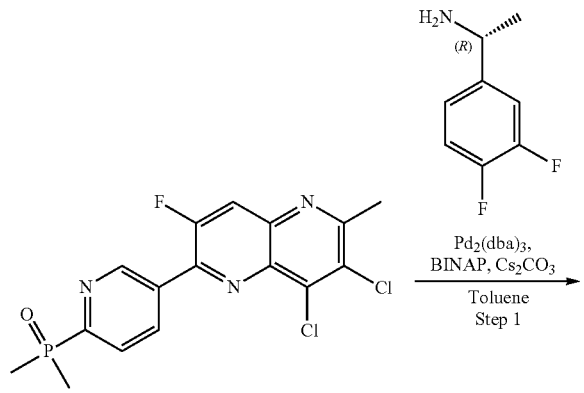

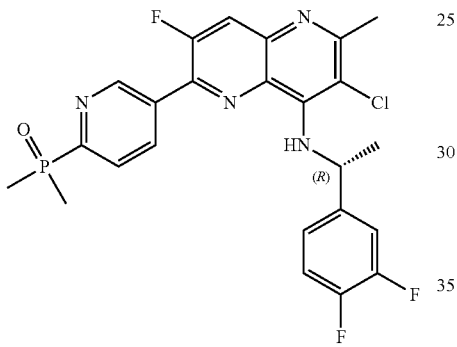

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-(3,4-difluorophenyl)ethanamine (49 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 30 B to 70 B in 40 min; 254/220 nm to afford 3-chloro-N-[(1R)-1-(3,4-difluorophenyl)ethyl]-6-[6-(dimethylphosphoryl)pyridin-3-yl]-7-fluoro-2-methyl-1,5-naphthyridin-4-amine (30 mg, 23%) as a light yellow solid. MS ESI calculated for $C_{24}H_{21}ClF_3N_4OP$ [M+H]$^+$, 505.11, found 504.95. $^1$H NMR (400 MHz, DMSO-$d_6$) δ 9.18 (s, 1H), 8.43-8.34 (m, 1H), 8.21-8.16 (m, 1H), 8.15-8.08 (m, 1H), 7.45-7.36 (m, 1H), 7.29-7.24 (m 1H), 7.20-7.11 (m, 1H), 6.91-6.79 (m, 1H), 6.16-6.10 (m, 1H), 2.64 (s, 3H), 1.76 (s, 3H), 1.72 (s, 3H), 1.65 (d, J=6.8 Hz, 3H). $^{19}$F NMR (377 MHz, DMSO-$d_6$) δ −121.11, −138.69, −138.75, −141.70, −141.76. $^{31}$P NMR (162 MHz, DMSO-$d_6$) δ 34.23.

270

Example 81: 3-chloro-6-[6-(dimethylphosphoryl)pyridin-3-yl]-7-fluoro-N-[(1R)-1-(2-methoxypyridin-4-yl)ethyl]-2-methyl-1,5-naphthyridin-4-amine

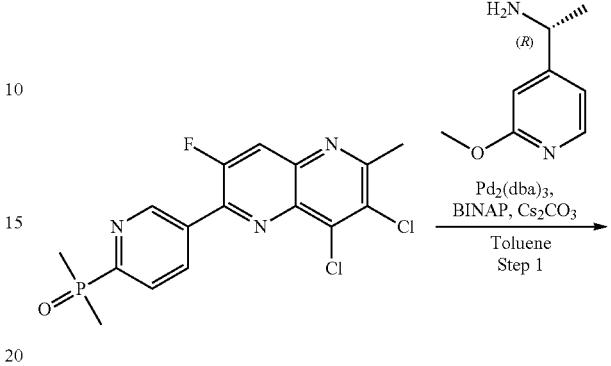

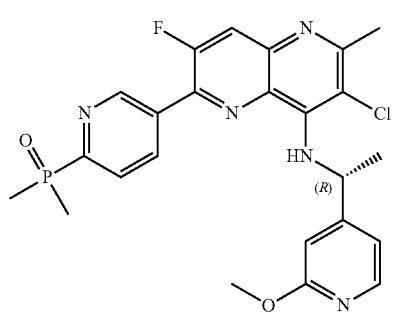

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-(2-methoxypyridin-4-yl)ethanamine (48 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 30 B to 70 B in 40 min; 254/220 nm to afford 3-chloro-6-[6-(dimethylphosphoryl)pyridin-3-yl]-7-fluoro-N-[(1R)-1-(2-methoxypyridin-4-yl)ethyl]-2-methyl-1,5-naphthyridin-4-amine (57 mg, 44%) as a light yellow solid. MS ESI calculated for $C_{24}H_{24}ClFN_5O_2P$ [M+H]$^+$, 500.13, found 500.10. $^1$H NMR (400 MHz, DMSO-$d_6$) δ 9.22 (s, 1H), 8.36-8.31 (m, 1H), 8.22-8.15 (m, 1H), 8.12-8.07 (m, 1H), 7.99 (d, J=5.3 Hz, 1H), 6.96-6.90 (m, 1H), 6.87 (d, J=8.5 Hz, 1H), 6.71-6.67 (m, 1H), 6.17-6.11 (m, 1H), 3.74 (s, 3H), 2.64 (s, 3H), 1.76 (s, 3H), 1.73 (s, 3H), 1.64 (d, J=6.8 Hz, 3H). $^{19}$F NMR (377 MHz, DMSO-$d_6$) δ −121.01. $^{31}$P NMR (162 MHz, DMSO-$d_6$) δ 34.20.

Example 82: 3-chloro-6-[6-(dimethylphosphoryl)pyridin-3-yl]-7-fluoro-2-methyl-N-[1-(pyridin-3-yl)propyl]-1,5-naphthyridin-4-amine

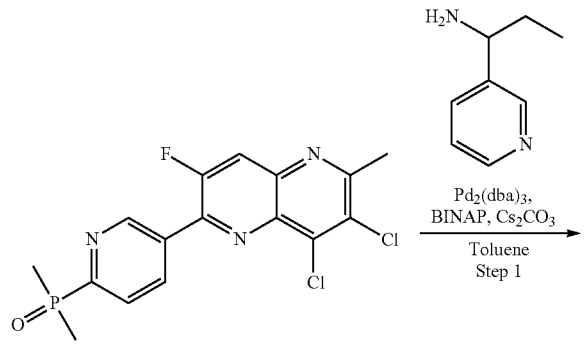

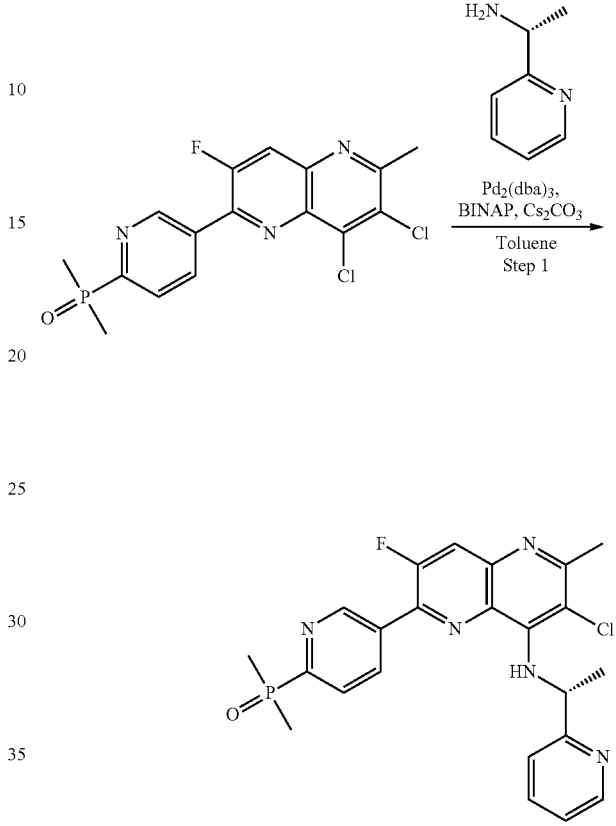

To a stirred solution of 3,4-dichloro-6-[6-(dimethylphosphoryl)pyridin-3-yl]-7-fluoro-2-methyl-1,5-naphthyridine (100 mg, 0.260 mmol) and 1-(pyridin-3-yl)propan-1-amine (43 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 30 B to 70 B in 40 min; 254/220 nm to afford 3-chloro-6-[6-(dimethylphosphoryl)pyridin-3-yl]-7-fluoro-2-methyl-N-[1-(pyridin-3-yl)propyl]-1,5-naphthyridin-4-amine (25 mg, 20%) as a light yellow solid. MS ESI calculated for $C_{24}H_{24}ClFN_5OP$ [M+H]$^+$, 484.14, found 483.95. $^1$H NMR (400 MHz, DMSO-$d_6$) δ 9.29 (s, 1H), 8.54 (d, J=2.3 Hz, 1H), 8.45-8.34 (m, 2H), 8.24-8.18 (m, 1H), 8.16-8.08 (m, 1H), 7.79-7.75 (m, 1H), 7.29-7.23 (m, 1H), 6.94 (d, J=8.9 Hz, 1H), 5.95-5.89 (m, 1H), 2.62 (s, 3H), 2.16-2.07 (m, 1H), 2.03-1.93 (m, 1H), 1.77 (s, 3H), 1.73 (s, 3H), 0.99-0.94 (m, 3H). $^{19}$F NMR (377 MHz, DMSO-$d_6$) δ −120.93. $^{31}$P NMR (162 MHz, DMSO-$d_6$) δ 34.24.

Example 83: 3-chloro-6-[6-(dimethylphosphoryl)pyridin-3-yl]-7-fluoro-2-methyl-N-[(1R)-1-(pyridin-2-yl)ethyl]-1,5-naphthyridin-4-amine To a solution of 3,4-dichloro-6-[6-(dimethylphosphoryl)pyridin-3-yl]-7-fluoro-2-methyl-1,5-naphthyridine (100 mg, 0.260 mmol) and (1R)-1-(pyridin-2-yl)ethanamine (40 mg, 0.325 mmol) in Toluene (2 mL) were added BINAP (41 mg, 0.065 mmol), $Cs_2CO_3$ (159 mg, 0.488 mmol) and $Pd_2(dba)_3$ (30 mg, 0.033 mmol). After stirring for overnight at 100° C. under a nitrogen atmosphere, the resulting mixture was concentrated under reduced pressure. The residue was purified by silica gel column chromatography, eluted with $CH_2Cl_2$/MeOH (8/1) followed by reversed-phase flash chromatography with the following conditions: column, C18 silica gel; mobile phase, $CH_3CN$ in water (10 mmol/L $NH_4HCO_3$), 30% to 70% gradient in 10 min; detector, 254 nm. This resulted in 3-chloro-6-[6-(dimethylphosphoryl)pyridin-3-yl]-7-fluoro-2-methyl-N-[(1R)-1-(pyridin-2-yl)ethyl]-1,5-naphthyridin-4-amine (51 mg, 33%) as a yellow solid. MS ESI calculated for $C_{23}H_{22}ClFN_5OP$ [M+H]$^+$, 470.12, found 469.90. $^1$H NMR (300 MHz, Chloroform-d) δ 9.45 (d, J=2.0 Hz, 1H), 8.72-8.66 (m, 1H), 8.62-8.53 (m, 1H), 8.35-8.28 (m, 1H), 8.05-7.92 (m, 2H), 7.73-7.65 (m, 1H), 7.33-7.22 (m, 2H), 6.27-6.13 (m, 1H), 2.77 (s, 3H), 1.90 (s, 3H), 1.86 (s, 3H), 1.69 (d, J=6.6 Hz, 3H). $^{19}$F NMR (282 MHz, Chloroform-d) δ −120.76. $^{31}$P NMR (121 MHz, Chloroform-d) δ 36.71.

Example 84: 3-chloro-6-[6-(dimethylphosphoryl)pyridin-3-yl]-7-fluoro-2-methyl-N-[(1R)-1-(pyridin-2-yl)propyl]-1,5-naphthyridin-4-amine

Example 85: 3-chloro-N-[(1R)-1-(3,5-difluorophenyl)ethyl]-6-[6-(dimethylphosphoryl)pyridin-3-yl]-7-fluoro-2-methyl-1,5-naphthyridin-4-amine

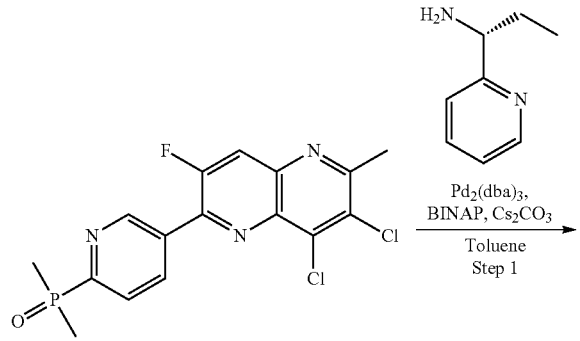

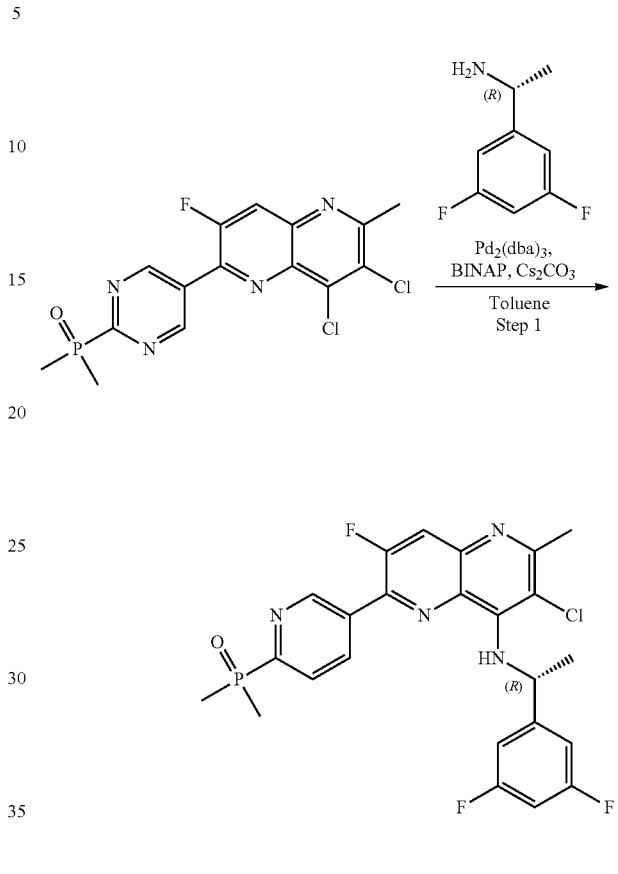

To a solution of 3,4-dichloro-6-[6-(dimethylphosphoryl)pyridin-3-yl]-7-fluoro-2-methyl-1,5-naphthyridine (100 mg, 0.260 mmol) and (1R)-1-(pyridin-2-yl)propan-1-amine (43 mg, 0.312 mmol) in Toluene (2 mL) were added BINAP (32 mg, 0.052 mmol), Cs$_2$CO$_3$ (127 mg, 0.390 mmol) and Pd$_2$(dba)$_3$ (24 mg, 0.026 mmol). After stirring for overnight at 100° C. under a nitrogen atmosphere, the resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 30% to 70% gradient in 10 min; detector, UV 254 nm. This resulted in 3-chloro-6-[6-(dimethylphosphoryl)pyridin-3-yl]-7-fluoro-2-methyl-N-[(1R)-1-(pyridin-2-yl)propyl]-1,5-naphthyridin-4-amine (47 mg, 37%) as a yellow solid. MS ESI calculated for C$_{24}$H$_{24}$ClFN$_5$OP [M+H]$^+$, 484.14, found 483.95. $^1$H NMR (300 MHz, Chloroform-d) δ 9.43 (s, 1H), 8.72-8.66 (m, 1H), 8.57-8.50 (m, 1H), 8.36-8.28 (m, 1H), 7.95 (d, J=11.9 Hz, 1H), 7.89-7.78 (m, 1H), 7.72-7.62 (m, 1H), 7.31-7.19 (m, 2H), 6.13-6.02 (m, 1H), 2.76 (s, 3H), 2.16-2.02 (m, 2H), 1.90 (s, 3H), 1.86 (s, 3H), 0.88 (t, J=7.4 Hz, 3H). $^{19}$F NMR (282 MHz, Chloroform-d) δ −120.83. $^{31}$P NMR (121 MHz, Chloroform-d) δ 36.73.

To a stirred solution of 3,4-dichloro-6-[6-(dimethylphosphoryl)pyridin-3-yl]-7-fluoro-2-methyl-1,5-naphthyridine (100 mg, 0.260 mmol) and ((1R)-1-(3,5-difluorophenyl)ethanamine (49 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 30 B to 70 B in 40 min; 254/220 nm to afford 3-chloro-N-[(1R)-1-(3,5-difluorophenyl)ethyl]-6-[6-(dimethylphosphoryl)pyridin-3-yl]-7-fluoro-2-methyl-1,5-naphthyridin-4-amine (41 mg, 31%) as a light yellow solid. MS ESI calculated for C$_{24}$H$_{21}$ClF$_3$N$_4$OP [M+H]$^+$, 505.11, found 504.90. $^1$H NMR (400 MHz, DMSO-d$_6$) δ 9.16 (s, 1H), 8.37-8.32 (m, 1H), 8.18 (d, J=11.8 Hz, 1H), 8.12-8.07 (m, 1H), 7.08-7.02 (m, 2H), 7.01-6.95 (m, 1H), 6.87 (d, J=8.4 Hz, 1H), 6.17-6.09 (m, 1H), 2.65 (s, 3H), 1.75 (s, 3H), 1.72 (s, 3H), 1.65 (d, J=6.8 Hz, 3H). $^{19}$F NMR (377 MHz, DMSO-d$_6$) δ −109.93, −121.17. $^{31}$P NMR (162 MHz, DMSO-d$_6$) δ 34.19.

Example 86: 3-chloro-6-[6-(dimethylphosphoryl)pyridin-3-yl]-7-fluoro-N-[(1R)-1-(3-fluorophenyl)ethyl]-2-methyl-1,5-naphthyridin-4-amine

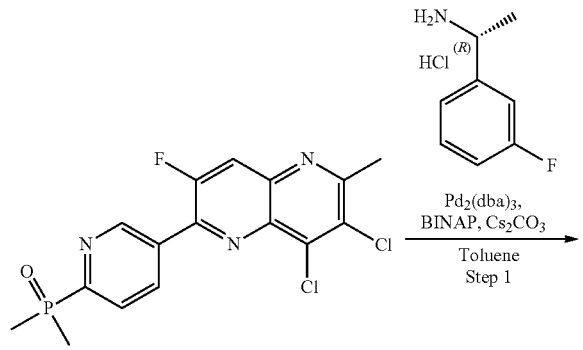

Example 87: 3-chloro-N-[(1R)-1-(2-chlorophenyl)ethyl]-6-[6-(dimethylphosphoryl)pyridin-3-yl]-7-fluoro-2-methyl-1,5-naphthyridin-4-amine

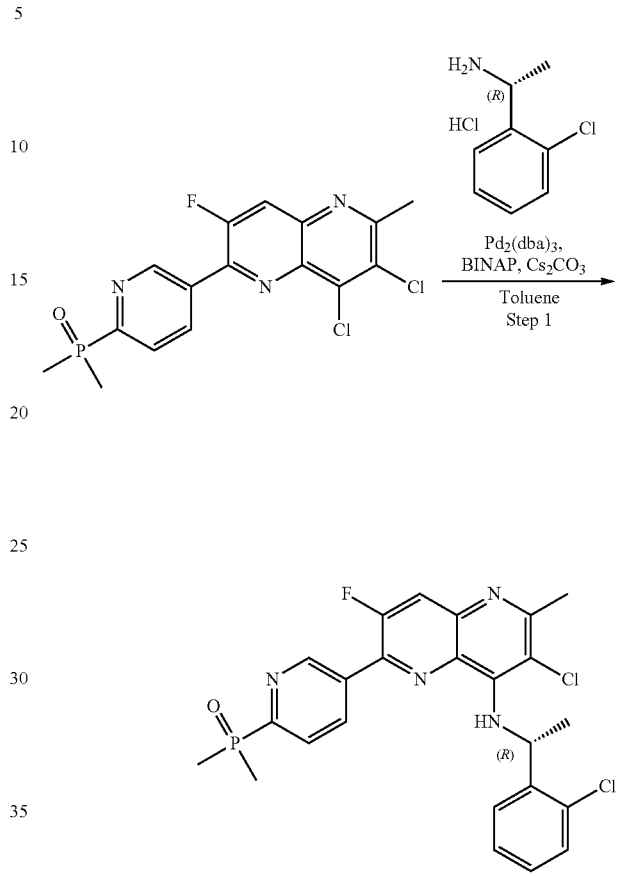

To a stirred mixture of 3,4-dichloro-6-[6-(dimethylphosphoryl)pyridin-3-yl]-7-fluoro-2-methyl-1,5-naphthyridine (80 mg, 0.208 mmol) and (1R)-1-(3-fluorophenyl)ethanamine (34 mg, 0.250 mmol) in Toluene (2 mL) were added $Cs_2CO_3$ (339 mg, 1.040 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20% B to 60% B in 25 min; 254/220 nm to afford 3-chloro-6-[6-(dimethylphosphoryl)pyridin-3-yl]-7-fluoro-N-[(1R)-1-(3-fluorophenyl)ethyl]-2-methyl-1,5-naphthyridin-4-amine (46 mg, 45%) as a yellow green solid. MS ESI calculated for $C_{24}H_{22}ClF_2N_4OP$ [M+H]$^+$, 487.12, found 487.20. $^1$H NMR (300 MHz, Chloroform-d) δ 9.25 (s, 1H), 8.31-8.21 (m, 2H), 7.99 (d, J=11.5 Hz, 1H), 7.30-7.18 (m, 1H), 7.11-7.03 (m, 1H), 7.03-6.84 (m, 2H), 6.45 (d, J=8.5 Hz, 1H), 6.25-6.13 (m, 1H), 2.76 (s, 3H), 1.89 (s, 3H), 1.85 (s, 3H), 1.71 (d, J=6.8 Hz, 3H). $^{19}$F NMR (282 MHz, Chloroform-d) δ −112.27, −120.60. $^{31}$P NMR (121 MHz, Chloroform-d) δ 36.56.

To a stirred mixture of 3,4-dichloro-6-[6-(dimethylphosphoryl)pyridin-3-yl]-7-fluoro-2-methyl-1,5-naphthyridine (80 mg, 0.208 mmol) and (1R)-1-(2-chlorophenyl)ethan-1-amine hydrochloride (48 mg, 0.250 mmol) in Toluene (2 mL) were added $Cs_2CO_3$ (169 mg, 0.520 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20% B to 60% B in 25 min; 254/220 nm to afford 3-chloro-N-[(1R)-1-(2-chlorophenyl)ethyl]-6-[6-(dimethylphosphoryl)pyridin-3-yl]-7-fluoro-2-methyl-1,5-naphthyridin-4-amine (65 mg, 62%) as a yellow green solid. MS ESI calculated for $C_{24}H_{22}Cl_2FN_4OP$ [M+H]$^+$, 503.09, found 503.20. $^1$H NMR (300 MHz, Chloroform-d) δ 9.25-9.23 (m, 1H), 8.32-8.23 (m, 2H), 7.97 (d, J=11.4 Hz, 1H), 7.32-7.27 (m, 2H), 7.21-7.13 (m, 2H), 6.64 (d, J=7.5 Hz, 1H), 6.45-6.36 (m, 1H), 2.71 (s, 3H), 1.90 (s, 3H), 1.85 (s, 3H), 1.69 (d, J=6.7 Hz, 3H). $^{19}$F NMR (282 MHz, Chloroform-d) δ −112.76. $^{31}$P NMR (121 MHz, Chloroform-d) δ 36.53.

Example 88: 3-chloro-N-[(1R)-1-(2,4-difluorophenyl)ethyl]-6-[6-(dimethylphosphoryl)pyridin-3-yl]-7-fluoro-2-methyl-1,5-naphthyridin-4-amine

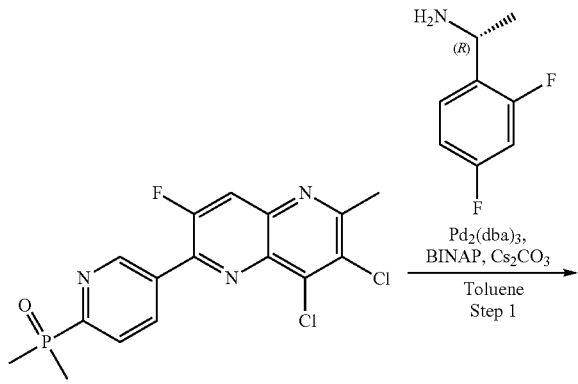

Example 89: 3-chloro-6-[6-(dimethylphosphoryl)pyridin-3-yl]-7-fluoro-2-methyl-N-[(1R)-1-(2,3,6-trifluorophenyl)ethyl]-1,5-naphthyridin-4-amine

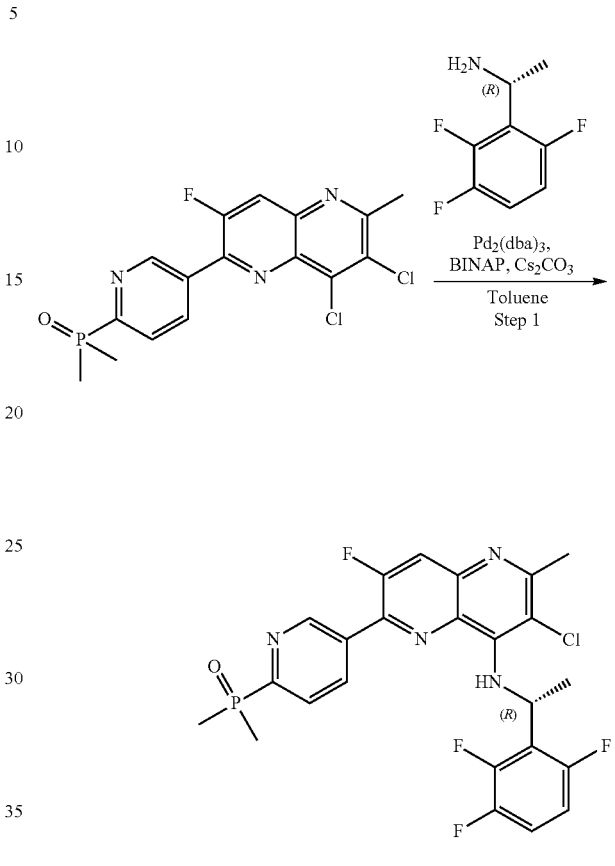

To a stirred mixture of 3,4-dichloro-6-[6-(dimethylphosphoryl)pyridin-3-yl]-7-fluoro-2-methyl-1,5-naphthyridine (80 mg, 0.208 mmol) and (1R)-1-(2,4-difluorophenyl)ethanamine (39 mg, 0.250 mmol) in Toluene (2 mL) were added $Cs_2CO_3$ (101 mg, 0.312 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20% B to 60% B in 25 min; 254/220 nm to afford 3-chloro-N-[(1R)-1-(2,4-difluorophenyl)ethyl]-6-[6-(dimethylphosphoryl)pyridin-3-yl]-7-fluoro-2-methyl-1,5-naphthyridin-4-amine (46 mg, 43%) as a yellow green solid. MS ESI calculated for $C_{24}H_{21}ClF_3N_4OP$ [M+H]$^+$, 505.11, found 505.20. $^1$H NMR (400 MHz, Chloroform-d) δ 9.27 (d, J=2.0 Hz, 1H), 8.38-8.34 (m, 1H), 8.30-8.26 (m, 1H), 7.97 (d, J=10.7 Hz, 1H), 7.21-7.15 (m, 1H), 6.76-6.70 (m, 2H), 6.54 (s, 1H), 6.42-6.31 (m, 1H), 2.73 (s, 3H), 1.88 (s, 3H), 1.84 (s, 3H), 1.70 (d, J=6.7 Hz, 3H). $^{19}$F NMR (377 MHz, Chloroform-d) δ −111.58, −114.55, −120.76. $^{31}$P NMR (162 MHz, Chloroform-d) δ 36.46.

To a stirred mixture of 3,4-dichloro-6-[6-(dimethylphosphoryl)pyridin-3-yl]-7-fluoro-2-methyl-1,5-naphthyridine (80 mg, 0.208 mmol) and (1R)-1-(2,3,6-trifluorophenyl)ethanamine (43 mg, 0.250 mmol) in Toluene (1 mL) were added $Cs_2CO_3$ (101 mg, 0.312 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20 B to 60 B in 25 min; 254/220 nm to afford 3-chloro-6-[6-(dimethylphosphoryl)pyridin-3-yl]-7-fluoro-2-methyl-N-[(1R)-1-(2,3,6-trifluorophenyl)ethyl]-1,5-naphthyridin-4-amine (30 mg, 27%) as a yellow green solid. MS ESI calculated for $C_{24}H_{20}ClF_4N_4OP$ [M+H]$^+$, 523.10, found 523.05. $^1$H NMR (400 MHz, Chloroform-d) δ 9.36 (d, J=2.0 Hz, 1H), 8.48-8.46 (m, 1H), 8.32-8.28 (m, 1H), 7.94 (d, J=11.6 Hz, 1H), 7.04-6.92 (m, 2H), 6.81-6.67 (m, 2H), 2.72 (s, 3H), 1.88 (s, 3H), 1.85 (s, 3H), 1.76 (d, J=6.9 Hz, 3H). $^{19}$F NMR (377 MHz, Chloroform-d) δ −120.42, −138.74, −141.40. $^{31}$P NMR (162 MHz, Chloroform-d) δ 36.66.

Example 90: 3-chloro-6-[6-(dimethylphosphoryl)pyridin-3-yl]-7-fluoro-2-methyl-N-[(1R)-1-phenylethyl]-1,5-naphthyridin-4-amine

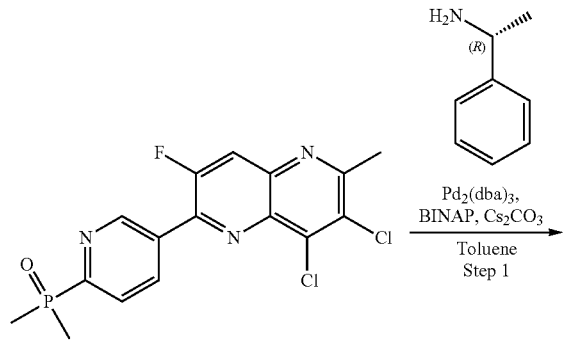

Example 91: 3-chloro-N-[(1R)-1-(3-chlorophenyl)ethyl]-6-[6-(dimethylphosphoryl)pyridin-3-yl]-7-fluoro-2-methyl-1,5-naphthyridin-4-amine

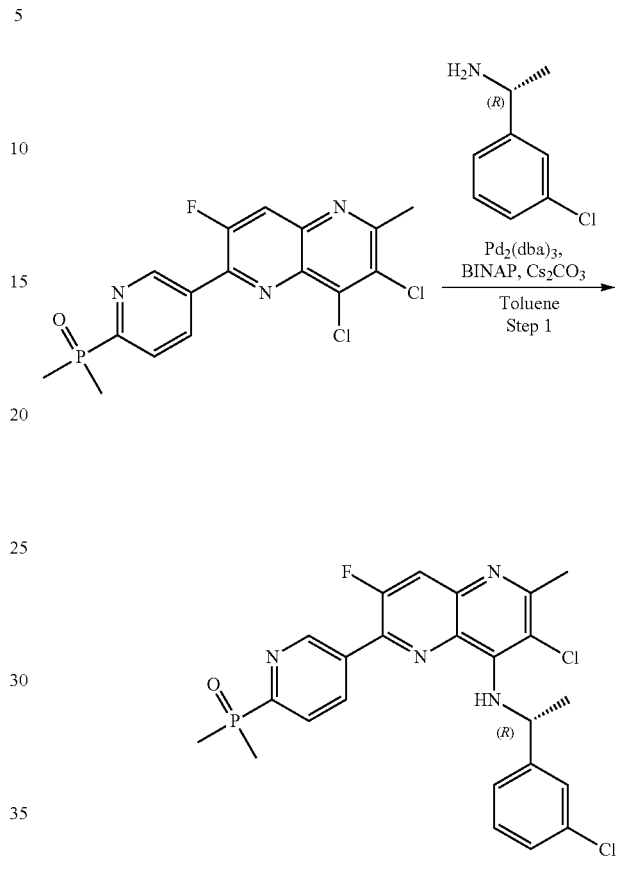

To a stirred mixture of 3,4-dichloro-6-[6-(dimethylphosphoryl)pyridin-3-yl]-7-fluoro-2-methyl-1,5-naphthyridine (80 mg, 0.208 mmol) and (R)-1-phenylethan-1-amine (30 mg, 0.250 mmol) in Toluene (2 mL) were added $Cs_2CO_3$ (101 mg, 0.312 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20 B to 60 B in 25 min; 254/220 nm to afford 3-chloro-6-[6-(dimethylphosphoryl)pyridin-3-yl]-7-fluoro-2-methyl-N-[(1R)-1-phenylethyl]-1,5-naphthyridin-4-amine (26 mg, 26%) as a yellow green solid. MS ESI calculated for $C_{24}H_{23}ClFN_4OP$ $[M+H]^+$, 469.13, found 469.05. $^1H$ NMR (400 MHz, Chloroform-d) δ 9.28 (s, 1H), 8.27-8.21 (m, 2H), 7.92 (d, J=11.6 Hz, 1H), 7.31-7.27 (m, 4H), 7.24-7.19 (m, 1H), 6.46 (d, J=8.6 Hz, 1H), 6.22-6.15 (m, 1H), 2.72 (s, 3H), 1.87 (s, 3H), 1.83 (s, 3H), 1.70 (d, J=6.7 Hz, 3H). $^{19}F$ NMR (377 MHz, Chloroform-d) δ −120.97. $^{31}P$ NMR (162 MHz, Chloroform-d) δ 36.47.

To a stirred mixture of 8-chloro-2-[6-(dimethylphosphoryl)pyridin-3-yl]-3-fluoro-1,5-naphthyridine (80 mg, 0.238 mmol) and (1R)-1-(3-chlorophenyl)ethanamine (44 mg, 0.286 mmol) in Toluene (1 mL) were added $Cs_2CO_3$ (101 mg, 0.312 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20% B to 60% B in 25 min; 254/220 nm to afford 3-chloro-N-[(1R)-1-(3-chlorophenyl)ethyl]-6-[6-(dimethylphosphoryl)pyridin-3-yl]-7-fluoro-2-methyl-1,5-naphthyridin-4-amine (31 mg, 26%) as a yellow green solid. MS ESI calculated for $C_{24}H_{22}Cl_2FN_4OP$ $[M+H]^+$, 503.09, found 503.05. $^1H$ NMR (300 MHz, Chloroform-d) δ 9.25-9.23 (m, 1H), 8.32-8.23 (m, 2H), 7.97 (d, J=11.4 Hz, 1H), 7.32-7.27 (m, 2H), 7.21-7.13 (m, 2H), 6.64 (d, J=7.5 Hz, 1H), 6.45-6.36 (m, 1H), 2.71 (s, 3H), 1.87 (s, 3H), 1.83 (s, 3H), 1.69 (d, J=6.7 Hz, 3H). $^{19}F$ NMR (377 MHz, Chloroform-d) δ −120.74. $^{31}P$ NMR (162 MHz, Chloroform-d) δ 36.46.

Example 92: 3-chloro-N-[(1R)-1-[3-(difluoromethyl)phenyl]ethyl]-6-[6-(dimethylphosphoryl)pyridin-3-yl]-7-fluoro-2-methyl-1,5-naphthyridin-4-amine

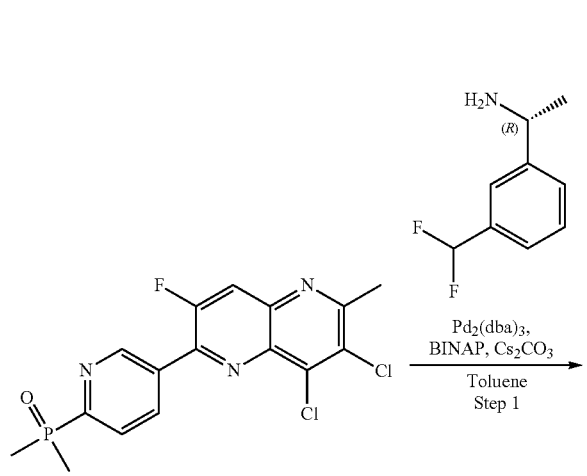

Example 93: 3-chloro-6-[6-(dimethylphosphoryl)pyridin-3-yl]-7-fluoro-2-methyl-N-[(1R)-1-[3-(trifluoromethyl)phenyl]ethyl]-1,5-naphthyridin-4-amine

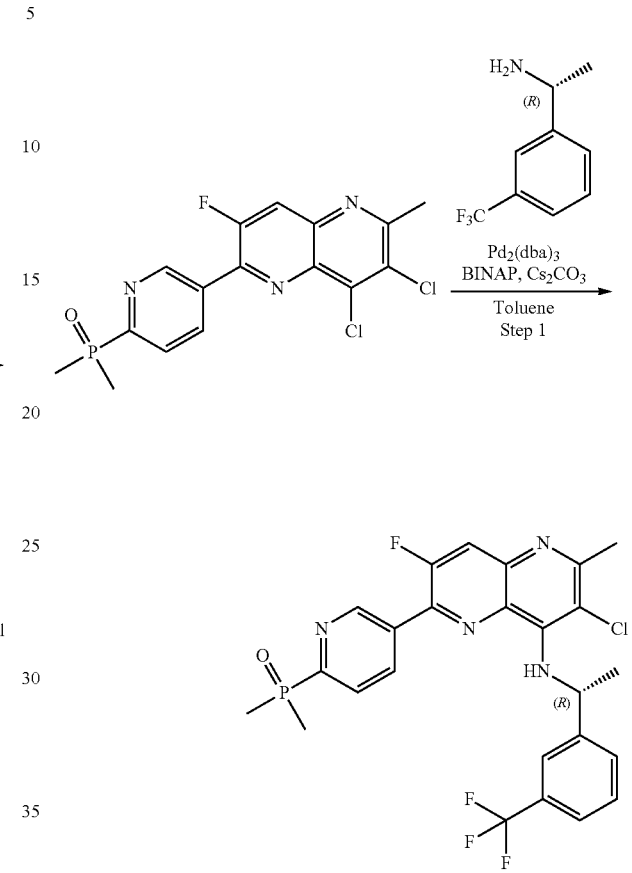

To a stirred mixture of 8-chloro-2-[6-(dimethylphosphoryl)pyridin-3-yl]-3-fluoro-1,5-naphthyridine (80 mg, 0.238 mmol) and (1R)-1-[3-(difluoromethyl)phenyl]ethanamine (42 mg, 0.250 mmol) in Toluene (1 mL) were added $Cs_2CO_3$ (101 mg, 0.312 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20% B to 605 B in 25 min; 254/220 nm to afford 3-chloro-N-[(1R)-1-[3-(difluoromethyl)phenyl]ethyl]-6-[6-(dimethylphosphoryl)pyridin-3-yl]-7-fluoro-2-methyl-1,5-naphthyridin-4-amine (28 mg, 25%) as a yellow green solid. MS ESI calculated for $C_{25}H_{23}ClF_3N_4OP$ $[M+H]^+$, 519.13, found 519.05. $^1H$ NMR (400 MHz, Chloroform-d) δ 9.24 (d, J=2.4 Hz, 1H), 8.31-8.22 (m, 2H), 7.98 (d, J=11.4 Hz, 1H), 7.42 (s, 1H), 7.39-7.32 (m, 3H), 6.52 (t, J=56.5 Hz, 2H), 6.26-6.20 (m, 1H), 2.75 (s, 3H), 1.87 (s, 3H), 1.84 (s, 3H), 1.72 (d, J=6.7 Hz, 3H). $^{19}F$ NMR (377 MHz, Chloroform-d) δ −110.82, −110.86, −120.66. $^{31}P$ NMR (162 MHz, Chloroform-d) δ 36.48.

To a stirred mixture of 8-chloro-2-[6-(dimethylphosphoryl)pyridin-3-yl]-3-fluoro-1,5-naphthyridine (80 mg, 0.238 mmol) and (1R)-1-[3-(trifluoromethyl)phenyl]ethanamine (47 mg, 0.250 mmol) in Toluene (1 mL) were added $Cs_2CO_3$ (101 mg, 0.312 mmol), $Pd_2(dba)_3$ (19 mg, 0.021 mmol) and BINAP (25 mg, 0.042 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20% B to 60% B in 25 min; 254/220 nm to afford 3-chloro-6-[6-(dimethylphosphoryl)pyridin-3-yl]-7-fluoro-2-methyl-N-[(1R)-1-[3-(trifluoromethyl)phenyl]ethyl]-1,5-naphthyridin-4-amine (38 mg, 34%) as a yellow green solid. MS ESI calculated for $C_{25}H_{22}ClF_4N_4OP$ $[M+H]^+$, 537.12, found 537.05. $^1H$ NMR (400 MHz, Chloroform-d) δ 9.23 (s, 1H), 8.32-8.23 (m, 2H), 7.92 (d, J=11.5 Hz, 1H), 7.49 (d, J=2.1 Hz, 1H), 7.46-7.42 (m, 2H), 7.38-7.34 (m, 1H), 6.40-6.35 (m, 1H), 6.28-6.20 (m, 1H), 2.73 (s, 3H), 1.87 (s, 3H), 1.84 (s, 3H), 1.72 (d, J=6.7 Hz, 3H). $^{19}F$ NMR (377 MHz, Chloroform-d) δ −62.66, −120.77. $^{31}P$ NMR (162 MHz, Chloroform-d) δ 36.48.

Example 94: 3-chloro-6-[6-(dimethylphosphoryl)pyridin-3-yl]-7-fluoro-N-[1-(3-fluoropyridin-2-yl)ethyl]-2-methyl-1,5-naphthyridin-4-amine

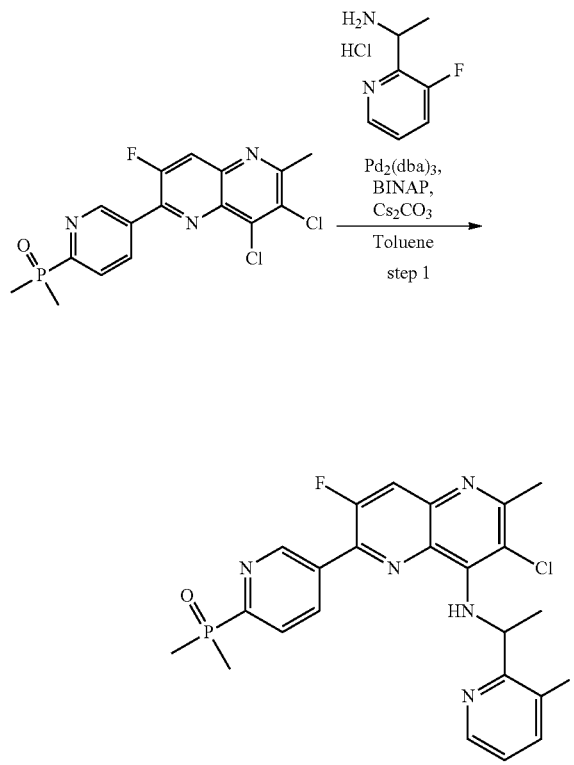

To a stirred solution of 1-(3-fluoropyridin-2-yl)ethanamine dihydrochloride (100 mg, 0.468 mmol) and 3,4-dichloro-6-[6-(dimethylphosphoryl)pyridin-3-yl]-7-fluoro-2-methyl-1,5-naphthyridine (150 mg, 0.390 mmol) in Toluene (2 mL) were added Pd$_2$(dba)$_3$ (36 mg, 0.039 mmol), BINAP (49 mg, 0.078 mmol) and Cs$_2$CO$_3$ (509 mg, 1.560 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in 3-chloro-6-[6-(dimethylphosphoryl)pyridin-3-yl]-7-fluoro-N-[(1R)-1-(3-fluoropyridin-2-yl)ethyl]-2-methyl-1,5-naphthyridin-4-amine (73 mg, 38%) as a yellow solid. MS ESI calculated for C$_{23}$H$_{21}$ClF$_2$N$_5$OP [M+H]$^+$, 488.11, found 487.90. $^1$H NMR (400 MHz, Chloroform-d) δ 9.50 (s, 1H), 8.67 (d, J=8.1 Hz, 1H), 8.52-8.47 (m, 1H), 8.38-8.29 (m, 1H), 8.25-8.10 (m, 1H), 8.03-7.88 (m, 1H), 7.43 (t, J=8.9 Hz, 1H), 7.35-7.28 (m, 1H), 6.72-6.59 (m, 1H), 2.76 (s, 3H), 1.88 (s, 3H), 1.85 (s, 3H), 1.64 (d, J=6.5 Hz, 3H). $^{19}$F NMR (376 MHz, Chloroform-d) δ −120.77, −126.91. $^{31}$P NMR (162 MHz, Chloroform-d) δ 36.75.

Example 95: (R)-(5-(7-chloro-8-((1-(2,3-difluorophenyl)propyl)amino)-3-fluoro-6-methyl-1,5-naphthyridin-2-yl)pyridin-2-yl)dimethylphosphine oxide Synthetic Scheme

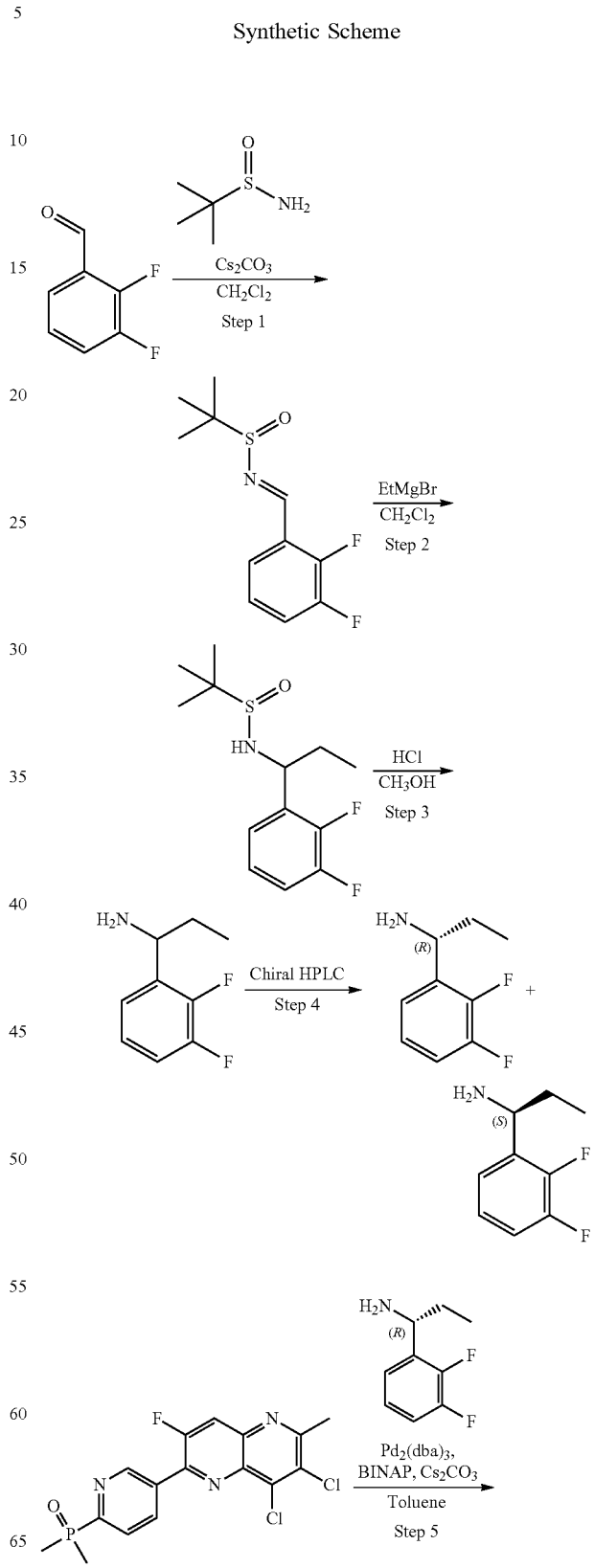

-continued

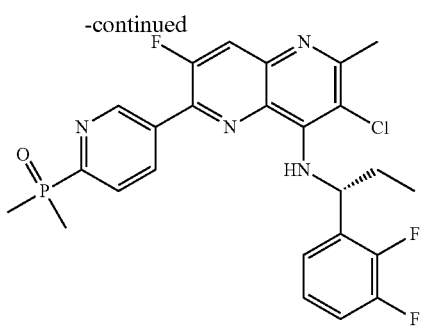

Preparation 95A: N-[(1E)-(2,3-difluorophenyl)methylidene]-2-methylpropane-2-sulfinamide

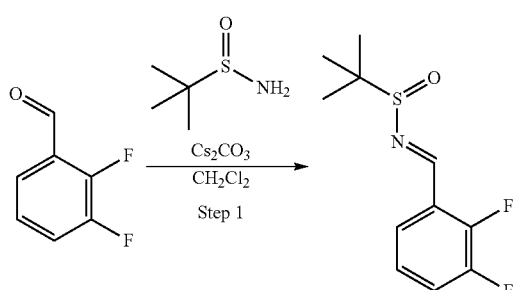

To a stirred solution of 2,3-difluorobenzaldehyde (5.00 g, 35.185 mmol) and tert-butanesulfinamide (5.12 g, 42.222 mmol) in DMF (50 mL) was added Cs$_2$CO$_3$ (22.93 g, 70.370 mmol) at room temperature. The resulting mixture was stirred for overnight at room temperature. The resulting mixture was concentrated under reduced pressure. The residue was purified by silica gel column chromatography, eluted with PE/EA (1/1) to afford N-[(1E)-(2,3-difluorophenyl)methylidene]-2-methylpropane-2-sulfinamide (7.79 g, 90%) as a yellow liquid. MS ESI calculated for C$_{11}$H$_{13}$F$_2$NOS [M+H]$^+$, 246.07, found 246.00. $^1$H NMR (400 MHz, Chloroform-d) δ 8.88 (s, 1H), 7.79-7.72 (m, 1H), 7.36-7.28 (m, 1H), 7.22-7.14 (m, 1H), 1.28 (s, 9H).

Preparation 95B: N-[1-(2,3-difluorophenyl)propyl]-2-methylpropane-2-sulfinamide

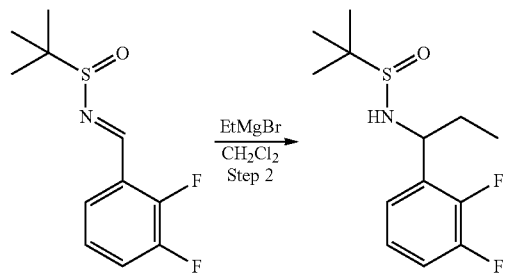

To a stirred solution of N-[(1E)-(2,3-difluorophenyl)methylidene]-2-methylpropane-2-sulfinamide (7.25 g, 29.557 mmol) in DCM (100 mL) was added ethylmagnesium bromide (17.4 mL, 59.114 mmol) dropwise at −35° C. under nitrogen atmosphere. The resulting mixture was stirred for 30 min at −35° C. under nitrogen atmosphere. The reaction was quenched by the addition of sat. NH$_4$Cl (aq.) (200 mL) at room temperature. The resulting mixture was extracted with CH$_2$Cl$_2$ (2×200 mL). The combined organic layers were washed with brine (2×200 mL), dried over anhydrous Na$_2$SO$_4$. After filtration, the filtrate was concentrated under reduced pressure. The residue was purified by silica gel column chromatography, eluted with PE/EA (1/1) to afford N-[1-(2,3-difluorophenyl)propyl]-2-methylpropane-2-sulfinamide (7.10 g, 87%) as a white solid. MS ESI calculated for C$_{13}$H$_{19}$F$_2$NO [M+H]$^+$, 276.12, found 276.00. $^1$H NMR (400 MHz, Chloroform-d) δ 7.14-6.93 (m, 3H), 4.68-4.43 (m, 1H), 3.61-3.42 (m, 1H), 2.11-1.76 (m, 2H), 1.20 (d, J=18.0 Hz, 9H), 0.95-0.83 (m, 3H).

Preparation 95C: 1-(2,3-difluorophenyl)propan-1-amine

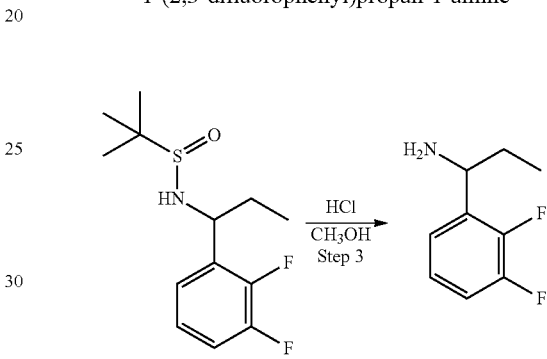

To a stirred solution of N-[1-(2,3-difluorophenyl)propyl]-2-methylpropane-2-sulfinamide (7.00 g, 25.421 mmol) in MeOH (30 mL) was added conc. HCl (10 mL) dropwise at room temperature. The resulting mixture was stirred for 1 h at room temperature. The reaction was quenched with sat. NH$_4$HCO$_3$ (aq.) at room temperature. The resulting mixture was extracted with CH$_2$Cl$_2$ (2×100 mL). The combined organic layers were washed with brine (2×100 mL), dried over anhydrous Na$_2$SO$_4$. After filtration, the filtrate was concentrated under reduced pressure. The residue was purified by silica gel column chromatography, eluted with CH$_2$Cl$_2$/MeOH (10/1) to afford 1-(2,3-difluorophenyl)propan-1-amine (1.80 g, 41%) as a yellow oil. MS ESI calculated for C$_9$H$_{11}$F$_2$N [M+H]$^+$, 172.09, found 172.25. $^1$H NMR (400 MHz, Chloroform-d) δ 7.18-7.08 (m, 1H), 7.11-6.98 (m, 2H), 4.15 (t, J=6.9 Hz, 1H), 1.80-1.71 (m, 2H), 0.97-0.84 (m, 3H).

Preparation 95D: (1R)-1-(2,3-difluorophenyl)propan-1-amine and (1S)-1-(2,3-difluorophenyl)propan-1-amine

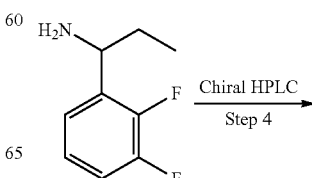

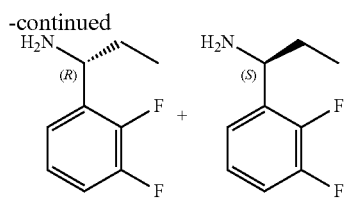

1-(2,3-difluorophenyl)propan-1-amine (1.80 g) was resolved by Chiral-Prep-HPLC with the following conditions (Column: CHIRAL CHIRALPAK IG-3, 0.46*5 cm, 3 um; Mobile Phase: Hex(10 mNH$_3$):IPA=98:2; Flow rate: 140 ml/min; 214 nm; RT1=9.5 min, RT2=13.9 min). The first peak afforded 630 mg (35%) as a yellow oil. The second peak afforded 530 mg (33%) as a yellow oil.

Example 95: (R)-(5-(7-chloro-8-((1-(2,3-difluorophenyl)propyl)amino)-3-fluoro-6-methyl-1,5-naphthyridin-2-yl)pyridin-2-yl)dimethylphosphine oxide

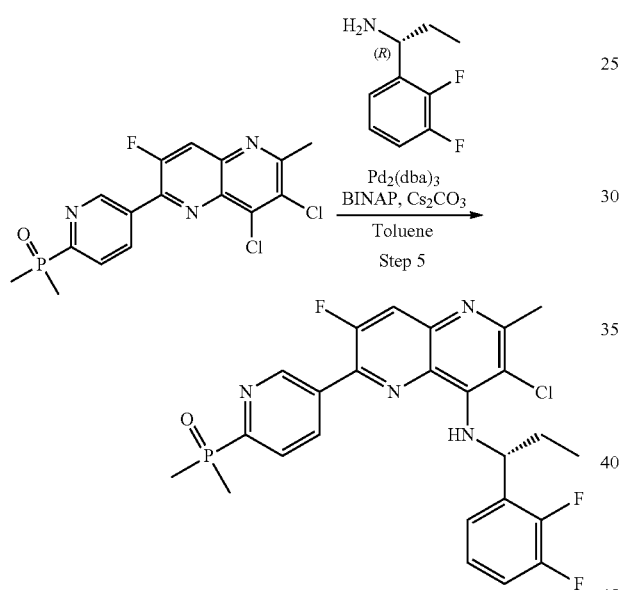

To a stirred solution of 3,4-dichloro-6-[6-(dimethylphosphoryl)pyridin-3-yl]-7-fluoro-2-methyl-1,5-naphthyridine (100 mg, 0.260 mmol) and (R)-1-(2,3-difluorophenyl)propan-1-amine (53 mg, 0.312 mmol,) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in (R)-(5-(7-chloro-8-((1-(2,3-difluorophenyl)propyl)amino)-3-fluoro-6-methyl-1,5-naphthyridin-2-yl)pyridin-2-yl)dimethylphosphine oxide (46 mg, 34%) as a yellow solid. MS ESI calculated for C$_{25}$H$_{23}$ClF$_3$N$_4$OP [M+H]$^+$, 519.13, found 519.00. $^1$H NMR (400 MHz, Chloroform-d) δ 9.22 (s, 1H), 8.38-8.31 (m, 1H), 8.32-8.24 (m, 1H), 7.97 (d, J=11.5 Hz, 1H), 7.06-6.90 (m, 3H), 6.62 (s, 1H), 6.19 (q, J=7.5 Hz, 1H), 2.73 (s, 3H), 2.10-1.97 (m, 2H), 1.88 (s, 3H), 1.85 (s, 3H), 1.07 (t, J=7.4 Hz, 3H). $^{19}$F NMR (376 MHz, Chloroform-d) δ −120.72, −137.78, −137.84, −143.67, −143.72. $^{31}$P NMR (162 MHz, Chloroform-d) δ 36.61.

Example 96: (S)-(5-(7-chloro-8-((1-(2,3-difluorophenyl)propyl)amino)-3-fluoro-6-methyl-1,5-naphthyridin-2-yl)pyridin-2-yl)dimethylphosphine oxide

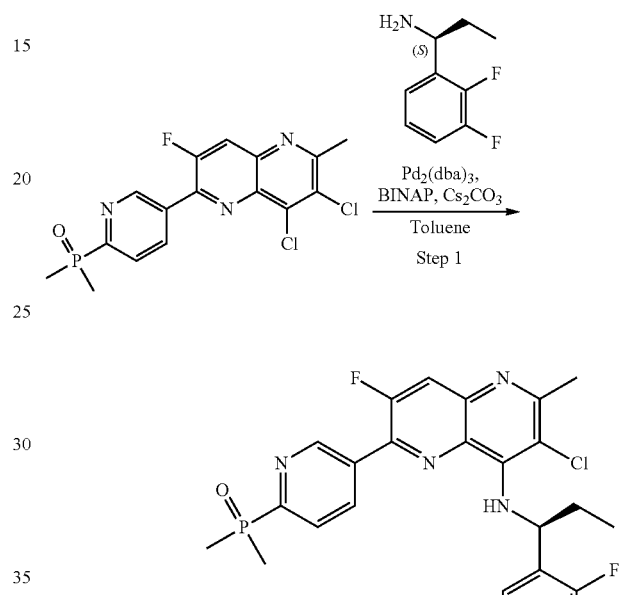

To a stirred solution of 3,4-dichloro-6-[6-(dimethylphosphoryl)pyridin-3-yl]-7-fluoro-2-methyl-1,5-naphthyridine (100 mg, 0.260 mmol) and (S)-1-(2,3-difluorophenyl)propan-1-amine (53 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in (S)-(5-(7-chloro-8-((1-(2,3-difluorophenyl)propyl)amino)-3-fluoro-6-methyl-1,5-naphthyridin-2-yl)pyridin-2-yl)dimethylphosphine oxide (47 mg, 34%) as a yellow solid. MS ESI calculated for C$_{25}$H$_{23}$ClF$_3$N$_4$OP [M+H]$^+$, 519.13, found 218.95. $^1$H NMR (400 MHz, Chloroform-d) δ 9.21 (s, 1H), 8.38-8.31 (m, 1H), 8.31-8.25 (m, 1H), 8.01 (s, 1H), 7.06-6.90 (m, 3H), 6.65 (s, 1H), 6.20 (d, J=8.1 Hz, 1H), 2.74 (s, 3H), 2.14-1 99 (m, 2H), 1.88 (s, 3H), 1.85 (s, 3H), 1.07 (t, J=7.4 Hz, 3H). $^{19}$F NMR (376 MHz, Chloroform-d) δ −120.61, −137.75, −143.66. $^{31}$P NMR (162 MHz, Chloroform-d) δ 36.65.

Example 97: 3-chloro-6-[6-(dimethylphosphoryl)pyridin-3-yl]-5,7-difluoro-N-[1-(3-fluoropyridin-2-yl)ethyl]-2-methylquinolin-4-amine

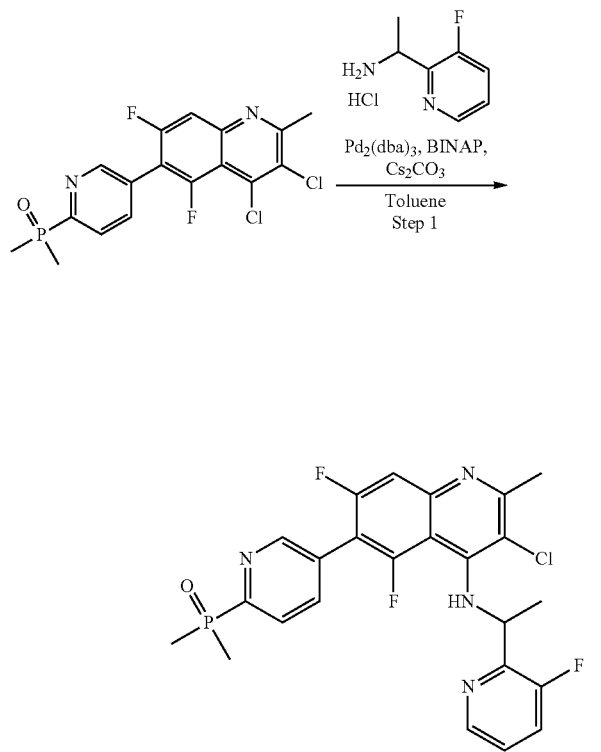

To a stirred mixture of 3,4-dichloro-6-[6-(dimethylphosphoryl)pyridin-3-yl]-5,7-difluoro-2-methylquinoline (150 mg, 0.374 mmol) and 1-(3-fluoropyridin-2-yl)ethan-1-amine dihydrochloride (95 mg, 0.449 mmol) in Toluene (2 mL) were added $Cs_2CO_3$ (609 mg, 1.870 mmol), $Pd_2(dba)_3$ (34 mg, 0.037 mmol) and BINAP (46 mg, 0.075 mmol) at room temperature under nitrogen atmosphere. The resulting mixture was stirred for 4 h at 100° C. under nitrogen atmosphere. The mixture was allowed to cool down to room temperature. The residue was purified by silica gel column chromatography, eluted with $CH_2Cl_2$/MeOH (9/1) followed by reverse phase flash with the following conditions (Column: C18, 120 g; Mobile Phase A: Water/0.05% $NH_4HCO_3$, Mobile Phase B: ACN; Flow rate: 60 mL/min; Gradient: 5% B to 30% B in 5 min; 30% B to 65% B in 20 min; Detector, 254 nm) to afford 3-chloro-6-[6-(dimethylphosphoryl)pyridin-3-yl]-5,7-difluoro-N-[1-(3-fluoropyridin-2-yl)ethyl]-2-methylquinolin-4-amine (31 mg, 16%) as a white solid. MS ESI calculated for $C_{24}H_{21}ClF_3N_4OP$ [M+H]$^+$, 505.11, found 505.10. $^1$H NMR (400 MHz, Chloroform-d) δ 8.88 (d, J=2.1 Hz, 1H), 8.4-8.38 (m, 1H), 8.28-8.24 (m, 1H), 8.04-8.00 (m, 1H), 7.54-7.50 (m, 1H), 7.38-7.34 (m, 1H), 7.25-7.21 (m, 1H), 7.09 (t, J=12.2 Hz, 1H), 5.82-5.74 (m, 1H), 2.72 (s, 3H), 1.87 (s, 3H), 1.84 (s, 3H), 1.52 (d, J=6.6 Hz, 3H). $^{19}$F NMR (377 MHz, Chloroform-d) δ −112.79, −113.63, −127.23.

Example 98: 3-chloro-6-[6-(dimethylphosphoryl)pyridin-3-yl]-N-[(1R)-1-(5-ethynyl-2-fluorophenyl)ethyl]-7-fluoro-2-methyl-1,5-naphthyridin-4-amine Synthetic Scheme

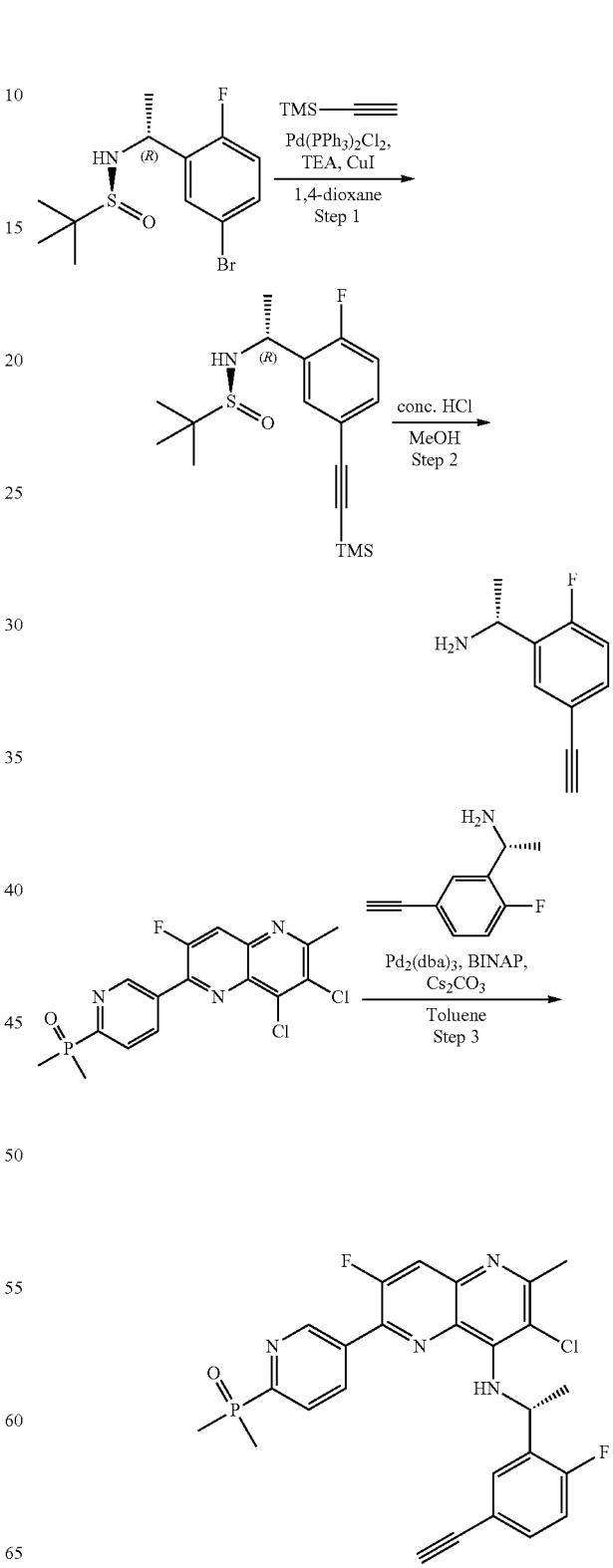

Preparation 98A: (S)—N-[(1R)-1-{2-fluoro-5-[2-(trimethylsilyl)ethynyl]phenyl}ethyl]-2-methylpropane-2-sulfinamide

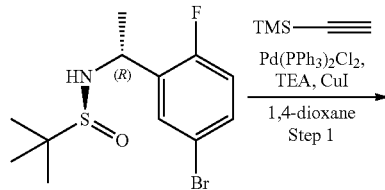

A mixture of (S)—N-[(1R)-1-(5-bromo-2-fluorophenyl)ethyl]-2-methylpropane-2-sulfinamide (1.00 g, 3.103 mmol), trimethylsilylacetylene (1.52 g, 15.515 mmol), Pd(PPh$_3$)$_2$Cl$_2$ (217 mg, 0.310 mmol) and CuI (29 mg, 0.155 mmol) in TEA (10 mL) and 1,4-dioxane (10 mL) was stirred for overnight at 100° C. under nitrogen atmosphere. The resulting mixture was concentrated under vacuum. The residue was purified by silica gel column chromatography, eluted with CH$_2$Cl$_2$/MeOH (20/1) to afford (S)—N-[(1R)-1-{2-fluoro-5-[2-(trimethylsilyl)ethynyl]phenyl}ethyl]-2-methylpropane-2-sulfinamide (840 mg, 79%) as a colorless oil. MS ESI calculated for C$_{17}$H$_{26}$FNOSSi [M+H]$^+$, 340.15, found 340.10. $^1$H NMR (300 MHz, Chloroform-d) δ 7.46-7.43 (m, 1H), 7.38-7.33 (m, 1H), 7.00-6.94 (m, 1H), 4.83-4.75 (m, 1H), 3.34 (d, J=5.2 Hz, 1H), 1.59 (d, J=2.5 Hz, 3H), 1.20 (s, 9H), 0.24 (s, 9H).

Preparation 98B: (1R)-1-(5-ethynyl-2-fluorophenyl)ethanamine

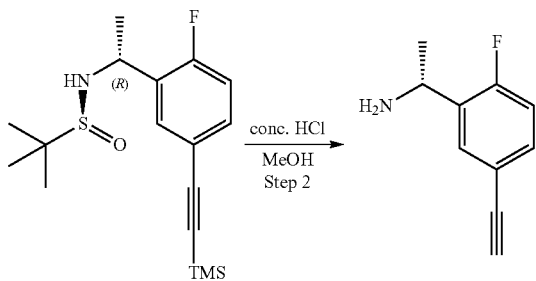

A solution of (S)—N-[(1R)-1-{2-fluoro-5-[2-(trimethylsilyl)ethynyl]phenyl}ethyl]-2-methylpropane-2-sulfinamide (840 mg, 2.474 mmol) in conc. HCl (2 mL) and MeOH (6 mL) was stirred for 2 h at room temperature. The resulting mixture was concentrated under reduced pressure. The residue was purified by silica gel column chromatography, eluted with CH$_2$Cl$_2$/MeOH (8/1) to afford (1R)-1-(5-ethynyl-2-fluorophenyl)ethanamine (95 mg, 21%) as a yellow oil. MS ESI calculated for C$_{10}$H$_{10}$FN [M+H]$^+$, 164.08, found 164.10. $^1$H NMR (400 MHz, DMSO-d$_6$) δ 7.71-7.69 (m, 1H), 7.38-7.34 (m, 1H), 7.16-7.11 (m, 1H), 4.24-4.19 (m, 1H), 4.14 (s, 1H), 2.30-2.11 (m, 2H), 1.23 (d, J=6.6 Hz, 3H).

Example 98: 3-chloro-6-[6-(dimethylphosphoryl)pyridin-3-yl]-N-[(1R)-1-(5-ethynyl-2-fluorophenyl)ethyl]-7-fluoro-2-methyl-1,5-naphthyridin-4-amine

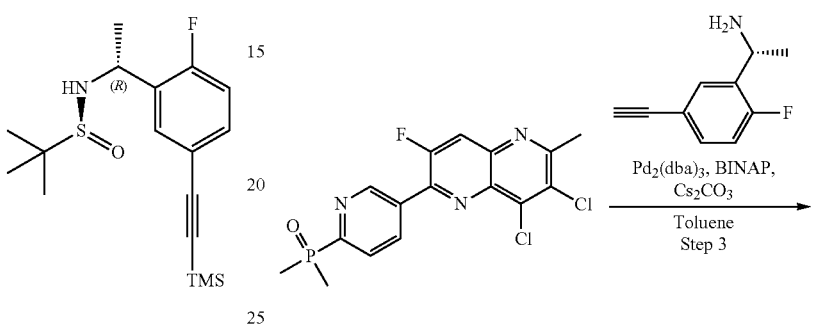

A mixture of (1R)-1-(5-ethynyl-2-fluorophenyl)ethanamine (50 mg, 0.312 mmol), 3,4-dichloro-6-[6-(dimethylphosphoryl)pyridin-3-yl]-7-fluoro-2-methyl-1,5-naphthyridine (100 mg, 0.260 mmol), Pd$_2$(dba)$_3$ (23 mg, 0.026 mmol), BINAP (32 mg, 0.052 mmol) and Cs$_2$CO$_3$ (212 mg, 0.650 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-chloro-6-[6-(dimethylphosphoryl)pyridin-3-yl]-N-[(1R)-1-(5-ethynyl-2-fluorophenyl)ethyl]-7-fluoro-2-methyl-1,5-naphthyridin-4-amine (45 mg, 33%) as a yellow solid. MS ESI calculated for C$_{26}$H$_{22}$ClF$_2$N$_4$OP [M+H]$^+$, 511.12, found 511.25. $^1$H NMR (400 MHz, Chloroform-d) δ 9.25 (s, 1H), 8.33-8.24 (m, 2H), 7.96 (d, J=12.2 Hz, 1H), 7.40-7.38 (m, 1H), 7.36-7.29 (m, 1H), 6.96-6.91 (m, 1H), 6.49 (s, 1H), 6.40-6.33 (m, 1H), 2.98 (s, 1H), 2.74 (s, 3H), 1.87 (s, 3H), 1.84 (s, 3H), 1.70 (d, J=6.7 Hz, 3H); $^{19}$F NMR (377 MHz, Chloroform-d) δ −115.84, −120.86. $^{31}$P NMR (162 MHz, Chloroform-d) δ 36.48.

Example 99: 3-[(1R)-1-({3-chloro-6-[6-(dimethylphosphoryl)pyridin-3-yl]-7-fluoro-2-methyl-1,5-naphthyridin-4-yl}amino)ethyl]-5-fluorobenzonitrile Synthetic Scheme

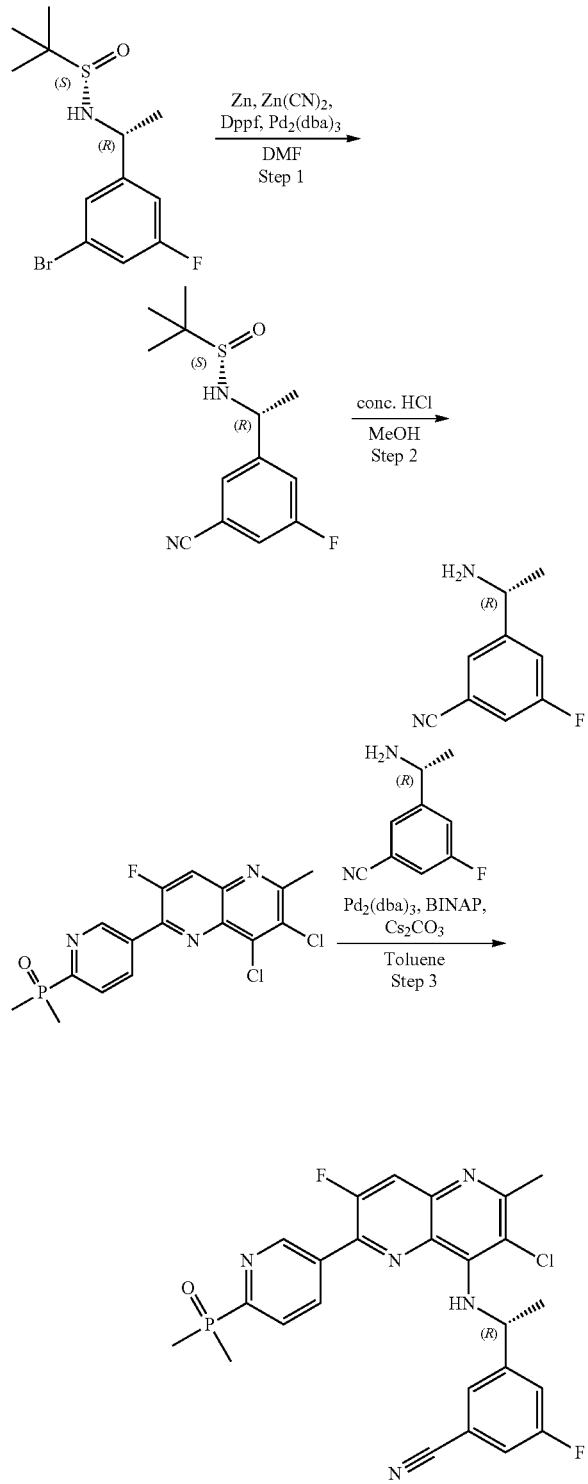

Preparation 99A: (S)—N-[(1R)-1-(3-cyano-5-fluorophenyl)ethyl]-2-methylpropane-2-sulfinamide

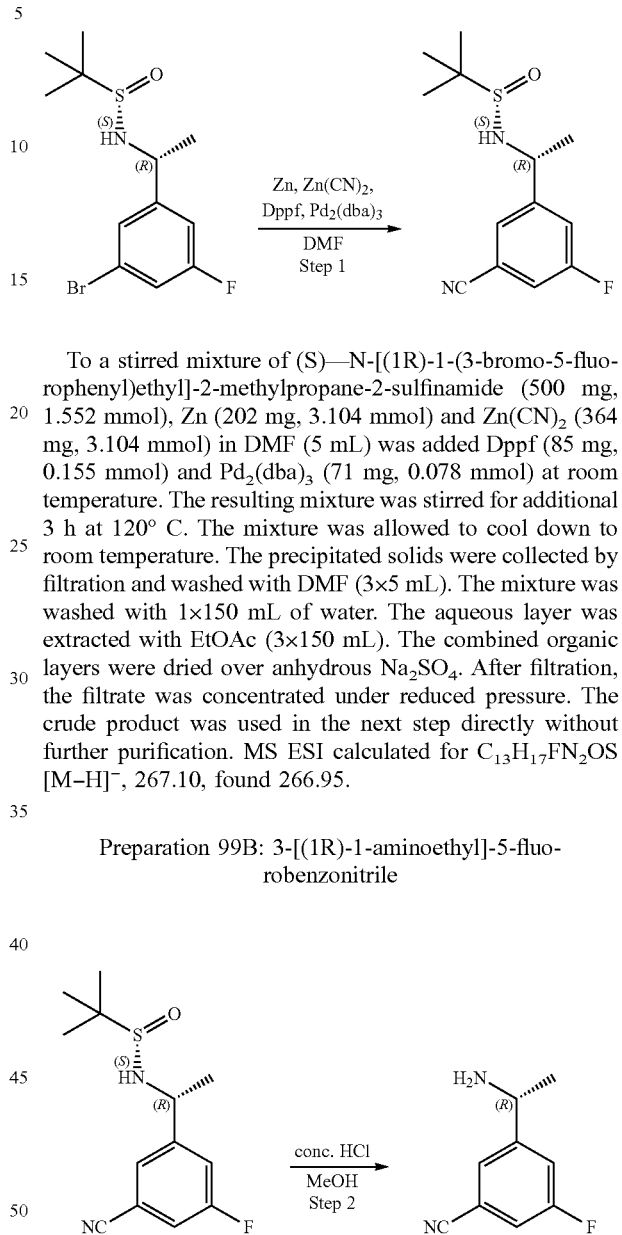

To a stirred mixture of (S)—N-[(1R)-1-(3-bromo-5-fluorophenyl)ethyl]-2-methylpropane-2-sulfinamide (500 mg, 1.552 mmol), Zn (202 mg, 3.104 mmol) and Zn(CN)$_2$ (364 mg, 3.104 mmol) in DMF (5 mL) was added Dppf (85 mg, 0.155 mmol) and Pd$_2$(dba)$_3$ (71 mg, 0.078 mmol) at room temperature. The resulting mixture was stirred for additional 3 h at 120° C. The mixture was allowed to cool down to room temperature. The precipitated solids were collected by filtration and washed with DMF (3×5 mL). The mixture was washed with 1×150 mL of water. The aqueous layer was extracted with EtOAc (3×150 mL). The combined organic layers were dried over anhydrous Na$_2$SO$_4$. After filtration, the filtrate was concentrated under reduced pressure. The crude product was used in the next step directly without further purification. MS ESI calculated for C$_{13}$H$_{17}$FN$_2$OS [M−H]$^-$, 267.10, found 266.95.

Preparation 99B: 3-[(1R)-1-aminoethyl]-5-fluorobenzonitrile

To a stirred solution of (S)—N-[(1R)-1-(3-cyano-5-fluorophenyl)ethyl]-2-methylpropane-2-sulfinamide (330 mg, 1.230 mmol) in MeOH (3 mL) was added conc. HCl (1 mL) dropwise at room temperature. The resulting mixture was stirred for 1 h at room temperature. The resulting mixture was concentrated under reduced pressure. The resulting mixture was extracted with CH$_2$Cl$_2$ (3×60 mL). The aqueous layer was basified to pH 10 with saturated Na$_2$CO$_3$ (aq.) and extracted with EtOAc (4×50 mL). The combined organic layers were dried over anhydrous Na$_2$SO$_4$. After filtration, the filtrate was concentrated under reduced pressure. This resulted in 3-[(1R)-1-aminoethyl]-5-fluorobenzonitrile (100 mg, 49%) as a brown oil. MS ESI calculated for C$_9$H$_9$FN$_2$ [M+H]$^+$, 165.07, found 165.05.

295

Example 99: 3-[(1R)-1-({3-chloro-6-[6-(dimethylphosphoryl)pyridin-3-yl]-7-fluoro-2-methyl-1,5-naphthyridin-4-yl}amino)ethyl]-5-fluorobenzonitrile

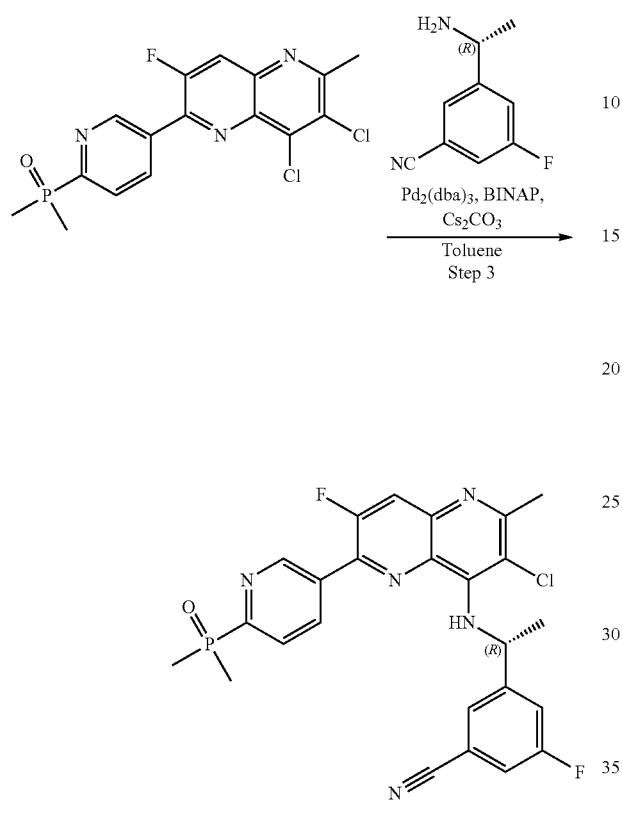

To a stirred mixture of 3,4-dichloro-6-[6-(dimethylphosphoryl)pyridin-3-yl]-7-fluoro-2-methyl-1,5-naphthyridine (100 mg, 0.260 mmol), 3-[(1R)-1-aminoethyl]-5-fluorobenzonitrile (51 mg, 0.312 mmol) and $Cs_2CO_3$ (127 mg, 0.390 mmol) in Toluene (1 mL) were added $Pd_2(dba)_3$ (23 mg, 0.026 mmol) and BINAP (32 mg, 0.052 mmol) at room temperature under nitrogen atmosphere. The resulting mixture was stirred for 3 h at 100° C. under nitrogen atmosphere. The mixture was allowed to cool down to room temperature. The residue was purified by silica gel column chromatography, eluted with $CH_2Cl_2$/MeOH (12/1) followed by reversed-phase flash chromatography with the following conditions: Column: C18 Column 120 g; Mobile Phase A: water (0.1% $NH_4HCO_3$), Mobile Phase B: $CH_3CN$; Flow rate: 50 mL/min; Gradient: 35% B to 70% B in 30 min; 254/220 nm to afford 3-[(1R)-1-({3-chloro-6-[6-(dimethylphosphoryl)pyridin-3-yl]-7-fluoro-2-methyl-1,5-naphthyridin-4-yl}amino)ethyl]-5-fluorobenzonitrile (58 mg, 43%) as a greenish solid. MS ESI calculated for $C_{25}H_{21}ClF_2N_5OP$ [M+H]$^+$, 512.11, found 512.00. $^1$H NMR (300 MHz, Chloroform-d) δ 9.09 (s, 1H), 8.31-8.26 (m, 2H), 8.00 (d, J=11.3 Hz, 1H), 7.33 (d, J=1.6 Hz, 1H), 7.22-7.13 (m, 2H), 6.35 (s, 1H), 6.20-6.11 (m, 1H), 2.76 (s, 3H), 1.88 (s, 3H), 1.84 (s, 3H), 1.70 (d, J=6.8 Hz, 3H). $^{19}$F NMR (282 MHz, Chloroform-d) δ −108.84, −122.43. $^{31}$P NMR (121 MHz, Chloroform-d) δ 36.60.

296

Example 100 and 101: (R)-(5-(3-chloro-7-fluoro-2-methyl-4-((1-(pyrimidin-5-yl)ethyl)amino)quinolin-6-yl)pyridin-2-yl)dimethylphosphine oxide and (S)-(5-(3-chloro-7-fluoro-2-methyl-4-((1-(pyrimidin-5-yl)ethyl)amino)quinolin-6-yl)pyridin-2-yl)dimethylphosphine oxide Synthetic Scheme

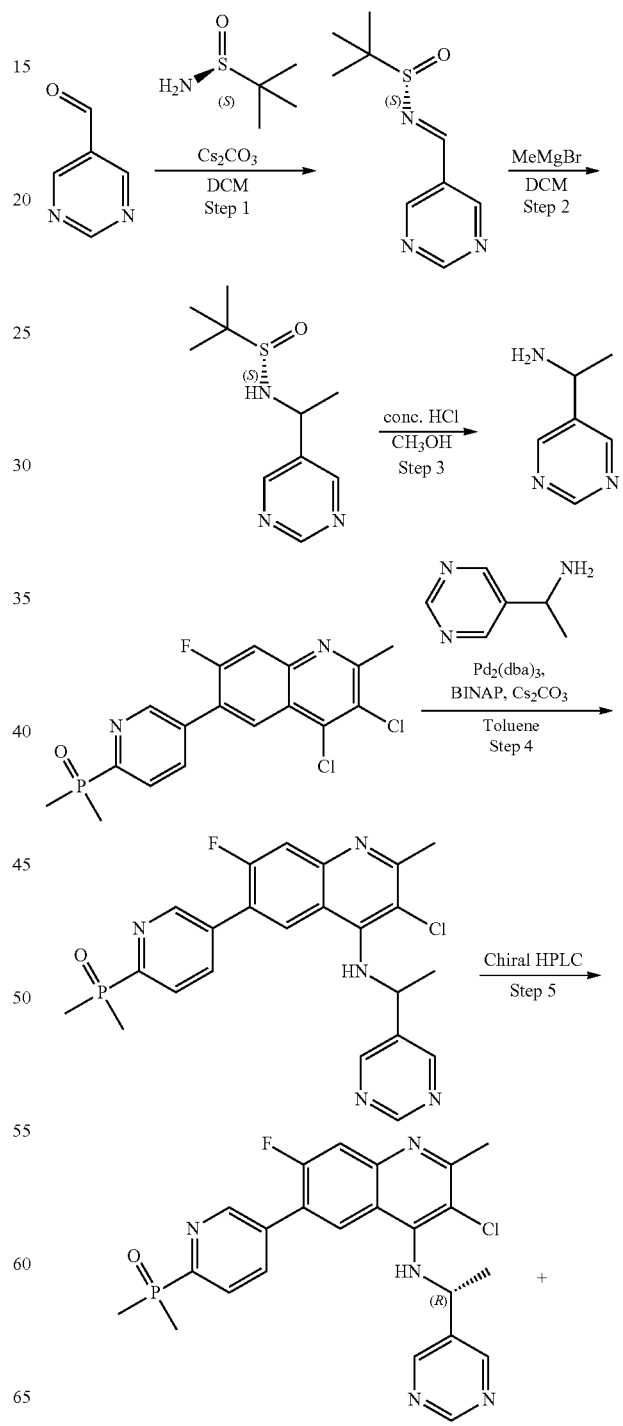

-continued

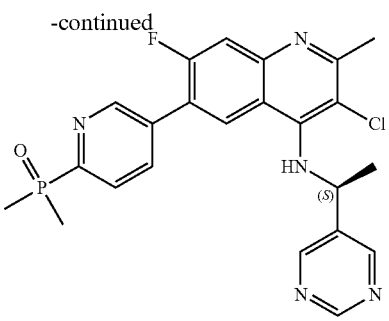

Preparation 100A: (S)-2-methyl-N-(pyrimidin-5-ylmethylidene)propane-2-sulfinamide

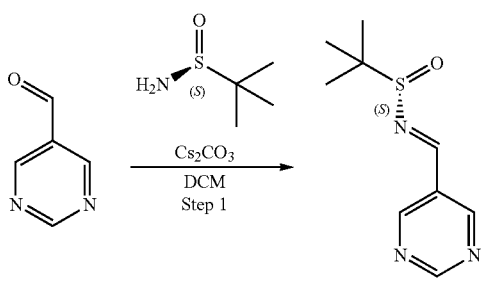

A mixture of pyrimidine-5-carbaldehyde (5.00 g, 46.253 mmol), (S)-2-methylpropane-2-sulfinamide (6.73 g, 55.504 mmol) and Cs$_2$CO$_3$ (30.14 g, 92.506 mmol) in DCM (50 mL) was stirred for overnight at room temperature under nitrogen atmosphere. The resulting mixture was filtered, and the filter cake was washed with DCM (3×100 mL). The filtrate was concentrated under reduced pressure. The residue was purified by silica gel column chromatography, eluted with PE/EA (7/1) to afford (S)-2-methyl-N-(pyrimidin-5-ylmethylidene)propane-2-sulfinamide (7.68 g, 78%) as a white solid. MS ESI calculated for C$_9$H$_{13}$N$_3$OS [M+H]$^+$, 212.08, found 212.00. $^1$H NMR (400 MHz, Chloroform-d) δ 9.31 (s, 1H), 9.15 (s, 2H), 8.64 (s, 1H), 1.27 (s, 9H).

Preparation 100B: (S)-2-methyl-N-(1-(pyrimidin-5-yl)ethyl)propane-2-sulfinamide

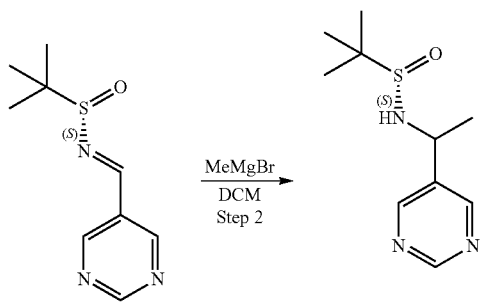

To a stirred solution of (S)-2-methyl-N-(pyrimidin-5-ylmethylidene)propane-2-sulfinamide (3.00 g, 14.199 mmol) in DCM (30 mL) was added 1 M of bromo(methyl) magnesium in THF (28.4 mL, 28.398 mmol) dropwise at −35° C. under nitrogen atmosphere. The resulting mixture was stirred for 30 min at −35° C. under nitrogen atmosphere. The reaction was quenched with sat. NH$_4$Cl (aq.) at 0° C. The resulting mixture was filtered, and the filter cake was washed with DCM (3×50 mL). The filtrate was concentrated under reduced pressure. The resulting mixture was extracted with CH$_2$Cl$_2$ (3×50 mL). The combined organic layers were dried over anhydrous Na$_2$SO$_4$. After filtration, the filtrate was concentrated under reduced pressure. The residue was purified by silica gel column chromatography, eluted with CH$_2$Cl$_2$/MeOH (12/1) to afford (S)-2-methyl-N-[(1S)-1-(pyrimidin-5-yl)ethyl]propane-2-sulfinamide (830 mg, 25%) as a yellow solid. MS ESI calculated for C$_{10}$H$_{17}$N$_3$OS [M+H]$^+$, 228.11, found 228.10. $^1$H NMR (300 MHz, Chloroform-d) δ 9.14 (d, J=3.9 Hz, 1H), 8.73 (d, J=9.4 Hz, 2H), 4.66-4.54 (m, 1H), 3.56-3.42 (m, 1H), 1.61-1.58 (m, 3H), 1.21 (d, J=7.3 Hz, 9H).

Preparation 100C: 1-(Pyrimidin-5-yl)ethan-1-amine

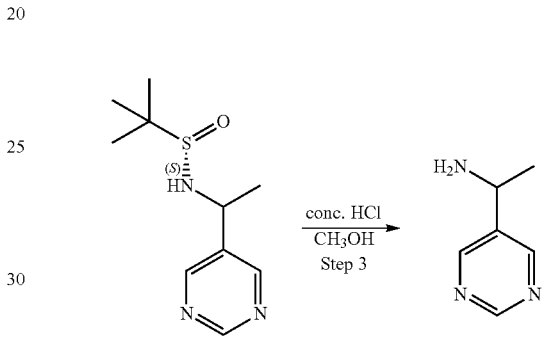

To a stirred solution of (S)-2-methyl-N-[(1S)-1-(pyrimidin-5-yl)ethyl]propane-2-sulfinamide (400 mg, 1.760 mmol) in MeOH (3 mL) was added conc. HCl (1 mL) dropwise at room temperature. The resulting mixture was stirred for 1 h at room temperature under air atmosphere. The resulting mixture was concentrated under reduced pressure. The resulting mixture was extracted with CH$_2$Cl$_2$ (1×50 mL). The mixture was basified to pH 10 with saturated Na$_2$CO$_3$ (aq.). The aqueous layer was extracted with EtOAc (4×50 mL). The combined organic layers were dried over anhydrous Na$_2$SO$_4$. After filtration, the filtrate was concentrated under reduced pressure. This resulted in (1S)-1-(pyrimidin-5-yl)ethanamine (165 mg, 76%) as a yellow green oil. MS ESI calculated for C$_6$H$_9$N$_3$ [M+H]$^+$, 124.08, found 124.10. $^1$H NMR (400 MHz, Methanol-d$_4$) δ 9.04 (s, 1H), 8.82 (s, 2H), 4.17-4.12 (m, 1H), 1.45 (d, J=6.8 Hz, 3H).

Preparation 100D: (5-(3-Chloro-7-fluoro-2-methyl-4-((1-(pyrimidin-5-yl)ethyl)amino)quinolin-6-yl)pyridin-2-yl)dimethylphosphine oxide

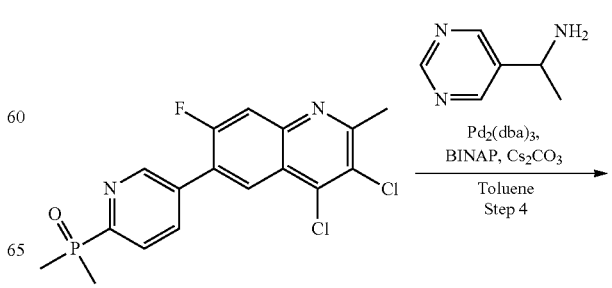

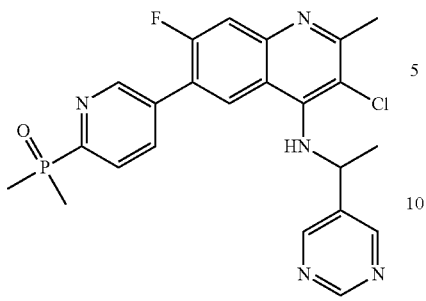

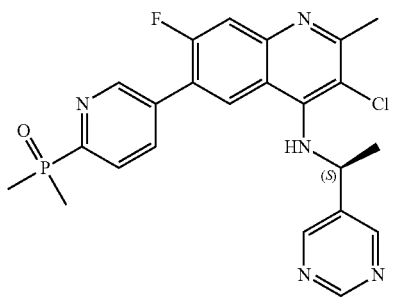

To a stirred mixture of 3,4-dichloro-6-[6-(dimethylphosphoryl)pyridin-3-yl]-7-fluoro-2-methylquinoline (100 mg, 0.261 mmol), 1-(pyrimidin-5-yl)ethanamine (38 mg, 0.313 mmol) and Cs$_2$CO$_3$ (127 mg, 0.392 mmol) in Toluene (1 mL) were added Pd$_2$(dba)$_3$ (23 mg, 0.026 mmol) and BINAP (32 mg, 0.052 mmol) at room temperature under nitrogen atmosphere. The resulting mixture was stirred for 3 h at 100° C. under nitrogen atmosphere. The resulting mixture was concentrated under reduced pressure. The residue was purified by silica gel column chromatography, eluted with CH$_2$Cl$_2$/MeOH (10/1) to afford (5-(3-chloro-7-fluoro-2-methyl-4-((1-(pyrimidin-5-yl)ethyl)amino)quinolin-6-yl)pyridin-2-yl)dimethylphosphine oxide (60 mg). MS ESI calculated for C$_{23}$H$_{22}$ClFN$_5$OP [M+H]$^+$, 470.12, found 470.15.

Example 100 and 101: (R)-(5-(3-chloro-7-fluoro-2-methyl-4-((1-(pyrimidin-5-yl)ethyl)amino)quinolin-6-yl)pyridin-2-yl)dimethylphosphine oxide and (S)-(5-(3-chloro-7-fluoro-2-methyl-4-((1-(pyrimidin-5-yl)ethyl)amino)quinolin-6-yl)pyridin-2-yl)dimethylphosphine oxide

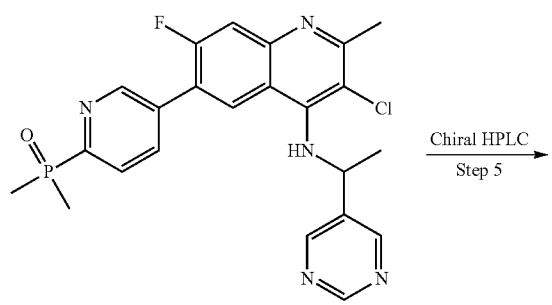

(5-(3-chloro-7-fluoro-2-methyl-4-((1-(pyrimidin-5-yl)ethyl)amino)quinolin-6-yl)pyridin-2-yl)dimethylphosphine oxide (60 mg) was resolved by Chiral-Prep-HPLC with the following conditions (Column: CHIRAL ART Cellulose-SB, :0.46*5 cm·3 um; Mobile Phase A: Hex(10 mM NH$_3$), Mobile Phase B: IPA; Flow rate: 20 mL/min; Gradient: 20% B; 220 nm; RT1=20.37 min, RT2=28.64 min). The first peak afforded 23 mg (18%) as a white solid. MS ESI calculated for C$_{23}$H$_{22}$ClFN$_5$OP [M+H]$^+$, 470.12, found 470.00. 1H NMR (300 MHz, Chloroform-d) δ 9.14 (s, 1H), 8.84 (s, 1H), 8.76 (s, 2H), 8.13 (d, J=6.4 Hz, 1H), 8.08-7.91 (m, 1H), 7.90-7.73 (m, 1H), 5.13 (s, 2H), 2.78 (s, 3H), 1.94-1.75 (m, 9H). $^{19}$F NMR (282 MHz, Chloroform-d) δ -114.53. $^{31}$P NMR (121 MHz, Chloroform-d) δ 36.55.

The second peak afforded 14 mg (11%) as a white solid. MS ESI calculated for C23H$_{22}$ClFN$_5$OP [M+H]$^+$, 470.12, found 470.00. 1H NMR (300 MHz, Chloroform-d) δ 9.14 (s, 1H), 8.84 (d, J=2.0 Hz, 1H), 8.75 (s, 2H), 8.17-8.12 (m, 1H), 7.99-7.91 (m, 1H), 7.77 (d, J=11.5 Hz, 1H), 5.12 (s, 2H), 2.77 (s, 3H), 1.94-1.75 (m, 9H). $^{19}$F NMR (282 MHz, Chloroform-d) δ -114.39. $^{31}$P NMR (121 MHz, Chloroform-d) δ 36.54.

Example 102: 3-chloro-6-[6-(dimethylphosphoryl)pyridin-3-yl]-7-fluoro-N-[(1R)-1-(3-fluoropyridin-2-yl)propyl]-2-methylquinolin-4-amine

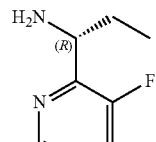

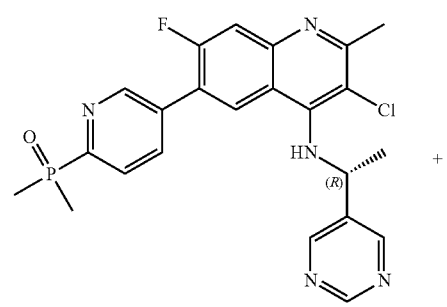

301

-continued

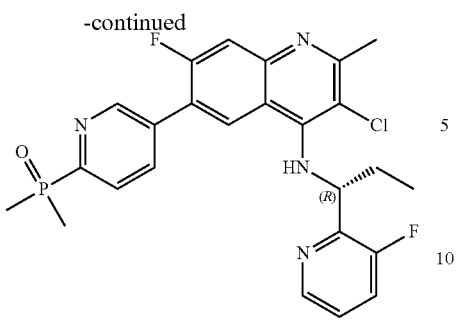

A mixture of 3,4-dichloro-6-[6-(dimethylphosphoryl)pyridin-3-yl]-7-fluoro-2-methylquinoline (100 mg, 0.261 mmol), (1R)-1-(3-fluoropyridin-2-yl)propan-1-amine (48 mg, 0.313 mmol), Pd₂(dba)₃ (24 mg, 0.026 mmol), BINAP (32 mg, 0.052 mmol) and Cs₂CO₃ (127 mg, 0.392 mmol) in Toluene (2 mL) was stirred for overnight at 100° C. under nitrogen atmosphere. The residue was purified by silica gel column chromatography, eluted with CH₂Cl₂/MeOH (10/1) to afford crude product. The residue was purified by reversed-phase flash chromatography with the following conditions: column, C18 silica gel; mobile phase, CH₃CN in water (10 mmol/L NH₄HCO₃), 45% to 55% gradient in 15 min; detector, 254 nm. This resulted in 3-chloro-6-[6-(dimethylphosphoryl)pyridin-3-yl]-7-fluoro-N-[(1R)-1-(3-fluoropyridin-2-yl)propyl]-2-methylquinolin-4-amine (73 mg, 55%) as a white solid. MS ESI calculated for $C_{25}H_{24}ClF_2N_4OP$ [M+H]⁺, 501.13, found 501.20. ¹H NMR (400 MHz, Methanol-d₄) δ 9.05 (s, 1H), 8.44-8.39 (m, 1H), 8.37-8.30 (m, 1H), 8.30-8.23 (m, 1H), 8.21-8.23 (m, 1H), 7.64-7.58 (m, 1H), 7.57-7.50 (m, 1H), 7.40-7.31 (m, 1H), 5.58-5.47 (m, 1H), 2.72-2.67 (m, 3H), 2.20-2.09 (m, 1H), 2.09-1.99 (m, 1H), 1.92 (s, 3H), 1.87 (s, 3H), 0.95-0.87 (m, 3H). ¹⁹F NMR (377 MHz, Methanol-d₄) δ -116.80, -128.38. ³¹P NMR (162 MHz, Methanol-d₄) δ 41.63.

Example 103: 4-[5-(3-chloro-4-{[(1R)-1-(2,3-difluorophenyl)ethyl]amino}-7-fluoro-2-methylquinolin-6-yl)pyridin-2-yl]-1,4lambda5-oxaphosphinan-4-one Synthetic Scheme

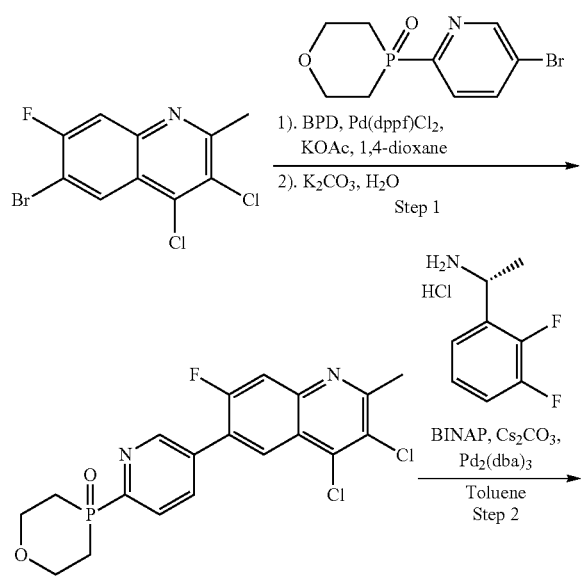

302

-continued

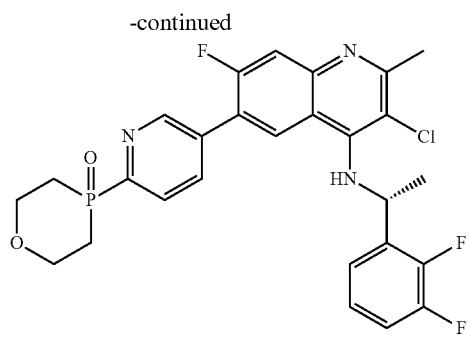

Preparation 103A: 4-[5-(3,4-dichloro-7-fluoro-2-methylquinolin-6-yl)pyridin-2-yl]-1,4lambda5-oxa-phosphinan-4-one

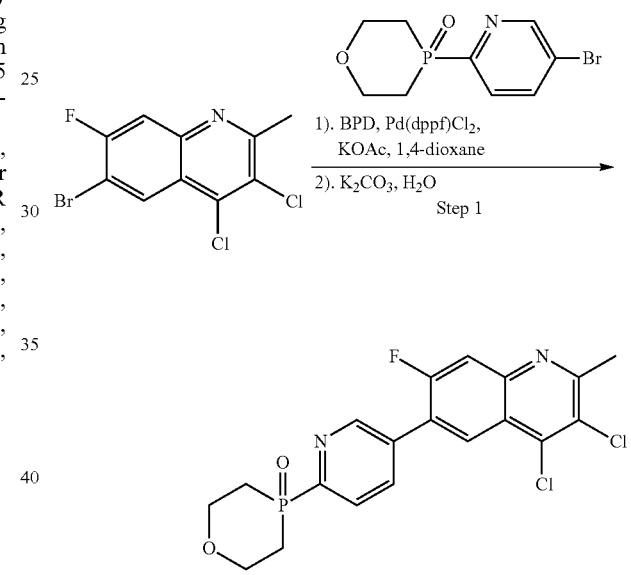

A mixture of 4-(5-bromopyridin-2-yl)-1,4lambda5-oxaphosphinan-4-one (147 mg, 0.533 mmol), BPD (210 mg, 0.825 mmol), KOAc (119.12 mg, 1.212 mmol) and Pd(dppf)Cl₂·CH₂Cl₂ (40 mg, 0.049 mmol) in 1,4-dioxane (2 mL) was stirred for 2 h at 100° C. under nitrogen atmosphere. The mixture was allowed to cool down to room temperature. To the above mixture were added 6-bromo-3,4-dichloro-7-fluoro-2-methylquinoline (150 mg, 0.485 mmol), K₂CO₃ (134 mg, 0.970 mmol) and H₂O (0.4 mL) at room temperature under nitrogen atmosphere. The resulting mixture was stirred for additional 2 h at 80° C. The resulting mixture was concentrated under reduced pressure. The residue was purified by silica gel column chromatography, eluted with CH₂Cl₂/MeOH (20/1) to afford 4-[5-(3,4-dichloro-7-fluoro-2-methylquinolin-6-yl)pyridin-2-yl]-1,4lambda5-oxaphosphinan-4-one (166 mg, 80%) as a brown yellow solid. MS ESI calculated for $C_{19}H_{16}Cl_2FN_2O_2P$ [M+H]⁺, 425.03, found 424.90. ¹H NMR (400 MHz, Chloroform-d) δ 9.04 (s, 1H), 8.32-8.23 (m, 2H), 8.19-8.13 (m, 1H), 7.84 (d, J=11.2 Hz, 1H), 4.36-4.16 (m, 4H), 2.88 (s, 3H), 2.62-2.50 (m, 2H), 2.19-2.08 (m, 2H).

303

Example 103: 4-[5-(3-chloro-4-{[(1R)-1-(2,3-difluorophenyl)ethyl]amino}-7-fluoro-2-methylquinolin-6-yl)pyridin-2-yl]-1,4lambda5-oxaphosphinan-4-one

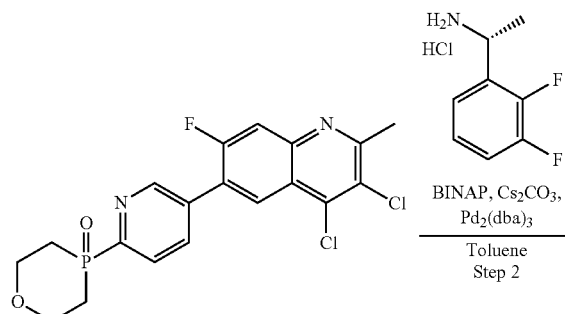

To a stirred solution of 4-[5-(3,4-dichloro-7-fluoro-2-methylquinolin-6-yl)pyridin-2-yl]-1,4lambda5-oxaphosphinan-4-one (100 mg, 0.235 mmol) and (1R)-1-(2,3-difluorophenyl)ethanamine hydrochloride (55 mg, 0.282 mmol) in Toluene (2 mL) were added Pd$_2$(dba)$_3$ (22 mg, 0.024 mmol), BINAP (29 mg, 0.047 mmol) and Cs$_2$CO$_3$ (192 mg, 0.587 mmol) at room temperature under nitrogen atmosphere. The resulting mixture was stirred for 16 h at 100° C. under nitrogen atmosphere. The resulting mixture was concentrated under reduced pressure. The residue was purified by silica gel column chromatography, eluted with CH$_2$Cl$_2$/MeOH (15/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in 4-[5-(3-chloro-4-{[(1R)-1-(2,3-difluorophenyl)ethyl]amino}-7-fluoro-2-methylquinolin-6-yl)pyridin-2-yl]-1,4lambda5-oxaphosphinan-4-one (44 mg, 34%) as a white solid. MS ESI calculated for C$_{27}$H$_{24}$ClF$_3$N$_3$O$_2$P [M+H]$^+$, 546.12, found 546.15. $^1$H NMR (400 MHz, Chloroform-d) δ 8.75 (s, 1H), 8.21-8.12 (m, 1H), 7.92-7.82 (m, 2H), 7.78-7.64 (m, 1H), 7.26-7.22 (m, 1H), 7.17-7.05 (m, 2H), 5.35-5.17 (m, 2H), 4.32-4.18 (m, 4H), 2.78 (s, 3H), 2.63-2.47 (m, 2H), 2.19-2.05 (m, 2H), 1.82-1.56 (m, 3H). $^{19}$F NMR (377 MHz, Chloroform-d) δ −115.09, −137.11, −137.17, −144.20, −144.26. $^{31}$P NMR (162 MHz, Chloroform-d) δ 25.43.

304

Example 104: 3-chloro-6-[6-(dimethylphosphoryl)pyridin-3-yl]-7-fluoro-2-methyl-N-[1-(1-methylpyrazol-4-yl)propyl]-1,5-naphthyridin-4-amine Synthetic Scheme

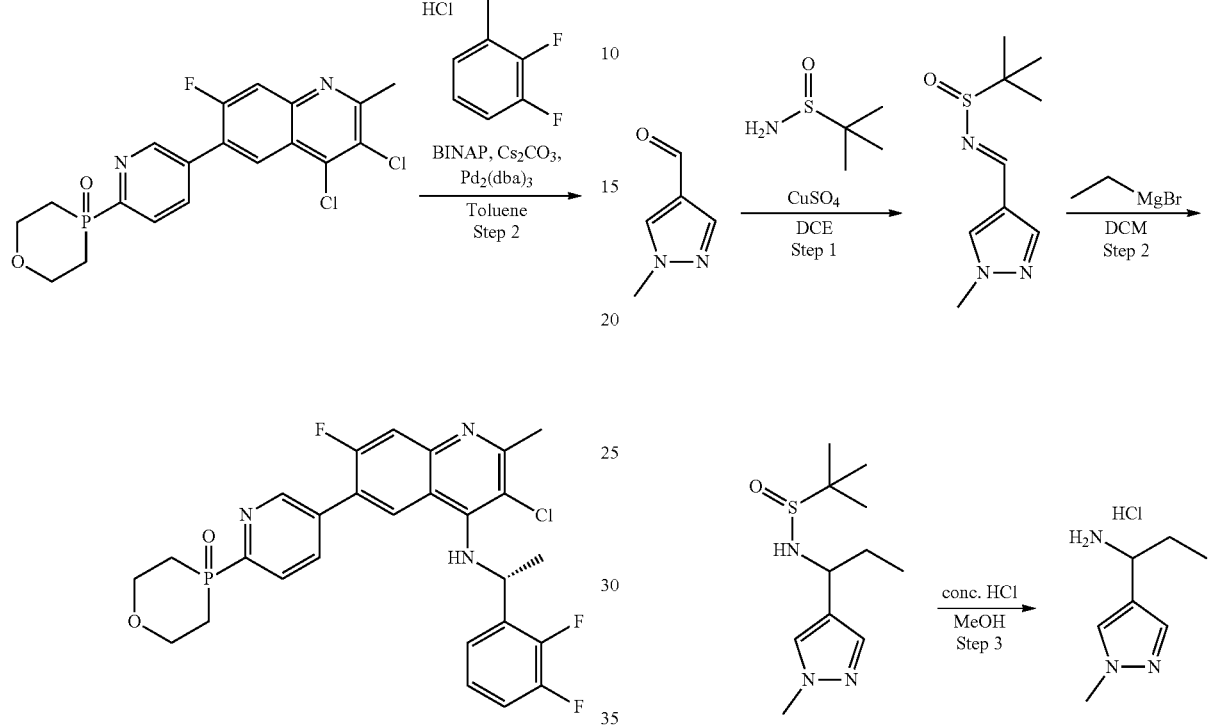

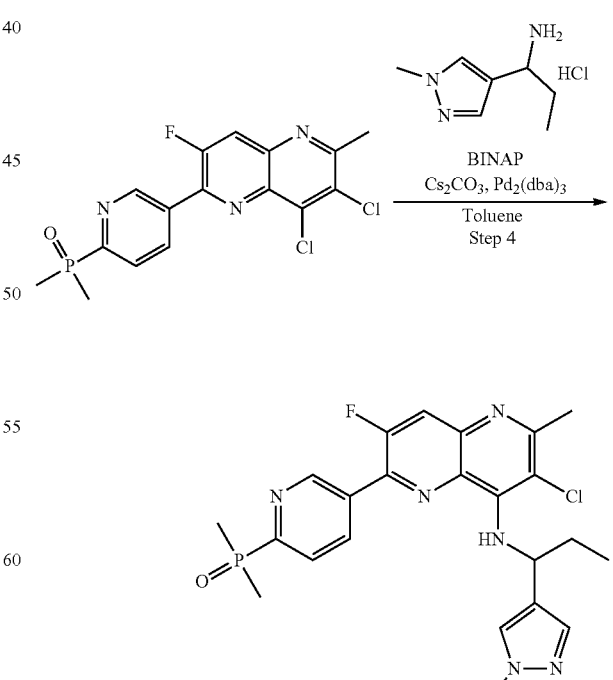

Preparation 104A: 2-methyl-N-[(1E)-(1-methylpyrazol-4-yl)methylidene]propane-2-sulfinamide

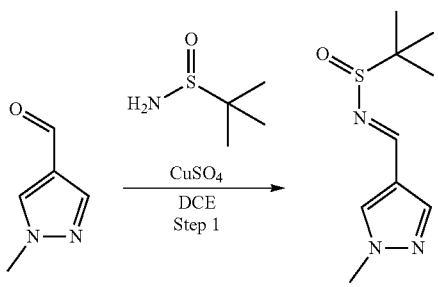

A mixture of 1-methylpyrazole-4-carbaldehyde (2.00 g, 18.163 mmol), tert-butanesulfinamide (2.64 g, 21.796 mmol) and cupric sulfate (5.80 g, 36.326 mmol) in DCE (20 mL) was stirred for overnight at 55° C. The resulting mixture was filtered, and the filter cake was washed with DCM (2×100 mL). The filtrate was concentrated under reduced pressure. The residue was purified by silica gel column chromatography, eluted with PE/EA (1/1) to afford 2-methyl-N-[(1E)-(1-methylpyrazol-4-yl)methylidene]propane-2-sulfinamide (3.30 g, 83%) as a yellow oil. MS ESI calculated for $C_9H_{15}N_3OS$ [M+H]$^+$, 214.09, found 214.10.

Preparation 104B: 2-methyl-N-[1-(1-methylpyrazol-4-yl)propyl]propane-2-sulfinamide

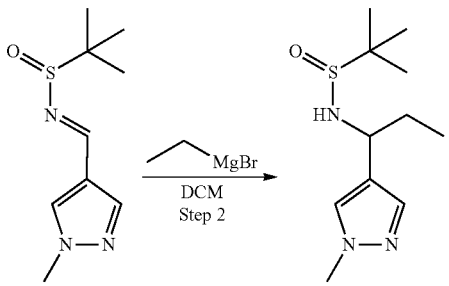

To a stirred mixture of 2-methyl-N-[(1E)-(1-methylpyrazol-4-yl)methylidene]propane-2-sulfinamide (3.30 g, 15.471 mmol) in DCM (35 mL) were added ethylmagnesium bromide (3.4 M in THF, 13.7 mL, 46.413 mmol) dropwise at −35° C. under nitrogen atmosphere for 30 min. The reaction was quenched with sat. NH$_4$Cl (aq.) at room temperature. The resulting mixture was filtered, and the filter cake was washed with ethyl acetate. The resulting mixture was extracted with EtOAc (2×100 mL). The combined organic layers dried over anhydrous Na$_2$SO$_4$. After filtration, the filtrate was concentrated under reduced pressure to afford 2-methyl-N-[1-(1-methylpyrazol-4-yl)propyl]propane-2-sulfinamide (2.90 g, 77%) as a yellow oil. MS ESI calculated for $C_{11}H_{21}N_3OS$ [M+H]$^+$, 244.14, found 244.00. $^1$H NMR (400 MHz, Chloroform-d) δ 7.47-7.37 (m, 1H), 7.32-7.26 (m, 1H), 4.36-4.22 (m, 1H), 3.91-3.85 (m, 3H), 1.92-1.74 (m, 2H), 1.25-1.15 (m, 9H), 0.98-0.85 (m, 3H).

Preparation 104C: 1-(1-methylpyrazol-4-yl)propan-1-amine hydrochloride

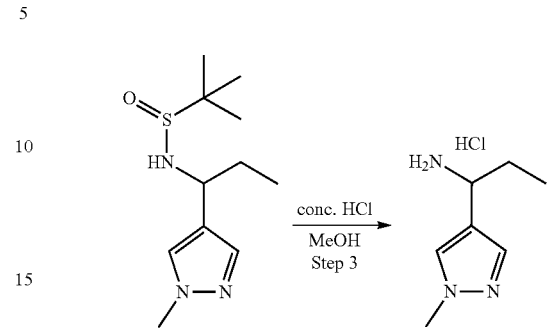

To a stirred solution of 2-methyl-N-[1-(1-methylpyrazol-4-yl)propyl]propane-2-sulfinamide (500 mg, 2.054 mmol) in methanol (3 mL) was added conc.HCl (1 mL) dropwise at room temperature. The resulting mixture was stirred for 1 h at room temperature. The resulting mixture was concentrated under vacuum to afford 1-(1-methylpyrazol-4-yl)propan-1-amine hydrochloride (260 mg, 72%) as a yellow oil. MS ESI calculated for $C_7H_{13}N_3$[M+H]$^+$, 140.11, found 141.05. $^1$H NMR (300 MHz, Methanol-d$_4$) δ 8.07 (s, 1H), 7.96 (s, 1H), 4.37-4.28 (m, 1H), 4.05 (s, 3H), 2.13-1.93 (m, 2H), 0.99 (t, J=7.4 Hz, 3H).

Example 104: 3-chloro-6-[6-(dimethylphosphoryl)pyridin-3-yl]-7-fluoro-2-methyl-N-[1-(1-methylpyrazol-4-yl)propyl]-1,5-naphthyridin-4-amine

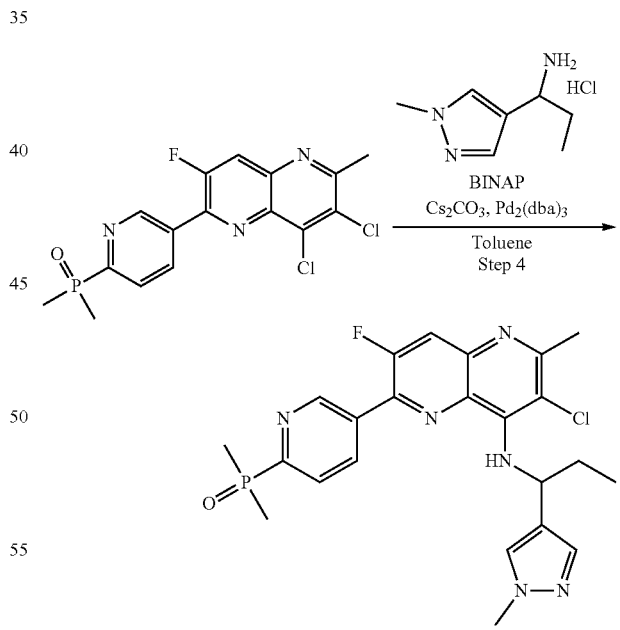

To a stirred mixture of 3,4-dichloro-6-[6-(dimethylphosphoryl)pyridin-3-yl]-7-fluoro-2-methyl-1,5-naphthyridine (80 mg, 0.208 mmol), Cs$_2$CO$_3$ (203 mg, 0.624 mmol) and 1-(1-methylpyrazol-4-yl)propan-1-amine hydrochloride (73 mg, 0.416 mmol) in Toluene (1 mL) were added BINAP (25 mg, 0.042 mmol) and Pd$_2$(dba)$_3$ (19 mg, 0.021 mmol) at room temperature under nitrogen atmosphere. The resulting mixture was stirred for 16 h at 80° C. under nitrogen atmosphere. The resulting mixture was concentrated under reduced pressure. The mixture was purified by silica gel column chromatography, eluted with CH₂Cl₂/MeOH (12/1) followed by reversed-phase flash chromatography with the following conditions: column, C18 silica gel; mobile phase, CH₃CN in water (10 mmol/L NH₄HCO₃), 40% to 70% gradient in 30 min; detector, 254 nm. This resulted in 3-chloro-6-[6-(dimethylphosphoryl)pyridin-3-yl]-7-fluoro-2-methyl-N-[1-(1-methylpyrazol-4-yl)propyl]-1,5-naphthyridin-4-amine (47 mg, 46%) as a yellow green solid. MS ESI calculated for $C_{23}H_{25}ClFN_6OP$ $[M+H]^+$, 487.15, found 487.00. ¹H NMR (400 MHz, Chloroform-d) δ 9.29 (s, 1H), 8.41-8.35 (m, 1H), 8.26-8.23 (m, 1H), 7.93 (d, J=11.7 Hz, 1H), 7.42-7.38 (m, 1H), 7.23 (s, 1H), 6.45-6.22 (m, 1H), 6.05-5.99 (m, 1H), 3.86-3.82 (m, 3H), 2.76-2.71 (m, 3H), 2.03-1.96 (m, 2H), 1.85 (s, 3H), 1.83 (s, 3H), 1.03-0.99 (m, 3H). ¹⁹F NMR (377 MHz, Chloroform-d) δ −120.83. ³¹P NMR (162 MHz, Chloroform-d) δ 36.41.

Example 105: 3-chloro-6-{6-[(dimethylphosphoryl)methoxy]pyridin-3-yl}-7-fluoro-N-[(1R)-1-(2-fluorophenyl)ethyl]-2-methylquinolin-4-amine Synthetic Scheme

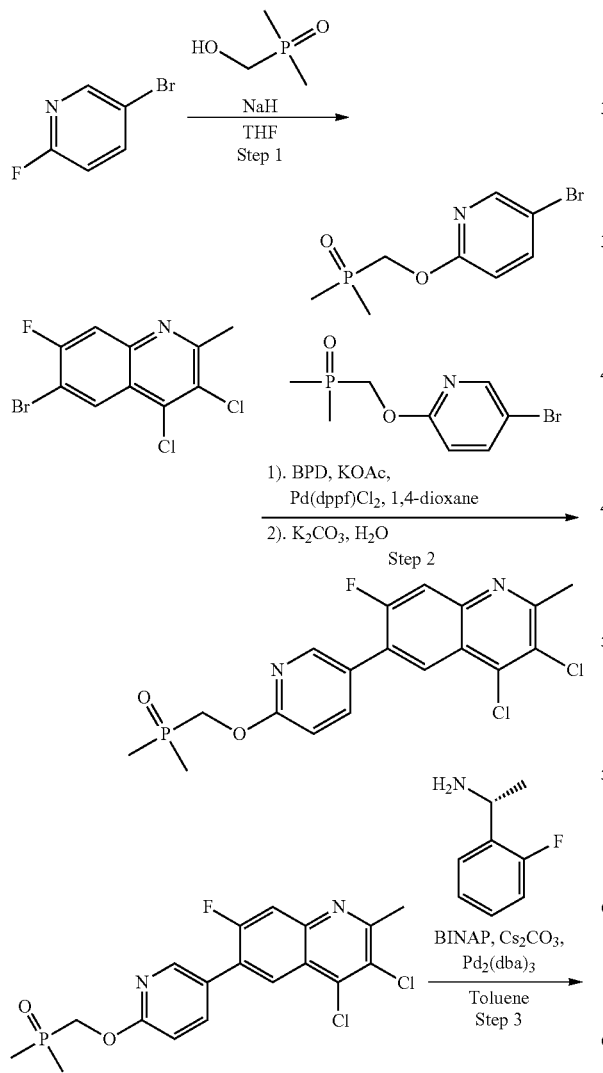

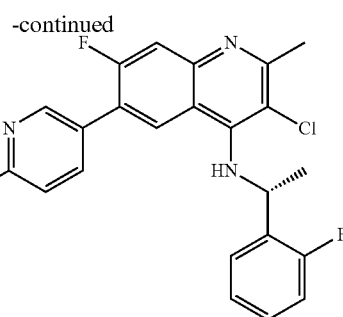

Preparation 105A 5-bromo-2-[(dimethylphosphoryl)methoxy]pyridine

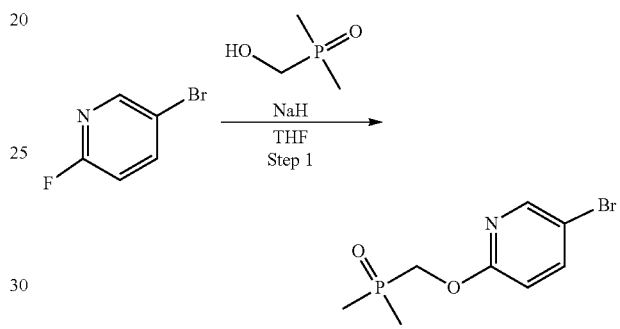

To a solution of (dimethylphosphoryl)methanol (307 mg, 2.841 mmol) in THF (10 mL) was added sodium hydride (60% in oil, 125 mg) at 0 degrees C. The mixture was stirred for 30 min at room temperature. 5-bromo-2-fluoropyridine (500 mg, 2.841 mmol) was added and the mixture was allowed to warm to room temperature and stirred for 3 h. The reaction mixture was quenched by water and extracted with DCM (3×25 mL). The residue was purified by reversed-phase flash chromatography with the following conditions: column, C18 silica gel; mobile phase, CH₃CN in water (10 mmol/L NH₄HCO₃), 10% to 50% gradient in 30 min; detector, 254 nm. This resulted in 5-bromo-2-[(dimethylphosphoryl)methoxy]pyridine (700 mg, 93%) as a white solid. MS ESI calculated for $C_8H_{11}BrNO_2P$ $[M+H]^+$, 263.97, found 264.00. ¹H NMR (400 MHz, Chloroform-d) δ 8.22-8.19 (m, 1H), 7.73-7.68 (m, 1H), 6.77-6.73 (m, 1H), 4.62 (d, J=5.9 Hz, 2H), 1.60 (s, 3H), 1.57 (s, 3H).

Preparation 105B: 3,4-dichloro-6-{6-[(dimethylphosphoryl)methoxy]pyridin-3-yl}-7-fluoro-2-methylquinoline

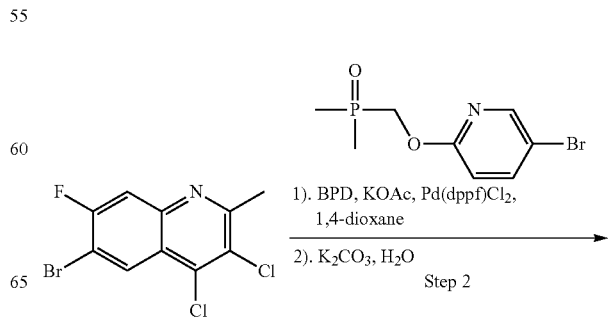

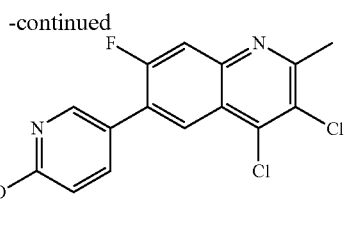

To a solution of 5-bromo-2-[(dimethylphosphoryl)methoxy]pyridine (470 mg, 1.780 mmol) and BPD (501 mg, 1.974 mmol) in 1,4-dioxane (5 mL) were added potassium acetate (476 mg, 4.854 mmol) and Pd(dppf)Cl$_2$·CH$_2$Cl$_2$ (132 mg, 0.162 mmol). After stirring for 2 h at 80° C. under a nitrogen atmosphere, to the above mixture was added 6-bromo-3,4-dichloro-7-fluoro-2-methylquinoline (500 mg, 1.618 mmol), K$_2$CO$_3$ (447 mg, 3.236 mmol) in H$_2$O (1 mL) at room temperature. The resulting mixture was stirred for additional 3 h at 80° C. The residue was purified by silica gel column chromatography, eluted with CH$_2$Cl$_2$/MeOH (9/1) to afford 3,4-dichloro-6-{6-[(dimethylphosphoryl)methoxy]pyridin-3-yl}-7-fluoro-2-methylquinoline (200 mg, 29%) as a brown solid. MS ESI calculated for C$_{18}$H$_{16}$Cl$_2$FN$_2$O$_2$P [M+H]$^+$, 413.03, found 413.10. $^1$H NMR (400 MHz, Chloroform-d) δ 8.49-8.40 (m, 1H), 8.17 (d, J=8.0 Hz, 1H), 7.99-7.88 (m, 1H), 7.82-7.67 (m, 1H), 6.99-6.93 (m, 1H), 4.81-4.76 (m, 2H), 2.87 (s, 3H), 1.65 (s, 3H), 1.68 (s, 3H).

Example 105: 3-chloro-6-{6-[(dimethylphosphoryl)methoxy]pyridin-3-yl}-7-fluoro-N-[(1R)-1-(2-fluorophenyl)ethyl]-2-methylquinolin-4-amine

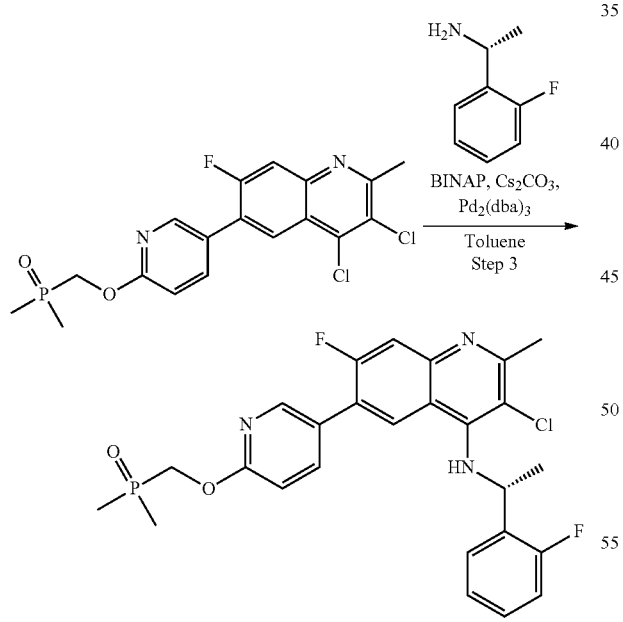

To a solution of 3,4-dichloro-6-{6-[(dimethylphosphoryl)methoxy]pyridin-3-yl}-7-fluoro-2-methylquinoline (200 mg, 0.484 mmol), BINAP (60 mg, 0.097 mmol) and (1R)-1-(2-fluorophenyl)ethanamine (74 mg, 0.532 mmol) in Toluene (2 mL) were added Cs$_2$CO$_3$ (237 mg, 0.726 mmol) and Pd$_2$(dba)$_3$ (44 mg, 0.048 mmol). After stirring for 4 h at 100° C. under a nitrogen atmosphere, the resulting mixture was concentrated under reduced pressure. The resulting mixture was filtered; the filter cake was washed with MeOH (3×10 mL). The filtrate was concentrated under reduced pressure. The residue was purified by reversed-phase flash chromatography with the following conditions: column, C18 silica gel; mobile phase, CH$_3$CN in water (10 mmol/L NH$_4$HCO$_3$), 20% to 50% gradient in 30 min; detector, 254 nm. This resulted in 3-chloro-6-{6-[(dimethylphosphoryl)methoxy]pyridin-3-yl}-7-fluoro-N-[(1R)-1-(2-fluorophenyl)ethyl]-2-methylquinolin-4-amine (68 mg, 27%) as a white solid. MS ESI calculated for C$_{26}$H$_{25}$ClF$_2$N$_3$O$_2$P [M+H]$^+$, 516.13, found 516.10. $^1$H NMR (400 MHz, Chloroform-d) δ 8.23-8.19 (m, 1H), 7.86 (d, J=8.2 Hz, 1H), 7.68-7.57 (m, 2H), 7.51-7.44 (m, 1H), 7.32-7.24 (m, 1H), 7.18-7.11 (m, 1H), 7.10-7.02 (m, 1H), 6.85 (d, J=8.6 Hz, 1H), 5.39-5.13 (m, 2H), 4.76 (d, J=6.0 Hz, 2H), 2.75 (s, 3H), 1.70-1.66 (m, 6H), 1.64 (s, 3H). $^{19}$F NMR (377 MHz, Chloroform-d) δ −114.94, −118.96. $^{31}$P NMR (162 MHz, Chloroform-d) δ 41.87.

Example 106: 3-[(1R)-1-({3-chloro-6-[6-(dimethylphosphoryl)pyridin-3-yl]-7-fluoro-2-methyl-1,5-naphthyridin-4-yl}amino)ethyl]-4,5-difluorobenzonitrile Synthetic Scheme

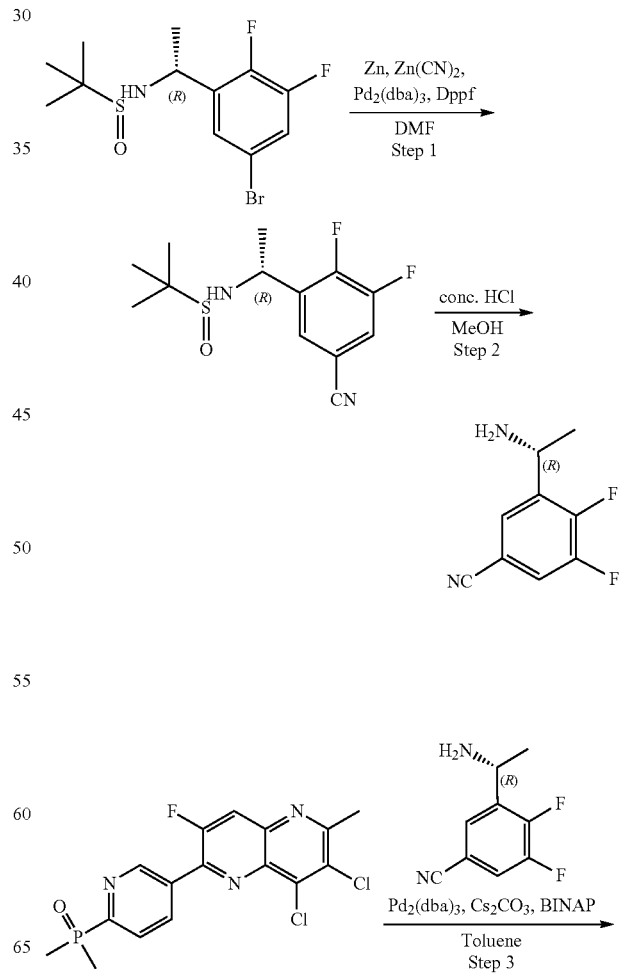

-continued

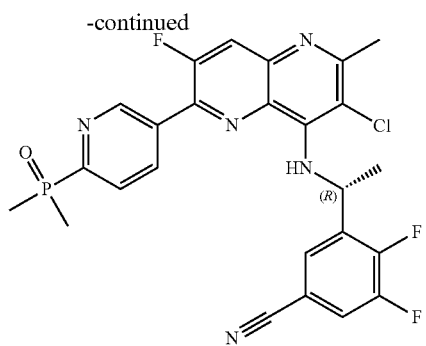

Preparation 106A: (S)—N-[(1R)-1-(5-cyano-2,3-difluorophenyl)ethyl]-2-methylpropane-2-sulfinamide

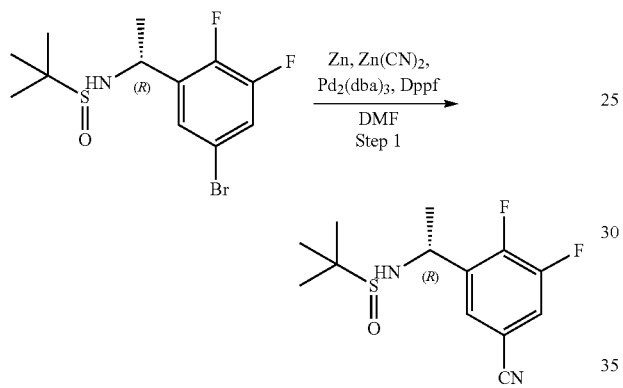

To a stirred solution of (S)—N-[(1R)-1-(5-bromo-2,3-difluorophenyl)ethyl]-2-methylpropane-2-sulfinamide (2.00 g, 5.878 mmol) and zinc cyanide (1.38 g, 11.756 mmol) in DMF (20 mL) were added Zn (0.77 g, 11.756 mmol), Pd$_2$(dba)$_3$ (0.54 g, 0.588 mmol) and Dppf (0.65 g, 1.176 mmol) at room temperature. The resulting mixture was stirred for 16 h at 100° C. under nitrogen atmosphere. The resulting mixture was concentrated under reduced pressure. The residue was purified by silica gel column chromatography, eluted with PE/EA (5:1) to afford (S)—N-[(1R)-1-(5-cyano-2,3-difluorophenyl)ethyl]-2-methylpropane-2-sulfinamide (1.40 g, 83%) as a yellow solid. MS ESI calculated for C$_{13}$H$_{16}$F$_2$N$_2$OS [M+H]$^+$, 287.10, found 287.05. $^1$H NMR (300 MHz, DMSO-d$_6$) δ 8.12-8.02 (m, 1H), 7.89-7.83 (m, 1H), 5.68 (d, J=6.4 Hz, 1H), 4.81-4.67 (m, 1H), 1.56-1.46 (m, 3H), 1.10 (s, 9H).

Preparation 106B: 3-[(1R)-1-aminoethyl]-4,5-difluorobenzonitrile

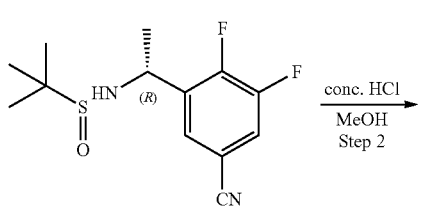

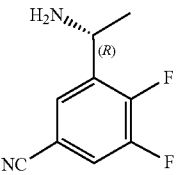

To a stirred solution of (S)—N-[(1R)-1-(5-cyano-2,3-difluorophenyl)ethyl]-2-methylpropane-2-sulfinamide (1.40 g, 4.889 mmol) in MeOH (15 mL) was added conc. HCl (5 mL) dropwise at room temperature. The resulting mixture was stirred for 2 h at room temperature under. The resulting mixture was concentrated under reduced pressure. The residue was dissolved in water (100 mL). The resulting mixture was washed with 2×50 mL of CH$_2$Cl$_2$. The combined aqueous layers were basified to pH 8 with saturated NaHCO$_3$ (aq.). The aqueous layer was extracted with CH$_2$Cl$_2$ (3×100 mL). The combined organic layers were washed with brine (2×100 mL), dried over anhydrous Na$_2$SO$_4$. After filtration, the filtrate was concentrated under reduced pressure. This resulted in 3-[(1R)-1-aminoethyl]-4,5-difluorobenzonitrile (750 mg, 84%) as a colorless oil. MS ESI calculated for C$_9$H$_8$F$_2$N$_2$[M+H]$^+$, 183.07, found 183.00. $^1$H NMR (300 MHz, Chloroform-d) δ 7.71-7.64 (m, 1H), 7.42-7.33 (m, 1H), 4.56-4.42 (m, 1H), 1.45-1.38 (m, 3H).

Example 106: 3-[(1R)-1-({3-chloro-6-[6-(dimethylphosphoryl)pyridin-3-yl]-7-fluoro-2-methyl-1,5-naphthyridin-4-yl}amino)ethyl]-4,5-difluorobenzonitrile

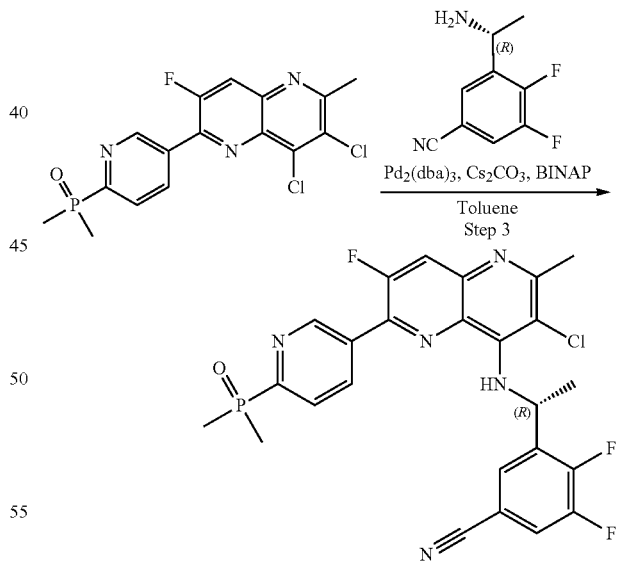

To a stirred solution of 3-[(1R)-1-aminoethyl]-4,5-difluorobenzonitrile (100 mg, 0.549 mmol) and 3,4-dichloro-6-[6-(dimethylphosphoryl)pyridin-3-yl]-7-fluoro-2-methyl-1,5-naphthyridine (169 mg, 0.439 mmol) in Toluene (2 mL) were added Cs$_2$CO$_3$ (268 mg, 0.824 mmol), Pd(PPh$_3$)$_4$(63 mg, 0.055 mmol) and BINAP (68 mg, 0.110 mmol) at room temperature under nitrogen atmosphere. The resulting mixture was stirred for 3 h at 100° C. under nitrogen atmosphere. The resulting mixture was concentrated under reduced pressure. The residue was purified by reversed-phase flash chromatography with the following conditions: column, C18 silica gel; mobile phase, CH$_3$CN in water (10 mmol/L NH$_4$HCO$_3$), 40% to 50% gradient in 20 min; detector, 254 nm. This resulted in 3-[(1R)-1-({3-chloro-6-[6-(dimethylphosphoryl)pyridin-3-yl]-7-fluoro-2-methyl-1,5-naphthyridin-4-yl}amino)ethyl]-4,5-difluorobenzonitrile (33 mg, 11%) as a light yellow solid. MS ESI calculated for C$_{25}$H$_{20}$ClF$_3$N$_5$OP [M+H]$^+$, 530.10, found 529.95. $^1$H NMR (300 MHz, DMSO-d$_6$) δ 8.96 (s, 1H), 8.32-8.24 (m, 1H), 8.18 (d, J=11.6 Hz, 1H), 8.11-8.05 (m, 1H), 8.01-7.93 (m, 1H), 7.91-7.85 (m, 1H), 6.91 (d, J=8.1 Hz, 1H), 6.34-6.19 (m, 1H), 2.66 (s, 3H), 1.76 (d, J=3.5 Hz, 3H), 1.72 (d, J=3.5 Hz, 3H), 1.65 (d, J=6.8 Hz, 3H). $^{19}$F NMR (282 MHz, DMSO-d$_6$) δ −121.30, −134.77, −135.61. $^{31}$P NMR (122 MHz, DMSO-d$_6$) δ 34.24.

Example 107: 3-chloro-N-[(1R)-1-(2,3-difluorophenyl)ethyl]-6-[6-(dimethylphosphoryl)-5-fluoropyridin-3-yl]-7-fluoro-2-methyl-1,5-naphthyridin-4-amine

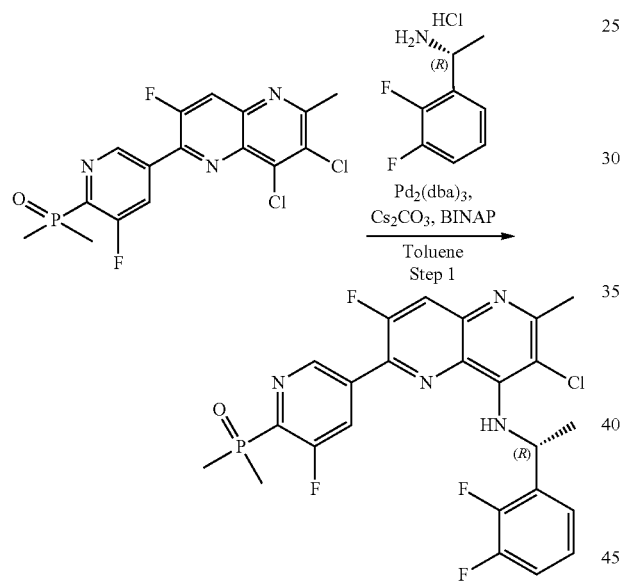

To a stirred solution of 3,4-dichloro-6-[6-(dimethylphosphoryl)-5-fluoropyridin-3-yl]-7-fluoro-2-methyl-1,5-naphthyridine (100 mg, 0.249 mmol) and (1R)-1-(2,3-difluorophenyl)ethan-1-amine hydrochloride (58 mg, 0.299 mmol) in Toluene (2 mL) were added Cs$_2$CO$_3$ (203 mg, 0.623 mmol), BINAP (31 mg, 0.050 mmol) and Pd$_2$(dba)$_3$ (23 mg, 0.025 mmol) at room temperature. The resulting mixture was stirred for 5 h at 100° C. under nitrogen atmosphere. The resulting mixture was concentrated under vacuum. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 30% to 60% gradient in 30 min; detector, 254 nm. This resulted in 3-chloro-N-[(1R)-1-(2,3-difluorophenyl)ethyl]-6-[6-(dimethylphosphoryl)-5-fluoropyridin-3-yl]-7-fluoro-2-methyl-1,5-naphthyridin-4-amine (33 mg, 25%) as a yellow solid. MS ESI calculated for C$_{24}$H$_{20}$ClF$_4$N$_4$OP [M+H]$^+$, 523.10, found 523.05. $^1$H NMR (400 MHz, DMSO-d$_6$) δ 8.96 (s, 1H), 8.24-8.10 (m, 2H), 7.34-7.17 (m, 2H), 7.13-7.09 (m, 1H), 6.97-6.84 (m, 1H), 6.41-6.28 (m, 1H), 2.68-2.60 (m, 3H), 1.88 (s, 3H), 1.85 (s, 3H), 1.67 (d, J=6.8 Hz, 3H). $^{19}$F NMR (376 MHz, DMSO-d$_6$) δ −117.77, −117.80, −120.70, −120.72, −139.47, −139.52, −145.22, −145.28. $^{31}$P NMR (162 MHz, DMSO-d$_6$) δ 34.36.

Example 108: 3-chloro-6-{6-[(dimethylphosphoryl)methoxy]pyridin-3-yl}-7-fluoro-N-[(1R)-1-(3-fluoropyridin-2-yl)propyl]-2-methyl-1,5-naphthyridin-4-amine

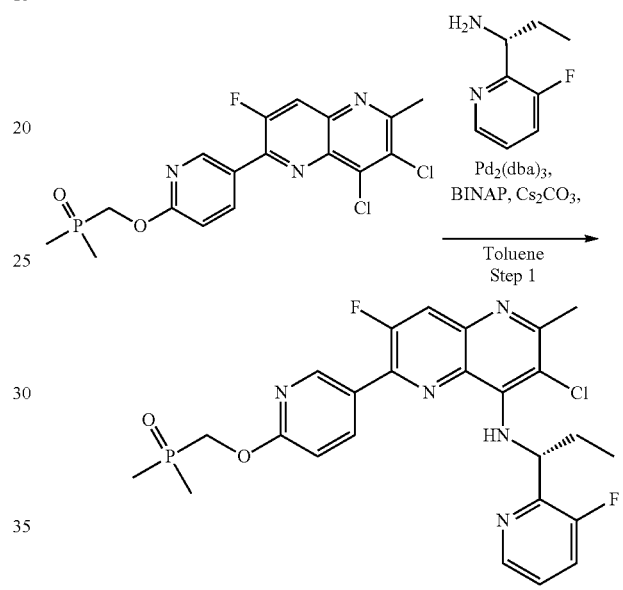

To a stirred solution of 3,4-dichloro-6-{6-[(dimethylphosphoryl)methoxy]pyridin-3-yl}-7-fluoro-2-methyl-1,5-naphthyridine (100 mg, 0.241 mmol) and (1R)-1-(3-fluoropyridin-2-yl)propan-1-amine (45 mg, 0.289 mmol) in Toluene (2 mL) were added Cs$_2$CO$_3$ (197 mg, 0.603 mmol), BINAP (30 mg, 0.048 mmol) and Pd$_2$(dba)$_3$ (22 mg, 0.024 mmol) at room temperature. The resulting mixture was stirred for 3 h at 100° C. under nitrogen atmosphere. The resulting mixture was concentrated under vacuum. The residue was purified by silica gel column chromatography, eluted with CH$_2$Cl$_2$/MeOH (10:1) followed by reversed-phase flash chromatography with the following conditions: column, C18 silica gel; mobile phase, CH$_3$CN in water (10 mmol/L NH$_4$HCO$_3$), 30% to 60% gradient in 30 min; detector, 254 nm. The resulting mixture was concentrated under vacuum. This resulted in 3-chloro-6-{6-[(dimethylphosphoryl)methoxy]pyridin-3-yl}-7-fluoro-N-[(1R)-1-(3-fluoropyridin-2-yl)propyl]-2-methyl-1,5-naphthyridin-4-amine (44 mg, 34%) as a white solid. MS ESI calculated for C$_{25}$H$_{25}$ClF$_2$N$_5$O$_2$P [M+H]$^+$, 532.14, found 532.05. $^1$H NMR (400 MHz, DMSO-d$_6$) δ 8.87 (d, J=12.3 Hz, 1H), 8.60-8.50 (m, 1H), 8.48-8.36 (m, 1H), 8.23-8.01 (m, 1H), 7.81-7.81 (m, 1H), 7.68 (s, 1H), 752-7.47 (m, 1H), 7.29-7.16 (m, 1H), 6.56 (s, 1H), 4.73 (d, J=5.2 Hz, 2H), 2.68-2.59 (m, 3H), 2.06-1.84 (m, 2H), 1.57 (s, 3H), 1.54 (s, 3H), 0.77-0.65 (m, 3H). $^{19}$F NMR (376 MHz, DMSO-d$_6$) δ −120.44, −127.01. $^{31}$P NMR (162 MHz, DMSO-d$_6$) δ 37.95.

Example 109 and 110: (R)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide and (S)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide Synthetic Scheme Preparation 109A: (5-(7-Chloro-3-fluoro-6-methyl-8-((1-(2,3,4-trifluorophenyl)ethyl)amino)-1,5-naphthyridin-2-yl)pyridin-2-yl)dimethylphosphine oxide

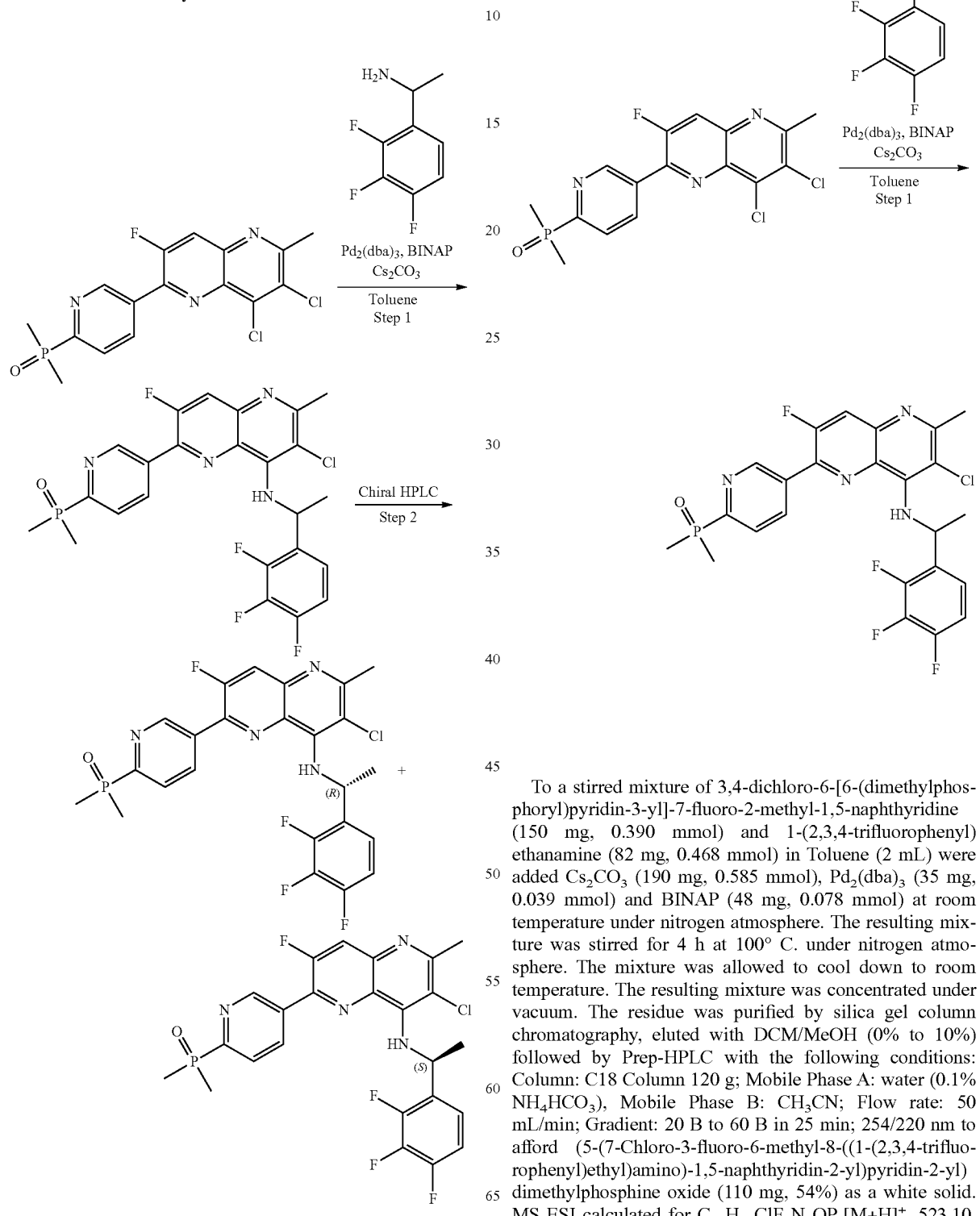

To a stirred mixture of 3,4-dichloro-6-[6-(dimethylphosphoryl)pyridin-3-yl]-7-fluoro-2-methyl-1,5-naphthyridine (150 mg, 0.390 mmol) and 1-(2,3,4-trifluorophenyl)ethanamine (82 mg, 0.468 mmol) in Toluene (2 mL) were added $Cs_2CO_3$ (190 mg, 0.585 mmol), $Pd_2(dba)_3$ (35 mg, 0.039 mmol) and BINAP (48 mg, 0.078 mmol) at room temperature under nitrogen atmosphere. The resulting mixture was stirred for 4 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 20 B to 60 B in 25 min; 254/220 nm to afford (5-(7-Chloro-3-fluoro-6-methyl-8-((1-(2,3,4-trifluorophenyl)ethyl)amino)-1,5-naphthyridin-2-yl)pyridin-2-yl)dimethylphosphine oxide (110 mg, 54%) as a white solid. MS ESI calculated for $C_{24}H_{20}ClF_4N_4OP$ $[M+H]^+$, 523.10, found 523.05.

Example 109 and 110: (R)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide and (S)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide

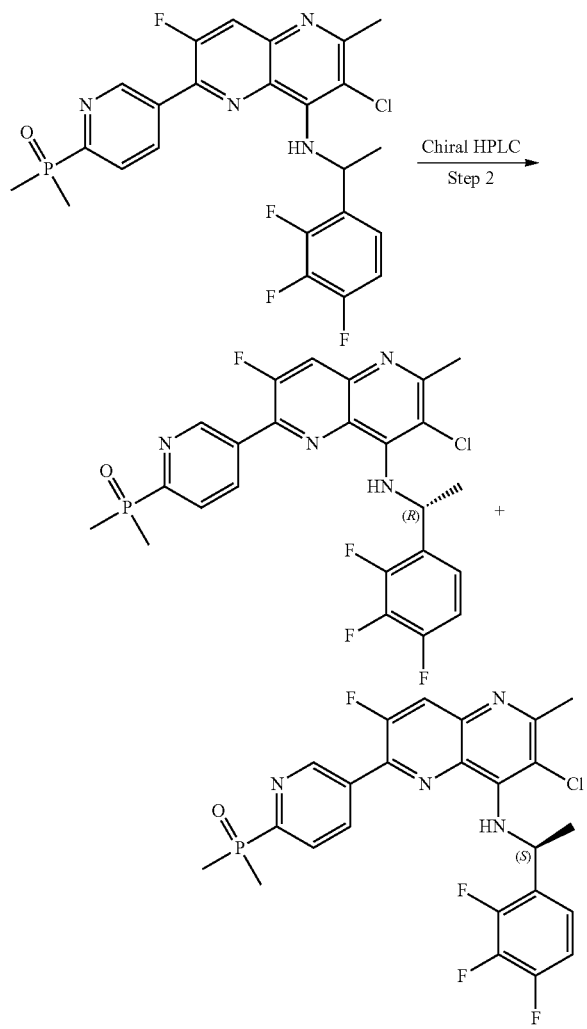

The racemic (110 mg) was resolved by Chiral-Prep-HPLC with the following conditions (Column: CHIRAL ART Cellulose-SB 2*25 cm, 5 m; Mobile Phase A: Hex(10 mM $NH_3$-MeOH), Mobile Phase B: IPA; Flow rate: 20 mL/min; Gradient: isocratic 20; Wave Length: 209/277 nm; RT1(min): 9.25; RT2(min): 11.1;). The first peak afforded 38 mg (18%) as a light green solid. MS ESI calculated for $C_{24}H_{20}ClF_4N_4OP$ $[M+H]^+$, 523.10, found 523.05. $^1H$ NMR (300 MHz, DMSO-$d_6$) δ 8.97 (s, 1H), 8.36-8.30 (m, 1H), 8.19 (d, J=11.7 Hz, 1H), 8.01-8.07 (m, 1H), 7.33-7.16 (m, 2H), 6.91 (d, J=8.2 Hz, 1H), 6.32-6.22 (m, 1H), 2.65 (s, 3H), 1.76 (d, J=3.6 Hz, 3H), 1.71 (d, J=3.6 Hz, 3H), 1.64 (d, J=6.8 Hz, 3H). $^{19}F$ NMR (282 MHz, DMSO-$d_6$) δ −121.10, −137.66, −140.64, −161.74. $^{31}P$ NMR (121 MHz, DMSO-$d_6$) δ 34.27. The second peak afforded 36 mg (18%) as a light green solid. MS ESI calculated for $C_{24}H_{20}ClF_4N_4OP$ $[M+H]^+$, 523.10, found 523.05. $^1H$ NMR (300 MHz, DMSO-$d_6$) δ 8.97 (s, 1H), 8.34 (d, J=7.7 Hz, 1H), 8.20 (d, J=11.7 Hz, 1H), 8.12-8.06 (m, 1H), 7.32-7.16 (m, 2H), 6.88 (d, J=8.2 Hz, 1H), 6.33-6.23 (m, 1H), 2.65 (s, 3H), 1.76 (d, J=3.6 Hz, 3H), 1.71 (d, J=3.6 Hz, 3H), 1.64 (d, J=6.8 Hz, 3H). $^{19}F$ NMR (282 MHz, DMSO-$d_6$) δ −121.19, −137.62, −140.66, −161.75. $^{31}P$ NMR (121 MHz, DMSO-$d_6$) δ 34.26.

Example 111: 3-chloro-6-[6-(dimethylphosphoryl)pyridin-3-yl]-7-fluoro-2-methyl-N-[1-(pyridin-2-yl)cyclopropyl]-1,5-naphthyridin-4-amine

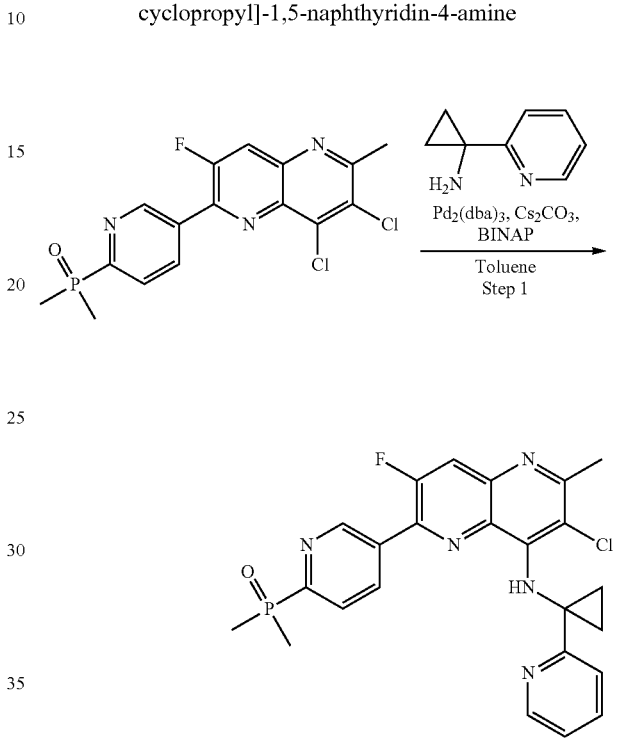

To a stirred mixture of 3,4-dichloro-6-[6-(dimethylphosphoryl)pyridin-3-yl]-7-fluoro-2-methyl-1,5-naphthyridine (80 mg, 0.208 mmol), 1-(pyridin-2-yl)cyclopropan-1-amine (33 mg, 0.250 mmol) and $Cs_2CO_3$ (101 mg, 0.312 mmol) in Toluene (1 mL) were added $Pd_2(dba)_3$ (21 mg, 0.021 mmol) and BINAP (25 mg, 0.042 mmol) at room temperature under nitrogen atmosphere. The resulting mixture was stirred for overnight at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 30% B to 60% B in 25 min; 254/220 nm to afford 3-chloro-6-[6-(dimethylphosphoryl)pyridin-3-yl]-7-fluoro-2-methyl-N-[1-(pyridin-2-yl)cyclopropyl]-1,5-naphthyridin-4-amine (33 mg, 33%) as a greenish solid. MS ESI calculated for $C_{24}H_{22}ClFN_5OP$ $[M+H]^+$, 582.12, found 482.00. $^1H$ NMR (300 MHz, Chloroform-d) δ 9.13 (s, 1H), 8.52-8.51 (m, 1H), 8.13 (t, J=6.6 Hz, 1H), 8.02 (d, J=11.8 Hz, 2H), 7.56-7.52 (m, 2H), 7.18-7.05 (m, 2H), 2.75 (s, 3H), 1.90 (d, J=3.0 Hz, 2H), 1.84 (s, 3H), 1.80 (s, 3H), 1.45 (d, J=2.9 Hz, 2H). $^{19}F$ NMR (282 MHz, Chloroform-d) δ −120.37. $^{31}P$ NMR (122 MHz, Chloroform-d) δ 36.50.

Example 112: 3-chloro-N-[(1R)-1-(3,5-difluorophenyl)ethyl]-6-[6-(dimethylphosphoryl)pyridin-3-yl]-7-fluoro-2-methylquinolin-4-amine

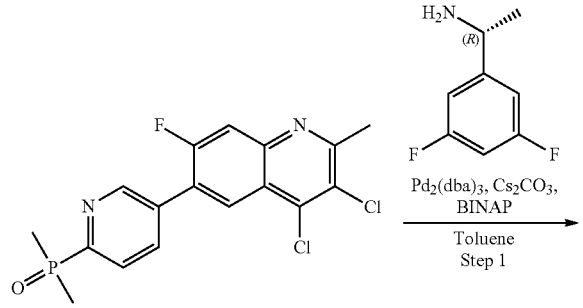

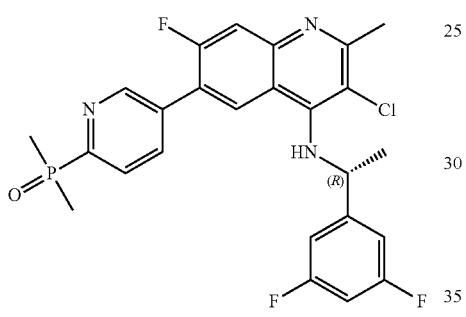

To a stirred mixture of 3,4-dichloro-6-[6-(dimethylphosphoryl)pyridin-3-yl]-fluoro-2-methylquinoline (80 mg, 0.209 mmol), (1R)-1-(3,5-difluorophenyl)ethanamine (39 mg, 0.251 mmol) and $Cs_2CO_3$ (102 mg, 0.314 mmol) in Toluene (1 mL) were added $Pd_2(dba)_3$ (19 mg, 0.021 mmol) and BINAP (26 mg, 0.042 mmol) at room temperature under nitrogen atmosphere. The resulting mixture was stirred for 3 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 50 mL/min; Gradient: 25% B to 60% B in 25 min; 254/220 nm to afford 3-chloro-N-[(1R)-1-(3,5-difluorophenyl)ethyl]-6-[6-(dimethylphosphoryl)pyridin-3-yl]-7-fluoro-2-methylquinolin-4-amine (50 mg, 47%) as a white solid. MS ESI calculated for $C_{25}H_{22}ClF_3N_3OP$ $[M+H]^+$, 504.11, found 503.90. $^1H$ NMR (300 MHz, Chloroform-d) δ 8.66 (s, 1H), 8.16-8.12 (m, 1H), 7.85-7.76 (m, 3H), 6.95-6.91 (m, 2H), 6.80-6.72 (m, 1H), 5.16 (s, 1H), 4.98 (s, 1H), 2.80 (s, 3H), 1.84 (d, J=3.7 Hz, 3H), 1.80 (d, J=3.7 Hz, 3H), 1.69 (d, J=6.6 Hz, 3H). $^{19}F$ NMR (282 MHz, Chloroform-d) δ −107.70, −115.00. $^{31}P$ NMR (122 MHz, Chloroform-d) δ 36.50.

Example 113: (R)-(5-(7-chloro-8-((1-(2,3-difluorophenyl)propyl)amino)-3-fluoro-6-methyl-1,5-naphthyridin-2-yl)pyrimidin-2-yl)dimethylphosphine oxide

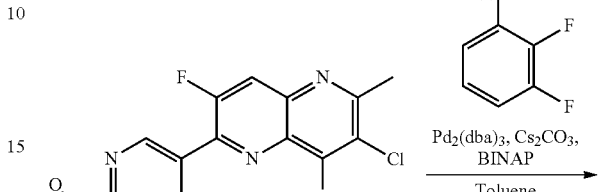

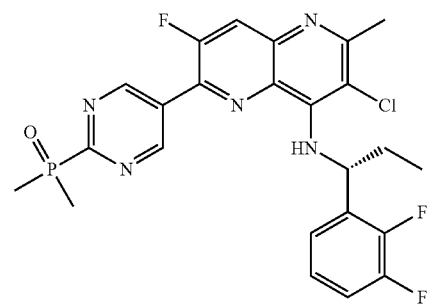

To a stirred solution of 3,4-dichloro-6-[2-(dimethylphosphoryl)pyrimidin-5-yl]-7-fluoro-2-methyl-1,5-naphthyridine (80 mg, 0.208 mmol) and (R)-1-(2,3-difluorophenyl)propan-1-amine (43 mg, 0.250 mmol) in Toluene (2 mL) were added $Pd_2(dba)_3$ (19 mg, 0.021 mmol), BINAP (26 mg, 0.042 mmol) and $Cs_2CO_3$ (169 mg, 0.520 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with $CH_2Cl_2$/MeOH (20/1) followed by reversed-phase flash chromatography with the following conditions: column, C18 silica gel; mobile phase, $CH_3CN$ in water (10 mmol/L $NH_4HCO_3$), 40% to 60% gradient in 30 min; detector, 254 nm. This resulted in (R)-(5-(7-chloro-8-((1-(2,3-difluorophenyl)propyl)amino)-3-fluoro-6-methyl-1,5-naphthyridin-2-yl)pyrimidin-2-yl)dimethylphosphine oxide (20 mg, 18%) as a yellow solid. MS ESI calculated for $C_{24}H_{22}ClF_3N_5OP$ $[M+H]^+$, 520.12, found 520.05. $^1H$ NMR (400 MHz, Chloroform-d) δ 9.38 (s, 2H), 7.96 (d, J=11.4 Hz, 1H), 7.08-6.92 (m, 3H), 6.56 (d, J=8.4 Hz, 1H), 6.15 (q, J=7.4 Hz, 1H), 2.72 (s, 3H), 2.11-1.93 (m, 8H), 1.08 (t, J=7.4 Hz, 3H). $^{19}F$ NMR (377 MHz, Chloroform-d) δ −121.12, −137.74, −137.79, −143.94, −144.00. $^{31}P$ NMR (162 MHz, Chloroform-d) δ 34.92.

Example 114: (R)-(5-(3-chloro-4-((1-(2,3-difluorophenyl)propyl)amino)-7-fluoro-2-methylquinolin-6-yl)pyrimidin-2-yl)dimethylphosphine oxide

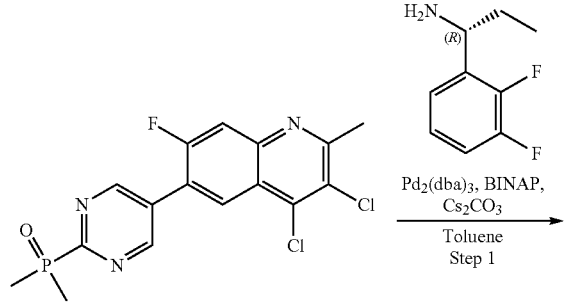

Example 115: (S)-(5-(3-chloro-4-((1-(2,3-difluorophenyl)propyl)amino)-7-fluoro-2-methylquinolin-6-yl)pyrimidin-2-yl)dimethylphosphine oxide

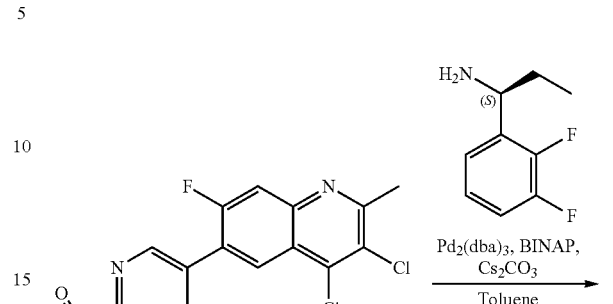

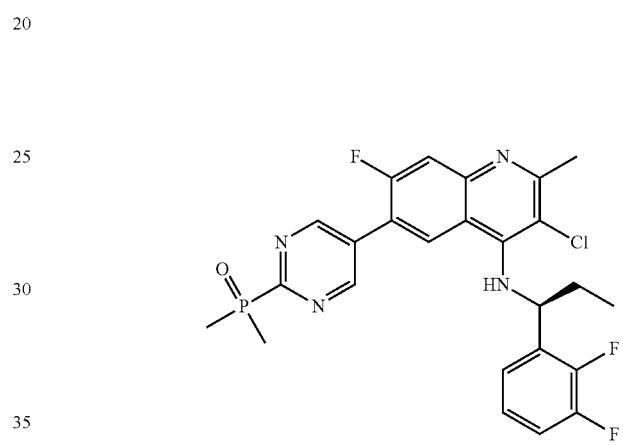

To a stirred solution of 3,4-dichloro-6-[2-(dimethylphosphoryl)pyrimidin-5-yl]-7-fluoro-2-methylquinoline (100 mg, 0.260 mmol) and (R)-1-(2,3-difluorophenyl)propan-1-amine (53 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in (R)-(5-(3-chloro-4-((1-(2,3-difluorophenyl)propyl)amino)-7-fluoro-2-methylquinolin-6-yl)pyrimidin-2-yl)dimethylphosphine oxide (33 mg, 24%) as a white solid. MS ESI calculated for C$_{25}$H$_{23}$ClF$_3$N$_4$OP [M+H]$^+$, 519.13, found 519.05. $^1$H NMR (400 MHz, Chloroform-d) δ 8.90 (s, 2H), 7.89 (d, J=7.9 Hz, 1H), 7.72 (d, J=11.7 Hz, 1H), 7.23-6.98 (m, 3H), 5.35 (s, 1H), 5.05 (q, J=7.3 Hz, 1H), 2.78 (s, 3H), 2.11-1.81 (m, 8H), 1.02 (t, J=7.4 Hz, 3H). $^{19}$F NMR (377 MHz, Chloroform-d) δ −115.34, −137.01, −144.07, −144.13. $^{31}$P NMR (121 MHz, Chloroform-d) δ 34.68.

To a stirred solution of 3,4-dichloro-6-[2-(dimethylphosphoryl)pyrimidin-5-yl]-7-fluoro-2-methylquinoline (100 mg, 0.260 mmol) and (S)-1-(2,3-difluorophenyl)propan-1-amine (53 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (9/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in (S)-(5-(3-chloro-4-((1-(2,3-difluorophenyl)propyl)amino)-7-fluoro-2-methylquinolin-6-yl)pyrimidin-2-yl)dimethylphosphine oxide (35 mg, 26%) as a white solid. MS ESI calculated for C$_{25}$H$_{23}$ClF$_3$N$_4$OP [M+H]$^+$, 519.13, found 519.05. $^1$H NMR (400 MHz, Chloroform-d) δ 8.89 (s, 2H), 7.89 (d, J=7.9 Hz, 1H), 7.74 (s, 1H), 7.22-7.04 (m, 3H), 5.37 (s, 1H), 5.11-5.03 (m, 1H), 2.79 (s, 3H), 2.16-1.84 (m, 8H), 1.02 (t, J=7.4 Hz, 3H). $^{19}$F NMR (377 MHz, Chloroform-d) δ −115.27, −136.96, −144.05, −144.10. $^{31}$P NMR (121 MHz, Chloroform-d) δ 34.70.

Example 116 and 117: (R)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide and (S)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide

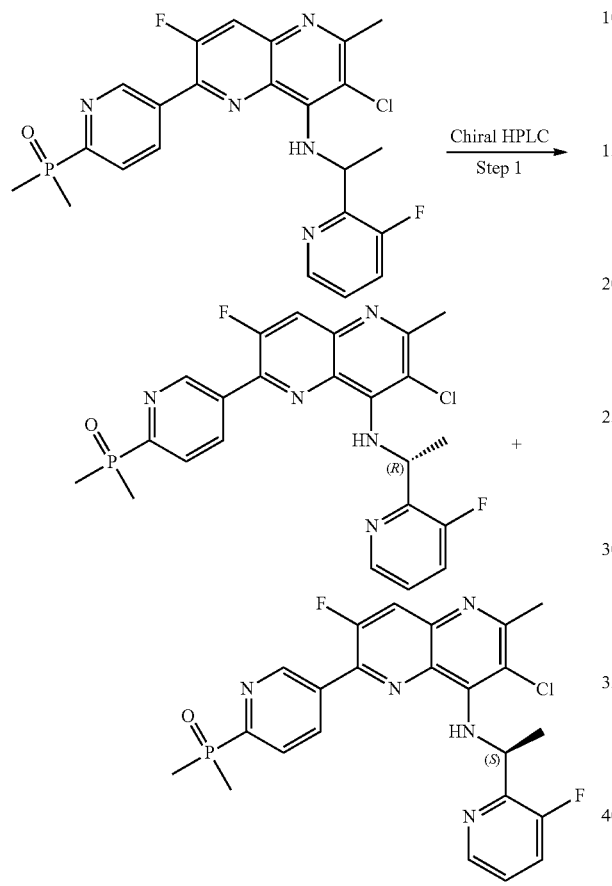

3-chloro-6-[6-(dimethylphosphoryl)pyridin-3-yl]-7-fluoro-N-[(1R)-1-(3-fluoropyridin-2-yl)ethyl]-2-methyl-1,5-naphthyridin-4-amine (110 mg) was resolved by Chiral-Prep-HPLC with the following conditions (Column: CHIRALPAK IH 2*25 cm, 5 m; Mobile Phase A: Hex(10 mM $NH_3$-MeOH), Mobile Phase B: EtOH; Flow rate: 20 mL/min; Gradient: isocratic 20; Wave Length: 212/286 nm; RT1(min): 7.0075; RT2(min): 8.93;). The first peak afforded 55 mg (50%) as a yellow solid. MS ESI calculated for $C_{23}H_{21}ClF_2N_5OP$ [M+H]$^+$, 488.11, found 488.00. $^1$H NMR (400 MHz, Chloroform-d) δ 9.49 (d, J=2.1 Hz, 1H), 8.70-8.63 (m, 1H), 8.52-8.48 (m, 1H), 8.37-8.30 (m, 1H), 8.20 (s, 1H), 7.98 (d, J=12.0 Hz, 1H), 7.47-7.39 (m, 1H), 7.33-7.28 (m, 1H), 6.66 (s, 1H), 2.77 (s, 3H), 1.88 (s, 3H), 1.85 (s, 3H), 1.64 (d, J=6.5 Hz, 3H). $^{19}$F NMR (377 MHz, Chloroform-d) δ −120.62, −126.91. $^{31}$P NMR (162 MHz, Chloroform-d) δ 36.72. The second peak afforded 52 mg (47%) as a white solid. MS ESI calculated for $C_{23}H_{21}ClF_2N_5OP$ [M+H]$^+$, 488.11, found 488.05. $^1$H NMR (400 MHz, Chloroform-d) δ 9.50 (s, 1H), 8.67 (d, J=8.1 Hz, 1H), 8.53-8.48 (m, 1H), 8.38-8.31 (m, 1H), 8.23 (s, 1H), 8.00 (d, J=11.9 Hz, 1H), 7.47-7.40 (m 1H), 7.35-7.29 (m, 1H), 6.67 (s, 1H), 2.77 (s, 3H), 1.88 (s, 3H), 1.85 (s, 3H), 1.64 (d, J=6.5 Hz, 3H). $^{19}$F NMR (377 MHz, Chloroform-d) δ −120.58, −126.91. $^{31}$P NMR (162 MHz, Chloroform-d) δ 36.71.

Example 118: 3-chloro-N-[(1R)-1-(3-chloro-2-fluorophenyl)ethyl]-6-[4-(dimethylphosphoryl)-3-fluorophenyl]-7-fluoro-2-methyl-1,5-naphthyridin-4-amine Synthetic Scheme

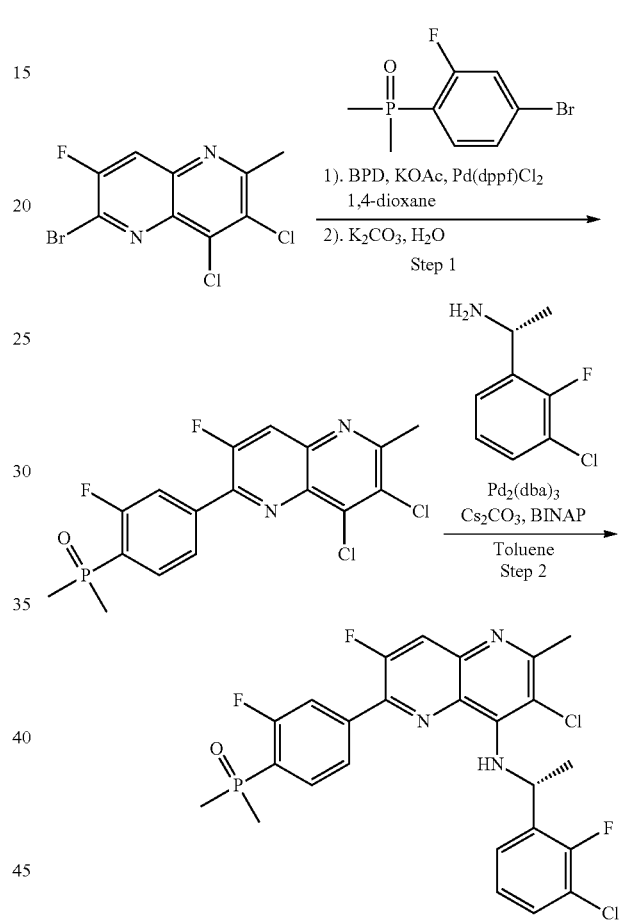

Preparation 118A: 3,4-dichloro-6-[4-(dimethylphosphoryl)-3-fluorophenyl]-7-fluoro-2-methyl-1,5-naphthyridine

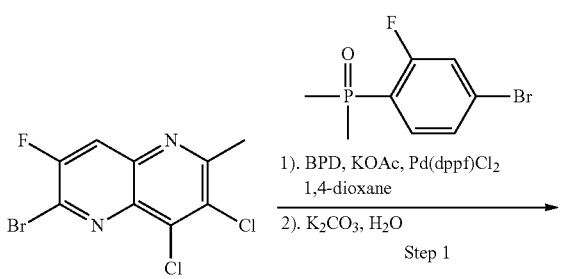

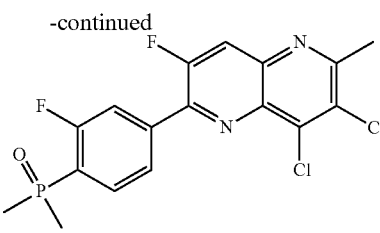

To a solution of 4-bromo-1-(dimethylphosphoryl)-2-fluorobenzene (294 mg, 1.171 mmol) and BPD (324 mg, 1.278 mmol) in 1,4-dioxane (5 mL) were added KOAc (313 mg, 3.195 mmol) and Pd(dppf)Cl$_2$·CH$_2$Cl$_2$ (104 mg, 0.128 mmol). After stirring for 2 h at 80° C. under a nitrogen atmosphere. To the above mixture were added 6-bromo-3,4-dichloro-7-fluoro-2-methyl-1,5-naphthyridine (330 mg, 1.065 mmol), K$_2$CO$_3$ (294 mg, 2.130 mmol) in H$_2$O (1 mL) at room temperature. The resulting mixture was stirred for additional 2 h at 80° C. The resulting mixture was concentrated under vacuum. The residue was purified by silica gel column chromatography, eluted with CH$_2$Cl$_2$/MeOH (12/1) to afford 3,4-dichloro-6-[4-(dimethylphosphoryl)-3-fluorophenyl]-7-fluoro-2-methyl-1,5-naphthyridine (184 mg, 43%) as a brown solid. MS ESI calculated for C$_{17}$H$_{13}$Cl$_2$F$_2$N$_2$OP [M+H]$^+$, 401.01, found 400.90. $^1$H NMR (400 MHz, Chloroform-d) δ 8.21-8.13 (m, 2H), 8.10 (d, J=11.2 Hz, 1H), 8.05-7.98 (m, 1H), 2.90 (s, 3H), 1.89 (s, 3H), 1.86 (s, 3H).

Example 118: 3-chloro-N-[(1R)-1-(3-chloro-2-fluorophenyl)ethyl]-6-[4-(dimethylphosphoryl)-3-fluorophenyl]-7-fluoro-2-methyl-1,5-naphthyridin-4-amine

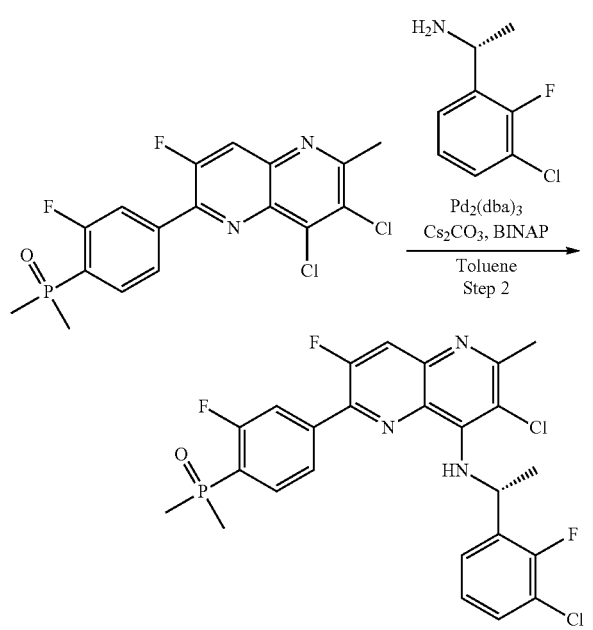

To a solution of 3,4-dichloro-6-[4-(dimethylphosphoryl)-3-fluorophenyl]-7-fluoro-2-methyl-1,5-naphthyridine (50 mg, 0.125 mmol), BINAP (16 mg, 0.025 mmol) and (1R)-1-(3-chloro-2-fluorophenyl)ethanamine hydrochloride (29 mg, 0.138 mmol) in Toluene (1 mL) were added Cs$_2$CO$_3$ (102 mg, 0.313 mmol) and Pd$_2$(dba)$_3$ (11 mg, 0.013 mmol). After stirring for 16 h at 100° C. under a nitrogen atmosphere. The resulting mixture was filtered, and the filter cake was washed with MeOH (3×5 mL). The filtrate was concentrated under reduced pressure. The residue was purified by reversed-phase flash chromatography with the following conditions: column, C18 silica gel; mobile phase, CH$_3$CN in water (10 mmol/L NH$_4$HCO$_3$), 40% to 70% gradient in 30 min; detector, 254 nm. This resulted in 3-chloro-N-[(1R)-1-(3-chloro-2-fluorophenyl)ethyl]-6-[4-(dimethylphosphoryl)-3-fluorophenyl]-7-fluoro-2-methyl-1,5-naphthyridin-4-amine (21 mg, 32%) as a yellow solid. MS ESI calculated for C$_{25}$H$_{21}$Cl$_2$F$_3$N$_3$OP [M+H]$^+$, 538.08, found 538.00. $^1$H NMR (400 MHz, Chloroform-d) δ 8.22-7.92 (m, 2H), 7.85 (s, 1H), 7.68-7.56 (m, 1H), 7.25-7.20 (m, 1H), 7.17-7.06 (m, 1H), 6.99-6.91 (m, 1H), 6.60-6.37 (m, 2H), 2.76 (s, 3H), 1.91 (s, 3H), 1.89 (s, 3H), 1.73 (d, J=6.1 Hz, 3H).

Example 119: 3-[(1R)-1-({6-[6-(dimethylphosphoryl)pyridin-3-yl]-7-fluoro-2,3-dimethyl-1,5-naphthyridin-4-yl}amino)ethyl]-4-fluorobenzonitrile

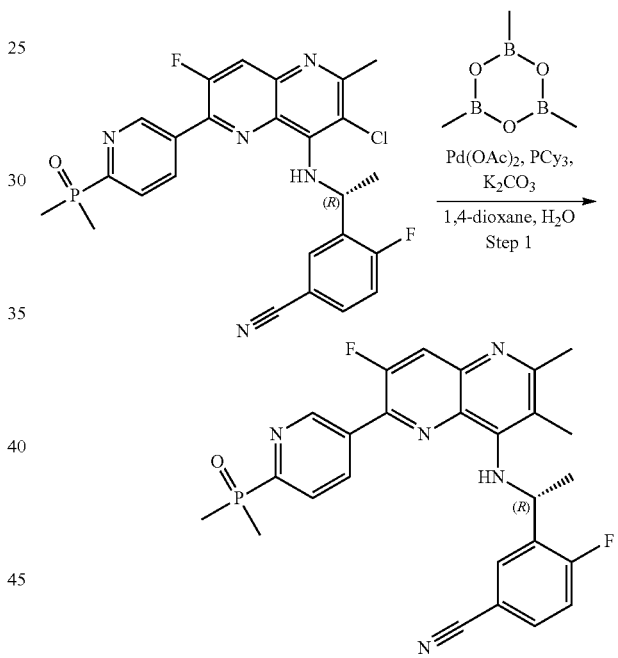

A solution of 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile (100 mg, 0.195 mmol), trimethyl-1,3,5,2,4,6-trioxatriborinane (0.28 mL, 0.975 mmol), Pd(OAc)$_2$ (4 mg, 0.020 mmol), PCy$_3$ (5 mg, 0.020 mmol) and K$_2$CO$_3$ (54 mg, 0.390 mmol) in 1,4-dioxane (2 mL) and H$_2$O (0.2 mL) was stirred for overnight at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-[(1R)-1-({6-[6-(dimethylphosphoryl)pyridin-3-yl]-7-fluoro-2,3-dimethyl-1,5-naphthyridin-4-yl}amino)ethyl]-4-fluorobenzonitrile (26 mg, 27%) as a yellow solid. MS ESI calculated for $C_{26}H_{24}F_2N_5OP$ [M+H]+, 492.17, found 492.25. $^1$H NMR (400 MHz, Chloroform-d) δ 9.35 (s, 1H), 8.46-8.42 (m, 1H), 8.31-8.28 (m, 1H), 8.00 (d, J=11.6 Hz, 1H), 7.72-7.70 (m, 1H), 7.54-7.50 (m, 1H), 7.13-7.09 (m, 1H), 6.43 (d, J=9.2 Hz, 1H), 5.53-5.46 (m, 1H), 2.66 (s, 3H), 2.32 (s, 3H), 1.88 (s, 3H), 1.85 (s, 3H), 1.69 (d, J=6.7 Hz, 3H). $^{19}$F NMR (377 MHz, Chloroform-d) δ −109.29, −121.91. $^{31}$P NMR (162 MHz, Chloroform-d) δ 36.46.

Example 120: 3-[(1R)-1-({3-chloro-6-[6-(dimethylphosphoryl)-5-fluoropyridin-3-yl]-7-fluoro-2-methyl-1,5-naphthyridin-4-yl}amino)ethyl]-4-fluorobenzonitrile Synthetic Scheme

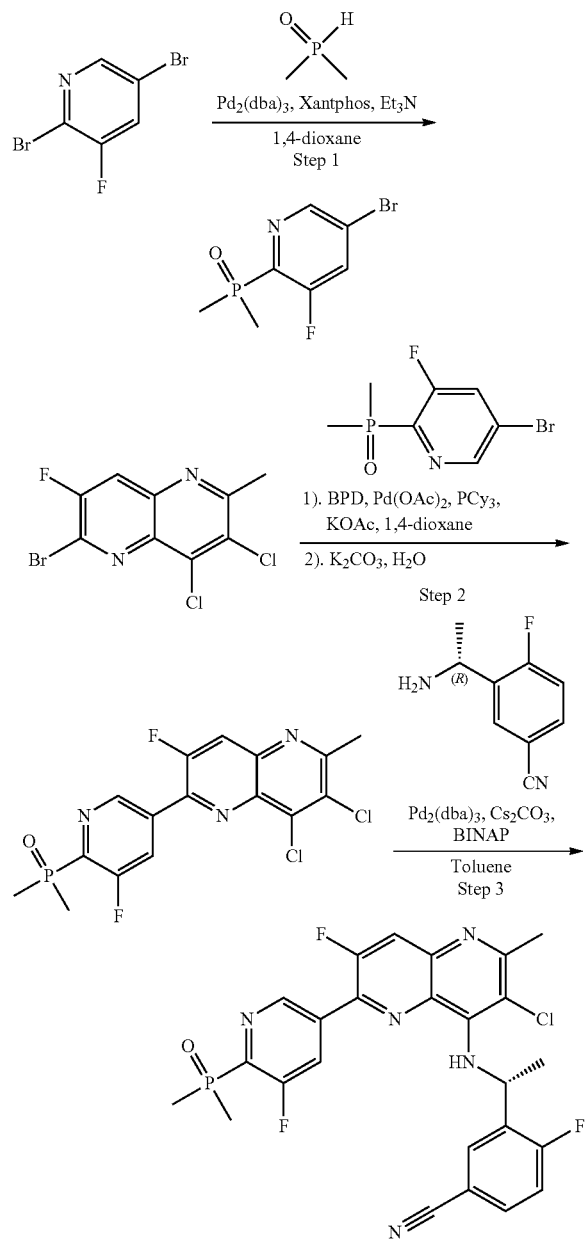

Preparation 120A:
5-bromo-2-(dimethylphosphoryl)-3-fluoropyridine

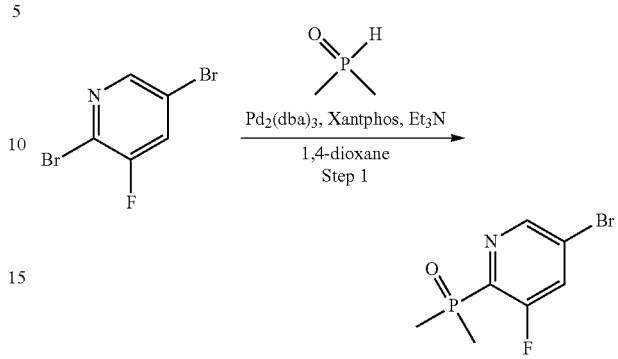

To a stirred solution of 2,5-dibromo-3-fluoropyridine (5.00 g, 19.617 mmol) and (methylphosphonoyl)methane (1.68 g, 21.579 mmol) in 1,4-dioxane (50 mL) were added $Pd_2(dba)_3$ (898 mg, 0.981 mmol) and TEA (3 mL, 23.540 mmol) at room temperature. The resulting mixture was stirred for overnight at 90° C. under nitrogen atmosphere. The resulting mixture was concentrated under reduced pressure. The residue was purified by silica gel column chromatography, eluted with $CH_2Cl_2$/MeOH (10:1) to afford 5-bromo-2-(dimethylphosphoryl)-3-fluoropyridine (1.78 g, 36%) as a brown solid. MS ESI calculated for $C_7H_8BrFNOP$ [M+H]+, 251.95 253.95, found 251.95 253.95. $^1$H NMR (400 MHz, Chloroform-d) δ 8.65-8.64 (m, 1H), 7.74-7.70 (m, 1H), 1.90 (s, 3H), 1.87 (s, 3H). $^{31}$P NMR (162 MHz, Chloroform-d) δ 35.40, 35.34.

Preparation 120B: 3,4-dichloro-6-[6-(dimethylphosphoryl)-5-fluoropyridin-3-yl]-7-fluoro-2-methyl-1,5-naphthyridine

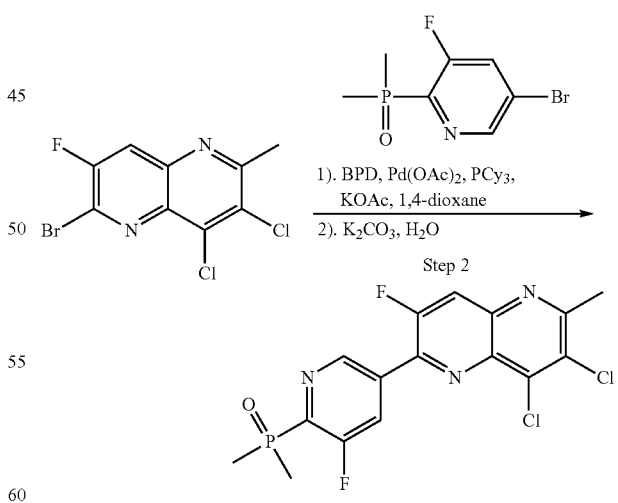

To a stirred solution of 5-bromo-2-(dimethylphosphoryl)-3-fluoropyridine (980 mg, 3.871 mmol) and BPD (2.46 g, 9.678 mmol) in 1,4-dioxane (10 mL) were added KOAc (0.76 g, 7.742 mmol) and $Pd(dppf)Cl_2 \cdot CH_2Cl_2$ (260 mg, 0.323 mmol) at room temperature. The resulting mixture was stirred for 1.5 h at 80° C. under nitrogen atmosphere. To the above mixture was added 6-bromo-3,4-dichloro-7-fluoro-2-methyl-1,5-naphthyridine (1 g, 3.226 mmol), $K_2CO_3$ (0.89 g, 6.452 mmol) and $H_2O$ (1 mL) at room temperature. The resulting mixture was stirred for additional 2 h at 80° C. The resulting liquid was dried $Na_2SO_4$. The residue was washed with DCM (3×15 mL). The resulting mixture was concentrated under reduced pressure. The residue was purified by silica gel column chromatography, eluted with $CH_2Cl_2$/MeOH (10:1) to afford 3,4-dichloro-6-[6-(dimethylphosphoryl)-5-fluoropyridin-3-yl]-7-fluoro-2-methyl-1,5-naphthyridine (560 mg, 43%) as a brown solid. MS ESI calculated for $C_{16}H_{12}Cl_2F_2N_3OP$ [M+H]$^+$, 402.01, found 402.00. $^1$H NMR (400 MHz, Chloroform-d) δ 9.43-9.41 (m, 1H), 8.47-8.34 (m, 1H), 8.15 (d, J=11.2 Hz, 1H), 2.91 (s, 3H), 1.98 (s, 3H), 1.95 (s, 3H). $^{19}$F NMR (376 MHz, Chloroform-d) δ −116.24, −116.27, −118.29. $^{31}$P NMR (162 MHz, Chloroform-d) δ 35.57, 35.51.

Example 120: 3-[(1R)-1-({3-chloro-6-[6-(dimethylphosphoryl)-5-fluoropyridin-3-yl]-7-fluoro-2-methyl-1,5-naphthyridin-4-yl}amino)ethyl]-4-fluorobenzonitrile

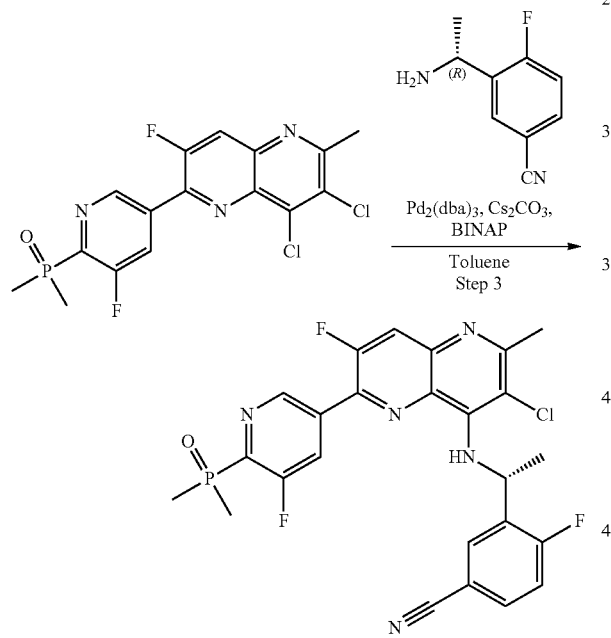

To a stirred solution of 3,4-dichloro-6-[6-(dimethylphosphoryl)-5-fluoropyridin-3-yl]-7-fluoro-2-methyl-1,5-naphthyridine (100 mg, 0.249 mmol) and 3-[(1R)-1-aminoethyl]-4-fluorobenzonitrile (49 mg, 0.299 mmol) in Toluene (2 mL) were added $Cs_2CO_3$ (122 mg, 0.373 mmol), BINAP (31 mg, 0.050 mmol) and $Pd_2(dba)_3$ (23 mg, 0.025 mmol) at room temperature. The resulting mixture was stirred for 5 h at 100° C. under nitrogen atmosphere. The resulting mixture was concentrated under vacuum. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in water (10 mmol/L $NH_4HCO_3$), 20% to 60% gradient in 30 min; detector, 254 nm. This resulted in 3-[(1R)-1-({3-chloro-6-[6-(dimethylphosphoryl)-5-fluoropyridin-3-yl]-7-fluoro-2-methyl-1,5-naphthyridin-4-yl}amino)ethyl]-4-fluorobenzonitrile (58 mg, 43%) as a yellow solid. MS ESI calculated for $C_{25}H_{20}ClF_3N_5OP$ [M+H]$^+$, 530.10, found 529.95. $^1$H NMR (400 MHz, DMSO-$d_6$) δ 9.01 (s, 1H), 8.25-8.16 (m, 2H), 8.05-7.99 (m, 1H), 7.80-7.75 (m, 1H), 7.35-7.22 (m, 1H), 6.99 (d, J=8.4 Hz, 1H), 6.31 (d, J=8.2 Hz, 1H), 2.71-2.61 (m, 3H), 1.90 (s, 3H), 1.86 (s, 3H), 1.66 (d, J=6.8 Hz, 3H). $^{19}$F NMR (376 MHz, DMSO-$d_6$) δ −109.43, −117.67, −117.70, −120.70. $^{31}$P NMR (162 MHz, DMSO-$d_6$) δ 34.46, 34.40.

Example 121: 3-[(1R)-1-[(3-chloro-6-{2-[(dimethylphosphoryl)methoxy]pyrimidin-5-yl}-7-fluoro-2-methyl-1,5-naphthyridin-4-yl)amino]ethyl]-4-fluorobenzonitrile Synthetic Scheme

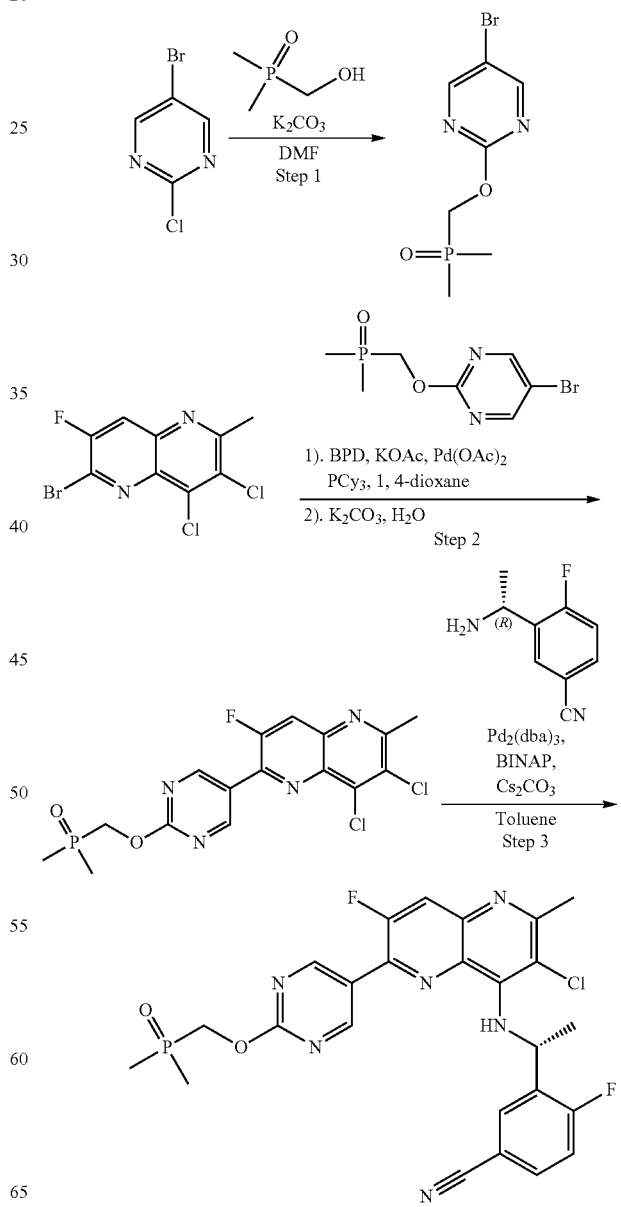

Preparation 121A: 5-bromo-2-[(dimethylphosphoryl)methoxy]pyrimidine

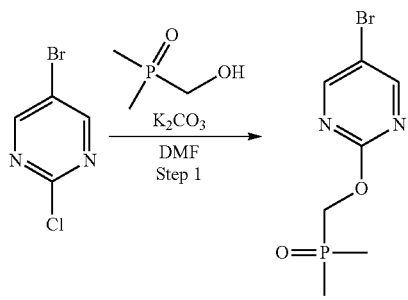

To a stirred solution of 5-bromo-2-chloropyrimidine (3.50 g, 18.094 mmol) and (dimethylphosphoryl) methanol (2.35 g, 21.713 mmol) in DMF (40 mL) were added $K_2CO_3$ (7.50 g, 54.282 mmol) at room temperature under nitrogen atmosphere. The resulting mixture was stirred for 16 h at 80° C. under nitrogen atmosphere. The resulting mixture was extracted with $CH_2Cl_2$ (3×100 mL). The combined organic layers were washed with brine (5×50 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford 5-bromo-2-[(dimethylphosphoryl) methoxy]pyrimidine (3.90 g, 81%) as a white solid. MS ESI calculated for $C_7H_{10}BrN_2O_2P$ [M+H]+, 264.97 266.97, found 264.85 266.85. $^1$H NMR (400 MHz, Methanol-$d_4$) δ 8.70 (s, 2H), 4.78 (d, J=5.5 Hz, 2H), 1.69 (s, 3H), 1.65 (s, 3H).

Preparation 121B: 3,4-dichloro-6-{2-[(dimethylphosphoryl)methoxy]pyrimidin-5-yl}-7-fluoro-2-methyl-1,5-naphthyridine

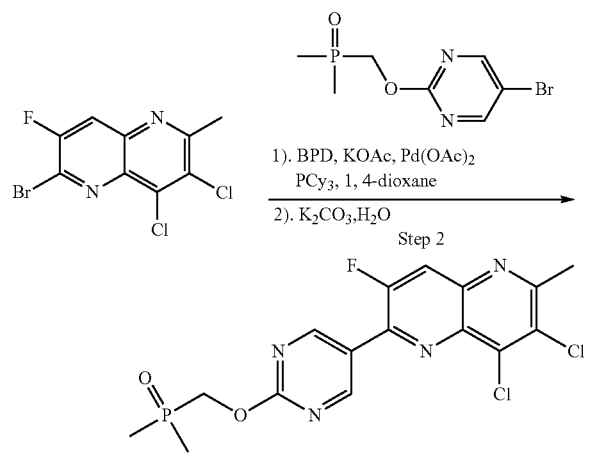

To a stirred mixture of 5-bromo-2-[(dimethylphosphoryl) methoxy]pyrimidine (1.00 g, 3.773 mmol) and BPD (2.40 g, 9.433 mmol) in 1,4-dioxane (10 mL) were added $Pd(OAc)_2$ (71 mg, 0.314 mmol), $PCy_3$ (88 mg, 0.314 mmol) and KOAc (771 mg, 7.860 mmol) at room temperature under nitrogen atmosphere. The resulting mixture was stirred for 2 h at 100° C. under nitrogen atmosphere. The mixture was allowed to cool down to room temperature. To the above mixture was added 6-bromo-3,4-dichloro-7-fluoro-2-methyl-1,5-naphthyridine (975 mg, 3.144 mmol), $K_2CO_3$ (1.09 g, 7.860 mmol) and $H_2O$ (1 mL) at room temperature. The resulting mixture was stirred for additional 16 h at 100° C. The resulting mixture was concentrated under reduced pressure. The residue was purified by silica gel column chromatography, eluted with $CH_2Cl_2$/MeOH (10:1) to afford 3,4-dichloro-6-{2-[(dimethylphosphoryl) methoxy]pyrimidin-5-yl}-7-fluoro-2-methyl-1,5-naphthyridine (840 mg, 64%) as a brown solid. MS ESI calculated for $C_{16}H_{14}Cl_2FN_4O_2P$ [M+H]+, 415.02, found 415.00. $^1$H NMR (300 MHz, Chloroform-d) δ 9.41 (d, J=1.3 Hz, 2H), 8.15-8.07 (m, 1H), 4.87 (d, J=5.8 Hz, 2H), 2.90 (s, 3H), 1.75 (s, 3H), 1.70 (s, 3H).

Example 121: 3-[(1R)-1-[(3-chloro-6-{2-[(dimethylphosphoryl)methoxy]pyrimidin-5-yl}-7-fluoro-2-methyl-1,5-naphthyridin-4-yl)amino]ethyl]-4-fluorobenzonitrile

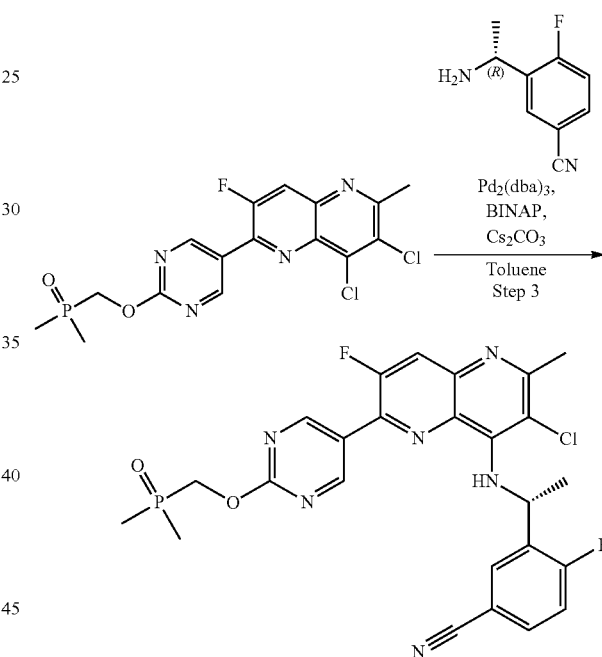

To a stirred solution of 3,4-dichloro-6-{2-[(dimethylphosphoryl)methoxy]pyrimidin-5-yl}-7-fluoro-2-methyl-1,5-naphthyridine (100 mg, 0.241 mmol) and 3-[(1R)-1-aminoethyl]-4-fluorobenzonitrile (47 mg, 0.289 mmol) in Toluene (2 mL) were added $Pd_2(dba)_3$ (22 mg, 0.024 mmol), BINAP (30 mg, 0.048 mmol) and $Cs_2CO_3$ (196 mg, 0.603 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 30 B to 70 B in 40 min; 254/220 nm to afford 3-[(1R)-1-[(3-chloro-6-{2-[(dimethylphosphoryl) methoxy]pyrimidin-5-yl}-7-fluoro-2-methyl-1,5-naphthyridin-4-yl)amino] ethyl]-4-fluorobenzonitrile (37 mg, 28%) as a white solid. MS ESI calculated for $C_{25}H_{22}ClF_2N_6O_2P$ [M+H]$^+$, 543.13, found 543.00. $^1$H NMR (400 MHz, DMSO-d$_6$) δ 9.08 (d, J=1.5 Hz, 2H), 8.18 (d, J=11.7 Hz, 1H), 8.05-8.00 (m, 1H), 7.82-7.76 (m, 1H), 7.36-7.32 (m, 1H), 6.97 (d, J=8.5 Hz, 1H), 6.38-6.28 (m, 1H), 4.78 (d, J=5.2 Hz, 2H), 2.64 (s, 3H), 1.66 (d, J=6.8 Hz, 3H), 1.58 (s, 3H), 1.55 (s, 3H). $^{19}$F NMR (377 MHz, DMSO-d$_6$) δ −109.61, −120.91. $^{31}$P NMR (162 MHz, DMSO-d$_6$) δ 37.46.

Example 122: 6-[(1S)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile Synthetic Scheme

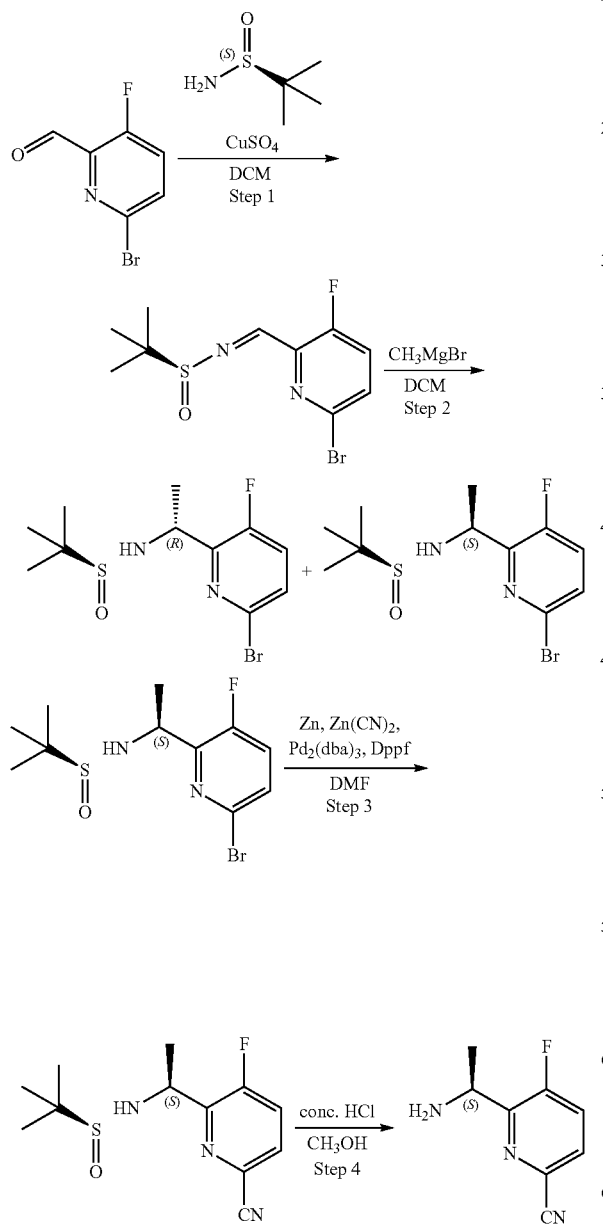

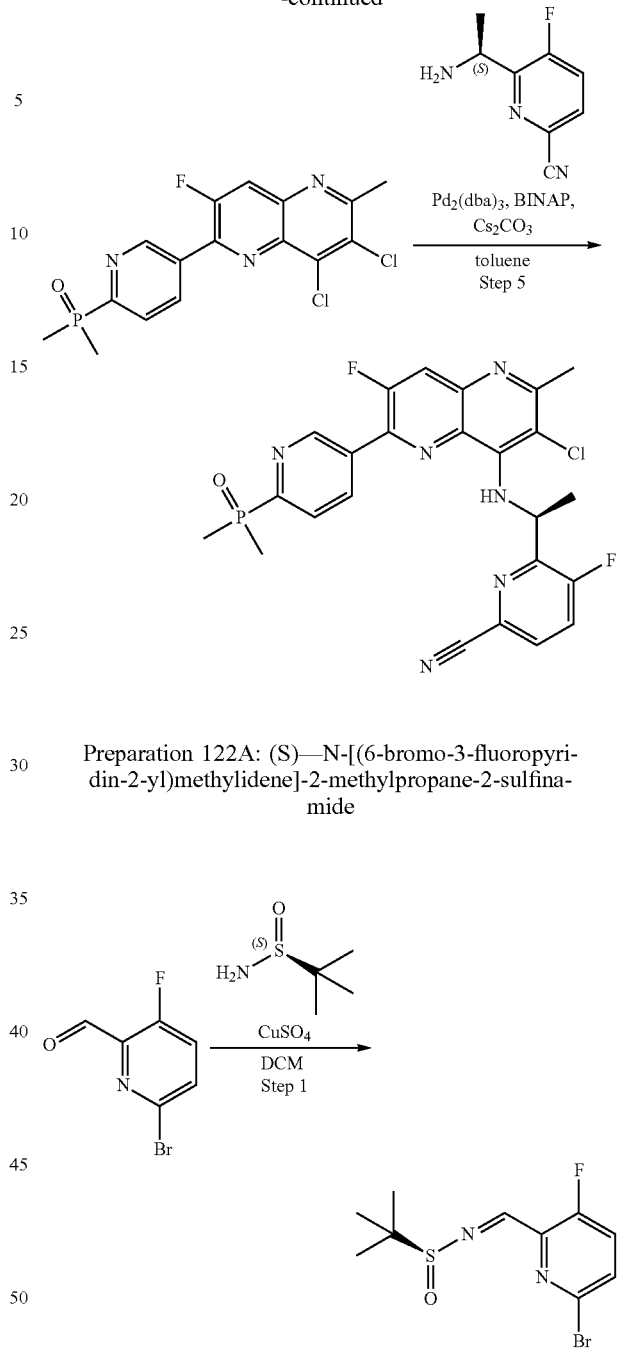

Preparation 122A: (S)—N-[(6-bromo-3-fluoropyridin-2-yl)methylidene]-2-methylpropane-2-sulfinamide A mixture of 6-bromo-3-fluoropyridine-2-carbaldehyde (10.00 g, 49.020 mmol), (S)-2-methylpropane-2-sulfinamide (7.13 g, 58.824 mmol) and CuSO$_4$ (15.65 g, 98.040 mmol) in DCM (100 mL) was stirred for overnight at room temperature. The precipitated solids were collected by filtration and washed with DCM (3×30 mL). The combined filtrate was concentrated under reduced pressure. The residue was purified by silica gel column chromatography, eluted with PE/EA (10:1) to afford (S)—N-[(6-bromo-3-fluoropyridin-2-yl)methylidene]-2-methylpropane-2-sulfinamide (14.00 g, 93%) as a white solid. MS ESI calculated for $C_{10}H_{12}BrFN_2OS$ [M+H]$^+$, 306.98 308.98, found 307.00 309.00. $^1$H NMR (400 MHz, Chloroform-d) δ 8.76 (s, 1H), 7.63-7.58 (m, 1H), 7.45 (t, J=8.9 Hz, 1H), 1.30 (s, 9H).

Preparation 122B: (S)—N-[(1R)-1-(6-bromo-3-fluoropyridin-2-yl)ethyl]-2-methylpropane-2-sulfinamide and (S)—N-[(1S)-1-(6-bromo-3-fluoropyridin-2-yl)ethyl]-2-methylpropane-2-sulfinamide

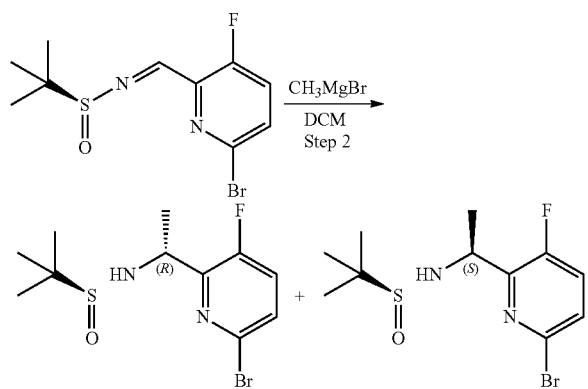

To a stirred solution of (S)—N-[(6-bromo-3-fluoropyridin-2-yl)methylidene]-2-methylpropane-2-sulfinamide (14.00 g, 45.576 mmol) in DCM (100 ml) was added 3M of bromo(methyl)magnesium (30.4 mL, 91.152 mmol) dropwise at −35° C. under nitrogen atmosphere. The resulting mixture was stirred for additional 30 min at −35° C. Then the resulting mixture was stirred for another 30 min at room temperature. The reaction was quenched with water at room temperature. The aqueous layer was extracted with EtOAc (4×300 mL). The resulting mixture was concentrated under reduced pressure. The residue was purified by silica gel column chromatography, eluted with PE/EA (2:1) followed by reversed-phase flash chromatography with the following conditions: column, C18 silica gel; mobile phase, CH$_3$CN in water (10 mmol/L NH$_4$HCO$_3$), 20% to 50% gradient in 40 min; detector, 254 nm. The first peak afforded (S)—N-[(1S)-1-(6-bromo-3-fluoropyridin-2-yl)ethyl]-2-methylpropane-2-sulfinamide (2.50 g, 17%) as a yellow oil. MS ESI calculated for C$_{11}$H$_{16}$BrFN$_2$OS [M+H]$^+$, 323.02 325.02, found 323.00 325.00. $^1$H NMR (400 MHz, Chloroform-d) δ 7.43-7.34 (m, 1H), 7.27 (t, J=8.6 Hz, 1H), 4.98-4.82 (m, 1H), 4.06 (d, J=8.8 Hz, 1H), 1.62 (d, J=6.8 Hz, 3H), 1.19 (s, 9H). The second peak afforded (S)—N-[(1R)-1-(6-bromo-3-fluoropyridin-2-yl)ethyl]-2-methylpropane-2-sulfinamide (8.30 g, 56%) as a yellow oil. MS ESI calculated for C$_{11}$H$_{16}$BrFN$_2$OS [M+H]$^+$, 323.02 325.02, found 323.00 325.00. $^1$H NMR (400 MHz, Chloroform-d) δ 7.40-7.33 (m, 1H), 7.26 (t, J=8.6 Hz, 1H), 4.87-4.77 (m, 1H), 4.64 (d, J=8.0 Hz, 1H), 1.48 (d, J=6.8 Hz, 3H), 1.25 (s, 9H).

Preparation 122C: (S)—N-[(1S)-1-(6-cyano-3-fluoropyridin-2-yl)ethyl]-2-methylpropane-2-sulfinamide

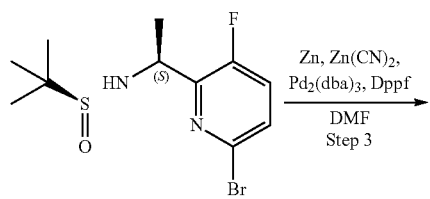

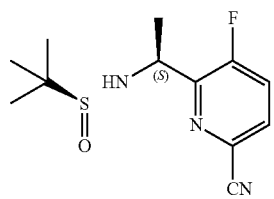

A mixture of (S)—N-[(1S)-1-(6-bromo-3-fluoropyridin-2-yl)ethyl]-2-methylpropane-2-sulfinamide (500 mg, 1.547 mmol), Zn (202 mg, 3.094 mmol), Zn(CN)$_2$ (363 mg, 3.094 mmol), Pd$_2$(dba)$_3$ (141 mg, 0.155 mmol) and Dppf (170 mg, 0.309 mmol) in DMF (10 ml) was stirred for overnight at 100° C. under nitrogen atmosphere. The resulting mixture was diluted with water (50 mL). The aqueous layer was extracted with EtOAc (3×75 mL). The resulting mixture was concentrated under reduced pressure. The residue was purified by silica gel column chromatography, eluted with CH$_2$Cl$_2$/MeOH (12/1) to afford (S)—N-[(1S)-1-(6-cyano-3-fluoropyridin-2-yl)ethyl]-2-methylpropane-2-sulfinamide (312 mg, 74%) as a yellow oil. MS ESI calculated for C$_{12}$H$_{16}$FN$_3$OS [M+H]$^+$, 270.10, found 270.10.

Preparation 122D: 6-[(1S)-1-aminoethyl]-5-fluoropyridine-2-carbonitrile

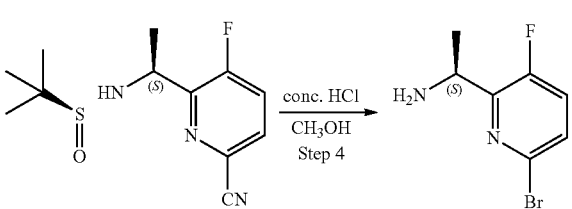

A mixture of (S)—N-[(1S)-1-(6-cyano-3-fluoropyridin-2-yl)ethyl]-2-methylpropane-2-sulfinamide (312 mg, 1.158 mmol) and conc. HCl (4 mL) in MeOH (12 mL) was stirred for 30 min at room temperature. The resulting mixture was concentrated under reduced pressure. The mixture was basified to pH 7 with saturated NaHCO$_3$ (aq.). The aqueous layer was extracted with EtOAc (5×30 mL). The resulting mixture was concentrated under reduced pressure. This resulted in 6-[(1S)-1-aminoethyl]-5-fluoropyridine-2-carbonitrile (80 mg, 41%) as a yellow oil. MS ESI calculated for C$_8$H$_8$FN$_3$ [M+H]$^+$, 166.07, found 166.15.

Example 122: 6-[(1S)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile

Example 123: 6-[(1R)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile Synthetic Scheme

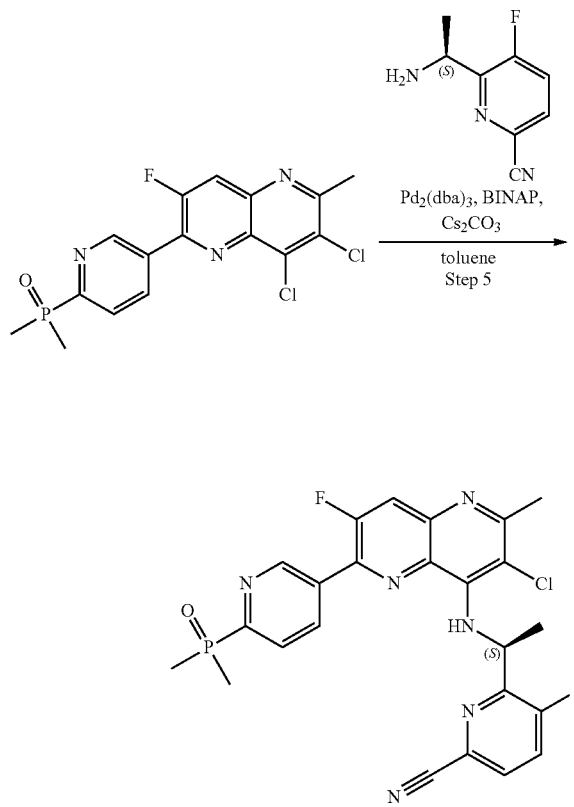

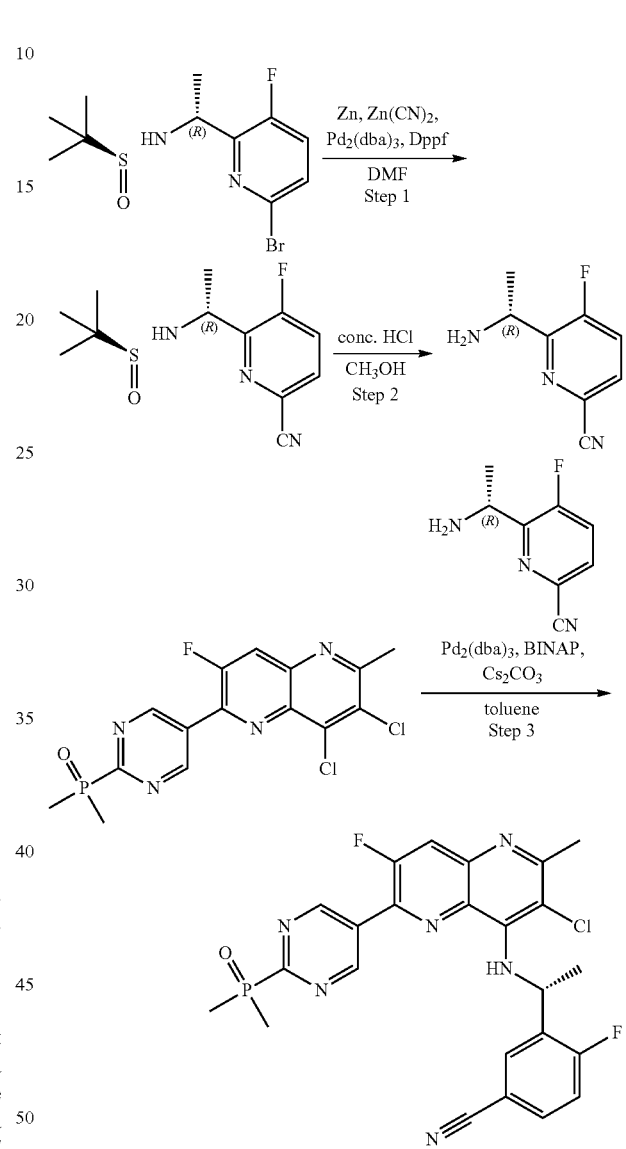

A mixture of 6-[(1S)-1-aminoethyl]-5-fluoropyridine-2-carbonitrile (80 mg, 0.484 mmol), 3,4-dichloro-6-[6-(dimethylphosphoryl)pyridin-3-yl]-7-fluoro-2-methyl-1,5-naphthyridine (223 mg, 0.581 mmol), Pd$_2$(dba)$_3$ (44 mg, 0.048 mmol), BINAP (60 mg, 0.097 mmol) and Cs$_2$CO$_3$ (236 mg, 0.726 mmol) in toluene (2 mL) was stirred for overnight at 80° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 70 mL/min; Gradient: 5 B to 70 B in 30 min; 254/220 nm to afford 6-[(1S)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile (35 mg, 13%) as a yellow solid. MS ESI calculated for C$_{24}$H$_{20}$ClF$_2$N$_6$OP [M+H]$^+$, 513.11, found 513.05. $^1$H NMR (400 MHz, DMSO-d$_6$) δ 9.28 (s, 1H), 8.53 (d, J=7.9 Hz, 1H), 8.29-8.09 (m, 3H), 7.98 (t, J=9.0 Hz, 1H), 7.49 (d, J=8.2 Hz, 1H), 6.58 (s, 1H), 2.67 (s, 3H), 1.77 (s, 3H), 1.74 (s, 3H), 1.60 (d, J=6.7 Hz, 3H). $^{19}$F NMR (377 MHz, DMSO-d$_6$) δ −117.52, −120.76. $^{31}$P NMR (162 MHz, DMSO-d$_6$) δ 34.33.

Preparation 123A: (S)—N-[(1R)-1-(6-cyano-3-fluoropyridin-2-yl)ethyl]-2-methylpropane-2-sulfinamide

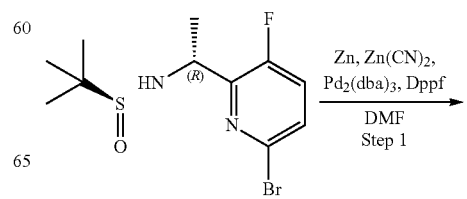

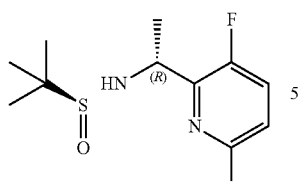

A mixture of (S)—N-[(1R)-1-(6-bromo-3-fluoropyridin-2-yl)ethyl]-2-methylpropane-2-sulfinamide (1.00 g, 3.094 mmol), Zn(CN)$_2$ (0.73 g, 6.188 mmol), Zn (0.40 g, 6.188 mmol), Pd$_2$(dba)$_3$ (0.28 g, 0.309 mmol) and Dppf (0.34 g, 0.619 mmol) in DMF (20 mL) was stirred for overnight at 100° C. under nitrogen atmosphere. The resulting mixture was diluted with water (100 mL). The aqueous layer was extracted with EtOAc (3×150 mL). The resulting mixture was concentrated under reduced pressure. The residue was purified by silica gel column chromatography, eluted with CH$_2$Cl$_2$/MeOH (12/1) to afford (S)—N-[(1R)-1-(6-cyano-3-fluoropyridin-2-yl)ethyl]-2-methylpropane-2-sulfinamide (594 mg, 71%) as a yellow oil. MS ESI calculated for C$_{12}$H$_{16}$FN$_3$OS [M+H]$^+$, 270.10, found 270.15. $^1$H NMR (400 MHz, Chloroform-d) δ 7.69-7.64 (m, 1H), 7.57-7.47 (m, 1H), 4.95-4.86 (m, 1H), 4.69 (d, J=8.5 Hz, 1H), 1.50 (d, J=6.8 Hz, 3H), 1.26 (s, 9H).

Preparation 123B: 6-[(1R)-1-aminoethyl]-5-fluoro-pyridine-2-carbonitrile

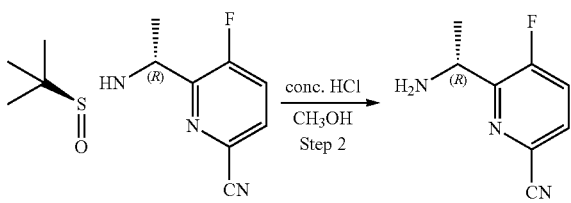

A mixture of (S)—N-[(1R)-1-(6-cyano-3-fluoropyridin-2-yl)ethyl]-2-methylpropane-2-sulfinamide (594 mg, 2.205 mmol) and conc. HCl (4 mL) in MeOH (12 mL) was stirred for 30 min at room temperature. The resulting mixture was concentrated under reduced pressure. The mixture was basified to pH 7 with saturated NaHCO$_3$ (aq.). The aqueous layer was extracted with EtOAc (5×30 mL). The combined organic layers were concentrated under reduced pressure. This resulted in 6-[(1R)-1-aminoethyl]-5-fluoropyridine-2-carbonitrile (300 mg, 82%) as a yellow oil. MS ESI calculated for C$_8$H$_8$FN$_3$ [M+H]$^+$, 166.07, found 166.15.

Example 123: 6-[(1R)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile

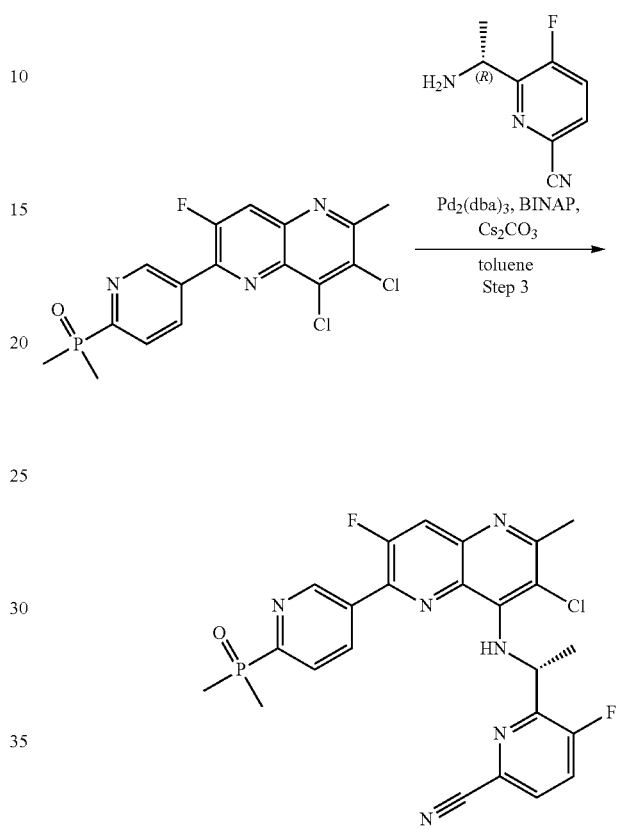

A mixture of 6-[(1R)-1-aminoethyl]-5-fluoropyridine-2-carbonitrile (100 mg, 0.605 mmol), 3,4-dichloro-6-[6-(dimethylphosphoryl)pyridin-3-yl]-7-fluoro-2-methyl-1,5-naphthyridine (279 mg, 0.726 mmol), Pd$_2$(dba)$_3$ (55 mg, 0.060 mmol), BINAP (75 mg, 0.121 mmol) and Cs$_2$CO$_3$ (295 mg, 0.907 mmol) in Toluene (2 mL) was stirred for overnight at 80° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 70 mL/min; Gradient: 5 B to 70 B in 30 min; 254/220 nm to afford 6-[(1R)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile (42 mg, 13%) as a yellow solid. MS ESI calculated for C$_{24}$H$_{20}$ClF$_2$N$_6$OP [M+H]$^+$, 513.11, found 513.10. $^1$H NMR (400 MHz, DMSO-d$_6$) δ 9.27 (s, 1H), 8.51 (d, J=7.9 Hz, 1H), 8.24-8.09 (m, 3H), 7.99 (t, J=8.9 Hz, 1H), 7.61-7.43 (m, 1H), 6.55 (d, J=9.0 Hz, 1H), 2.65 (s, 3H), 1.77 (s, 3H), 1.74 (s, 3H), 1.58 (d, J=6.6 Hz, 3H). $^{19}$F NMR (377 MHz, DMSO-d$_6$) δ −117.56, −120.70. $^{31}$P NMR (162 MHz, DMSO-d$_6$) δ 34.33.

Example 124: 3-chloro-N-[(1R)-1-(2,3-difluorophenyl)ethyl]-6-{2-[(dimethylphosphoryl)methoxy]pyrimidin-5-yl}-7-fluoro-2-methyl-1,5-naphthyridin-4-amine

Example 125: 3-chloro-N-[(1R)-1-(2,3-difluorophenyl)propyl]-6-{2-[(dimethylphosphoryl)methoxy]pyrimidin-5-yl}-7-fluoro-2-methyl-1,5-naphthyridin-4-amine

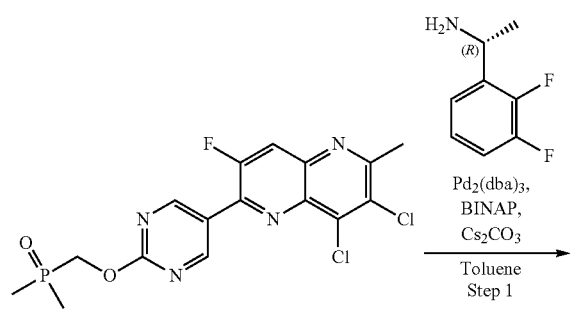

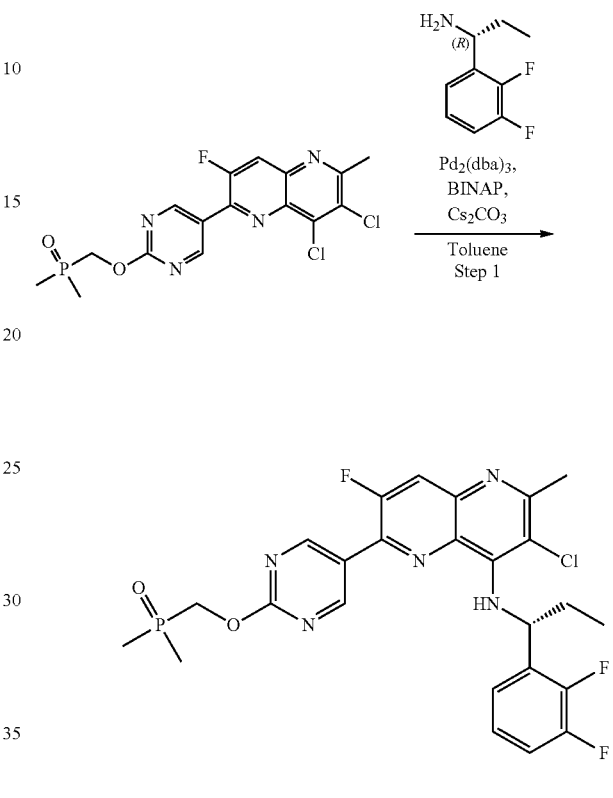

To a stirred solution of 3,4-dichloro-6-{2-[(dimethylphosphoryl)methoxy]pyrimidin-5-yl}-7-fluoro-2-methyl-1,5-naphthyridine (100 mg, 0.241 mmol) and (1R)-1-(2,3-difluorophenyl)ethanamine (45 mg, 0.289 mmol) in Toluene (2 mL) were added $Pd_2(dba)_3$ (22 mg, 0.024 mmol) and $Cs_2CO_3$ (196 mg, 0.603 mmol) at room temperature under nitrogen atmosphere. The resulting mixture was stirred for 16 h at 100° C. under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 40% to 70% gradient in 30 min; detector, 254 nm. This resulted in 3-chloro-N-[(1R)-1-(2,3-difluorophenyl)ethyl]-6-{2-[(dimethylphosphoryl)methoxy]pyrimidin-5-yl}-7-fluoro-2-methyl-1,5-naphthyridin-4-amine (51 mg, 40%) as a white solid. MS ESI calculated for $C_{24}H_{22}ClF_3N_5O_2P$ [M+H]$^+$, 536.12, found 536.00. $^1$H NMR (400 MHz, DMSO-$d_6$) δ 9.09 (d, J=1.5 Hz, 2H), 8.16 (d, J=11.7 Hz, 1H), 7.28-7.19 (m, 2H), 7.13-7.07 (m, 1H), 6.90 (d, J=8.6 Hz, 1H), 6.43-6.36 (m, 1H), 4.78 (d, J=5.2 Hz, 2H), 2.63 (s, 3H), 1.67 (d, J=6.8 Hz, 3H), 1.58 (s, 3H), 1.54 (s, 3H). $^{19}$F NMR (377 MHz, DMSO-$d_6$) δ −120.90, −139.21, −145.52. $^{31}$P NMR (162 MHz, DMSO-$d_6$) δ 37.51.

To a stirred solution of 3,4-dichloro-6-{2-[(dimethylphosphoryl)methoxy]pyrimidin-5-yl}-7-fluoro-2-methyl-1,5-naphthyridine (100 mg, 0.241 mmol) and (1R)-1-(2,3-difluorophenyl)propan-1-amine (50 mg, 0.289 mmol) in Toluene (2 mL) were added $Pd_2(dba)_3$ (22 mg, 0.024 mmol), BINAP (30 mg, 0.048 mmol) and $Cs_2CO_3$ (118 mg, 0.361 mmol) at room temperature under nitrogen atmosphere. The resulting mixture was stirred for 16 h at 100° C. under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 40% to 70% gradient in 30 min; detector, 254 nm. This resulted in 3-chloro-N-[(1R)-1-(2,3-difluorophenyl)propyl]-6-{2-[(dimethylphosphoryl)methoxy]pyrimidin-5-yl}-7-fluoro-2-methyl-1,5-naphthyridin-4-amine (20 mg, 15%) as a white solid. MS ESI calculated for $C_{25}H_{24}ClF_3N_5O_2P$ [M+H]$^+$, 550.13, found 550.00. $^1$H NMR (400 MHz, DMSO-$d_6$) δ 9.10 (d, J=1.5 Hz, 2H), 8.19 (d, J=11.7 Hz, 1H), 7.36-7.19 (m, 2H), 7.17-7.07 (m, 1H), 6.91 (d, J=8.8 Hz, 1H), 6.16-6.09 (m 1H), 4.78 (d, J=5.2 Hz, 2H), 2.63 (s, 3H), 2.15-2.05 (m, 1H), 1.97-1.88 (m, 1H), 1.57 (s, 3H), 1.54 (s, 3H), 1.02-0.97 (m, 3H). $^{19}$F NMR (377 MHz, DMSO-$d_6$) δ −120.84, −139.12, −145.30. $^{31}$P NMR (162 MHz, DMSO-$d_6$) δ 37.49.

Example 126: 3-chloro-N-[(1S)-1-(2,3-difluorophenyl)propyl]-6-{2-[(dimethylphosphoryl)methoxy]pyrimidin-5-yl}-7-fluoro-2-methyl-1,5-naphthyridin-4-amine

Example 127: 3-chloro-N-[(1S)-1-(2,3-difluorophenyl)propyl]-6-[2-(dimethylphosphoryl)pyrimidin-5-yl]-7-fluoro-2-methyl-1,5-naphthyridin-4-amine

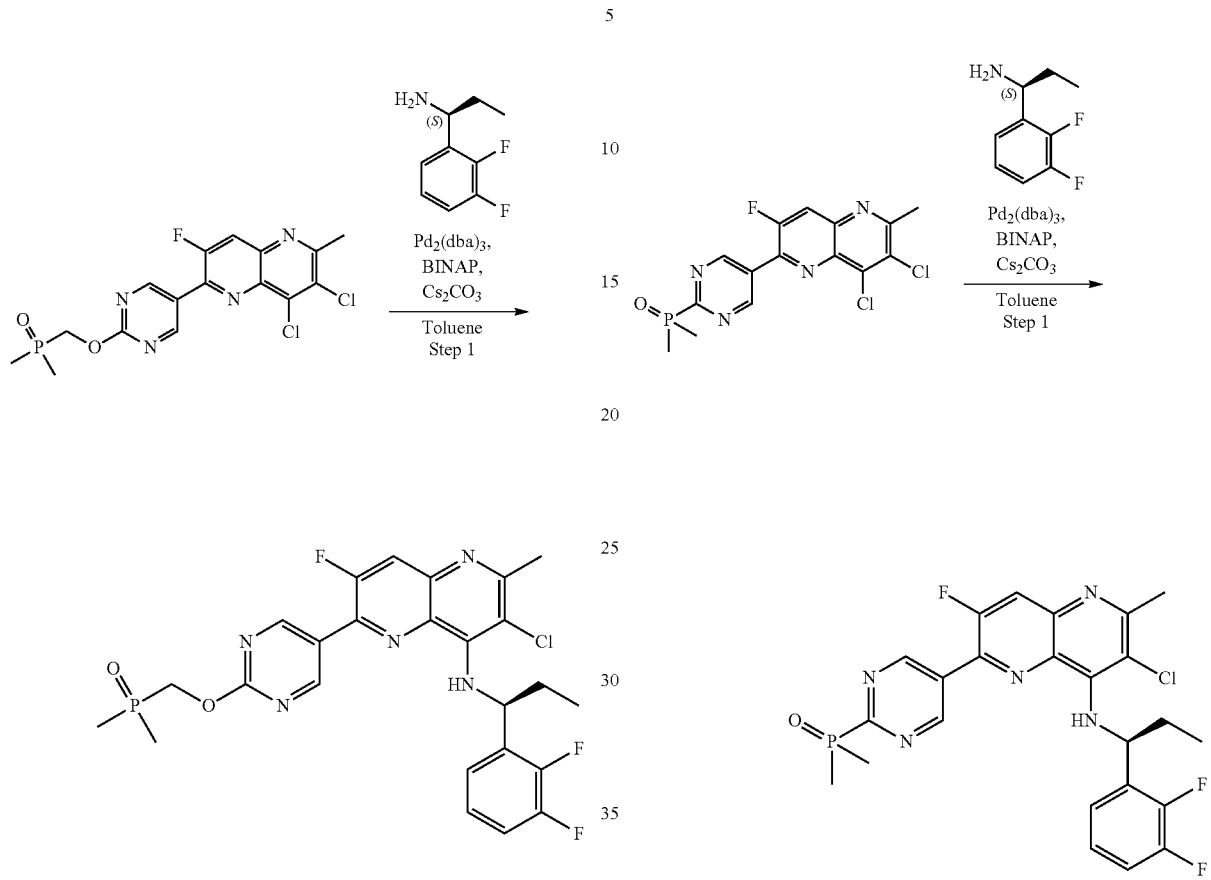

To a stirred solution of 3,4-dichloro-6-{2-[(dimethylphosphoryl)methoxy]pyrimidin-5-yl}-7-fluoro-2-methyl-1,5-naphthyridine (100 mg, 0.241 mmol) and (1S)-1-(2,3-difluorophenyl)propan-1-amine (50 mg, 0.289 mmol) in Toluene (2 mL) were added $Pd_2(dba)_3$ (22 mg, 0.024 mmol), BINAP (30 mg, 0.048 mmol) and $Cs_2CO_3$ (118 mg, 0.361 mmol) at room temperature under nitrogen atmosphere. The resulting mixture was stirred for 16 h at 100° C. under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 40% to 70% gradient in 30 min; detector, 254 nm. This resulted in 3-chloro-N-[(1S)-1-(2,3-difluorophenyl)propyl]-6-{2-[(dimethylphosphoryl)methoxy]pyrimidin-5-yl}-7-fluoro-2-methyl-1,5-naphthyridin-4-amine (27 mg, 20%) as a white solid. MS ESI calculated for $C_{25}H_{24}ClF_3N_5O_2P$ [M+H]$^+$, 550.13, found 550.00. $^1$H NMR (400 MHz, DMSO-$d_6$) δ 9.10 (d, J=1.5 Hz, 2H), 8.19 (d, J=11.7 Hz, 1H), 7.34-7.20 (m, 2H), 7.16-7.08 (m, 1H), 6.91 (d, J=8.8 Hz, 1H), 6.17-6.08 (m, 1H), 4.78 (d, J=5.2 Hz, 2H), 2.63 (s, 3H), 2.13-2.05 (m, 1H), 1.97-1.89 (m, 1H), 1.58 (s, 3H), 1.54 (s, 3H), 1.02-0.96 (m, 3H). $^{19}$F NMR (377 MHz, DMSO-$d_6$) δ −120.85, −139.00, −145.31. $^{31}$P NMR (162 MHz, DMSO-$d_6$) δ 37.50.

To a stirred solution of 5-{[(5-chloro-4-iodopyridin-3-yl)oxy]methyl}pyridine-2-carbonitrile (100 mg, 0.269 mmol) and (1S)-1-(2,3-difluorophenyl)propan-1-amine (53 mg, 0.312 mmol) in Toluene (2 mL) were added $Pd_2(dba)_3$ (24 mg, 0.026 mmol), BINAP (32 mg, 0.052 mmol) and $Cs_2CO_3$ (211 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with $CH_2Cl_2$/MeOH (19/1) followed by reversed-phase flash chromatography with the following conditions: column, C18 silica gel; mobile phase, $CH_3CN$ in water (10 mmol/L $NH_4HCO_3$), 40% to 60% gradient in 30 min; detector, 254 nm. This resulted in 3-chloro-N-[(1S)-1-(2,3-difluorophenyl)propyl]-6-[2-(dimethylphosphoryl)pyrimidin-5-yl]-7-fluoro-2-methyl-1,5-naphthyridin-4-amine (20 mg, 14%) as a yellow solid. MS ESI calculated for $C_{24}H_{22}ClF_3N_5OP$ [M+H]$^+$, 520.12, found 520.00. $^1$H NMR (400 MHz, Chloroform-d) δ 9.38 (s, 2H), 8.11 (s, 1H), 7.08-6.92 (m, 3H), 6.70 (s, 1H), 6.19 (s, 1H), 2.77 (s, 3H), 2.10-2.01 (m, 2H), 1.99 (s, 3H), 1.95 (s, 3H), 1.08 (t, J=7.4 Hz, 3H). $^{31}$P NMR (162 MHz, Chloroform-d) δ 34.84.

Example 128: 3-chloro-N-[(1R)-1-(3,5-difluorophenyl)ethyl]-6-[6-(dimethylphosphoryl)-5-fluoropyridin-3-yl]-7-fluoro-2-methyl-1,5-naphthyridin-4-amine

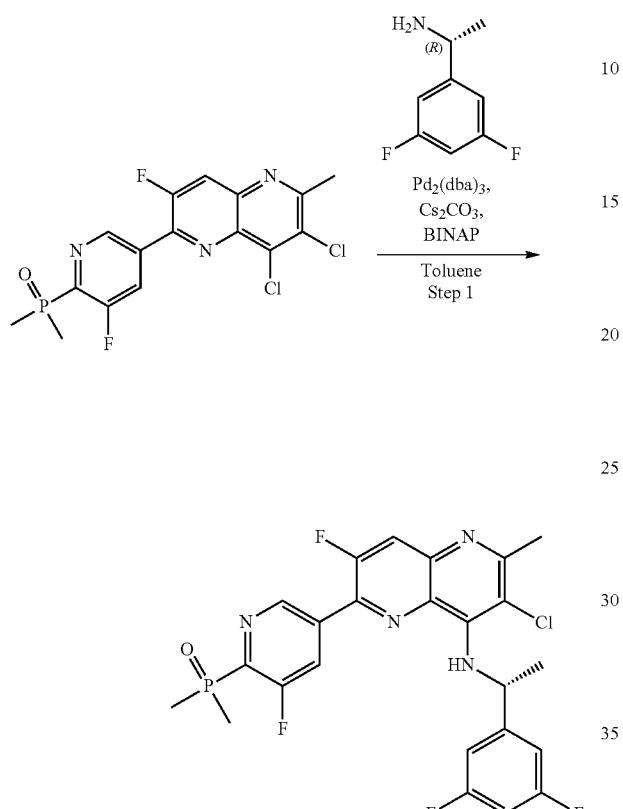

To a stirred solution of 3,4-dichloro-6-[6-(dimethylphosphoryl)-5-fluoropyridin-3-yl]-7-fluoro-2-methyl-1,5-naphthyridine (100 mg, 0.249 mmol) and (1R)-1-(3,5-difluorophenyl)ethanamine (47 mg, 0.299 mmol) in Toluene (2 mL) were added Pd$_2$(dba)$_3$ (23 mg, 0.025 mmol), BINAP (31 mg, 0.050 mmol) and Cs$_2$CO$_3$ (203 mg, 0.623 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (15/1) followed by reversed-phase flash chromatography with the following conditions: column, C18 silica gel; mobile phase, CH$_3$CN in Water (10 mmol/L NH$_4$HCO$_3$), 40% to 60% gradient in 30 min; detector, 254 nm. This resulted in 3-chloro-N-[(1R)-1-(3,5-difluorophenyl)ethyl]-6-[6-(dimethylphosphoryl)-5-fluoropyridin-3-yl]-7-fluoro-2-methyl-1,5-naphthyridin-4-amine (44 mg, 34%) as a yellow solid. MS ESI calculated for C$_{24}$H$_{20}$ClF$_4$N$_4$OP [M+H]$^+$, 523.10, found 522.95. $^1$H NMR (400 MHz, Chloroform-d) δ 9.07 (s, 1H), 8.00-7.84 (m, 2H), 6.83-6.73 (m, 2H), 6.67-6.60 (m, 1H), 6.32-6.22 (m, 1H), 6.16-6.07 (m, 1H), 2.74 (s, 3H), 1.99 (s, 3H), 1.96 (s, 3H), 1.69 (d, J=6.8 Hz, 3H). $^{19}$F NMR (377 MHz, Chloroform-d) δ −108.75, −116.37, −116.40, −120.62. $^{31}$P NMR (162 MHz, Chloroform-d) δ 35.16, 35.10.

Example 129: 3-chloro-N-[(1R)-1-(3,5-difluorophenyl)ethyl]-6-[6-(dimethylphosphoryl)-5-fluoropyridin-3-yl]-7-fluoro-2-methylquinolin-4-amine Synthetic Scheme

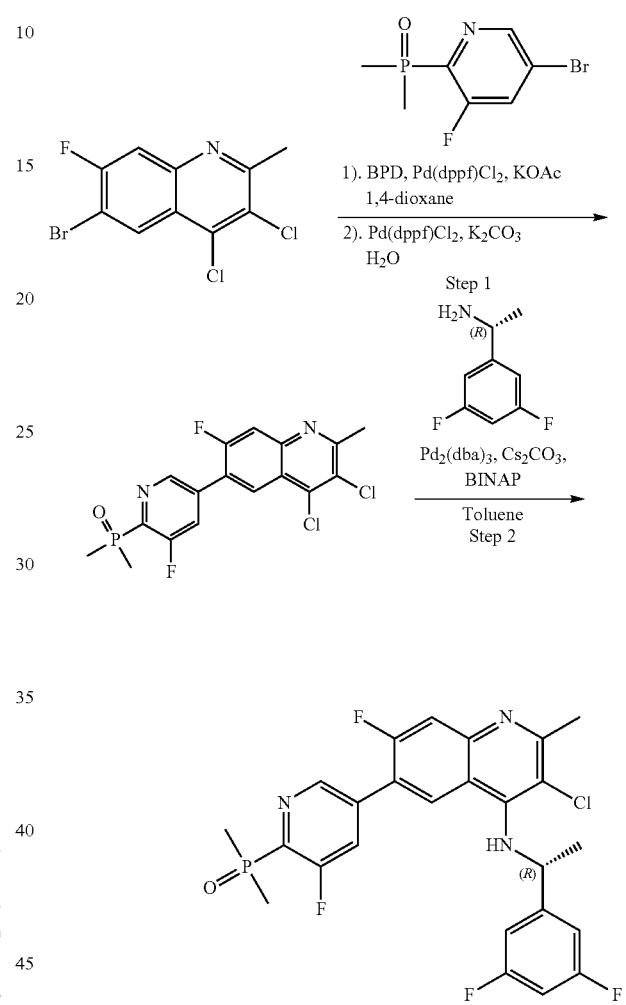

Preparation 129A: 3,4-dichloro-6-[6-(dimethylphosphoryl)-5-fluoropyridin-3-yl]-7-fluoro-2-methylquinoline

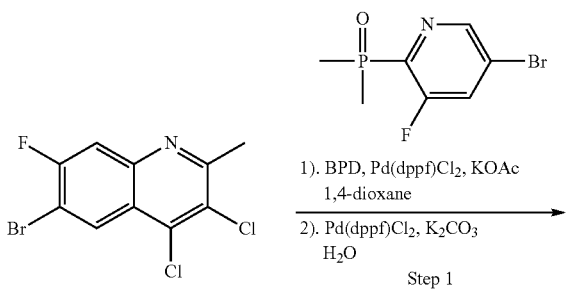

-continued

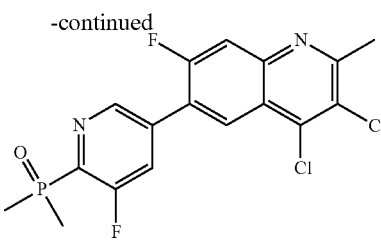

To a stirred solution of 5-bromo-2-(dimethylphosphoryl)-3-fluoropyridine (392 mg, 1.554 mmol) and BPD (986 mg, 3.885 mmol) in 1,4-dioxane (8 mL) were added KOAc (305 mg, 3.108 mmol) and Pd(dppf)Cl$_2$·CH$_2$Cl$_2$ (105 mg, 0.130 mmol) at room temperature. The resulting mixture was stirred for 1.5 h at 80° C. under nitrogen atmosphere. To the above mixture was added 6-bromo-3,4-dichloro-7-fluoro-2-methylquinoline (400 mg, 1.295 mmol), Pd(dppf)Cl$_2$·CH$_2$Cl$_2$ (105 mg, 0.130 mmol), K$_2$CO$_3$ (358 mg, 2.590 mmol) and H$_2$O (0.8 mL) at room temperature. The resulting mixture was stirred for additional 2 h at 80° C. The resulting mixture was concentrated under reduced pressure. The residue was purified by silica gel column chromatography, eluted with CH$_2$Cl$_2$/MeOH (18/1) to afford 3,4-dichloro-6-[6-(dimethylphosphoryl)-5-fluoropyridin-3-yl]-7-fluoro-2-methylquinoline (260 mg, 50%) as a brown solid. MS ESI calculated for C$_{17}$H$_{13}$Cl$_2$F$_2$N$_2$OP [M+H]$^+$, 401.01, found 400.95. $^1$H NMR (400 MHz, Chloroform-d) δ 8.88 (s, 1H), 8.26 (d, J=7.8 Hz, 1H), 7.89-7.78 (m, 2H), 2.89 (s, 3H), 1.99 (s, 3H), 1.96 (s, 3H). $^{19}$F NMR (377 MHz, Chloroform-d) δ −113.24, −116.36. $^{31}$P NMR (162 MHz, Chloroform-d) δ 35.44.

Example 129: 3-chloro-N-[(1R)-1-(3,5-difluorophenyl)ethyl]-6-[6-(dimethylphosphoryl)-5-fluoropyridin-3-yl]-7-fluoro-2-methylquinolin-4-amine

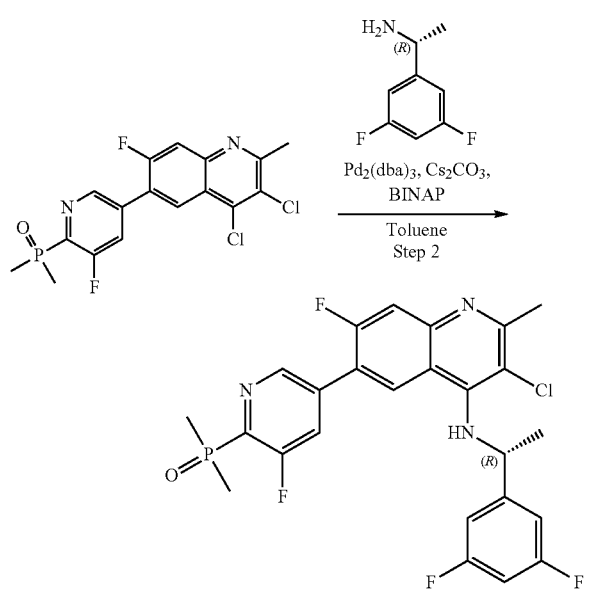

To a stirred solution of 3,4-dichloro-6-[6-(dimethylphosphoryl)-5-fluoropyridin-3-yl]-7-fluoro-2-methylquinoline (60 mg, 0.150 mmol) and (1R)-1-(3,5-difluorophenyl)ethanamine (28 mg, 0.180 mmol) in Toluene (1 mL) were added Pd$_2$(dba)$_3$ (14 mg, 0.015 mmol), BINAP (19 mg, 0.030 mmol) and Cs$_2$CO$_3$ (122 mg, 0.375 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (15/1) followed by reversed-phase flash chromatography with the following conditions: column, C18 silica gel; mobile phase, CH$_3$CN in Water (10 mmol/L NH$_4$HCO$_3$), 40% to 60% gradient in 30 min; detector, 254 nm. This resulted in 3-chloro-N-[(1R)-1-(3,5-difluorophenyl)ethyl]-6-[6-(dimethylphosphoryl)-5-fluoropyridin-3-yl]-7-fluoro-2-methylquinolin-4-amine (22 mg, 28%) as a white solid. MS ESI calculated for C$_{25}$H$_{21}$ClF$_4$N$_3$OP [M+H]$^+$, 522.10, found 522.00. $^1$H NMR (400 MHz, Chloroform-d) δ 8.57-8.47 (m, 1H), 7.86 (d, J=8.0 Hz, 1H), 7.70 (d, J=11.9 Hz, 1H), 7.48-7.40 (m, 1H), 6.99-6.90 (m, 2H), 6.82-6.73 (m, 1H), 5.18 (s, 1H), 5.00-4.87 (m, 1H), 2.78 (s, 3H), 1.96 (s, 3H), 1.92 (s, 3H), 1.69 (d, J=6.7 Hz, 3H). $^{19}$F NMR (377 MHz, Chloroform-d) δ −107.56, −116.68, −116.71. $^{31}$P NMR (162 MHz, Chloroform-d) δ 35.37, 35.30.

Example 130: 3-chloro-N-[(1R)-1-(3-chloro-5-fluorophenyl)ethyl]-6-[6-(dimethylphosphoryl)pyridin-3-yl]-7-fluoro-2-methyl-1,5-naphthyridin-4-amine

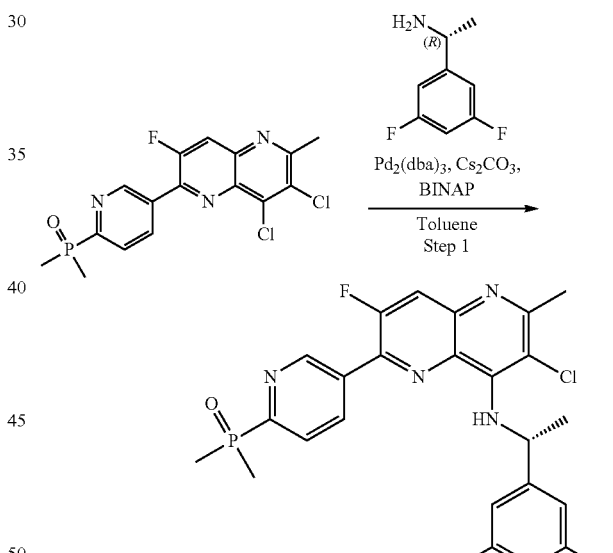

To a stirred mixture of 3,4-dichloro-6-[6-(dimethylphosphoryl)pyridin-3-yl]-7-fluoro-2-methyl-1,5-naphthyridine (80 mg, 0.208 mmol), (1R)-1-(3-chloro-5-fluorophenyl)ethanamine (43 mg, 0.250 mmol) and Cs$_2$CO$_3$ (23 mg, 0.312 mmol) in Toluene (1 mL) were added Pd$_2$(dba)$_3$ (19 mg, 0.021 mmol) and BINAP (25 mg, 0.042 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 50 mL/min; Gradient: 35% B to 65% B in 25 min; 254/220 nm to afford 3-chloro-N-[(1R)-1-(3-chloro-5-fluorophenyl)ethyl]-6-[6-(dimethylphosphoryl)pyridin-3-yl]-7-fluoro-2-methyl-1,5-naphthyridin-4-amine (25 mg, 23%) as an off-white solid. MS ESI calculated for $C_{24}H_{21}Cl_2F_2N_4OP$ [M+H]$^+$, 521.08, found 520.95. $^1$H NMR (300 MHz, Chloroform-d) δ 9.18 (d, J=1.9 Hz, 1H), 8.30-8.25 (m, 2H), 8.08-7.90 (m, 1H), 7.07-7.02 (m, 1H), 6.92-6.81 (m, 2H), 6.43-6.26 (m, 1H), 6.17-6.07 (m, 1H), 2.75 (s, 3H), 1.88 (s, 3H), 1.84 (s, 3H), 1.70 (d, J=6.7 Hz, 3H). $^{19}$F NMR (282 MHz, Chloroform-d) δ −110.01, −120.77. $^{31}$P NMR (121 MHz, Chloroform-d) δ 36.47.

Example 131: 3-[(1R)-1-({3-chloro-6-[2-(dimethylphosphoryl)pyrimidin-5-yl]-7-fluoro-2-methyl-1,5-naphthyridin-4-yl}amino)ethyl]-4,5-difluorobenzonitrile

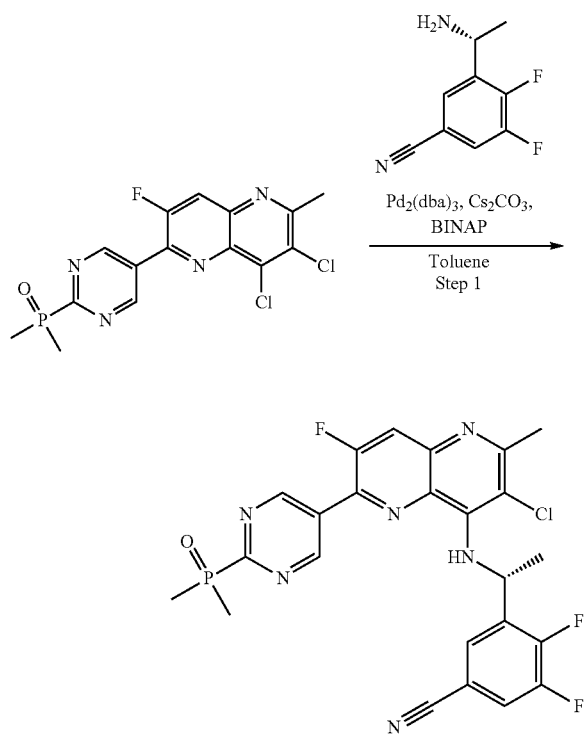

To a solution of 3,4-dichloro-6-[2-(dimethylphosphoryl)pyrimidin-5-yl]-7-fluoro-2-methyl-1,5-naphthyridine (150 mg, 0.389 mmol) and 3-[(1R)-1-aminoethyl]-4,5-difluorobenzonitrile (85 mg, 0.467 mmol) and BINAP (49 mg, 0.078 mmol) in Toluene (3 mL) were added $Cs_2CO_3$ (190 mg, 0.584 mmol) and $Pd_2(dba)_3$ (36 mg, 0.039 mmol). After stirring for 16 h at 100° C. under a nitrogen atmosphere, the resulting mixture was concentrated under reduced pressure. The residue was purified by silica gel column chromatography, eluted with $CH_2Cl_2$/MeOH (9/1) followed by reversed-phase flash chromatography with the following conditions: column, C18 silica gel; mobile phase, $CH_3CN$ in water (10 mmol/L $NH_4HCO_3$), 30% to 60% gradient in 30 min; detector, 254 nm. This resulted in 3-[(1R)-1-({3-chloro-6-[2-(dimethylphosphoryl)pyrimidin-5-yl]-7-fluoro-2-methyl-1,5-naphthyridin-4-yl}amino)ethyl]-4,5-difluorobenzonitrile (50 mg, 24%) as a yellow solid. MS ESI calculated for $C_{24}H_{19}ClF_3N_6OP$ [M+H]$^+$, 531.10, found 531.05. $^1$H NMR (400 MHz, Chloroform-d) δ 9.32 (s, 2H), 8.00 (d, J=11.1 Hz, 1H), 7.40-7.31 (m, 2H), 6.41-6.28 (m, 2H), 2.75 (s, 3H), 1.99 (s, 3H), 1.95 (s, 3H), 1.73 (d, J=6.5 Hz, 3H). $^{19}$F NMR (377 MHz, Chloroform-d) δ −120.73, −133.18, −133.24, −133.83, −133.89. $^{31}$P NMR (162 MHz, Chloroform-d) δ 34.89.

Example 132: 3-chloro-6-[2-(dimethylphosphoryl)pyrimidin-5-yl]-7-fluoro-N-[(1S)-1-(3-fluoropyridin-2-yl)propyl]-2-methyl-1,5-naphthyridin-4-amine

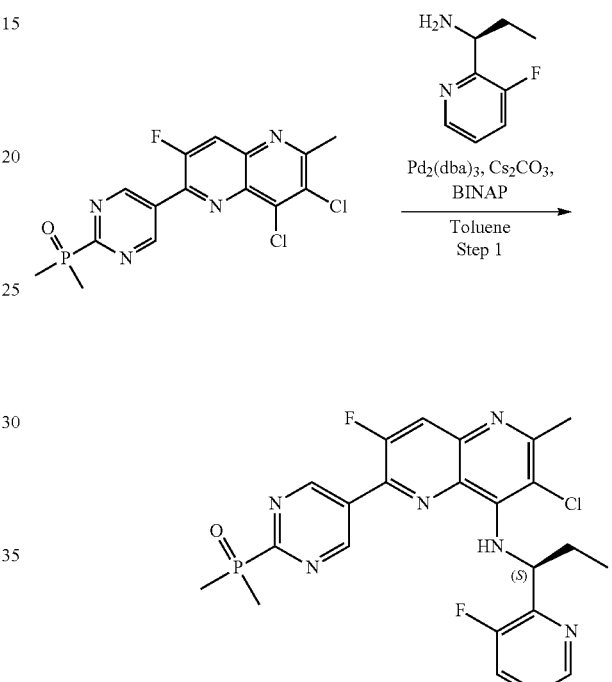

To a solution of 3,4-dichloro-6-[2-(dimethylphosphoryl)pyrimidin-5-yl]-7-fluoro-2-methyl-1,5-naphthyridine (100 mg, 0.260 mmol) and (1S)-1-(3-fluoropyridin-2-yl)propan-1-amine (48 mg, 0.312 mmol) and BINAP (32 mg, 0.052 mmol) in Toluene (2 mL) were added $Cs_2CO_3$ (127 mg, 0.390 mmol) and $Pd_2(dba)_3$ (24 mg, 0.026 mmol). After 16 h at 80° C. under a nitrogen atmosphere, the resulting mixture was concentrated under reduced pressure. The residue was purified by silica gel column chromatography, eluted with $CH_2Cl_2$/MeOH (9/1) followed by reversed-phase flash chromatography with the following conditions: column, C18 silica gel; mobile phase, $CH_3CN$ in water (10 mmol/L $NH_4HCO_3$), 30% to 60% gradient in 20 min; detector, 254 nm. This resulted in 3-chloro-6-[2-(dimethylphosphoryl)pyrimidin-5-yl]-7-fluoro-N-[(1S)-1-(3-fluoropyridin-2-yl)propyl]-2-methyl-1,5-naphthyridin-4-amine (38 mg, 29%) as a yellow solid. MS ESI calculated for $C_{23}H_{22}ClF_2N_6OP$ [M+H]$^+$, 503.12, found 503.00. $^1$H NMR (400 MHz, Chloroform-d) δ 9.64 (d, J=1.3 Hz, 2H), 8.55-8.49 (m, 1H), 8.15-7.94 (m, 2H), 7.46-7.38 (m, 1H), 7.32-7.27 (m, 1H), 6.60 (s, 1H), 2.77 (s, 3H), 2.16-2.01 (m, 2H), 1.99 (s, 3H), 1.96 (s, 3H), 0.88-0.80 (m, 3H). $^{19}$F NMR (377 MHz, Chloroform-d) δ −120.94, −126.33. $^{31}$P NMR (162 MHz, Chloroform-d) δ 34.87.

Example 133: N-[(1R)-1-(2,3-difluorophenyl)ethyl]-6-[6-(dimethylphosphoryl)pyridin-3-yl]-7-fluoro-2,3-dimethyl-1,5-naphthyridin-4-amine

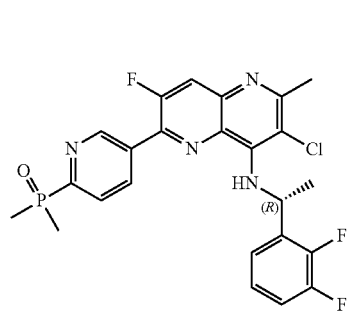 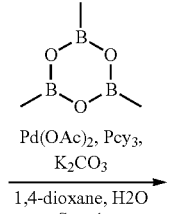

Pd(OAc)₂, PCy₃, K₂CO₃
1,4-dioxane, H2O
Step 1

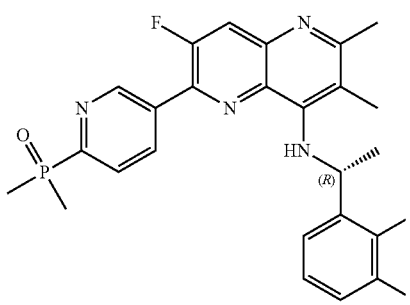

A solution of 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine (80 mg, 0.158 mmol), trimethyl-1,3,5,2,4,6-trioxatriborinane (0.23 mL, 0.790 mmol), Pd(OAc)₂ (4 mg, 0.020 mmol), PCy₃ (5, 0.020 mmol) and K₂CO₃ (54 mg, 0.396 mmol) in 1,4-dioxane (1 mL) and H₂O (0.2 mL) was stirred for 2 h at 100° C. under nitrogen atmosphere. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH₄HCO₃), Mobile Phase B: CH₃CN; Flow rate: 60 mL/min; Gradient: 30% B to 70% B in 20 min; 254/220 nm to afford N-[(1R)-1-(2,3-difluorophenyl)ethyl]-6-[6-(dimethylphosphoryl)pyridin-3-yl]-7-fluoro-2,3-dimethyl-1,5-naphthyridin-4-amine (31 mg, 41%) as a yellow solid. MS ESI calculated for C₂₅H₂₄F₃N₄OP [M+H]⁺, 485.16, found 485.30. ¹H NMR (400 MHz, DMSO-d₆) δ 9.17 (s, 1H), 8.42-8.31 (m, 1H), 8.15-7.99 (m, 2H), 7.36-7.28 (m, 1H), 7.24-7.17 (m, 1H), 7.15-7.01 (m, 1H), 6.46 (d, J=9.1 Hz, 1H), 5.94-5.78 (m, 1H), 2.57 (s, 3H), 2.34 (s, 3H), 1.76 (s, 3H), 1.72 (s, 3H), 1.63 (d, J=6.8 Hz, 3H). ¹⁹F NMR (377 MHz, DMSO-d₆) δ −122.97, −139.47, −139.53, −145.42, −145.48. ³¹P NMR (162 MHz, DMSO-d₆) δ 34.20.

Example 134: 3-cyclopropyl-N-[(1R)-1-(2,3-difluorophenyl)ethyl]-6-[6-(dimethylphosphoryl)pyridin-3-yl]-7-fluoro-2-methyl-1,5-naphthyridin-4-amine

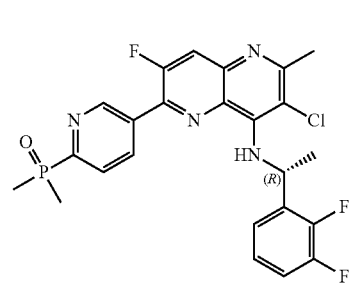 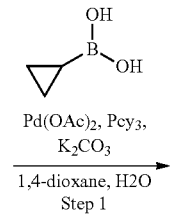

Pd(OAc)₂, PCy₃, K₂CO₃
1,4-dioxane, H2O
Step 1

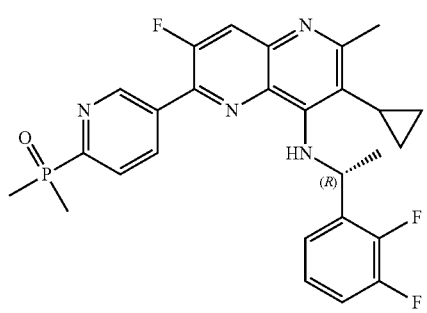

A solution of 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine (100 mg, 0.198 mmol), cyclopropylboronic acid (85 mg, 0.990 mmol), Pd(OAc)₂ (4 mg, 0.020 mmol), PCy₃ (5, 0.020 mmol) and K₂CO₃ (54 mg, 0.396 mmol) in 1,4-dioxane (1 mL) and H₂O (0.2 mL) was stirred for 2 h at 100° C. under nitrogen atmosphere. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH₄HCO₃), Mobile Phase B: CH₃CN; Flow rate: 60 mL/min; Gradient: 30% B to 70% B in 20 min; 254/220 nm to afford 3-cyclopropyl-N-[(1R)-1-(2,3-difluorophenyl)ethyl]-6-[6-(dimethylphosphoryl)pyridin-3-yl]-7-fluoro-2-methyl-1,5-naphthyridin-4-amine (36 mg, 36%) as a yellow solid. MS ESI calculated for C₂₇H₂₆F₃N₄OP [M+H]⁺, 511.18, found 511.30. ¹H NMR (400 MHz, DMSO-d₆) δ 9.22 (s, 1H), 8.41-8.45 (m, 1H), 8.17-8.04 (m, 2H), 7.33-7.14 (m, 2H), 7.12-7.03 (m, 1H), 6.77 (d, J=9.8 Hz, 1H), 6.14-6.03 (m, 1H), 2.66 (s, 3H), 1.98-1.90 (m, 1H), 1.76 (s, 3H), 1.73 (s, 3H), 1.66 (d, J=6.8 Hz, 3H), 1.21-1.15 (m, 2H), 0.75-0.69 (m, 1H), 0.56-0.46 (m, 1H). ¹⁹F NMR (377 MHz, DMSO-d₆) δ −122.45, −139.24, −139.30, −145.52, −145.58. ³¹P NMR (162 MHz, DMSO-d₆) δ 34.19.

Example 135: 3-chloro-N-[(1R)-1-(2,3-difluorophenyl)ethyl]-6-[6-(dimethylphosphoryl)-5-fluoropyridin-3-yl]-7-fluoro-2-methylquinolin-4-amine

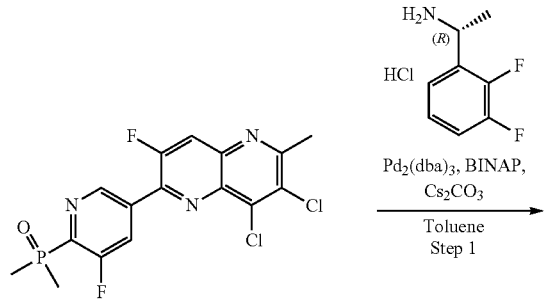

Example 136: 3-chloro-N-[cyclopropyl(3-fluoropyridin-2-yl)methyl]-6-[6-(dimethylphosphoryl)pyridin-3-yl]-7-fluoro-2-methyl-1,5-naphthyridin-4-amine Synthetic Scheme

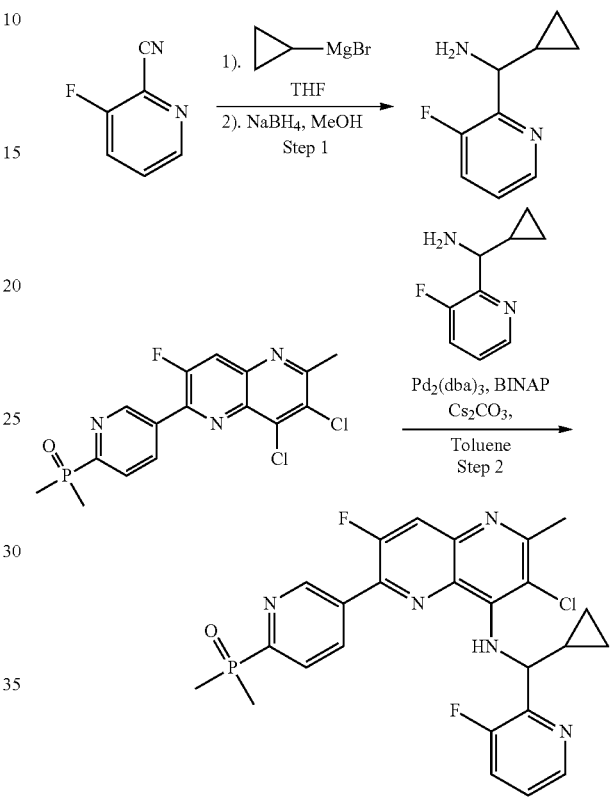

To a stirred solution of 3,4-dichloro-6-[6-(dimethylphosphoryl)-5-fluoropyridin-3-yl]-7-fluoro-2-methylquinoline (100 mg, 0.249 mmol) and (1R)-1-(2,3-difluorophenyl)ethan-1-amine hydrochloride (58 mg, 0.299 mmol) in Toluene (2 mL) were added $Pd_2(dba)_3$ (23 mg, 0.025 mmol), BINAP (31 mg, 0.050 mmol) and $Cs_2CO_3$ (203 mg, 0.623 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with $CH_2Cl_2$/MeOH (19/1) followed by reversed-phase flash chromatography with the following conditions: column, C18 silica gel; mobile phase, $CH_3CN$ in water (10 mmol/L $NH_4HCO_3$), 40% to 60% gradient in 30 min; detector, 254 nm. This resulted in 3-chloro-N-[(1R)-1-(2,3-difluorophenyl)ethyl]-6-[6-(dimethylphosphoryl)-5-fluoropyridin-3-yl]-7-fluoro-2-methylquinolin-4-amine (59 mg, 44%) as a white solid. MS ESI calculated for $C_{25}H_{21}ClF_4N_3OP$ [M+H]$^+$, 522.10, found 522.00. $^1H$ NMR (300 MHz, Chloroform-d) δ 8.60 (s, 1H), 7.92 (d, J=8.0 Hz, 1H), 7.84-7.66 (M, 1H), 7.57-7.48 (m, 1H), 7.28-7.24 (m, 1H), 7.20-7.10 (m, 2H), 5.29 (s, 2H), 2.81 (s, 3H), 2.00 (s, 3H), 1.95 (s, 3H), 1.74 (d, J=5.9 Hz, 3H). $^{19}F$ NMR (282 MHz, Chloroform-d) δ −115.05, −116.67, −116.71, −137.05, −144.18, −144.26. $^{31}P$ NMR (121 MHz, Chloroform-d) δ 35.45, 35.36.

Preparation 136A: 1-cyclopropyl-1-(3-fluoropyridin-2-yl)methanamine

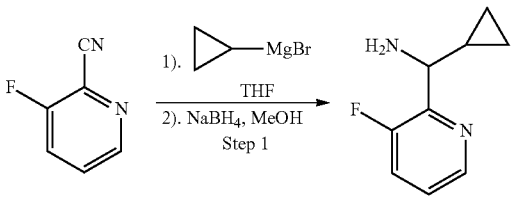

A solution of 3-fluoropyridine-2-carbonitrile (200 mg, 1.638 mmol) and bromo(cyclopropyl)magnesium (476 mg, 3.276 mmol) in THF (1 mL) was stirred for 1 h at 100° C. under nitrogen atmosphere. The mixture was allowed to cool down to room temperature. To the above mixture was added $NaBH_4$ (124 mg, 3.276 mmol) in MeOH (2 mL) dropwise over 1 min at 0° C. The resulting mixture was stirred for additional 1 h at room temperature. The reaction was quenched by the addition of sat. $NH_4Cl$ (aq.) (1 mL) at 0° C. The resulting mixture was extracted with EtOAc (3×50 mL). The combined organic layers were washed with brine (3×30 mL), dried over anhydrous $Na_2SO_4$. After filtration, the filtrate was concentrated under reduced pressure. The residue was purified by silica gel column chromatography, eluted with PE/EA (3/1) to afford 1-cyclopropyl-1-(3-fluoropyridin-2-yl)methanamine (230 mg, 84%) as a brown yellow oil. MS ESI calculated for $C_9H_{11}FN_2$ [M+H]$^+$, 167.09, found 167.10. $^1$H NMR (400 MHz, Chloroform-d) δ 8.43-8.37 (m, 1H), 7.43-7.35 (m, 1H), 7.26-7.21 (m, 1H), 3.93-3.84 (m, 1H), 0.73-0.65 (m, 1H), 0.58-0.43 (m, 4H).

Example 136: 3-chloro-N-[cyclopropyl(3-fluoropyridin-2-yl)methyl]-6-[6-(dimethylphosphoryl)pyridin-3-yl]-7-fluoro-2-methyl-1,5-naphthyridin-4-amine

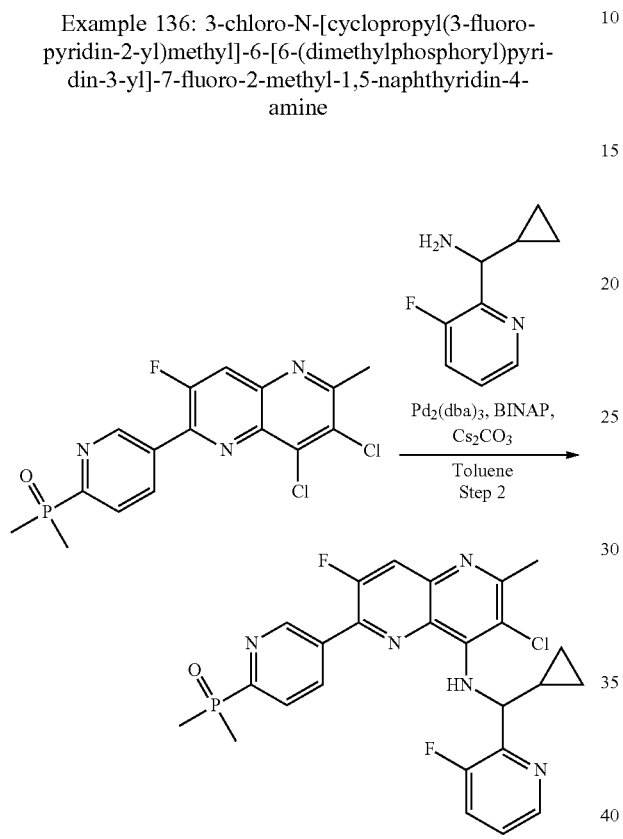

To a stirred solution of 3,4-dichloro-6-[6-(dimethylphosphoryl)pyridin-3-yl]-7-fluoro-2-methyl-1,5-naphthyridine (100 mg, 0.260 mmol) and 1-cyclopropyl-1-(3-fluoropyridin-2-yl)methanamine (52 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (127 mg, 0.390 mmol) at room temperature under nitrogen atmosphere. The resulting mixture was stirred for 16 h at 100° C. under nitrogen atmosphere. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 40 B to 70 B in 30 min; 254/220 nm to afford 3-chloro-N-[cyclopropyl(3-fluoropyridin-2-yl)methyl]-6-[6-(dimethylphosphoryl)pyridin-3-yl]-7-fluoro-2-methyl-1,5-naphthyridin-4-amine (28 mg, 21%) as a white solid. MS ESI calculated for $C_{25}H_{23}ClF_2N_5OP$ [M+H]$^+$, 514.13, found 514.05. $^1$H NMR (400 MHz, Chloroform-d) δ 9.47 (s, 1H), 8.68-8.61 (m, 1H), 8.46-8.43 (m, 1H), 8.35-8.31 (m, 1H), 8.07-7.90 (m, 1H), 7.79 (s, 1H), 7.45-7.34 (m, 1H), 7.26-7.23 (m, 1H), 6.60 (s, 1H), 2.76 (s, 3H), 1.89 (s, 3H), 1.86 (s, 3H), 1.48-1.43 (m, 1H), 0.49-0.41 (m, 4H). $^{19}$F NMR (377 MHz, Chloroform-d) δ -120.63, -126.35. $^{31}$P NMR (162 MHz, Chloroform-d) δ 36.60.

Example 137: 3-chloro-N—[(R)-cyclopropyl(phenyl)methyl]-6-[6-(dimethylphosphoryl)pyridin-3-yl]-7-fluoro-2-methyl-1,5-naphthyridin-4-amine

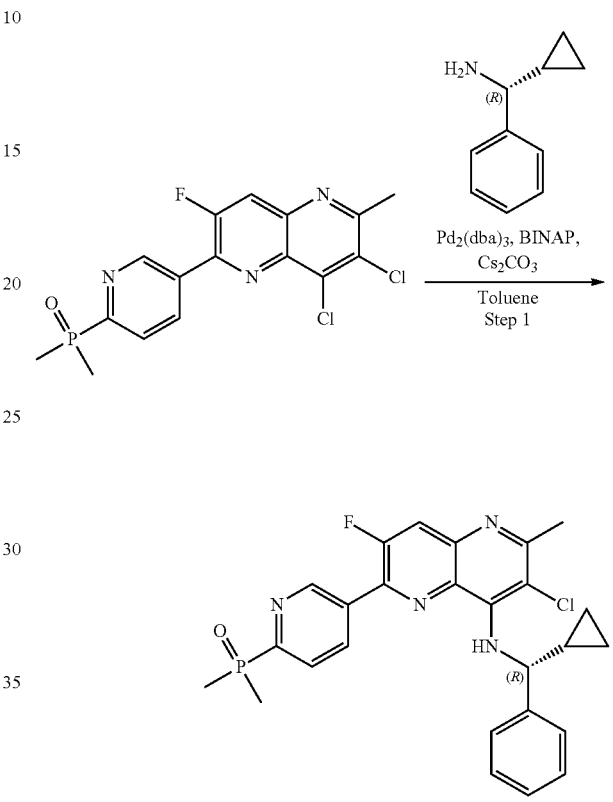

To a stirred solution of 3,4-dichloro-6-[6-(dimethylphosphoryl)pyridin-3-yl]-7-fluoro-2-methyl-1,5-naphthyridine (100 mg, 0.260 mmol) and (1R)-1-cyclopropyl-1-phenyl-methanamine (46 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (19/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in 3-chloro-N—[(R)-cyclopropyl(phenyl)methyl]-6-[6-(dimethylphosphoryl)pyridin-3-yl]-7-fluoro-2-methyl-1,5-naphthyridin-4-amine (34 mg, 26%) as a yellow solid. MS ESI calculated for $C_{26}H_{25}ClFN_4OP$ [M+H]$^+$, 495.14, found 495.05. $^1$H NMR (400 MHz, DMSO-d$_6$) δ 9.27 (d, J=2.1 Hz, 1H), 8.44-8.35 (m, 1H), 8.22-8.10 (m, 2H), 7.36-7.29 (m, 2H), 7.25-7.07 (m, 4H), 5.45 (t, J=8.7 Hz, 1H), 2.61 (s, 3H), 1.77 (s, 3H), 1.73 (s, 3H), 1.58-1.47 (m, 1H), 0.68-0.54 (m, 2H), 0.53-0.38 (m, 2H). $^{19}$F NMR (377 MHz, DMSO-d$_6$) -121.02. $^{31}$P NMR (162 MHz, DMSO-d$_6$) δ 34.25.

357

Example 138: 3-chloro-N—[(R)-cyclopropyl(3,5-difluorophenyl)methyl]-6-[6-(dimethylphosphoryl)pyridin-3-yl]-7-fluoro-2-methyl-1,5-naphthyridin-4-amine

Synthetic Scheme

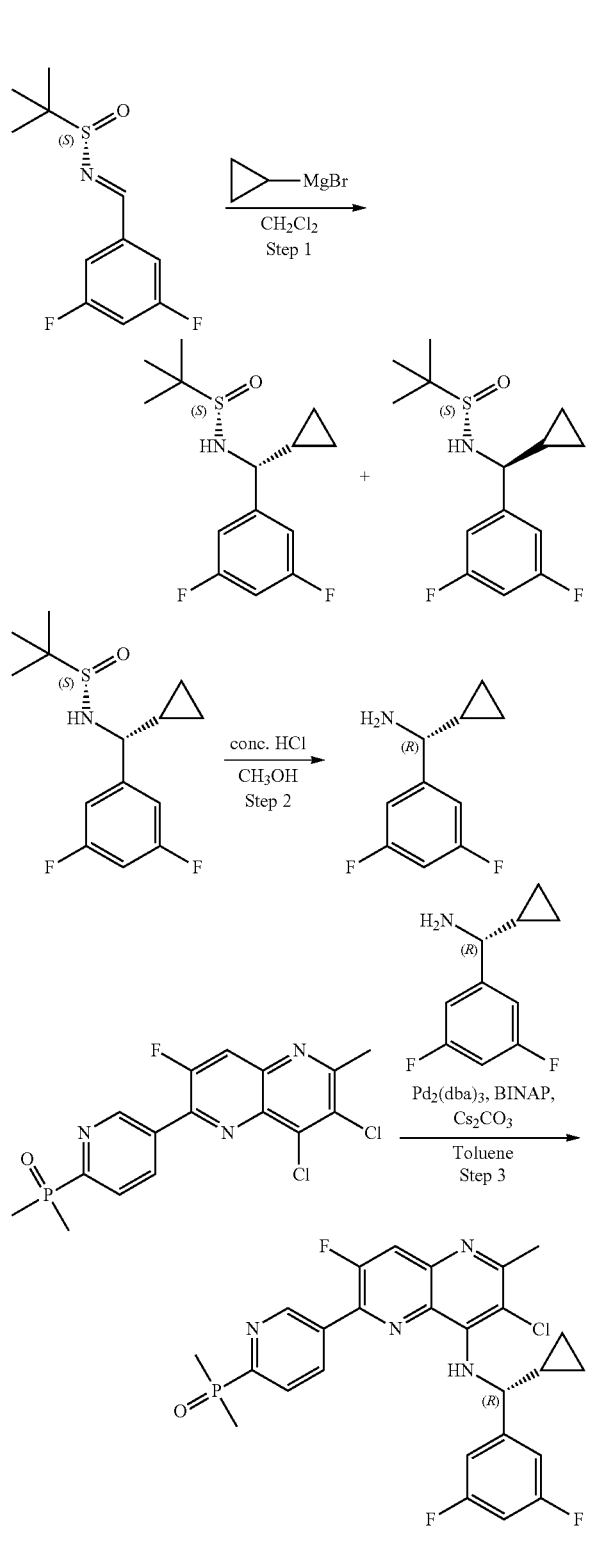

358

Preparation 138A: (S)—N—[(R)-cyclopropyl(3,5-difluorophenyl)methyl]-2-methylpropane-2-sulfinamide and (S)—N—[(S)-cyclopropyl(3,5-difluorophenyl)methyl]-2-methylpropane-2-sulfinamide

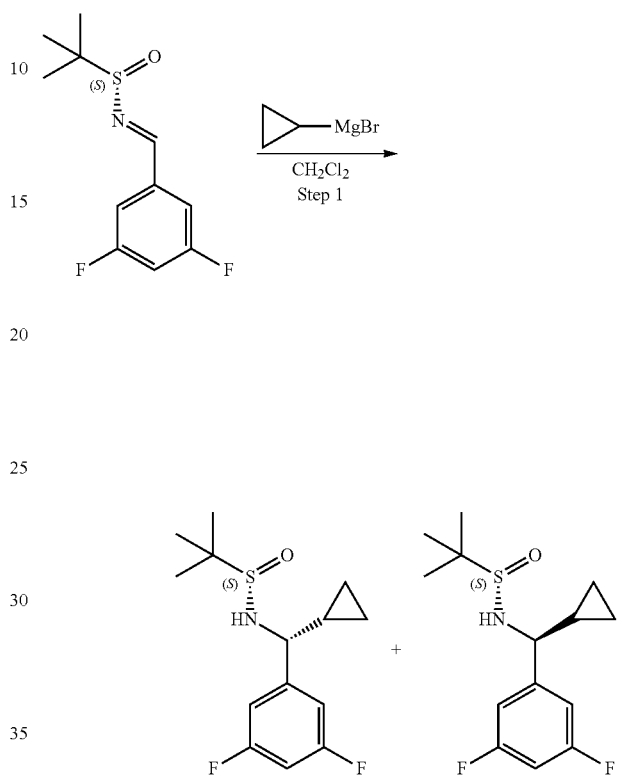

To a stirred solution of (S)—N-[(3,5-difluorophenyl)methylidene]-2-methylpropane-2-sulfinamide (5.00 g, 20.384 mmol) in DCM (50 mL) was added 1M of bromo(cyclopropyl)magnesium in THF (40 mL, 40.768 mmol) dropwise at −35° C. under nitrogen atmosphere. The resulting mixture was stirred for 1 h at −35° C. under nitrogen atmosphere. The reaction was quenched by the addition of sat. NH₄Cl (aq.) (100 mL) at 0° C. The resulting mixture was extracted with CH₂Cl2 (3×100 mL). The combined organic layers were washed with brine (3×50 mL), dried over anhydrous Na₂SO₄. After filtration, the filtrate was concentrated under reduced pressure. The residue was purified by silica gel column chromatography, eluted with PE/EA (3:1) to afford two isomers. The first peak afforded (S)—N—[(R)-cyclopropyl(3,5-difluorophenyl)methyl]-2-methylpropane-2-sulfinamide (2.20 g, 37%) as a white solid. $^1$H NMR (300 MHz, Chloroform-d) δ 6.97-6.88 (m, 2H), 6.78-6.70 (m, 1H), 3.67-3.62 (m, 1H), 1.25 (s, 9H), 1.15-1.02 (m, 1H), 0.92-0.71 (m, 1H), 0.70-0.49 (m, 2H), 0.32-0.20 (m, 1H).

The second peak afforded (S)—N—[(S)-cyclopropyl(3,5-difluorophenyl)methyl]-2-methylpropane-2-sulfinamide (1.40 g, 23%) as a light yellow oil. $^1$H NMR (300 MHz, Chloroform-d) δ 6.94-6.84 (m, 2H), 6.75-6.70 (m, 1H), 3.55-3.49 (m, 1H), 1.24 (s, 9H), 1.18-1.06 (m, 1H), 0.75-0.39 (m, 4H).

359

Preparation 138B: (1R)-1-cyclopropyl-1-(3,5-difluorophenyl)methanamine

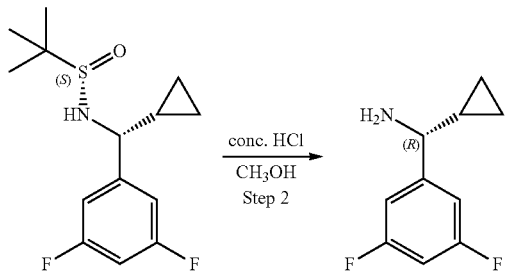

To a stirred solution of (S)—N—[(R)-cyclopropyl(3,5-difluorophenyl)methyl]-2-methylpropane-2-sulfinamide (1.40 g, 4.872 mmol) in MeOH (10 mL) was added conc. HCl (3 mL) dropwise at 0° C. The resulting mixture was stirred for 1 h at room temperature. The resulting mixture was concentrated under reduced pressure. The residue was dissolved in water (50 mL). The aqueous layer was extracted with $CH_2Cl_2$ (3×100 mL). The aqueous layer was basified to pH 8 with KOH (aq.). The resulting mixture was extracted with $CH_2Cl_2$ (3×100 mL). The combined organic layers were washed with brine (3×50 mL), dried over anhydrous $Na_2SO_4$. After filtration, the filtrate was concentrated under reduced pressure. This resulted in (1R)-1-cyclopropyl-1-(3,5-difluorophenyl)methanamine (840 mg, 94%) as a light yellow oil. MS ESI calculated for $C_{10}H_{11}F_2N$ $[M+H]^+$, 184.09, found 184.10. $^1H$ NMR (400 MHz, Chloroform-d) δ 6.99-6.95 (m, 2H), 6.73-6.66 (m, 1H), 3.18 (d, J=8.7 Hz, 1H), 1.07-0.96 (m, 1H), 0.67-0.49 (m, 2H), 0.38-0.27 (m, 2H).

Example 138: 3-chloro-N—[(R)-cyclopropyl(3,5-difluorophenyl)methyl]-6-[6-(dimethylphosphoryl)pyridin-3-yl]-7-fluoro-2-methyl-1,5-naphthyridin-4-amine

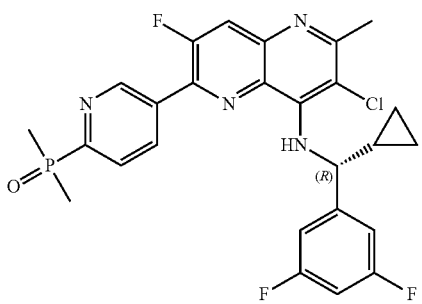

To a stirred mixture of 3,4-dichloro-6-[6-(dimethylphosphoryl)pyridin-3-yl]-7-fluoro-2-methyl-1,5-naphthyridine (100 mg, 0.260 mmol) and (1R)-1-cyclopropyl-1-(3,5-difluorophenyl)methanamine (57 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 40 B to 70 B in 30 min; 254/220 nm to afford 3-chloro-N—[(R)-cyclopropyl(3,5-difluorophenyl)methyl]-6-[6-(dimethylphosphoryl)pyridin-3-yl]-7-fluoro-2-methyl-1,5-naphthyridin-4-amine (42 mg, 30%) as a light yellow solid. MS ESI calculated for $C_{26}H_{23}ClF_3N_4OP$ $[M+H]^+$, 531.13, found 531.05. $^1H$ NMR (300 MHz, DMSO-$d_6$) δ 9.15 (s, 1H), 8.35 (d, J=8.1 Hz, 1H), 8.22-8.09 (m, 2H), 7.14-6.95 (m, 4H), 5.24 (t, J=8.6 Hz, 1H), 2.68-2.60 (m, 3H), 1.76 (s, 3H), 1.71 (s, 3H), 1.59-1.43 (m, 1H), 0.62 (d, J=6.8 Hz, 3H), 0.46-0.41 (m, 1H). $^{19}F$ NMR (282 MHz, DMSO-$d_6$) δ −110.05, −121.16. $^{31}P$ NMR (122 MHz, DMSO-$d_6$) δ 34.23.

Example 139: 3-chloro-N—[(S)-cyclopropyl(3,5-difluorophenyl)methyl]-6-[6-(dimethylphosphoryl)pyridin-3-yl]-7-fluoro-2-methyl-1,5-naphthyridin-4-amine Synthetic Scheme

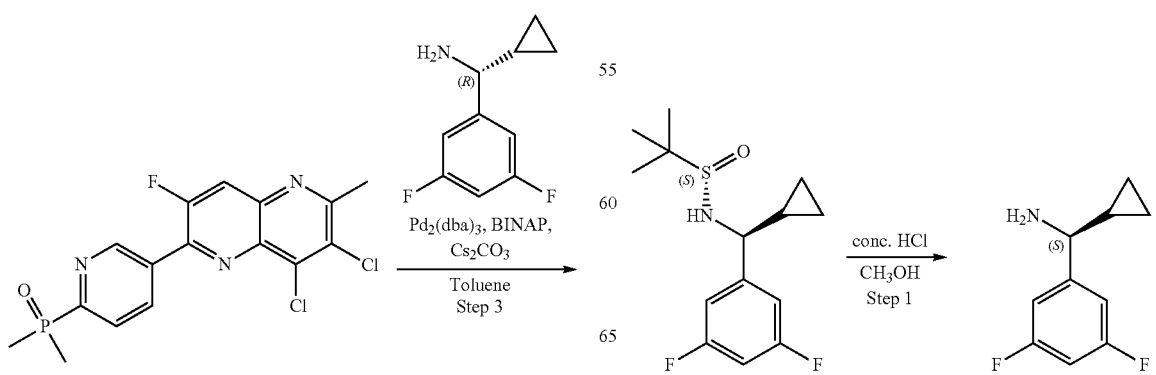

-continued

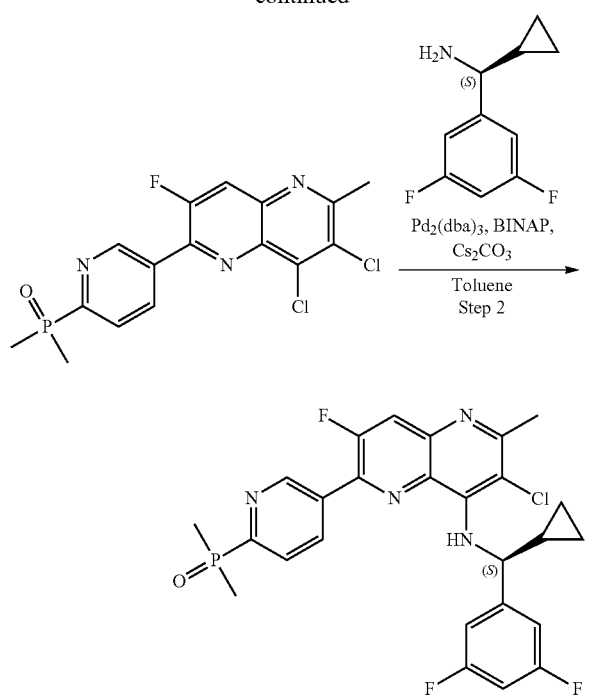

Preparation 139A: (1S)-1-cyclopropyl-1-(3,5-difluorophenyl)methanamine

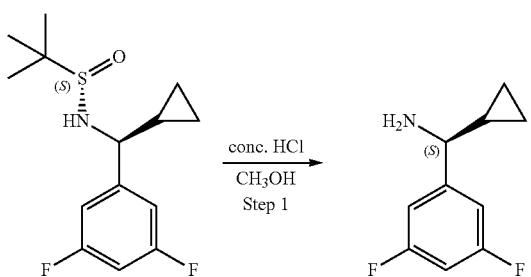

To a stirred solution of (S)—N—[(S)-cyclopropyl(3,5-difluorophenyl)methyl]-2-methylpropane-2-sulfinamide (2.20 g, 7.656 mmol) in MeOH (15 mL) was added conc. HCl (5 mL) dropwise at 0° C. The resulting mixture was stirred for 1 h at room temperature. The resulting mixture was concentrated under reduced pressure. The residue was dissolved in water (50 mL). The aqueous layer was extracted with CH$_2$Cl$_2$ (3×100 mL). The aqueous layer was basified to pH 8 with KOH (aq.). The resulting mixture was extracted with CH$_2$Cl$_2$ (3×100 mL). The combined organic layers were washed with brine (3×50 mL), dried over anhydrous Na$_2$SO$_4$. After filtration, the filtrate was concentrated under reduced pressure. MS ESI calculated for C$_{10}$H$_{11}$F$_2$N [M+H]$^+$, 184.09, found 184.10. This resulted in (1S)-1-cyclopropyl-1-(3,5-difluorophenyl)methanamine (1.20 g, 85%) as a light yellow oil. $^1$H NMR (400 MHz, Chloroform-d) δ 6.99-6.93 (m, 2H), 6.72-6.66 (m, 1H), 3.18 (d, J=8.6 Hz, 1H), 1.06-0.99 (m, 1H), 0.68-0.47 (m, 2H), 0.39-0.25 (m, 2H).

Example 139: 3-chloro-N—[(S)-cyclopropyl(3,5-difluorophenyl)methyl]-6-[6-(dimethylphosphoryl)pyridin-3-yl]-7-fluoro-2-methyl-1,5-naphthyridin-4-amine

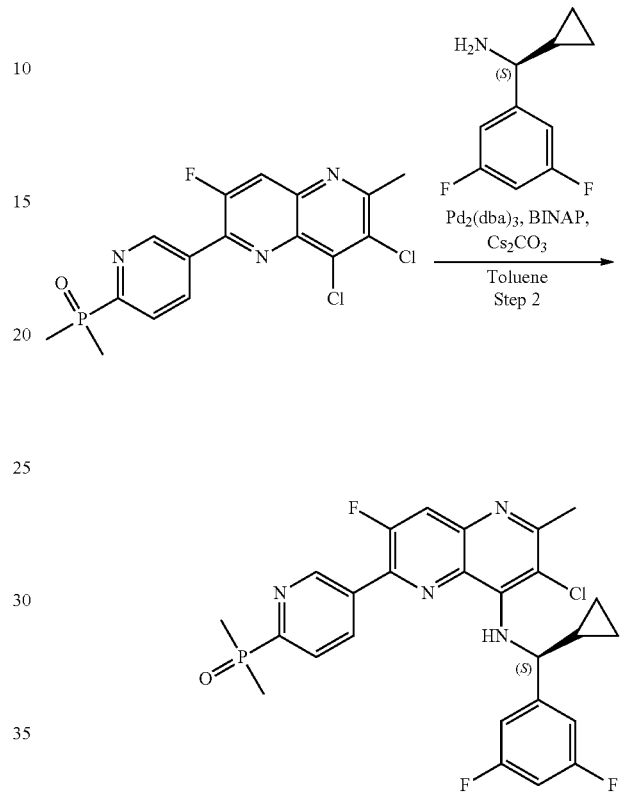

To a stirred mixture of 3,4-dichloro-6-[6-(dimethylphosphoryl)pyridin-3-yl]-7-fluoro-2-methyl-1,5-naphthyridine (100 mg, 0.260 mmol) and (1S)-1-cyclopropyl-1-(3,5-difluorophenyl)methanamine (57 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% NH$_4$HCO$_3$), Mobile Phase B: CH$_3$CN; Flow rate: 60 mL/min; Gradient: 40 B to 70 B in 30 min; 254/220 nm to afford 3-chloro-N—[(S)-cyclopropyl(3,5-difluorophenyl)methyl]-6-[6-(dimethylphosphoryl)pyridin-3-yl]-7-fluoro-2-methyl-1,5-naphthyridin-4-amine (40 mg, 29%) as a light yellow solid. MS ESI calculated for C$_{26}$H$_{23}$ClF$_3$N$_4$OP [M+H]$^+$, 531.13, found 531.05. $^1$H NMR (300 MHz, DMSO-d$_6$) δ 9.15 (s, 1H), 8.42-8.30 (m, 1H), 8.19 (d, J=11.8 Hz, 1H), 8.15-8.09 (m, 1H), 7.15-6.95 (m, 4H), 5.24 (t, J=8.6 Hz, 1H), 2.64 (s, 3H), 1.76 (s, 3H), 1.72 (s, 3H), 1.58-1.46 (m, 1H), 0.62 (d, J=7.2 Hz, 3H), 0.48-0.38 (m, 1H). $^{19}$F NMR (282 MHz, DMSO-d$_6$) δ −110.05, −121.16. $^{31}$P NMR (122 MHz, DMSO-d$_6$) δ 34.28.

Example 140: 3-chloro-N—[(S)-cyclopropyl(phenyl)methyl]-6-[6-(dimethylphosphoryl)pyridin-3-yl]-7-fluoro-2-methyl-1,5-naphthyridin-4-amine

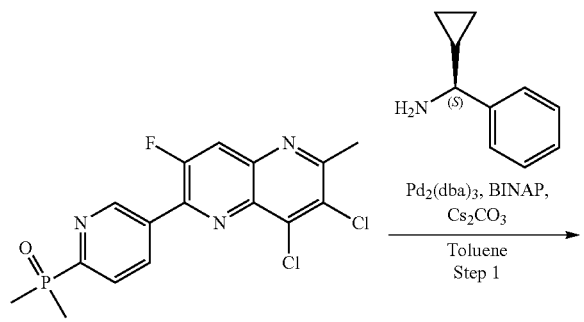

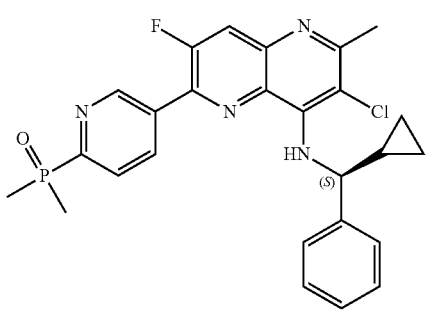

To a stirred solution of 3,4-dichloro-6-[6-(dimethylphosphoryl)pyridin-3-yl]-7-fluoro-2-methyl-1,5-naphthyridine (100 mg, 0.260 mmol) and (1S)-1-cyclopropyl-1-phenylmethanamine (46 mg, 0.312 mmol) in Toluene (2 mL) were added Pd$_2$(dba)$_3$ (24 mg, 0.026 mmol), BINAP (32 mg, 0.052 mmol) and Cs$_2$CO$_3$ (212 mg, 0.650 mmol) at room temperature under nitrogen atmosphere. The resulting mixture was stirred for 4 h at 100° C. under nitrogen atmosphere. The resulting mixture was concentrated under reduced pressure. The residue was purified by silica gel column chromatography, eluted with CH$_2$Cl$_2$/MeOH (19/1) followed by reversed-phase flash chromatography with the following conditions: column, C18 silica gel; mobile phase, CH$_3$CN in water (10 mmol/L NH$_4$HCO$_3$), 40% to 60% gradient in 30 min; detector, 254 nm. This resulted in 3-chloro-N—[(S)-cyclopropyl(phenyl)methyl]-6-[6-(dimethylphosphoryl)pyridin-3-yl]-7-fluoro-2-methyl-1,5-naphthyridin-4-amine (46 mg, 36%) as a yellow solid. MS ESI calculated for C$_{26}$H$_{25}$ClFN$_4$OP [M+H]$^+$, 495.14, found 495.00. $^1$H NMR (400 MHz, DMSO-d$_6$) δ 9.27 (s, 1H), 8.41 (d, J=7.9 Hz, 1H), 8.20 (d, J=11.8 Hz, 1H), 8.16-8.10 (m, 1H), 7.36-7.29 (m, 2H), 7.27-7.08 (m, 4H), 5.46 (t, J=8.7 Hz, 1H), 2.61 (s, 3H), 1.77 (s, 3H), 1.73 (s, 3H), 1.58-1.46 (m, 1H), 0.69-0.54 (m, 2H), 0.53-0.37 (m, 2H). $^{19}$F NMR (377 MHz, DMSO-d$_6$) δ −121.02. $^{31}$P NMR (162 MHz, DMSO-d$_6$) 34.26.

Example 141: 3-[(1R)-1-({3-chloro-7-fluoro-2-methyl-6-[6-(4-oxo-1,4lambda5-oxaphosphinan-4-yl)pyridin-3-yl]-1,5-naphthyridin-4-yl}amino)ethyl]-4-fluorobenzonitrile

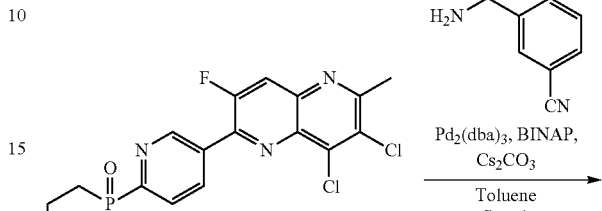

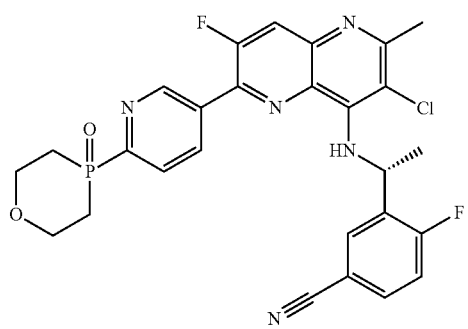

To a stirred solution of 4-[5-(7,8-dichloro-3-fluoro-6-methyl-1,5-naphthyridin-2-yl)pyridin-2-yl]-1,4lambda5-oxaphosphinan-4-one (100 mg, 0.235 mmol) and 3-[(1R)-1-aminoethyl]-4-fluorobenzonitrile (46 mg, 0.282 mmol) in Toluene (2 mL) were added Pd$_2$(dba)$_3$ (21 mg, 0.024 mmol), BINAP (29 mg, 0.047 mmol) and Cs$_2$CO$_3$ (191 mg, 0.587 mmol) at room temperature under nitrogen atmosphere. The resulting mixture was stirred for overnight at 100° C. under nitrogen atmosphere. The resulting mixture was concentrated under reduced pressure. The residue was purified by silica gel column chromatography, eluted with CH$_2$Cl$_2$/MeOH (15/1) followed by reversed-phase flash chromatography with the following conditions: column, C18 silica gel; mobile phase, CH$_3$CN in water (10 mmol/L NH$_4$HCO$_3$), 30% to 50% gradient in 30 min; detector, 254 nm. This resulted in 3-[(1R)-1-({3-chloro-7-fluoro-2-methyl-6-[6-(4-oxo-1,4lambda5-oxaphosphinan-4-yl)pyridin-3-yl]-1,5-naphthyridin-4-yl}amino)ethyl]-4-fluorobenzonitrile (33 mg, 25%) as a light yellow solid. MS ESI calculated for C$_{27}$H$_{23}$ClF$_2$N$_5$O$_2$P [M+H]$^+$, 554.12, found 554.05. $^1$H NMR (400 MHz, Chloroform-d) δ 9.23 (s, 1H), 8.30 (s, 2H), 8.00 (d, J=11.3 Hz, 1H), 7.59-7.47 (m, 2H), 7.14-7.02 (m, 1H), 6.56-6.29 (m, 2H), 4.35-4.19 (m, 4H), 2.75 (s, 3H), 2.68-2.51 (m, 2H), 2.13 (t, J=16.0 Hz, 2H), 1.73 (d, J=6.4 Hz, 3H). $^{19}$F NMR (377 MHz, Chloroform-d) δ −108.54, −120.40. $^{31}$P NMR (162 MHz, Chloroform-d) δ 25.73.

Example 142: 3-chloro-N-[1-(2,3-difluorophenyl)-2,2-difluoropropyl]-6-[6-(dimethylphosphoryl)pyridin-3-yl]-7-fluoro-2-methyl-1,5-naphthyridin-4-amine Synthetic Scheme

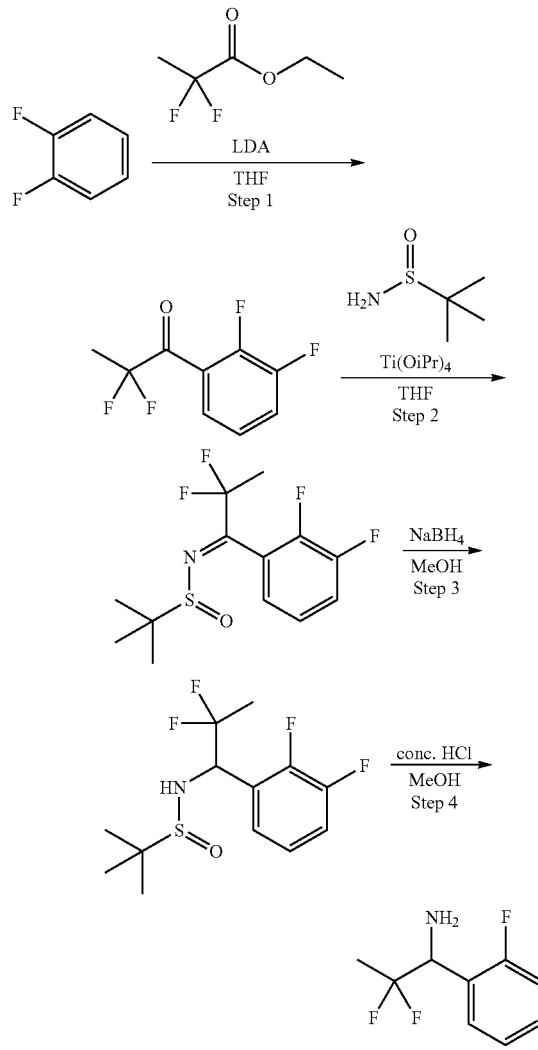

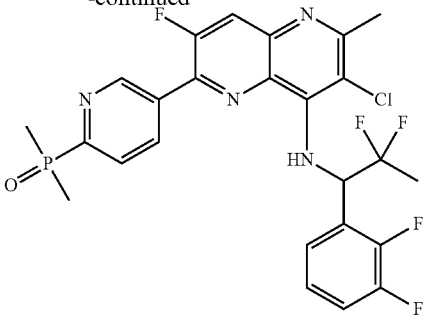

Preparation 142A: 1-(2,3-difluorophenyl)-2,2-difluoropropan-1-one

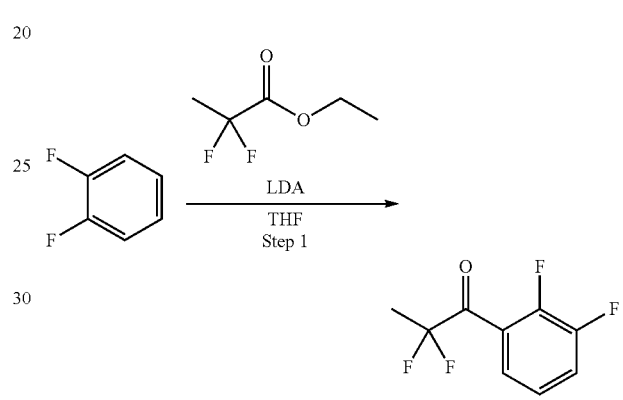

To a stirred solution of diisopropylamine (9.76 g, 96.411 mmol) in THF (50 mL) were added n-BuLi (38.6 mL, 96.411 mmol) dropwise at −78° C. under nitrogen atmosphere. The resulting mixture was stirred for additional 30 min at −78° C. Then, the solution of 1,2-difluorobenzene (10.00 g, 87.646 mmol) in THF (50 mL) were added the above solution dropwise at −78° C. under nitrogen atmosphere. The resulting mixture was stirred for additional 30 min at −78° C. To the above mixture was added ethyl 2,2-difluoropropanoate (14.53 g, 105.175 mmol) dropwise 30 min at −78° C. The resulting mixture was stirred for additional 30 min at −78° C. Then, the above solution was stirred for another 30 min. The reaction was quenched with water at room temperature. The aqueous layer was extracted with n-hexane (3×100 mL). The resulting mixture was concentrated under reduced pressure at room temperature. The crude product (7.70 g) was used in the next step directly without further purification.

Preparation 142B: N-[1-(2,3-difluorophenyl)-2,2-difluoropropylidene]-2-methylpropane-2-sulfinamide

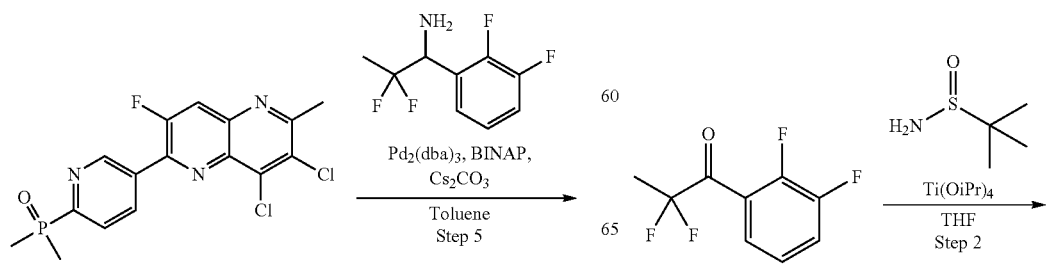

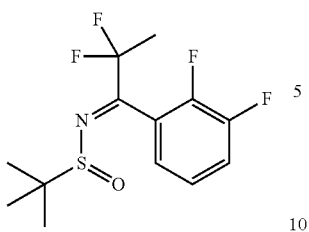

A mixture of 1-(2,3-difluorophenyl)-2,2-difluoropropan-1-one (7.70 g, 37.353 mmol), 2-methylpropane-2-sulfinamide (5.43 g, 44.824 mmol) and Ti(OiPr)$_4$ (21.23 g, 74.706 mmol) in THF (100 mL) was stirred for overnight at 80° C. The reaction was quenched with sat. sodium hyposulfite (aq.) at room temperature. The resulting mixture was diluted with EtOAc (150 mL). The resulting mixture was filtered, and the filter cake was washed with EtOAc (3×50 mL). The aqueous layer was extracted with EtOAc (3×150 mL). The resulting mixture was concentrated under reduced pressure. The crude product (8.00 g) was used in the next step directly without further purification.

Preparation 142C: N-[1-(2,3-difluorophenyl)-2,2-difluoropropyl]-2-methylpropane-2-sulfinamide

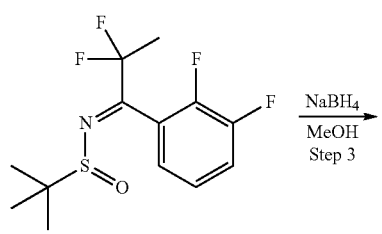

To a stirred solution of N-[1-(2,3-difluorophenyl)-2,2-difluoropropylidene]-2-methylpropane-2-sulfinamide (8.00 g, 25.863 mmol) in MeOH (80 mL) were added NaBH$_4$ (1.17 g, 31.036 mmol) in portions at 0° C. The reaction was quenched with water at room temperature. The resulting mixture was concentrated under reduced pressure. The aqueous layer was extracted with EtOAc (3×100 mL). The resulting mixture was concentrated under reduced pressure. The residue was purified by silica gel column chromatography, eluted with CH$_2$Cl$_2$/MeOH (99/1) to afford (S)—N-[1-(2,3-difluorophenyl)-2,2-difluoropropyl]-2-methyl propane-2-sulfinamide (5.60 g, 3 steps 20%) as a yellow solid. MS ESI calculated for C$_{13}$H$_{17}$F$_4$NOS [M+H]$^+$, 312.10, found 312.15. $^1$H NMR (400 MHz, Chloroform-d) δ 7.24-7.07 (m, 3H), 4.88 (m, 1H), 4.02 (d, J=8.1 Hz, 1H), 1.73-1.60 (m, 3H), 1.23 (d, J=12.8 Hz, 9H).

Preparation 142D: 1-(2,3-difluorophenyl)-2,2-difluoropropan-1-amine

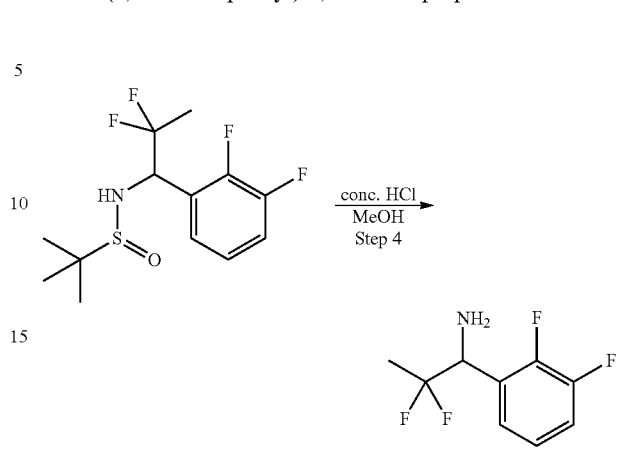

A mixture of N-[1-(2,3-difluorophenyl)-2,2-difluoropropyl]-2-methylpropane-2-sulfinamide (1.00 g, 3.212 mmol) and conc. HCl (7 mL) in CH$_3$OH (21 mL) was stirred for 30 min at room temperature. The resulting mixture was concentrated under reduced pressure. The mixture was basified to pH 7 with saturated NaHCO$_3$ (aq.). The aqueous layer was extracted with EtOAc (5×50 mL). The resulting mixture was concentrated under reduced pressure. This result in 1-(2,3-difluorophenyl)-2,2-difluoropropan-1-amine (600 mg, 90%) as a yellow oil. MS ESI calculated for C$_9$H$_9$F$_4$N [M+H]$^+$, 208.07, found 208.15. $^1$H NMR (400 MHz, Chloroform-d) δ 7.25 (t, J=7.1 Hz, 1H), 7.18-7.08 (m, 2H), 4.68-4.46 (m, 1H), 1.59 (t, J=18.8 Hz, 3H).

Example 142: 3-chloro-N-[1-(2,3-difluorophenyl)-2,2-difluoropropyl]-6-[6-(dimethylphosphoryl)pyridin-3-yl]-7-fluoro-2-methyl-1,5-naphthyridin-4-amine

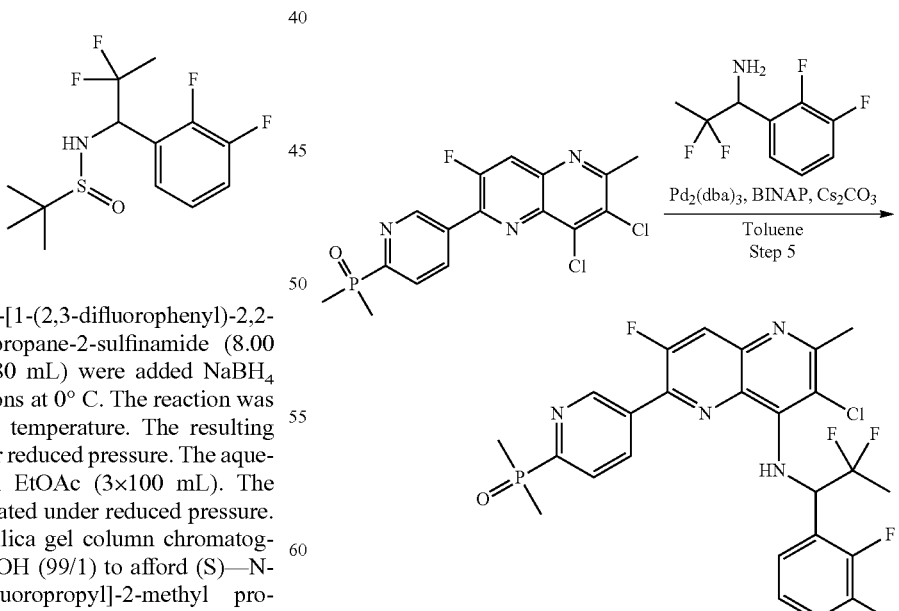

A mixture of 1-(2,3-difluorophenyl)-2,2-difluoropropan-1-amine (100 mg, 0.483 mmol), 3,4-dichloro-6-[6-(dimethylphosphoryl)pyridin-3-yl]-7-fluoro-2-methyl-1,5-naphthyridine (222 mg, 0.580 mmol), Pd$_2$(dba)$_3$ (44 mg, 0.048 mmol), BINAP (60 mg, 0.097 mmol) and Cs$_2$CO$_3$ (235 mg, 0.724 mmol) in Toluene (2 mL) was stirred for overnight at 80° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 70 mL/min; Gradient: 5 B to 70 B in 30 min; 254/220 nm to afford 3-chloro-N-[1-(2,3-difluorophenyl)-2,2-difluoropropyl]-6-[6-(dimethylphosphoryl)pyridin-3-yl]-7-fluoro-2-methyl-1,5-naphthyridin-4-amine (98 mg, 36%) as a white solid. MS ESI calculated for C$_{25}$H$_{21}$ClF$_5$N$_4$OP [M+H]$^+$, 555.11, found 554.95. $^1$H NMR (400 MHz, DMSO-d$_6$) δ 9.18 (s, 1H), 8.45-8.39 (m, 1H), 8.33 (d, J=11.3 Hz, 1H), 8.19-8.12 (m, 1H), 7.58-7.36 (m, 2H), 7.24 (s, 1H), 7.10-1.01 (m, 1H), 6.68-6.51 (m, 1H), 2.68 (s, 3H), 1.84-1.70 (m, 9H). $^{19}$F NMR (377 MHz, DMSO-d$_6$) δ -97.78, -97.81, -98.42, -98.45, -99.49, -99.51, -100.13, -100.15, -120.35, -138.49, -138.55, -141.93. $^{31}$P NMR (162 MHz, DMSO-d$_6$) δ 34.29.

Example 143: 4-[5-(7-chloro-8-{[(1R)-1-(2,3-difluorophenyl)ethyl]amino}-3-fluoro-6-methyl-1,5-naphthyridin-2-yl)pyridin-2-yl]-1,4lambda5-oxaphosphinan-4-one Synthetic Scheme

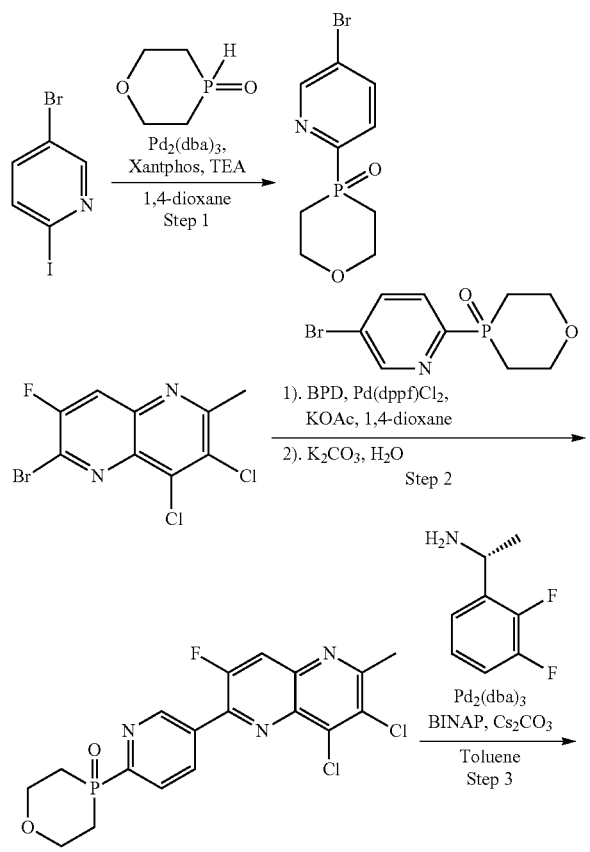

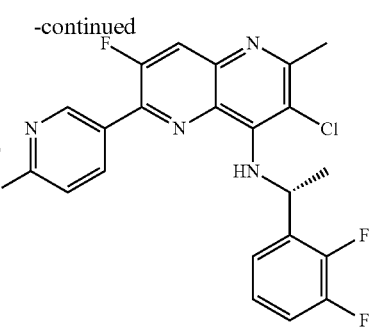

Preparation 143A: 4-(5-bromopyridin-2-yl)-1,4lambda5-oxaphosphinan-4-one

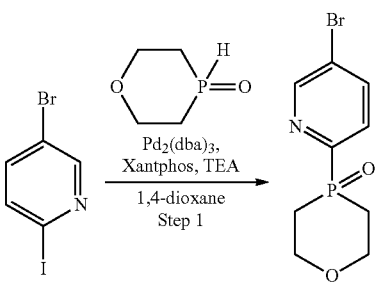

A mixture of Pd$_2$(dba)$_3$ (194 mg, 0.211 mmol) and Xantphos (245 mg, 0.423 mmol) in 1,4-dioxane (5 mL) was stirred for 10 min at room temperature under nitrogen atmosphere. To the above mixture were added a solution of 5-bromo-2-iodopyridine (600 mg, 2.113 mmol), 1,4lambda5-oxaphosphinan-4-one (1.01 g, 8.452 mmol) and TEA (321 mg, 3.170 mmol) in 1,4-dioxane (10 mL) at room temperature. The resulting mixture was stirred for additional overnight at 80° C. under nitrogen atmosphere. The resulting mixture was concentrated under reduced pressure. The residue was purified by silica gel column chromatography, eluted with CH$_2$Cl$_2$/MeOH (20/1) to afford 4-(5-bromopyridin-2-yl)-1,4lambda5-oxaphosphinan-4-one (260 mg, 44%) as a white solid. MS ESI calculated for C$_9$H$_{11}$BrNO$_2$P [M+H]$^+$, 275.97 277.97, found 275.95 277.97. $^1$H NMR (400 MHz, Chloroform-d) δ 8.82 (s, 1H), 8.04-8.00 (m, 2H), 4.26-4.24 (m, 4H), 2.52-2.38 (m, 2H), 2.12-1.97 (m, 2H). $^{31}$P NMR (162 MHz, Chloroform-d) δ 25.64.

Preparation 143B: 4-[5-(7,8-dichloro-3-fluoro-6-methyl-1,5-naphthyridin-2-yl)pyridin-2-yl]-1,4lambda5-oxaphosphinan-4-one

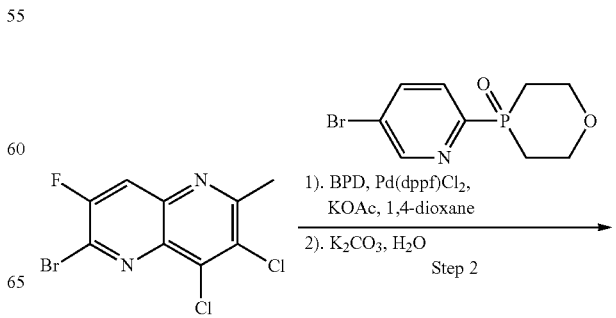

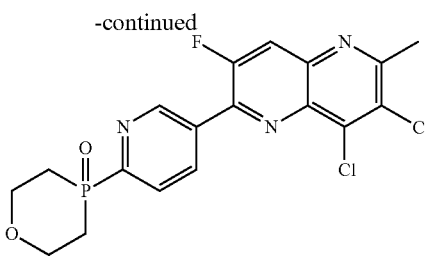

A mixture of 4-(5-bromopyridin-2-yl)-1,4lambda5-oxaphosphinan-4-one (176 mg, 0.639 mmol), BPD (251 mg, 0.988 mmol), KOAc (142 mg, 1.452 mmol) and Pd(dppf)Cl₂·CH₂Cl₂ (47 mg, 0.058 mmol) in 1,4-dioxane (2 mL) was stirred for 2 h at 100° C. under nitrogen atmosphere. The mixture was allowed to cool down to room temperature. To the above mixture were added 6-bromo-3,4-dichloro-7-fluoro-2-methyl-1,5-naphthyridine (180 mg, 0.581 mmol), K₂CO₃ (160 mg, 1.162 mmol) in H₂O (0.4 mL) at room temperature under nitrogen atmosphere. The resulting mixture was stirred for additional 2 h at 80° C. The resulting mixture was concentrated under reduced pressure. The residue was purified by silica gel column chromatography, eluted with CH₂Cl₂/MeOH (19/1) to afford 4-[5-(7,8-dichloro-3-fluoro-6-methyl-1,5-naphthyridin-2-yl)pyridin-2-yl]-1,4lambda5-oxaphosphinan-4-one (219 mg, 88%) as a yellow solid. MS ESI calculated for $C_{18}H_{15}Cl_2FN_3O_2P$ [M+H]⁺, 426.03, found 425.95. ¹H NMR (300 MHz, Chloroform-d) δ 9.57 (s, 1H), 8.66 (d, J=6.9 Hz, 1H), 8.32 (s, 1H), 8.14 (d, J=11.0 Hz, 1H), 4.26 (d, J=15.2 Hz, 4H), 2.91 (s, 3H), 2.58 (s, 2H), 2.10 (d, J=10.6 Hz, 2H). ¹⁹F NMR (282 MHz, Chloroform-d) δ −118.65.

Example 143: 4-[5-(7-chloro-8-{[(1R)-1-(2,3-difluorophenyl)ethyl]amino}-3-fluoro-6-methyl-1,5-naphthyridin-2-yl)pyridin-2-yl]-1,4lambda5-oxaphosphinan-4-one

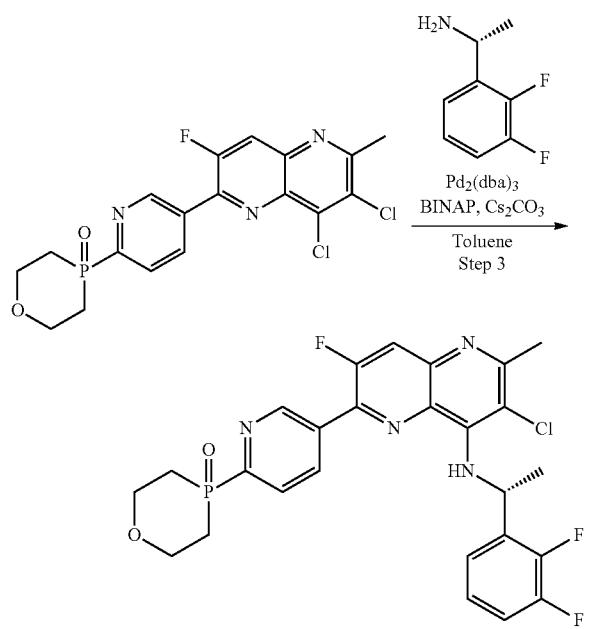

To a stirred solution of 4-[5-(7,8-dichloro-3-fluoro-6-methyl-1,5-naphthyridin-2-yl)pyridin-2-yl]-1,4lambda5-oxaphosphinan-4-one (100 mg, 0.235 mmol) and (1R)-1-(2,3-difluorophenyl)ethan-1-amine hydrochloride (54 mg, 0.282 mmol) in Toluene (2 mL) were added Pd₂(dba)₃ (21 mg, 0.024 mmol), BINAP (29 mg, 0.047 mmol) and Cs₂CO₃ (191 mg, 0.587 mmol) at room temperature under nitrogen atmosphere. The resulting mixture was stirred for overnight at 100° C. under nitrogen atmosphere. The resulting mixture was concentrated under reduced pressure. The residue was purified by silica gel column chromatography, eluted with CH₂Cl₂/MeOH (15/1) followed by reversed-phase flash chromatography with the following conditions: column, C18 silica gel; mobile phase, CH₃CN in water (10 mmol/L NH₄HCO₃), 40% to 60% gradient in 30 min; detector, 254 nm. This resulted in 4-[5-(7-chloro-8-{[(1R)-1-(2,3-difluorophenyl)ethyl]amino}-3-fluoro-6-methyl-1,5-naphthyridin-2-yl)pyridin-2-yl]-1,4lambda5-oxaphosphinan-4-one (48 mg, 36%) as a light yellow solid. MS ESI calculated for $C_{26}H_{23}ClF_3N_4O_2P$ [M+H]⁺, 547.12, found 547.05. ¹H NMR (400 MHz, Chloroform-d) δ 9.20 (s, 1H), 8.36-8.23 (m, 2H), 7.96 (d, J=11.4 Hz, 1H), 7.07-6.88 (m, 3H), 6.54-6.36 (m, 2H), 4.37-4.18 (m, 4H), 2.74 (s, 3H), 2.66-2.51 (m, 2H), 2.21-2.06 (m, 2H), 1.72 (d, J=6.2 Hz, 3H). ¹⁹F NMR (377 MHz, Chloroform-d) δ −120.69, −137.87, −137.93, −144.04, −144.10. ³¹P NMR (162 MHz, Chloroform-d) δ 25.65.

Example 144: 4-{[(1R)-1-(2,3-difluorophenyl)ethyl]amino}-6-[6-(dimethylphosphoryl)pyridin-3-yl]-7-fluoro-2-methyl-1,5-naphthyridine-3-carbonitrile

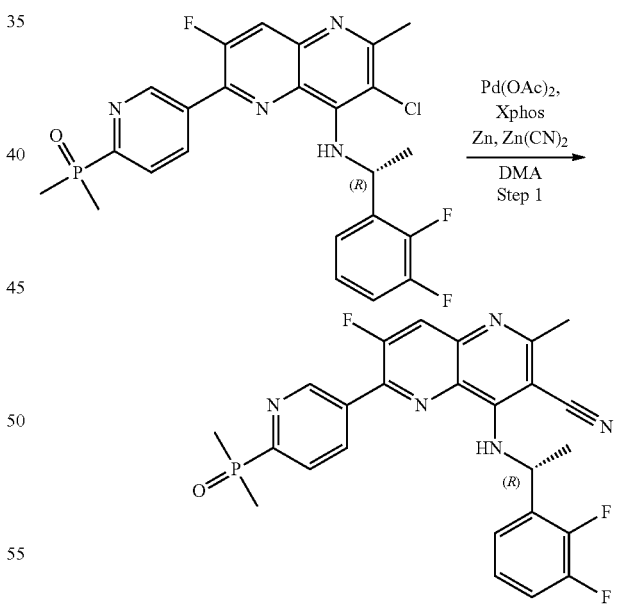

A mixture of 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine (100 mg, 0.198 mmol), Pd(OAc)₂ (1 mg, 0.004 mmol), Xantphos (4 mg, 0.008 mmol), Zn (1 mg, 0.002 mmol) and Zn(CN)₂ (13 mg, 0.119 mmol) in DMA (2 mL) was stirred for 16 h at 120° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 55% B in 20 min; 254/220 nm to afford 4-{[(1R)-1-(2,3-difluorophenyl)ethyl]amino}-6-[6-(dimethylphosphoryl)pyridin-3-yl]-7-fluoro-2-methyl-1,5-naphthyridine-3-carbonitrile (14 mg, 14%) as a white solid. MS ESI calculated for C$_{25}$H$_{21}$F$_3$N$_5$OP [M+H]$^+$, 496.14, found 496.25. $^1$H NMR (300 MHz, Chloroform-d) δ 9.38 (s, 1H), 8.49 (d, J=6.3 Hz, 1H), 8.40-8.29 (m, 1H), 8.13-7.90 (m, 2H), 7.25-7.03 (m, 3H), 6.19-6.05 (m, 1H), 2.79 (s, 3H), 1.90 (s, 3H), 1.87 (s, 3H), 1.85 (d, J=6.8 Hz, 3H); $^{19}$F NMR (282 MHz, Chloroform-d) δ −116.91, −136.81, −136.88, −143.20, −143.27. $^{31}$P NMR (121 MHz, Chloroform-d) δ 36.54.

Example 145 and 146: (S)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide and (R)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide Synthetic Scheme

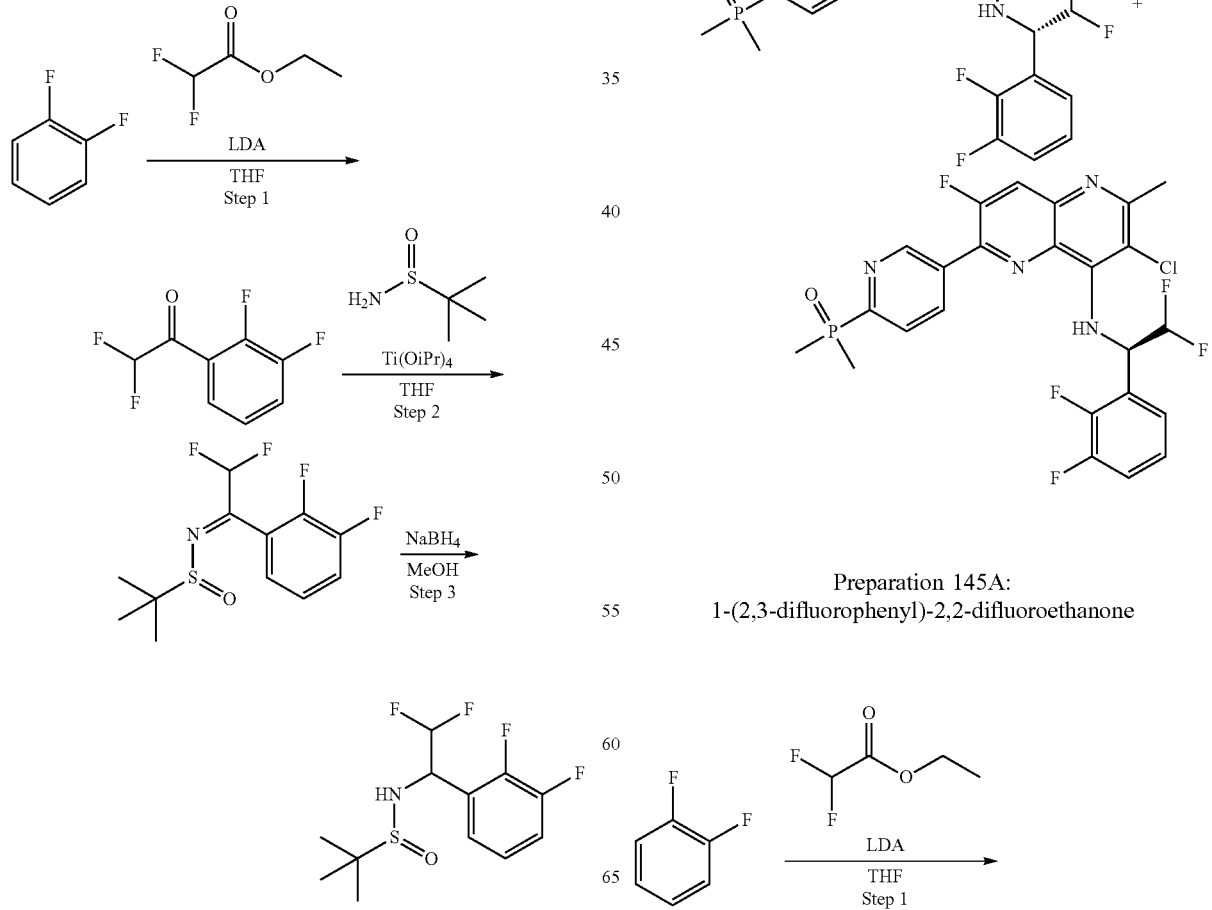

Preparation 145A:
1-(2,3-difluorophenyl)-2,2-difluoroethanone

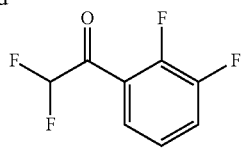

To a stirred solution of diisopropylamine (9.76 g, 96.411 mmol) in THF (50 mL) were added n-BuLi (38.6 mL, 96.411 mmol, 3M in THF) dropwise at −78° C. under nitrogen atmosphere. The resulting mixture was stirred for additional 30 min at −78° C. Then the solution of 1,2-difluorobenzene (10.00 g, 87.646 mmol) in THF (50 mL) were added the above solution dropwise at −78° C. under nitrogen atmosphere. The resulting mixture was stirred for additional 30 min at −78° C. To the above mixture was added ethyl 2,2-difluoroacetate (13.05 g, 105.175 mmol) dropwise 30 min at −78° C. The resulting mixture was stirred for additional 30 min at −78° C. Then the above solution was stirred for another 30 min. The reaction was quenched with water at room temperature. The aqueous layer was extracted with n-hexane (3×100 mL). The resulting mixture was concentrated under reduced pressure at room temperature. The crude product was used in the next step directly without further purification. MS ESI calculated for $C_8H_4F_4O$ [M+H]$^+$, 193.02, found N/A.

Preparation 145B: N-[1-(2,3-difluorophenyl)-2,2-difluoroethylidene]-2-methylpropane-2-sulfinamide

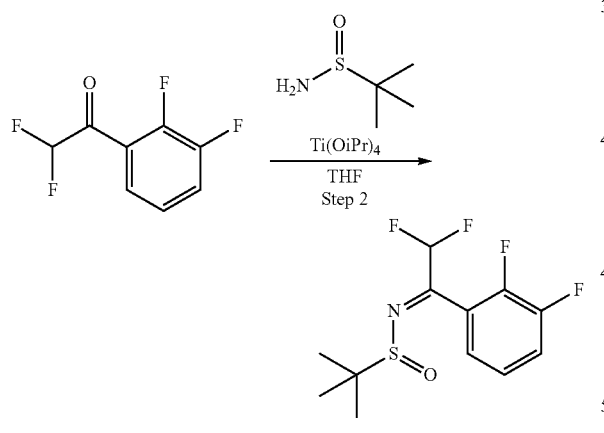

A mixture of 1-(2,3-difluorophenyl)-2,2-difluoroethanone (7.70 g, 40.081 mmol), 2-methylpropane-2-sulfinamide (5.83 g, 48.097 mmol) and Ti(OiPr)$_4$ (22.78 g, 80.162 mmol) in THF (100 mL) was stirred for overnight at 80° C. The reaction was quenched by the addition of sat. NaHCO$_3$(aq.) (100 mL) at room temperature. The residue was dissolved in EtOAc (150 mL). The resulting mixture was filtered, the filter cake was washed with EtOAc (3×50 mL). The aqueous layer was extracted with EtOAc (3×150 mL). The resulting mixture was concentrated under reduced pressure. This resulted in N-[1-(2,3-difluorophenyl)-2,2-difluoroethylidene]-2-methylpropane-2-sulfinamide (8.00 g, 68%) as a yellow oil. The crude product was used in the next step directly without further purification. MS ESI calculated for $C_{12}H_{13}F_4NOS$ [M+H]$^+$, 296.07, found N/A.

Preparation 145C: N-[1-(2,3-difluorophenyl)-2,2-difluoroethyl]-2-methylpropane-2-sulfinamide

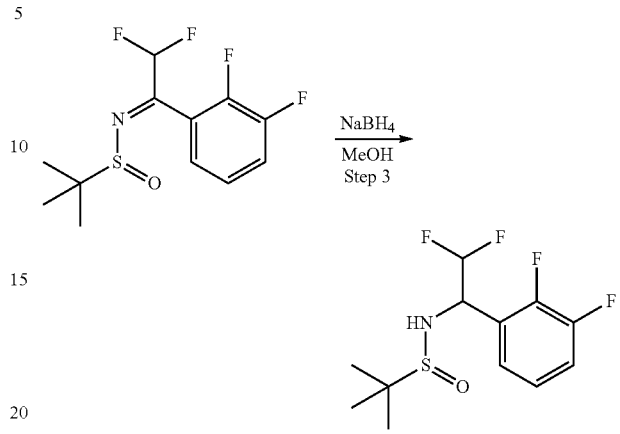

To a stirred solution of N-[1-(2,3-difluorophenyl)-2,2-difluoroethylidene]-2-methylpropane-2-sulfinamide (8.00 g, 27.091 mmol) in MeOH (80 mL) was added NaBH$_4$ (1.23 g, 32.509 mmol) in portions at 0° C. The resulting mixture was stirred for additional overnight at room temperature. The reaction was quenched with water at 0° C. The resulting mixture was concentrated under reduced pressure. The aqueous layer was extracted with EtOAc (3×75 mL). The resulting mixture was concentrated under reduced pressure. The residue was purified by silica gel column chromatography, eluted with CH$_2$Cl$_2$/MeOH (99:1) to afford N-[1-(2,3-difluorophenyl)-2,2-difluoroethyl]-2-methylpropane-2-sulfinamide (3.90 g, 48%) as a yellow oil. MS ESI calculated for $C_{12}H_{15}F_4NOS$ [M+H]$^+$, 298.08, found 298.10. $^1$H NMR (400 MHz, Chloroform-d) δ 7.26-7.09 (m, 3H), 6.26-5.83 (m, 1H), 5.03-4.85 (m, 1H), 4.15-4.25 (m, 1H), 1.24 (s, 9H).

Preparation 145D: 1-(2,3-difluorophenyl)-2,2-difluoroethanamine

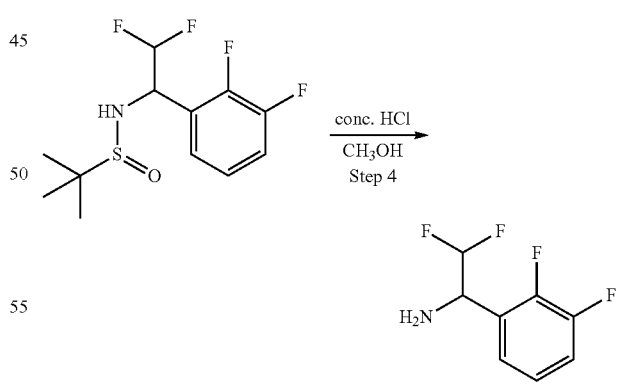

A mixture of N-[1-(2,3-difluorophenyl)-2,2-difluoroethyl]-2-methylpropane-2-sulfinamide (1.00 g, 3.363 mmol) and conc. HCl (3 mL) in CH$_3$OH (21 mL) was stirred for 30 min at room temperature. The resulting mixture was concentrated under reduced pressure. The mixture was basified to pH 7 with saturated NaHCO$_3$ (aq.). The aqueous layer was extracted with EtOAc (5×50 mL). The resulting mixture was concentrated under reduced pressure. This result in 1-(2,3- difluorophenyl)-2,2-difluoroethanamine (590 mg, 91%) as a yellow oil. MS ESI calculated for $C_8H_7F_4N$ [M+H]+, 194.05, found 194.00. $^1$H NMR (400 MHz, Chloroform-d) δ 7.25-7.08 (m, 3H), 6.05-5.71 (m, 1H), 4.59-4.50 (m, 1H).

Example 145 and 146: (S)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide and (R)-(5-(7-chloro-8-((1-(2,3-difluorophenyl)-2,2-difluoroethyl)amino)-3-fluoro-6-methyl-1,5-naphthyridin-2-yl)pyridin-2-yl) dimethylphosphine oxide

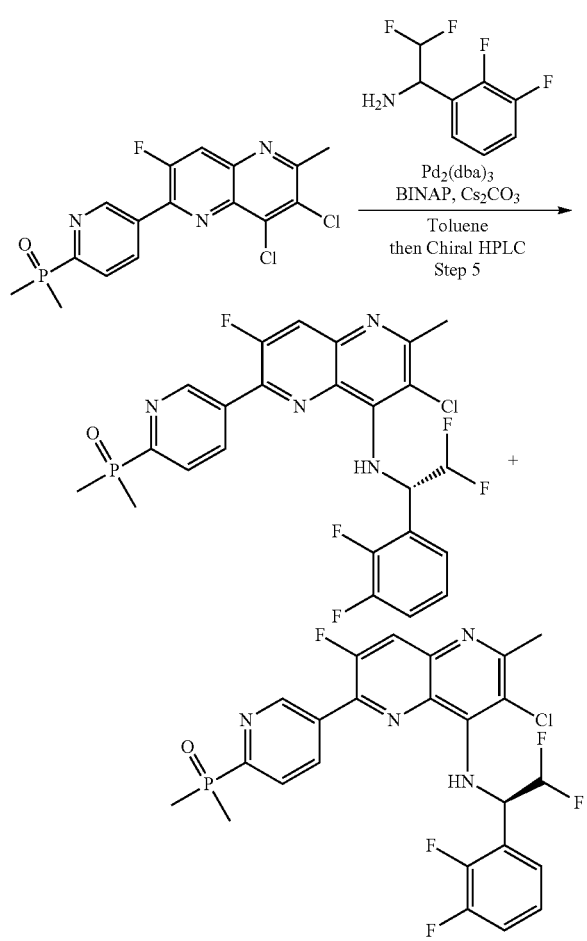

A mixture of 1-(2,3-difluorophenyl)-2,2-difluoroethanamine (150 mg, 0.777 mmol), 3,4-dichloro-6-[6-(dimethylphosphoryl)pyridin-3-yl]-7-fluoro-2-methyl-1,5-naphthyridine (358 mg, 0.932 mmol), $Pd_2(dba)_3$ (71 mg, 0.078 mmol), BINAP (97 mg, 0.155 mmol) and $Cs_2CO_3$ (380 mg, 1.165 mmol) in Toluene (4 mL) was stirred for overnight at 80° C. under nitrogen atmosphere. The resulting mixture was concentrated under reduced pressure. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in water (10 mmol/L $NH_4HCO_3$), 10% to 70% gradient in 15 min; detector, 254 nm. This result in (5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide (250 mg) as a light yellow solid. The racemic (250 mg) was resolved by SFC with the following conditions (Column: CHIRALPAK IG 3*25 cm, 5 μm; Mobile Phase A: $CO_2$, Mobile Phase B: MeOH (0.1% 2M $NH_3$-MeOH); Flow rate: 100 mL/min; Gradient: isocratic 35% B; Column Temperature(° C.): 35; Back Pressure(bar): 100; Wave Length: 267/210 nm; RT1 (min): 4.28; RT2(min): 5.28.). The first peak afforded 80 mg (19%) as a white solid. MS ESI calculated for $C_{24}H_{19}ClF_5N_4OP$ [M+H]+, 541.09, found 541.15. $^1$H NMR (400 MHz, DMSO-$d_6$) δ 9.12 (s, 1H), 8.45-8.22 (m, 2H), 8.17-8.09 (m, 1H), 7.60-7.49 (m, 1H), 7.48-7.36 (m, 1H), 7.32-7.22 (m, 1H), 7.16 (d, J=9.5 Hz, 1H), 6.88-6.43 (m, 2H), 2.68 (d, J=5.7 Hz, 3H), 1.85-1.67 (m, 6H). $^{19}$F NMR (377 MHz, DMSO-$d_6$) δ −120.49, −124.67, −125.41, −125.56, −126.31, −138.50, −138.57, −142.42, −142.48. $^{31}$P NMR (162 MHz, DMSO-$d_6$) δ 34.32.

The last peak afforded 82 mg (20%) as a white solid. MS ESI calculated for $C_{24}H_{19}ClF_5N_4OP$ [M+H]+, 541.09, found 541.15. $^1$H NMR (400 MHz, DMSO-$d_6$) δ 9.12 (s, 1H), 8.45-8.26 (m, 2H), 8.20-8.07 (m, 1H), 7.52 (t, J=6.9 Hz, 1H), 7.49-7.38 (m, 1H), 7.30-7.24 (m, 1H), 7.16 (d, J=9.5 Hz, 1H), 6.93-6.44 (m, 2H), 2.79-2.63 (m, 3H), 1.88-1.69 (m, 6H). $^{19}$F NMR (377 MHz, DMSO-$d_6$) δ −120.49, −124.65, −125.40, −125.57, −126.33, −138.52, −138.56, −142.41, −142.49. $^{31}$P NMR (162 MHz, DMSO-$d_6$) δ 34.33.

Example 147: 3-chloro-N-[(1R)-1-(3,5-difluorophenyl)propyl]-6-[6-(dimethylphosphoryl)pyridin-3-yl]-7-fluoro-2-methyl-1,5-naphthyridin-4-amine Synthetic Scheme

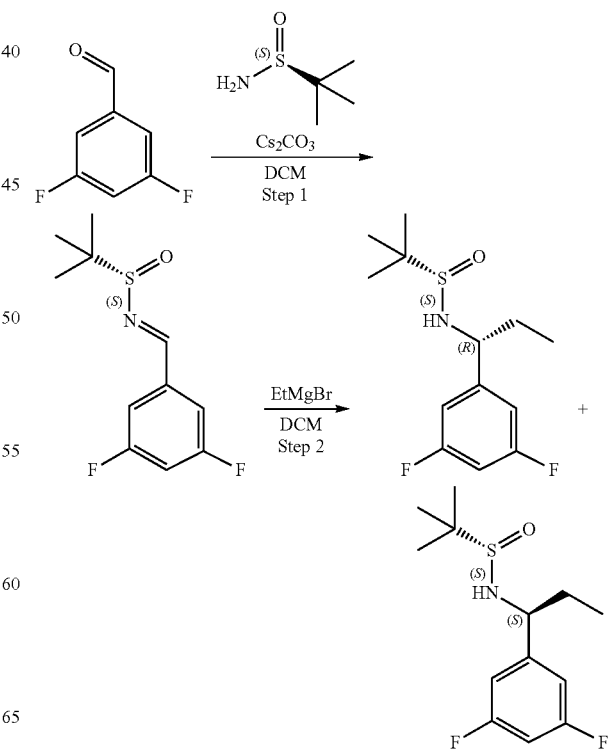

-continued

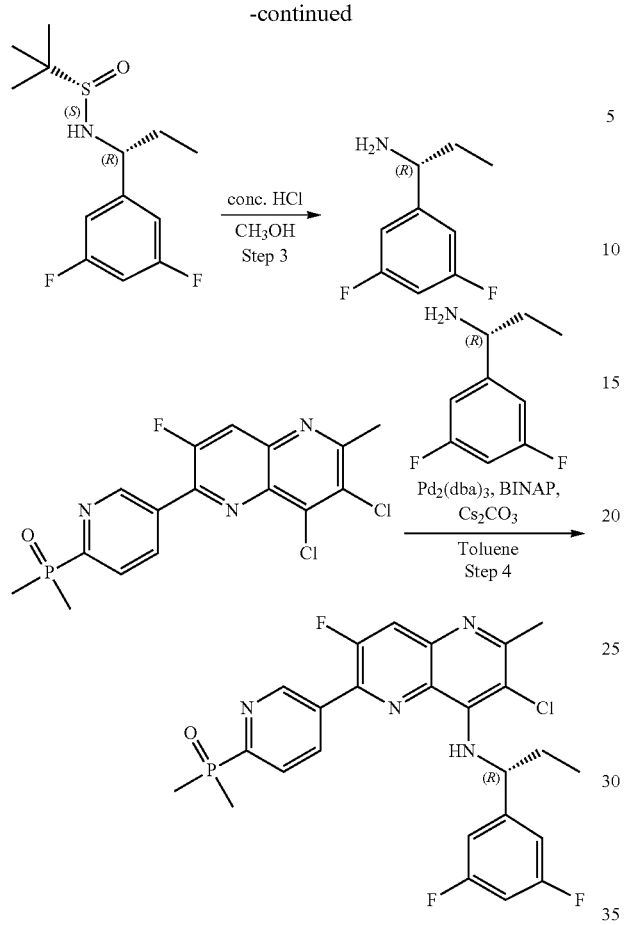

Preparation 147A: (S)—N-[(3,5-difluorophenyl)methylidene]-2-methylpropane-2-sulfinamide

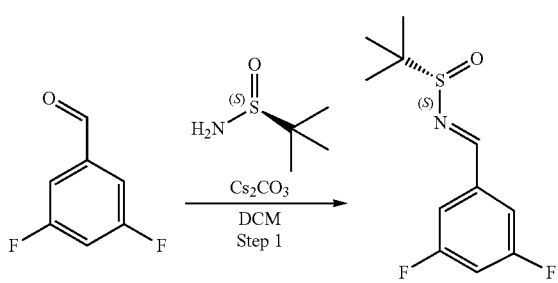

To a stirred mixture of 3,5-difluorobenzaldehyde (10.00 g, 70.371 mmol) and (S)-2-methylpropane-2-sulfinamide (10.23 g, 84.445 mmol) in DCM (200 mL) was added Cs₂CO₃ (45.86 g, 140.742 mmol) at room temperature. The resulting mixture was stirred for 16 h at room temperature. The resulting mixture was filtered, and the filter cake was washed with CH₂Cl₂ (3×100 mL). The filtrate was concentrated under reduced pressure. The residue was purified by silica gel column chromatography, eluted with PE/EA (5:1) to afford (S)—N-[(3,5-difluorophenyl)methylidene]-2-methylpropane-2-sulfinamide (17.00 g, 98%) as a white solid. ¹H NMR (400 MHz, Chloroform-d) δ 8.52 (s, 1H), 7.41-7.33 (m, 2H), 7.01-6.94 (m, 1H), 1.27 (s, 9H).

Preparation 147B: (S)—N-[(1R)-1-(3,5-difluorophenyl)propyl]-2-methylpropane-2-sulfinamide and (S)—N-[(1S)-1-(3,5-difluorophenyl)propyl]-2-methylpropane-2-sulfinamide

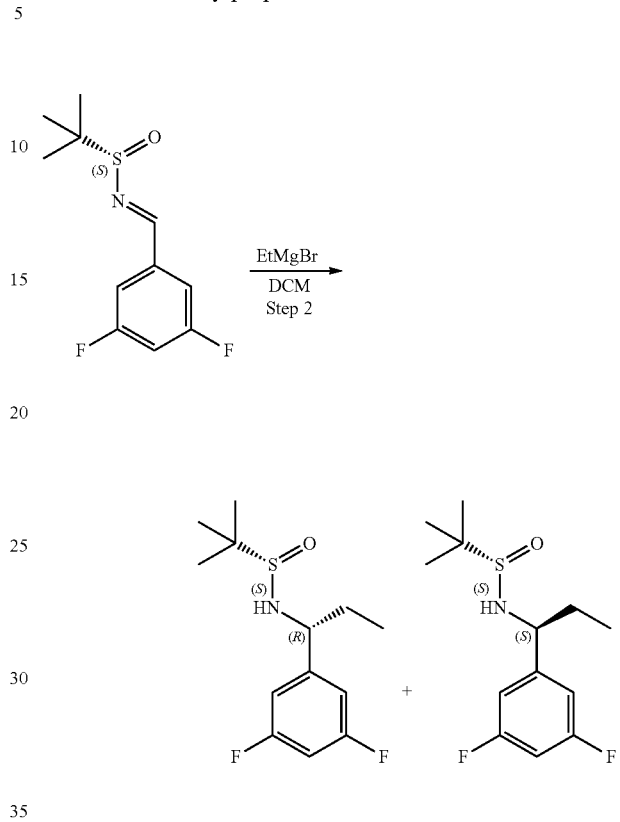

To a stirred solution of (S)—N-[(3,5-difluorophenyl)methylidene]-2-methylpropane-2-sulfinamide (5.00 g, 20.384 mmol) in DCM (50 mL) was added 1M of ethylmagnesium bromide in THF (40.8 mL, 40.768 mmol) dropwise at −35° C. under nitrogen atmosphere. The resulting mixture was stirred for 1 h at −35° C. under nitrogen atmosphere. The reaction was quenched by the addition of sat. NH₄Cl (aq.) (10 mL) at 0° C. The resulting mixture was extracted with CH₂Cl₂ (3×100 mL). The combined organic layers were washed with brine (3×50 mL), dried over anhydrous Na₂SO₄. After filtration, the filtrate was concentrated under reduced pressure. The residue was purified by silica gel column chromatography, eluted with PE/EA (3:1) to afford two isomers. The first peak afforded (S)—N-[(1S)-1-(3,5-difluorophenyl)propyl]-2-methylpropane-2-sulfinamide (1.90 g, 33%) as a light yellow oil. MS ESI calculated for C₁₃H₁₉F₂NOS [M+H]⁺, 276.12, found 276.00. ¹H NMR (300 MHz, Chloroform-d) δ 6.91-6.81 (m, 2H), 6.75-6.69 (m, 1H), 4.28-4.21 (m, 1H), 2.07-1.95 (m, 1H), 1.81-1.65 (m, 1H), 1.24 (s, 9H), 0.86-0.78 (m, 3H).

The second peak afforded (S)—N-[(1R)-1-(3,5-difluorophenyl)propyl]-2-methylpropane-2-sulfinamide (3.70 g, 65%). MS ESI calculated for C₁₃H₁₉F₂NOS [M+H]⁺, 276.12, found 276.00. ¹H NMR (300 MHz, Chloroform-d) δ 6.87-6.79 (m, 2H), 6.74-6.69 (m, 1H), 4.31-4.25 (m, 1H), 1.88-1.70 (m, 2H), 1.21 (s, 9H), 0.98-0.79 (m, 3H).

Preparation 147C: (1R 1-(3,5-difluorophenyl)propan-1-amine

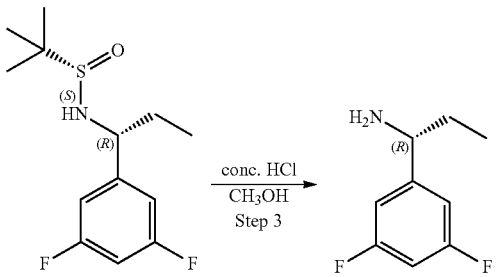

To a stirred solution of (S)—N-[(1R)-1-(3,5-difluorophenyl)propyl]-2-methylpropane-2-sulfinamide (3.40 g, 12.347 mmol) in MeOH (30 mL) was added conc. HCl (10 mL) dropwise at 0° C. The resulting mixture was stirred for 1 h at room temperature. The resulting mixture was concentrated under reduced pressure. The residue was dissolved in water (50 mL). The resulting mixture was extracted with $CH_2Cl_2$ (3×100 mL). The aqueous layer was basified to pH 8 with NaOH (aq.). The resulting mixture was extracted with $CH_2Cl_2$ (3×100 mL). The combined organic layers were washed with brine (3×50 mL), dried over anhydrous $Na_2SO_4$. After filtration, the filtrate was concentrated under reduced pressure. This resulted in (1R)-1-(3,5-difluorophenyl)propan-1-amine (1.90 g, 89%) as a light yellow oil. as a light yellow oil. MS ESI calculated for $C_9H_{11}F_2N$ $[M+H]^+$, 172.09, found 172.05. $^1$H NMR (400 MHz, Chloroform-d) δ 6.89-6.81 (m, 2H), 6.69-6.63 (m, 1H), 3.84-3.77 (m, 1H), 1.67-1.61 (m, 2H), 0.89-0.83 (m, 3H).

Example 147: 3-chloro-N-[(1R)-1-(3,5-difluorophenyl)propyl]-6-[6-(dimethylphosphoryl)pyridin-3-yl]-7-fluoro-2-methyl-1,5-naphthyridin-4-amine

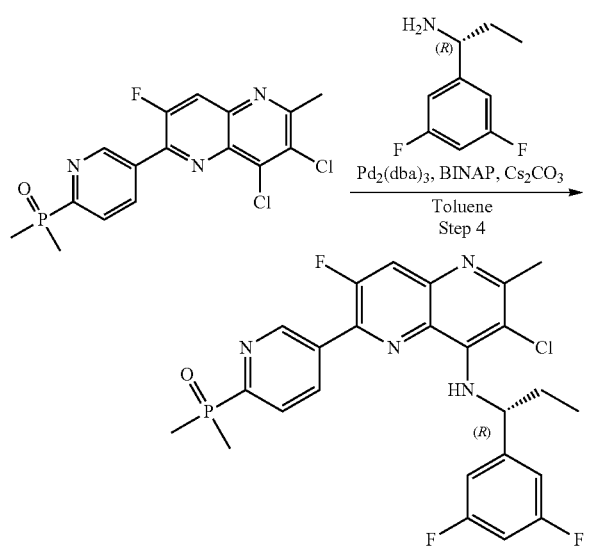

To a stirred mixture of 3,4-dichloro-6-[6-(dimethylphosphoryl)pyridin-3-yl]-7-fluoro-2-methyl-1,5-naphthyridine (100 mg, 0.260 mmol) and (1R)-1-(3,5-difluorophenyl)propan-1-amine (54 mg, 0.312 mmol) in Toluene (2 mL) were added $Pd_2(dba)_3$ (24 mg, 0.026 mmol), BINAP (32.42 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 40 B to 70 B in 30 min; 254/220 nm to afford 3-chloro-N-[(1R)-1-(3,5-difluorophenyl)propyl]-6-[6-(dimethylphosphoryl)pyridin-3-yl]-7-fluoro-2-methyl-1,5-naphthyridin-4-amine (51 mg, 38%) as a light yellow solid. MS ESI calculated for $C_{25}H_{23}ClF_3N_4OP$ $[M+H]^+$, 519.13, found 519.05. $^1$H NMR (400 MHz, DMSO-$d_6$) δ 9.16 (s, 1H), 8.36 (d, J=7.9 Hz, 1H), 8.22-8.17 (m, 1H), 8.13-8.07 (m, 1H), 7.12-7.04 (m, 2H), 7.01-6.97 (m, 1H), 6.86 (d, J=8.6 Hz, 1H), 5.85-5.81 (m, 1H), 2.65 (d, J=1.1 Hz, 3H), 2.08-1.92 (m, 2H), 1.75 (s, 3H), 1.72 (s, 3H), 0.97 (t, J=7.3 Hz, 3H). $^{19}$F NMR (377 MHz, DMSO-$d_6$) δ −110.06, −121.14. $^{31}$P NMR (162 MHz, DMSO-$d_6$) δ 34.21.

Example 148: 3-chloro-N-[(1S)-1-(3,5-difluorophenyl)propyl]-6-[6-(dimethylphosphoryl)pyridin-3-yl]-7-fluoro-2-methyl-1,5-naphthyridin-4-amine Synthetic Scheme

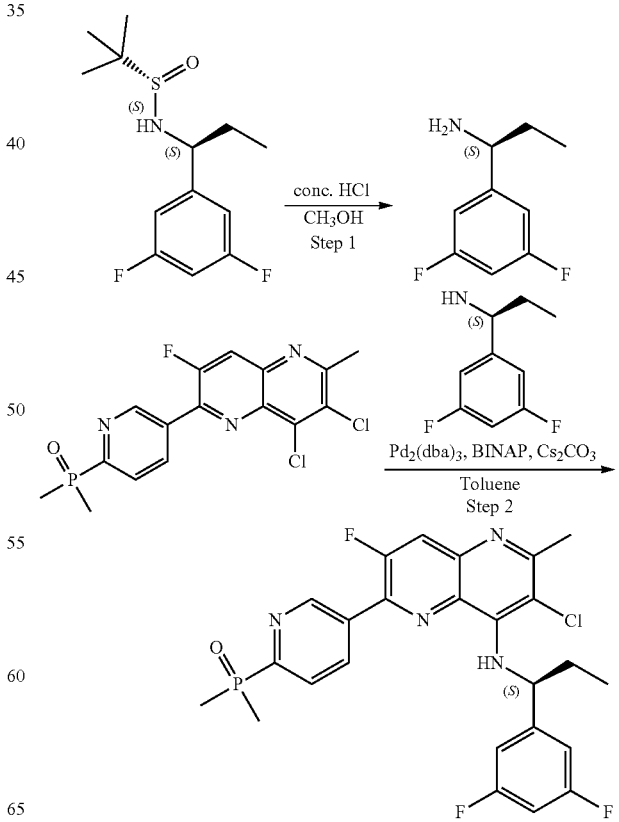

383

Preparation 148A: (1S)-1-(3,5-difluorophenyl)propan-1-amine

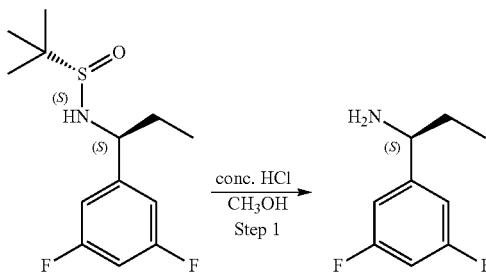

To a stirred solution of (S)—N-[(1S)-1-(3,5-difluorophenyl)propyl]-2-methylpropane-2-sulfinamide (1.90 g, 6.900 mmol) in MeOH (30 mL) was added conc. HCl (10 mL) dropwise at 0° C. The resulting mixture was stirred for 1 h at room temperature. The resulting mixture was concentrated under reduced pressure. The residue was dissolved in water (50 mL). The resulting mixture was extracted with $CH_2Cl_2$ (3×100 mL). The aqueous layer was basified to pH 8 with NaOH (aq.). The resulting mixture was extracted with $CH_2Cl_2$ (3×100 mL). The combined organic layers were washed with brine (3×50 mL), dried over anhydrous $Na_2SO_4$. After filtration, the filtrate was concentrated under reduced pressure. This resulted in (1S)-1-(3,5-difluorophenyl)propan-1-amine (1.00 g, 84%) as a light yellow oil. MS ESI calculated for $C_9H_{11}F_2N$ $[M+H]^+$, 172.09, found 172.05. $^1$H NMR (400 MHz, Chloroform-d) δ 6.87-6.83 (m, 2H), 6.69-6.64 (m, 1H), 3.84-3.77 (m, 1H), 1.67-1.62 (m, 2H), 0.89-0.85 (m, 3H).

Example 148: 3-chloro-N-[(1S)-1-(3,5-difluorophenyl)propyl]-6-[6-(dimethylphosphoryl)pyridin-3-yl]-7-fluoro-2-methyl-1,5-naphthyridin-4-amine

384

To a stirred mixture of 3,4-dichloro-6-[6-(dimethylphosphoryl)pyridin-3-yl]-7-fluoro-2-methyl-1,5-naphthyridine (100 mg, 0.260 mmol) and (1R)-1-(3,5-difluorophenyl)propan-1-amine (54 mg, 0.312 mmol) in Toluene (2 mL) were added $Pd_2(dba)_3$ (24 mg, 0.026 mmol), BINAP (32 mg, 0.052 mmol) and $Cs_2CO_3$ (127 mg, 0.390 mmol) at room temperature under nitrogen atmosphere. The resulting mixture was stirred for 16 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (0.1% $NH_4HCO_3$), Mobile Phase B: $CH_3CN$; Flow rate: 60 mL/min; Gradient: 40 B to 70 B in 30 min; 254/220 nm to afford 3-chloro-N-[(1S)-1-(3,5-difluorophenyl)propyl]-6-[6-(dimethylphosphoryl)pyridin-3-yl]-7-fluoro-2-methyl-1,5-naphthyridin-4-amine (43 mg, 31%) as a light yellow solid. MS ESI calculated for $C_{25}H_{23}ClF_3N_4OP$ $[M+H]^+$, 519.13, found 519.00. $^1$H NMR (400 MHz, DMSO-$d_6$) δ 9.16 (s, 1H), 8.36 (d, J=7.9 Hz, 1H), 8.20 (d, J=11.7 Hz, 1H), 8.12-8.07 (m, 1H), 7.11-7.04 (m, 2H), 7.02-6.97 (m, 1H), 6.86 (d, J=8.6 Hz, 1H), 5.85-5.80 (m, 1H), 2.65 (s, 3H), 2.09-1.90 (m, 2H), 1.75 (s, 3H), 1.72 (s, 3H), 0.97 (t, J=7.3 Hz, 3H). $^{19}$F NMR (377 MHz, DMSO-$d_6$) δ −110.06, −121.14. $^{31}$P NMR (162 MHz, DMSO-$d_6$) δ 34.18.

Example 149: 3-chloro-6-[6-(dimethylphosphoryl)pyridin-3-yl]-7-fluoro-2-methyl-N-[1-(1-methylpyrazol-3-yl)propyl]-1,5-naphthyridin-4-amine Synthetic Scheme

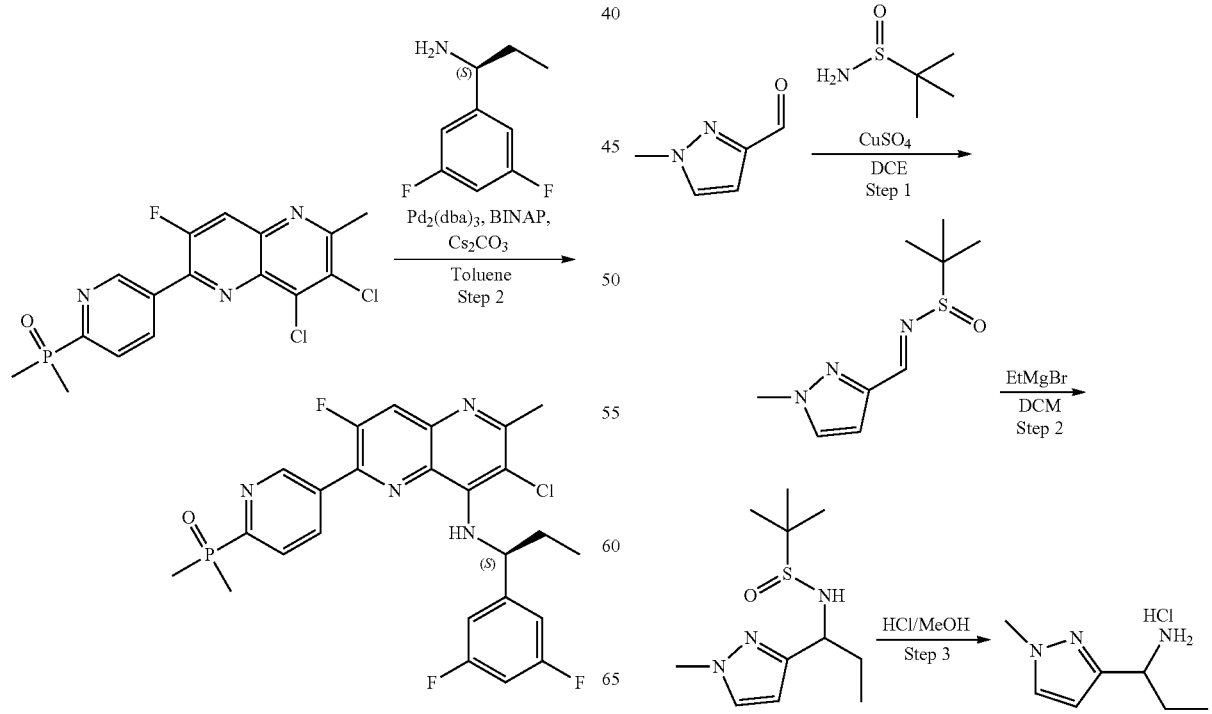

-continued

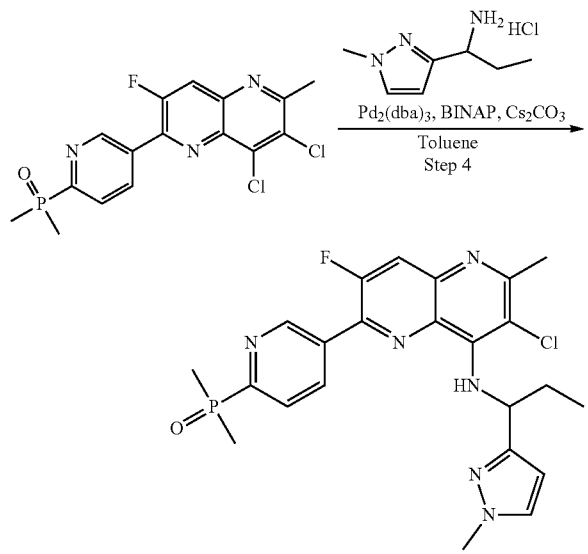

Preparation 149A: 2-methyl-N-[(1E)-(1-methylpyrazol-3-yl)methylidene]propane-2-sulfinamide

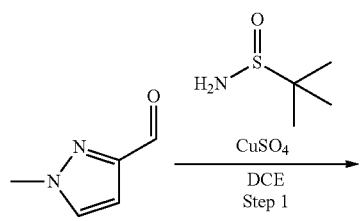

A mixture of 1-methylpyrazole-3-carbaldehyde (2.00 g, 18.163 mmol), tert-butanesulfinamide (2.64 g, 21.796 mmol) and dioxo(sulfonylidene)copper (5.80 g, 36.326 mmol) in DCE (20 mL) was stirred for overnight at 55° C. The resulting mixture was filtered, and the filter cake was washed with DCM (200 mL). The filtrate was concentrated under reduced pressure. The residue was purified by silica gel column chromatography, eluted with PE/EA (1/1) to afford 2-methyl-N-[(1E)-(1-methylpyrazol-3-yl)methylidene]propane-2-sulfinamide (2.50 g, 64%) as a yellow oil. MS ESI calculated for $C_9H_{15}N_3OS$ [M+H]$^+$, 214.09, found 214.10. $^1$H NMR (400 MHz, Chloroform-d) δ 8.63 (s, 1H), 7.41 (d, J=2.4 Hz, 1H), 6.77 (d, J=2.4 Hz, 1H), 3.99 (s, 3H), 1.25 (s, 9H).

Preparation 149B: 2-methyl-N-[1-(1-methylpyrazol-3-yl)propyl]propane-2-sulfinamide

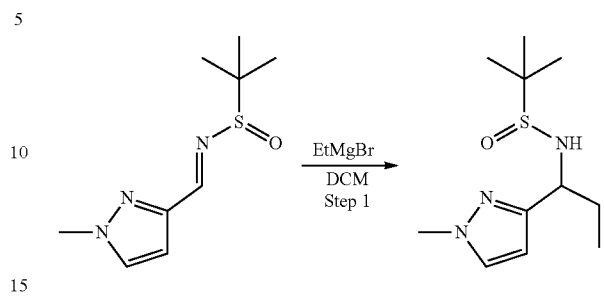

To a stirred solution of 2-methyl-N-[(1E)-(1-methylpyrazol-3-yl)methylidene]propane-2-sulfinamide (1.50 g, 7.032 mmol) in DCM (20 mL) were added ethylmagnesium bromide (3.4 M in THF, 6.2 mL, 21.096 mmol) dropwise at −35° C. under nitrogen atmosphere for 30 min. The reaction was quenched with sat. NH$_4$Cl (aq.) at room temperature. The resulting mixture was filtered, and the filter cake was washed with ethyl acetate. The resulting mixture was extracted with EtOAc (15 mL). The combined organic layers dried over anhydrous Na$_2$SO$_4$. After filtration, the filtrate was concentrated under reduced pressure to afford 2-methyl-N-[1-(1-methylpyrazol-3-yl)propyl]propane-2-sulfinamide (1.10 g, 64%) as a yellow oil. MS ESI calculated for $C_{11}H_{21}N_3OS$ [M+H]$^+$, 244.14, found 244.05.

Preparation 149C: 1-(1-methylpyrazol-3-yl)propan-1-amine hydrochloride

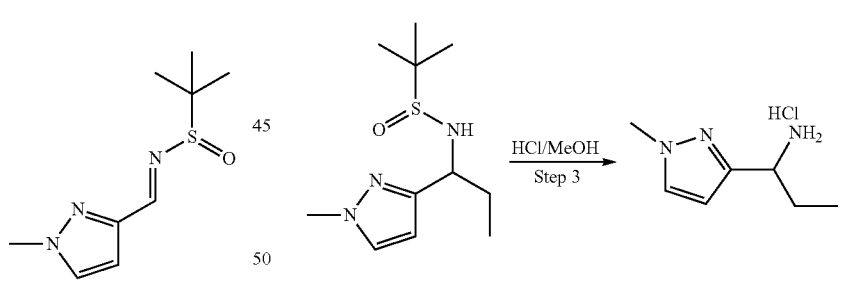

To a stirred solution of 2-methyl-N-[1-(1-methylpyrazol-3-yl)propyl]propane-2-sulfinamide (250 mg, 1.027 mmol) in methanol (1.5 mL) was added conc. HCl (0.5 mL) dropwise at room temperature. The resulting mixture was stirred for 1 h at room temperature. The resulting mixture was concentrated under vacuum. This result in 1-(1-methylpyrazol-3-yl)propan-1-amine hydrochloride (100 mg, 55%) as a yellow oil. MS ESI calculated for $C_7H_{13}N_3$[M+H]$^+$, 140.11, found 140.00. $^1$H NMR (400 MHz, Methanol-d$_4$) δ 7.66 (t, J=2.4 Hz, 1H), 6.41-6.36 (m, 1H), 4.25 (t, J=7.2 Hz, 1H), 3.91 (d, J=1.1 Hz, 3H), 2.05-1.93 (m, 2H), 0.95 (t, J=7.5 Hz, 3H).

Example 149: 3-chloro-6-[6-(dimethylphosphoryl)pyridin-3-yl]-7-fluoro-2-methyl-N-[1-(1-methylpyrazol-3-yl)propyl]-1,5-naphthyridin-4-amine

Example 150: 3-chloro-N-[(1R)-1-(5-cyclopropyl-2-fluorophenyl)ethyl]-6-[6-(dimethylphosphoryl)pyridin-3-yl]-7-fluoro-2-methyl-1,5-naphthyridin-4-amine Synthetic Scheme

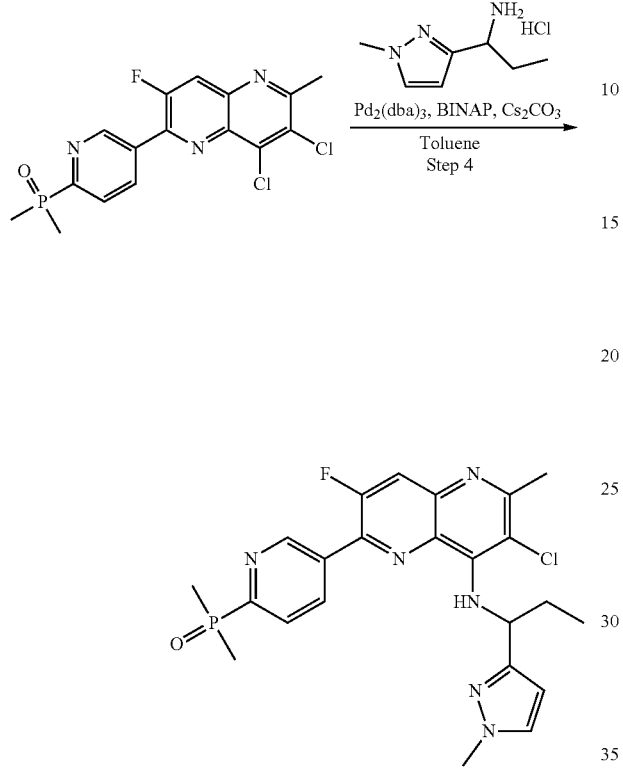

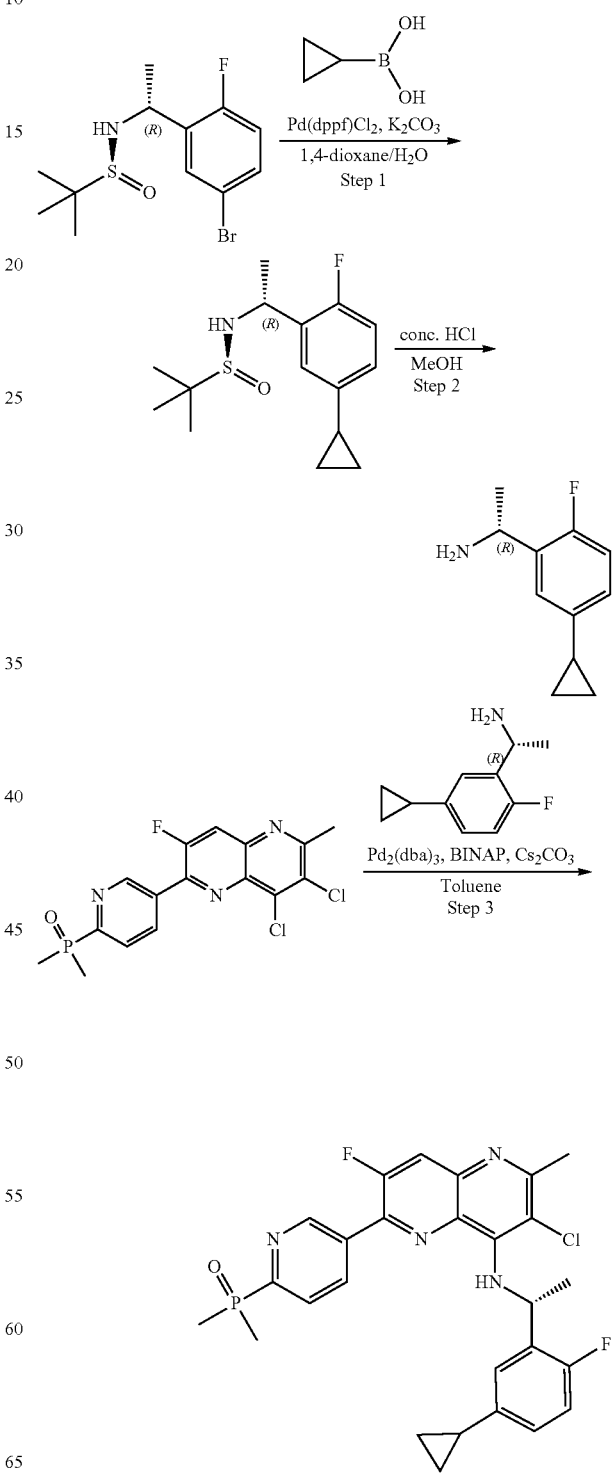

To a stirred mixture of 3,4-dichloro-6-[6-(dimethylphosphoryl)pyridin-3-yl]-7-fluoro-2-methyl-1,5-naphthyridine (80 mg, 0.208 mmol), $Cs_2CO_3$ (203 mg, 0.624 mmol) and 1-(1-methylpyrazol-3-yl)propan-1-amine hydrochloride (73 mg, 0.416 mmol) in Toluene (2 mL) were added BINAP (26 mg, 0.042 mmol) and $Pd_2(dba)_3$ (19 mg, 0.021 mmol) at room temperature under nitrogen atmosphere. The resulting mixture was stirred for overnight at 80° C. under nitrogen atmosphere. The resulting mixture was concentrated under reduced pressure. The residue was purified by silica gel column chromatography, eluted with $CH_2Cl_2$/MeOH (12/1) followed by reversed-phase flash chromatography with the following conditions: column, C18 silica gel; mobile phase, $CH_3CN$ in water (10 mmol/L $NH_4HCO_3$), 35% to 70% gradient in 25 min; detector, 254 nm to afford 3-chloro-6-[6-(dimethylphosphoryl)pyridin-3-yl]-7-fluoro-2-methyl-N-[1-(1-methylpyrazol-3-yl)propyl]-1,5-naphthyridin-4-amine (12 mg, 12%) as a yellow solid. MS ESI calculated for $C_{23}H_{25}ClFN_6OP$ [M+H]$^+$, 487.15, found 487.05. $^1$H NMR (400 MHz, Chloroform-d) δ 9.40 (s, 1H), 8.53 (d, J=8.2 Hz, 1H), 8.28-8.25 (m, 1H), 7.92 (d, J=11.8 Hz, 1H), 7.30 (d, J=2.2 Hz, 1H), 6.99 (s, 1H), 6.13 (d, J=2.2 Hz, 1H), 6.07 (d, J=8.0 Hz, 1H), 3.91 (s, 3H), 2.74 (s, 3H), 2.09-2.02 (m, 2H), 1.86 (s, 3H), 1.83 (s, 3H), 0.93 (t, J=7.4 Hz, 3H). $^{19}$F NMR (377 MHz, Chloroform-d) δ −121.05. $^{31}$P NMR (162 MHz, Chloroform-d) δ 36.64.

Preparation 150A: (S)—N-[(1R)-1-(5-cyclopropyl-2-fluorophenyl)ethyl]-2-methylpropane-2-sulfinamide

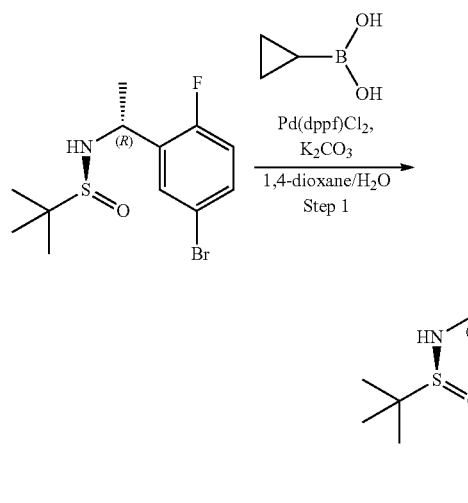

A solution of (S)—N-[(1R)-1-(5-bromo-2-fluorophenyl)ethyl]-2-methylpropane-2-sulfinamide (1.00 g, 3.103 mmol), cyclopropylboronic acid (399 mg, 4.655 mmol), Pd(dppf)Cl$_2$·CH$_2$Cl$_2$ (379 mg, 0.465 mmol) and K$_2$CO$_3$ (1.29 g, 9.309 mmol) in 1,4-dioxane (10 mL) and H$_2$O (1 mL) was stirred for overnight at 100° C. under nitrogen atmosphere. The mixture was allowed to cool down to room temperature. The resulting mixture was concentrated under reduced pressure. The residue was purified by silica gel column chromatography, eluted with CH$_2$Cl$_2$/MeOH (20/1) to afford (S)—N-[(1R)-1-(5-cyclopropyl-2-fluorophenyl)ethyl]-2-methylpropane-2-sulfinamide (760 mg, 86%) as a yellow oil. MS ESI calculated for C$_{15}$H$_{22}$FNOS [M+H]$^+$, 284.14, found 284.20. $^1$H NMR (300 MHz, Chloroform-d) δ 7.06-7.03 (m, 1H), 6.95-6.89 (m, 2H), 4.85-4.74 (m, 1H), 3.36 (d, J=4.9 Hz, 1H), 1.91-1.82 (m, 1H), 1.57 (d, J=6.7 Hz, 3H), 1.20 (s, 9H), 0.99-0.89 (m, 2H), 0.68-0.57 (m, 2H).

Preparation 150B: (1R)-1-(5-cyclopropyl-2-fluorophenyl)ethanamine

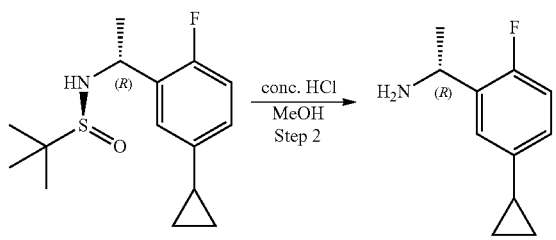

A solution of (S)—N-[(1R)-1-(5-cyclopropyl-2-fluorophenyl)ethyl]-2-methylpropane-2-sulfinamide (760 mg, 2.682 mmol) in conc. HCl (2 mL) and MeOH (6 mL) was stirred for 2 h at room temperature. The resulting mixture was concentrated under vacuum. The residue was purified by silica gel column chromatography, eluted with CH$_2$Cl$_2$/MeOH (10/1) to afford (1R)-1-(5-cyclopropyl-2-fluorophenyl)ethanamine (400 mg, 83%) as a yellow oil. MS ESI calculated for C$_{11}$H$_{14}$FN [M+H]$^+$, 180.11, found 180.12. $^1$H NMR (400 MHz, DMSO-d$_6$) δ 8.51 (s, 2H), 7.35 (d, J=7.0 Hz, 1H), 7.14 (d, J=8.5 Hz, 2H), 4.55 (d, J=6.7 Hz, 1H), 1.49 (d, J=6.7 Hz, 3H), 1.11 (s, 1H), 0.97-0.94 (m, 2H), 0.73-0.65 (m, 2H).

Example 150: 3-chloro-N-[(1R)-1-(5-cyclopropyl-2-fluorophenyl)ethyl]-6-[6-(dimethylphosphoryl)pyridin-3-yl]-7-fluoro-2-methyl-1,5-naphthyridin-4-amine

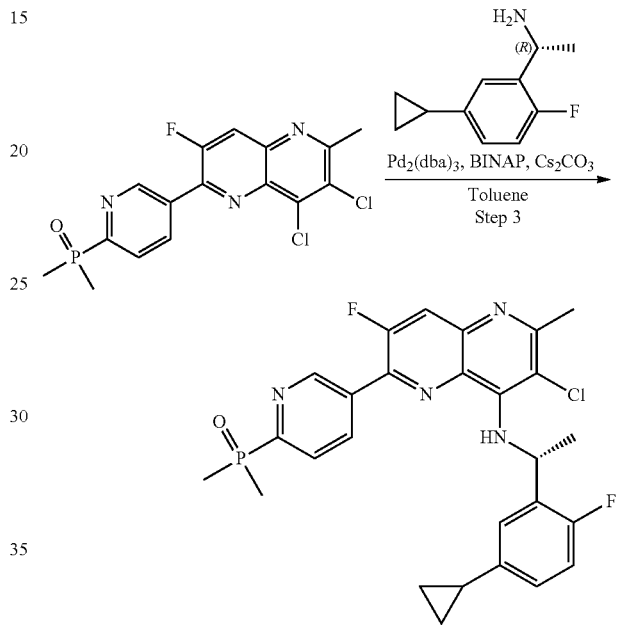

A mixture of (1R)-1-(5-cyclopropyl-2-fluorophenyl)ethanamine (55 mg, 0.312 mmol), 3,4-dichloro-6-[6-(dimethylphosphoryl)pyridin-3-yl]-7-fluoro-2-methyl-1,5-naphthyridine (100 mg, 0.260 mmol), Pd$_2$(dba)$_3$ (23 mg, 0.026 mmol), BINAP (32 mg, 0.052 mmol) and Cs$_2$CO$_3$ (212 mg, 0.650 mmol) in Toluene (2 mL) was stirred for 2 h at 100° C. under nitrogen atmosphere. The mixture was allowed to cool down to room temperature. The resulting mixture was concentrated under vacuum. The residue was purified by silica gel column chromatography, eluted with DCM/MeOH (0% to 10%) followed by Prep-HPLC with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B in 20 min; 254/220 nm to afford 3-chloro-N-[(1R)-1-(5-cyclopropyl-2-fluorophenyl)ethyl]-6-[6-(dimethylphosphoryl)pyridin-3-yl]-7-fluoro-2-methyl-1,5-naphthyridin-4-amine (62 mg, 44%) as a yellow solid. MS ESI calculated for C$_{27}$H$_{26}$ClF$_2$N$_4$OP [M+H]$^+$, 527.15, found 527.25. $^1$H NMR (400 MHz, Chloroform-d) δ 9.33 (s, 1H), 8.37 (d, J=7.9 Hz, 1H), 8.30-8.26 (m, 1H), 7.96 (s, 1H), 6.97-6.89 (m, 1H), 6.88-6.84 (m, 2H), 6.58 (s, 1H), 6.45-6.30 (m, 1H), 2.74 (s, 3H), 1.87 (s, 3H), 1.84 (s, 3H), 1.76-1.72 (m, 1H), 1.70 (d, J=6.8 Hz, 3H), 0.87-0.80 (m, 2H), 0.50-0.37 (m, 2H); $^{19}$F NMR (377 MHz, Chloroform-d) δ −120.90, −123.56. $^{31}$P NMR (162 MHz, Chloroform-d) δ 36.44.

II. Biological Evaluation
TNF-α Induced HEK Bluet Cellular Assay

Test articles were diluted in DMSO and serially diluted into 384 well assay plate (Corning 3765), at final concentrations ranging from 30 mM to 0.5 nM. HEK Blue™ TNFα reporter cells were added at a final density of 10,000 cell per well in assay media [DMEM (Gibco, cat #21063-029), 10% fetal bovine serum (ExcelBio, cat #FND500), 1% Penicillin-Streptomycin (Solarbio, cat #P1400-100]. TNF-α (R&D 210-TA-020/CF) was then added to the assay plate at a final concentration of 100 pg/ml. This plate was then incubated for 24 hrs at 37° C. and 5% $CO_2$. Secreted alkaline phosphatase expression was then measured using QUANTI-Blue™ (Invivogen), according to manufacturer instructions and read on an Envision microplate reader at 620 nm.

Inhibition data for test compound over a range of concentration was plotted as percentage inhibition of the test compound (100%=maximum inhibition). $IC_{50}$ values were determined after correcting for background [(sample read-mean of low control)/(mean of high control-mean of low control)] where by the low control is DMSO without stimulation and high control is DMSO with stimulation. The $IC_{50}$ is defined as the concentration of test compound which produces 50% inhibition and was quantified using the 4 parameter logistic equation to fit the data.

Representative data for exemplary compounds is presented in Table 3.

TABLE 3

| Ex. No | $IC_{50}$ value |
|---|---|
| 1 | A |
| 2 | A |
| 3 | A |
| 4 | B |
| 5 | A |
| 6 | B |
| 7 | B |
| 8 | A |
| 9 | A |
| 10 | A |
| 11 | A |
| 12 | B |
| 13 | A |
| 14 | B |
| 15 | A |
| 16 | A |
| 17 | B |
| 18 | A |
| 19 | A |
| 20 | A |
| 21 | B |
| 22 | A |
| 23 | A |
| 24 | B |
| 25 | A |
| 26 | C |
| 27 | A |
| 28 | A |
| 29 | B |
| 30 | A |
| 31 | A |
| 32 | A |
| 33 | A |
| 34 | A |
| 35 | B |
| 36 | B |
| 37 | D |
| 38 | B |
| 39 | B |
| 40 | A |
| 41 | B |
| 42 | A |
| 43 | A |

TABLE 3-continued

| Ex. No | $IC_{50}$ value |
|---|---|
| 44 | A |
| 45 | A |
| 46 | A |
| 47 | B |
| 48 | A |
| 49 | A |
| 50 | A |
| 51 | A |
| 52 | B |
| 53 | B |
| 54 | B |
| 55 | D |
| 56 | A |
| 57 | A |
| 58 | A |
| 59 | D |
| 60 | D |
| 61 | B |
| 62 | B |
| 63 | D |
| 64 | D |
| 65 | B |
| 66 | B |
| 67 | A |
| 68 | A |
| 69 | B |
| 70 | A |
| 71 | B |
| 72 | B |
| 73 | B |
| 74 | B |
| 75 | A |
| 76 | A |
| 77 | B |
| 78 | A |
| 79 | A |
| 80 | B |
| 81 | D |
| 82 | A |
| 83 | B |
| 84 | B |
| 85 | B |
| 86 | A |
| 87 | C |
| 88 | D |
| 89 | D |
| 90 | A |
| 91 | A |
| 92 | A |
| 93 | A |
| 94 | B |
| 95 | A |
| 96 | A |
| 97 | B |
| 98 | B |
| 99 | B |
| 100 | D |
| 101 | D |
| 102 | B |
| 103 | D |
| 104 | B |
| 105 | B |
| 106 | A |
| 107 | B |
| 108 | B |
| 109 | A |
| 110 | A |
| 111 | A |
| 112 | B |
| 113 | B |
| 114 | A |
| 115 | B |
| 116 | A |
| 117 | C |
| 118 | B |
| 119 | B |
| 120 | A |
| 121 | A |

TABLE 3-continued

| Ex. No | IC$_{50}$ value |
|---|---|
| 122 | A |
| 123 | B |
| 124 | B |
| 125 | B |
| 126 | A |
| 127 | B |
| 128 | D |
| 129 | D |
| 130 | B |
| 131 | B |
| 132 | B |
| 133 | A |
| 134 | C |
| 135 | A |
| 136 | B |
| 137 | B |
| 138 | B |
| 139 | B |
| 140 | B |
| 141 | C |
| 142 | C |
| 143 | D |
| 144 | D |
| 145 | D |
| 146 | C |
| 147 | C |
| 148 | C |
| 149 | D |
| 150 | B |

Note:
IC$_{50}$ data are designated within the following ranges:
A: ≤0.1 µM
B: ≤1.0 µM
C: >1 µM to ≤10 µM
D: >10 µM to ≤30 µM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

I claim:
1. A compound, or pharmaceutically acceptable salt or solvate thereof, selected from the group consisting of:
   3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile;
   3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzamide;
   3-[(1R)-1-({3-chloro-6-[6-(dimethylphosphoryl)pyridin-3-yl]-7-fluoro-1,5-naphthyridin-4-yl}amino)ethyl]-4-fluorobenzonitrile;
   3-chloro-6-[6-(dimethylphosphoryl)pyridin-3-yl]-7-fluoro-N-[(1R)-1-(2-fluorophenyl)ethyl]-2-methyl-1,5-naphthyridin-4-amine;
   3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile;
   methyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate;
   3-chloro-6-[6-(dimethylphosphoryl)pyridin-3-yl]-7-fluoro-N-[(1R)-1-(2-fluorophenyl)propyl]-2-methyl-1,5-naphthyridin-4-amine;
   3-chloro-6-[6-(dimethylphosphoryl)pyridin-3-yl]-7-fluoro-N-[(1S)-1-(2-fluorophenyl)propyl]-2-methyl-1,5-naphthyridin-4-amine;
   (S)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide;
   (R)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide;
   3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile;
   diethyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate;
   3-[(1R)-1-[(3-chloro-6-{6-[(dimethylphosphoryl)methoxy]pyridin-3-yl}-7-fluoro-2-methyl-1,5-naphthyridin-4-yl)amino]ethyl]-4-fluorobenzonitrile;
   (S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile;
   (R)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile;
   5-(7-chloro-8-{[(1R)-1-(5-cyano-2-fluorophenyl)ethyl]amino}-3-fluoro-6-methyl-1,5-naphthyridin-2-yl)pyridin-2-ylphosphonate;
   (R)-3-(1-((3-chloro-6-(6-((dimethylphosphoryl)methyl)pyridin-3-yl)-7-fluoro-2-methyl-1,5-naphthyridin-4-yl)amino)ethyl)-4-fluorobenzonitrile;
   3-[(1R)-1-({3-chloro-6-[6-(dimethylphosphoryl)pyridin-3-yl]-2-methyl-1,5-naphthyridin-4-yl}amino)ethyl]-4-fluorobenzonitrile;
   3-[(1R)-1-({3-chloro-6-[6-(diethylphosphoryl)pyridin-3-yl]-7-fluoro-2-methyl-1,5-naphthyridin-4-yl}amino)ethyl]-4-fluorobenzonitrile;
   3-[(1R)-1-({3-chloro-6-[6-(dimethylphosphoryl)pyridin-3-yl]-7-fluoro-2-methyl-1,5-naphthyridin-4-yl}amino)ethyl]benzonitrile;
   3-[(1S)-1-({3-chloro-6-[6-(dimethylphosphoryl)pyridin-3-yl]-7-fluoro-2-methyl-1,5-naphthyridin-4-yl}amino)propyl]-4-fluorobenzonitrile;
   3-chloro-N-[(1S)-1-(2,3-difluorophenyl)ethyl]-6-[6-(dimethylphosphoryl)pyridin-3-yl]-7-fluoro-2-methyl-1,5-naphthyridin-4-amine;
   3-[(1R)-1-({3-chloro-6-[6-(dimethylphosphoryl)pyridin-3-yl]-7-fluoro-2-methyl-1,5-naphthyridin-4-yl}amino)propyl]benzonitrile;
   3-chloro-N-[(1R)-1-(2,3-difluorophenyl)ethyl]-6-[6-(dimethylphosphoryl)pyridin-3-yl]7-fluoro-2-methyl-1,5-naphthyridin-4-amine;

3-chloro-N-[(1S)-1-(2,5-difluorophenyl)ethyl]-6-[6-(dimethylphosphoryl)pyridin-3-yl]-7-fluoro-2-methyl-1,5-naphthyridin-4-amine;
3-chloro-N-[(1R)-1-(2,6-difluorophenyl)ethyl]-6-[6-(dimethylphosphoryl)pyridin-3-yl]-7-fluoro-2-methyl-1,5-naphthyridin-4-amine;
3-chloro-N-[(1R)-1-(2,5-difluorophenyl)ethyl]-6-[6-(dimethylphosphoryl)pyridin-3-yl]-7-fluoro-2-methyl-1,5-naphthyridin-4-amine;
3-chloro-N-[(1S)-1-(2,6-difluorophenyl)ethyl]-6-[6-(dimethylphosphoryl)pyridin-3-yl]-7-fluoro-2-methyl-1,5-naphthyridin-4-amine;
(R)-3-(1-((3-chloro-6-(6-(diethylphosphoryl)pyridin-3-yl)-7-fluoro-2-methyl-1,5-naphthyridin-4-yl)amino)ethyl)-4-fluorobenzonitrile;
3-((R)-1-((3-chloro-6-(6-((S)-ethyl(methyl)phosphoryl)pyridin-3-yl)-7-fluoro-2-methyl-1,5-naphthyridin-4-yl)amino)ethyl)-4-fluorobenzonitrile;
(2R)-2-({3-chloro-6-[6-(dimethylphosphoryl)pyridin-3-yl]-7-fluoro-2-methyl-1,5-naphthyridin-4-yl}amino)-2-(2-fluorophenyl)ethanol;
3-[(1R)-1-({3-chloro-6-[6-(dimethylphosphoryl)-4-methylpyridin-3-yl]-7-fluoro-2-methyl-1,5-naphthyridin-4-yl}amino)ethyl]-4-fluorobenzonitrile;
3-chloro-6-[6-(dimethylphosphoryl)-4-methylpyridin-3-yl]-7-fluoro-N-[(1R)-1-(2-fluorophenyl)ethyl]-2-methyl-1,5-naphthyridin-4-amine;
(S)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile;
(R)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile;
3-chloro-6-[6-(dimethylphosphoryl)pyridin-3-yl]-7-fluoro-N-[(1R)-1-[2-fluoro-5-(4-methylimidazol-1-yl)phenyl]ethyl]-2-methyl-1,5-naphthyridin-4-amine;
(S)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide;
(R)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide;
3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine;
3-chloro-6-[6-(dimethylphosphoryl)pyridin-3-yl]-7-fluoro-2-methyl-N-[(1R)-1-(pyridin-3-yl)ethyl]-1,5-naphthyridin-4-amine;
3-chloro-6-[6-(dimethylphosphoryl)pyridin-3-yl]-7-fluoro-2-methyl-N-[(1S)-1-(pyridin-2-yl)propyl]-1,5-naphthyridin-4-amine;
6-[6-(dimethylphosphoryl)pyridin-3-yl]-3,7-difluoro-N-[(1R)-1-(2-fluorophenyl)propyl]-2-methyl-1,5-naphthyridin-4-amine;
3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-2-methyl-N-[(1R)-1-phenylpropyl]-1,5-naphthyridin-4-amine;
3-chloro-N-[(1R)-1-(3,4-difluorophenyl)ethyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-N-[(1R)-1-(2-methoxypyridin-4-yl)ethyl]-2-methyl-1,5-naphthyridin-4-amine;
3-chloro-6-[6-(dimethylphosphoryl)pyridin-3-yl]-7-fluoro-2-methyl-N-[1-(pyridin-3-yl)propyl]-1,5-naphthyridin-4-amine;
3-chloro-6-[6-(dimethylphosphoryl)pyridin-3-yl]-7-fluoro-2-methyl-N-[(1R)-1-(pyridin-2-yl)ethyl]-1,5-naphthyridin-4-amine;
3-chloro-6-[6-(dimethylphosphoryl)pyridin-3-yl]-7-fluoro-2-methyl-N-[(1R)-1-(pyridin-2-yl)propyl]-1,5-naphthyridin-4-amine;
3-chloro-N-[(1R)-1-(3,5-difluorophenyl)ethyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-N-[(1R)-1-(3-fluorophenyl)ethyl]-2-methyl-1,5-naphthyridin-4-amine;
3-chloro-N-[(1R)-1-(2-chlorophenyl)ethyl]-6-[6-(dimethylphosphoryl)pyridin-3-yl]-7-fluoro-2-methyl-1,5-naphthyridin-4-amine;
3-chloro-N-[(1R)-1-(2,4-difluorophenyl)ethyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-2-methyl-N-[(1R)-1-(2,3,6-trifluorophenyl)ethyl]-1,5-naphthyridin-4-amine;
3-chloro-6-[6-(dimethylphosphoryl)pyridin-3-yl]-7-fluoro-2-methyl-N-[(1R)-1-phenylethyl]-1,5-naphthyridin-4-amine;
3-chloro-N-[(1R)-1-(3-chlorophenyl)ethyl]-6-[6-(dimethylphosphoryl)pyridin-3-yl]-7-fluoro-2-methyl-1,5-naphthyridin-4-amine;
3-chloro-N-[(1R)-1-[3-(difluoromethyl)phenyl]ethyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-2-methyl-N-[(1R)-1-[3-(trifluoromethyl)phenyl]ethyl]-1,5-naphthyridin-4-amine;
3-chloro-6-[6-(dimethylphosphoryl)pyridin-3-yl]-7-fluoro-N-[1-(3-fluoropyridin-2-yl)ethyl]-2-methyl-1,5-naphthyridin-4-amine;
(R)-(5-(7-chloro-8-((1-(2,3-difluorophenyl)propyl)amino)-3-fluoro-6-methyl-1,5-naphthyridin-2-yl)pyridin-2-yl)dimethylphosphine oxide;
(S)-(5-(7-chloro-8-((1-(2,3-difluorophenyl)propyl)amino)-3-fluoro-6-methyl-1,5-naphthyridin-2-yl)pyridin-2-yl)dimethylphosphine oxide;
3-chloro-6-[6-(dimethylphosphoryl)pyridin-3-yl]-N-[(1R)-1-(5-ethynyl-2-fluorophenyl)ethyl]-7-fluoro-2-methyl-1,5-naphthyridin-4-amine;
3-[(1R)-1-({3-chloro-6-[6-(dimethylphosphoryl)pyridin-3-yl]-7-fluoro-2-methyl-1,5-naphthyridin-4-yl}amino)ethyl]-5-fluorobenzonitrile;
3-chloro-6-[6-(dimethylphosphoryl)pyridin-3-yl]-7-fluoro-2-methyl-N-[1-(1-methylpyrazol-4-yl)propyl]-1,5-naphthyridin-4-amine;
3-[(1R)-1-({3-chloro-6-[6-(dimethylphosphoryl)pyridin-3-yl]-7-fluoro-2-methyl-1,5-naphthyridin-4-yl}amino)ethyl]-4,5-difluorobenzonitrile;
3-chloro-N-[(1R)-1-(2,3-difluorophenyl)ethyl]-6-[6-(dimethylphosphoryl)-5-fluoropyridin-3-yl]-7-fluoro-2-methyl-1,5-naphthyridin-4-amine;
(R)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide;
(S)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide;

3-chloro-6-[6-(dimethylphosphoryl)pyridin-3-yl]-7-fluoro-2-methyl-N-[1-(pyridin-2-yl)cyclopropyl]-1,5-naphthyridin-4-amine;
(R)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide;
(S)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide;
3-[(1R)-1-({6-[6-(dimethylphosphoryl)pyridin-3-yl]-7-fluoro-2,3-dimethyl-1,5-naphthyridin-4-yl}amino)ethyl]-4-fluorobenzonitrile;
3-[(1R)-1-({3-chloro-6-[6-(dimethylphosphoryl)-5-fluoropyridin-3-yl]-7-fluoro-2-methyl-1,5-naphthyridin-4-yl}amino)ethyl]-4-fluorobenzonitrile;
6-[(1S)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile;
6-[(1R)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile;
3-chloro-N-[(1R)-1-(3,5-difluorophenyl)ethyl]-6-[6-(dimethylphosphoryl)-5-fluoropyridin-3-yl]-7-fluoro-2-methyl-1,5-naphthyridin-4-amine;
3-chloro-N-[(1R)-1-(3-chloro-5-fluorophenyl)ethyl]-6-[6-(dimethylphosphoryl)pyridin-3-yl]-7-fluoro-2-methyl-1,5-naphthyridin-4-amine;
N-[(1R)-1-(2,3-difluorophenyl)ethyl]-6-[6-(dimethylphosphoryl)pyridin-3-yl]-7-fluoro-2,3-dimethyl-1,5-naphthyridin-4-amine;
3-cyclopropyl-N-[(1R)-1-(2,3-difluorophenyl)ethyl]-6-[6-(dimethylphosphoryl)pyridin-3-yl]-7-fluoro-2-methyl-1,5-naphthyridin-4-amine;
3-chloro-N-[cyclopropyl(3-fluoropyridin-2-yl)methyl]-6-[6-(dimethylphosphoryl)pyridin-3-yl]-7-fluoro-2-methyl-1,5-naphthyridin-4-amine;
3-chloro-N—[(R)-cyclopropyl(phenyl)methyl]-6-[6-(dimethylphosphoryl)pyridin-3-yl]-7-fluoro-2-methyl-1,5-naphthyridin-4-amine;
3-chloro-N—[(R)-cyclopropyl(3,5-difluorophenyl)methyl]-6-[6-(dimethylphosphoryl)pyridin-3-yl]-7-fluoro-2-methyl-1,5-naphthyridin-4-amine;
3-chloro-N—[(S)-cyclopropyl(3,5-difluorophenyl)methyl]-6-[6-(dimethylphosphoryl)pyridin-3-yl]-7-fluoro-2-methyl-1,5-naphthyridin-4-amine;
3-chloro-N—[(S)-cyclopropyl(phenyl)methyl]-6-[6-(dimethylphosphoryl)pyridin-3-yl]-7-fluoro-2-methyl-1,5-naphthyridin-4-amine;
3-[(1R)-1-({3-chloro-7-fluoro-2-methyl-6-[6-(4-oxo-1,4lambda5-oxaphosphinan-4-yl)pyridin-3-yl]-1,5-naphthyridin-4-yl}amino)ethyl]-4-fluorobenzonitrile;
3-chloro-N-[1-(2,3-difluorophenyl)-2,2-difluoropropyl]-6-[6-(dimethylphosphoryl)pyridin-3-yl]-7-fluoro-2-methyl-1,5-naphthyridin-4-amine;
4-[5-(7-chloro-8-{[(1R)-1-(2,3-difluorophenyl)ethyl]amino}-3-fluoro-6-methyl-1,5-naphthyridin-2-yl)pyridin-2-yl]-1,4lambda5-oxaphosphinan-4-one;
4-{[(1R)-1-(2,3-difluorophenyl)ethyl]amino}-6-[6-(dimethylphosphoryl)pyridin-3-yl]-7-fluoro-2-methyl-1,5-naphthyridine-3-carbonitrile;
(S)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide;
(R)-(5-(7-chloro-8-((1-(2,3-difluorophenyl)-2,2-difluoroethyl)amino)-3-fluoro-6-methyl-1,5-naphthyridin-2-yl)pyridin-2-yl)dimethylphosphine oxide;
3-chloro-N-[(1R)-1-(3,5-difluorophenyl)propyl]-6-[6-(dimethylphosphoryl)pyridin-3-yl]-7-fluoro-2-methyl-1,5-naphthyridin-4-amine;
3-chloro-N-[(1S)-1-(3,5-difluorophenyl)propyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-2-methyl-N-[1-(1-methylpyrazol-3-yl)propyl]-1,5-naphthyridin-4-amine; and
3-chloro-N-[(1R)-1-(5-cyclopropyl-2-fluorophenyl)ethyl]-6-[6-(dimethylphosphoryl)pyridin-3-yl]-7-fluoro-2-methyl-1,5-naphthyridin-4-amine.

2. The compound of claim 1, or pharmaceutically acceptable salt or solvate thereof wherein the compound is selected from the group consisting of:
3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile;
3-chloro-6-[6-(dimethylphosphoryl)pyridin-3-yl]-7-fluoro-N-[(1R)-1-(2-fluorophenyl)ethyl]-2-methyl-1,5-naphthyridin-4-amine;
3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile;
(S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile;
3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine;
3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine;
3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine; and
3-chloro-6-[6-(dimethylphosphoryl)pyridin-3-yl]-7-fluoro-2-methyl-N-[(1R)-1-(pyridin-2-yl)ethyl]-1,5-naphthyridin-4-amine.

3. The compound of claim 2, or pharmaceutically acceptable salt or solvate thereof, wherein the compound is 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile.

4. The compound of claim 2, or pharmaceutically acceptable salt or solvate thereof, wherein the compound is 3-chloro-6-[6-(dimethylphosphoryl)pyridin-3-yl]-7-fluoro-N-[(1R)-1-(2-fluorophenyl)ethyl]-2-methyl-1,5-naphthyridin-4-amine.

5. The compound of claim 2, or pharmaceutically acceptable salt or solvate thereof, wherein the compound is 3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile.

6. The compound of claim 2, or pharmaceutically acceptable salt or solvate thereof, wherein the compound is(S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile.

7. The compound of claim 2, or pharmaceutically acceptable salt or solvate thereof, wherein the compound is 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine.

8. The compound of claim 2, or pharmaceutically acceptable salt or solvate thereof, wherein the compound is 3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine.

9. The compound of claim 2, or pharmaceutically acceptable salt or solvate thereof, wherein the compound is 3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine.

10. The compound of claim 2, or pharmaceutically acceptable salt or solvate thereof, wherein the compound is 3-chloro-6-[6-(dimethylphosphoryl)pyridin-3-yl]-7-fluoro-2-methyl-N-[(1R)-1-(pyridin-2-yl)ethyl]-1,5-naphthyridin-4-amine.

11. A pharmaceutical composition comprising at least one pharmaceutically acceptable excipient and a compound, or pharmaceutically acceptable salt or solvate thereof, selected from the group consisting of:

- 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile;
- 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzamide;
- 3-[(1R)-1-({3-chloro-6-[6-(dimethylphosphoryl)pyridin-3-yl]-7-fluoro-1,5-naphthyridin-4-yl}amino)ethyl]-4-fluorobenzonitrile;
- 3-chloro-6-[6-(dimethylphosphoryl)pyridin-3-yl]-7-fluoro-N-[(1R)-1-(2-fluorophenyl)ethyl]-2-methyl-1,5-naphthyridin-4-amine;
- 3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile;
- methyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate;
- 3-chloro-6-[6-(dimethylphosphoryl)pyridin-3-yl]-7-fluoro-N-[(1R)-1-(2-fluorophenyl)propyl]-2-methyl-1,5-naphthyridin-4-amine;
- 3-chloro-6-[6-(dimethylphosphoryl)pyridin-3-yl]-7-fluoro-N-[(1S)-1-(2-fluorophenyl)propyl]-2-methyl-1,5-naphthyridin-4-amine;
- (S)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide;
- (R)-(5-(7-chloro-8-((2,2-difluoro-1-(2-fluorophenyl)ethyl)amino)-3-fluoro-6-methyl-1,5-naphthyridin-2-yl)pyridin-2-yl)dimethylphosphine oxide;
- 3-[(1R)-1-({3-chloro-7-fluoro-2-methyl-6-[6-(1-oxo-1lambda5-phospholan-1-yl)pyridin-3-yl]-1,5-naphthyridin-4-yl}amino)ethyl]-4-fluorobenzonitrile;
- diethyl 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate;
- 3-[(1R)-1-[(3-chloro-6-{6-[(dimethylphosphoryl)methoxy]pyridin-3-yl}-7-fluoro-2-methyl-1,5-naphthyridin-4-yl)amino]ethyl]-4-fluorobenzonitrile;
- (S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile;
- (R)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile;
- 5-(7-chloro-8-{[(1R)-1-(5-cyano-2-fluorophenyl)ethyl]amino}-3-fluoro-6-methyl-1,5-naphthyridin-2-yl)pyridin-2-ylphosphonate;
- (R)-3-(1-((3-chloro-6-(6-((dimethylphosphoryl)methyl)pyridin-3-yl)-7-fluoro-2-methyl-1,5-naphthyridin-4-yl)amino)ethyl)-4-fluorobenzonitrile;
- 3-[(1R)-1-({3-chloro-6-[6-(dimethylphosphoryl)pyridin-3-yl]-2-methyl-1,5-naphthyridin-4-yl}amino)ethyl]-4-fluorobenzonitrile;
- 3-[(1R)-1-({3-chloro-6-[6-(diethylphosphoryl)pyridin-3-yl]-7-fluoro-2-methyl-1,5-naphthyridin-4-yl}amino)ethyl]-4-fluorobenzonitrile;
- 3-[(1R)-1-({3-chloro-6-[6-(dimethylphosphoryl)pyridin-3-yl]-7-fluoro-2-methyl-1,5-naphthyridin-4-yl}amino)ethyl]benzonitrile;
- 3-[(1S)-1-({3-chloro-6-[6-(dimethylphosphoryl)pyridin-3-yl]-7-fluoro-2-methyl-1,5-naphthyridin-4-yl}amino)propyl]-4-fluorobenzonitrile;
- 3-chloro-N-[(1S)-1-(2,3-difluorophenyl)ethyl]-6-[6-(dimethylphosphoryl)pyridin-3-yl]-7-fluoro-2-methyl-1,5-naphthyridin-4-amine;
- 3-[(1R)-1-({3-chloro-6-[6-(dimethylphosphoryl)pyridin-3-yl]-7-fluoro-2-methyl-1,5-naphthyridin-4-yl}amino)propyl]benzonitrile;
- 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine;
- 3-chloro-N-[(1S)-1-(2,5-difluorophenyl)ethyl]-6-[6-(dimethylphosphoryl)pyridin-3-yl]-7-fluoro-2-methyl-1,5-naphthyridin-4-amine;
- 3-chloro-N-[(1R)-1-(2,6-difluorophenyl)ethyl]-6-[6-(dimethylphosphoryl)pyridin-3-yl]-7-fluoro-2-methyl-1,5-naphthyridin-4-amine;
- 3-chloro-N-[(1R)-1-(2,5-difluorophenyl)ethyl]-6-[6-(dimethylphosphoryl)pyridin-3-yl]-7-fluoro-2-methyl-1,5-naphthyridin-4-amine;
- 3-chloro-N-[(1S)-1-(2,6-difluorophenyl)ethyl]-6-[6-(dimethylphosphoryl)pyridin-3-yl]-7-fluoro-2-methyl-1,5-naphthyridin-4-amine;
- (R)-3-(1-((3-chloro-6-(6-(diethylphosphoryl)pyridin-3-yl)-7-fluoro-2-methyl-1,5-naphthyridin-4-yl)amino)ethyl)-4-fluorobenzonitrile;
- 3-((R)-1-((3-chloro-6-(6-((S)-ethyl(methyl)phosphoryl)pyridin-3-yl)-7-fluoro-2-methyl-1,5-naphthyridin-4-yl)amino)ethyl)-4-fluorobenzonitrile;
- (2R)-2-({3-chloro-6-[6-(dimethylphosphoryl)pyridin-3-yl]-7-fluoro-2-methyl-1,5-naphthyridin-4-yl}amino)-2-(2-fluorophenyl)ethanol;
- 3-[(1R)-1-({3-chloro-6-[6-(dimethylphosphoryl)-4-methylpyridin-3-yl]-7-fluoro-2-methyl-1,5-naphthyridin-4-yl}amino)ethyl]-4-fluorobenzonitrile;
- 3-chloro-6-[6-(dimethylphosphoryl)-4-methylpyridin-3-yl]-7-fluoro-N-[(1R)-1-(2-fluorophenyl)ethyl]-2-methyl-1,5-naphthyridin-4-amine;
- (S)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile;
- (R)-3-(1-((3-chloro-6-(6-(dimethylphosphoryl)pyridin-3-yl)-7-fluoro-2-methyl-1,5-naphthyridin-4-yl)amino)-2-hydroxyethyl)-4-fluorobenzonitrile;
- 3-chloro-6-[6-(dimethylphosphoryl)pyridin-3-yl]-7-fluoro-N-[(1R)-1-[2-fluoro-5-(4-methylimidazol-1-yl)phenyl]ethyl]-2-methyl-1,5-naphthyridin-4-amine;
- (S)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide;
- (R)-(5-(7-chloro-3-fluoro-8-((1-(3-fluoropyridin-2-yl)propyl)amino)-6-methyl-1,5-naphthyridin-2-yl)pyridin-2-yl)dimethylphosphine oxide;

3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine;

3-chloro-6-[6-(dimethylphosphoryl)pyridin-3-yl]-7-fluoro-2-methyl-N-[(1R)-1-(pyridin-3-yl)ethyl]-1,5-naphthyridin-4-amine;

3-chloro-6-[6-(dimethylphosphoryl)pyridin-3-yl]-7-fluoro-2-methyl-N-[(1S)-1-(pyridin-2-yl)propyl]-1,5-naphthyridin-4-amine;

6-[6-(dimethylphosphoryl)pyridin-3-yl]-3,7-difluoro-N-[(1R)-1-(2-fluorophenyl)propyl]-2-methyl-1,5-naphthyridin-4-amine;

3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine;

3-chloro-6-[6-(dimethylphosphoryl)pyridin-3-yl]-7-fluoro-2-methyl-N-[(1R)-1-phenylpropyl]-1,5-naphthyridin-4-amine;

3-chloro-N-[(1R)-1-(3,4-difluorophenyl)ethyl]-6-[6-(dimethylphosphoryl)pyridin-3-yl]-7-fluoro-2-methyl-1,5-naphthyridin-4-amine;

3-chloro-6-[6-(dimethylphosphoryl)pyridin-3-yl]-7-fluoro-N-[(1R)-1-(2-methoxypyridin-4-yl)ethyl]-2-methyl-1,5-naphthyridin-4-amine;

3-chloro-6-[6-(dimethylphosphoryl)pyridin-3-yl]-7-fluoro-2-methyl-N-[1-(pyridin-3-yl)propyl]-1,5-naphthyridin-4-amine;

3-chloro-6-[6-(dimethylphosphoryl)pyridin-3-yl]-7-fluoro-2-methyl-N-[(1R)-1-(pyridin-2-yl)ethyl]-1,5-naphthyridin-4-amine;

3-chloro-6-[6-(dimethylphosphoryl)pyridin-3-yl]-7-fluoro-2-methyl-N-[(1R)-1-(pyridin-2-yl)propyl]-1,5-naphthyridin-4-amine;

3-chloro-N-[(1R)-1-(3,5-difluorophenyl)ethyl]-6-[6-(dimethylphosphoryl)pyridin-3-yl]-7-fluoro-2-methyl-1,5-naphthyridin-4-amine;

3-chloro-6-[6-(dimethylphosphoryl)pyridin-3-yl]-7-fluoro-N-[(1R)-1-(3-fluorophenyl)ethyl]-2-methyl-1,5-naphthyridin-4-amine;

3-chloro-N-[(1R)-1-(2-chlorophenyl)ethyl]-6-[6-(dimethylphosphoryl)pyridin-3-yl]-7-fluoro-2-methyl-1,5-naphthyridin-4-amine;

3-chloro-N-[(1R)-1-(2,4-difluorophenyl)ethyl]-6-[6-(dimethylphosphoryl)pyridin-3-yl]-7-fluoro-2-methyl-1,5-naphthyridin-4-amine;

3-chloro-6-[6-(dimethylphosphoryl)pyridin-3-yl]-7-fluoro-2-methyl-N-[(1R)-1-(2,3,6-trifluorophenyl)ethyl]-1,5-naphthyridin-4-amine;

3-chloro-6-[6-(dimethylphosphoryl)pyridin-3-yl]-7-fluoro-2-methyl-N-[(1R)-1-phenylethyl]-1,5-naphthyridin-4-amine;

3-chloro-N-[(1R)-1-(3-chlorophenyl)ethyl]-6-[6-(dimethylphosphoryl)pyridin-3-yl]-7-fluoro-2-methyl-1,5-naphthyridin-4-amine;

3-chloro-N-[(1R)-1-[3-(difluoromethyl)phenyl]ethyl]-6-[6-(dimethylphosphoryl)pyridin-3-yl]-7-fluoro-2-methyl-1,5-naphthyridin-4-amine;

3-chloro-6-[6-(dimethylphosphoryl)pyridin-3-yl]-7-fluoro-2-methyl-N-[(1R)-1-[3-(trifluoromethyl)phenyl]ethyl]-1,5-naphthyridin-4-amine;

3-chloro-6-[6-(dimethylphosphoryl)pyridin-3-yl]-7-fluoro-N-[1-(3-fluoropyridin-2-yl)ethyl]-2-methyl-1,5-naphthyridin-4-amine;

(R)-(5-(7-chloro-8-((1-(2,3-difluorophenyl)propyl)amino)-3-fluoro-6-methyl-1,5-naphthyridin-2-yl)pyridin-2-yl)dimethylphosphine oxide;

(S)-(5-(7-chloro-8-((1-(2,3-difluorophenyl)propyl)amino)-3-fluoro-6-methyl-1,5-naphthyridin-2-yl)pyridin-2-yl)dimethylphosphine oxide;

3-chloro-6-[6-(dimethylphosphoryl)pyridin-3-yl]-N-[(1R)-1-(5-ethynyl-2-fluorophenyl)ethyl]-7-fluoro-2-methyl-1,5-naphthyridin-4-amine;

3-[(1R)-1-({3-chloro-6-[6-(dimethylphosphoryl)pyridin-3-yl]-7-fluoro-2-methyl-1,5-naphthyridin-4-yl}amino)ethyl]-5-fluorobenzonitrile;

3-chloro-6-[6-(dimethylphosphoryl)pyridin-3-yl]-7-fluoro-2-methyl-N-[1-(1-methylpyrazol-4-yl)propyl]-1,5-naphthyridin-4-amine;

3-[(1R)-1-({3-chloro-6-[6-(dimethylphosphoryl)pyridin-3-yl]-7-fluoro-2-methyl-1,5-naphthyridin-4-yl}amino)ethyl]-4,5-difluorobenzonitrile;

3-chloro-N-[(1R)-1-(2,3-difluorophenyl)ethyl]-6-[6-(dimethylphosphoryl)-5-fluoropyridin-3-yl]-7-fluoro-2-methyl-1,5-naphthyridin-4-amine;

(R)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide;

(S)-(5-(7-chloro-3-fluoro-6-methyl-8-((1-(2,3,4-trifluorophenyl)ethyl)amino)-1,5-naphthyridin-2-yl)pyridin-2-yl)dimethylphosphine oxide;

3-chloro-6-[6-(dimethylphosphoryl)pyridin-3-yl]-7-fluoro-2-methyl-N-[1-(pyridin-2-yl)cyclopropyl]-1,5-naphthyridin-4-amine;

(R)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide;

(S)-(5-(7-chloro-3-fluoro-8-((1-(3-fluoropyridin-2-yl)ethyl)amino)-6-methyl-1,5-naphthyridin-2-yl)pyridin-2-yl)dimethylphosphine oxide;

3-[(1R)-1-({6-[6-(dimethylphosphoryl)pyridin-3-yl]-7-fluoro-2,3-dimethyl-1,5-naphthyridin-4-yl}amino)ethyl]-4-fluorobenzonitrile;

3-[(1R)-1-({3-chloro-6-[6-(dimethylphosphoryl)-5-fluoropyridin-3-yl]-7-fluoro-2-methyl-1,5-naphthyridin-4-yl}amino)ethyl]-4-fluorobenzonitrile;

6-[(1S)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile;

6-[(1R)-1-({3-chloro-6-[6-(dimethylphosphoryl)pyridin-3-yl]-7-fluoro-2-methyl-1,5-naphthyridin-4-yl}amino)ethyl]-5-fluoropyridine-2-carbonitrile;

3-chloro-N-[(1R)-1-(3,5-difluorophenyl)ethyl]-6-[6-(dimethylphosphoryl)-5-fluoropyridin-3-yl]-7-fluoro-2-methyl-1,5-naphthyridin-4-amine;

3-chloro-N-[(1R)-1-(3-chloro-5-fluorophenyl)ethyl]-6-[6-(dimethylphosphoryl)pyridin-3-yl]-7-fluoro-2-methyl-1,5-naphthyridin-4-amine;

N-[(1R)-1-(2,3-difluorophenyl)ethyl]-6-[6-(dimethylphosphoryl)pyridin-3-yl]-7-fluoro-2,3-dimethyl-1,5-naphthyridin-4-amine;

3-cyclopropyl-N-[(1R)-1-(2,3-difluorophenyl)ethyl]-6-[6-(dimethylphosphoryl)pyridin-3-yl]-7-fluoro-2-methyl-1,5-naphthyridin-4-amine;

3-chloro-N-[cyclopropyl(3-fluoropyridin-2-yl)methyl]-6-[6-(dimethylphosphoryl)pyridin-3-yl]-7-fluoro-2-methyl-1,5-naphthyridin-4-amine;

3-chloro-N—[(R)-cyclopropyl(phenyl)methyl]-6-[6-(dimethylphosphoryl)pyridin-3-yl]-7-fluoro-2-methyl-1,5-naphthyridin-4-amine;

3-chloro-N—[(R)-cyclopropyl(3,5-difluorophenyl)methyl]-6-[6-(dimethylphosphoryl)pyridin-3-yl]-7-fluoro-2-methyl-1,5-naphthyridin-4-amine;

3-chloro-N—[(S)-cyclopropyl(3,5-difluorophenyl)
  methyl]-6-[6-(dimethylphosphoryl)pyridin-3-yl]-7-
  fluoro-2-methyl-1,5-naphthyridin-4-amine;
3-chloro-N—[(S)-cyclopropyl(phenyl)methyl]-6-[6-(dimethylphosphoryl)pyridin-3-yl]-7-fluoro-2-methyl-1,
  5-naphthyridin-4-amine;
3-[(1R)-1-({3-chloro-7-fluoro-2-methyl-6-[6-(4-oxo-1,
  4lambda5-oxaphosphinan-4-yl)pyridin-3-yl]-1,5-naphthyridin-4-yl}amino)ethyl]-4-fluorobenzonitrile;
3-chloro-N-[1-(2,3-difluorophenyl)-2,2-difluoropropyl]-
  6-[6-(dimethylphosphoryl)pyridin-3-yl]-7-fluoro-2-
  methyl-1,5-naphthyridin-4-amine;
4-[5-(7-chloro-8-{[(1R)-1-(2,3-difluorophenyl)ethyl]
  amino}-3-fluoro-6-methyl-1,5-naphthyridin-2-yl)pyridin-2-yl]-1,4lambda5-oxaphosphinan-4-one;
4-{[(1R)-1-(2,3-difluorophenyl)ethyl]amino}-6-[6-(dimethylphosphoryl)pyridin-3-yl]-7-fluoro-2-methyl-1,5-
  naphthyridine-3-carbonitrile;
(S)-(5-(7-chloro-8-((1-(2,3-difluorophenyl)-2,2-difluoroethyl)amino)-3-fluoro-6-methyl-1,5-naphthyridin-2-
  yl)pyridin-2-yl)dimethylphosphine oxide;
(R)-(5-(7-chloro-8-((1-(2,3-difluorophenyl)-2,2-difluoroethyl)amino)-3-fluoro-6-methyl-1,5-naphthyridin-2-
  yl)pyridin-2-yl)dimethylphosphine oxide;
3-chloro-N-[(1R)-1-(3,5-difluorophenyl)propyl]-6-[6-
  (dimethylphosphoryl)pyridin-3-yl]-7-fluoro-2-methyl-
  1,5-naphthyridin-4-amine;
3-chloro-N-[(1S)-1-(3,5-difluorophenyl)propyl]-6-[6-(dimethylphosphoryl)pyridin-3-yl]-7-fluoro-2-methyl-1,
  5-naphthyridin-4-amine;
3-chloro-6-[6-(dimethylphosphoryl)pyridin-3-yl]-7-
  fluoro-2-methyl-N-[1-(1-methylpyrazol-3-yl)propyl]-
  1,5-naphthyridin-4-amine; and
3-chloro-N-[(1R)-1-(5-cyclopropyl-2-fluorophenyl)
  ethyl]-6-[6-(dimethylphosphoryl)pyridin-3-yl]-7-
  fluoro-2-methyl-1,5-naphthyridin-4-amine.

12. The pharmaceutical composition of claim 11, wherein the compound, or pharmaceutically acceptable salt or solvate thereof, is selected from the group consisting of:
3-[(1R)-1-({3-chloro-6-[6-(dimethylphosphoryl)pyridin-
  3-yl]-7-fluoro-2-methyl-1,5-naphthyridin-4-yl}amino)
  ethyl]-4-fluorobenzonitrile;
3-chloro-6-[6-(dimethylphosphoryl)pyridin-3-yl]-7-
  fluoro-N-[(1R)-1-(2-fluorophenyl)ethyl]-2-methyl-1,
  5-naphthyridin-4-amine;
3-[(1R)-1-({3-chloro-6-[6-(dimethylphosphoryl)pyridin-
  3-yl]-7-fluoro-2-methyl-1,5-naphthyridin-4-yl}amino)
  propyl]-4-fluorobenzonitrile;
(S)-3-(1-((3-chloro-6-(6-(dimethylphosphoryl)pyridin-3-
  yl)-7-fluoro-2-methyl-1,5-naphthyridin-4-yl)amino)-2,
  2-difluoroethyl)-4-fluorobenzonitrile;
3-chloro-N-[(1R)-1-(2,3-difluorophenyl)ethyl]-6-[6-(dimethylphosphoryl)pyridin-3-yl]-7-fluoro-2-methyl-1,
  5-naphthyridin-4-amine;
3-chloro-6-[6-(dimethylphosphoryl)pyridin-3-yl]-7-
  fluoro-2-methyl-N-[(1S)-2,2,2-trifluoro-1-(2-fluorophenyl)ethyl]-1,5-naphthyridin-4-amine;
3-chloro-N-[(1R)-1-(3-chloro-2-fluorophenyl)ethyl]-6-
  [6-(dimethylphosphoryl)pyridin-3-yl]-7-fluoro-2-
  methyl-1,5-naphthyridin-4-amine; and
3-chloro-6-[6-(dimethylphosphoryl)pyridin-3-yl]-7-
  fluoro-2-methyl-N-[(1R)-1-(pyridin-2-yl)ethyl]-1,5-
  naphthyridin-4-amine.

13. The pharmaceutical composition of claim 12 wherein the compound is 3-[(1R)-1-({3-chloro-6-[6-(dimethylphosphoryl)pyridin-3-yl]-7-fluoro-2-methyl-1,5-naphthyridin-4-yl}amino)ethyl]-4-fluorobenzonitrile, or a pharmaceutically acceptable salt or solvate thereof.

14. The pharmaceutical composition of claim 12 wherein the compound is 3-chloro-6-[6-(dimethylphosphoryl)pyridin-3-yl]-7-fluoro-N-[(1R)-1-(2-fluorophenyl)ethyl]-2-methyl-1,5-naphthyridin-4-amine, or a pharmaceutically acceptable salt or solvate thereof.

15. The pharmaceutical composition of claim 12 wherein the compound is 3-[(1R)-1-({3-chloro-6-[6-(dimethylphosphoryl)pyridin-3-yl]-7-fluoro-2-methyl-1,5-naphthyridin-4-yl}amino)propyl]-4-fluorobenzonitrile, or a pharmaceutically acceptable salt or solvate thereof.

16. The pharmaceutical composition of claim 12 wherein the compound is(S)-3-(1-((3-chloro-6-(6-(dimethylphosphoryl)pyridin-3-yl)-7-fluoro-2-methyl-1,5-naphthyridin-4-yl)amino)-2,2-difluoroethyl)-4-fluorobenzonitrile, or a pharmaceutically acceptable salt or solvate thereof.

17. The pharmaceutical composition of claim 12 wherein the compound is 3-chloro-N-[(1R)-1-(2,3-difluorophenyl)ethyl]-6-[6-(dimethylphosphoryl)pyridin-3-yl]-7-fluoro-2-methyl-1,5-naphthyridin-4-amine, or a pharmaceutically acceptable salt or solvate thereof.

18. The pharmaceutical composition of claim 12 wherein the compound is 3-chloro-6-[6-(dimethylphosphoryl)pyridin-3-yl]-7-fluoro-2-methyl-N-[(1S)-2,2,2-trifluoro-1-(2-fluorophenyl)ethyl]-1,5-naphthyridin-4-amine, or a pharmaceutically acceptable salt or solvate thereof.

19. The pharmaceutical composition of claim 12, or pharmaceutically acceptable salt or solvate thereof, wherein the compound is 3-chloro-N-[(1R)-1-(3-chloro-2-fluorophenyl)ethyl]-6-[6-(dimethylphosphoryl)pyridin-3-yl]-7-fluoro-2-methyl-1,5-naphthyridin-4-amine, or a pharmaceutically acceptable salt or solvate thereof.

20. The pharmaceutical composition of claim 12 wherein the compound is 3-chloro-6-[6-(dimethylphosphoryl)pyridin-3-yl]-7-fluoro-2-methyl-N-[(1R)-1-(pyridin-2-yl)ethyl]-1,5-naphthyridin-4-amine, or a pharmaceutically acceptable salt or solvate thereof.

\* \* \* \* \*